United States Patent
Roy et al.

(10) Patent No.: US 10,286,086 B2
(45) Date of Patent: May 14, 2019

(54) ALTERNATIVE NUCLEIC ACID MOLECULES AND USES THEREOF

(71) Applicant: ModernaTX, Inc., Cambridge, MA (US)

(72) Inventors: Atanu Roy, Stoneham, MA (US); Christopher R. Conlee, Watertown, MA (US); Antonin De Fougerolles, Waterloo (BE); Andrew W. Fraley, Arlington, MA (US); Gabor Butora, Cambridge, MA (US); Matthew Stanton, Marlton, NJ (US)

(73) Assignee: ModernaTX, Inc., Cambridge, MA (US)

( * ) Notice: Subject to any disclaimer, the term of this patent is extended or adjusted under 35 U.S.C. 154(b) by 73 days.

(21) Appl. No.: 15/319,840

(22) PCT Filed: Jun. 19, 2015

(86) PCT No.: PCT/US2015/036771
§ 371 (c)(1),
(2) Date: Dec. 19, 2016

(87) PCT Pub. No.: WO2015/196128
PCT Pub. Date: Dec. 23, 2015

(65) Prior Publication Data
US 2017/0136131 A1    May 18, 2017

Related U.S. Application Data

(60) Provisional application No. 62/014,620, filed on Jun. 19, 2014, provisional application No. 62/036,880, filed on Aug. 13, 2014.

(51) Int. Cl.

| | | |
|---|---|---|
| A61K 48/00 | (2006.01) |
| C07F 9/6558 | (2006.01) |
| C07H 19/06 | (2006.01) |
| C07H 19/16 | (2006.01) |
| C12N 15/11 | (2006.01) |
| C12N 15/67 | (2006.01) |
| C07H 21/02 | (2006.01) |
| C07F 9/6561 | (2006.01) |
| C07D 405/04 | (2006.01) |
| C07D 239/54 | (2006.01) |
| C07H 19/067 | (2006.01) |
| C07H 19/10 | (2006.01) |
| C07H 19/14 | (2006.01) |
| C07H 19/167 | (2006.01) |
| C07H 19/20 | (2006.01) |
| C07H 19/23 | (2006.01) |
| C07D 473/16 | (2006.01) |
| C07D 473/18 | (2006.01) |
| C07D 473/30 | (2006.01) |
| C07D 473/34 | (2006.01) |
| C07D 473/38 | (2006.01) |
| C07D 473/40 | (2006.01) |
| C07D 487/04 | (2006.01) |
| C07D 487/16 | (2006.01) |
| C07D 498/22 | (2006.01) |
| C12N 15/87 | (2006.01) |

(52) U.S. Cl.
CPC ........ *A61K 48/0066* (2013.01); *C07D 239/54* (2013.01); *C07D 405/04* (2013.01); *C07D 473/16* (2013.01); *C07D 473/18* (2013.01); *C07D 473/30* (2013.01); *C07D 473/34* (2013.01); *C07D 473/38* (2013.01); *C07D 473/40* (2013.01); *C07D 487/04* (2013.01); *C07D 487/16* (2013.01); *C07D 498/22* (2013.01); *C07F 9/6561* (2013.01); *C07F 9/65586* (2013.01); *C07F 9/65616* (2013.01); *C07H 19/06* (2013.01); *C07H 19/067* (2013.01); *C07H 19/10* (2013.01); *C07H 19/14* (2013.01); *C07H 19/16* (2013.01); *C07H 19/167* (2013.01); *C07H 19/20* (2013.01); *C07H 19/23* (2013.01); *C07H 21/02* (2013.01); *C12N 15/11* (2013.01); *C12N 15/67* (2013.01); *C12N 15/87* (2013.01); *C12N 2310/334* (2013.01); *C12N 2310/335* (2013.01); *C12N 2310/3341* (2013.01)

(58) Field of Classification Search
None
See application file for complete search history.

(56) References Cited

U.S. PATENT DOCUMENTS

| | | |
|---|---|---|
| 5,426,180 A | 6/1995 | Kool |
| 5,489,677 A | 2/1996 | Sanghvi et al. |
| 5,512,439 A | 4/1996 | Hornes et al. |
| 5,591,722 A | 1/1997 | Montgomery et al. |
| 5,637,459 A | 6/1997 | Burke et al. |
| 5,639,873 A | 6/1997 | Barascut et al. |
| 5,789,578 A | 8/1998 | Burton et al. |
| 5,808,039 A | 9/1998 | Reddy et al. |
| 5,989,911 A | 11/1999 | Fournier et al. |
| 6,022,737 A | 2/2000 | Niven et al. |

(Continued)

FOREIGN PATENT DOCUMENTS

| | | |
|---|---|---|
| CA | 2028849 A1 | 9/1991 |
| CA | 2473135 A1 | 6/2003 |

(Continued)

OTHER PUBLICATIONS

Li, et al. (2016) "Effects of Chemically Modified Messenger RNA on Protein Expression", Bioconjugate Chemistry, 27: 849-53.*

(Continued)

*Primary Examiner* — Robert M Kelly
(74) *Attorney, Agent, or Firm* — Clark & Elbing LLP

(57) ABSTRACT

The present disclosure provides alternative nucleosides, nucleotides, and nucleic acids, and methods of using them.

14 Claims, No Drawings
Specification includes a Sequence Listing.

(56) References Cited

U.S. PATENT DOCUMENTS

| | | |
|---|---|---|
| 6,248,268 B1 | 6/2001 | Cook |
| 6,423,492 B1 | 7/2002 | Harbron |
| 6,511,832 B1 | 1/2003 | Guarino et al. |
| 6,521,411 B2 | 2/2003 | Hecker et al. |
| 7,691,569 B2 | 4/2010 | Wohlgemuth et al. |
| 8,093,367 B2 | 1/2012 | Kore et al. |
| 8,664,194 B2 | 3/2014 | de Fougerolles et al. |
| 8,680,069 B2 | 3/2014 | de Fougerolles et al. |
| 8,710,200 B2 | 4/2014 | Schrum et al. |
| 8,716,465 B2 | 5/2014 | Rossi et al. |
| 8,802,438 B2 | 8/2014 | Rossi et al. |
| 8,822,663 B2 | 9/2014 | Schrum et al. |
| 8,883,506 B2 | 11/2014 | Rossi et al. |
| 8,898,864 B1 | 12/2014 | Porter |
| 8,980,864 B2 | 3/2015 | Hoge et al. |
| 8,999,380 B2 | 4/2015 | Bancel et al. |
| 9,050,297 B2 | 6/2015 | Chakraborty et al. |
| 9,061,059 B2 | 6/2015 | Chakraborty et al. |
| 9,089,604 B2 | 7/2015 | Chakraborty et al. |
| 9,095,552 B2 | 8/2015 | Chakraborty et al. |
| 9,107,886 B2 | 8/2015 | Chakraborty et al. |
| 9,114,113 B2 | 8/2015 | Chakraborty et al. |
| 9,149,506 B2 | 10/2015 | Chakraborty et al. |
| 9,428,535 B2 | 8/2016 | de Fougerolles et al. |
| 9,533,047 B2 | 1/2017 | de Fougerolles et al. |
| 9,675,668 B2 | 6/2017 | Bancel et al. |
| 9,751,925 B2 | 9/2017 | Hoge et al. |
| 9,803,177 B2 | 10/2017 | Rossi et al. |
| 9,872,900 B2 | 1/2018 | Ciaramella et al. |
| 10,022,435 B2 | 7/2018 | Ciaramella et al. |
| 10,064,935 B2 | 9/2018 | Ciaramella et al. |
| 10,072,057 B2 | 9/2018 | Hoge et al. |
| 2001/0025097 A1 | 9/2001 | Sheridan et al. |
| 2002/0001812 A1 | 1/2002 | Smith et al. |
| 2002/0016450 A1 | 2/2002 | Laugharn et al. |
| 2002/0114784 A1 | 8/2002 | Li et al. |
| 2002/0153312 A1 | 10/2002 | Gjerde et al. |
| 2003/0120035 A1 | 6/2003 | Gao et al. |
| 2003/0170876 A1 | 9/2003 | Widner et al. |
| 2003/0170891 A1 | 9/2003 | McSwiggen |
| 2003/0180754 A1 | 9/2003 | Bergholtz et al. |
| 2003/0180779 A1 | 9/2003 | Lofton-Day et al. |
| 2004/0038278 A1 | 2/2004 | Tzertzinis et al. |
| 2004/0142433 A1 | 7/2004 | Padgett et al. |
| 2004/0220127 A1 | 11/2004 | Sternberg et al. |
| 2004/0259097 A1 | 12/2004 | De Backer et al. |
| 2005/0003496 A1 | 1/2005 | McGall et al. |
| 2005/0130196 A1 | 6/2005 | Hofstadler et al. |
| 2006/0058266 A1 | 3/2006 | Manoharan et al. |
| 2006/0121441 A1 | 6/2006 | Spira |
| 2006/0223081 A1 | 10/2006 | Jarrell et al. |
| 2007/0020678 A1 | 1/2007 | Ault-Riche et al. |
| 2007/0037148 A1 | 2/2007 | Fong et al. |
| 2007/0037770 A1 | 2/2007 | Gryaznov et al. |
| 2007/0244062 A1 | 10/2007 | Laux et al. |
| 2007/0281336 A1 | 12/2007 | Jendrisak et al. |
| 2008/0076910 A1 | 3/2008 | Takkellapati et al. |
| 2009/0215125 A1 | 8/2009 | Reed et al. |
| 2009/0286852 A1 | 11/2009 | Kariko et al. |
| 2010/0047261 A1 | 2/2010 | Hoerr et al. |
| 2010/0178272 A1 | 7/2010 | Hartmann et al. |
| 2010/0183639 A1 | 7/2010 | Uhlmann et al. |
| 2010/0261228 A1 | 10/2010 | Gharib et al. |
| 2010/0261231 A1 | 10/2010 | Kore et al. |
| 2010/0317532 A1 | 12/2010 | Liu et al. |
| 2011/0130440 A1 | 6/2011 | Manoharan et al. |
| 2011/0143397 A1 | 6/2011 | Kariko et al. |
| 2011/0218170 A1 | 9/2011 | Thottassery et al. |
| 2011/0281938 A1 | 11/2011 | Schaub et al. |
| 2012/0046346 A1 | 2/2012 | Rossi et al. |
| 2012/0100136 A1 | 4/2012 | Patel et al. |
| 2012/0129261 A1 | 5/2012 | Eberwine et al. |
| 2012/0251618 A1 | 10/2012 | Schrum et al. |
| 2013/0046084 A1 | 2/2013 | Brown et al. |
| 2013/0052721 A1 | 2/2013 | Hollander et al. |
| 2013/0058894 A1 | 3/2013 | Maldonado et al. |
| 2013/0115272 A1 | 5/2013 | de Fougerolles et al. |
| 2013/0123481 A1 | 5/2013 | de Fougerolles et al. |
| 2013/0156849 A1 | 6/2013 | de Fougerolles et al. |
| 2013/0165504 A1 | 6/2013 | Bancel et al. |
| 2013/0197068 A1 | 8/2013 | Kariko et al. |
| 2013/0203115 A1 | 8/2013 | Schrum et al. |
| 2013/0244282 A1 | 9/2013 | Schrum et al. |
| 2013/0245103 A1 | 9/2013 | de Fougerolles et al. |
| 2013/0245106 A1 | 9/2013 | de Fougerolles et al. |
| 2013/0251618 A1 | 9/2013 | Li et al. |
| 2013/0259923 A1 | 10/2013 | Bancel et al. |
| 2013/0259924 A1 | 10/2013 | Bancel et al. |
| 2014/0010861 A1 | 1/2014 | Bancel et al. |
| 2014/0105964 A1 | 4/2014 | Bancel et al. |
| 2014/0105966 A1 | 4/2014 | Bancel et al. |
| 2014/0147454 A1 | 5/2014 | Chakraborty et al. |
| 2014/0200261 A1 | 7/2014 | Hoge et al. |
| 2014/0206752 A1 | 7/2014 | Afeyan et al. |
| 2014/0206852 A1 | 7/2014 | Hoge et al. |
| 2014/0243399 A1 | 8/2014 | Schrum et al. |
| 2014/0273230 A1 | 9/2014 | Chen et al. |
| 2014/0275227 A1 | 9/2014 | Hoge et al. |
| 2014/0343129 A1 | 11/2014 | de Fougerolles et al. |
| 2015/0005372 A1 | 1/2015 | Hoge et al. |
| 2015/0017211 A1 | 1/2015 | de Fougerolles et al. |
| 2015/0030576 A1 | 1/2015 | Bancel |
| 2015/0050354 A1 | 2/2015 | Bouchon et al. |
| 2015/0050738 A1 | 2/2015 | Ozsolak et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064725 A1 | 3/2015 | Schrum et al. |
| 2015/0086614 A1 | 3/2015 | Bancel et al. |
| 2015/0111248 A1 | 4/2015 | Bancel et al. |
| 2015/0141269 A1 | 5/2015 | Soldatov et al. |
| 2015/0141499 A1 | 5/2015 | Bancel et al. |
| 2015/0166616 A1 | 6/2015 | Bancel et al. |
| 2015/0167017 A1 | 6/2015 | Roy et al. |
| 2015/0211039 A1 | 7/2015 | Wang et al. |
| 2015/0307542 A1 | 10/2015 | Roy et al. |
| 2016/0017313 A1 | 1/2016 | Spivak et al. |
| 2016/0024140 A1 | 1/2016 | Issa et al. |
| 2016/0024141 A1 | 1/2016 | Issa et al. |
| 2016/0024492 A1 | 1/2016 | Issa et al. |
| 2016/0024547 A1 | 1/2016 | Bancel et al. |
| 2016/0032273 A1 | 2/2016 | Shahrokh et al. |
| 2016/0038612 A1 | 2/2016 | Hoge et al. |
| 2016/0177295 A1 | 6/2016 | Rudolph et al. |
| 2016/0194368 A1 | 7/2016 | Hoge et al. |
| 2016/0194625 A1 | 7/2016 | Hoge et al. |
| 2016/0237108 A1 | 8/2016 | Fraley et al. |
| 2016/0244742 A1 | 8/2016 | Linnarsson et al. |
| 2016/0326575 A1 | 11/2016 | Von Der Mulbe et al. |
| 2016/0354490 A1 | 12/2016 | Roy et al. |
| 2016/0354491 A1 | 12/2016 | Roy et al. |
| 2016/0354492 A1 | 12/2016 | Roy et al. |
| 2016/0354493 A1 | 12/2016 | Roy et al. |
| 2017/0136131 A1 | 5/2017 | Roy et al. |
| 2017/0136132 A1 | 5/2017 | Roy et al. |
| 2017/0175129 A1 | 6/2017 | Roy et al. |

FOREIGN PATENT DOCUMENTS

| | | | |
|---|---|---|---|
| EP | 0366400 | A2 | 5/1990 |
| EP | 1083232 | B1 | 2/2005 |
| EP | 1619254 | A1 | 1/2006 |
| EP | 1383556 | B9 | 3/2008 |
| EP | 1831160 | B1 | 6/2010 |
| EP | 2092064 | B1 | 9/2010 |
| EP | 2377938 | A1 | 10/2011 |
| EP | 2484770 | A1 | 8/2012 |
| EP | 2188379 | B1 | 1/2013 |
| EP | 2548960 | A1 | 1/2013 |
| JP | 2011-130725 | A | 7/2011 |
| RU | 2540017 | C2 | 1/2015 |
| WO | WO-91/05058 | A1 | 4/1991 |

(56) References Cited

FOREIGN PATENT DOCUMENTS

| | | |
|---|---|---|
| WO | WO-93/03052 A1 | 2/1993 |
| WO | WO-93/13121 A1 | 7/1993 |
| WO | WO-01/55306 A2 | 8/2001 |
| WO | WO-02/44399 A2 | 6/2002 |
| WO | WO-02/098443 A2 | 12/2002 |
| WO | WO-03/039523 A2 | 5/2003 |
| WO | WO-03/051881 A1 | 6/2003 |
| WO | WO-2004/020575 A2 | 3/2004 |
| WO | WO-2004/064782 A2 | 8/2004 |
| WO | WO-2006/015445 A1 | 2/2006 |
| WO | WO-2007/024708 A2 | 3/2007 |
| WO | WO-2007/024798 A2 | 3/2007 |
| WO | WO-2007/089607 A2 | 8/2007 |
| WO | WO-2007/120863 A2 | 10/2007 |
| WO | WO-2008/039669 A1 | 4/2008 |
| WO | WO-2008/045505 A2 | 4/2008 |
| WO | WO-2008/083949 A2 | 7/2008 |
| WO | WO-2008/120016 A1 | 10/2008 |
| WO | WO-2009/042971 A2 | 4/2009 |
| WO | WO-2009/051451 A2 | 4/2009 |
| WO | WO-2009/127060 A1 | 10/2009 |
| WO | WO-2009/127230 A1 | 10/2009 |
| WO | WO-2009/147519 A1 | 12/2009 |
| WO | WO-2009/149253 A2 | 12/2009 |
| WO | WO-2010/014895 A2 | 2/2010 |
| WO | WO-2010/017510 A1 | 2/2010 |
| WO | WO-2010/109289 A1 | 9/2010 |
| WO | WO-2011/005850 A1 | 1/2011 |
| WO | WO-2011/012316 A2 | 2/2011 |
| WO | WO-2011/071931 A2 | 6/2011 |
| WO | WO-2011/127933 A1 | 10/2011 |
| WO | WO-2011/133868 A2 | 10/2011 |
| WO | WO-2011/140627 A1 | 11/2011 |
| WO | WO-2012/019168 A2 | 2/2012 |
| WO | WO-2012/135805 A2 | 10/2012 |
| WO | WO-2012/138530 A1 | 10/2012 |
| WO | WO-2012/158736 A1 | 11/2012 |
| WO | WO-2012/164565 A1 | 12/2012 |
| WO | WO-2013/039861 A2 | 3/2013 |
| WO | WO-2013/052523 A1 | 4/2013 |
| WO | WO-2013/090186 A1 | 6/2013 |
| WO | WO-2013/090294 A1 | 6/2013 |
| WO | WO-2013/090648 A1 | 6/2013 |
| WO | WO-2013/090897 A1 | 6/2013 |
| WO | WO-2013/096709 A2 | 6/2013 |
| WO | WO-2013/101690 A1 | 7/2013 |
| WO | WO-2013/113326 A1 | 8/2013 |
| WO | WO-2013/113501 A1 | 8/2013 |
| WO | WO-2013/113502 A1 | 8/2013 |
| WO | WO-2013/130161 A1 | 9/2013 |
| WO | WO-2013/151663 A1 | 10/2013 |
| WO | WO-2013/151664 A1 | 10/2013 |
| WO | WO-2013/151665 A2 | 10/2013 |
| WO | WO-2013/151666 A2 | 10/2013 |
| WO | WO-2013/151667 A1 | 10/2013 |
| WO | WO-2013/151668 A2 | 10/2013 |
| WO | WO-2013/151669 A1 | 10/2013 |
| WO | WO-2013/151670 A2 | 10/2013 |
| WO | WO-2013/151671 A1 | 10/2013 |
| WO | WO-2013/151672 A2 | 10/2013 |
| WO | WO-2013/151736 A2 | 10/2013 |
| WO | WO-2013/184976 A2 | 12/2013 |
| WO | WO-2013/185069 A1 | 12/2013 |
| WO | WO-2014/028429 A2 | 2/2014 |
| WO | WO-2014/081507 A1 | 5/2014 |
| WO | WO-2014/093574 A1 | 6/2014 |
| WO | WO-2014/093622 A2 | 6/2014 |
| WO | WO-2014/093924 A1 | 6/2014 |
| WO | WO-2014/113089 A2 | 7/2014 |
| WO | WO-2014/144039 A1 | 9/2014 |
| WO | WO-2014/144711 A1 | 9/2014 |
| WO | WO-2014/144767 A1 | 9/2014 |
| WO | WO-2014/152027 A1 | 9/2014 |
| WO | WO-2014/152030 A1 | 9/2014 |
| WO | WO-2014/152031 A1 | 9/2014 |
| WO | WO-2014/152211 A1 | 9/2014 |
| WO | WO-2014/152513 A1 | 9/2014 |
| WO | WO-2014/152540 A1 | 9/2014 |
| WO | WO-2014/152659 A1 | 9/2014 |
| WO | WO-2014/152673 A1 | 9/2014 |
| WO | WO-2014/160243 A1 | 10/2014 |
| WO | WO-2014/160284 A1 | 10/2014 |
| WO | WO-2014/164253 A1 | 10/2014 |
| WO | WO-2015/006747 A2 | 1/2015 |
| WO | WO-2015/034925 A1 | 3/2015 |
| WO | WO-2015/034928 A1 | 3/2015 |
| WO | WO-2015/038892 A1 | 3/2015 |
| WO | WO-2015/048744 A2 | 4/2015 |
| WO | WO-2015/051169 A2 | 4/2015 |
| WO | WO-2015/051173 A2 | 4/2015 |
| WO | WO-2015/051214 A1 | 4/2015 |
| WO | WO-2015/058069 A1 | 4/2015 |
| WO | WO-2015/070413 A1 | 5/2015 |
| WO | WO-2015/085318 A2 | 6/2015 |
| WO | WO-2015/089511 A2 | 6/2015 |
| WO | WO-2015/101416 A1 | 7/2015 |
| WO | WO-2015/105926 A1 | 7/2015 |
| WO | WO-2015/196118 A1 | 12/2015 |
| WO | WO-2015/196128 A2 | 12/2015 |
| WO | WO-2015/196130 A2 | 12/2015 |
| WO | WO-2016/010840 A1 | 1/2016 |
| WO | WO-2016/011222 A2 | 1/2016 |
| WO | WO-2016/011226 A1 | 1/2016 |
| WO | WO-2016/034620 A1 | 3/2016 |
| WO | WO-2016/036902 A1 | 3/2016 |
| WO | WO-2016/077125 A1 | 5/2016 |
| WO | WO-2016/118724 A1 | 7/2016 |
| WO | WO-2016/118725 A1 | 7/2016 |

OTHER PUBLICATIONS

Anderson et al., "Incorporation of pseudouridine into mRNA enhances translation by diminishing PKR activation," Nucleic Acids Res. 38(17):5884-92 (2010).

Anderson et al., "Nucleoside modifications in RNA limit activation of 2'-5'-oligoadenylate synthetase and increase resistance to cleavage by RNase L," Nucleic Acids Res. 39(21): 9329-38 (2011) (10 pages).

Bangs et al., "Mass Spectrometry of mRNA cap 4 from trypanosomatids reveals two novel nucleosides," J Biol Chem. 267(14):9805-15 (1992).

Bhaduri et al., "Procedure for the preparation of milligram quantities of adenovirus messenger ribonucleic acid," J Virol. 10(6):1126-9 (1972).

Deltcheva et al., "CRISPR RNA maturation by trans-encoded small RNA and host factor RNase III," available in PMC Sep. 30, 2011, published in final edited form as: Nature 471(7340):602-7 (2011) (54 pages).

Derrigo et al., "RNA-protein interactions in the control of stability and localization of messenger RNA (review)," Int J Mol Med. 5(2):111-23 (2000).

Extended European Search Report for European Application No. 15809963.0, dated Jan. 22, 2018 (11 pages).

Fath et al., "Multiparameter RNA and codon optimization: a standardized tool to assess and enhance autologous mammalian gene expression," PLoS One 6(3):e17596 (2011) (14 pages).

Gaj et al., "ZFN, TALEN, and CRISPR/Cas-based methods for genome engineering," Trends Biotechnol. 31(7):397-405 (2013).

Gilbert et al., "CRISPR-mediated modular RNA-guided regulation of transcription in eukaryotes," Cell 154(2):442-51 (2013) (15 pages).

Grosjean, Modification and editing of RNA: historical overview and important facts to remember. *Fine-Tuning of RNA Functions by Modification and Editing.* Grosjean H, 1-22 (2005).

Hansen et al., "Circular RNA and miR-7 in Cancer," Cancer Res. 73(18):5609-12 (2013).

Hansen et al., "Natural RNA circles function as efficient microRNA sponges," Nature. 495(7441):384-8 (2013) (7 pages).

(56) References Cited

OTHER PUBLICATIONS

Hikishima et al., "Synthesis of 1,8-naphthyridine C-nucleosides and their base-pairing properties in oligodeoxynucleotides: thermally stable naphthyridine:imidazopyridopyrimidine base-pairing motifs," Angew Chem Int Ed. 44:596-8 (2005).
International Search Report and Written Opinion for International Patent Application No. PCT/US15/36771, dated Dec. 18, 2015 (15 pages).
Invitation to Pay Additional Fees for International Application No. PCT/US15/36771, dated Oct. 2, 2015 (4 pages).
Irier et al., "Translational regulation of GluR2 mRNAs in rat hippocampus by alternative 3' untranslated regions," available in PMC Aug. 17, 2009, published in final edited form as: J Neurochem. 109(2):584-594 (2009) (18 pages).
Jani et al., "In vitro transcription and capping of Gaussia luciferase mRNA followed by HeLa cell transfection," J Vis Exp. 61:e3702 (2012) (9 pages).
Karikó et al., "Incorporation of pseudouridine into mRNA yields superior nonimmunogenic vector with increased translational capacity and biological stability." Mol Ther. 16(11):1833-40 (2008).
Karikó et al., "mRNA is an endogenous ligand for Toll-like receptor 3," J Biol Chem. 279(13): 12542-50 (2004).
Karikó et al., "Suppression of RNA recognition by Toll-like receptors: the impact of nucleoside modification and the evolutionary origin of RNA," Immunity. 23(2):165-75 (2005).
Kluiver et al., "Rapid generation of MicroRNA Sponges for MicroRNA Inhibition ," PLoS One. 7(1):E29275(2012) (8 pages).
Kore et al., "Synthesis and application of 2'-fluoro-substituted cap analogs." Bioorg Med Chem Letters. 17:5295-9 (2007).
Kormann et al., "Expression of therapeutic proteins after delivery of chemically modified mRNA in mice," Nat Biotechnol. 29(2):154-7 (2011) (6 pages).
Kuwahara et al., "Molecular evolution of functional nucleic acids with chemical modifications," Molecules. 15(8):5423-44 (2010).
Liu et al., "Construction of circular miRNA sponges targeting miR-21 or miR-221 and demonstration of their excellent anticancer effects on malignant melanoma cells," Int J Biochem Cell Biol. 45(11):2643-50 (2013).
Maeder et al., "CRISPR RNA-guided activation of endogenous human genes," Nat Methods 10(10):977-9 (2013).
Melton et al., "Efficient in vitro synthesis of biologically active RNA and RNA hybridization probes from plasmids containing a bacteriophage SP6 promoter," Nucleic Acids Res. 12(18):7035-56 (1984).
Memczak et al., "Circular RNAs are a large class of animal RNAs with regulatory potency," Nature. 495(7441):333-8 (2013) (10 pages).
Mestas et al., "Of mice and not men: differences between mouse and human immunology," J Immunol. 172(5):2731-8 (2004).
Park et al., "Reverse transcriptase-coupled quantitative real time PCR analysis of cell-free transcription on the chromatin-assembled p21 promoter," PLoS One 6(8):e23617 (2011) (6 pages).
Pascolo, Chapter 3: Vaccination With Messenger RNA. *Methods in Molecular Medicine, vol. 127: DNA Vaccines: Methods and Protocols: Second Edition.* Saltzman et al., Humana Press Inc., 23-40 (2006).
Perez-Pinera et al., "RNA-guided gene activation by CRISPR-Cas9-based transcription factors," Nat Methods 10(10):973-6 (2013).
PubChem entry CID 10374519, <https://pubchem.ncbi.nlm.nih.gov/compound/10374519#section=Top>, created Oct. 25, 2006, accessed Sep. 13, 2015 (10 pages).
PubChem entry CID 10630529, <https://pubchem.ncbi.nlm.nih.gov/compound/10630529#section=Names-and-Identifiers>, created Oct. 25, 2006, accessed Sep. 13, 2015 (12 pages).
PubChem entry CID 22086948, <https://pubchem.ncbi.nlm.nih.gov/compound/22086948#section=2D-Structure>, created Dec. 5, 2007, accessed Sep. 13, 2015 (10 pages).
PubChem entry CID 57336529, <https://pubchem.ncbi.nlm.nih.gov/compound/57336529>, created Jun. 21, 2012, accessed Sep. 13, 2015 (10 pages).
Qiu et al., "Creating a flexible multiple microRNA expression vector by linking precursor microRNAs," Biochem Biophys Res Commun. 411(2):276-80 (2011).
Sasaki et al., "Construction of a normalized cDNA library by introduction of a semi-solid mRNA-cDNA hybridization system," Nucleic Acids Res. 22(6):987-92 (1994).
Tavernier et al., "mRNA as gene therapeutic: how to control protein expression," J Control Release. 150(3):238-47 (2011).
Wang et al., "One-step generation of mice carrying mutations in multiple genes by CRISPR/Cas-mediated genome engineering," Cell 153(4):910-8 (2013).
Warren et al., "Highly efficient reprogramming to pluripotency and directed differentiation of human cells with synthetic modified mRNA," Cell Stem Cell. 7(5):618-30 (2010).
Weiss et al., "Prophylactic mRNA vaccination against allergy," Curr Opin Allergy Clin Immunol. 10(6):567-74 (2010) (8 pages).
Wilusz et al., "Molecular Biology. A circuitous route to noncoding RNA," Science. 340(6131):440-1 (2013).
Yamamoto et al., "Current prospects for mRNA gene delivery," Eur J Pharm Biopharm. 71(3):484-9 (2009).
Andries et al., "N1-methylpseudouridine-incorporated mRNA outperforms pseudouridine-incorporated mRNA by providing enhanced protein expression and reduced immunogenicity in mammalian cell lines and mice," J Control Release. 217:337-44 (2015).
Pardi et al., "Expression kinetics of nucleoside-modified mRNA delivered in lipid nanoparticles to mice by various routes," available in PMC Nov. 10, 2016, published in final edited form as: J Control Release. 217:345-51 (2015) (18 pages).
Olesiak et al., "The synthesis of di- and oligo-nucleotides containing a phosphorodithioate internucleotide linkage with one of the sulfur atoms in a 5'-bridging position," Org Biomol Chem. 7(10):2162-9 (2009).
Applied Biosystems DNA Synthesizer model 380B operation manual, 2001 (327 pages).
Aviv et al., "Purification of Biologically Active Globin Messenger RNA by Chromatography on Oligothymidylic acid-Cellulose," Proc Nat Acad Sci USA 69(6):1408-1412 (1972).
Gilham, "The Synthesis of Polynucleotide-Celluloses and Their Use in the Fractionation of Polynucleotides," J Am Chem Soc 86(22):4982-4985 (1964).
Gustafsson et al., "Codon bias and heterologous protein expression," Trends Biotechnol. 22(7):346-353 (2004).
Henke et al., "microRNA-122 stimulates translation of hepatitis C virus RNA," EMBO J. 27(24):3300-10 (2008).
Meyer et al., "Combinatorial recombination of gene fragments to construct a library of chimeras," Curr Protoc Protein Sci. Chapter 26:Unit 26.2 (2006) (17 pages).
Miyoshi-Akiyama et al., "Complete genome sequence of *Streptococcus pyogenes* M1 476, isolated from a patient with streptococcal toxic shock syndrome," J Bacteriology. 194(19):5466 (2012).
Moretti et al., "Mechanism of translational regulation by miR-2 from sites in the 5' untranslated region or the open reading frame," RNA. 16(12):2493-502 (2010).
Motorin, "RNA modification," *eLS*. John Wiley & Sons, DOI:10.1002/9780470015902.a0000528.pub3 (2015) (18 pages).
Nakazato et al., "Purification of messenger RNA and heterogeneous nuclear RNA containing poly(A) sequences," Methods Enzymol. 29:431-443 (1974).
Nielsen et al., "An mRNA is capped by a 2',5' lariat catalyzed by a group I-like ribozyme," Science. 309(5740):1584-7 (2005).
Rodriguez et al., "Magnetic poly (styrene/divinylbenzene/acrylic acid)-based hybrid microspheres for bio-molecular recognition," Micro Nano Lett. 6(6):349-352 (2011).
Takita et al., "Precise sequential DNA ligation on a solid substrate: solid-based rapid sequential ligation of multiple DNA molecules," DNA Res. 20(6):583-92 (2013).
Virnekäs et al., "Trinucleotide phosphoramidites: ideal reagents for the synthesis of mixed oligonucleotides for random mutagenesis," Nucleic Acids Res. 22(25):5600-7 (1994).

\* cited by examiner

ALTERNATIVE NUCLEIC ACID MOLECULES AND USES THEREOF

REFERENCE TO A SEQUENCE LISTING

This application contains a Sequence Listing in computer readable form. The computer readable form is incorporated herein by reference.

TECHNICAL FIELD

The present disclosure provides compositions and methods using alternative nucleic acids to modulate cellular function. The alternative nucleic acids of the invention may encode peptides, polypeptides or multiple proteins. The encoded molecules may be used as therapeutics and/or diagnostics.

BACKGROUND OF THE INVENTION

There are multiple problems with prior methodologies of effecting protein expression. For example, heterologous DNA introduced into a cell can be inherited by daughter cells (whether or not the heterologous DNA has integrated into the chromosome) or by offspring. Introduced DNA can integrate into host cell genomic DNA at some frequency, resulting in alterations and/or damage to the host cell genomic DNA. In addition, multiple steps must occur before a protein is made. Once inside the cell, DNA must be transported into the nucleus where it is transcribed into RNA. The RNA transcribed from DNA must then enter the cytoplasm where it is translated into protein. This need for multiple processing steps creates lag times before the generation of a protein of interest. Further, it is difficult to obtain DNA expression in cells; frequently DNA enters cells but is not expressed or not expressed at reasonable rates or concentrations. This can be a particular problem when DNA is introduced into cells such as primary cells or modified cell lines.

Naturally occurring RNAs are synthesized from four basic ribonucleotides: ATP, CTP, UTP and GTP, but may contain post-transcriptionally modified nucleotides. Further, approximately one hundred different nucleoside alterations have been identified in RNA (Rozenski, J, Crain, P, and McCloskey, J. (1999). The RNA Modification Database: 1999 update. Nucl Acids Res 27: 196-197).

There is a need in the art for biological modalities to address the modulation of intracellular translation of nucleic acids. The present invention solves this problem by providing new mRNA molecules incorporating chemical alterations which impart properties which are advantageous to therapeutic development.

SUMMARY OF THE INVENTION

The present disclosure provides, inter alia, alternative nucleosides, alternative nucleotides, and alternative nucleic acids including an alternative nucleobase, sugar or backbone.

In one aspect, the invention features an mRNA encoding a polypeptide of interest, wherein said mRNA contains an alternative uracil and alternative cytosine in the percentages recited in any one of Tables A1-A22 (e.g., the percentages recited in Table A1, the percentages recited in Table A2, the percentages recited in Table A3, the percentages recited in Table A4, the percentages recited in Table A5, the percentages recited in Table A6, the percentages recited in Table A7, the percentages recited in Table A8, the percentages recited in Table A9, the percentages recited in Table A10, the percentages recited in Table A11, the percentages recited in Table A12, the percentages recited in Table A13, the percentages recited in Table A14, the percentages recited in Table A15, the percentages recited in Table A16, the percentages recited in Table A17, the percentages recited in Table A18, the percentages recited in Table A19, the percentages recited in Table A20, the percentages recited in Table A21, or the percentages recited in Table A22).

In some embodiments, the alternative uracil represents about 5%, about 10%, about 15%, about 20%, about 25%, about 30%, about 35%, about 40%, about 45%, about 50%, about 55%, about 60%, about 65%, about 70%, or about 75% of the uracils in the mRNA and said alternative cytosine represents about 5%, about 10%, about 12.5%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% of the cytosines in the mRNA.

In other embodiments, the alternative uracil and the alternative cytosine are 1-methyl-pseudouracil and 5-methyl-cytosine, pseudouracil and 5-methyl-cytosine, 1-methyl-pseudouracil and 5-iodo-cytosine, 1-methyl-pseudouracil and 5-methyl-cytosine, pseudouracil and 5-methyl-cytosine, 5-methoxy-uracil and 5-trifluoromethyl-cytosine, 5-methoxy-uracil and 5-hydroxymethyl-cytosine, 5-methoxy-uracil and 5-bromo-cytosine, 2-thio-uracil and 5-methyl-cytosine, 1-methyl-pseudouracil and 5-bromo-cytosine, 5-methoxy-uracil and N4-acetyl-cytosine, 5-methoxy-uracil and N4-methyl-cytosine, 5-methoxy-uracil and pseudoisocytosine, 5-methoxy-uracil and 5-formyl-cytosine, 5-methoxy-uracil and 5-aminoallyl-cytosine, 5-methoxy-uracil and 5-fluoro-cytosine, 5-methoxy-uracil and 5-iodo-cytosine, 5-methoxy-uracil and 5-ethyl-cytosine, 5-methoxy-uracil and 5-methoxy-cytosine, 5-methoxy-uracil and 5-ethynyl-cytosine, 5-methoxy-uracil and 5-phenyl-cytosine, 5-methoxy-uracil and N4-benzoyl-cytosine, or 5-methoxy-uracil and 5-carboxy-cytosine.

In another aspect, the invention features an mRNA encoding a polypeptide of interest, wherein at least two bases are pseudouracil and 5-hydroxymethyl-cytosine, pseudouracil and 5-iodo-cytosine, pseudouracil and N4-acetyl-cytosine, 1-ethyl-pseudouracil and 5-methyl-cytosine, 1-propyl-uracil and 5-methyl-cytosine, 1-benzyl-uracil and 5-methyl-cytosine, 1-methyl-pseudouracil and 5-ethyl-cytosine, 1-methyl-pseudouracil and 5-methoxy-cytosine, 1-methyl-pseudouracil and 5-ethynyl-cytosine, pseudouracil and 5-ethynyl-cytosine, 1-methyl-pseudouracil and N4-methyl-cytosine, 1-methyl-pseudouracil and 5-fluoro-cytosine, 5-methoxy-uracil and 5-fluoro-cytosine, 1-methyl-pseudouracil and 5-phenyl-cytosine, 1-methyl-pseudouracil and N4-benzoyl-cytosine, 1-methyl-pseudouracil and N6-isopentenyl-cytosine, or 5-methoxy-uracil and N6-isopentenyl-cytosine.

In another aspect, the invention features an mRNA encoding a polypeptide of interest, wherein an alternative uracil represents about 25%-100% (e.g., about 25%-35%, about 30% to 40%, about 35%-45%, about 40%-50%, about 45%-55%, about 50%-60%, about 55%-65%, about 60%-70%, about 65%-75%, about 70%-80%, about 75%-85%, about 80%-90%, about 85%-95%, about 90%-100%, about 95%-100%, about 25%-50%, about 25%-75%, about 50%-75%) of the uracils in the mRNA, wherein the alternative uracil is 5-isopentenyl-aminomethyl-uracil, 5-hydroxy-uracil, 5-carbamoyl-methyl-uracil, 5-methyl-uracil, 5-methyl-2-thio-uracil, 4-thio-uracil, or 5-methoxy-carbonylmethyl-uracil.

In some embodiments of any of the foregoing mRNA, the alternative uracil represents about 25%, about 50%, about 75%, or about 100% of the uracils in the mRNA.

In another aspect, the invention features an mRNA encoding a polypeptide of interest, wherein at least one base is 1-methyl-pseudouracil and one base is 5-methoxy-uracil.

In some embodiments, 1-methyl-pseudouracil represents about 25% of the uracils and 5-methoxy-uracil represents about 75% of the uracils, 1-methyl-pseudouracil represents about 50% of the uracils and 5-methoxy-uracil represents about 50% of the uracils, or 1-methyl-pseudouracil represents about 75% of the uracils and 5-methoxy-uracil represents about 25% of the uracils.

In other embodiments, at least one base is 5-methyl-cytosine.

In certain embodiments, 5-methylcytosine represents about 5%, about 10%, about 20%, about 25%, about 30%, about 35%, about 40%, about 45%, about 50%, about 55%, about 60%, about 65%, about 70%, about 75%, about 80%, about 85%, about 90%, about 95%, or about 100% of the cytosines.

In another aspect, the invention features an mRNA encoding a polypeptide of interest, wherein at least one base is 2-pyridone, 6-flouro-2-pyridone, 3-methyl-2-pyridone, 6-methyl-2-pyridone, 5-methyl-5,6-dihydro-uracil, or 1-benzyl-pseudouracil.

In some embodiments, at least one base is 5-methyl-cytosine.

In other embodiments of any of the foregoing mRNA, at least one base is an alternative adenine and/or an alternative guanine (e.g., 8-methyl-adenine, N6-isopentenyl-adenine, N6-methyl-adenine, 8-azido-adenine, N6-methyl-2-amino-purine, 2-amino-purine, 2-amino-6-chloro-purine, 06-methyl-guanine, 7-deaza-guanine, or N7-methyl-guanine).

In certain embodiments, the alternative adenine and/or alternative guanine represents about 25%-100% (e.g., about 25%-35%, about 30% to 40%, about 35%-45%, about 40%-50%, about 45%-55%, about 50%-60%, about 55%-65%, about 60%-70%, about 65%-75%, about 70%-80%, about 75%-85%, about 80%-90%, about 85%-95%, about 90%-100%, about 95%-100%, about 25%-50%, about 25%-75%, about 50%-75%) of the adenines and/or guanines in the mRNA.

In some embodiments, the alternative adenine and/or guanine represents about 5%, about 10%, about 20%, about 25%, about 30%, about 35%, about 40%, about 45%, about 50%, about 55%, about 60%, about 65%, about 70%, about 75%, about 80%, about 85%, about 90%, about 95%, or about 100% of the adenines and/or guanines in the mRNA.

In another aspect, the invention features an mRNA encoding a polypeptide of interest, wherein said mRNA contains an alternative uridine and alternative cytidine in the percentages of Tables B1-B22 (e.g., the percentages recited in Table B1, the percentages recited in Table B2, the percentages recited in Table B3, the percentages recited in Table B4, the percentages recited in Table B5, the percentages recited in Table B6, the percentages recited in Table B7, the percentages recited in Table B8, the percentages recited in Table B9, the percentages recited in Table B10, the percentages recited in Table B11, the percentages recited in Table B12, the percentages recited in Table B13, the percentages recited in Table B14, the percentages recited in Table B15, the percentages recited in Table B16, the percentages recited in Table B17, the percentages recited in Table B18, the percentages recited in Table B19, the percentages recited in Table B20, the percentages recited in Table B21, or the percentages recited in Table B22).

In some embodiments, the alternative uridine represents about 5%, about 10%, about 15%, about 20%, about 25%, about 30%, about 35%, about 40%, about 45%, about 50%, about 55%, about 60%, about 65%, about 70%, or about 75% of the uridines in the mRNA and said alternative cytidine represents about 5%, about 10%, about 12.5%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% of the cytidines in the mRNA.

In other embodiments, the alternative uridine and the alternative cytidine are 1-methyl-pseudouridine and 5-methyl-cytidine, pseudouridine and 5-methyl-cytidine, 1-methyl-pseudouridine and 5-iodo-cytidine, 1-methyl-pseudouridine and 5-methyl-cytidine, pseudouridine and 5-methyl-cytidine, 5-methoxy-uridine and 5-trifluorom-ethyl-cytidine, 5-methoxy-uridine and 5-hydroxymethyl-cytidine, 5-methoxy-uridine and 5-bromo-cytidine, 2-thio-uridine and 5-methyl-cytidine, 1-methyl-pseudouridine and 5-bromo-cytidine, 5-methoxy-uridine and N4-acetyl-cytidine, 5-methoxy-uridine and N4-methyl-cytidine, 5-methoxy-uridine and pseudoisocytidine, 5-methoxy-uridine and 5-formyl-cytidine, 5-methoxy-uridine and 5-aminoallyl-cytidine, 5-methoxy-uridine and 5-fluoro-cytidine, 5-methoxy-uridine and 5-iodo-cytidine, 5-methoxy-uridine and 5-ethyl-cytidine, 5-methoxy-uridine and 5-methoxy-cytidine, 5-methoxy-uridine and 5-ethynyl-cytidine, 5-methoxy-uridine and 5-phenyl-cytidine, 5-methoxy-uridine and N4-benzoyl-cytidine, or 5-methoxy-uridine and 5-carboxy-cytidine.

In another aspect, the invention features an mRNA encoding a polypeptide of interest, wherein at least two bases are pseudouridine and 5-hydroxymethyl-cytidine, pseudouridine and 5-iodo-cytidine, pseudouridine and N4-acetyl-cytidine, 1-ethyl-pseudouridine and 5-methyl-cytidine, 1-propyl-uridine and 5-methyl-cytidine, 1-benzyl-uridine and 5-methyl-cytidine, 1-methyl-pseudouridine and 5-ethyl-cytidine, 1-methyl-pseudouridine and 5-methoxy-cytidine, 1-methyl-pseudouridine and 5-ethynyl-cytidine, pseudouridine and 5-ethynyl-cytidine, 1-methyl-pseudouridine and N4-methyl-cytidine, 1-methyl-pseudouridine and 5-fluoro-cytidine, 5-methoxy-uridine and 5-fluoro-cytidine, 1-methyl-pseudouridine and 5-phenyl-cytidine, 1-methyl-pseudouridine and N4-benzoyl-cytidine, 1-methyl-pseudouridine and N6-isopentenyl-cytidine, or 5-methoxy-uridine and N6-isopentenyl-cytidine.

In another aspect, the invention features an mRNA encoding a polypeptide of interest, wherein an alternative uridine represents about 25%-100% (e.g., about 25%-35%, about 30% to 40%, about 35%-45%, about 40%-50%, about 45%-55%, about 50%-60%, about 55%-65%, about 60%-70%, about 65%-75%, about 70%-80%, about 75%-85%, about 80%-90%, about 85%-95%, about 90%-100%, about 95%-100%, about 25%-50%, about 25%-75%, about 50%-75%) of the uridines in the mRNA, wherein the alternative uridine is 5-isopentenyl-aminomethyl-uridine, 5-hydroxy-uridine, 5-carbamoyl-methyl-uridine, 5-methyl-uridine, 5-methyl-2-thio-uridine, 4-thio-uridine, or 5-methoxy-carbonylmethyl-uridine.

In some embodiments of any of the foregoing mRNA, the alternative uridine represents about 25%, about 50%, about 75%, or about 100% of the uridines in the mRNA.

In another aspect, the invention features an mRNA encoding a polypeptide of interest, wherein at least one base is 1-methyl-pseudouridine and one base is 5-methoxy-uridine.

In some embodiments, 1-methyl-pseudouridine represents about 25% of the uridines and 5-methoxy-uridine represents about 75% of the uridines, 1-methyl-pseudouridine represents about 50% of the uridines and 5-methoxy-uridine represents about 50% of the uridines, or 1-methyl-pseudouridine represents about 75% of the uridines and 5-methoxy-uridine represents about 25% of the uridines.

In other embodiments, at least one base is 5-methyl-cytidine.

In certain embodiments, 5-methylcytidine represents about 5%, about 10%, about 20%, about 25%, about 30%, about 35%, about 40%, about 45%, about 50%, about 55%, about 60%, about 65%, about 70%, about 75%, about 80%, about 85%, about 90%, about 95%, or about 100% of the cytidines.

In another aspect, the invention features an mRNA encoding a polypeptide of interest, wherein at least one base is 2-pyridone, 6-flouro-2-pyridone, 3-methyl-2-pyridone, 6-methyl-2-pyridone, 5-methyl-5,6-dihydro-uracil, or 1-benzyl-pseudouracil.

In some embodiments, at least one base is 5-methyl-cytidine.

In other embodiments of any of the foregoing mRNA, at least one base is an alternative adenine and/or an alternative guanine (e.g., 8-methyl-adenine, N6-isopentenyl-adenine, N6-methyl-adenine, 8-azido-adenine, N6-methyl-2-amino-purine, 2-amino-purine, 2-amino-6-chloro-purine, 06-methyl-guanine, 7-deaza-guanine, or N7-methyl-guanine).

In certain embodiments, the alternative adenine and/or alternative guanine represents about 25%-100% (e.g., about 25%-35%, about 30% to 40%, about 35%-45%, about 40%-50%, about 45%-55%, about 50%-60%, about 55%-65%, about 60%-70%, about 65%-75%, about 70%-80%, about 75%-85%, about 80%-90%, about 85%-95%, about 90%-100%, about 95%-100%, about 25%-50%, about 25%-75%, about 50%-75%) of the adenines and/or guanines in the mRNA.

In some embodiments, the alternative adenine and/or guanine represents about 5%, about 10%, about 20%, about 25%, about 30%, about 35%, about 40%, about 45%, about 50%, about 55%, about 60%, about 65%, about 70%, about 75%, about 80%, about 85%, about 90%, about 95%, or about 100% of the adenines and/or guanines in the mRNA.

In some embodiments of any of the foregoing mRNA, at least one nucleotide is alpha-thio-adenosine, alpha-thio-guanosine, and/or alpha-thio-cytidine (e.g., alpha-thio-adenosine and/or alpha-thio-guanosine).

In other embodiments, alpha-thio-adenosine, alpha-thio-guanosine, and/or alpha-thio-cytidine represent about 2%-100% (e.g., about 2%-10%, about 5%-15%, about 10%-20%, about 15%-25%, about 25%-35%, about 30% to 40%, about 35%-45%, about 40%-50%, about 45%-55%, about 50%-60%, about 55%-65%, about 60%-70%, about 65%-75%, about 70%-80%, about 75%-85%, about 80%-90%, about 85%-95%, about 90%-100%, about 95%-100%, about 25%-50%, about 25%-75%, about 50%-75%) of the adenosines, guanosines, and/or cytidines in the mRNA.

In certain embodiments, alpha-thio-adenosine, alpha-thio-guanosine, and/or alpha-thio-cytidine represent about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% of the adenosines, guanosines, and/or cytidines in the mRNA.

In some embodiments, any of the foregoing mRNA further include:
(i) at least one 5' cap structure;
(ii) a 5' UTR optionally including a Kozak sequence; and
(iii) a 3' UTR.

In other embodiments, the at least one 5' cap structure is Cap0, Cap1, ARCA, inosine, N1-methyl-guanosine, 2'-fluoro-guanosine, 7-deaza-guanosine, 8-oxo-guanosine, 2-amino-guanosine, LNA-guanosine, or 2-azido-guanosine.

In some embodiments, any of the foregoing mRNA further include a poly-A tail.

In other embodiments, any of the foregoing mRNA are purified.

In certain embodiments, any of the foregoing mRNA are codon optimized (e.g., the mRNA comprises an open reading frame that is codon optimized and/or the mRNA is codon optimized to minimize base runs that impair gene expression).

In another aspect, the invention features a pharmaceutical composition including any of the foregoing mRNA and a pharmaceutically acceptable excipient.

In another aspect, the invention features a method of expressing a polypeptide of interest in a mammalian cell, said method comprising the steps of:
(i) providing any of the foregoing mRNA; and
(ii) introducing said mRNA to a mammalian cell under conditions that permit the expression of the polypeptide of interest by the mammalian cell.

In some embodiments, the innate immune response associated with the mRNA is reduced by at least 50% relative to the innate immune response induced by a corresponding unmodified mRNA.

In another aspect, the invention features an mRNA encoding a polypeptide of interest, wherein 5-methoxy-uracil represents from 10% to 50% (e.g., 10% to 20%, 15% to 25%, 20% to 30%, 25% to 35%, 30% to 40%, 35% to 45%, or 40% to 50%) of the uracils in the mRNA and 5-methyl-cytosine represents 50-100% (e.g., 50% to 60%, 55% to 65%, 60% to 70%, 65% to 75%, 70% to 80%, 75% to 85%, 80%, to 90%, 85% to 95%, 90% to 100%, or 95% to 100%) of the cytosines in the mRNA.

In some embodiments, 5-methoxy-uracil represents from 15% to 35% of the uracils in the mRNA and 5-methyl-cytosine represents 75-100% of the cytosines in the mRNA.

In other embodiments, wherein 5-methoxy-uracil represents about 25% of the uracils in the mRNA and 5-methyl-cytosine represents about 100% of the cytosines in the mRNA.

In another aspect, the invention features an mRNA encoding a polypeptide of interest, the mRNA including at least one 5' cap structure; a 5' UTR (e.g., a 5' UTR including a Kozak sequence); and a 3' UTR, wherein 5-methoxy-uracil represents from 10% to 50% (e.g., 10% to 20%, 15% to 25%, 20% to 30%, 25% to 35%, 30% to 40%, 35% to 45%, or 40% to 50%) of the uracils in the mRNA and the alternative cytosine represents from 50% to 100% (e.g., 50% to 60%, 55% to 65%, 60% to 70%, 65% to 75%, 70% to 80%, 75% to 85%, 80%, to 90%, 85% to 95%, 90% to 100%, or 95% to 100%) of the cytosines in the mRNA.

In another aspect, the invention features an mRNA encoding a polypeptide of interest, wherein 5-methoxy-uridine represents from 10% to 50% (e.g., 10% to 20%, 15% to 25%, 20% to 30%, 25% to 35%, 30% to 40%, 35% to 45%, or 40% to 50%) of the uridines in the mRNA and 5-methylcytidine represents 50-100% (e.g., 50% to 60%, 55% to 65%, 60% to 70%, 65% to 75%, 70% to 80%, 75% to 85%, 80%, to 90%, 85% to 95%, 90% to 100%, or 95% to 100%) of the cytidines in the mRNA.

In some embodiments, 5-methoxy-uridine represents from 15% to 35% of the uridines in the mRNA and 5-methyl-cytidine represents 75-100% of the cytidines in the mRNA.

In other embodiments, 5-methoxy-uridine represents about 25% of the uridines in the mRNA and 5-methyl-cytidine represents about 100% of the cytidines in the mRNA.

In certain embodiments of any of the above aspects, the mRNA further includes:

(i) at least one 5' cap structure;
(ii) a 5' UTR optionally including a Kozak sequence; and
(iii) a 3' UTR.

In some embodiments, the at least one 5' cap structure is Cap0, Cap1, ARCA, inosine, N1-methyl-guanosine, 2'-fluoro-guanosine, 7-deaza-guanosine, 8-oxo-guanosine, 2-amino-guanosine, LNA-guanosine, or 2-azido-guanosine.

In other embodiments, the mRNA further includes a poly-A tail.

In some embodiments, the mRNA is purified.

In other embodiments of the foregoing aspects, the mRNA is codon optimized (e.g., the mRNA includes an open reading frame that is codon optimized and/or the mRNA is codon optimized to minimize base runs that impair gene expression).

In another aspect, the invention features a pharmaceutical composition including any of the foregoing mRNAs and a pharmaceutically acceptable excipient.

In another aspect, the invention features any of the foregoing mRNAs or pharmaceutical compositions for use in therapy.

In another aspect, the invention features a method of expressing a polypeptide of interest in a mammalian cell, said method including the steps of:

(i) providing an mRNA encoding a polypeptide of interest, wherein 5-methoxy-uracil represents from 10% to 50% (e.g., 10% to 20%, 15% to 25%, 20% to 30%, 25% to 35%, 30% to 40%, 35% to 45%, or 40% to 50%) of the uracils in the mRNA and 5-methyl-cytosine represents from 50% to 100% (e.g., 50% to 60%, 55% to 65%, 60% to 70%, 65% to 75%, 70% to 80%, 75% to 85%, 80%, to 90%, 85% to 95%, 90% to 100%, or 95% to 100%) of the cytosines in the mRNA; and (ii) introducing the mRNA to a mammalian cell under conditions that permit the expression of the polypeptide of interest by the mammalian cell.

In another aspect, the invention features a method of expressing a polypeptide of interest in a mammalian cell, said method comprising the steps of:

(i) providing an mRNA encoding the polypeptide of interest, the mRNA comprising at least one 5' cap structure; a 5' UTR (e.g., a 5' UTR including a Kozak sequence); and a 3' UTR, wherein 5-methoxy-uracil represents from 10% to 50% (e.g., 10% to 20%, 15% to 25%, 20% to 30%, 25% to 35%, 30% to 40%, 35% to 45%, or 40% to 50%) of the uracils in the mRNA and 5-methyl-cytosine represents from 50% to 100% (e.g., 50% to 60%, 55% to 65%, 60% to 70%, 65% to 75%, 70% to 80%, 75% to 85%, 80%, to 90%, 85% to 95%, 90% to 100%, or 95% to 100%) of the cytosines in the mRNA; and (ii) introducing the mRNA to a mammalian cell capable of expressing the polypeptide of interest under conditions that permit the expression of the polypeptide of interest by the mammalian cell.

In certain embodiments of any of the foregoing methods, 5-methoxy-uracil represents from 15% to 35% of the uracils in the mRNA and 5-methyl-cytosine represents 75% to 100% of the cytosines in the mRNA.

In particular embodiments, 5-methoxy-uracil represents about 25% of the uracils in the mRNA and 5-methyl-cytosine represents about 100% of the cytosines in the mRNA.

In another aspect, the invention features a method of expressing a polypeptide of interest in a mammalian cell, said method including the steps of:

(i) providing an mRNA encoding a polypeptide of interest, wherein 5-methoxy-uridine represents from 10% to 50% (e.g., 10% to 20%, 15% to 25%, 20% to 30%, 25% to 35%, 30% to 40%, 35% to 45%, or 40% to 50%) of the uridines in the mRNA and 5-methyl-cytidine represents from 50% to 100% (e.g., 50% to 60%, 55% to 65%, 60% to 70%, 65% to 75%, 70% to 80%, 75% to 85%, 80%, to 90%, 85% to 95%, 90% to 100%, or 95% to 100%) of the cytidines in the mRNA; and (ii) introducing the mRNA to a mammalian cell under conditions that permit the expression of the polypeptide of interest by the mammalian cell.

In another aspect, the invention features a method of expressing a polypeptide of interest in a mammalian cell, said method comprising the steps of:

(i) providing an mRNA encoding the polypeptide of interest, the mRNA comprising at least one 5' cap structure; a 5' UTR (e.g., a 5' UTR including a Kozak sequence); and a 3' UTR, wherein 5-methoxy-uridine represents from 10% to 50% (e.g., 10% to 20%, 15% to 25%, 20% to 30%, 25% to 35%, 30% to 40%, 35% to 45%, or 40% to 50%) of the uridines in the mRNA and 5-methyl-cytidine represents from 50% to 100% (e.g., 50% to 60%, 55% to 65%, 60% to 70%, 65% to 75%, 70% to 80%, 75% to 85%, 80%, to 90%, 85% to 95%, 90% to 100%, or 95% to 100%) of the cytidines in the mRNA; and (ii) introducing the mRNA to a mammalian cell capable of expressing the polypeptide of interest under conditions that permit the expression of the polypeptide of interest by the mammalian cell.

In some embodiments of any of the foregoing methods, the at least one 5' cap structure is Cap0, Cap1, ARCA, inosine, N1-methyl-guanosine, 2'-fluoro-guanosine, 7-deaza-guanosine, 8-oxo-guanosine, 2-amino-guanosine, LNA-guanosine, or 2-azido-guanosine.

In other embodiments of any of the foregoing methods, the mRNA further includes a poly-A tail.

In certain embodiments of any of the foregoing methods, 5-methoxy-uridine represents from 15% to 35% of the uridines in the mRNA and 5-methyl-cytidine represents 75% to 100% of the cytidines in the mRNA.

In some embodiments of any of the foregoing methods, 5-methoxy-uridine represents about 25% of the uridines in the mRNA and 5-methyl-cytidine represents about 100% of the cytidines in the mRNA.

In other embodiments of any of the foregoing methods, the innate immune response associated with the mRNA is reduced by at least 50% (e.g., at least 60%, at least 70%, at least 80%, at least 90%, at least 95%) relative to the innate immune response induced by a corresponding unaltered mRNA.

In certain embodiments of any of the foregoing methods, the mRNA further includes a poly-A tail.

In certain embodiments of any of the foregoing methods, the mRNA is codon optimized.

In another aspect, the invention features a method for producing an mRNA encoding a polypeptide of interest including contacting a cDNA that encodes the protein of interest with an RNA polymerase in the presence of a nucleotide triphosphate mix, wherein from 10% to 50% (e.g., 10% to 20%, 15% to 25%, 20% to 30%, 25% to 35%, 30% to 40%, 35% to 45%, or 40% to 50%) of the uridine triphosphate includes 5-methoxy-uracil and 50% to 100% (e.g., 50% to 60%, 55% to 65%, 60% to 70%, 65% to 75%, 70% to 80%, 75% to 85%, 80%, to 90%, 85% to 95%, 90% to 100%, or 95% to 100%) of the cytidine triphosphate includes 5-methyl-cytosine.

In some embodiments, from 15% to 35% of the uridine triphosphate includes 5-methoxy-uracil and 75% to 100% of the cytidine triphosphate includes 5-methyl-cytosine, or wherein about 25% of the uridine triphosphate includes 5-methoxy-uracil and about 75% of the cytidine triphosphate includes 5-methyl-cytosine.

In other embodiments, the RNA polymerase is T7 RNA polymerase.

In another aspect, the invention features an mRNA produced by any of the foregoing methods.

In another aspect, the invention features a polynucleotide (e.g., an mRNA), wherein at least two bases are 5-trifluoromethyl-cytosine and 1-methyl-pseudo-uracil; 5-hydroxymethyl-cytosine and 1-methyl-pseudo-uracil; 5-bromo-cytosine and 1-methyl-pseudo-uracil; 5-trifluoromethyl-cytosine and pseudo-uracil; 5-hydroxymethyl-cytosine and pseudo-uracil; 5-bromo-cytosine and pseudo-uracil; cytosine and 5-methoxy-uracil; 5-methyl-cytosine and 5-methoxy-uracil; 5-trifluoromethyl-cytosine and 5-methoxy-uracil; 5-hydroxymethyl-cytosine and 5-methoxy-uracil; or 5-bromo-cytosine and 5-methoxy-uracil.

In some embodiments, at least two bases are 5-trifluoromethyl-cytosine and 5-methoxy-uracil; 5-hydroxymethyl-cytosine and 5-methoxy-uracil; or 5-bromo-cytosine and 5-methoxy-uracil.

In other embodiments, at least two bases are 5-bromo-cytosine and 5-methoxy-uracil.

In another aspect, the invention features a polynucleotide (e.g., an mRNA), wherein at least one base is 1,6-Dimethyl-pseudo-uracil, 1-(optionally substituted $C_1$-$C_6$ Alkyl)-6-(1-propynyl)-pseudo-uracil, 1-(optionally substituted $C_1$-$C_6$ Alkyl)-6-(2-propynyl)-pseudo-uracil, 1-(optionally substituted $C_1$-$C_6$ Alkyl)-6-allyl-pseudo-uracil, 1-(optionally substituted $C_1$-$C_6$ Alkyl)-6-ethynyl-pseudo-uracil, 1-(optionally substituted $C_1$-$C_6$ Alkyl)-6-homoallyl-pseudo-uracil, 1-(optionally substituted $C_1$-$C_6$ Alkyl)-6-vinyl-pseudo-uracil, 1-Methyl-6-(2,2,2-Trifluoroethyl)pseudo-uracil, 1-Methyl-6-(4-morpholino)-pseudo-uracil, 1-Methyl-6-(4-thiomorpholino)-pseudo-uracil, 1-Methyl-6-(optionally substituted phenyl)pseudo-uracil, 1-Methyl-6-amino-pseudo-uracil, 1-Methyl-6-azido-pseudo-uracil, 1-Methyl-6-bromo-pseudo-uracil, 1-Methyl-6-butyl-pseudo-uracil, 1-Methyl-6-chloro-pseudo-uracil, 1-Methyl-6-cyano-pseudo-uracil, 1-Methyl-6-dimethylamino-pseudo-uracil, 1-Methyl-6-ethoxy-pseudo-uracil, 1-Methyl-6-ethylcarboxylate-pseudo-uracil, 1-Methyl-6-ethyl-pseudo-uracil, 1-Methyl-6-fluoro-pseudo-uracil, 1-Methyl-6-formyl-pseudo-uracil, 1-Methyl-6-hydroxyamino-pseudo-uracil, 1-Methyl-6-hydroxy-pseudo-uracil, 1-Methyl-6-iodo-pseudo-uracil, 1-Methyl-6-iso-propyl-pseudo-uracil, 1-Methyl-6-methoxy-pseudo-uracil, 1-Methyl-6-methylamino-pseudo-uracil, 1-Methyl-6-phenyl-pseudo-uracil, 1-Methyl-6-propyl-pseudo-uracil, 1-Methyl-6-tert-butyl-pseudo-uracil, 1-Methyl-6-trifluoromethoxy-pseudo-uracil, 1-Methyl-6-trifluoromethyl-pseudo-uracil, 6-(2,2,2-Trifluoroethyl)-pseudo-uracil, 6-(4-Morpholino)-pseudo-uracil, 6-(4-Thiomorpholino)-pseudo-uracil, 6-(optionally substituted-Phenyl)-pseudo-uracil, 6-Amino-pseudo-uracil, 6-Azido-pseudo-uracil, 6-Bromo-pseudo-uracil, 6-Butyl-pseudo-uracil, 6-Chloro-pseudo-uracil, 6-Cyano-pseudo-uracil, 6-Dimethylamino-pseudo-uracil, 6-Ethoxy-pseudo-uracil, 6-Ethylcarboxylate-pseudo-uracil, 6-Ethyl-pseudo-uracil, 6-Fluoro-pseudo-uracil, 6-Formyl-pseudo-uracil, 6-Hydroxyamino-pseudo-uracil, 6-Hydroxy-pseudo-uracil, 6-Iodo-pseudo-uracil, 6-iso-Propyl-pseudo-uracil, 6-Methoxy-pseudo-uracil, 6-Methylamino-pseudo-uracil, 6-Methyl-pseudo-uracil, 6-Phenyl-pseudo-uracil, 6-Propyl-pseudo-uracil, 6-tert-Butyl-pseudo-uracil, 6-Trifluoromethoxy-pseudo-uracil, 6-Trifluoromethyl-pseudo-uracil, 1-(3-Amino-3-carboxypropyl)pseudo-uracil, 1-(2,2,2-Trifluoroethyl)-pseudo-uracil, 1-(2,4,6-Trimethyl-benzyl)pseudo-uracil, 1-(2,4,6-Trimethyl-phenyl)pseudo-uracil, 1-(2-Amino-2-carboxyethyl)pseudo-uracil, 1-(2-Amino-ethyl)pseudo-uracil, 1-(3-Amino-propyl)pseudo-uracil, 1-(4-Amino-4-carboxybutyl)pseudo-uracil, 1-(4-Amino-benzyl)pseudo-uracil, 1-(4-Amino-butyl)pseudo-uracil, 1-(4-Amino-phenyl)pseudo-uracil, 1-(4-Methoxy-benzyl)pseudo-uracil, 1-(4-Methoxy-phenyl)pseudo-uracil, 1-(4-Methyl-benzyl)pseudo-uracil, 1-(4-Nitro-benzyl)pseudo-uracil, 1(4-Nitro-phenyl)pseudo-uracil, 1-(5-Amino-pentyl)pseudo-uracil, 1-(6-Amino-hexyl)pseudo-uracil, 1-Aminomethyl-pseudo-uracil, 1-Benzyl-pseudo-uracil, 1-Butyl-pseudo-uracil, 1-Cyclobutylmethyl-pseudo-uracil, 1-Cyclobutyl-pseudo-uracil, 1-Cycloheptylmethyl-pseudo-uracil, 1-Cycloheptyl-pseudo-uracil, 1-Cyclohexylmethyl-pseudo-uracil, 1-Cyclohexyl-pseudo-uracil, 1-Cyclooctylmethyl-pseudo-uracil, 1-Cyclooctyl-pseudo-uracil, 1-Cyclopentylmethyl-pseudo-uracil, 1-Cyclopentyl-pseudo-uracil, 1-Cyclopropylmethyl-pseudo-uracil, 1-Cyclopropyl-pseudo-uracil, 1-Ethyl-pseudo-uracil, 1-Hexyl-pseudo-uracil, 1-iso-Propyl-pseudo-uracil 1-Pentyl-pseudo-uracil, 1-Phenyl-pseudo-uracil, 1-Propyl-pseudo-uracil, 1-p-toluyl-pseudo-uracil, 1-tert-Butyl-pseudo-uracil, 1-Trifluoromethyl-pseudo-uracil, 3-(optionally substituted $C_1$-$C_6$ Alkyl)-pseudo-uracil, Pseudo-uracil-N1-2-ethanoic acid, Pseudo-uracil-N1-3-propionic acid, Pseudo-uracil-N1-4-butanoic acid, Pseudo-uracil-N1-5-pentanoic acid, Pseudo-uracil-N1-6-hexanoic acid, Pseudo-uracil-N1-7-heptanoic acid, Pseudo-uracil-N1-methyl-p-benzoic acid, 6-phenyl-pseudo-uracil, 6-azido-pseudo-uracil, Pseudo-uracil-N1-p-benzoic acid, N3-Methyl-pseudo-uracil, 5-Methyl-amino-methyl-uracil, 5-Carboxy-methyl-amino-methyl-uracil, 5-(carboxyhydroxymethyl)uracil methyl ester 5-(carboxyhydroxymethyl) uracil, 2-anhydro-cytosine, 2-anhydro-uracil, 5-Methoxycarbonylmethyl-2-thio-uracil, 5-Methylaminomethyl-2-seleno-uracil, 5-(iso-Pentenylaminomethyl)-uracil, 5-(iso-Pentenylaminomethyl)-2-thio-uracil, 5-(iso-Pentenylaminomethyl)-uracil, 5-Trideuteromethyl-6-deutero-uracil, 5-(2-Chloro-phenyl)-2-thio-cytosine, 5-(4-Amino-phenyl)-2-thio-cytosine, 5-(2-Furanyl)-uracil, 8-Trifluoromethyl-adenine, 2-Trifluoromethyl-adenine, 3-Deaza-3-fluoro-adenine, 3-Deaza-3-bromo-adenine, 3-Deaza-3-iodo-adenine, 1-Hydroxymethyl-pseudo-uracil, 1-(2-Hydroxyethyl)-pseudo-uracil, 1-Methoxymethyl-pseudo-uracil, 1-(2-Methoxyethyl)-pseudo-uracil, 1-(2,2-Diethoxyethyl)-pseudo-uracil, 1-(2-Hydroxypropyl)-pseudo-uracil, (2R)-1-(2-Hydroxypropyl)-pseudo-uracil, (2S)-1-(2-Hydroxypropyl)-pseudo-uracil, 1-Cyanomethyl-pseudo-uracil, 1-Morpholinomethyl-pseudo-uracil, 1-Thiomorpholinomethyl-pseudo-uracil, 1-Benzyloxymethyl-pseudo-uracil, 1-(2,2,3,3,3-Pentafluoropropyl)-pseudo-uracil, 1-Thiomethoxymethyl-pseudo-uracil, 1-Methanesulfonylmethyl-pseudo-uracil, 1-Vinyl-pseudo-uracil, 1-Allyl-pseudo-uracil, 1-Homoallyl-pseudo-uracil, 1-Propargyl-pseudo-uracil, 1-(4-Fluorobenzyl)-pseudo-uracil, 1-(4-Chlorobenzyl)-pseudo-uracil, 1-(4-Bromobenzyl)-pseudo-uracil, 1-(4-Iodobenzyl)-pseudo-uracil, 1-(4-Methylbenzyl)-pseudo-uracil, 1-(4-Trifluoromethylbenzyl)-pseudo-uracil, 1-(4-Methoxybenzyl)-pseudo-uracil, 1-(4-Trifluoromethoxybenzyl)-pseudo-uracil, 1-(4-Thiomethoxybenzyl)-pseudo-uracil, 1-(4-Methanesulfonylbenzyl)-pseudo-uracil, Pseudo-uracil 1-(4-methylbenzoic acid), Pseudo-uracil 1-(4-methylbenzenesulfonic acid), 1-(2,4,6-Trimethylbenzyl)-pseudo-uracil, 1-(4-Nitrobenzyl)-pseudo-uracil, 1-(4-Azidobenzyl)-pseudo-uracil, 1-(3,4-Dimethoxybenzyl)-pseudo-uracil, 1-(3,4-Bis-trifluoromethoxybenzyl)-pseudo-uracil, 1-Acetyl-pseudo-uracil, 1-Trifluoroacetyl-pseudo-uracil, 1-Benzoyl-pseudo-uracil, 1-Pivaloyl-pseudo-uracil, 1-(3-Cyclopropyl-prop-2-ynyl)-pseudo-uracil, Pseudo-uracil 1-methylphosphonic acid diethyl ester, Pseudo-uracil 1-methylphosphonic acid, Pseudo-uracil 1-[3-(2-ethoxy)] propionic acid, Pseudo-uracil 1-[3-{2-(2-ethoxy)-ethoxy}] propionic acid, Pseudo-uracil 1-[3-{2-(2-[2-ethoxy]-ethoxy)-ethoxy}]propionic acid, Pseudo-uracil 1-[3-{2-(2-[2-(2-ethoxy)-ethoxy]-ethoxy)-ethoxy}]propionic acid, Pseudo-uracil 1-[3-{2-(2-[2-{2(2-ethoxy)-ethoxy}-ethoxy]-ethoxy)-ethoxy}]propionic acid, 1-{3-[2-(2-Aminoethoxy)-ethoxy]-propionyl} pseudo-uracil, 1-[3-(2-{2-[2-(2-Aminoethoxy)-ethoxy]-ethoxy}-ethoxy)-propionyl]-pseudo-uracil, 1-Biotinyl-pseudo-uracil, 1-Biotinyl-PEG2-pseudo-uracil, 5-($C_{3-8}$ cycloalkyl)-cytosine, 5-methyl-N6-acetyl-1-cytosine, 5-(carboxymethyl)-N6-trifluoroacetyl-cytosine trifluoromethyl ester, N6-propionyl-cytosine, 5-monofluoromethyl-cytosine, 5-trifluoromethoxy-cytosine, N6-(1,1,1-trifluoro-propionyl)-cytosine, 4-acetyl-pseudo-isocytosine, 1-ethyl-pseudo-isocytosine, 1-hydroxy-pseudo-isocytosine, or 1-(2,2,2-trifluoroethyl)-pseudo-uracil.

In some embodiments, at least one base is 1,6-Dimethyl-pseudo-uracil, 1-(optionally substituted $C_1$-$C_6$ Alkyl)-6-(1-propynyl)-pseudo-uracil, 1-(optionally substituted $C_1$-$C_6$ Alkyl)-6-(2-propynyl)-pseudo-uracil, 1-(optionally substituted $C_1$-$C_6$ Alkyl)-6-allyl-pseudo-uracil, 1-(optionally substituted $C_1$-$C_6$ Alkyl)-6-ethynyl-pseudo-uracil, 1-(optionally substituted $C_1$-$C_6$ Alkyl)-6-homoallyl-pseudo-uracil, 1-(optionally substituted $C_1$-$C_6$ Alkyl)-6-vinyl-pseudo-uracil, 1-Methyl-6-(2,2,2-Trifluoroethyl)pseudo-uracil, 1-Methyl-6-(4-morpholino)-pseudo-uracil, 1-Methyl-6-(4-thiomorpholino)-pseudo-uracil, 1-Methyl-6-(optionally substituted phenyl)pseudo-uracil, 1-Methyl-6-amino-pseudo-uracil, 1-Methyl-6-azido-pseudo-uracil, 1-Methyl-6-bromo-pseudo-uracil, 1-Methyl-6-butyl-pseudo-uracil, 1-Methyl-6-chloro-pseudo-uracil, 1-Methyl-6-cyano-pseudo-uracil, 1-Methyl-6-dimethylamino-pseudo-uracil, 1-Methyl-6-ethoxy-pseudo-uracil, 1-Methyl-6-ethylcarboxylate-pseudo-uracil, 1-Methyl-6-ethyl-pseudo-uracil, 1-Methyl-6-fluoro-pseudo-uracil, 1-Methyl-6-formyl-pseudo-uracil, 1-Methyl-6-hydroxyamino-pseudo-uracil, 1-Methyl-6-hydroxy-pseudo-uracil, 1-Methyl-6-iodo-pseudo-uracil, 1-Methyl-6-iso-propyl-pseudo-uracil, 1-Methyl-6-methoxy-pseudo-uracil, 1-Methyl-6-methylamino-pseudo-uracil, 1-Methyl-6-phenyl-pseudo-uracil, 1-Methyl-6-propyl-pseudo-uracil, 1-Methyl-6-tert-butyl-pseudo-uracil, 1-Methyl-6-trifluoromethoxy-pseudo-uracil, 1-Methyl-6-trifluoromethyl-pseudo-uracil, 6-(2,2,2-Trifluoroethyl)-pseudo-uracil, 6-(4-Morpholino)-pseudo-uracil, 6-(4-Thiomorpholino)-pseudo-uracil, 6-(Substituted-Phenyl)-pseudo-uracil, 6-Amino-pseudo-uracil, 6-Azido-pseudo-uracil, 6-Bromo-pseudo-uracil, 6-Butyl-pseudo-uracil, 6-Chloro-pseudo-uracil, 6-Cyano-pseudo-uracil, 6-Dimethylamino-pseudo-uracil, 6-Ethoxy-pseudo-uracil, 6-Ethylcarboxylate-pseudo-uracil, 6-Ethyl-pseudo-uracil, 6-Fluoro-pseudo-uracil, 6-Formyl-pseudo-uracil, 6-Hydroxyamino-pseudo-uracil, 6-Hydroxy-pseudo-uracil, 6-Iodo-pseudo-uracil, 6-iso-Propyl-pseudo-uracil, 6-Methoxy-pseudo-uracil, 6-Methylamino-pseudo-uracil, 6-Methyl-pseudo-uracil, 6-Phenyl-pseudo-uracil, 6-Phenyl-pseudo-uracil, 6-Propyl-pseudo-uracil, 6-tert-Butyl-pseudo-uracil, 6-Trifluoromethoxy-pseudo-uracil, 6-Trifluoromethyl-pseudo-uracil, 1-(3-Amino-3-carboxypropyl)pseudo-uracil, 1-(2,2,2-Trifluoroethyl)-pseudo-uracil, 1-(2,4,6-Trimethyl-benzyl)pseudo-uracil, 1-(2,4,6-Trimethyl-phenyl)pseudo-uracil, 1-(2-Amino-2-carboxyethyl)pseudo-uracil, 1-(2-Amino-ethyl)pseudo-uracil, 1-(3-Amino-propyl)pseudo-uracil, 1-(4-Amino-4-carboxybutyl)pseudo-uracil, 1-(4-Amino-benzyl)pseudo-uracil, 1-(4-Amino-butyl)pseudo-uracil, 1-(4-Amino-phenyl)pseudo-uracil, 1-(4-Methoxy-benzyl)pseudo-uracil, 1-(4-Methoxy-phenyl)pseudo-uracil, 1-(4-Methyl-benzyl)pseudo-uracil, 1-(4-Nitro-benzyl)pseudo-uracil, 1 (4-Nitro-phenyl)pseudo-uracil, 1-(5-Amino-pentyl)pseudo-uracil, 1-(6-Amino-hexyl)pseudo-uracil, 1-Aminomethyl-pseudo-uracil, 1-Benzyl-pseudo-uracil, 1-Butyl-pseudo-uracil, 1-Cyclobutylmethyl-pseudo-uracil, 1-Cyclobutyl-pseudo-uracil, 1-Cycloheptylmethyl-pseudo-uracil, 1-Cycloheptyl-pseudo-uracil, 1-Cyclohexylmethyl-pseudo-uracil, 1-Cyclohexyl-pseudo-uracil, 1-Cyclooctylmethyl-pseudo-uracil, 1-Cyclooctyl-pseudo-uracil, 1-Cyclopentylmethyl-pseudo-uracil, 1-Cyclopentyl-pseudo-uracil, 1-Cyclopropylmethyl-pseudo-uracil, 1-Cyclopropyl-pseudo-uracil, 1-Ethyl-pseudo-uracil, 1-Hexyl-pseudo-uracil, 1-iso-Propyl-pseudo-uracil, 1-Pentyl-pseudo-uracil, 1-Phenyl-pseudo-uracil, 1-Propyl-pseudo-uracil, 1-p-tolyl-pseudo-uracil, 1-tert-Butyl-pseudo-uracil, 1-Trifluoromethyl-pseudo-uracil, 3-(optionally substituted $C_1$-$C_6$ Alkyl)-pseudo-uracil, Pseudo-uracil-N1-2-ethanoic acid, Pseudo-uracil-N1-3-propionic acid, Pseudo-uracil-N1-4-butanoic acid, Pseudo-uracil-N1-5-pentanoic acid, Pseudo-uracil-N1-6-hexanoic acid, Pseudo-uracil-N1-7-heptanoic acid, Pseudo-uracil-N1-methyl-p-benzoic acid, 6-phenyl-pseudo-uracil, 6-azido-pseudo-uracil, or Pseudo-uracil-N1-p-benzoic acid.

In other embodiments, at least one base is N3-Methyl-pseudo-uracil, 5-Methyl-amino-methyl-uracil, 5-Carboxymethyl-amino-methyl-uracil, 5-(carboxyhydroxymethyl) uracil methyl ester or 5-(carboxyhydroxymethyl) uracil.

In certain embodiments, at least one base is 2-anhydro-cytosine hydrochloride or 2-anhydro-uracil.

In some embodiments, at least one base is 5-Methoxycarbonylmethyl-2-thio-uracil, 5-Methylaminomethyl-2-seleno-uracil, 5-(iso-Pentenylaminomethyl)-uracil, 5-(iso-Pentenylaminomethyl)-2-thio-uracil, or 5-(iso-Pentenylaminomethyl)-uracil.

In other embodiments, at least one base is 5-Trideuteromethyl-6-deutero-uracil, 5-(2-Chloro-phenyl)-2-thio-cytosine, 5-(4-Amino-phenyl)-2-thio-cytosine, 5-(2-Furanyl)-uracil, N4-methyl-cytosine, 8-Trifluoromethyl-adenine, 2-Trifluoromethyl-adenine, 3-Deaza-3-fluoro-adenine, 3-Deaza-3-bromo-adenine, or 3-Deaza-3-iodo-adenine.

In certain embodiments, at least one base is 1-Hydroxymethyl-pseudo-uracil, 1-(2-Hydroxyethyl)-pseudo-uracil, 1-Methoxymethyl-pseudo-uracil, 1-(2-Methoxyethyl)-pseudo-uracil, 1-(2,2-Diethoxyethyl)-pseudo-uracil, (±)1-

(2-Hydroxypropyl)-pseudo-uracil, (2R)-1-(2-Hydroxypropyl)-pseudo-uracil, (2S)-1-(2-Hydroxypropyl)-pseudo-uracil, 1-Cyanomethyl-pseudo-uracil, 1-Morpholinomethyl-pseudo-uracil, 1-Thiomorpholinomethyl-pseudo-uracil, 1-Benzyloxymethyl-pseudo-uracil, 1-(2,2,3,3,3-Pentafluoropropyl)-pseudo-uracil, 1-Thiomethoxymethyl-pseudo-uracil, 1-Methanesulfonylmethyl-pseudo-uracil, 1-Vinyl-pseudo-uracil, 1-Allyl-pseudo-uracil, 1-Homoallyl-pseudo-uracil, 1-Propargyl-pseudo-uracil, 1-(4-Fluorobenzyl)-pseudo-uracil, 1-(4-Chlorobenzyl)-pseudo-uracil, 1-(4-Bromobenzyl)-pseudo-uracil, 1-(4-Iodobenzyl)-pseudo-uracil, 1-(4-Methylbenzyl)-pseudo-uracil, 1-(4-Trifluoromethylbenzyl)-pseudo-uracil, 1-(4-Methoxybenzyl)-pseudo-uracil, 1-(4-Trifluoromethoxybenzyl)-pseudo-uracil, 1-(4-Thiomethoxybenzyl)-pseudo-uracil, 1-(4-Methanesulfonylbenzyl)-pseudo-uracil, Pseudo-uracil 1-(4-methylbenzoic acid), Pseudo-uracil 1-(4-methylbenzenesulfonic acid), 1-(2,4,6-Trimethylbenzyl)-pseudo-uracil, 1-(4-Nitrobenzyl)-pseudo-uracil, 1-(4-Azidobenzyl)-pseudo-uracil, 1-(3,4-Dimethoxybenzyl)-pseudo-uracil, 1-(3,4-Bis-trifluoromethoxybenzyl)-pseudo-uracil, 1-Acetyl-pseudo-uracil, 1-Trifluoroacetyl-pseudo-uracil, 1-Benzoyl-pseudo-uracil, 1-Pivaloyl-pseudo-uracil, 1-(3-Cyclopropyl-prop-2-ynyl)-pseudo-uracil, Pseudo-uracil 1-methylphosphonic acid diethyl ester, Pseudo-uracil 1-methylphosphonic acid, Pseudo-uracil 1-[3-(2-ethoxy)]propionic acid, Pseudo-uracil 1-[3-{2-(2-ethoxy)-ethoxy}]propionic acid, Pseudo-uracil 1-[3-{2-(2-[2-ethoxy]-ethoxy)-ethoxy}]propionic acid, Pseudo-uracil 1-[3-{2-(2-[2-(2-ethoxy)-ethoxy]-ethoxy)-ethoxy}]propionic acid, Pseudo-uracil 1-[3-{2-(2-[2-{2(2-ethoxy)-ethoxy}-ethoxy]-ethoxy)-ethoxy}]propionic acid, 1-{3-[2-(2-Aminoethoxy)-ethoxy]-propionyl}pseudo-uracil, 1-[3-(2-{2-[2-(2-Aminoethoxy)-ethoxy]-ethoxy}-ethoxy)-propionyl]-pseudo-uracil, 1-Biotinyl-pseudo-uracil, or 1-Biotinyl-PEG2-pseudo-uracil.

In some embodiments, at least one base is 5-cyclopropyl-cytosine, 5-methyl-N6-acetyl-1-cytosine, 5-(carboxymethyl)-N6-trifluoroacetyl-cytosine trifluoromethyl ester, N6-propionyl-cytosine, 5-monofluoromethyl-cytosine, 5-trifluoromethoxy-cytosine, N6-(1,1,1-trifluoro-propionyl)-cytosine, 4-acetyl-pseudo-isocytosine, 1-ethyl-pseudo-isocytosine, or 1-hydroxy-pseudo-isocytosine.

In other embodiments, at least one base is 1-(2,2,2-trifluoroethyl)-pseudo-uracil.

In another aspect, the invention features a polynucleotide (e.g., an mRNA), wherein at least one base has the structure of Formula b15:

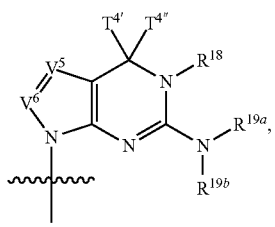

or a pharmaceutically acceptable salt thereof, wherein
T$^{4'}$ and T$^{4''}$ combine to form O (oxo); V$^5$ is N or CR$^{Vd}$; V$^6$ is CR$^{Vd}$; each R$^{Vd}$ is, independently, hydrogen, nitro, chloro, iodo, optionally substituted C$_1$-C$_6$ aminoalkyl, or optionally substituted C$_1$-C$_6$ alkoxyalkyl; and R$^{18}$, R$^{19a}$, and R$^{19b}$ are each hydrogen, provided that, when V$^5$ is N, R$^{Vd}$ is not hydrogen, and, V$^5$ and V$^6$ are not both CH.

In some embodiments, at least one base has the structure of Formula b50:

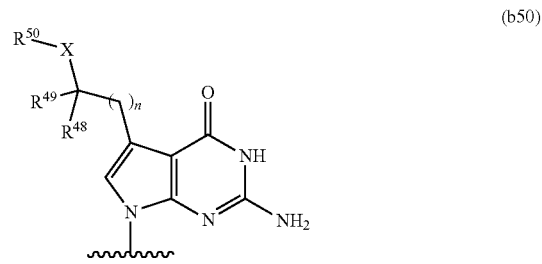

or a pharmaceutically acceptable salt thereof, wherein
n is 0, 1, 2, or 3; X is O or NR$^{51}$; R$^{48}$ and R$^{49}$ are independently hydrogen or optionally substituted C$_1$-C$_6$ alkyl, or combine to form an optionally substituted C$_3$-C$_8$ cycloalkyl; and R$^{50}$ and R$^{51}$ are independently hydrogen or optionally substituted C$_1$-C$_6$ alkyl.

In other embodiments, at least one base has the structure of Formula b51:

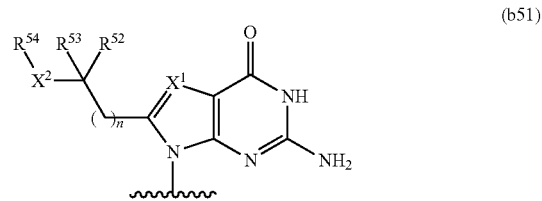

or a pharmaceutically acceptable salt thereof, wherein
n is 0, 1, 2, or 3; X$^1$ is N or CH; X$^2$ is O or NR$^{55}$; R$^{52}$ and R$^{53}$ are independently hydrogen or optionally substituted C$_1$-C$_6$ alkyl, or combine to form an optionally substituted C$_3$-C$_8$ cycloalkyl; and R$^{54}$ and R$^{55}$ are independently hydrogen or optionally substituted C$_1$-C$_6$ alkyl.

In some embodiments, at least one base has the structure:

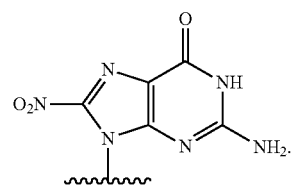 [SMILES: *n1c([N+](=O)[O-])nc2c(=O)[nH]c(N)nc21]

In other embodiments, at least one base has the structure:

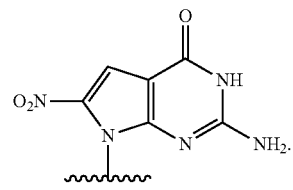 [SMILES: *n1c([N+](=O)[O-])cc2c(=O)[nH]c(N)nc21]

In certain embodiments, at least one base has the structure:

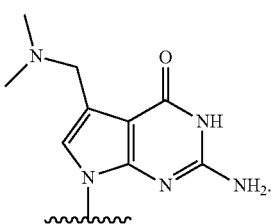 [SMILES: *n1cc(CN(C)C)c2c(=O)[nH]c(N)nc21]

In some embodiments, at least one base has the structure:

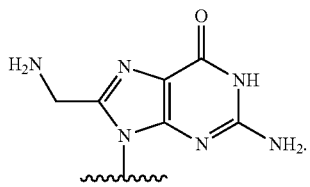 [SMILES: *n1c(CN)nc2c(=O)[nH]c(N)nc21]

In other embodiments, at least one base has the structure:

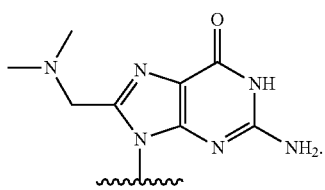 [SMILES: *n1c(CN(C)C)nc2c(=O)[nH]c(N)nc21]

In certain embodiments, at least one base has the structure:

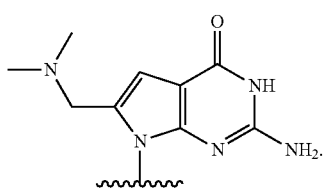 [SMILES: *n1c(CN(C)C)cc2c(=O)[nH]c(N)nc21]

In some embodiments, at least one base has the structure:

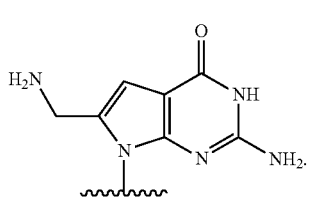 [SMILES: *n1c(CN)cc2c(=O)[nH]c(N)nc21]

In another aspect, the invention features a polynucleotide (e.g., an mRNA), wherein at least one base has the structure of Formula b45:

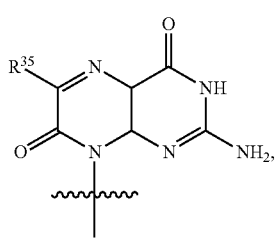

(b45)

or a pharmaceutically acceptable salt thereof,
wherein $R^{35}$ is hydrogen or optionally substituted $C_1$-$C_6$ alkyl.

In some embodiments, at least one base has the structure:

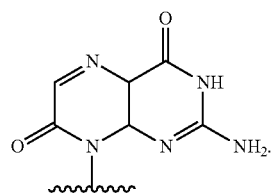 [SMILES: *N1C(=O)C=NC2C(=O)NC(N)=NC21]

In another aspect, the invention features a polynucleotide (e.g., an mRNA), wherein at least one base has the structure of Formula b16:

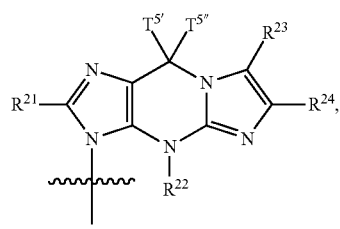

(b16)

or a pharmaceutically acceptable salt thereof, wherein
$T^{5'}$ and $T^{5''}$ combine to form O (oxo); $R^{21}$ is hydrogen, chloro, bromo, iodo, nitro, or optionally substituted $C_1$-$C_6$ alkyl; and each of $R^{22}$, $R^{23}$, and $R^{24}$ is, independently hydrogen or optionally substituted $C_1$-$C_6$ alkyl,
wherein said base does not have the structure:

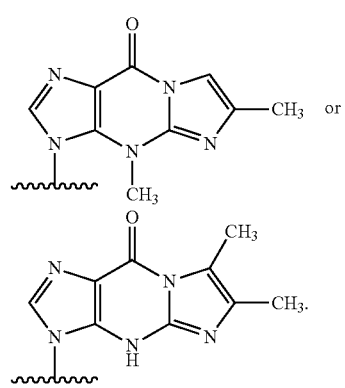

In another aspect, the invention features a polynucleotide (e.g., an mRNA), wherein at least one base has the structure of Formula b3:

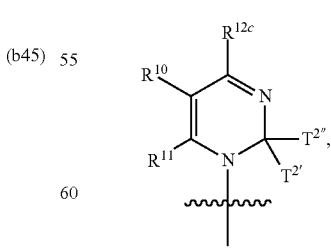

(b3)

or a pharmaceutically acceptable salt thereof, wherein
$T^{2'}$ and $T^{2''}$ combine to form O (oxo); $R^{11}$ is H; and $R^{12c}$ combines with $R^{10}$ to form an optionally substituted $C_2$-$C_9$ heterocyclyl.

In some embodiments, at least one base has the structure of Formula b47:

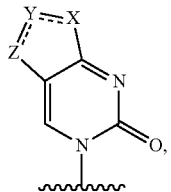
(b47)

or a pharmaceutically acceptable salt thereof, wherein
the dotted lines represent optional double bonds, provided that no more than one double bond is present, X, Y, and Z are independently O, $NR^{45}$, or $CR^{46}R^{47}$, and $R^{45}$, $R^{46}$, and $R^{47}$ are independently absent, hydrogen, or optionally substituted $C_1$-$C_6$ alkyl, provided that at least one of X, Y, and Z is O or $NR^{45}$.

In other embodiments, at least one base has the structure:

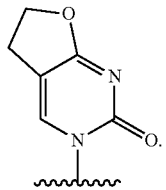

In another aspect, the invention features a polynucleotide (e.g., an mRNA), wherein at least one base has the structure of Formula b30:

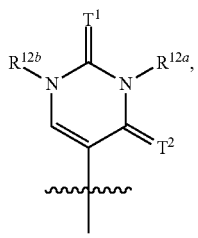
(b30)

or a pharmaceutically acceptable salt thereof, wherein
each of $T^1$ and $T^2$ is O (oxo); $R^{12a}$ is H; and $R^{12b}$ is optionally substituted amino or optionally substituted $C_{1-6}$ hydroxyalkyl.

In some embodiments, at least one base has the structure:

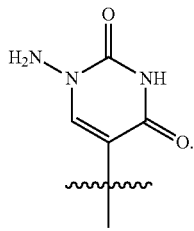

In another aspect, the invention features a polynucleotide (e.g., an mRNA), wherein at least one base has the structure of Formula b29:

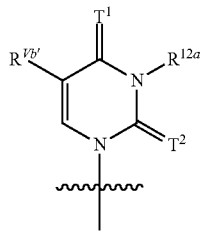
(b29)

or a pharmaceutically acceptable salt thereof, wherein
each of $T^1$ and $T^2$ is O (oxo); $R^{12a}$ is H; and $R^{Vb'}$ is optionally substituted $C_6$-$C_{10}$ aryl, optionally substituted $C_3$-$C_9$ heteroaryl, optionally substituted $C_1$-$C_6$ aminoalkyl, optionally substituted $C_1$-$C_6$ alkoxyalkyl, or optionally substituted $C_1$-$C_6$ hydroxyalkyl.

In certain embodiments, at least one base has the structure of Formula b52:

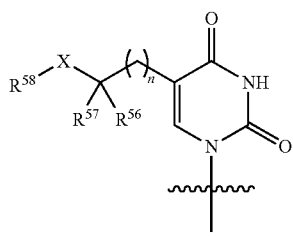
(b52)

or a pharmaceutically acceptable salt thereof, wherein
n is 0, 1, 2, or 3, X is O or $NR^{59}$; $R^{56}$ and $R^{57}$ are independently hydrogen or optionally substituted $C_1$-$C_6$ alkyl, or combine to form an optionally substituted $C_3$-$C_8$ cycloalkyl; and $R^{58}$ and $R^{59}$ are independently hydrogen or optionally substituted $C_1$-$C_6$ alkyl.

In some embodiments, at least one base has the structure:

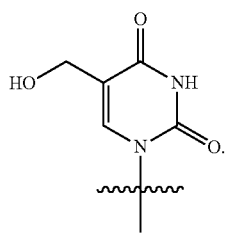 [SMILES: *n1cc(CO)c(=O)[nH]c1=O]

In another aspect, the invention features a polynucleotide (e.g., an mRNA), wherein at least one base is replaced with a structure of Formula b44:

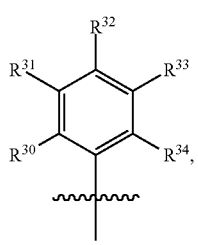
(b44)

or a pharmaceutically acceptable salt thereof, wherein each of $R^{30}$, $R^{31}$, $R^{32}$, $R^{33}$, and $R^{34}$ is independently hydrogen, fluoro, or optionally substituted $C_1$-$C_6$ alkyl.

In some embodiments, at least one base is replaced with the structure:

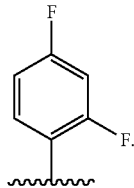 [SMILES: *c1ccc(F)cc1F]

In other embodiments, at least one base is replaced with the structure:

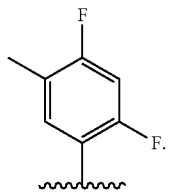

In another aspect, the invention features a polynucleotide (e.g., an mRNA), wherein at least one base has the structure of Formula b46:

have the structure of Formula (b46):

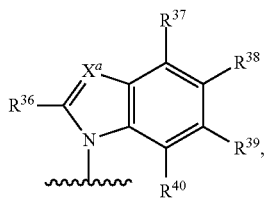

(b46)

or a pharmaceutically acceptable salt thereof,
wherein $X^a$ is N or $CR^{41}$;
$R^{36}$ is hydrogen, chloro, bromo, iodo, nitro, or optionally substituted $C_1$-$C_6$ alkyl;
$R^{37}$, $R^{38}$, $R^{39}$, and $R^{40}$ are independently hydrogen or fluoro; and
$R^{41}$ is hydrogen or optionally substituted $C_1$-$C_6$ alkyl.

In another aspect, the invention features a polynucleotide (e.g., an mRNA), wherein at least one base has the structure of Formula b7:

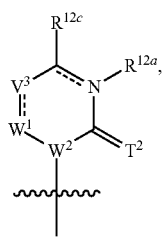

(b7)

or a pharmaceutically acceptable salt thereof,
wherein ⇌ is a single or double bond;
$T^2$ is O (oxo); $V^3$ is $CR^{Va}$ and $R^{Va}$ is H; $W^1$ is $CR^{Wa}$ and $R^{Wa}$ is H; $W^2$ is N; and $R^{12a}$ and $R^{12c}$ combine to form optionally substituted $C_2$-$C_9$ heterocyclyl.

In some embodiments, at least one base has the structure of Formula b48:

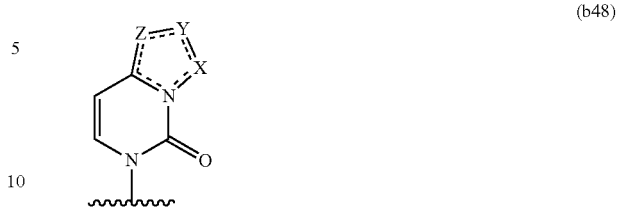

(b48)

or a pharmaceutically acceptable salt thereof, wherein
the dotted lines represent optional double bonds, provided that no two double bonds are adjacent, X, Y, and Z are independently O, $NR^{45}$, or $CR^{46}R^{47}$, and $R^{45}$, $R^{46}$, and $R^{47}$ are independently absent, hydrogen, or optionally substituted $C_1$-$C_6$ alkyl.

In another aspect, the invention features a polynucleotide (e.g., an mRNA), wherein at least one base has the structure of Formula b8:

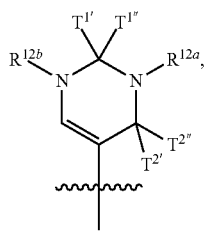

(b8)

or a pharmaceutically acceptable salt thereof, wherein
$T^{1'}$ and $T^{1''}$ combine to form O (oxo); $R^{12b}$ is H; and $R^{12a}$ and $T^{2'}$ combine to form optionally substituted $C_2$-$C_9$ heterocyclyl.

In some embodiments, at least one base has the structure of Formula b49:

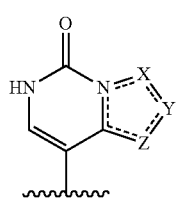

(b49)

or a pharmaceutically acceptable salt thereof, wherein
the dotted lines represent optional double bonds, provided that no two double bonds are adjacent, X, Y, and Z are independently O, $NR^{45}$, or $CR^{46}R^{47}$, and $R^{45}$, $R^{46}$, and $R^{47}$ are independently absent, hydrogen or optionally substituted $C_1$-$C_6$ alkyl.

In another aspect, the invention features a polynucleotide (e.g., an mRNA), wherein at least one base has the structure of Formula b47:

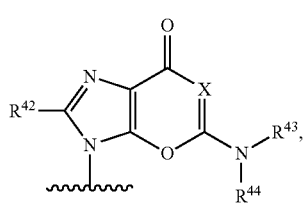

(b47)

or a pharmaceutically acceptable salt thereof,
wherein X is N or CH;
$R^{42}$ is hydrogen, chloro, bromo, iodo, nitro, or optionally substituted $C_1$-$C_6$ alkyl; and $R^{43}$ and $R^{44}$ are independently hydrogen or optionally substituted $C_1$-$C_6$ alkyl.

In another aspect, the invention features a polynucleotide (e.g., an mRNA), wherein at least one base has the structure of Formula b20:

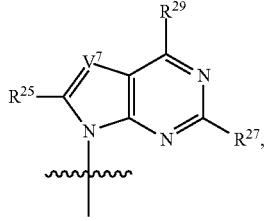

(b20)

or a pharmaceutically acceptable salt thereof, wherein $V^7$ is N; $R^{27}$ is optionally substituted amino; $R^{25}$ is H, chloro, bromo, iodo, nitro, or optionally substituted $C_1$-$C_6$ alkyl; and $R^{29}$ is optionally substituted $C_1$-$C_6$ alkyl, optionally substituted $C_6$-$C_{10}$ aryl, or optionally substituted $C_2$-$C_9$ heteroaryl.

In certain embodiments, the polynucleotide includes at least one backbone moiety of Formula VIII-XII:

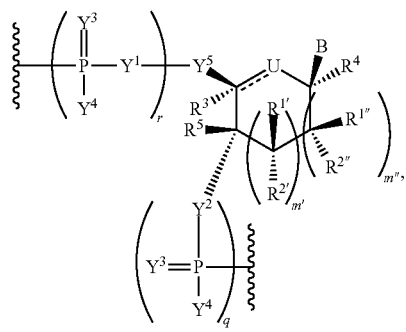

Formula VIII

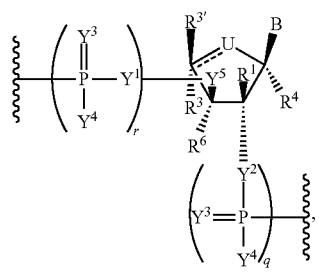

Formula IX

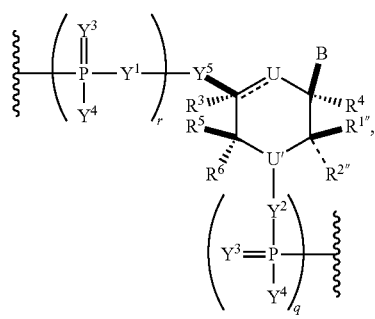

Formula X

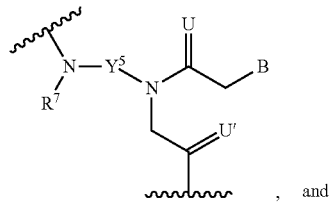

Formula XI

, and

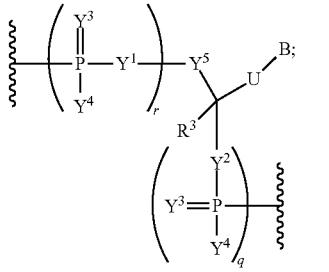

Formula XII wherein the dashed line represents an optional double bond;

B is a nucleobase;

each of U and U' is, independently, O, S, $N(R^U)_{nu}$, or $C(R^U)_{nu}$, wherein nu is an integer from 0 to 2 (e.g., 0 or 1 for $N(R^U)_{nu}$ and 1 or 2 for $C(R^U)_{nu}$) and each $R^U$ is, independently, H, halo, or optionally substituted $C_1$-$C_6$ alkyl;

each of $R^{1'}$, $R^{2'}$, $R^{1''}$, $R^{2''}$, $R^1$, $R^{3'}$, $R^4$, $R^5$, $R^6$, and $R^7$ is, independently, H, halo, hydroxy, thiol, optionally substituted $C_1$-$C_6$ alkyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, optionally substituted $C_6$-$C_{10}$ aryl; or $R^5$ can join together with one or more of $R^{1'}$, $R^{1''}$, $R^{2'}$, or $R^{2''}$ to form together with the carbons to which they are attached, an optionally substituted $C_3$-$C_9$ heterocyclyl or an optionally substituted $C_3$-$C_9$ cycloalkyl; or $R^4$ can join together with one or more of $R^{1'}$, $R^{1''}$, $R^{2'}$, $R^{2''}$, $R^3$, or $R^5$ to form together with the carbons to which they are attached, provide an optionally substituted $C_3$-$C_9$ heterocyclyl or an optionally substituted $C_3$-$C_9$ cycloalkyl;

$R^3$ is H, halo, hydroxy, thiol, optionally substituted $C_1$-$C_6$ alkyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, optionally substituted $C_6$-$C_{10}$ aryl; or $R^3$ can join together with one or more of $R^{1'}$, $R^{1''}$, $R^{2'}$, $R^{2''}$, and, taken together with the carbons to which they are attached, provide an optionally substituted $C_3$-$C_9$ heterocyclyl or an optionally substituted $C_3$-$C_9$ cycloalkyl; wherein if said optional double bond is present, $R^3$ is absent;

each of m' and m" is, independently, an integer from 0 to 3;

each of q and r is independently, an integer from 0 to 5;

each of $Y^1$, $Y^2$, and $Y^3$, is, independently, hydrogen, O, S, Se, $-NR^{N1}-$, optionally substituted $C_1$-$C_6$ alkylene, or optionally substituted $C_1$-$C_6$ heteroalkylene, wherein $R^{N1}$ is H, optionally substituted $C_1$-$C_6$ alkyl, optionally substituted $C_2$-$C_6$ alkenyl, optionally substituted $C_2$-$C_6$ alkynyl, or optionally substituted $C_6$-$C_{10}$ aryl;

each $Y^4$ is, independently, H, hydroxyl, protected hydroxyl, halo, thiol, boranyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, or absent; and $Y^5$ is O, S, Se, optionally substituted $C_1$-$C_6$ alkylene, or optionally substituted $C_1$-$C_6$ heteroalkylene.

In some embodiments, the polynucleotide further includes:

(a) a 5' UTR optionally including at least one Kozak sequence;

(b) a 3' UTR; and (c) at least one 5' cap structure.

In other embodiments, the at least one 5' cap structure is Cap0, Cap1, ARCA, inosine, N1-methyl-guanosine, 2'-fluoro-guanosine, 7-deaza-guanosine, 8-oxo-guanosine, 2-amino-guanosine, LNA-guanosine, or 2-azido-guanosine.

In certain embodiments, the polynucleotide further includes a poly-A tail.

In some embodiments, the polynucleotide encodes a protein of interest.

In other embodiments, the polynucleotide is purified.

In certain embodiments, the polynucleotide is codon optimized.

In another aspect, the invention features an isolated polynucleotide (e.g., an mRNA) encoding a polypeptide of interest, the isolated polynucleotide including:

(a) a 5' UTR optionally including at least one Kozak sequence;

(b) a 3' UTR; and (c) at least one 5' cap structure, wherein at least one base is 1-Methyl-3-(3-amino-3-carboxypropyl)pseudo-uracil, 5-Oxyacetic acid-methyl ester-uracil, 5-Trifluoromethyl-cytosine, 5-Trifluoromethyl-uracil, 5-Carboxymethylaminomethyl-2-thio-uracil, 5-Methylaminomethyl-2-thio-uracil, 5-Methoxy-carbonylmethyl-uracil, 5-Oxyacetic acid-uracil, 3-(3-Amino-3-carboxypropyl)-uracil, 2-Amino-adenine, 8-Aza-adenine, Xanthosine, 5-Bromo-cytosine, 5-Aminoallyl-cytosine, 5-iodo-cytosine, 8-bromo-adenine, 8-bromo-guanine, N4-Benzoyl-cytosine, N4-Amino-cytosine, N6-Bz-adenine, N2-isobutyl-guanine, 5-Methylaminomethyl-2-thio-uracil, 5-Carbamoylmethyl-uracil, 1-Methyl-3-(3-amino-3-carboxypropyl)pseudo-uracil, 5-Methyldihydro-uracil, 5-(1-propynyl)cytosine, 5-Ethynylcytosine, 5-vinyl-uracil, (Z)-5-(2-Bromo-vinyl)-uracil, (E)-5-(2-Bromo-vinyl)-uracil, 5-Methoxy-cytosine, 5-Formyl-uracil, 5-Cyano-uracil, 5-Dimethylamino-uracil, 5-Cyano-cytosine, 5-Phenylethynyl-uracil, (E)-5-(2-Bromo-vinyl)-cytosine, 2-Mercapto-adenine, 2-Azido-adenine, 2-Fluoro-adenine, 2-Chloro-adenine, 2-Bromo-adenine, 2-Iodo-adenine, 7-Amino-1H-pyrazolo[4,3-d]pyrimidine, 2,4-dihydropyrazolo[4,3-d]pyrimidin-7-one, 2,4-dihydropyrazolo[4,3-d]pyrimidine-5,7-dione, pyrrolosine, 9-Deaza-adenine, 9-Deaza-guanine, 3-Deaza-adenine, 3-Deaza-3-chloro-adenine, 1-Deaza-adenine, 5-vinyl-cytosine, 5-phenyl-cytosine, 5-difluoromethyl-cytosine, 5-(1-propynyl)-uracil, 5-(1-propynyl)-cytosine, or 5-methoxymethyl-cytosine.

In some embodiments, at least one base is 1-Methyl-3-(3-amino-3-carboxypropyl)pseudo-uracil.

In other embodiments, at least one base is 5-Oxyacetic acid-methyl ester-uracil, 5-Trifluoromethyl-cytosine, 5-Trifluoromethyl-uracil, 5-Carboxymethylaminomethyl-2-thio-uracil, 5-Methylaminomethyl-2-thio-uracil, 5-Methoxy-carbonyl-methyl-uracil, 5-Oxyacetic acid-uracil, or 3-(3-Amino-3-carboxypropyl)-uracil.

In certain embodiments, at least one base is 2-Amino-adenine, 8-Aza-adenine, Xanthosine, 5-Bromo-cytosine, or 5-Aminoallyl-cytosine.

In some embodiments, at least one base is 5-iodo-cytosine, 8-bromo-adenine, 8-bromo-guanine, N4-Benzoyl-cytosine, N4-Amino-cytosine, N6-Bz-adenine, or N2-isobutyl-guanine.

In other embodiments, at least one base is 5-Methylaminomethyl-2-thio-uracil, 5-Carbamoylmethyl-uracil, 1-Methyl-3-(3-amino-3-carboxypropyl)pseudo-uracil, or 5-Methyldihydro-uracil.

In certain embodiments, at least one base is 5-(1-propynyl)cytosine, 5-Ethynylcytosine, 5-vinyl-uracil, (Z)-5-(2-Bromo-vinyl)-uracil, (E)-5-(2-Bromo-vinyl)-uracil, 5-Methoxy-cytosine, 5-Formyl-uracil, 5-Cyano-uracil, 5-Dimethylamino-uracil, 5-Cyano-cytosine, 5-Phenylethynyl-uracil, (E)-5-(2-Bromo-vinyl)-cytosine, 2-Mercapto-adenine, 2-Azido-adenine, 2-Fluoro-adenine, 2-Chloro-adenine, 2-Bromo-adenine, 2-Iodo-adenine, 7-Amino-1H-pyrazolo[4,3-d]pyrimidine, 2,4-dihydropyrazolo[4,3-d]pyrimidin-7-one, 2,4-dihydropyrazolo[4,3-d]pyrimidine-5,7-dione, pyrrolosine, 9-Deaza-adenine, 9-Deaza-guanine, 3-Deaza-adenine, 3-Deaza-3-chloro-adenine, or 1-Deaza-adenine.

In some embodiments, at least one base is 5-methoxy-uridine, 5-vinyl-cytosine, 5-phenyl-cytosine, 5-difluoromethyl-cytosine, or 5-methoxymethyl-cytosine.

In other embodiments, at least one base is 5-bromo-cytosine.

In certain embodiments, the polynucleotide further includes a poly-A tail.

In some embodiments, the polynucleotide is purified.

In other embodiments, the at least one 5' cap structure is Cap0, Cap1, ARCA, inosine, N1-methyl-guanosine, 2'-fluoro-guanosine, 7-deaza-guanosine, 8-oxo-guanosine, 2-amino-guanosine, LNA-guanosine, or 2-azido-guanosine.

In certain embodiments, the polynucleotide is codon optimized.

In another aspect, the invention features a compound of Formula I:

A-B,      Formula I wherein A is:

Formula II

Formula III

-continued

Formula IV

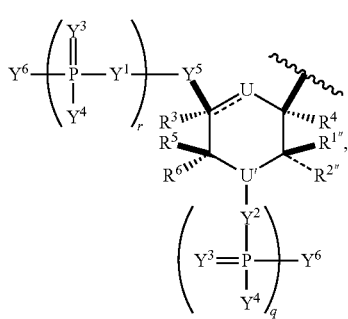

Formula V

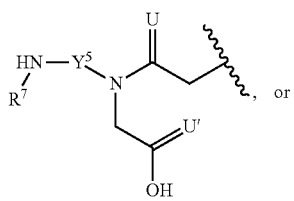

Formula VI

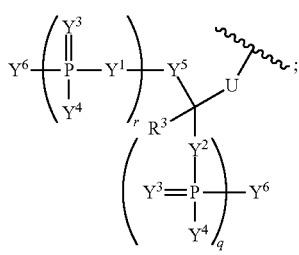

wherein the dashed line represents an optional double bond;

each of U and U' is, independently, O, S, $N(R^U)_{nu}$, or $C(R^U)_{nu}$, wherein nu is an integer from 0 to 2 (e.g., 0 or 1 for $N(R^U)_{nu}$ and 1 or 2 for $C(R^U)_{nu}$) and each $R^U$ is, independently, H, halo, or optionally substituted $C_1$-$C_6$ alkyl;

each of $R^{1'}$, $R^{2'}$, $R^{1''}$, $R^{2''}$, $R^1$, $R^{3'}$, $R^4$, $R^5$, $R^6$, and $R^7$ is, independently, H, halo, hydroxy, thiol, optionally substituted $C_1$-$C_6$ alkyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, optionally substituted $C_6$-$C_{10}$ aryl; or $R^5$ can join together with one or more of $R^{1'}$, $R^{1''}$, $R^{2'}$, or $R^{2''}$ to form together with the carbons to which they are attached, an optionally substituted $C_3$-$C_9$ heterocyclyl or an optionally substituted $C_3$-$C_9$ cycloalkyl; or $R^4$ can join together with one or more of $R^{1'}$, $R^{1''}$, $R^{2'}$, $R^{2''}$, $R^3$, or $R^5$ to form together with the carbons to which they are attached, an optionally substituted $C_3$-$C_9$ heterocyclyl or an optionally substituted $C_3$-$C_9$ cycloalkyl;

$R^3$ is H, halo, hydroxy, thiol, optionally substituted $C_1$-$C_6$ alkyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, optionally substituted $C_6$-$C_{10}$ aryl; or $R^3$ can join together with one or more of $R^{1'}$, $R^{1''}$, $R^{2'}$, $R^{2''}$, and, taken together with the carbons to which they are attached, provide an optionally substituted $C_3$-$C_9$ heterocyclyl or an optionally substituted $C_3$-$C_9$ cycloalkyl; wherein if said optional double bond is present, $R^3$ is absent;

each of m' and m'' is, independently, an integer from 0 to 3;

each of q and r is independently, an integer from 0 to 5;
each of $Y^1$, $Y^2$, and $Y^3$, is, independently, hydrogen, O, S, Se, $-NR^{N1}-$, optionally substituted $C_1$-$C_6$ alkylene, or optionally substituted $C_1$-$C_6$ heteroalkylene, wherein $R^{N1}$ is H, optionally substituted $C_1$-$C_6$ alkyl, optionally substituted $C_2$-$C_6$ alkenyl, optionally substituted $C_2$-$C_6$ alkynyl, or optionally substituted $C_6$-$C_{10}$ aryl;

each of $Y^4$ and $Y^6$ is, independently, H, hydroxyl, protected hydroxyl, halo, thiol, boranyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, or optionally substituted amino, or $Y^4$ is absent;

$Y^5$ is O, S, Se, optionally substituted $C_1$-$C_6$ alkylene, or optionally substituted $C_1$-$C_6$ heteroalkylene; and B is 1,6-Dimethyl-pseudo-uracil, 1-(optionally substituted $C_1$-$C_6$ Alkyl)-6-(1-propynyl)-pseudo-uracil, 1-(optionally substituted $C_1$-$C_6$ Alkyl)-6-(2-propynyl)-pseudo-uracil, 1-(optionally substituted $C_1$-$C_6$ Alkyl)-6-allyl-pseudo-uracil, 1-(optionally substituted $C_1$-$C_6$ Alkyl)-6-ethynyl-pseudo-uracil, 1-(optionally substituted $C_1$-$C_6$ Alkyl)-6-homoallyl-pseudo-uracil, 1-(optionally substituted $C_1$-$C_6$ Alkyl)-6-vinyl-pseudo-uracil, 1-Methyl-6-(2,2,2-Trifluoroethyl)pseudo-uracil, 1-Methyl-6-(4-morpholino)-pseudo-uracil, 1-Methyl-6-(4-thiomorpholino)-pseudo-uracil, 1-Methyl-6-(optionally substituted phenyl)pseudo-uracil, 1-Methyl-6-amino-pseudo-uracil, 1-Methyl-6-azido-pseudo-uracil, 1-Methyl-6-bromo-pseudo-uracil, 1-Methyl-6-butyl-pseudo-uracil, 1-Methyl-6-chloro-pseudo-uracil, 1-Methyl-6-cyano-pseudo-uracil, 1-Methyl-6-dimethyl-amino-pseudo-uracil, 1-Methyl-6-ethoxy-pseudo-uracil, 1-Methyl-6-ethylcarboxylate-pseudo-uracil, 1-Methyl-6-ethyl-pseudo-uracil, 1-Methyl-6-fluoro-pseudo-uracil, 1-Methyl-6-formyl-pseudo-uracil, 1-Methyl-6-hydroxyamino-pseudo-uracil, 1-Methyl-6-hydroxy-pseudo-uracil, 1-Methyl-6-iodo-pseudo-uracil, 1-Methyl-6-iso-propyl-pseudo-uracil, 1-Methyl-6-methoxy-pseudo-uracil, 1-Methyl-6-methylamino-pseudo-uracil, 1-Methyl-6-phenyl-pseudo-uracil, 1-Methyl-6-propyl-pseudo-uracil, 1-Methyl-6-tert-butyl-pseudo-uracil, 1-Methyl-6-trifluoromethoxy-pseudo-uracil, 1-Methyl-6-trifluoromethyl-pseudo-uracil, 6-(2,2,2-Trifluoroethyl)-pseudo-uracil, 6-(4-Morpholino)-pseudo-uracil, 6-(4-Thiomorpholino)-pseudo-uracil, 6-(optionally substituted-Phenyl)-pseudo-uracil, 6-Amino-pseudo-uracil, 6-Azido-pseudo-uracil, 6-Bromo-pseudo-uracil, 6-Butyl-pseudo-uracil, 6-Chloro-pseudo-uracil, 6-Cyano-pseudo-uracil, 6-Dimethylamino-pseudo-uracil, 6-Ethoxy-pseudo-uracil, 6-Ethylcarboxylate-pseudo-uracil, 6-Ethyl-pseudo-uracil, 6-Fluoro-pseudo-uracil, 6-Formyl-pseudo-uracil, 6-Hydroxyamino-pseudo-uracil, 6-Hydroxy-pseudo-uracil, 6-Iodo-pseudo-uracil, 6-iso-Propyl-pseudo-uracil, 6-Methoxy-pseudo-uracil, 6-Methylamino-pseudo-uracil, 6-Methyl-pseudo-uracil, 6-Phenyl-pseudo-uracil, 6-Propyl-pseudo-uracil, 6-tert-Butyl-pseudo-uracil, 6-Trifluoromethoxy-pseudo-uracil, 6-Trifluoromethyl-pseudo-uracil, 1-(3-Amino-3-carboxypropyl)pseudo-uracil, 1-(2,2,2-Trifluoroethyl)-pseudo-uracil, 1-(2,4,6-Trimethyl-benzyl)pseudo-uracil, 1-(2,4,6-Trimethyl-phenyl)pseudo-uracil, 1-(2-Amino-2-carboxyethyl)pseudo-uracil, 1-(2-Amino-ethyl)pseudo-uracil, 1-(3-Amino-propyl)pseudo-uracil, 1-(4-Amino-4-carboxybutyl)pseudo-uracil, 1-(4-Amino-benzyl)pseudo-uracil, 1-(4-Amino-butyl)pseudo-uracil, 1-(4-Amino-phenyl)pseudo-uracil, 1-(4-Methoxy-benzyl)pseudo-uracil, 1-(4-Methoxy-phenyl)pseudo-uracil, 1-(4-Methyl-benzyl)pseudo-uracil, 1-(4-Nitro-benzyl)pseudo-uracil, 1(4-Nitro-phenyl)pseudo-uracil, 1-(5-Amino-pentyl)pseudo-uracil, 1-(6-Amino-hexyl)pseudo-uracil, 1-Aminomethyl-pseudo-uracil, 1-Benzyl-pseudo-uracil, 1-Butyl-pseudo-uracil, 1-Cyclobutylmethyl-pseudo-uracil, 1-Cyclobutyl-pseudo-uracil, 1-Cycloheptylmethyl-pseudo-uracil, 1-Cycloheptyl-pseudo-uracil, 1-Cyclohexylmethyl-pseudo-uracil, 1-Cyclohexyl-pseudo-uracil, 1-Cyclooctylmethyl-pseudo-uracil, 1-Cyclooctyl-pseudo-uracil, 1-Cyclopentylmethyl-pseudo-uracil, 1-Cyclopentyl-pseudo-uracil, 1-Cyclopropylmethyl-pseudo-uracil, 1-Cyclopropyl-pseudo-uracil, 1-Ethyl-pseudo-uracil, 1-Hexyl-pseudo-uracil, 1-iso-Propyl-pseudo-uracil 1-Pentyl-pseudo-uracil, 1-Phenyl-pseudo-uracil, 1-Propyl-pseudo-uracil, 1-p-toluyl-pseudo-uracil, 1-tert-Butyl-pseudo-uracil, 1-Trifluoromethyl-pseudo-uracil, 3-(optionally substituted $C_1$-$C_6$ Alkyl)-pseudo-uracil, Pseudo-uracil-N1-2-ethanoic acid, Pseudo-uracil-N1-3-propionic acid, Pseudo-uracil-N1-4-butanoic acid, Pseudo-uracil-N1-5-pentanoic acid, Pseudo-uracil-N1-6-hexanoic acid, Pseudo-uracil-N1-7-heptanoic acid, Pseudo-uracil-N1-methyl-p-benzoic acid, 6-phenyl-pseudo-uracil, 6-azido-pseudo-uracil, Pseudo-uracil-N1-p-benzoic acid, N3-Methyl-pseudo-uracil, 5-Methyl-amino-methyl-uracil, 5-Carboxy-methyl-amino-methyl-uracil, 5-(carboxyhydroxymethyl)uracil methyl ester 5-(carboxyhydroxymethyl) uracil, 2-anhydro-cytosine, 2-anhydro-uracil, 5-Methoxycarbonylmethyl-2-thio-uracil, 5-Methylaminomethyl-2-seleno-uracil, 5-(iso-Pentenylaminomethyl)-uracil, 5-(iso-Pentenylaminomethyl)-2-thio-uracil, 5-(iso-Pentenylaminomethyl)-uracil, 5-Trideuteromethyl-6-deutero-uracil, 5-(2-Chloro-phenyl)-2-thio-cytosine, 5-(4-Amino-phenyl)-2-thio-cytosine, 5-(2-Furanyl)-uracil, 8-Trifluoromethyl-adenine, 2-Trifluoromethyl-adenine, 3-Deaza-3-fluoro-adenine, 3-Deaza-3-bromo-adenine, 3-Deaza-3-iodo-adenine, 1-Hydroxymethyl-pseudo-uracil, 1-(2-Hydroxyethyl)-pseudo-uracil, 1-Methoxymethyl-pseudo-uracil, 1-(2-Methoxyethyl)-pseudo-uracil, 1-(2,2-Diethoxyethyl)-pseudo-uracil, 1-(2-Hydroxypropyl)-pseudo-uracil, (2R)-1-(2-Hydroxypropyl)-pseudo-uracil, (2S)-1-(2-Hydroxypropyl)-pseudo-uracil, 1-Cyanomethyl-pseudo-uracil, 1-Morpholinomethyl-pseudo-uracil, 1-Thiomorpholinomethyl-pseudo-uracil, 1-Benzyloxymethyl-pseudo-uracil, 1-(2,2,3,3,3-Pentafluoropropyl)-pseudo-uracil, 1-Thiomethoxymethyl-pseudo-uracil, 1-Methanesulfonylmethyl-pseudo-uracil, 1-Vinyl-pseudo-uracil, 1-Allyl-pseudo-uracil, 1-Homoallyl-pseudo-uracil, 1-Propargyl-pseudo-uracil, 1-(4-Fluorobenzyl)-pseudo-uracil, 1-(4-Chlorobenzyl)-pseudo-uracil, 1-(4-Bromobenzyl)-pseudo-uracil, 1-(4-Iodobenzyl)-pseudo-uracil, 1-(4-Methylbenzyl)-pseudo-uracil, 1-(4-Trifluoromethylbenzyl)-pseudo-uracil, 1-(4-Methoxybenzyl)-pseudo-uracil, 1-(4-Trifluoromethoxybenzyl)-pseudo-uracil, 1-(4-Thiomethoxybenzyl)-pseudo-uracil, 1-(4-Methanesulfonylbenzyl)-pseudo-uracil, Pseudo-uracil 1-(4-methylbenzoic acid), Pseudo-uracil 1-(4-methylbenzenesulfonic acid), 1-(2,4,6-Trimethylbenzyl)-pseudo-uracil, 1-(4-Nitrobenzyl)-pseudo-uracil, 1-(4-Azidobenzyl)-pseudo-uracil, 1-(3,4-Dimethoxybenzyl)-pseudo-uracil, 1-(3,4-Bis-trifluoromethoxybenzyl)-pseudo-uracil, 1-Acetyl-pseudo-uracil, 1-Trifluoroacetyl-pseudo-uracil, 1-Benzoyl-pseudo-uracil, 1-Pivaloyl-pseudo-uracil, 1-(3-Cyclopropyl-prop-2-ynyl)-pseudo-uracil, Pseudo-uracil 1-methylphosphonic acid diethyl ester, Pseudo-uracil 1-methylphosphonic acid, Pseudo-uracil 1-[3-(2-ethoxy)] propionic acid, Pseudo-uracil 1-[3-{2-(2-ethoxy)-ethoxy}] propionic acid, Pseudo-uracil 1-[3-{2-(2-[2-ethoxy]-ethoxy)-ethoxy}]propionic acid, Pseudo-uracil 1-[3-{2-(2-[2-(2-ethoxy)-ethoxy]-ethoxy)-ethoxy}]propionic acid, Pseudo-uracil 1-[3-{2-(2-[2-{2(2-ethoxy)-ethoxy}-ethoxy]-ethoxy)-ethoxy}]propionic acid, 1-{3-[2-(2-Aminoethoxy)-ethoxy]-propionyl} pseudo-uracil, 1-[3-(2-{2-[2-(2-Aminoethoxy)-ethoxy]-ethoxy}-ethoxy)-propionyl]-pseudo-uracil, 1-Biotinyl-pseudo-uracil, 1-Biotinyl-PEG2-pseudo-uracil, 5-cyclopropyl-cytosine, 5-methyl-N6-acetyl-1-cytosine, 5-(carboxymethyl)-N6-trifluoroacetyl-cytosine trifluoromethyl ester, N6-propionyl-cytosine, 5-monofluoromethyl-cytosine, 5-trifluoromethoxy-cytosine, N6-(1,1,1-trifluoro-propionyl)-cytosine, 4-acetyl-pseudo-isocytosine, 1-ethyl-pseudo-isocytosine, 1-hydroxy-pseudo-isocytosine, or 1-(2,2,2-trifluoroethyl)-pseudo-uracil or has the structure:

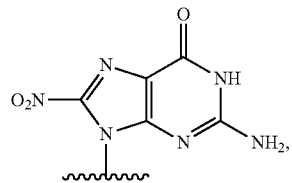

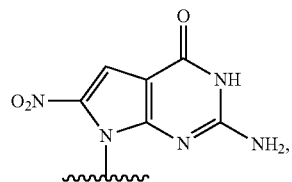

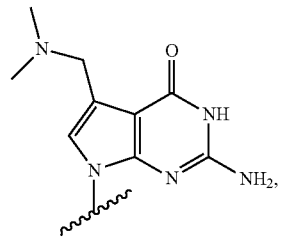

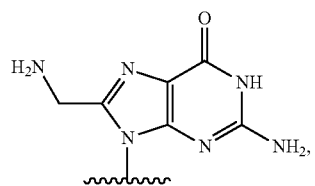

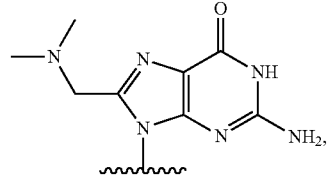

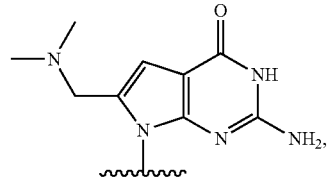

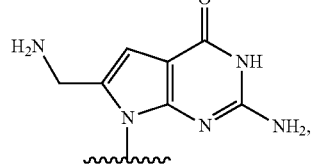

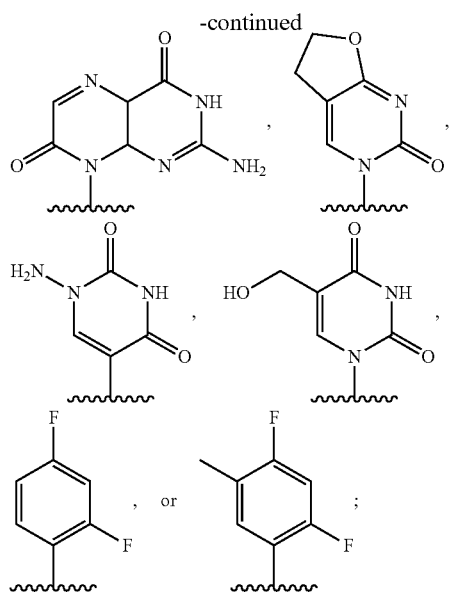

or a salt thereof.

In some embodiments, B is 1,6-Dimethyl-pseudo-uracil, 1-(optionally substituted $C_1$-$C_6$ Alkyl)-6-(1-propynyl)-pseudo-uracil, 1-(optionally substituted $C_1$-$C_6$ Alkyl)-6-(2-propynyl)-pseudo-uracil, 1-(optionally substituted $C_1$-$C_6$ Alkyl)-6-allyl-pseudo-uracil, 1-(optionally substituted $C_1$-$C_6$ Alkyl)-6-ethynyl-pseudo-uracil, 1-(optionally substituted $C_1$-$C_6$ Alkyl)-6-homoallyl-pseudo-uracil, 1-(optionally substituted $C_1$-$C_6$ Alkyl)-6-vinyl-pseudo-uracil, 1-Methyl-6-(2,2,2-Trifluoroethyl)pseudo-uracil, 1-Methyl-6-(4-morpholino)-pseudo-uracil, 1-Methyl-6-(4-thiomorpholino)-pseudo-uracil, 1-Methyl-6-(optionally substituted phenyl)pseudo-uracil, 1-Methyl-6-amino-pseudo-uracil, 1-Methyl-6-azido-pseudo-uracil, 1-Methyl-6-bromo-pseudo-uracil, 1-Methyl-6-butyl-pseudo-uracil, 1-Methyl-6-chloro-pseudo-uracil, 1-Methyl-6-cyano-pseudo-uracil, 1-Methyl-6-dimethylamino-pseudo-uracil, 1-Methyl-6-ethoxy-pseudo-uracil, 1-Methyl-6-ethylcarboxylate-pseudo-uracil, 1-Methyl-6-ethyl-pseudo-uracil, 1-Methyl-6-fluoro-pseudo-uracil, 1-Methyl-6-formyl-pseudo-uracil, 1-Methyl-6-hydroxyamino-pseudo-uracil, 1-Methyl-6-hydroxy-pseudo-uracil, 1-Methyl-6-iodo-pseudo-uracil, 1-Methyl-6-iso-propyl-pseudo-uracil, 1-Methyl-6-methoxy-pseudo-uracil, 1-Methyl-6-methylamino-pseudo-uracil, 1-Methyl-6-phenyl-pseudo-uracil, 1-Methyl-6-propyl-pseudo-uracil, 1-Methyl-6-tert-butyl-pseudo-uracil, 1-Methyl-6-trifluoromethoxy-pseudo-uracil, 1-Methyl-6-trifluoromethyl-pseudo-uracil, 6-(2,2,2-Trifluoroethyl)-pseudo-uracil, 6-(4-Morpholino)-pseudo-uracil, 6-(4-Thiomorpholino)-pseudo-uracil, 6-(Substituted-Phenyl)-pseudo-uracil, 6-Amino-pseudo-uracil, 6-Azido-pseudo-uracil, 6-Bromo-pseudo-uracil, 6-Butyl-pseudo-uracil, 6-Chloro-pseudo-uracil, 6-Cyano-pseudo-uracil, 6-Dimethylamino-pseudo-uracil, 6-Ethoxy-pseudo-uracil, 6-Ethylcarboxylate-pseudo-uracil, 6-Ethyl-pseudo-uracil, 6-Fluoro-pseudo-uracil, 6-Formyl-pseudo-uracil, 6-Hydroxyamino-pseudo-uracil, 6-Hydroxy-pseudo-uracil, 6-Iodo-pseudo-uracil, 6-iso-Propyl-pseudo-uracil, 6-Methoxy-pseudo-uracil, 6-Methylamino-pseudo-uracil, 6-Methyl-pseudo-uracil, 6-Phenyl-pseudo-uracil, 6-Phenyl-pseudo-uracil, 6-Propyl-pseudo-uracil, 6-tert-Butyl-pseudo-uracil, 6-Trifluoromethoxy-pseudo-uracil, 6-Trifluoromethyl-pseudo-uracil, 1-(3-Amino-3-carboxypropyl)pseudo-uracil, 1-(2,2,2-Trifluoroethyl)-pseudo-uracil, 1-(2,4,6-Trimethyl-benzyl)pseudo-uracil, 1-(2,4,6-Trimethyl-phenyl)pseudo-uracil, 1-(2-Amino-2-carboxyethyl)pseudo-uracil, 1-(2-Amino-ethyl)pseudo-uracil, 1-(3-Amino-propyl)pseudo-uracil, 1-(4-Amino-4-carboxybutyl)pseudo-uracil, 1-(4-Amino-benzyl)pseudo-uracil, 1-(4-Amino-butyl)pseudo-uracil, 1-(4-Amino-phenyl)pseudo-uracil, 1-(4-Methoxy-benzyl)pseudo-uracil, 1-(4-Methoxy-phenyl)pseudo-uracil, 1-(4-Methyl-benzyl)pseudo-uracil, 1-(4-Nitro-benzyl)pseudo-uracil, 1 (4-Nitro-phenyl)pseudo-uracil, 1-(5-Amino-pentyl)pseudo-uracil, 1-(6-Amino-hexyl)pseudo-uracil, 1-Aminomethyl-pseudo-uracil, 1-Benzyl-pseudo-uracil, 1-Butyl-pseudo-uracil, 1-Cyclobutylmethyl-pseudo-uracil, 1-Cyclobutyl-pseudo-uracil, 1-Cycloheptylmethyl-pseudo-uracil, 1-Cycloheptyl-pseudo-uracil, 1-Cyclohexylmethyl-pseudo-uracil, 1-Cyclohexyl-pseudo-uracil, 1-Cyclooctylmethyl-pseudo-uracil, 1-Cyclooctyl-pseudo-uracil, 1-Cyclopentylmethyl-pseudo-uracil, 1-Cyclopentyl-pseudo-uracil, 1-Cyclopropylmethyl-pseudo-uracil, 1-Cyclopropyl-pseudo-uracil, 1-Ethyl-pseudo-uracil, 1-Hexyl-pseudo-uracil, 1-iso-Propyl-pseudo-uracil, 1-Pentyl-pseudo-uracil, 1-Phenyl-pseudo-uracil, 1-Propyl-pseudo-uracil, 1-p-tolyl-pseudo-uracil, 1-tert-Butyl-pseudo-uracil, 1-Trifluoromethyl-pseudo-uracil, 3-(optionally substituted $C_1$-$C_6$ Alkyl)-pseudo-uracil, Pseudo-uracil-N1-2-ethanoic acid, Pseudo-uracil-N1-3-propionic acid, Pseudo-uracil-N1-4-butanoic acid, Pseudo-uracil-N1-5-pentanoic acid, Pseudo-uracil-N1-6-hexanoic acid, Pseudo-uracil-N1-7-heptanoic acid, Pseudo-uracil-N1-methyl-p-benzoic acid, 6-phenyl-pseudo-uracil, 6-azido-pseudo-uracil, or Pseudo-uracil-N1-p-benzoic acid.

In other embodiments, B is N3-Methyl-pseudo-uracil, 5-Methyl-amino-methyl-uracil, 5-Carboxy-methyl-amino-methyl-uracil, 5-(carboxyhydroxymethyl)uracil methyl ester or 5-(carboxyhydroxymethyl) uracil.

In certain embodiments, B is 2-anhydro-cytosine hydrochloride or 2-anhydro-uracil.

In some embodiments, B is 5-Methoxycarbonylmethyl-2-thio-uracil, 5-Methylaminomethyl-2-seleno-uracil, 5-(iso-Pentenylaminomethyl)-uracil, 5-(iso-Pentenylaminomethyl)-2-thio-uracil, or 5-(iso-Pentenylaminomethyl)-uracil.

In other embodiments, B is 5-Trideuteromethyl-6-deutero-uracil, 5-(2-Chloro-phenyl)-2-thio-cytosine, 5-(4-Amino-phenyl)-2-thio-cytosine, 5-(2-Furanyl)-uracil, N4-methyl-cytosine, 8-Trifluoromethyl-adenine, 2-Trifluoromethyl-adenine, 3-Deaza-3-fluoro-adenine, 3-Deaza-3-bromo-adenine, or 3-Deaza-3-iodo-adenine.

In certain embodiments, B is 1-Hydroxymethyl-pseudo-uracil, 1-(2-Hydroxyethyl)-pseudo-uracil, 1-Methoxymethyl-pseudo-uracil, 1-(2-Methoxyethyl)-pseudo-uracil, 1-(2,2-Diethoxyethyl)-pseudo-uracil, (±)1-(2-Hydroxypropyl)-pseudo-uracil, (2R)-1-(2-Hydroxypropyl)-pseudo-uracil, (2S)-1-(2-Hydroxypropyl)-pseudo-uracil, 1-Cyanomethyl-pseudo-uracil, 1-Morpholinomethyl-pseudo-uracil, 1-Thiomorpholinomethyl-pseudo-uracil, 1-Benzyloxymethyl-pseudo-uracil, 1-(2,2,3,3,3-Pentafluoropropyl)-pseudo-uracil, 1-Thiomethoxymethyl-pseudo-uracil, 1-Methanesulfonylmethyl-pseudo-uracil, 1-Vinyl-pseudo-uracil, 1-Allyl-pseudo-uracil, 1-Homoallyl-pseudo-uracil, 1-Propargyl-pseudo-uracil, 1-(4-Fluorobenzyl)-pseudo-uracil, 1-(4-Chlorobenzyl)-pseudo-uracil, 1-(4-Bromobenzyl)-pseudo-uracil, 1-(4-Iodobenzyl)-pseudo-uracil, 1-(4-Methylbenzyl)-pseudo-uracil, 1-(4-Trifluoromethylbenzyl)-pseudo-uracil, 1-(4-Methoxybenzyl)-pseudo-uracil, 1-(4-Trifluoromethoxybenzyl)-pseudo-uracil, 1-(4-Thiomethoxybenzyl)-pseudo-uracil, 1-(4-Methanesulfonylbenzyl)-pseudo-uracil, Pseudo-uracil 1-(4-methylbenzoic acid), Pseudo-uracil 1-(4- methylbenzenesulfonic acid), 1-(2,4,6-Trimethylbenzyl)-pseudo-uracil, 1-(4-Nitrobenzyl)-pseudo-uracil, 1-(4-Azidobenzyl)-pseudo-uracil, 1-(3,4-Dimethoxybenzyl)-pseudo-uracil, 1-(3,4-Bis-trifluoromethoxybenzyl)-pseudo-uracil, 1-Acetyl-pseudo-uracil, 1-Trifluoroacetyl-pseudo-uracil, 1-Benzoyl-pseudo-uracil, 1-Pivaloyl-pseudo-uracil, 1-(3-Cyclopropyl-prop-2-ynyl)-pseudo-uracil, Pseudo-uracil 1-methylphosphonic acid diethyl ester, Pseudo-uracil 1-methylphosphonic acid, Pseudo-uracil 1-[3-(2-ethoxy)] propionic acid, Pseudo-uracil 1-[3-{2-(2-ethoxy)-ethoxy}] propionic acid, Pseudo-uracil 1-[3-{2-(2-[2-ethoxy]-ethoxy)-ethoxy}]propionic acid, Pseudo-uracil 1-[3-{2-(2-[2-(2-ethoxy)-ethoxy]-ethoxy)-ethoxy}]propionic acid, Pseudo-uracil 1-[3-{2-(2-[2-{2(2-ethoxy)-ethoxy}-ethoxy]-ethoxy)-ethoxy}]propionic acid, 1-{3-[2-(2-Aminoethoxy)-ethoxy]-propionyl} pseudo-uracil, 1-[3-(2-{2-[2-(2-Aminoethoxy)-ethoxy]-ethoxy}-ethoxy)-propionyl]-pseudo-uracil, 1-Biotinyl-pseudo-uracil, or 1-Biotinyl-PEG2-pseudo-uracil.

In some embodiments, B is 5-cyclopropyl-cytosine, 5-methyl-N6-acetyl-1-cytosine, 5-(carboxymethyl)-N6-trifluoroacetyl-cytosine trifluoromethyl ester, N6-propionyl-cytosine, 5-monofluoromethyl-cytosine, 5-trifluoromethoxy-cytosine, N6-(1,1,1-trifluoro-propionyl)-cytosine, 4-acetyl-pseudo-isocytosine, 1-ethyl-pseudo-isocytosine, or 1-hydroxy-pseudo-isocytosine.

In some embodiments, B has the structure:

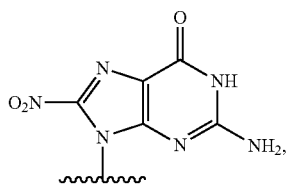

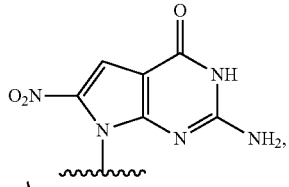

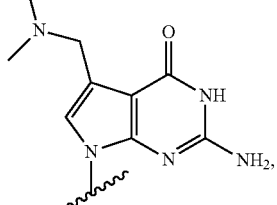

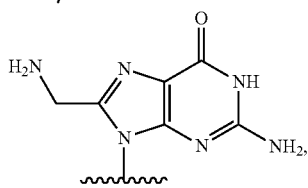

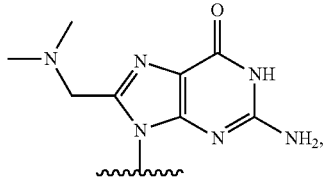

In other embodiments, B is 1-(2,2,2-trifluoroethyl)-pseudo-uracil.

In certain embodiments, A has the structure of Formula II.
In some embodiments, m' is 0.
In other embodiments, m" is 1.
In certain embodiments, $R^4$ is hydrogen.
In some embodiments, A is:

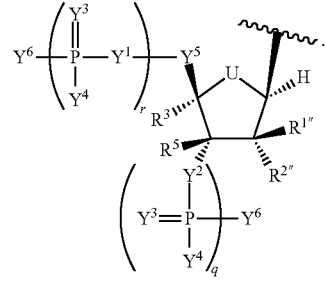

Formula VII wherein U is O, S, $N(R^U)_{nu}$, or $C(R^U)_{nu}$, wherein nu is an integer from 0 to 2 (e.g., 0 or 1 for $N(R^U)_{nu}$ and 1 or 2 for $C(R^U)_{nu}$) and each $R^U$ is, independently, H, halo, or optionally substituted $C_1$-$C_6$ alkyl;

each of $R^{1'}$, $R^{2''}$, and $R^5$ is, independently, H, halo, hydroxy, thiol, optionally substituted $C_1$-$C_6$ alkyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, optionally substituted $C_6$-$C_{10}$ aryl; or $R^5$ can join together with one or more of $R^{1''}$ or $R^{2''}$ to form together with the carbons to which they are attached, an optionally substituted $C_3$-$C_9$ heterocyclyl or an optionally substituted $C_3$-$C_9$ cycloalkyl; or;

$R^3$ is H, halo, hydroxy, thiol, optionally substituted $C_1$-$C_6$ alkyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, optionally substituted $C_6$-$C_{10}$ aryl; or $R^3$ can join together with one or more of $R^{1''}$ or $R^{2''}$, and, taken together with the carbons to which they are attached, provide an optionally substituted $C_3$-$C_9$ heterocyclyl or an optionally substituted $C_3$-$C_9$ cycloalkyl;

each of q and r is independently, an integer from 0 to 5;

each of $Y^1$, $Y^2$, and $Y^3$, is, independently, hydrogen, O, S, Se, $-NR^{N1}-$, optionally substituted $C_1$-$C_6$ alkylene, or optionally substituted $C_1$-$C_6$ heteroalkylene, wherein $R^{N1}$ is H, optionally substituted $C_1$-$C_6$ alkyl, optionally substituted $C_2$-$C_6$ alkenyl, optionally substituted $C_2$-$C_6$ alkynyl, or optionally substituted $C_6$-$C_{10}$ aryl; and each of $Y^4$ and $Y^6$ is, independently, H, hydroxyl, protected hydroxyl, halo, thiol, boranyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, or optionally substituted amino, or $Y^4$ is absent; and $Y^5$ is O, S, Se, optionally substituted $C_1$-$C_6$ alkylene, or optionally substituted $C_1$-$C_6$ heteroalkylene.

In some embodiments, $R^{2''}$ is hydroxyl.

In other embodiments, $R^{1''}$ is hydrogen.

In certain embodiments, $R^3$ is hydrogen and $R^5$ is hydrogen.

In some embodiments, $R^3$ is hydrogen and $R^5$ is optionally substituted $C_2$-$C_6$ alkynyl.

In other embodiments, the optionally substituted $C_2$-$C_6$ alkynyl is ethynyl.

In certain embodiments, $R^5$ is hydrogen.

In some embodiments, $R^3$ is azido or optionally substituted $C_2$-$C_6$ alkynyl.

In other embodiments, $R^3$ is azido.

In certain embodiments, $R^3$ is optionally substituted $C_2$-$C_6$ alkynyl, wherein said optionally substituted $C_2$-$C_6$ alkynyl is ethynyl.

In some embodiments, $R^3$ is hydrogen and $R^5$ is hydrogen.

In other embodiments, $R^{1''}$ is optionally substituted $C_1$-$C_6$ alkyl or optionally substituted $C_2$-$C_6$ alkynyl.

In certain embodiments, $R^{1''}$ is optionally substituted $C_1$-$C_6$ alkyl, wherein said optionally substituted $C_1$-$C_6$ alkyl is trifluoromethyl.

In some embodiments, $R^{1''}$ is optionally substituted $C_2$-$C_6$ alkynyl, wherein said optionally substituted $C_2$-$C_6$ alkynyl is ethynyl.

In other embodiments, $R^{2''}$ is hydrogen.

In certain embodiments, $R^3$ is hydrogen.

In some embodiments, $R^5$ is hydrogen.

In other embodiments, $R^{1''}$ is halo, thiol, optionally substituted $C_1$-$C_6$ heteroalkyl, azido, or amino.

In certain embodiments, halo is fluoro, chloro, bromo, or iodo.

In some embodiments, optionally substituted $C_1$-$C_6$ heteroalkyl is thiomethoxy.

In other embodiments, $R^3$ is hydrogen.

In certain embodiments, $R^5$ is hydrogen.

In some embodiments, $R^{1''}$ is hydroxy.

In other embodiments, $R^{2''}$ is hydrogen, optionally substituted $C_1$-$C_6$ alkyl, or optionally substituted $C_2$-$C_6$ alkynyl.

In certain embodiments, optionally substituted $C_1$-$C_6$ alkyl is trifluoromethyl.

In some embodiments, optionally substituted $C_2$-$C_6$ alkynyl is ethynyl.

In other embodiments, $R^{1''}$ is hydrogen.

In certain embodiments, $R^{2''}$ is thiol, optionally substituted $C_1$-$C_6$ heteroalkyl, azido, or amino.

In some embodiments, optionally substituted $C_1$-$C_6$ heteroalkyl is thiomethoxy.

In other embodiments, $R^{1''}$ is halo.

In certain embodiments, halo is fluoro.

In some embodiments, $R^{2''}$ is halo.

In other embodiments, halo is fluoro.

In certain embodiments, U is $C(R^U)_{nu}$.

In some embodiments, nu is 2.

In other embodiments, each $R^U$ is hydrogen.

In certain embodiments, q is 0 and $Y^6$ is hydroxyl.

In some embodiments, $R^5$ is hydroxyl.

In other embodiments, $Y^5$ is optionally substituted $C_1$-$C_6$ alkylene.

In certain embodiments, optionally substituted $C_1$-$C_6$ alkylene is methylene.

In some embodiments, r is 0 and $Y^6$ is hydroxyl.

In other embodiments, r is 3; each $Y^1$, $Y^3$, and $Y^4$ is O; and $Y^6$ is hydroxyl.

In certain embodiments, r is 3, each $Y^1$ and $Y^4$ is O; and $Y^6$ is hydroxyl.

In some embodiments, at least one $Y^3$ is S.

In some embodiments, the nucleobase is selected from a naturally occurring nucleobase or a non-naturally occurring nucleobase.

In some embodiments, the naturally occurring nucleobase is selected from the group consisting of pseudouracil or N1-methylpseudouracil.

In some embodiments, the nucleoside is not pseudouridine (ψ) or 5-methyl-cytidine ($m^5C$).

The present invention provides polynucleotides (e.g., mRNAs) which may be isolated and/or purified. These polynucleotides may encode one or more polypeptides of interest and comprise a sequence of n number of linked nucleosides or nucleotides including at least one alternative nucleoside or nucleotide as compared to the chemical structure of an A, G, U or C nucleoside or nucleotide. The polynucleotides may also contain a 5' UTR optionally including at least one Kozak sequence, a 3' UTR, and at least one 5' cap structure. The isolated polynucleotides may further contain a poly-A tail and may be purified.

In some embodiments, multiple alterations are included in the alternative nucleic acid or in one or more individual nucleoside or nucleotide. For example, alterations to a nucleoside may include one or more alterations to the nucleobase, the sugar, and/or the internucleoside linkage.

In some embodiments having at least one alteration, the polynucleotide includes a backbone moiety containing the nucleobase, sugar, and internucleoside linkage of: 5-methoxy-uridine-alpha-thio-TP, 5-methyl-cytidine-alpha-thio-TP, pseudouridine-alpha-thio-TP, 1-methyl-pseudouridine-alpha-thio-TP, 1-ethyl-pseudouridine-TP, 1-propyl-pseudouridine-TP, 1-(2,2,2-trifluoroethyl)-pseudouridine-TP, 2-amino-adenosine-TP, xanthosine, 5-bromo-cytidine, 5-aminoallyl-cytidine-TP, or 2-aminopurine-riboside-TP. It will be understood that after incorporation of the triphosphate, the internucleoside linkage will be a monophosphate.

In certain embodiments having at least one alteration, the polynucleotide includes a backbone moiety containing the nucleobase, sugar, and internucleoside linkage of: pseudouridine-alpha-thio-TP, 1-methyl-pseudouridine-alpha-thio-TP, 1-ethyl-pseudouridine-TP, 1-propyl-pseudouridine-TP, 5-bromo-cytidine, 5-aminoallyl-cytidine-TP, or 2-aminopurine-riboside-TP.

In other embodiments having at least one alteration, the polynucleotide includes a backbone moiety containing the nucleobase, sugar, and internucleoside linkage of: pseudouridine-alpha-thio-TP, 1-methyl-pseudouridine-alpha-thio-TP, or 5-bromo-cytidine-TP.

In other embodiments, the isolated polynucleotide includes at least two alternative nucleosides or nucleotides.

In certain embodiments having at least two alterations, the polynucleotide includes a backbone moiety containing the nucleobase, sugar, and internucleoside linkage of at least one of each of 5-bromo-cytidine-TP and 1-methyl-pseudouridine-TP or 5-methoxy-uridine-alpha-thio-TP and 5-methyl-cytidine-alpha-thio-TP.

In other embodiments having at least two alterations, the polynucleotide includes a backbone moiety containing the nucleobase, sugar, and internucleoside linkage of at least one of each of 5-bromo-cytidine-TP and pseudouridine-TP.

In some embodiments having at least one alteration, the polynucleotide includes a backbone moiety containing the nucleobase, sugar, and internucleoside linkage of: 2-thio-pseudouridine-TP, 5-trifluoromethyl-uridine-TP, 5-trifluoromethyl-cytidine-TP, 3-methyl-pseudouridine, 5-methyl-2-thio-uridine-TP, N4-methyl-cytidine-TP, 5-hydroxymethyl-cytidine-TP, 3-methyl-cytidine-TP, 5-oxyacetic acid methyl ester-uridine-TP, 5-methoxycarbonylmethyl-uridine-TP, 5-methylaminomethyl-uridine-TP, 5-methoxy-uridine-TP, N1-methyl-guanosine-TP, 8-aza-adenosine-TP, 2-thio-uridine-TP, 5-bromo-uridine-TP, 2-thio-cytidine-TP, alpha-thio-cytidine-TP, 5-aminoallyl-uridine-TP, alpha-thio-uridine-TP, or 4-thio-uridine-TP.

In other embodiments having at least two alterations, the polynucleotide includes a backbone moiety containing the nucleobase, sugar, and internucleoside linkage of at least one of each of 5-trifluoromethyl-cytidine-TP and 1-methyl-pseudouridine-TP; 5-hydroxymethyl-cytidine-TP and 1-methyl-pseudouridine-TP; 5-trifluoromethyl-cytidine-TP and pseudouridine-TP; or N4-acetyl-cytidine-TP and 5-methoxy-uridine-TP.

In some embodiments having at least one alteration, the polynucleotide includes a backbone moiety containing the nucleobase, sugar, and internucleoside linkage of: 2-thio-pseudouridine-TP, 5-trifluoromethyl-cytidine-TP, 5-methyl-2-thio-uridine-TP, 5-hydroxymethyl-cytidine-TP, 5-oxyacetic acid methyl ester-uridine-TP, 5-methoxy-uridine-TP, N4-acetyl-cytidine-TP, 2-thio-uridine-TP, 5-bromo-uridine-TP, alpha-thio-cytidine-TP, 5-aminoallyl-uridine-TP, or alpha-thio-uridine-TP.

In other embodiments having at least two alterations, the polynucleotide includes a backbone moiety containing the nucleobase, sugar, and internucleoside linkage of at least one of each of 5-trifluoromethyl-cytidine-TP and 1-methyl-pseudouridine-TP or 5-hydroxymethyl-cytidine-TP and 1-methyl-pseudouridine-TP.

In some embodiments having at least one alteration, the polynucleotide includes a backbone moiety containing the nucleobase, sugar, and internucleoside linkage of: 2-thio-pseudouridine-TP, 5-trifluoromethyl-cytidine-TP, 5-methyl-2-thio-uridine-TP, N4-methyl-cytidine-TP, 5-hydroxymethyl-cytidine-TP, 5-oxyacetic acid methyl ester-uridine-TP, 5-methoxycarbonylmethyl-uridine-TP, 5-methoxy-uridine-TP, 2-thio-uridine-TP, 5-bromo-uridine-TP, alpha-thio-cytidine-TP, 5-aminoallyl-uridine-TP, or alpha-thio-uridine-TP.

In some embodiments having at least one alteration, the polynucleotide includes a backbone moiety containing the nucleobase, sugar, and internucleoside linkage of: 2-thio-pseudouridine-TP, 5-trifluoromethyl-cytidine-TP, 5-hydroxymethyl-cytidine-TP, or 5-methoxy-uridine-TP.

In other embodiments having at least two alterations, the polynucleotide includes a backbone moiety containing the nucleobase, sugar, and internucleoside linkage of at least one of each of N4-acetyl-cytidine-TP and 5-methoxy-uridine-TP.

The present invention also provides for pharmaceutical compositions including the alternative polynucleotides described herein. These may also further include one or more pharmaceutically acceptable excipients selected from a solvent, aqueous solvent, non-aqueous solvent, dispersion media, diluent, dispersion, suspension aid, surface active agent, isotonic agent, thickening or emulsifying agent, preservative, lipid, lipidoids liposome, lipid nanoparticle, core-shell nanoparticles, polymer, lipoplexed peptide, protein, cell, hyaluronidase, and mixtures thereof. In certain embodiments, the mRNA is formulated in lipid nanoparticles.

Methods of using the polynucleotides and alternative nucleic acids of the invention are also provided. In this instance, the polynucleotides may be formulated by any means known in the art or administered via any of several routes including injection by intradermal, subcutaneous or intramuscular means.

Administration of the alternative nucleic acids of the invention may be via two or more equal or unequal split doses. In some embodiments, the level of the polypeptide produced by the subject by administering split doses of the polynucleotide is greater than the levels produced by administering the same total daily dose of polynucleotide as a single administration.

Detection of the alternative nucleic acids or the encoded polypeptides may be performed in the hair or bodily fluid of the subject or patient where the bodily fluid is selected from the group consisting of peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood.

In some embodiments, administration is according to a dosing regimen which occurs over the course of hours, days, weeks, months, or years and may be achieved by using one or more devices selected from multi-needle injection systems, catheter or lumen systems, and ultrasound, electrical or radiation based systems.

The names of nucleobases correspond to the name given to the base when part of a nucleoside or nucleotide. For example, "pseudo-uracil" refers to the nucleobase of pseudouridine and "pseudo-isocytosine" refers to the nucleobase of pseudoisocytidine.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present disclosure will be apparent from the following detailed description and figures, and from the claims.

DETAILED DESCRIPTION

The present disclosure provides, inter alia, alternative nucleosides, alternative nucleotides, and alternative nucleic acids that exhibit improved therapeutic properties including, but not limited to, a reduced innate immune response when introduced into a population of cells.

As there remains a need in the art for therapeutic modalities to address the myriad of barriers surrounding the efficacious modulation of intracellular translation and processing of nucleic acids encoding polypeptides or fragments thereof, the inventors have shown that certain alternative mRNA sequences have the potential as therapeutics with benefits beyond just evading, avoiding or diminishing the immune response.

The present invention addresses this need by providing nucleic acid based compounds or polynucleotides (e.g., alternative mRNAs) which encode a polypeptide of interest (e.g., alternative mRNA) and which have structural and/or chemical features that avoid one or more of the problems in the art, for example, features which are useful for optimizing nucleic acid-based therapeutics while retaining structural and functional integrity, overcoming the threshold of expression, improving expression rates, half life and/or protein concentrations, optimizing protein localization, and avoiding deleterious bio-responses such as the immune response and/or degradation pathways.

In particular, the inventors have identified that mRNA wherein a relatively low proportion of the uracils (such as from 10% to 50%, 15% to 35% or about 25%) are 5-methoxy-uracil and a relatively high proportion of the cytosines are 5-methyl-cytosine (such as from 50% to 100%, 75% to 100% or about 100%) may be particularly effective for use in therapeutic compositions, because they may benefit from both high expression levels and limited induction of the innate immune response, as shown in the Examples (in particular, high performance may be observed across the assays in Examples 83-87).

Polypeptides of interest, according to the present invention, may be selected from any of those disclosed in US 2013/0259924, US 2013/0259923, WO 2013/151663, WO 2013/151669, WO 2013/151670, WO 2013/151664, WO 2013/151665, WO 2013/151736, U.S. Provisional Patent Application No. 61/618,862, U.S. Provisional Patent Application No. 61/681,645, U.S. Provisional Patent Application No. 61/618,873, U.S. Provisional Patent Application No. 61/681,650, U.S. Provisional Patent Application No. 61/618,878, U.S. Provisional Patent Application No. 61/681,654, U.S. Provisional Patent Application No. 61/618,885, U.S. Provisional Patent Application No. 61/681,658, U.S. Provisional Patent Application No. 61/618,911, U.S. Provisional Patent Application No. 61/681,667, U.S. Provisional Patent Application No. 61/618,922, U.S. Provisional Patent Application No. 61/681,675, U.S. Provisional Patent Application No. 61/618,935, U.S. Provisional Patent Application No. 61/681,687, U.S. Provisional Patent Application No. 61/618,945, U.S. Provisional Patent Application No. 61/681,696, U.S. Provisional Patent Application No. 61/618,953, and U.S. Provisional Patent Application No. 61/681,704, the polypeptides of each of which are incorporated herein by reference in their entirety.

Provided herein, in part, are polynucleotides encoding polypeptides of interest which have been chemically modified to improve one or more of the stability and/or clearance in tissues, receptor uptake and/or kinetics, cellular access by the compositions, engagement with translational machinery, mRNA half-life, translation efficiency, immune evasion, protein production capacity, secretion efficiency (when applicable), accessibility to circulation, protein half-life and/or modulation of a cell's status, function and/or activity.

The alternative nucleosides, nucleotides, and nucleic acids of the invention, including the combination of alterations taught herein have superior properties making them more suitable as therapeutic modalities.

It has been determined that the "all or none" model in the art is sorely insufficient to describe the biological phenomena associated with the therapeutic utility of alternative mRNA. The present inventors have determined that to improve protein production, one may consider the nature of the alteration, or combination of alterations, the percent alteration and survey more than one cytokine or metric to determine the efficacy and risk profile of a particular alternative mRNA.

In one aspect of the invention, methods of determining the effectiveness of an alternative mRNA as compared to unaltered involves the measure and analysis of one or more cytokines whose expression is triggered by the administration of the exogenous nucleic acid of the invention. These values are compared to administration of an unaltered nucleic acid or to a standard metric such as cytokine response, PolyIC, R-848 or other standard known in the art.

One example of a standard metric developed herein is the measure of the ratio of the level or amount of encoded polypeptide (protein) produced in the cell, tissue or organism to the level or amount of one or more (or a panel) of cytokines whose expression is triggered in the cell, tissue or organism as a result of administration or contact with the alternative nucleic acid. Such ratios are referred to herein as the Protein:Cytokine Ratio or "PC" Ratio. The higher the PC ratio, the more efficacious the alternative nucleic acid (polynucleotide encoding the protein measured). Preferred PC Ratios, by cytokine, of the present invention may be greater than 1, greater than 10, greater than 100, greater than 1000, greater than 10,000 or more. Alternative nucleic acids having higher PC Ratios than an alternative nucleic acid of a different or unaltered construct are preferred.

The PC ratio may be further qualified by the percent alteration present in the polynucleotide. For example, normalized to a 100% alternative nucleic acid, the protein production as a function of cytokine (or risk) or cytokine profile can be determined.

In one embodiment, the present invention provides a method for determining, across chemistries, cytokines or percent alteration, the relative efficacy of any particular alternative polynucleotide by comparing the PC Ratio of the alternative nucleic acid (polynucleotide).

In another embodiment, the alternative mRNA are substantially non toxic and non mutagenic.

In one embodiment, the alternative nucleosides, alternative nucleotides, and alternative nucleic acids can be chemically modified, thereby disrupting interactions, which may cause innate immune responses. Further, these alternative nucleosides, alternative nucleotides, and alternative nucleic acids can be used to deliver a payload, e.g., detectable or therapeutic agent, to a biological target. For example, the nucleic acids can be covalently linked to a payload, e.g. a detectable or therapeutic agent, through a linker attached to the nucleobase or the sugar moiety. The compositions and methods described herein can be used, in vivo and in vitro, both extracellularly and intracellularly, as well as in assays such as cell free assays.

In another aspect, the present disclosure provides chemical alterations located on the sugar moiety of the nucleotide.

In another aspect, the present disclosure provides chemical alterations located on the phosphate backbone of the nucleic acid.

In another aspect, the present disclosure provides nucleotides that contain chemical alterations, wherein the nucleotide reduces the cellular innate immune response, as compared to the cellular innate immune induced by a corresponding unaltered nucleic acid.

In another aspect, the present disclosure provides compositions comprising a compound as described herein. In some embodiments, the composition is a reaction mixture. In some embodiments, the composition is a pharmaceutical composition. In some embodiments, the composition is a cell culture. In some embodiments, the composition further comprises an RNA polymerase and a cDNA template. In some embodiments, the composition further comprises a nucleotide selected from the group consisting of adenosine, cytidine, guanosine, and uridine.

In a further aspect, the present disclosure provides methods of making a pharmaceutical formulation comprising a physiologically active secreted protein, comprising transfecting a first population of human cells with the pharmaceutical nucleic acid made by the methods described herein, wherein the secreted protein is active upon a second population of human cells.

In some embodiments, the secreted protein is capable of interacting with a receptor on the surface of at least one cell present in the second population.

In certain embodiments, provided herein are combination therapeutics containing one or more alternative nucleic acids containing translatable regions that encode for a protein or proteins that boost a mammalian subject's immunity along with a protein that induces antibody-dependent cellular toxicity.

In one embodiment, it is intended that the compounds of the present disclosure are stable. It is further appreciated that certain features of the present disclosure, which are, for clarity, described in the context of separate embodiments, can also be provided in combination in a single embodiment. Conversely, various features of the present disclosure which are, for brevity, described in the context of a single embodiment, can also be provided separately or in any suitable subcombination.

Alternative Nucleotides, Nucleosides and Polynucleotides of the Invention

Herein, in a nucleotide, nucleoside or polynucleotide (such as the nucleic acids of the invention, e.g., mRNA molecule), the terms "alteration" or, as appropriate, "alternative" refer to alteration with respect to A, G, U or C ribonucleotides. Generally, herein, these terms are not intended to refer to the ribonucleotide alterations in naturally occurring 5'-terminal mRNA cap moieties. In a polypeptide, the term "alteration" refers to a alteration as compared to the canonical set of 20 amino acids, moiety)

The alterations may be various distinct alterations. In some embodiments, where the nucleic acid is an mRNA, the coding region, the flanking regions and/or the terminal regions may contain one, two, or more (optionally different) nucleoside or nucleotide alterations. In some embodiments, an alternative polynucleotide introduced to a cell may exhibit reduced degradation in the cell, as compared to an unaltered polynucleotide.

The polynucleotides can include any useful alteration, such as to the sugar, the nucleobase, or the internucleoside linkage (e.g. to a linking phosphate/to a phosphodiester linkage/to the phosphodiester backbone). In certain embodiments, alterations (e.g., one or more alterations) are present in each of the sugar and the internucleoside linkage. Alterations according to the present invention may be alterations of ribonucleic acids (RNAs) to deoxyribonucleic acids (DNAs), e.g., the substitution of the 2'OH of the ribofuranosyl ring to 2'H, threose nucleic acids (TNAs), glycol nucleic acids (GNAs), peptide nucleic acids (PNAs), locked nucleic acids (LNAs) or hybrids thereof). Additional alterations are described herein.

As described herein, the polynucleotides of the invention do not substantially induce an innate immune response of a cell into which the polynucleotide (e.g., mRNA) is introduced. Features of an induced innate immune response include 1) increased expression of pro-inflammatory cytokines, 2) activation of intracellular PRRs (e.g., RIG-I, MDA5) and/or 3) termination or reduction in protein translation.

In certain embodiments, it may desirable for an alternative nucleic acid molecule introduced into the cell to be degraded intracellularly. For example, degradation of an alternative nucleic acid molecule may be preferable if precise timing of protein production is desired. Thus, in some embodiments, the invention provides an alternative nucleic acid molecule containing a degradation domain, which is capable of being acted on in a directed manner within a cell.

The polynucleotides can optionally include other agents (e.g., RNAi-inducing agents, RNAi agents, siRNAs, shRNAs, miRNAs, antisense RNAs, ribozymes, catalytic DNA, tRNA, RNAs that induce triple helix formation, aptamers, and vectors). In some embodiments, the polynucleotides may include one or more messenger RNAs (mRNAs) having one or more alternative nucleoside or nucleotides (i.e., alternative mRNA molecules). Details for these polynucleotides follow.

Polynucleotides

According to Aduri et al (Journal of Chemical Theory and Computation. 2006. 3(4):1464-75) there are 107 naturally occurring nucleosides, including 1-methyladenosine, 2-methylthio-N6-hydroxynorvalyl carbamoyladenosine, 2-methyladenosine, 2-O-ribosylphosphate adenosine, N6-methyl-N6-threonylcarbamoyladenosine, N6-acetyladenosine, N6-glycinylcarbamoyladenosine, N6-isopentenyladenosine, N6-methyladenosine, N6-threonylcarbamoyladenosine, N6,N6-dimethyladenosine, N6-(cis-hydroxyisopentenyl)adenosine, N6-hydroxynorvalylcarbamoyladenosine, 1,2-O-dimethyladenosine, N6,2-O-dimethyladenosine, 2-O-methyladenosine, N6,N6,O-2-trimethyladenosine, 2-methylthio-N6-(cis-hydroxyisopentenyl) adenosine, 2-methylthio-N6-methyladenosine, 2-methylthio-N6-isopentenyladenosine, 2-methylthio-N6-threonyl carbamoyladenosine, 2-thiocytidine, 3-methylcytidine, N4-acetylcytidine, 5-formylcytidine, N4-methylcytidine, 5-methylcytidine, 5-hydroxymethylcytidine, lysidine, N4-acetyl-2-O-methylcytidine, 5-formyl-2-O-methylcytidine, 5,2-O-dimethylcytidine, 2-O-methylcytidine, N4,2-O-dimethylcytidine, N4,N4,2-O-trimethylcytidine, 1-methylguanosine, N2,7-dimethylguanosine, N2-methylguanosine, 2-O-ribosylphosphate guanosine, 7-methylguanosine, under modified hydroxywybutosine, 7-aminomethyl-7-deazaguanosine, 7-cyano-7-deazaguanosine, N2,N2-dimethylguanosine, 4-demethylwyosine, epoxyqueuosine, hydroxywybutosine, isowyosine, N2,7,2-O-trimethylguanosine, N2,2-O-dimethylguanosine, 1,2-O-dimethylguanosine, 2-O-methylguanosine, N2,N2,2-O-trimethylguanosine, N2,N2,7-trimethylguanosine, peroxywybutosine, galactosyl-queuosine, mannosyl-queuosine, queuosine, archaeosine, wybutosine, methylwyosine, wyosine, 2-thiouridine, 3-(3-amino-3-carboxypropyl)uridine, 3-methyluridine, 4-thiouridine, 5-methyl-2-thiouridine, 5-methylaminomethyluridine, 5-carboxymethyluridine, 5-carboxymethylaminomethyluridine, 5-hydroxyuridine, 5-methyluridine, 5-taurinomethyluridine, 5-carbamoylmethyluridine, 5-(carboxyhydroxymethyl)uridine methyl ester, dihydrouridine, 5-methyldihydrouridine, 5-methylaminomethyl-2-thiouridine, 5-(carboxyhydroxymethyl)uridine, 5-(isopentenylaminomethyl)uridine, 5-(isopentenylaminomethyl)-2-thiouridine, 3,2-O-dimethyluridine, 5-carboxymethylaminomethyl-2-O-methyluridine, 5-carbamoylmethyl-2-O-methyluridine, 5-methoxycarbonylmethyl-2-O-methyluridine, 5-(isopentenylaminomethyl)-2-O-methyluridine, 5,2-O-dimethyluridine, 2-O-methyluridine, 2-thio-2-O-methyluridine, uridine 5-oxyacetic acid, 5-methoxycarbonylmethyluridine, uridine 5-oxyacetic acid methyl ester, 5-methoxyuridine, 5-aminomethyl-2-thiouridine, 5-carboxymethylaminomethyl-2-thiouridine, 5-methylaminomethyl-2-selenouridine, 5-methoxycarbonylmethyl-2-thiouridine, 5-taurinomethyl-2-thiouridine, pseudouridine, 1-methyl-3-(3-amino-3-carboxypropyl)pseudouridine, 1-methylpseudouridine, 3-methylpseudouridine, 2-O-methylpseudouridine, inosine, 1-methylinosine, 1,2-O-dimethylinosine and 2-O-methylinosine. Each of these may be components of nucleic acids of the present invention.

The polynucleotides of the invention includes a first region of linked nucleosides encoding a polypeptide of interest, a first flanking region located at the 5' terminus of the first region, and a second flanking region located at the 3' terminus of the first region.

In some embodiments, the polynucleotide (e.g., the first region, first flanking region, or second flanking region) includes n number of linked nucleosides having Formula (Ia) or Formula (Ia-1)

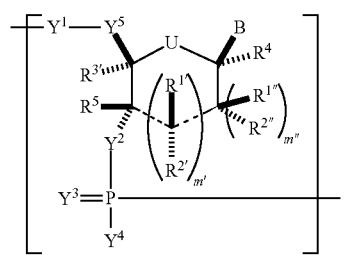

(Ia)

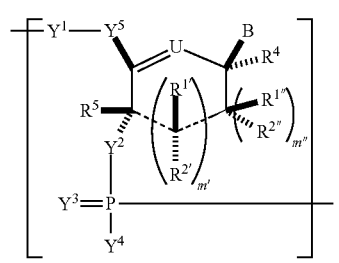

(Ia-1)

or a pharmaceutically acceptable salt or stereoisomer thereof, wherein U is O, S, $N(R^U)_{nu}$, or $C(R^U)_{nu}$, wherein nu is an integer from 0 to 2 and each $R^U$ is, independently, H, halo, or optionally substituted alkyl;

--- is a single bond or absent;

each of $R^{1'}$, $R^{2'}$, $R^{1''}$, $R^{2''}$, $R^3$, $R^4$, and $R^5$, if present, is, independently, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, optionally substituted aminoalkynyl, or absent; wherein the combination of $R^3$ with one or more of $R^{1'}$, $R^{1''}$, $R^{2'}$, $R^{2''}$, or $R^5$ (e.g., the combination of $R^{1'}$ and $R^3$, the combination of $R^{1''}$ and $R^3$, the combination of $R^{2'}$ and $R^3$, the combination of $R^{2''}$ and $R^3$, or the combination of $R^5$ and $R^3$) can join together to form, together with the carbons to which they are attached, an optionally substituted heterocyclyl (e.g., a bicyclic, tricyclic, or tetracyclic heterocyclyl) or cycloalkyl; wherein the combination of $R^5$ with one or more of $R^{1'}$, $R^{1''}$, $R^{2'}$, or $R^{2''}$ (e.g., the combination of $R^{1'}$ and $R^5$, the combination of $R^{1''}$ and $R^5$, the combination of $R^{2'}$ and $R^5$, or the combination of $R^{2''}$ and $R^5$) can join together to form, together with the carbons to which they are attached, an optionally substituted heterocyclyl (e.g., a bicyclic, tricyclic, or tetracyclic heterocyclyl) or cycloalkyl; and wherein the combination of $R^4$ and one or more of $R^{1'}$, $R^{1''}$, $R^{2'}$, $R^{2''}$, $R^3$ or $R^5$ can join together to form, together with the carbons to which they are attached, an optionally substituted heterocyclyl (e.g., a bicyclic, tricyclic, or tetracyclic heterocyclyl) or cycloalkyl;

each of m' and m" is, independently, an integer from 0 to 3 (e.g., from 0 to 2, from 0 to 1, from 1 to 3, or from 1 to 2);

each of $Y^1$, $Y^2$, and $Y^3$, is, independently, O, S, Se, $-NR^{N1}-$, optionally substituted alkylene, or optionally substituted heteroalkylene, wherein $R^{N1}$ is H, optionally substituted alkyl, optionally substituted alkenyl, optionally substituted alkynyl, or optionally substituted aryl;

each $Y^4$ is, independently, H, hydroxy, thiol, boranyl, optionally substituted alkyl, optionally substituted alkenyl, optionally substituted alkynyl, optionally substituted alkoxy, optionally substituted alkenyloxy, optionally substituted alkynyloxy, optionally substituted thioalkoxy, optionally substituted alkoxyalkoxy, or optionally substituted amino;

each $Y^5$ is O, S, Se, optionally substituted alkylene (e.g., methylene), or optionally substituted heteroalkylene;

n is an integer from 1 to 100,000; and

B is a nucleobase (e.g., a purine, a pyrimidine, or derivatives thereof), wherein the combination of B and $R^{1'}$, the combination of B and $R^{2'}$, the combination of B and $R^{1''}$, or the combination of B and $R^{2''}$ can, taken together with the carbons to which they are attached, optionally form a bicyclic group (e.g., a bicyclic heterocyclyl) or wherein the combination of B, $R^{1'}$, and $R^3$ or the combination of B, $R^{2''}$, and $R^3$ can optionally form a tricyclic or tetracyclic group (e.g., a tricyclic or tetracyclic heterocyclyl, such as in Formula (IIo)-(IIp) herein).

In some embodiments, the polynucleotide includes an alternative ribose. In some embodiments, the polynucleotide (e.g., the first region, the first flanking region, or the second flanking region) includes n number of linked nucleosides having Formula (Ia-2)-(Ia-5) or a pharmaceutically acceptable salt or stereoisomer thereof.

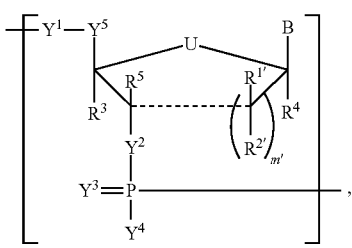
(Ia-2)

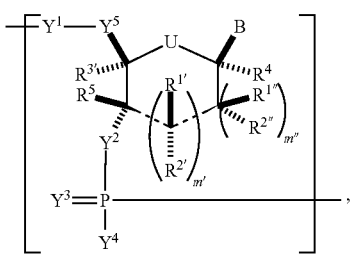
(Ia-3)

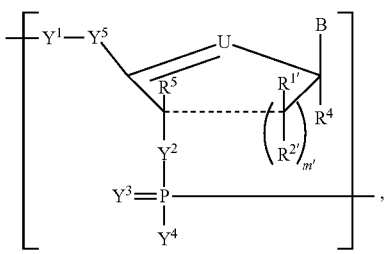
(Ia-4)

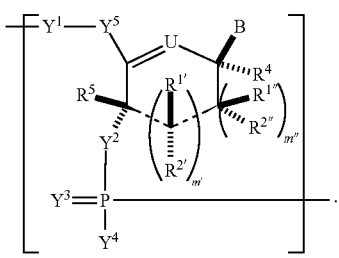
(Ia-5)

In some embodiments, the polynucleotide (e.g., the first region, the first flanking region, or the second flanking region) includes n number of linked nucleosides having Formula (Ib) or Formula (Ib-1):

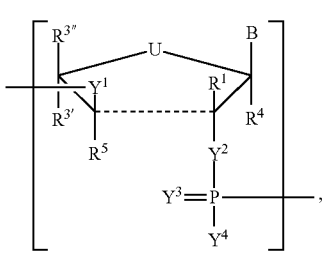
(Ib)

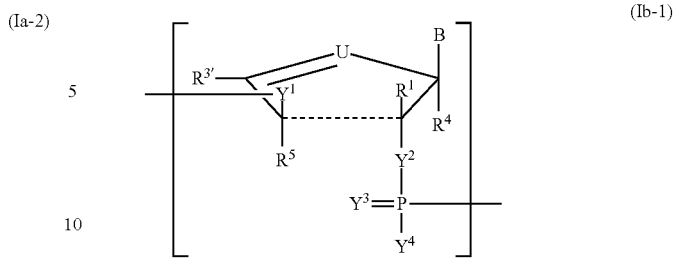
(Ib-1)

or a pharmaceutically acceptable salt or stereoisomer thereof, wherein

U is O, S, $N(R^U)_{nu}$, or $C(R^U)_{nu}$, wherein nu is an integer from 0 to 2 and each $R^U$ is, independently, H, halo, or optionally substituted alkyl;

--- is a single bond or absent;

each of $R^1$, $R^{3'}$, $R^{3''}$, and $R^4$ is, independently, H, halo, hydroxy, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, or optionally substituted aminoalkynyl; and wherein the combination of $R^1$ and $R^{3'}$ or the combination of $R^1$ and $R^{3''}$ can be taken together to form, together with the carbons to which they are attached, an optionally substituted heterocycle or cycloalkyl (e.g., to produce a locked nucleic acid);

each $R^5$ is, independently, H, halo, hydroxy, optionally substituted alkyl, optionally substituted alkoxy, optionally substituted alkenyloxy, optionally substituted alkynyloxy, optionally substituted aminoalkoxy, or optionally substituted alkoxyalkoxy;

each of $Y^1$, $Y^2$, and $Y^3$ is, independently, O, S, Se, $NR^{N1}$—, optionally substituted alkylene, or optionally substituted heteroalkylene, wherein $R^{N1}$ is H, optionally substituted alkyl, optionally substituted alkenyl, optionally substituted alkynyl, or optionally substituted aryl;

each $Y^4$ is, independently, H, hydroxy, thiol, boranyl, optionally substituted alkyl, optionally substituted alkenyl, optionally substituted alkynyl, optionally substituted alkoxy, optionally substituted alkenyloxy, optionally substituted alkynyloxy, optionally substituted alkoxyalkoxy, or optionally substituted amino;

n is an integer from 1 to 100,000; and

B is a nucleobase.

In some embodiments, the polynucleotide (e.g., the first region, first flanking region, or second flanking region) includes n number of linked nucleosides having Formula (Ic)

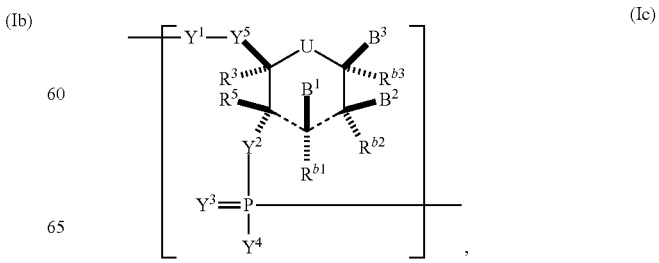
(Ic)

or a pharmaceutically acceptable salt or stereoisomer thereof, wherein

U is O, S, N(R$^U$)$_{nu}$, or C(R$^U$)$_{nu}$, wherein nu is an integer from 0 to 2 and each R$^U$ is, independently, H, halo, or optionally substituted alkyl;

--- is a single bond or absent;

each of B$^1$, B$^2$, and B$^3$ is, independently, a nucleobase (e.g., a purine, a pyrimidine, or derivatives thereof, as described herein), H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, or optionally substituted aminoalkynyl, wherein one and only one of B$^1$, B$^2$, and B$^3$ is a nucleobase;

each of R$^{b1}$, R$^{b2}$, R$^{b3}$, R$^3$, and R$^5$ is, independently, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, or optionally substituted aminoalkynyl;

each of Y$^1$, Y$^2$, and Y$^3$, is, independently, O, S, Se, —NR$^{N'}$—, optionally substituted alkylene, or optionally substituted heteroalkylene, wherein R$^{N1}$ is H, optionally substituted alkyl, optionally substituted alkenyl, optionally substituted alkynyl, or optionally substituted aryl;

each Y$^4$ is, independently, H, hydroxy, thiol, boranyl, optionally substituted alkyl, optionally substituted alkenyl, optionally substituted alkynyl, optionally substituted alkoxy, optionally substituted alkenyloxy, optionally substituted alkynyloxy, optionally substituted thioalkoxy, optionally substituted alkoxyalkoxy, or optionally substituted amino;

each Y$^5$ is O, S, Se, optionally substituted alkylene (e.g., methylene), or optionally substituted heteroalkylene;

n is an integer from 1 to 100,000; and wherein the ring including U can include one or more double bonds.

In particular embodiments, the ring including U does not have a double bond between U—CB$^3$R$^{b3}$ or between CB$^3$R$^{b3}$—C$^{B2}$R$^{b2}$.

In some embodiments, the polynucleotide (e.g., the first region, first flanking region, or second flanking region) includes n number of linked nucleosides having Formula (Id)

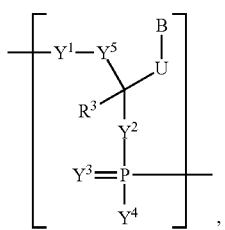

(Id)

or a pharmaceutically acceptable salt or stereoisomer thereof, wherein U is O, S, N(R$^U$)$_{nu}$, or C(R$^U$)$_{nu}$, wherein nu is an integer from 0 to 2 and each R$^U$ is, independently, H, halo, or optionally substituted alkyl;

each R$^3$ is, independently, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, or optionally substituted aminoalkynyl;

each of Y$^1$, Y$^2$, and Y$^3$, is, independently, O, S, Se, —NR$^{N1}$—, optionally substituted alkylene, or optionally substituted heteroalkylene, wherein R$^{N1}$ is H, optionally substituted alkyl, optionally substituted alkenyl, optionally substituted alkynyl, or optionally substituted aryl;

each Y$^4$ is, independently, H, hydroxy, thiol, boranyl, optionally substituted alkyl, optionally substituted alkenyl, optionally substituted alkynyl, optionally substituted alkoxy, optionally substituted alkenyloxy, optionally substituted alkynyloxy, optionally substituted thioalkoxy, optionally substituted alkoxyalkoxy, or optionally substituted amino;

each Y$^5$ is O, S, optionally substituted alkylene (e.g., methylene), or optionally substituted heteroalkylene;

n is an integer from 1 to 100,000; and

B is a nucleobase (e.g., a purine, a pyrimidine, or derivatives thereof).

In some embodiments, the polynucleotide (e.g., the first region, first flanking region, or second flanking region) includes n number of linked nucleosides having Formula (Ie)

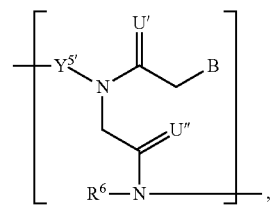

(Ie)

or a pharmaceutically acceptable salt or stereoisomer thereof, wherein each of U' and U" is, independently, O, S, N(R$^U$)$_{nu}$, or C(R$^U$)$_{nu}$, wherein nu is an integer from 0 to 2 and each R$^U$ is, independently, H, halo, or optionally substituted alkyl;

each R$^6$ is, independently, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, or optionally substituted aminoalkynyl;

each Y$^{5'}$ is, O, S, optionally substituted alkylene (e.g., methylene or ethylene), or optionally substituted heteroalkylene;

n is an integer from 1 to 100,000; and

B is a nucleobase (e.g., a purine, a pyrimidine, or derivatives thereof).

In some embodiments, the polynucleotide (e.g., the first region, first flanking region, or second flanking region) includes n number of linked nucleosides having Formula (If) or (If-1)

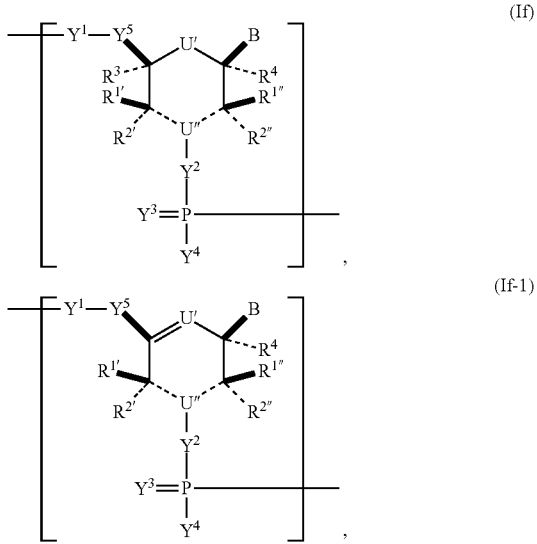

or a pharmaceutically acceptable salt or stereoisomer thereof, wherein each of U' and U" is, independently, O, S, N, N(R$^U$)$_{nu}$, or C(R$^U$)$_{nu}$, wherein nu is an integer from 0 to 2 and each R$^U$ is, independently, H, halo, or optionally substituted alkyl (e.g., U' is O and U" is N);

--- is a single bond or absent;

each of R$^{1'}$, R$^{2'}$, R$^{1"}$, R$^{2"}$, R$^3$, and R$^4$ is, independently, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkyl, optionally substituted amino, azido, optionally substituted aryl, optionally substituted aminoalkyl, optionally substituted aminoalkenyl, or optionally substituted aminoalkynyl; and wherein the combination of R$^{1'}$ and R$^3$, the combination of R$^{1"}$ and R$^3$, the combination of R$^{2'}$ and R$^3$, or the combination of R$^{2"}$ and R$^3$ can be taken together to form, with the carbons to which they are attached, an optionally substituted heterocyclyl or cycloalkyl (e.g., to produce a locked nucleic acid); each of m' and m" is, independently, an integer from 0 to 3 (e.g., from 0 to 2, from 0 to 1, from 1 to 3, or from 1 to 2);

each of Y$^1$, Y$^2$, and Y$^3$, is, independently, O, S, Se, —NR$^{N1}$—, optionally substituted alkylene, or optionally substituted heteroalkylene, wherein R$^{N1}$ is H, optionally substituted alkyl, optionally substituted alkenyl, optionally substituted alkynyl, or optionally substituted aryl;

each Y$^4$ is, independently, H, hydroxy, thiol, boranyl, optionally substituted alkyl, optionally substituted alkenyl, optionally substituted alkynyl, optionally substituted alkoxy, optionally substituted alkenyloxy, optionally substituted alkynyloxy, optionally substituted thioalkoxy, optionally substituted alkoxyalkoxy, or optionally substituted amino;

each Y$^5$ is O, S, Se, optionally substituted alkylene (e.g., methylene), or optionally substituted heteroalkylene;

n is an integer from 1 to 100,000; and

B is a nucleobase (e.g., a purine, a pyrimidine, or derivatives thereof).

In some embodiments of the polynucleotides (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IVl), and (IXa)-(IXr)), the ring including U has one or two double bonds.

In some embodiments of the polynucleotides (e.g., Formulas (Ia)-Ia-5), (Ib)-(If-1), (IIa)-(IIp), (IIb-1), (IIb-2), (IIc-1)-(IIc-2), (IIn-1), (IIn-2), (IVa)-(IVl), and (IXa)-(IXr)), each of R$^1$, R$^{1'}$, and R$^{1"}$, if present, is H. In further embodiments, each of R$^2$, R$^{2'}$, and R$^{2"}$, if present, is, independently, H, halo (e.g., fluoro), hydroxy, optionally substituted alkoxy (e.g., methoxy or ethoxy), or optionally substituted alkoxyalkoxy. In particular embodiments, alkoxyalkoxy is —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C$_{1-20}$ alkyl). In some embodiments, s2 is 0, s1 is 1 or 2, s3 is 0 or 1, and R' is C$_{1-6}$ alkyl.

In some embodiments of the polynucleotides (e.g., Formulas (Ia)-(Ia-5), (Ib)-(If), (IIa)-(IIp), (IIb-1), (IIb-2), (IIc-1)-(IIc-2), (IIn-1), (IIn-2), (IVa)-(IVl), and (IXa)-(IXr)), each of R$^2$, R$^{2'}$, and R$^{2"}$, if present, is H. In further embodiments, each of R$^1$, R$^{1'}$, and R$^{1"}$, if present, is, independently, H, halo (e.g., fluoro), hydroxy, optionally substituted alkoxy (e.g., methoxy or ethoxy), or optionally substituted alkoxyalkoxy. In particular embodiments, alkoxyalkoxy is —(CH$_2$)$_{s2}$(OCH$_2$CH$_2$)$_1$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C$_{1-20}$ alkyl). In some embodiments, s2 is 0, s1 is 1 or 2, s3 is 0 or 1, and R' is C$_{1-6}$ alkyl.

In some embodiments of the polynucleotides (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IVl), and (IXa)-(IXr)), each of R$^3$, R$^4$, and R$^5$ is, independently, H, halo (e.g., fluoro), hydroxy, optionally substituted alkyl, optionally substituted alkoxy (e.g., methoxy or ethoxy), or optionally substituted alkoxyalkoxy. In particular embodiments, R$^3$ is H, R$^4$ is H, R$^5$ is H, or R$^3$, R$^4$, and R$^5$ are all H. In particular embodiments, R$^3$ is C$_{1-6}$ alkyl, R$^4$ is C$_{1-6}$ alkyl, R$^5$ is C$_{1-6}$ alkyl, or R$^3$, R$^4$, and R$^5$ are all C$_{1-6}$ alkyl. In particular embodiments, R$^3$ and R$^4$ are both H, and R$^5$ is C$_{1-6}$ alkyl.

In some embodiments of the polynucleotides (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IVl), and (IXa)-(IXr)), R$^3$ and R$^5$ join together to form, taken together with the carbons to which they are attached, an optionally substituted heterocyclyl (e.g., a bicyclic, tricyclic, or tetracyclic heterocyclyl) or cycloalkyl, such as trans-3', 4' analogs, wherein R$^3$ and R$^5$ join together to form a heterocycle (e.g., a heterocycle including the structure —(CH$_2$)$_{b1}$O(CH$_2$)$_{b2}$O(CH$_2$)$_{b3}$—, wherein each of b1, b2, and b3 are, independently, an integer from 0 to 3).

In some embodiments of the polynucleotides (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IVl), and (IXa)-(IXr)), R$^3$ and one or more of R$^{1'}$, R$^{1"}$, R$^{2'}$, R$^{2"}$, or R$^5$ join together to form, taken together with the carbons to which they are attached, an optionally substituted heterocyclyl (e.g., a bicyclic, tricyclic, or tetracyclic heterocyclyl) or cycloalkyl, R$^3$ and one or more of R$^{1'}$, R$^{1"}$, R$^{2'}$, R$^{2"}$, or R$^5$ join together to form a heterocycle (e.g., a heterocycle including the structure —(CH$_2$)$_{b1}$O(CH$_2$)$_{b2}$O(CH$_2$)$_{b3}$—, wherein each of b1, b2, and b3 are, independently, an integer from 0 to 3).

In some embodiments of the polynucleotides (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IVl), and (IXa)-(IXr)), R$^5$ and one or more of R$^{1'}$, R$^{1"}$, R$^{2'}$, or R$^{2"}$ join together to form together with the carbons to which they are attached, an optionally substituted heterocyclyl (e.g., a bicyclic, tricyclic, or tetracyclic heterocyclyl) or cycloalkyl, $R^5$ and one or more of $R^{1'}$, $R^{1''}$, $R^{2'}$, or $R^{2''}$ join together to form a heterocycle (e.g., a heterocycle including the structure —$(CH_2)_{b1}O(CH_2)_{b2}O(CH_2)_{b3}$—, wherein each of b1, b2, and b3 are, independently, an integer from 0 to 3).

In some embodiments of the polynucleotides (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IVl), and (IXa)-(IXr)), each $Y^2$ is, independently, O, S, or —$NR^{N1}$—, wherein $R^{N1}$ is H, optionally substituted alkyl, optionally substituted alkenyl, optionally substituted alkynyl, or optionally substituted aryl. In particular embodiments, $Y^2$ is $NR^{N1}$—, wherein $R^{N1}$ is H or optionally substituted alkyl (e.g., $C_{1-6}$ alkyl, such as methyl, ethyl, isopropyl, or n-propyl).

In some embodiments of the polynucleotides (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IVl), and (IXa)-(IXr)), each $Y^3$ is, independently, O or S.

In some embodiments of the polynucleotides (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IVl), and (IXa)-(IXr)), $R^1$ is H; each $R^2$ is, independently, H, halo (e.g., fluoro), hydroxy, optionally substituted alkoxy (e.g., methoxy or ethoxy), or optionally substituted alkoxyalkoxy (e.g., —$(CH_2)_{s2}(OCH_2CH_2)_1(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, such as wherein s2 is 0, s1 is 1 or 2, s3 is 0 or 1, and R' is $C_{1-6}$ alkyl); each $Y^2$ is, independently, O or —$NR^{N1}$—, wherein $R^{N1}$ is H, optionally substituted alkyl, optionally substituted alkenyl, optionally substituted alkynyl, or optionally substituted aryl (e.g., wherein $R^{N1}$ is H or optionally substituted alkyl (e.g., $C_{1-6}$ alkyl, such as methyl, ethyl, isopropyl, or n-propyl)); and each $Y^3$ is, independently, O or S (e.g., S). In further embodiments, $R^3$ is H, halo (e.g., fluoro), hydroxy, optionally substituted alkyl, optionally substituted alkoxy (e.g., methoxy or ethoxy), or optionally substituted alkoxyalkoxy. In yet further embodiments, each $Y^1$ is, independently, O or —$NR^{N1}$—, wherein $R^{N1}$ is H, optionally substituted alkyl, optionally substituted alkenyl, optionally substituted alkynyl, or optionally substituted aryl (e.g., wherein $R^{N1}$ is H or optionally substituted alkyl (e.g., $C_{1-6}$ alkyl, such as methyl, ethyl, isopropyl, or n-propyl)); and each $Y^4$ is, independently, H, hydroxy, thiol, optionally substituted alkyl, optionally substituted alkoxy, optionally substituted thioalkoxy, optionally substituted alkoxyalkoxy, or optionally substituted amino.

In some embodiments of the polynucleotides (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IVl), and (IXa)-(IXr)), each $R^1$ is, independently, H, halo (e.g., fluoro), hydroxy, optionally substituted alkoxy (e.g., methoxy or ethoxy), or optionally substituted alkoxyalkoxy (e.g., —$(CH_2)_{s2}(OCH_2CH_2)_1(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, such as wherein s2 is 0, s1 is 1 or 2, s3 is 0 or 1, and R' is $C_{1-6}$ alkyl); $R^2$ is H; each $Y^2$ is, independently, O or —$NR^{N1}$—, wherein $R^{N1}$ is H, optionally substituted alkyl, optionally substituted alkenyl, optionally substituted alkynyl, or optionally substituted aryl (e.g., wherein $R^{N1}$ is H or optionally substituted alkyl (e.g., $C_{1-6}$ alkyl, such as methyl, ethyl, isopropyl, or n-propyl)); and each $Y^3$ is, independently, O or S (e.g., S). In further embodiments, $R^3$ is H, halo (e.g., fluoro), hydroxy, optionally substituted alkyl, optionally substituted alkoxy (e.g., methoxy or ethoxy), or optionally substituted alkoxyalkoxy. In yet further embodiments, each $Y^1$ is, independently, O or —$NR^{N1}$—, wherein $R^{N1}$ is H, optionally substituted alkyl, optionally substituted alkenyl, optionally substituted alkynyl, or optionally substituted aryl (e.g., wherein $R^{N1}$ is H or optionally substituted alkyl (e.g., $C_{1-6}$ alkyl, such as methyl, ethyl, isopropyl, or n-propyl)); and each $Y^4$ is, independently, H, hydroxy, thiol, optionally substituted alkyl, optionally substituted alkoxy, optionally substituted thioalkoxy, optionally substituted alkoxyalkoxy, or optionally substituted amino.

In some embodiments of the polynucleotides (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IVl), and (IXa)-(IXr)), the ring including U is in the β-D (e.g., β-D-ribo) configuration.

In some embodiments of the polynucleotides (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IVl), and (IXa)-(IXr)), the ring including U is in the α-L (e.g., α-L-ribo) configuration.

In some embodiments of the polynucleotides (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IVl), and (IXa)-(IXr)), one or more B is not pseudouracil (ψ) or 5-methyl-cytosine ($m^5C$).

In some embodiments, about 10% to about 100% of n number of B nucleobases is not ψ or $m^5C$ (e.g., from 10% to 20%, from 10% to 35%, from 10% to 50%, from 10% to 60%, from 10% to 75%, from 10% to 90%, from 10% to 95%, from 10% to 98%, from 10% to 99%, from 20% to 35%, from 20% to 50%, from 20% to 60%, from 20% to 75%, from 20% to 90%, from 20% to 95%, from 20% to 98%, from 20% to 99%, from 20% to 100%, from 50% to 60%, from 50% to 75%, from 50% to 90%, from 50% to 95%, from 50% to 98%, from 50% to 99%, from 50% to 100%, from 75% to 90%, from 75% to 95%, from 75% to 98%, from 75% to 99%, and from 75% to 100% of n number of B is not ψ or $m^5C$). In some embodiments, B is not ψ or $m^5C$.

In some embodiments of the polynucleotides (e.g., Formulas (Ia)-(Ia-5), (Ib)-(If-1), (IIa)-(IIp), (IIb-1), (IIb-2), (IIc-1)-(IIc-2), (IIn-1), (IIn-2), (IVa)-(IVl), and (IXa)-(IXr)), when B is an unaltered nucleobase selected from cytosine, guanine, uracil and adenine, then at least one of $Y^1$, $Y^2$, or $Y^3$ is not O.

In some embodiments, the polynucleotide includes an alternative ribose. In some embodiments, the polynucleotide (e.g., the first region, the first flanking region, or the second flanking region) includes n number of linked nucleosides having Formula (IIa)-(IIc):

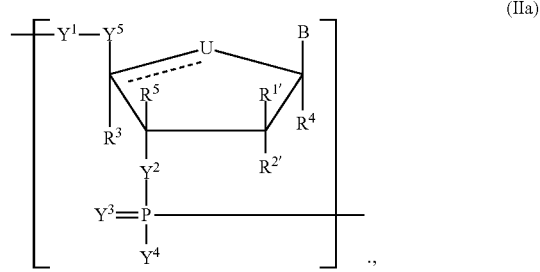

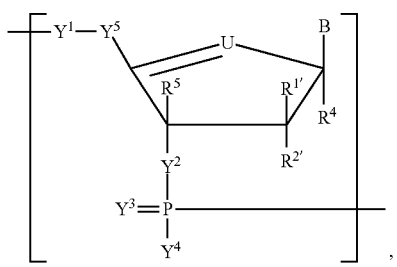

(IIb)

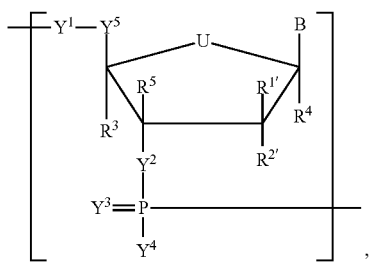

, or (IIc)

or a pharmaceutical acceptable salt or stereoisomer thereof. In particular embodiments, U is O or $C(R^U)_{nu}$, wherein nu is an integer from 0 to 2 and each $R^U$ is, independently, H, halo, or optionally substituted alkyl (e.g., U is —$CH_2$— or —CH—). In other embodiments, each of $R^{1'}$, $R^{2'}$, $R^3$, $R^4$, and $R^5$ is, independently, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, optionally substituted aminoalkynyl, or absent (e.g., each $R^1$ and $R^2$ is, independently H, halo, hydroxy, optionally substituted alkyl, or optionally substituted alkoxy; each $R^3$ and $R^4$ is, independently, H or optionally substituted alkyl; and $R^5$ is H or hydroxy), and ⇌ is a single bond or double bond.

In particular embodiments, the polynucleotide (e.g., the first region, the first flanking region, or the second flanking region) includes n number of linked nucleosides having Formula (IIb-1)-(IIb-2):

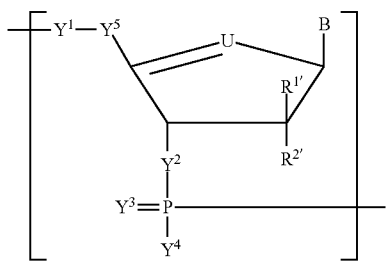

(IIb-1)

or

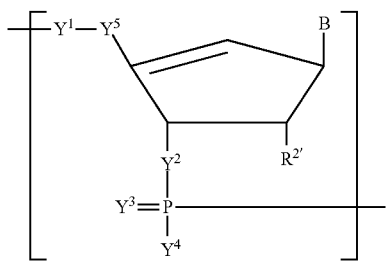

(IIb-2)

or a pharmaceutically acceptable salt or stereoisomer thereof. In some embodiments, U is O or $C(R^U)_{nu}$, wherein nu is an integer from 0 to 2 and each $R^U$ is, independently, H, halo, or optionally substituted alkyl (e.g., U is —$CH_2$— or —CH—). In other embodiments, each of $R^1$ and $R^2$ is, independently, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, optionally substituted aminoalkynyl, or absent (e.g., each $R^1$ and $R^2$ is, independently, H, halo, hydroxy, optionally substituted alkyl, or optionally substituted alkoxy, e.g., H, halo, hydroxy, alkyl, or alkoxy). In particular embodiments, $R^2$ is hydroxy or optionally substituted alkoxy (e.g., methoxy, ethoxy, or any described herein).

In particular embodiments, the polynucleotide (e.g., the first region, the first flanking region, or the second flanking region) includes n number of linked nucleosides having Formula (IIc-1)-(IIc-4):

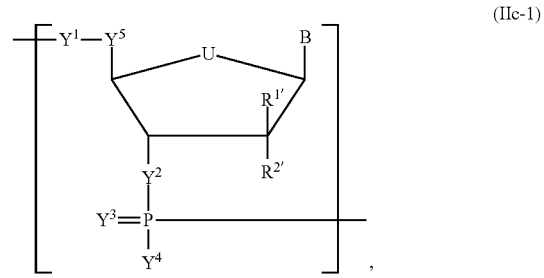

(IIc-1)

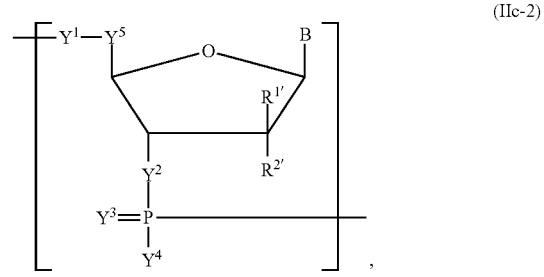

(IIc-2)

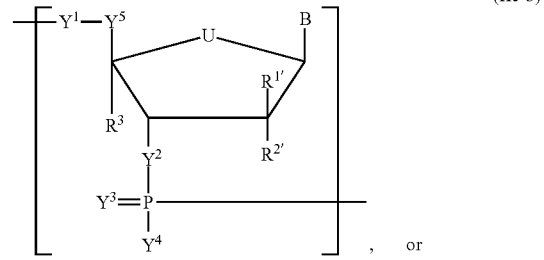

(IIc-3)

, or

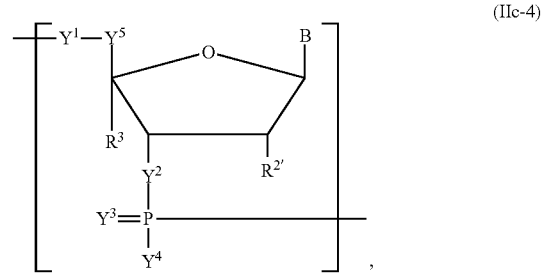

(IIc-4)

, or a pharmaceutically acceptable salt or stereoisomer thereof.

In some embodiments, U is O or C(R$^U$)$_{nu}$, wherein nu is an integer from 0 to 2 and each R$^U$ is, independently, H, halo, or optionally substituted alkyl (e.g., U is —CH$_2$— or —CH—). In some embodiments, each of R$^{1'}$, R$^{2'}$, and R$^3$ is, independently, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, optionally substituted aminoalkynyl, or absent (e.g., each R$^1$ and R$^2$ is, independently, H, halo, hydroxy, optionally substituted alkyl, or optionally substituted alkoxy, e.g., H, halo, hydroxy, alkyl, or alkoxy; and each R$^3$ is, independently, H or optionally substituted alkyl)). In particular embodiments, R$^2$ is optionally substituted alkoxy (e.g., methoxy or ethoxy, or any described herein). In particular embodiments, R$^1$ is optionally substituted alkyl, and R$^2$ is hydroxy. In other embodiments, R$^1$ is hydroxy, and R$^2$ is optionally substituted alkyl. In further embodiments, R$^3$ is optionally substituted alkyl.

In some embodiments, the polynucleotide includes an acyclic alternative ribose. In some embodiments, the polynucleotide (e.g., the first region, the first flanking region, or the second flanking region) includes n number of linked nucleosides having Formula (IId)-(IIf):

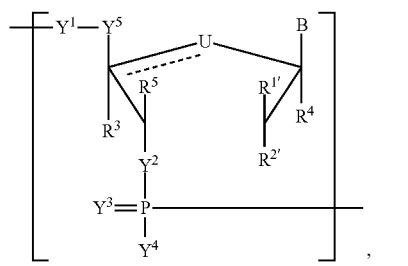

(IId)

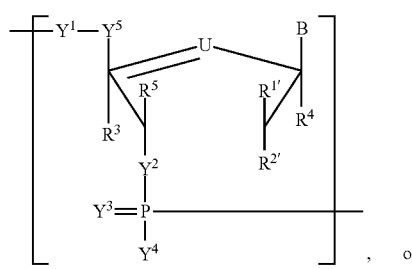

(IIe)

, or

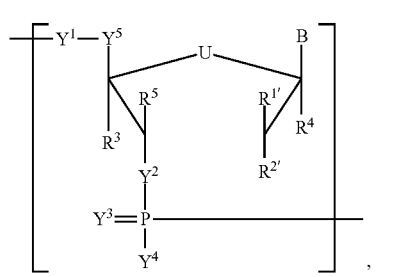

(IIf)

or a pharmaceutically acceptable salt or stereoisomer thereof.

In some embodiments, the polynucleotide includes an acyclic alternative hexitol. In some embodiments, the polynucleotide (e.g., the first region, the first flanking region, or the second flanking region) includes n number of linked nucleosides having Formula (IIg)-(IIj):

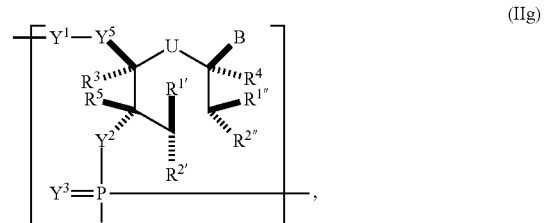

(IIg)

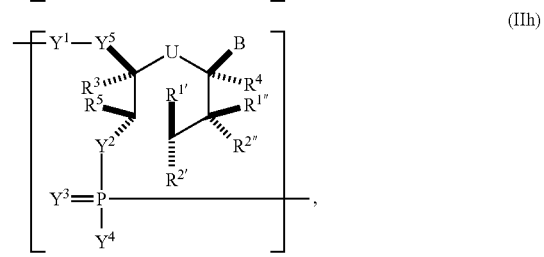

(IIh)

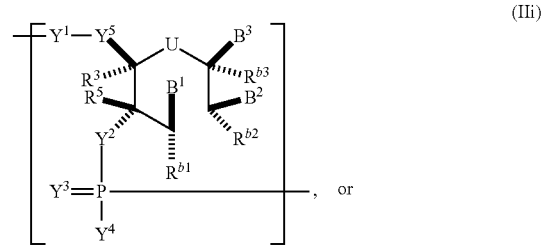

(IIi)

, or

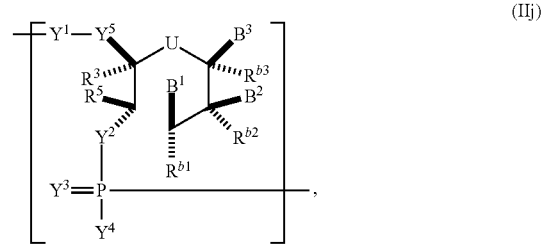

(IIj)

pharmaceutically acceptable salt or stereoisomer thereof.

In some embodiments, the polynucleotide includes a sugar moiety having a contracted or an expanded ribose ring. In some embodiments, the polynucleotide (e.g., the first region, the first flanking region, or the second flanking region) includes n number of linked nucleosides having Formula (IIk)-(IIm):

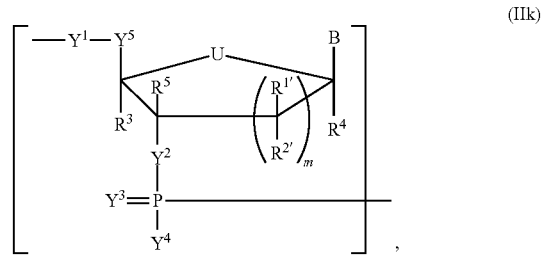

(IIk)

-continued

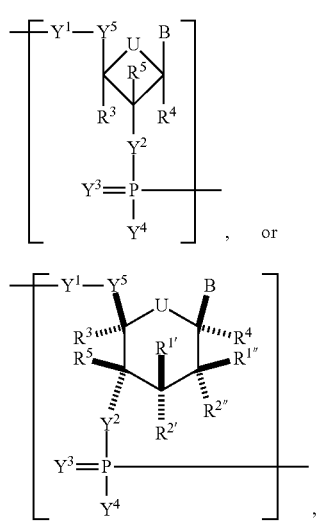

(III)

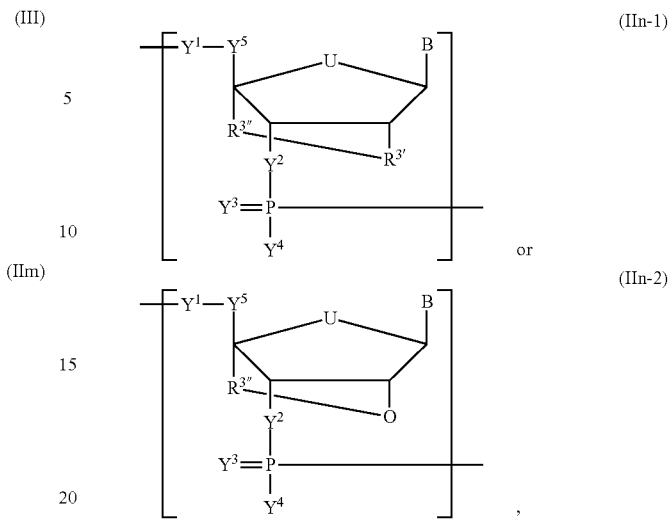

(IIn-1)

or (IIn-2)

(IIm)

or a pharmaceutically acceptable salt or stereoisomer thereof, wherein R$^{3'}$ is O, S, or —NR$^{N1}$—, wherein R$^{N1}$ is H, optionally substituted alkyl, optionally substituted alkenyl, optionally substituted alkynyl, or optionally substituted aryl and R$^{3''}$ is optionally substituted alkylene (e.g., —CH$_2$—, —CH$_2$CH$_2$—, or —CH$_2$CH$_2$CH$_2$—) or optionally substituted heteroalkylene (e.g., —CH$_2$NH—, —CH$_2$CH$_2$NH—, —CH$_2$OCH$_2$—, or —CH$_2$CH$_2$OCH$_2$—) (e.g., R$^{3'}$ is O and R$^{3''}$ is optionally substituted alkylene (e.g., —CH$_2$—, —CH$_2$CH$_2$—, or —CH$_2$CH$_2$CH$_2$—)).

or a pharmaceutically acceptable salt or stereoisomer thereof, wherein each of R$^{1'}$, R$^{1''}$, R$^{2'}$, and R$^{2''}$ is, independently, H, halo, hydroxy, optionally substituted alkyl, optionally substituted alkoxy, optionally substituted alkenyloxy, optionally substituted alkynyloxy, optionally substituted aminoalkoxy, optionally substituted alkoxyalkoxy, or absent; and wherein the combination of R$^{2'}$ and R$^3$ or the combination of R$^{2''}$ and R$^3$ can be taken together to form optionally substituted alkylene or optionally substituted heteroalkylene.

In some embodiments, the polynucleotide includes a locked alternative ribose. In some embodiments, the polynucleotide (e.g., the first region, the first flanking region, or the second flanking region) includes n number of linked nucleosides having Formula (IIn):

In some embodiments, the polynucleotide includes a locked alternative ribose that forms a tetracyclic heterocyclyl. In some embodiments, the polynucleotide (e.g., the first region, the first flanking region, or the second flanking region) includes n number of linked nucleosides having Formula (IIo):

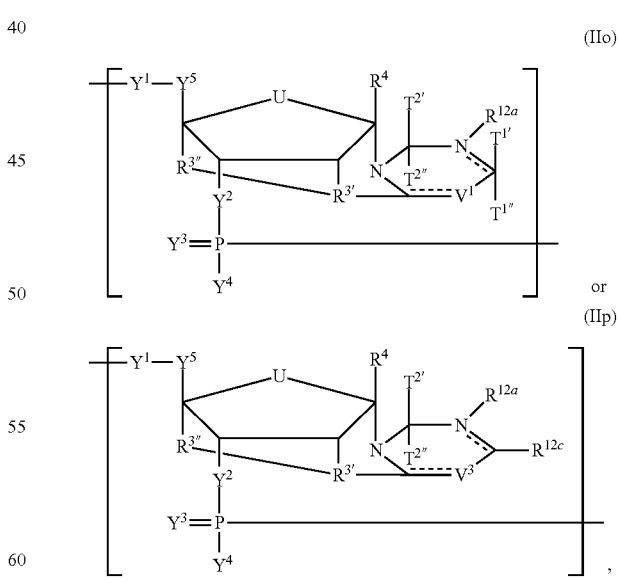

(IIo)

or (IIp)

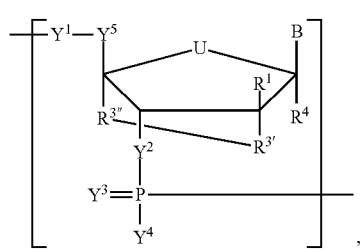

(IIn)

or a pharmaceutically acceptable salt or stereoisomer thereof, wherein R$^{3'}$ is O, S, or —NR$^{N1}$—, wherein R$^{N1}$ is H, optionally substituted alkyl, optionally substituted alkenyl, optionally substituted alkynyl, or optionally substituted aryl and R$^3$ is optionally substituted alkylene (e.g., —CH$_2$—, —CH$_2$CH$_2$—, or —CH$_2$CH$_2$CH$_2$—) or optionally substituted heteroalkylene (e.g., —CH$_2$NH—, —CH$_2$CH$_2$NH—, —CH$_2$OCH$_2$—, or —CH$_2$CH$_2$OCH$_2$—) (e.g., R$^{3'}$ is O and R$^{3''}$ is optionally substituted alkylene (e.g., —CH$_2$—, —CH$_2$CH$_2$—, or —CH$_2$CH$_2$CH$_2$—)).

In some embodiments, the polynucleotide (e.g., the first region, the first flanking region, or the second flanking region) includes n number of linked nucleosides having Formula (IIn-1)-(II-n2):

or a pharmaceutically acceptable salt or stereoisomer thereof, wherein R$^{12a}$, R$^{12c}$, T$^{1'}$, T$^{1''}$, T$^{2'}$, T$^{2''}$, V$^1$, and V$^3$ are as described herein.

Any of the formulas for the polynucleotides can include one or more nucleobases described herein (e.g., Formulas (b1)-(b43)).

In one embodiment, the present invention provides methods of preparing a polynucleotide comprising at least one nucleotide, wherein the polynucleotide comprises n number of nucleosides having Formula (Ia), as defined herein:

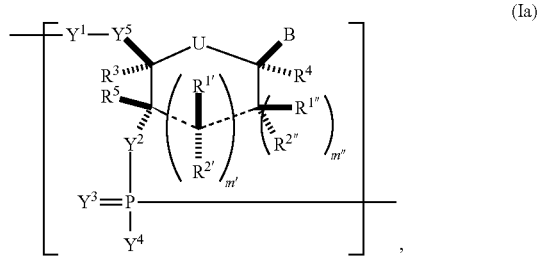

(Ia)

the method comprising reacting a compound of Formula (IIIa), as defined herein:

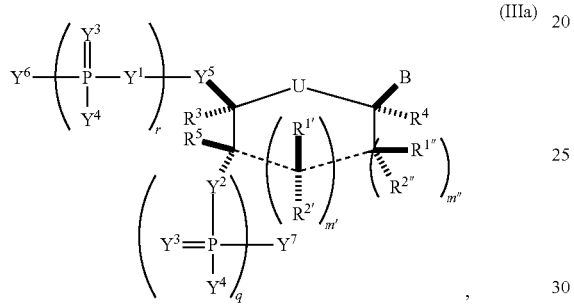

(IIIa)

with an RNA polymerase, and a cDNA template.

In one embodiment, the present invention provides methods of preparing a polynucleotide comprising at least one nucleotide, wherein the polynucleotide comprises n number of nucleosides having Formula (Ia-1), as defined herein:

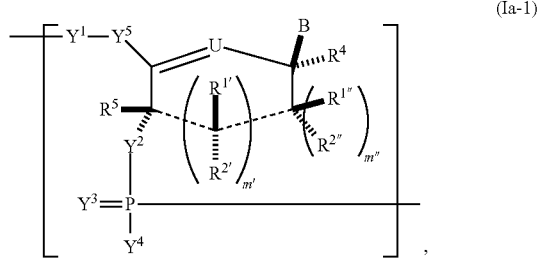

(Ia-1)

(Ia-1), the method comprising reacting a compound of Formula (IIIa-1), as defined herein:

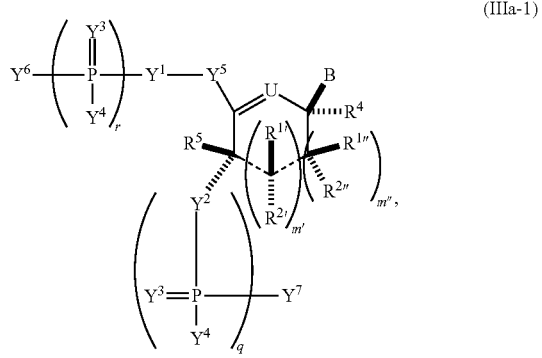

(IIIa-1)

with an RNA polymerase, and a cDNA template.

In a further embodiment, the present invention provides methods of amplifying a polynucleotide comprising at least one nucleotide (e.g., alternative mRNA molecule), the method comprising: reacting a compound of Formula (IIIa-1), as defined herein, with a primer, a cDNA template, and an RNA polymerase.

In one embodiment, the present invention provides methods of preparing a polynucleotide comprising at least one nucleotide, wherein the polynucleotide comprises n number of nucleosides having Formula (Ia-2), as defined herein:

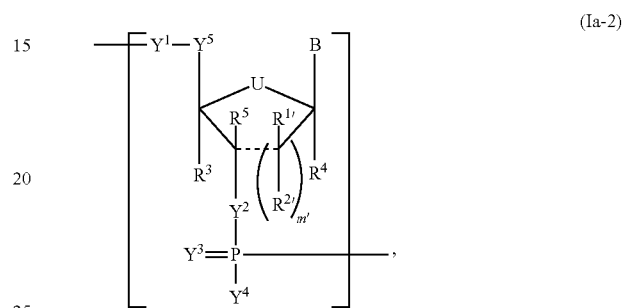

(Ia-2)

the method comprising reacting a compound of Formula (IIIa-2), as defined herein:

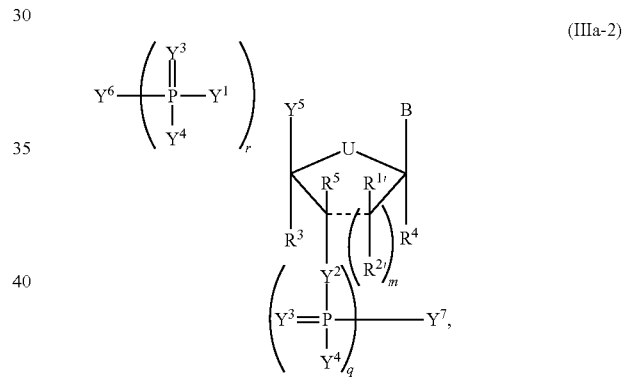

(IIIa-2)

with an RNA polymerase, and a cDNA template.

In a further embodiment, the present invention provides methods of amplifying a polynucleotide comprising at least one nucleotide (e.g., alternative mRNA molecule), the method comprising reacting a compound of Formula (IIIa-2), as defined herein, with a primer, a cDNA template, and an RNA polymerase.

In some embodiments, the reaction may be repeated from 1 to about 7,000 times. In any of the embodiments herein, B may be a nucleobase of Formula (b1)-(b43).

The polynucleotides can optionally include 5' and/or 3' flanking regions, which are described herein.

Alternative Nucleotides and Nucleosides

The present invention also includes the building blocks, e.g., alternative ribonucleosides, alternative ribonucleotides, of the polynucleotides, e.g., alternative RNA (or mRNA) molecules. For example, these building blocks can be useful for preparing the polynucleotides of the invention.

In some embodiments, the building block molecule has Formula (IIIa) or (IIIa-1):

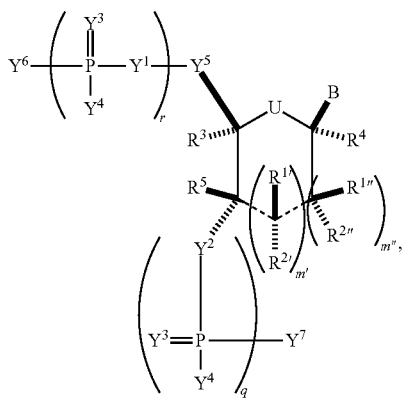

(IIIa)

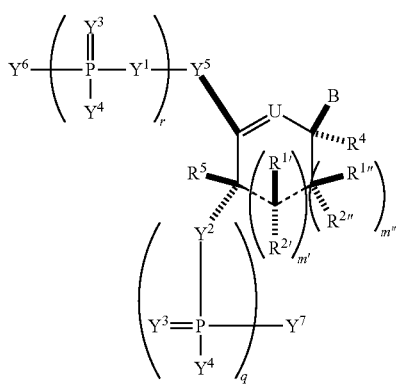

(IIIa)

or a pharmaceutically acceptable salt or stereoisomer thereof, wherein the substituents are as described herein (e.g., for Formula (Ia) and (Ia-1)), and wherein when B is an unaltered nucleobase selected from cytosine, guanine, uracil and adenine, then at least one of $Y^1$, $Y^2$, or $Y^3$ is not O.

In some embodiments, the building block molecule, which may be incorporated into a polynucleotide, has Formula (IVa)-(IVb):

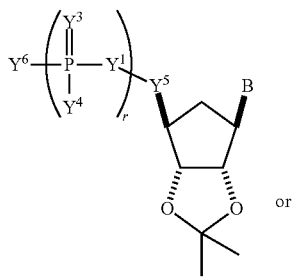

(IVa)

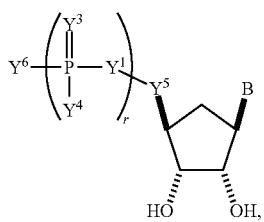

(IVb)

or a pharmaceutically acceptable salt or stereoisomer thereof, wherein B is as described herein (e.g., any one of (b1)-(b43)).

In particular embodiments, Formula (IVa) or (IVb) is combined with an alternative uracil (e.g., any one of formulas (b1)-(b9), (b21)-(b23), and (b28)-(b31), such as formula (b1), (b8), (b28), (b29), or (b30)). In particular embodiments, Formula (IVa) or (IVb) is combined with an alternative cytosine (e.g., any one of formulas (b10)-(b14), (b24), (b25), and (b32)-(b36), such as formula (b10) or (b32)). In particular embodiments, Formula (IVa) or (IVb) is combined with an alternative guanine (e.g., any one of formulas (b15)-(b17) and (b37)-(b40)). In particular embodiments, Formula (IVa) or (IVb) is combined with an alternative adenine (e.g., any one of formulas (b18)-(b20) and (b41)-(b43)).

In some embodiments, the building block molecule, which may be incorporated into a polynucleotide, has Formula (IVc)-(IVk):

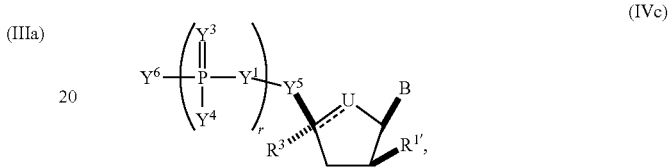

(IVc)

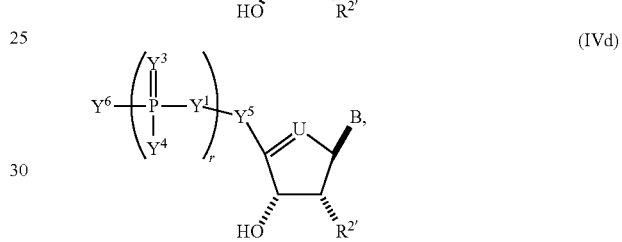

(IVd)

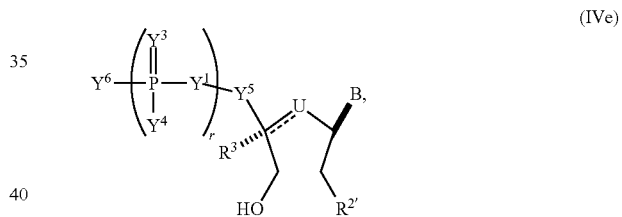

(IVe)

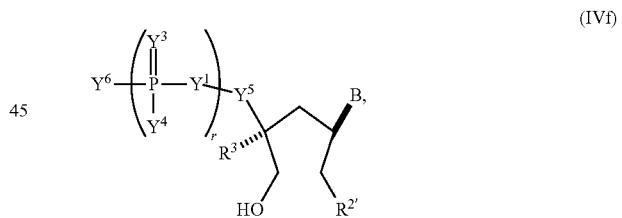

(IVf)

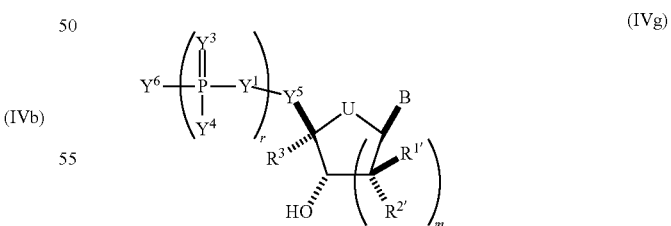

(IVg)

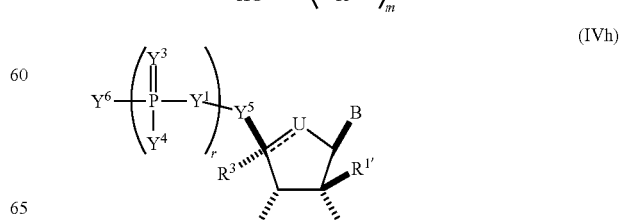

(IVh)

-continued

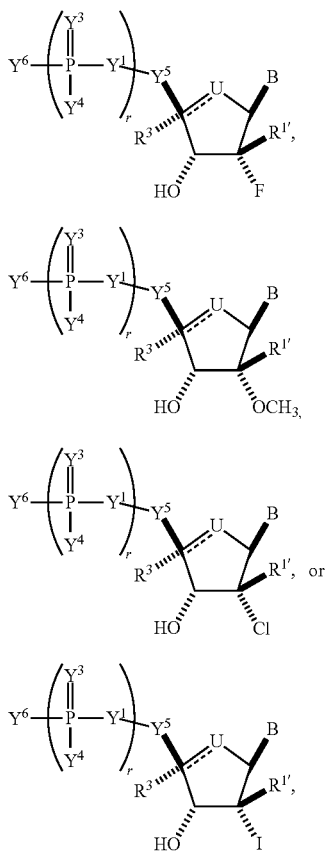
(IVi)
(IVj)
(IVk)
(IVl)

or a pharmaceutically acceptable salt or stereoisomer thereof, wherein B is as described herein (e.g., any one of (b1)-(b43)).

In particular embodiments, one of Formulas (IVc)-(IVk) is combined with an alternative uracil (e.g., any one of formulas (b1)-(b9), (b21)-(b23), and (b28)-(b31), such as formula (b1), (b8), (b28), (b29), or (b30)).

In particular embodiments, one of Formulas (IVc)-(IVk) is combined with an alternative cytosine (e.g., any one of formulas (b10)-(b14), (b24), (b25), and (b32)-(b36), such as formula (b10) or (b32)).

In particular embodiments, one of Formulas (IVc)-(IVk) is combined with an alternative guanine (e.g., any one of formulas (b15)-(b17) and (b37)-(b40)).

In particular embodiments, one of Formulas (IVc)-(IVk) is combined with an alternative adenine (e.g., any one of formulas (b18)-(b20) and (b41)-(b43)).

In other embodiments, the building block molecule, which may be incorporated into a polynucleotide has Formula (Va) or (Vb):

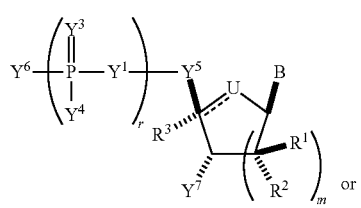
(Va)

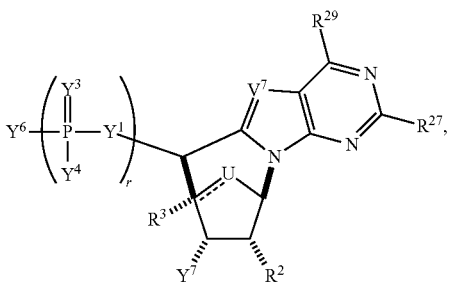
(Vb)

or a pharmaceutically acceptable salt or stereoisomer thereof, wherein B is as described herein (e.g., any one of (b1)-(b43)).

In other embodiments, the building block molecule, which may be incorporated into a polynucleotide has Formula (IXa)-(IXd):

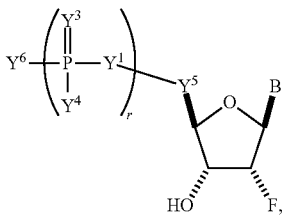
(IXa)

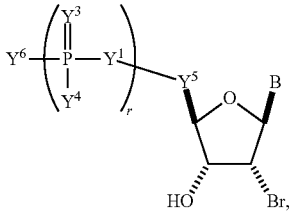
(IXb)

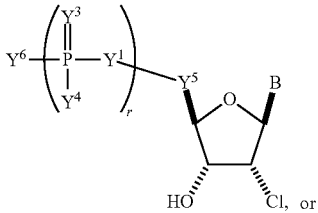
(IXc)

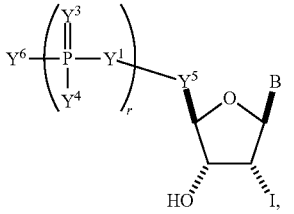
(IXd)

or a pharmaceutically acceptable salt or stereoisomer thereof, wherein B is as described herein (e.g., any one of (b1)-(b43)).

In particular embodiments, one of Formulas (IXa)-(IXd) is combined with an alternative uracil (e.g., any one of formulas (b1)-(b9), (b21)-(b23), and (b28)-(b31), such as formula (b1), (b8), (b28), (b29), or (b30)). In particular embodiments, one of Formulas (IXa)-(IXd) is combined with an alternative cytosine (e.g., any one of formulas (b10)-(b14), (b24), (b25), and (b32)-(b36), such as formula (b10) or (b32)).

In particular embodiments, one of Formulas (IXa)-(IXd) is combined with an alternative guanine (e.g., any one of formulas (b15)-(b17) and (b37)-(b40)).

In particular embodiments, one of Formulas (IXa)-(IXd) is combined with an alternative adenine (e.g., any one of formulas (b18)-(b20) and (b41)-(b43)).

In other embodiments, the building block molecule, which may be incorporated into a polynucleotide has Formula (IXe)-(IXg):

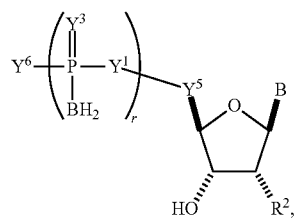
(IXe)

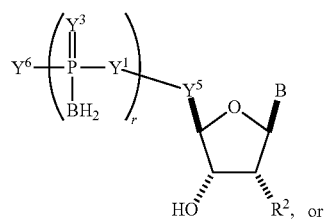
(IXf)

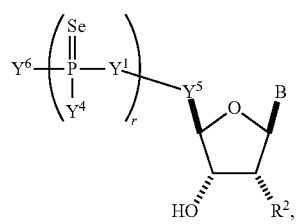
(IXg)

or a pharmaceutically acceptable salt or stereoisomer thereof, wherein B is as described herein (e.g., any one of (b1)-(b43)).

In particular embodiments, one of Formulas (IXe)-(IXg) is combined with an alternative uracil (e.g., any one of formulas (b1)-(b9), (b21)-(b23), and (b28)-(b31), such as formula (b1), (b8), (b28), (b29), or (b30)).

In particular embodiments, one of Formulas (IXe)-(IXg) is combined with an alternative cytosine (e.g., any one of formulas (b10)-(b14), (b24), (b25), and (b32)-(b36), such as formula (b10) or (b32)).

In particular embodiments, one of Formulas (IXe)-(IXg) is combined with an alternative guanine (e.g., any one of formulas (b15)-(b17) and (b37)-(b40)).

In particular embodiments, one of Formulas (IXe)-(IXg) is combined with an alternative adenine (e.g., any one of formulas (b18)-(b20) and (b41)-(b43)).

In other embodiments, the building block molecule, which may be incorporated into a polynucleotide has Formula (IXh)-(IXk):

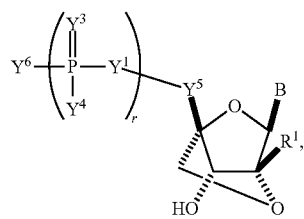
(IXh)

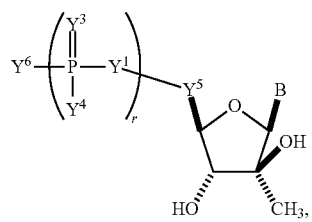
(IXi)

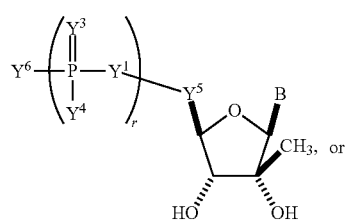
(IXj)

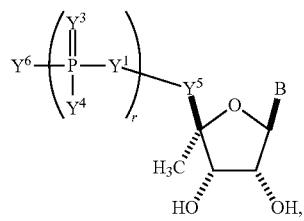
(IXk)

or a pharmaceutically acceptable salt or stereoisomer thereof, wherein B is as described herein (e.g., any one of (b1)-(b43)). In particular embodiments, one of Formulas (IXh)-(IXk) is combined with an alternative uracil (e.g., any one of formulas (b1)-(b9), (b21)-(b23), and (b28)-(b31), such as formula (b1), (b8), (b28), (b29), or (b30)). In particular embodiments, one of Formulas (IXh)-(IXk) is combined with an alternative cytosine (e.g., any one of formulas (b10)-(b14), (b24), (b25), and (b32)-(b36), such as formula (b10) or (b32)).

In particular embodiments, one of Formulas (IXh)-(IXk) is combined with an alternative guanine (e.g., any one of formulas (b15)-(b17) and (b37)-(b40)). In particular embodiments, one of Formulas (IXh)-(IXk) is combined with an alternative adenine (e.g., any one of formulas (b18)-(b20) and (b41)-(b43)).

In other embodiments, the building block molecule, which may be incorporated into a polynucleotide has Formula (IXl)-(IXr):

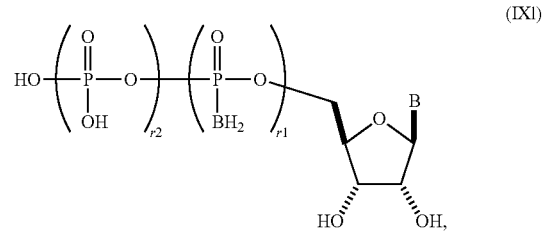
(IXl)

-continued

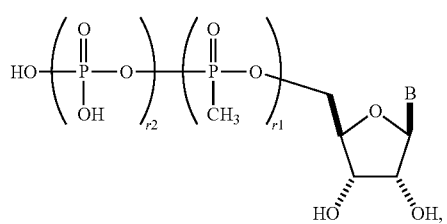 (IXm)

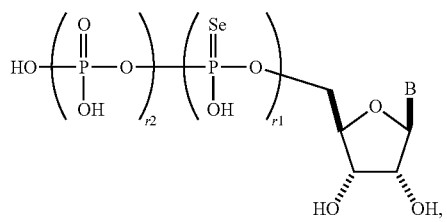 (IXn)

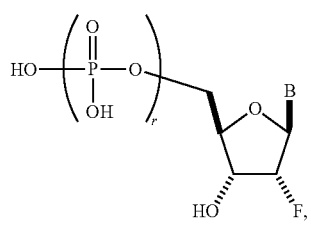 (IXo)

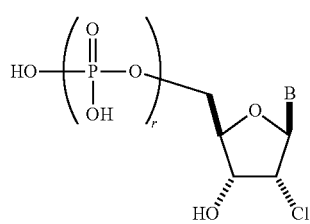 (IXp)

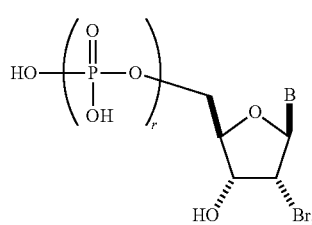 (IXq)

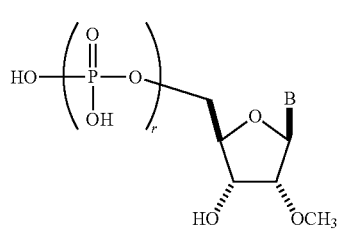 (IXr)

or a pharmaceutically acceptable salt or stereoisomer thereof, wherein each r1 and r2 is, independently, an integer from 0 to 5 (e.g., from 0 to 3, from 1 to 3, or from 1 to 5) and B is as described herein (e.g., any one of (b1)-(b43)).

In particular embodiments, one of Formulas (IXl)-(IXr) is combined with an alternative uracil (e.g., any one of formulas (b1)-(b9), (b21)-(b23), and (b28)-(b31), such as formula (b1), (b8), (b28), (b29), or (b30)).

In particular embodiments, one of Formulas (IXl)-(IXr) is combined with an alternative cytosine (e.g., any one of formulas (b10)-(b14), (b24), (b25), and (b32)-(b36), such as formula (b10) or (b32)).

In particular embodiments, one of Formulas (IXl)-(IXr) is combined with an alternative guanine (e.g., any one of formulas (b15)-(b17) and (b37)-(b40)). In particular embodiments, one of Formulas (IXl)-(IXr) is combined with an alternative adenine (e.g., any one of formulas (b18)-(b20) and (b41)-(b43)).

In some embodiments, the building block molecule, which may be incorporated into a polynucleotide can be selected from the group consisting of:

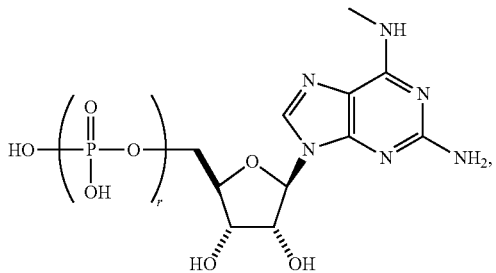 (BB-1)

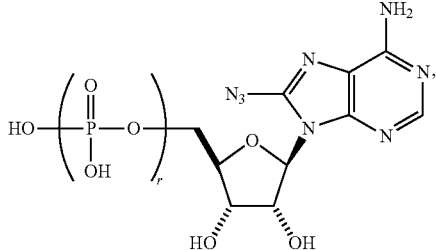 (BB-2)

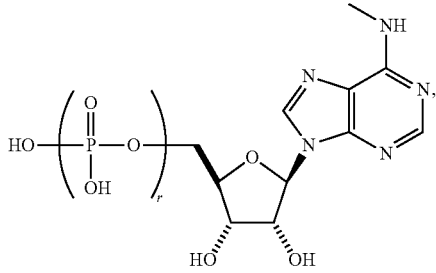 (BB-3)

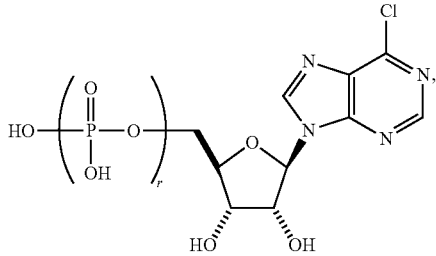 (BB-4)

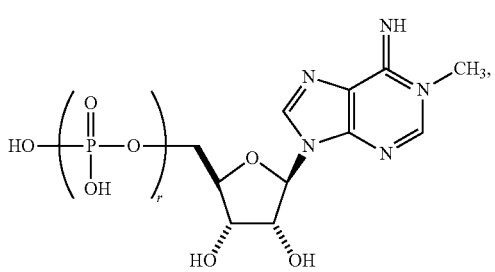 (BB-5)

(BB-6)
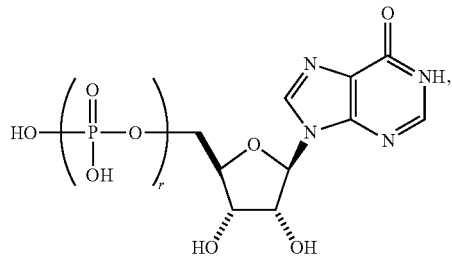
(BB-7)
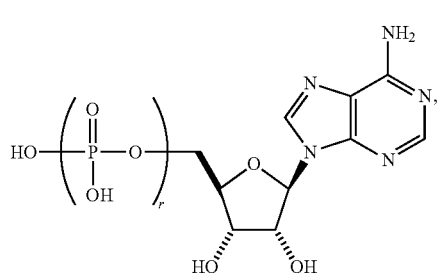
(BB-8)
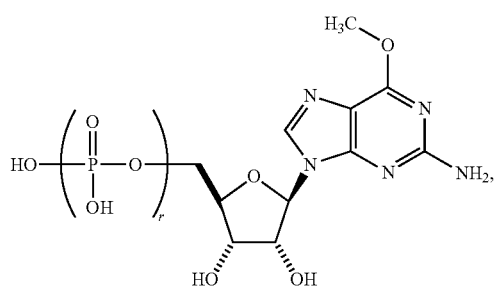
(BB-9)
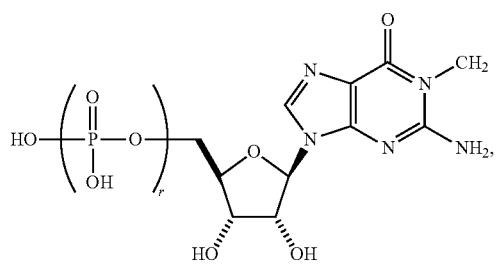
(BB-10)
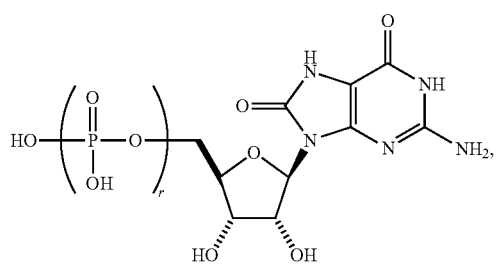
(BB-11)
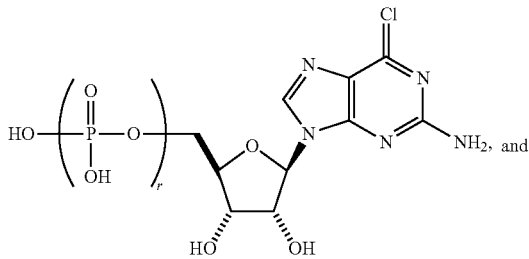
(BB-12)
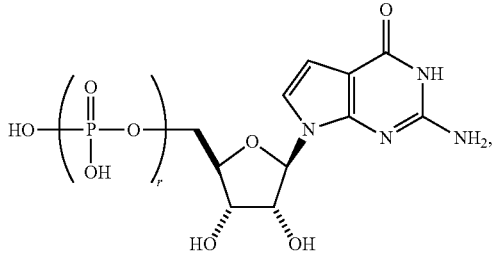
or a pharmaceutically acceptable salt or stereoisomer thereof, wherein each r is, independently, an integer from 0 to 5, (e.g., from 0 to 3, from 1 to 3, or from 1 to 5).
In some embodiments, the building block molecule, which may be incorporated into a polynucleotide can be selected from the group consisting of:
(BB-13)
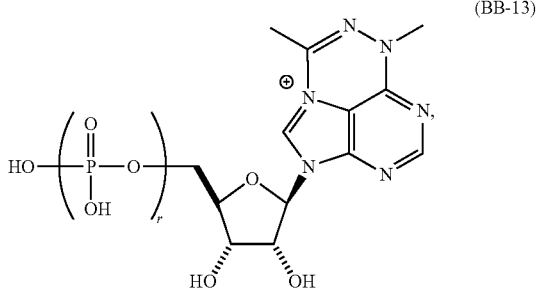
(BB-14)
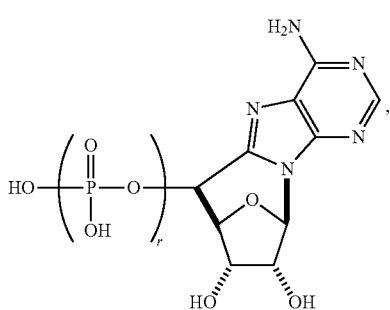
(BB-15)
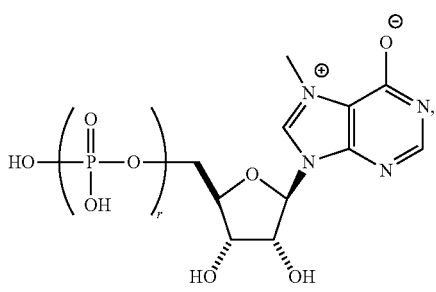

-continued

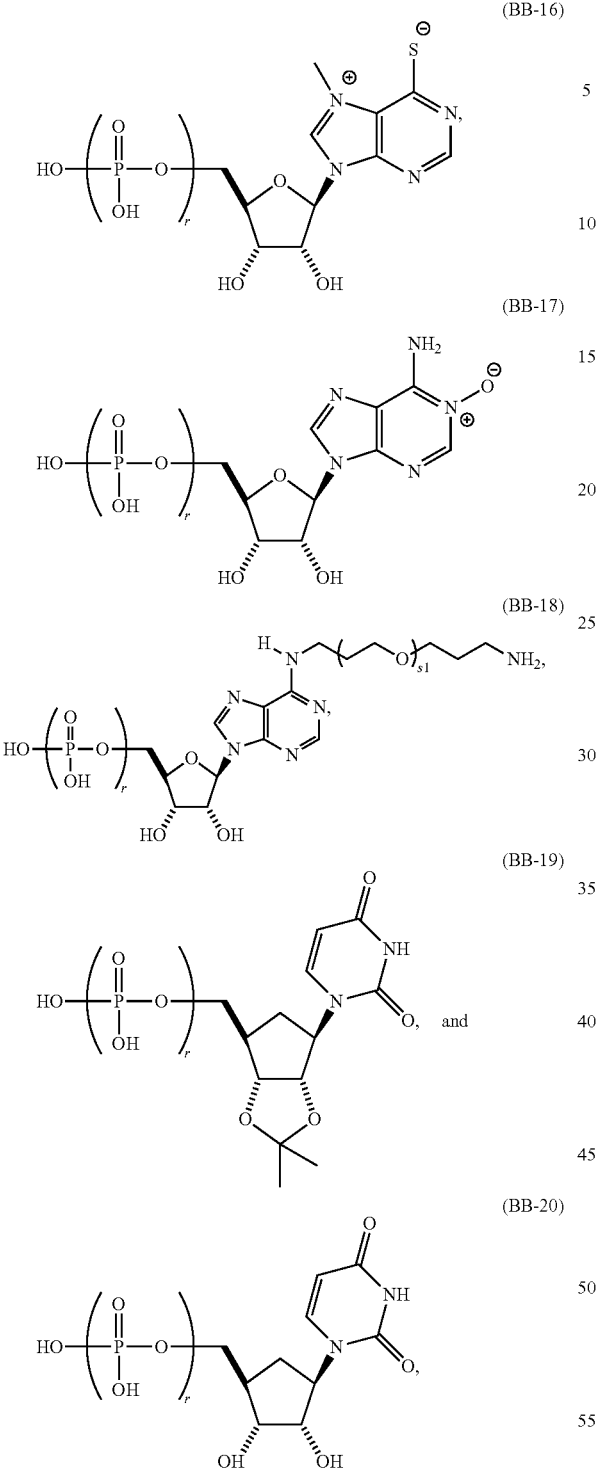

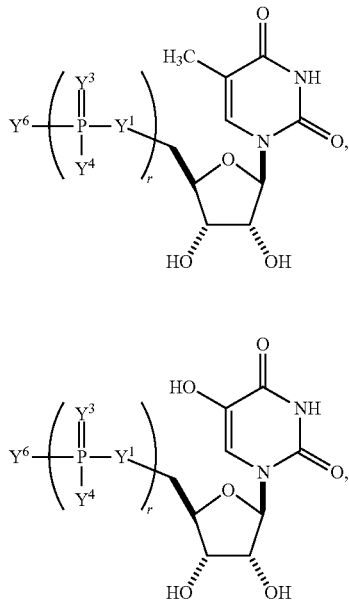

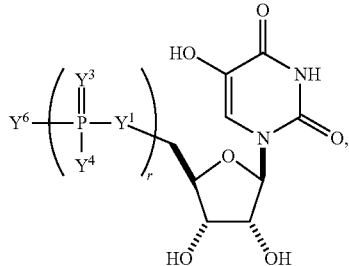

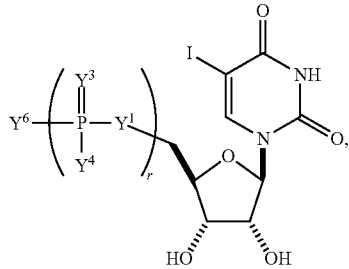

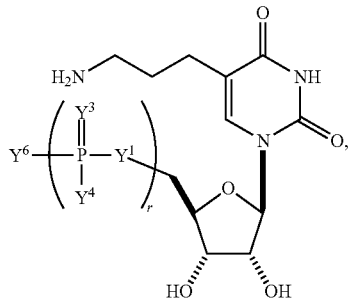

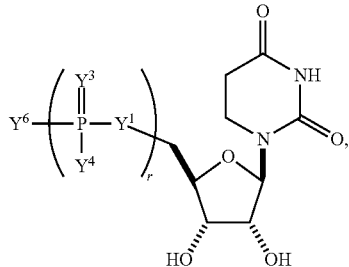

or a pharmaceutically acceptable salt or stereoisomer thereof, wherein each r is, independently, an integer from 0 to 5 (e.g., from 0 to 3, from 1 to 3, or from 1 to 5) and s1 is as described herein.

In some embodiments, the building block molecule, which may be incorporated into a nucleic acid (e.g., RNA, mRNA, polynucleotide), is an alternative uridine (e.g., selected from the group consisting of:

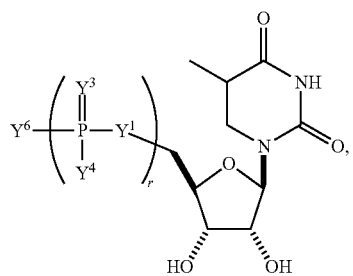
(BB-26)
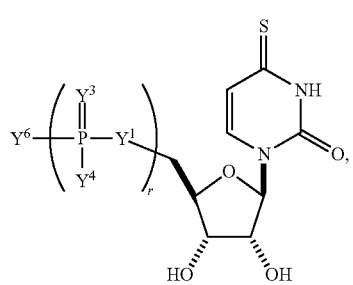
(BB-27)
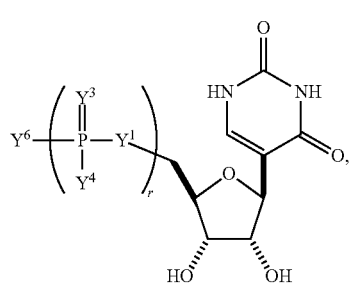
(BB-28)
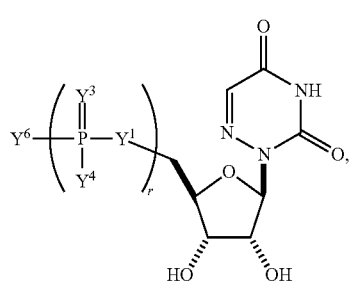
(BB-29)
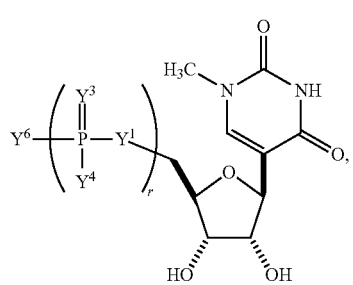
(BB-30)
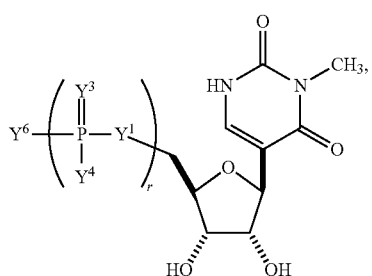
(BB-31)
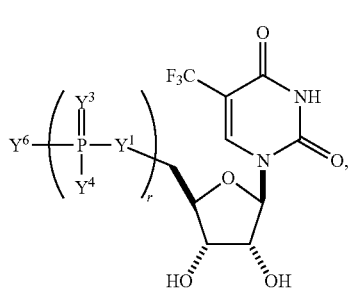
(BB-32)
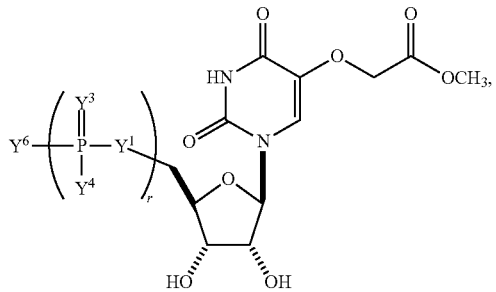
(BB-33)
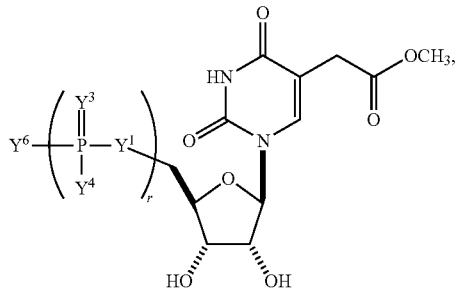
(BB-34)
(BB-35)

(BB-36)
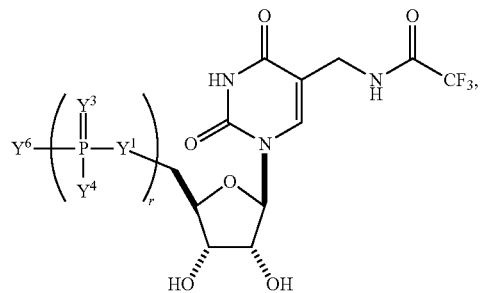
(BB-37)
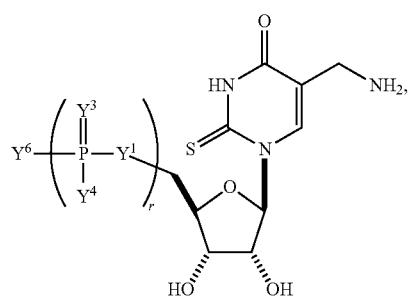
(BB-38)
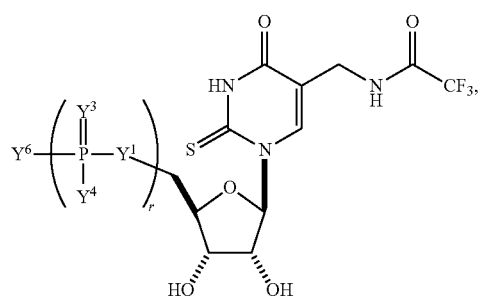
(BB-39)
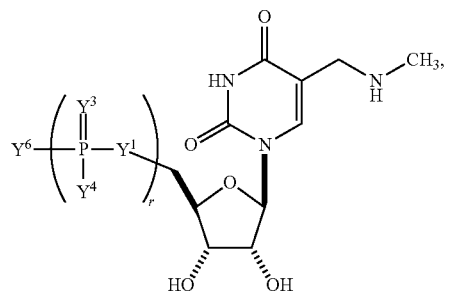
(BB-40)
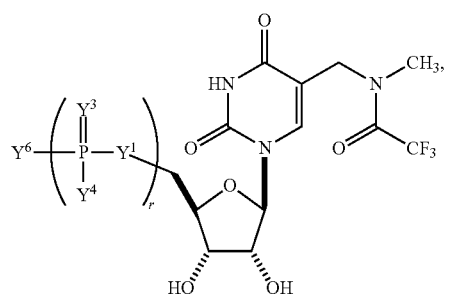
(BB-41)
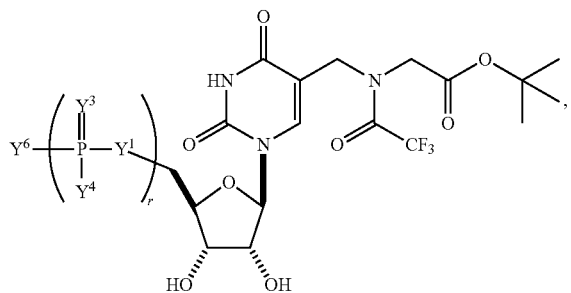
(BB-42)
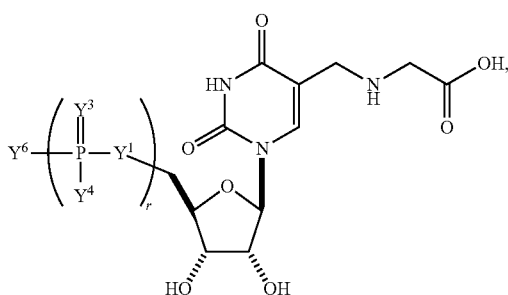
(BB-43)
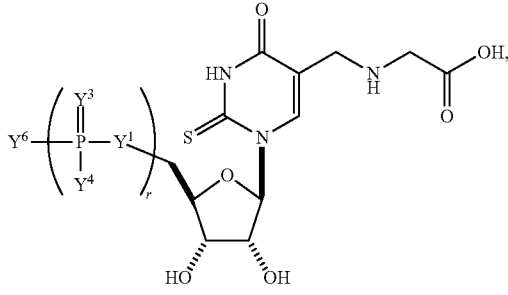
(BB-44)
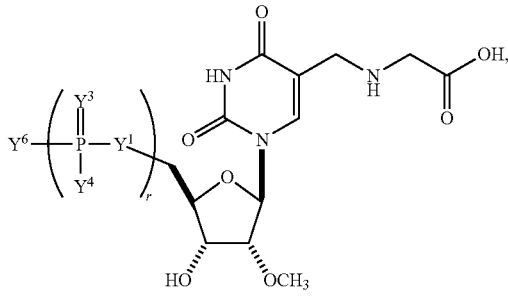
(BB-45)
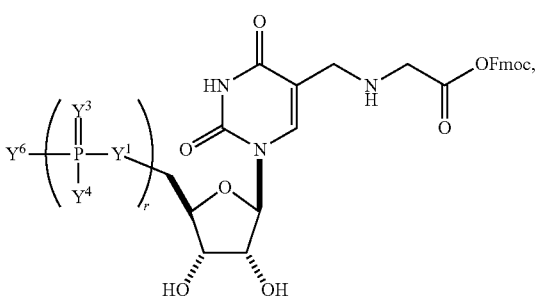

(BB-46)
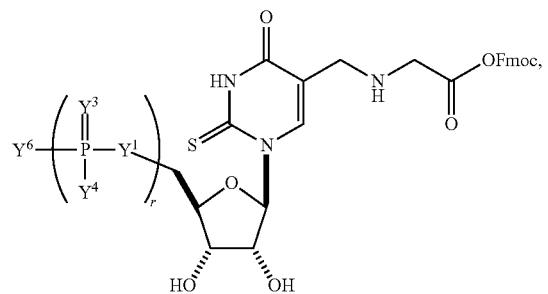
(BB-47)
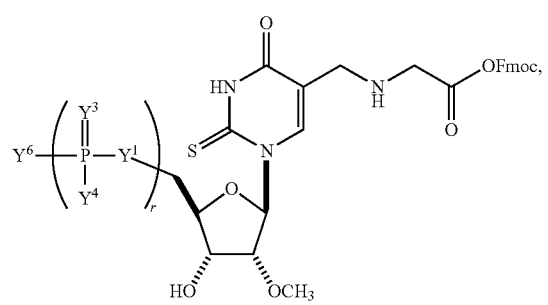
(BB-48)
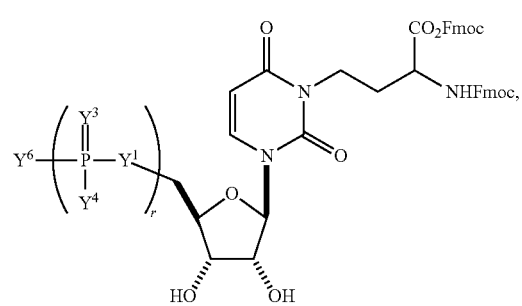
(BB-49)
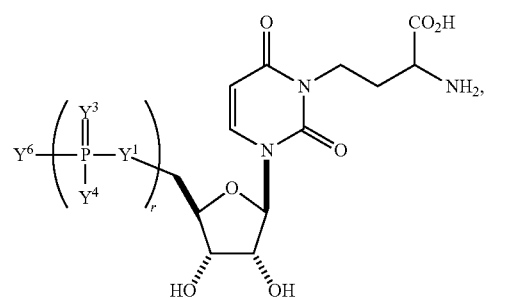
(BB-50)
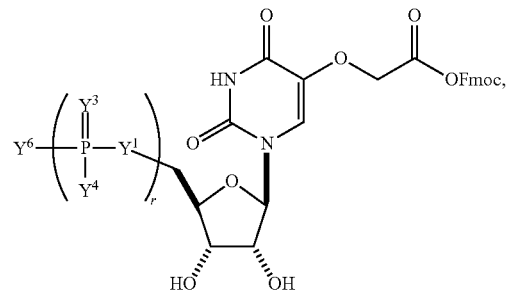
(BB-51)
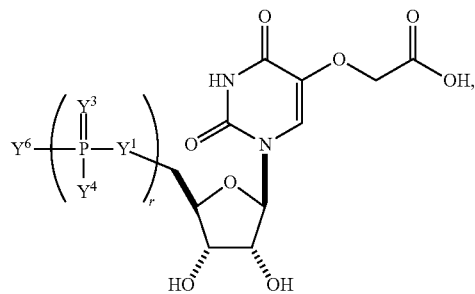
(BB-52)
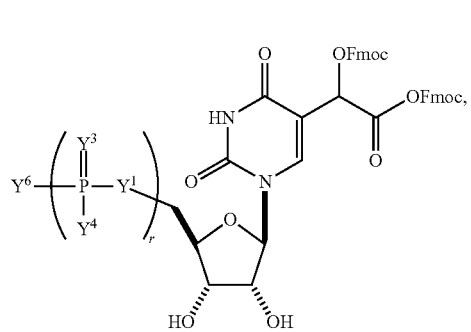
(BB-53)
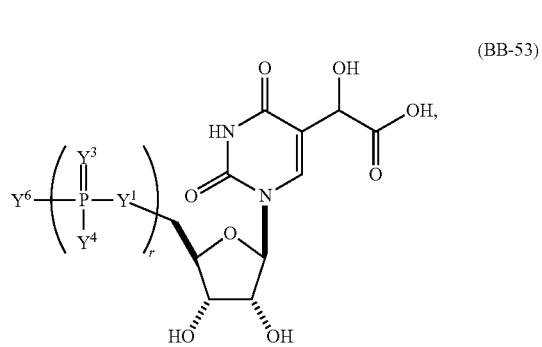
(BB-54)
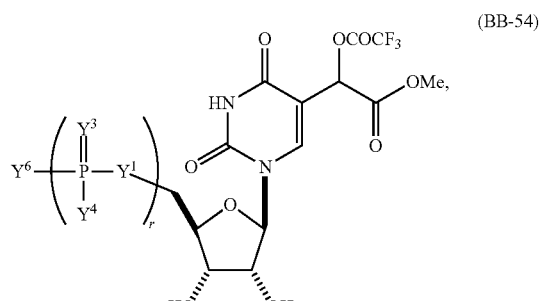
(BB-55)
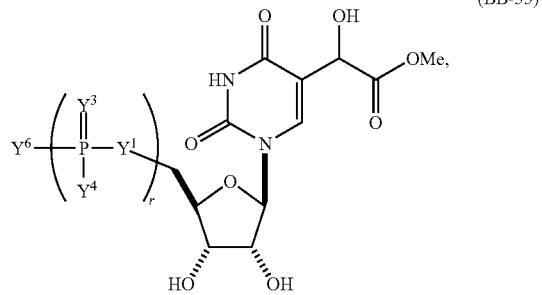

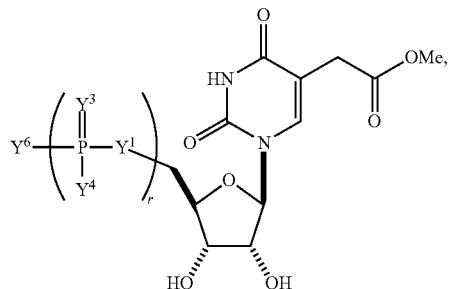 (BB-56)
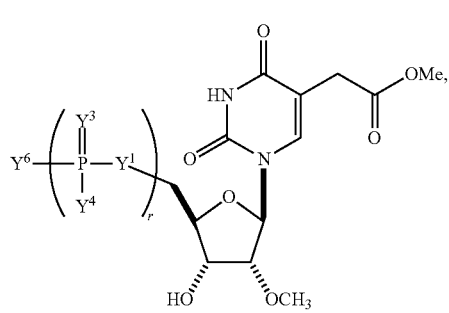 (BB-57)
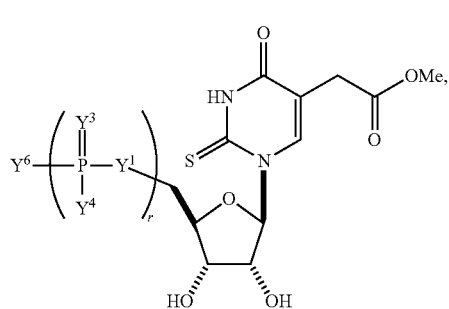 (BB-58)
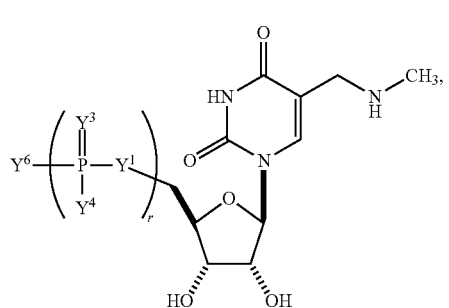 (BB-59)
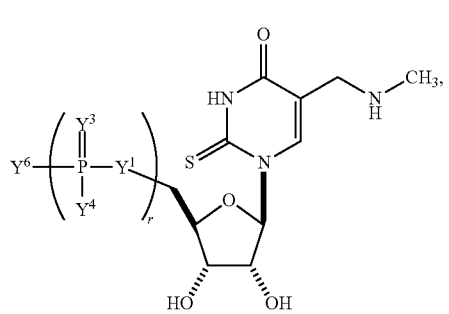 (BB-60)
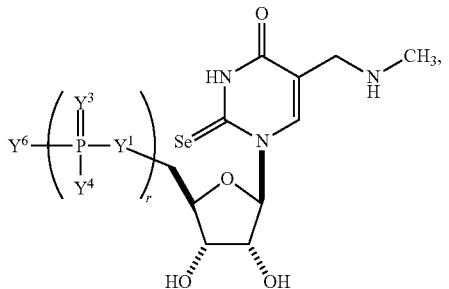 (BB-61)
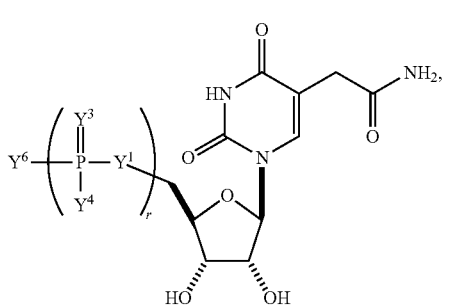 (BB-62)
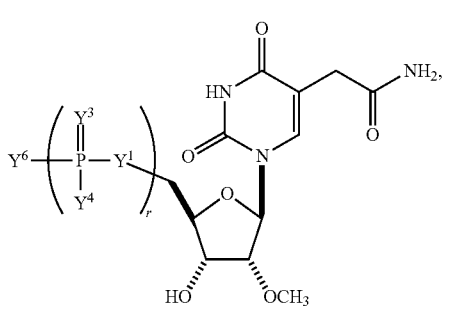 (BB-63)
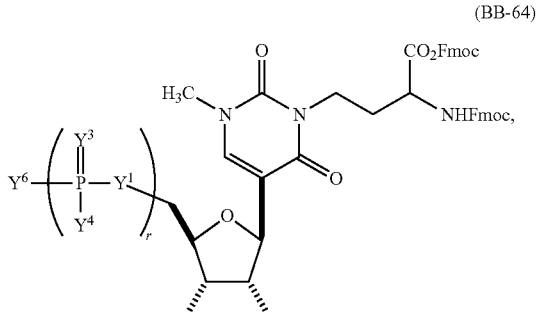 (BB-64)
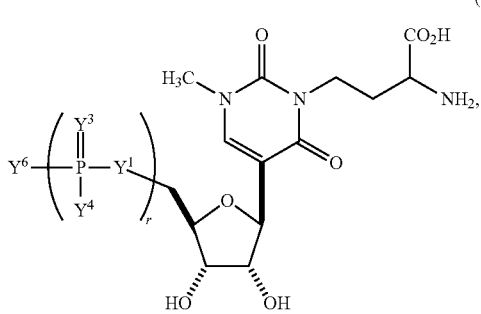 (BB-65)

(BB-66)
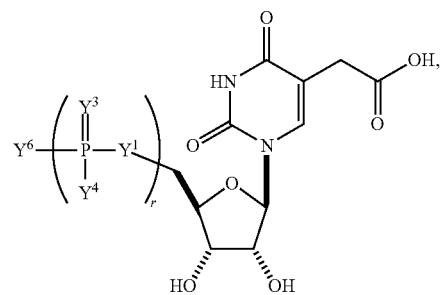
(BB-67)
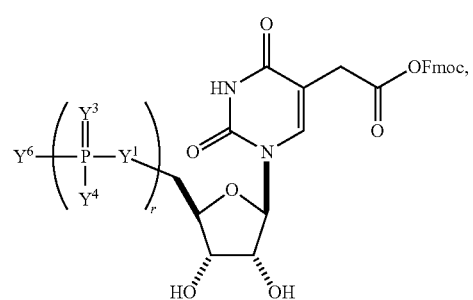
(BB-68)
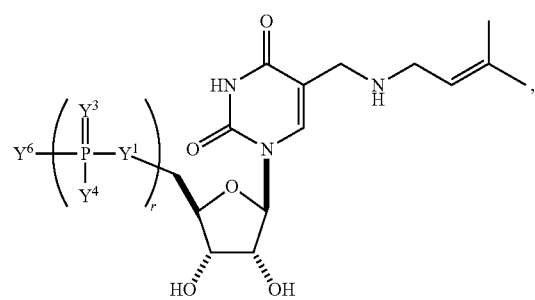
(BB-69)
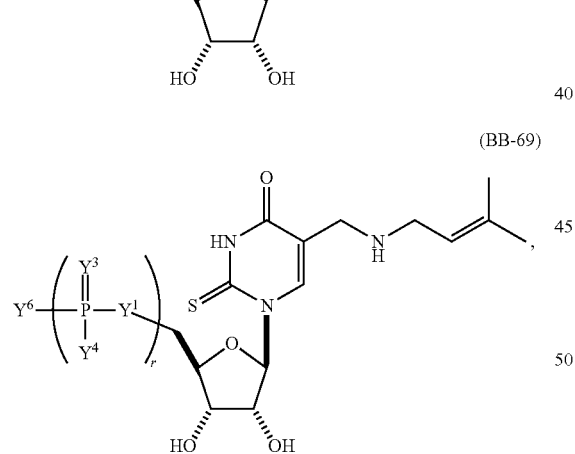
(BB-70)
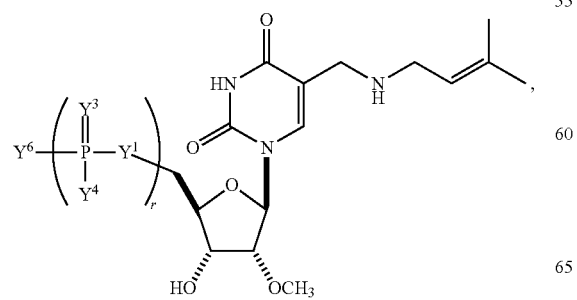
(BB-71)
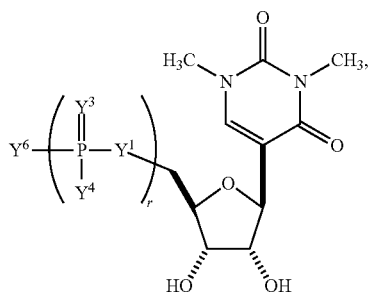
(BB-72)
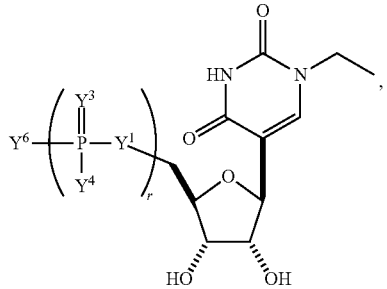
(BB-73)
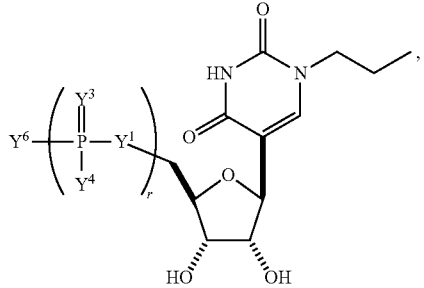
(BB-74)
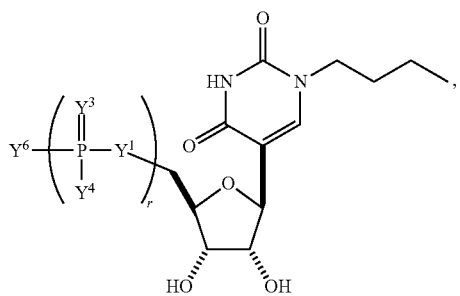
(BB-75)
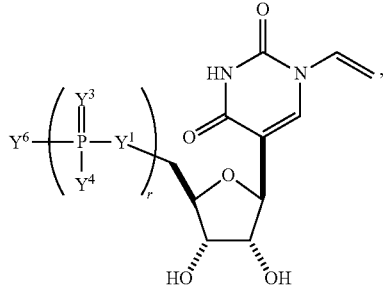

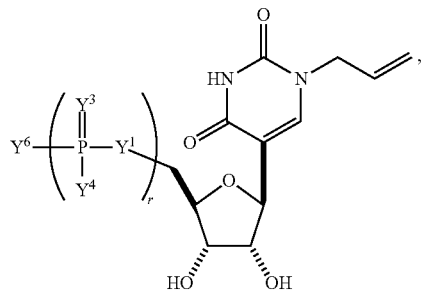
(BB-76)
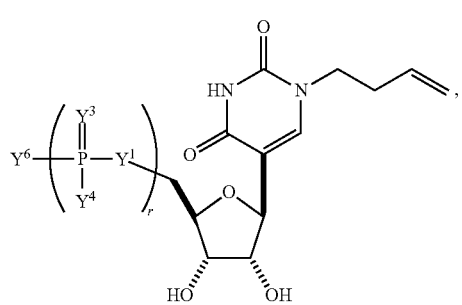
(BB-77)
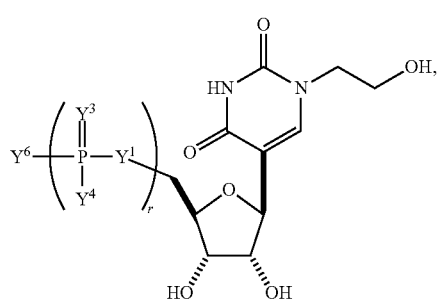
(BB-78)
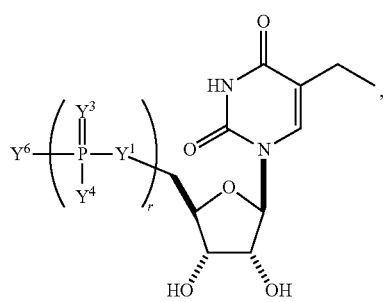
(BB-79)
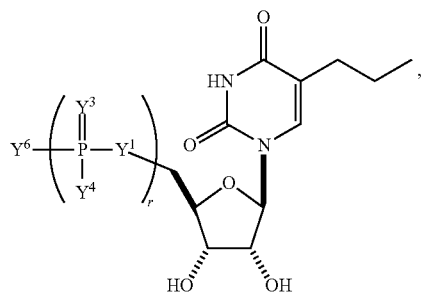
(BB-80)
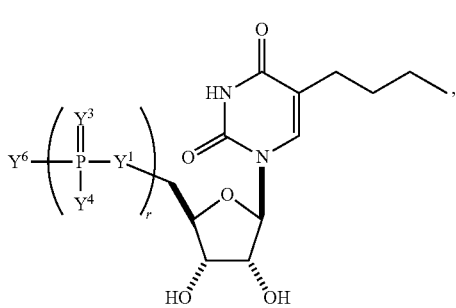
(BB-81)
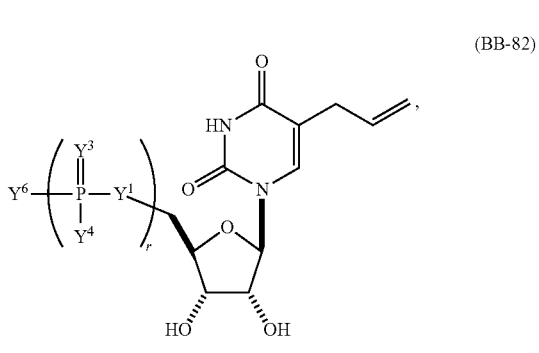
(BB-82)
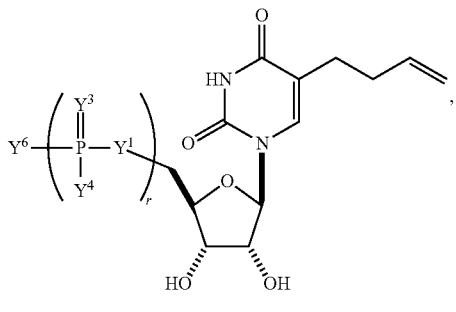
(BB-83)
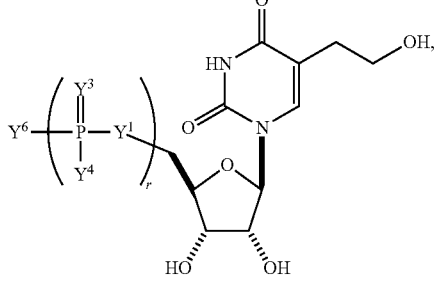
(BB-84)
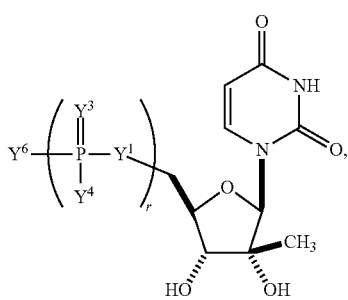
(BB-85)

(BB-86)
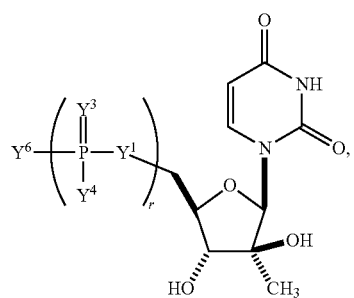
(BB-87)
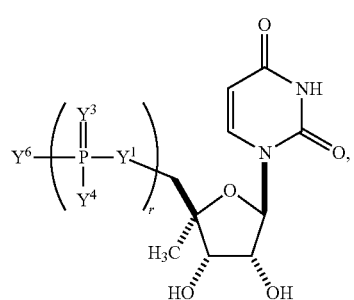
(BB-88)
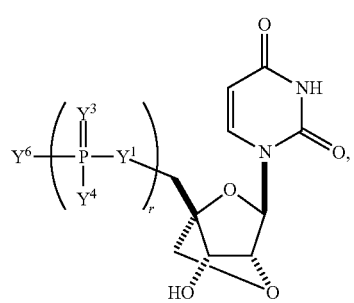
(BB-89)
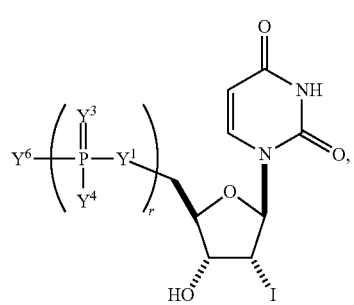
(BB-90)
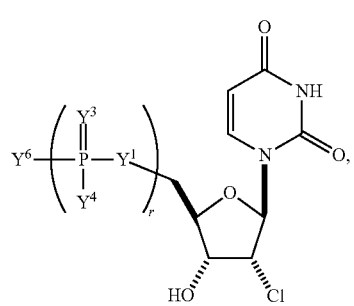
(BB-91)
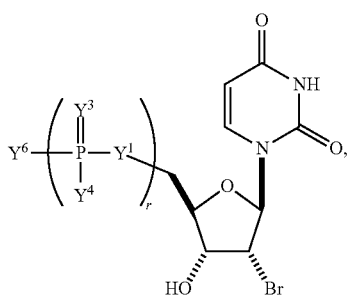
(BB-92)
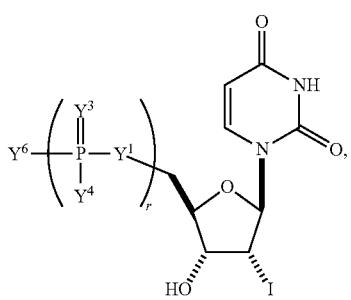
(BB-93)
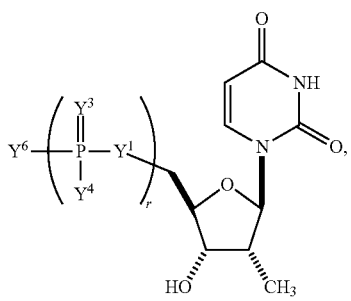
(BB-94)
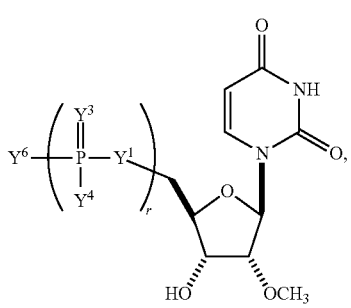
(BB-95)
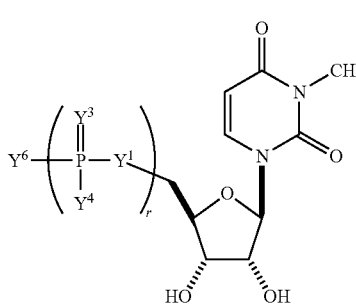

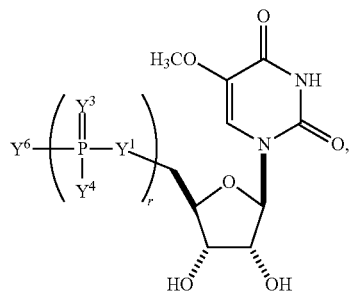
(BB-96)
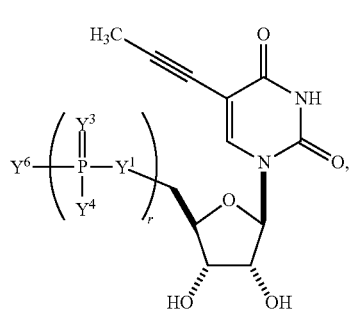
(BB-97)
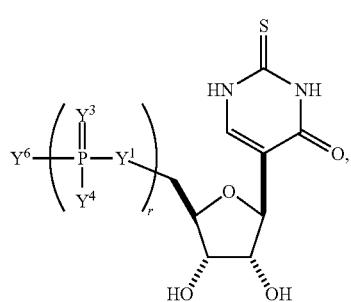
(BB-98)
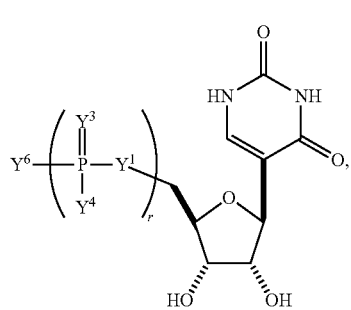
(BB-99)
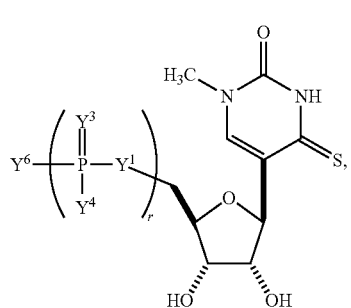
(BB-100)
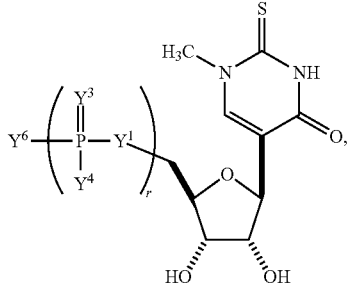
(BB-101)
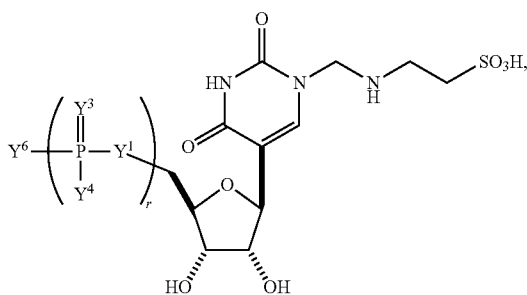
(BB-102)
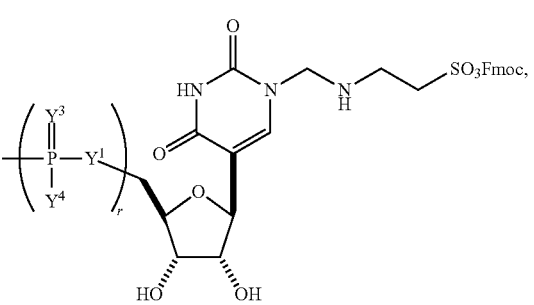
(BB-103)
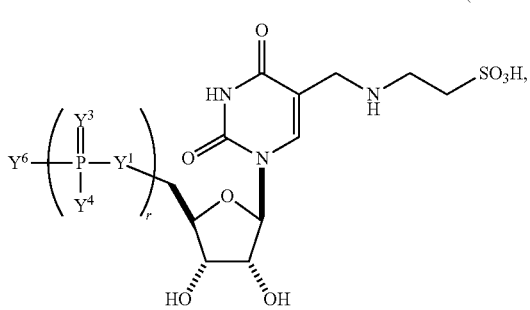
(BB-104)
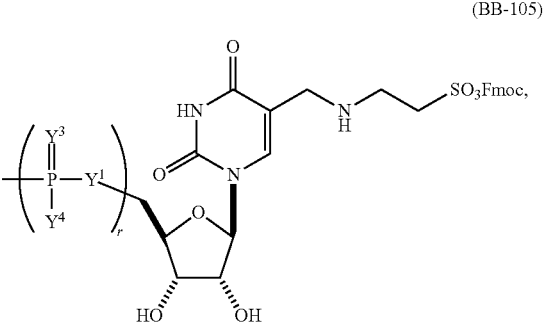
(BB-105)

(BB-106)
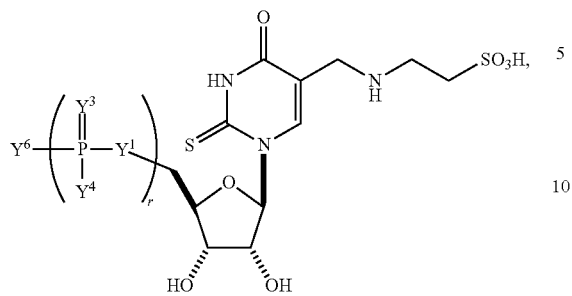
(BB-111)
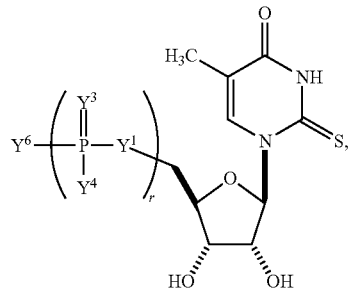
(BB-107)
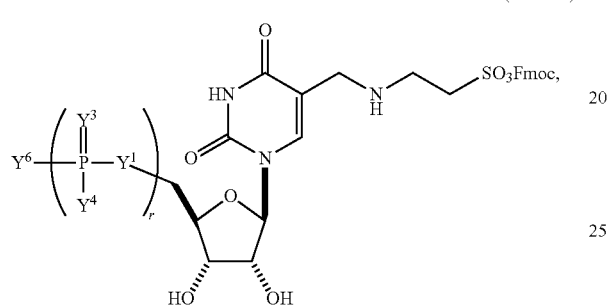
(BB-112)
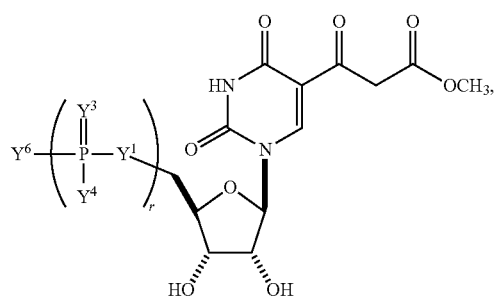
(BB-108)
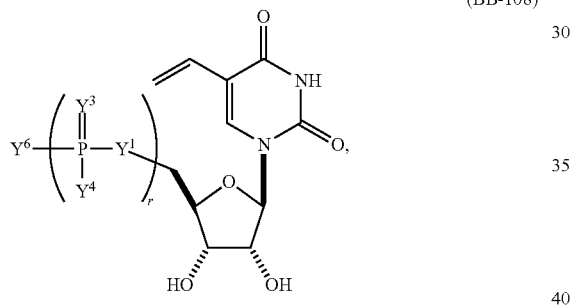
(BB-113)
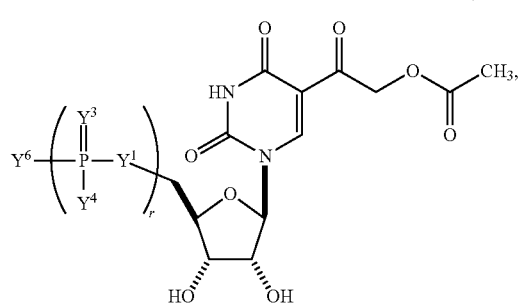
(BB-109)
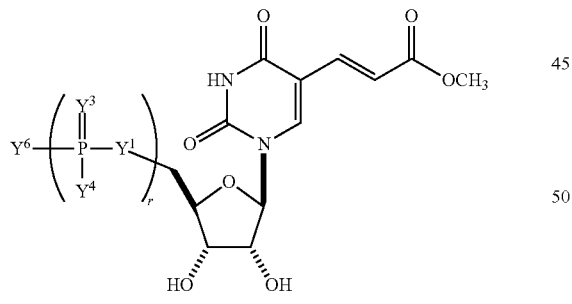
(BB-114)
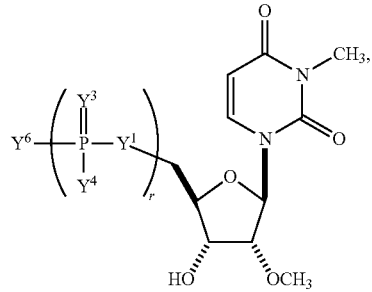
(BB-110)
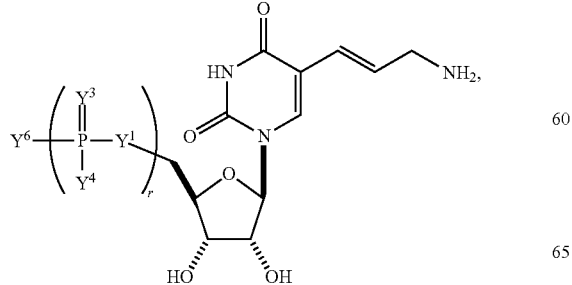
(BB-115)
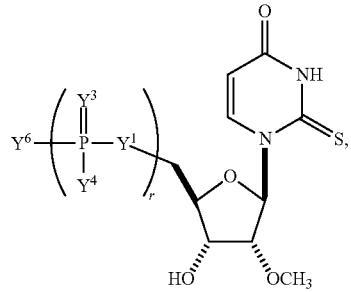

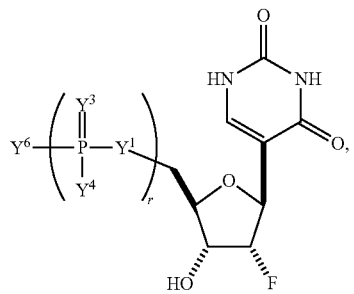
(BB-116)
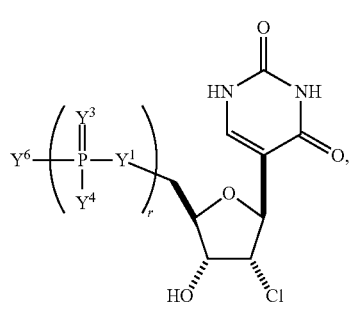
(BB-117)
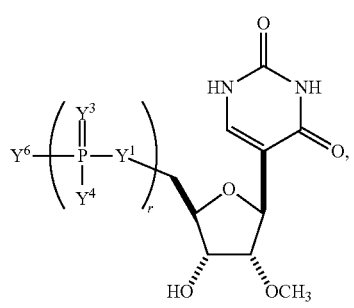
(BB-118)
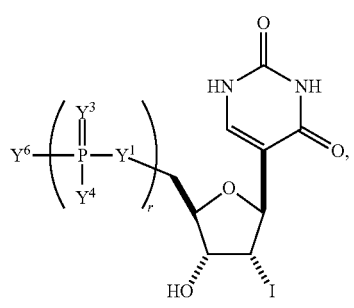
(BB-119)
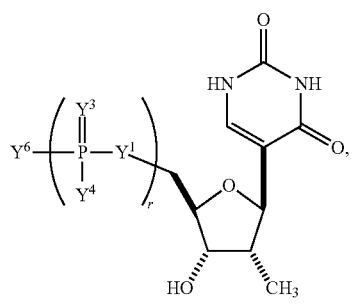
(BB-120)
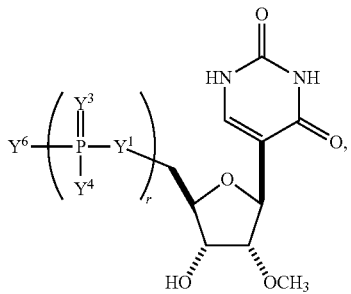
(BB-121)
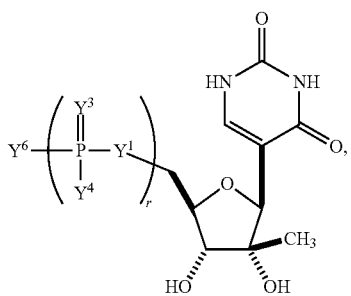
(BB-122)
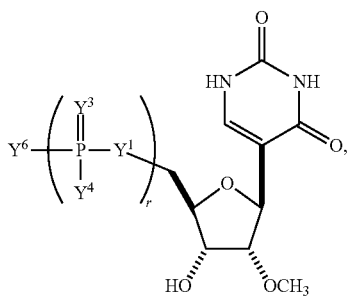
(BB-123)
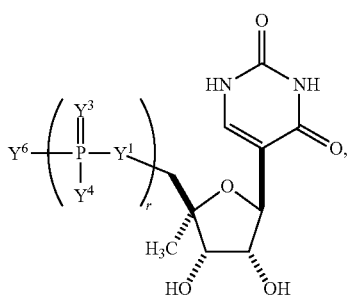
(BB-124)
and
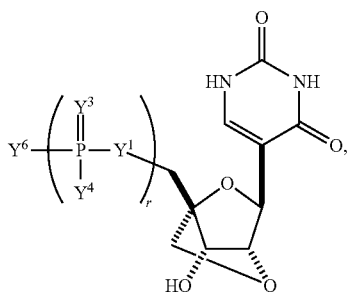
(BB-125)
or a pharmaceutically acceptable salt or stereoisomer thereof, wherein $Y^1$, $Y^3$, $Y^4$, $Y^6$, and r are as described herein (e.g., each r is, independently, an integer from 0 to 5, such as from 0 to 3, from 1 to 3, or from 1 to 5)).

In some embodiments, the building block molecule, which may be incorporated into a polynucleotide is an alternative cytidine (e.g., selected from the group consisting of:
(BB-126)
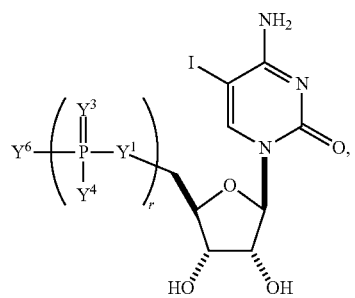
(BB-127)
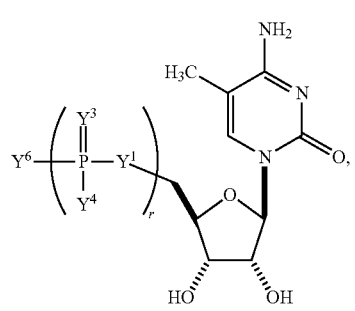
(BB-128)
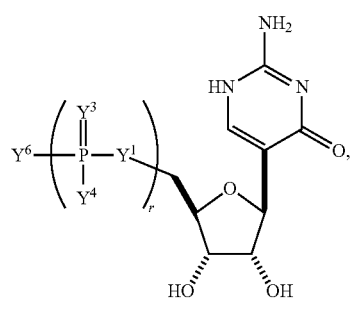
(BB-129)
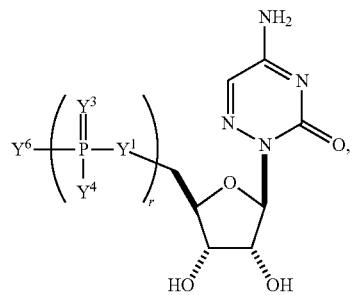
(BB-130)
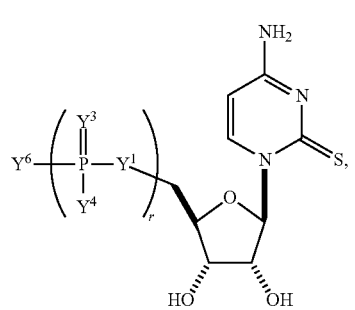
-continued
(BB-131)
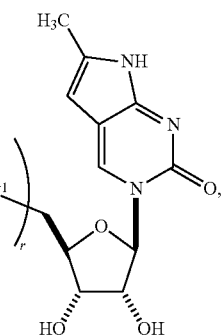
(BB-132)
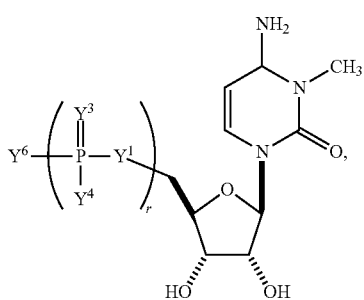
(BB-133)
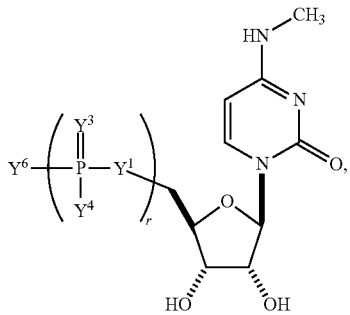
(BB-134)
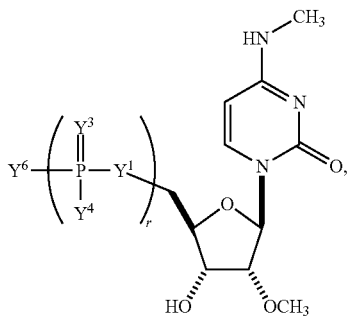
(BB-135)
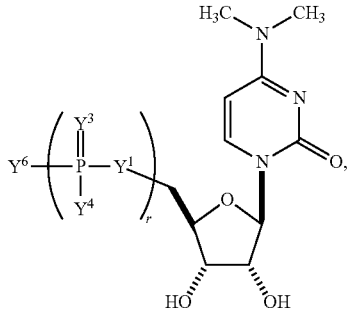

(BB-136) 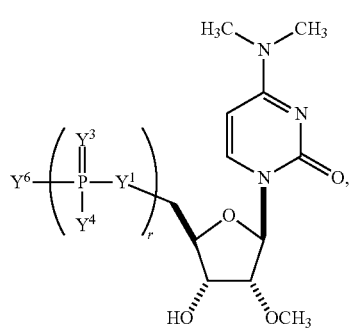
(BB-137) 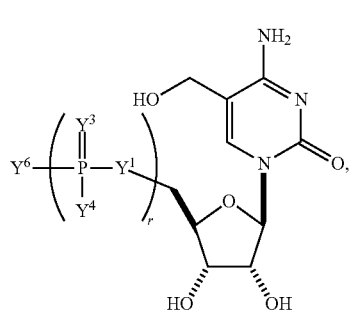
(BB-138) 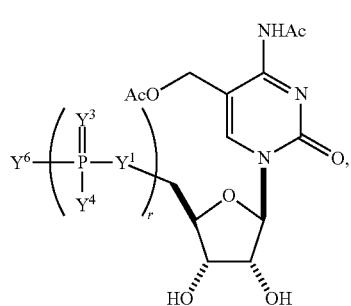
(BB-139) 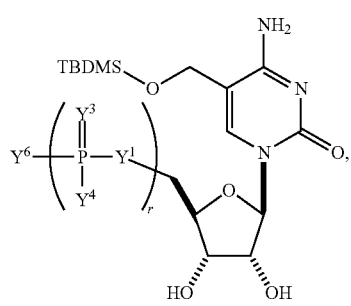
(BB-140) 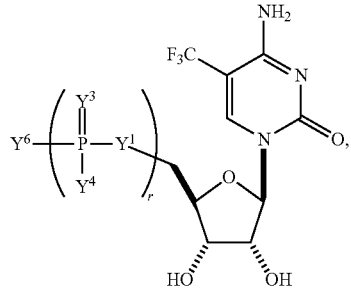
(BB-141) 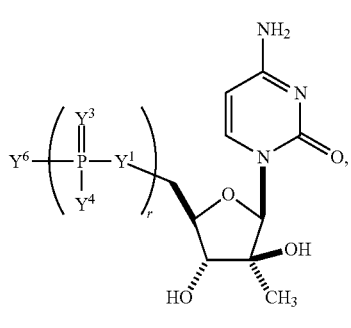
(BB-142) 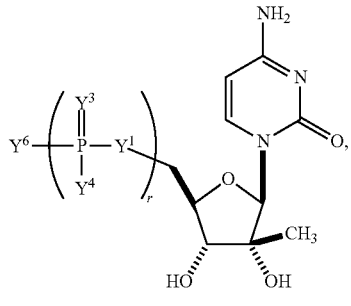
(BB-143) 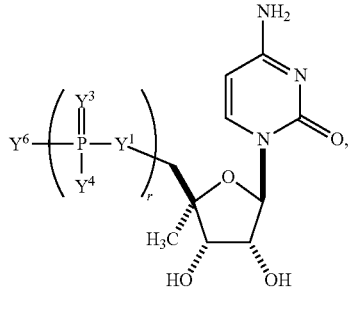
(BB-144) 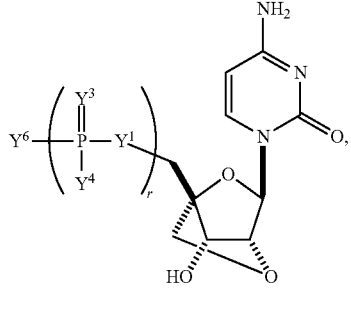
(BB-145) 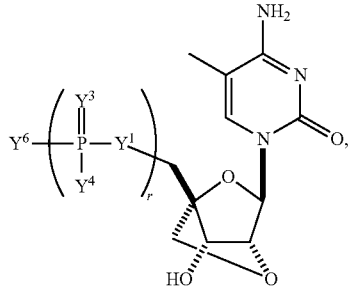

(BB-146)
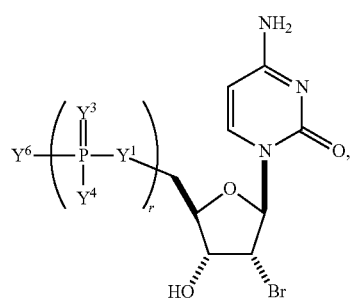
(BB-147)
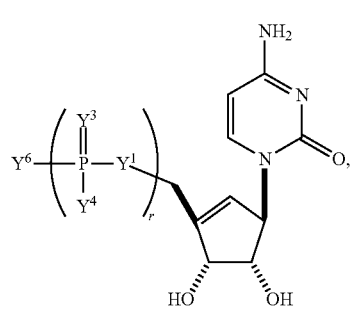
(BB-148)
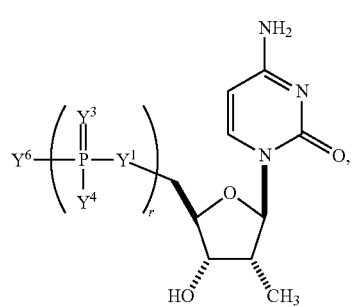
(BB-149)
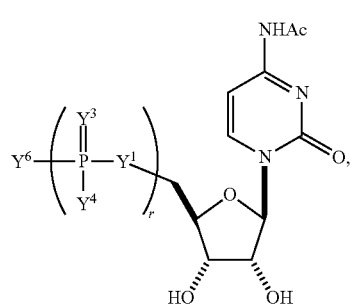
(BB-150)
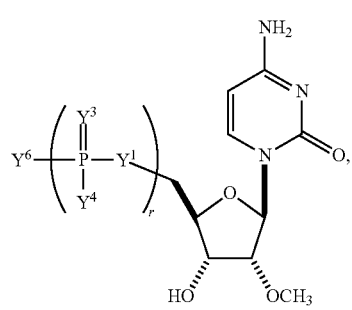
(BB-151)
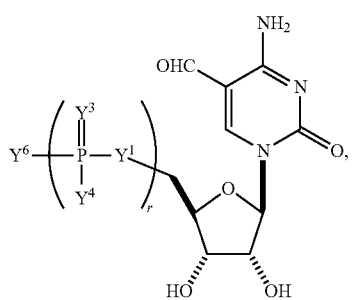
(BB-152)
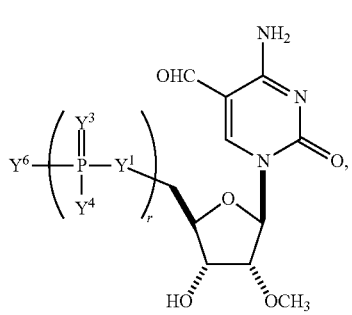
(BB-153)
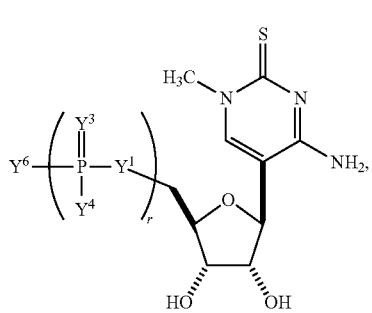
(BB-154)
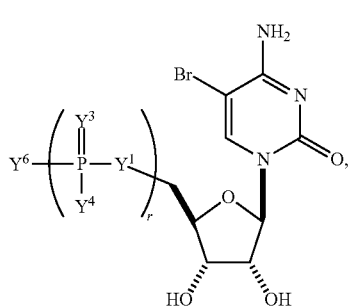
(BB-155)
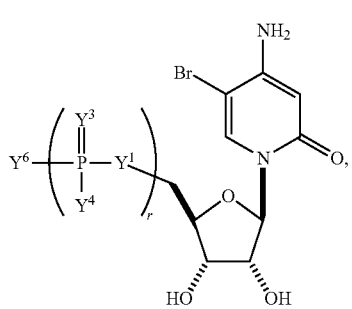

(BB-156)
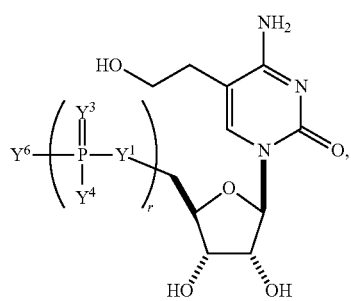

(BB-157)
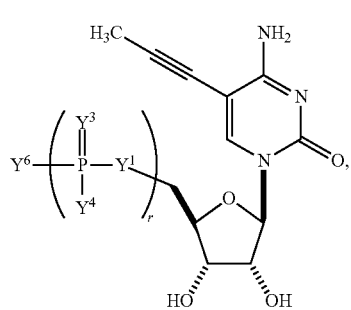

(BB-158)
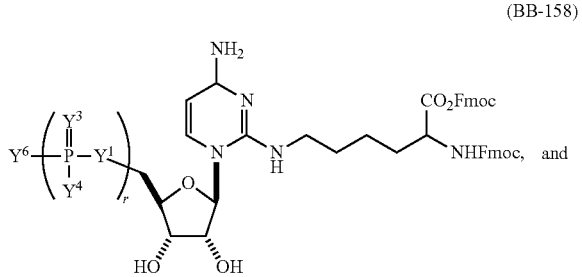

(BB-159)
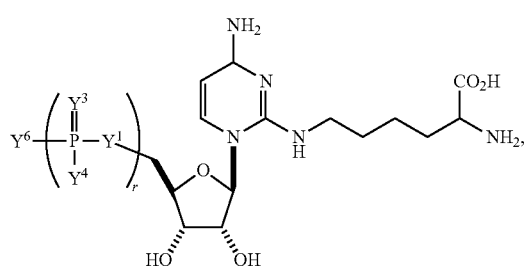

or a pharmaceutically acceptable salt or stereoisomer thereof, wherein $Y^1$, $Y^3$, $Y^4$, $Y^6$, and r are as described herein (e.g., each r is, independently, an integer from 0 to 5, such as from 0 to 3, from 1 to 3, or from 1 to 5)). For example, the building block molecule, which may be incorporated into a polynucleotide can be:

(BB-160)
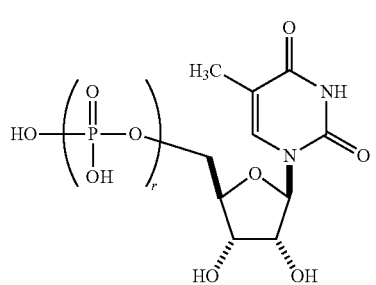
or (BB-161)
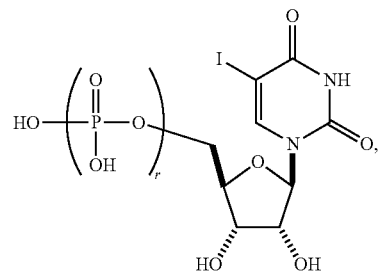

or a pharmaceutically acceptable salt or stereoisomer thereof, wherein each r is, independently, an integer from 0 to 5 (e.g., from 0 to 3, from 1 to 3, or from 1 to 5).

In some embodiments, the building block molecule, which may be incorporated into a polynucleotide is an alternative adenosine (e.g., selected from the group consisting of:

(BB-162)
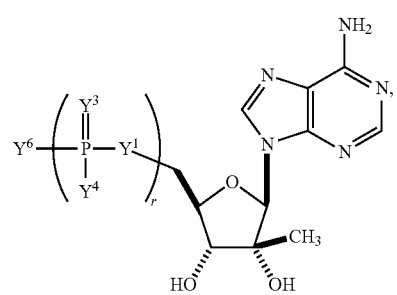

(BB-163)
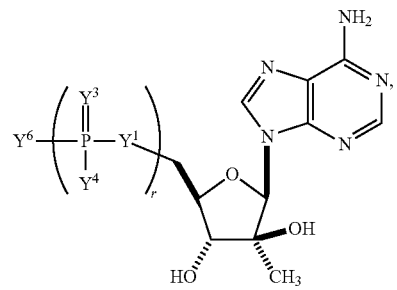

(BB-164)
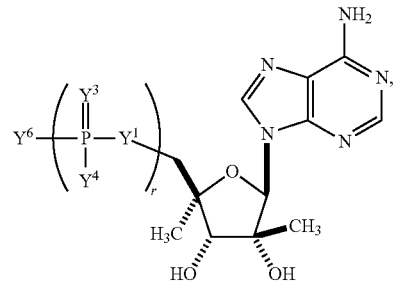

(BB-165)
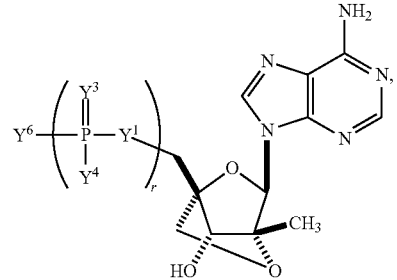

(BB-166)
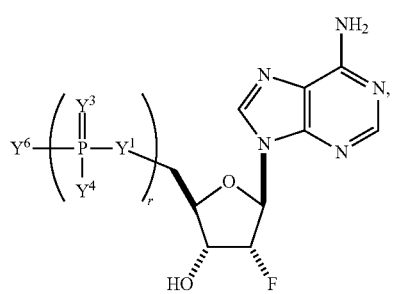
(BB-167)
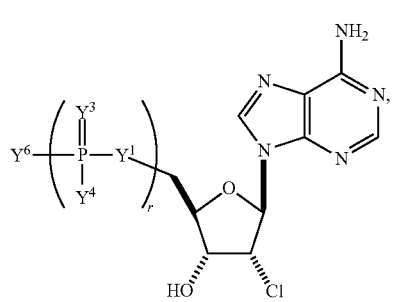
(BB-168)
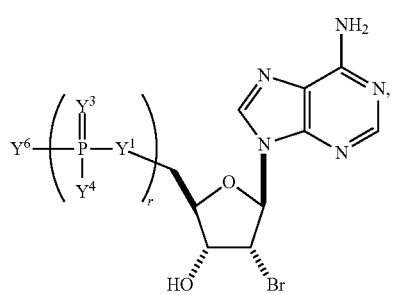
(BB-169)
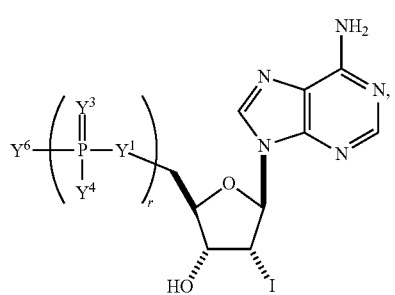
(BB-170)
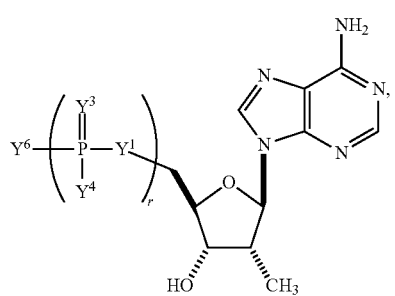
(BB-171)
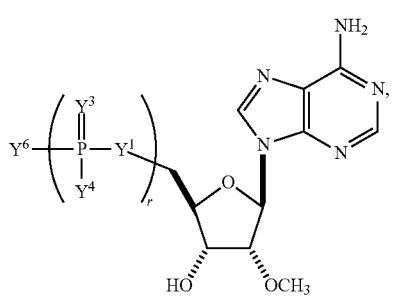
(BB-172)
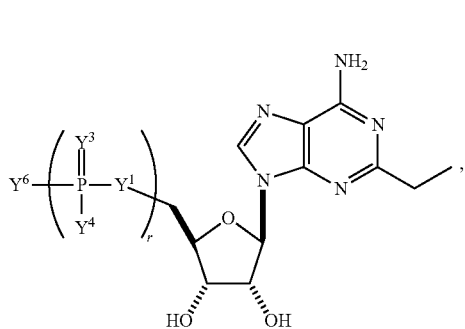
(BB-173)
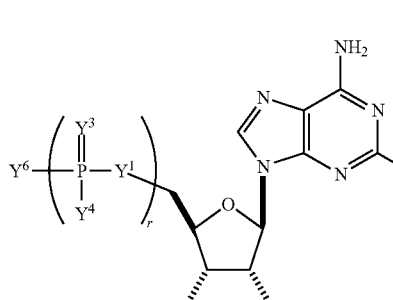
(BB-174)
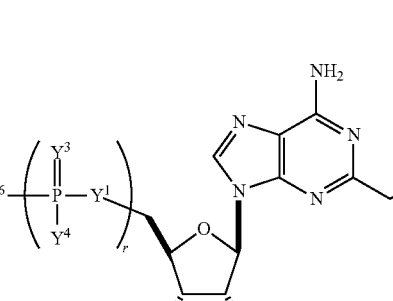
(BB-175)
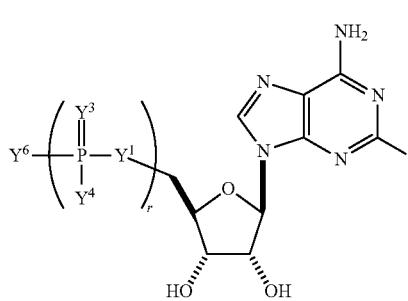

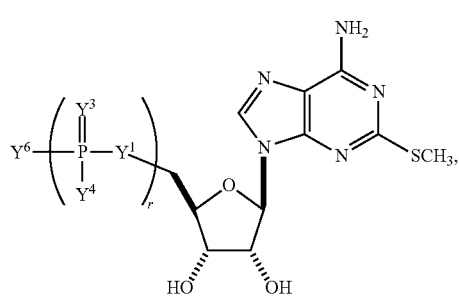
(BB-176)
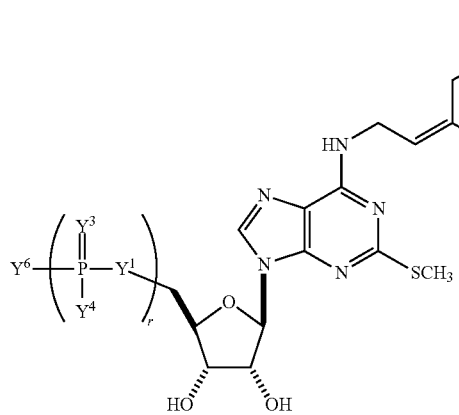
(BB-177)
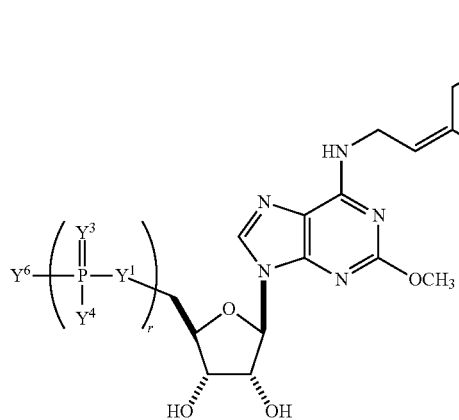
(BB-178)
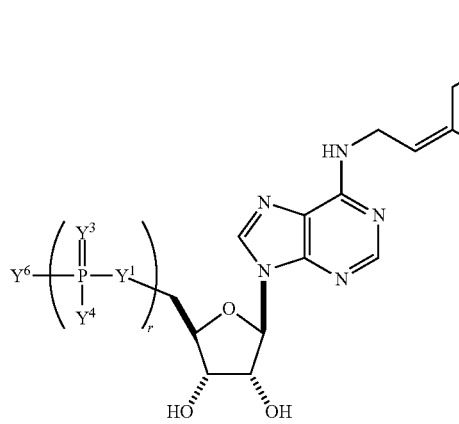
(BB-179)
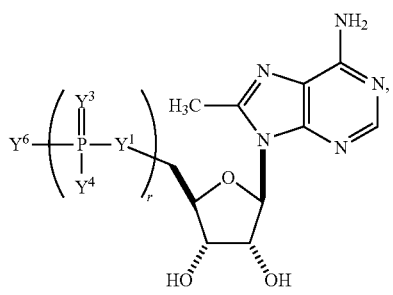
(BB-180)
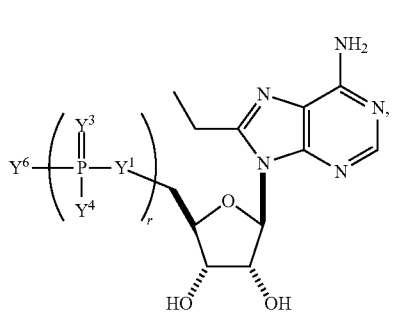
(BB-181)
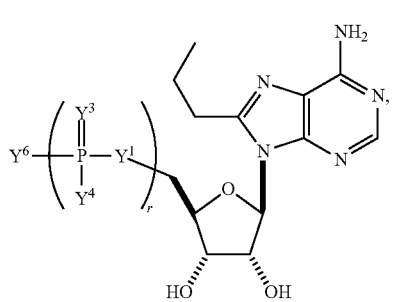
(BB-182)
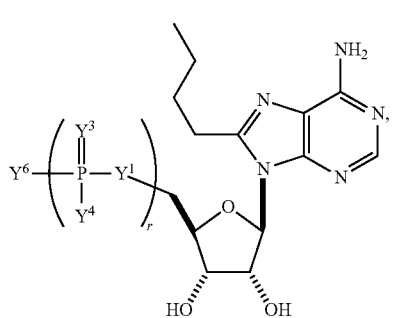
(BB-183)
(BB-184)

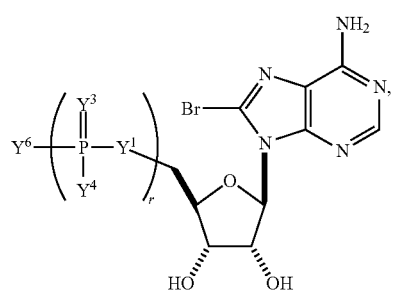 (BB-185)
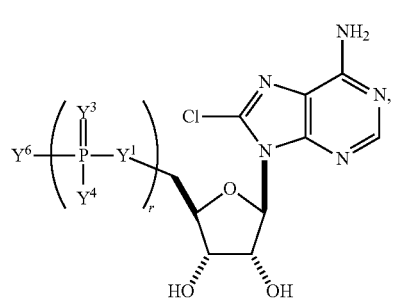 (BB-186)
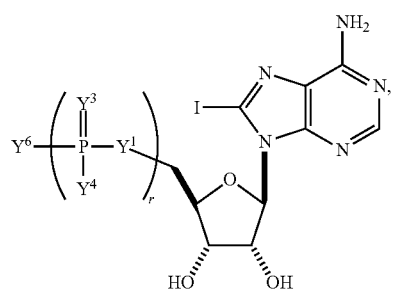 (BB-187)
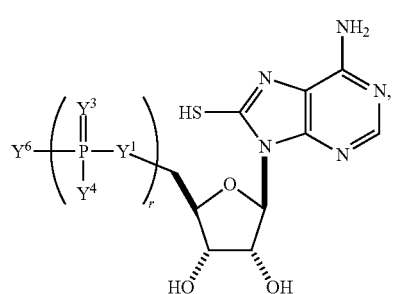 (BB-188)
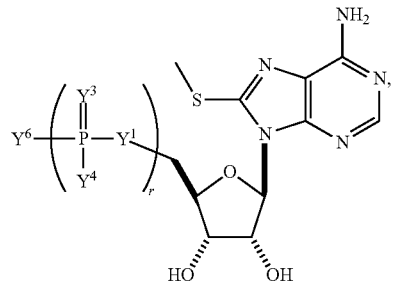 (BB-189)
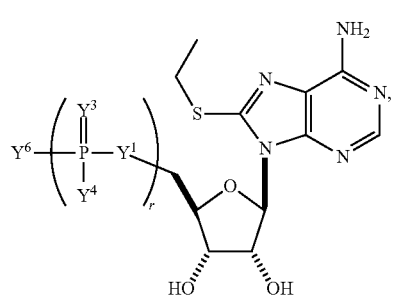 (BB-190)
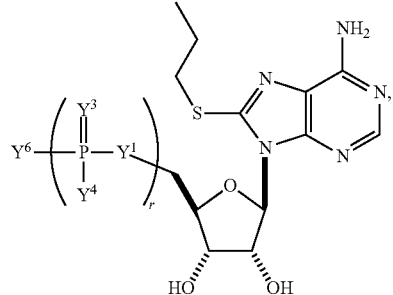 (BB-191)
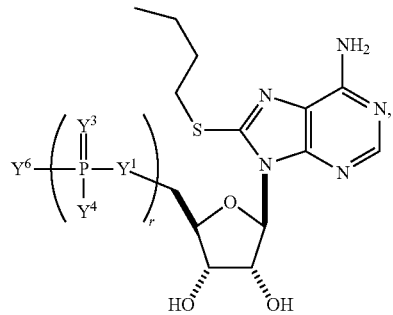 (BB-192)
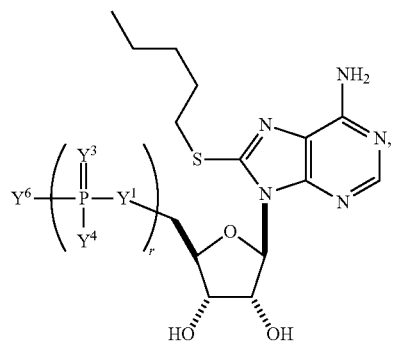 (BB-193)
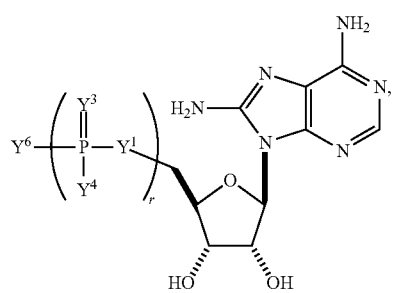 (BB-194)

(BB-195)
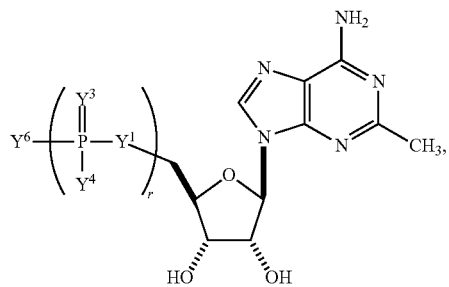

(BB-196)
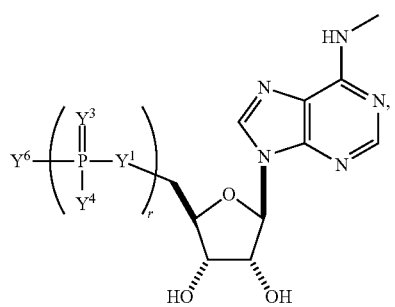

(BB-197)
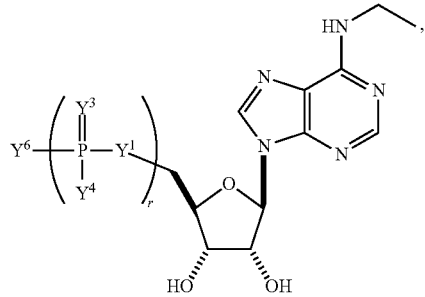

(BB-198)
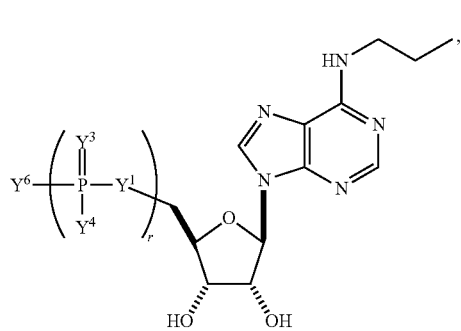

(BB-199), and
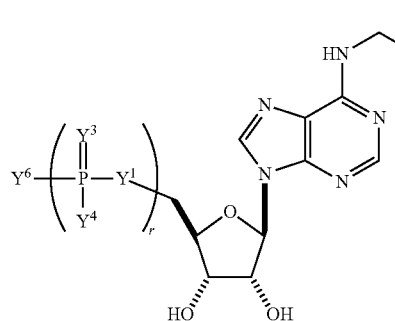

(BB-200)
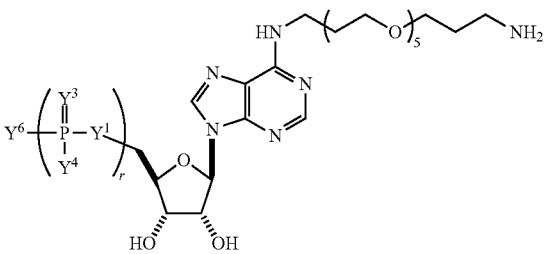

or a pharmaceutically acceptable salt or stereoisomer thereof, wherein $Y^1$, $Y^3$, $Y^4$, $Y^6$, and r are as described herein (e.g., each r is, independently, an integer from 0 to 5, such as from 0 to 3, from 1 to 3, or from 1 to 5)).

In some embodiments, the building block molecule, which may be incorporated into a polynucleotide, is an alternative guanosine (e.g., selected from the group consisting of:

(BB-201)
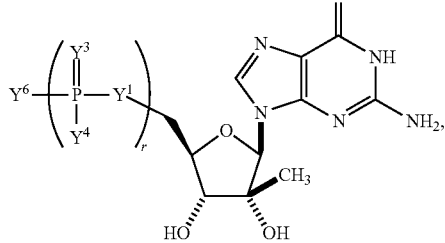

(BB-202)
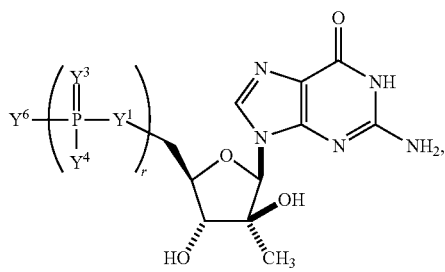

(BB-203)
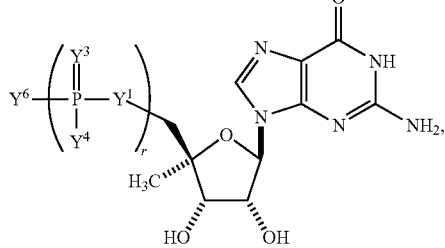

(BB-204)
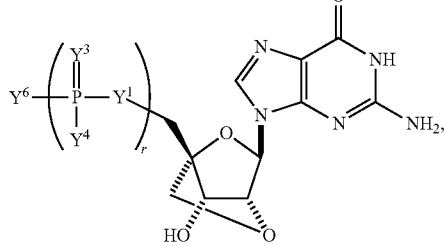

(BB-205)
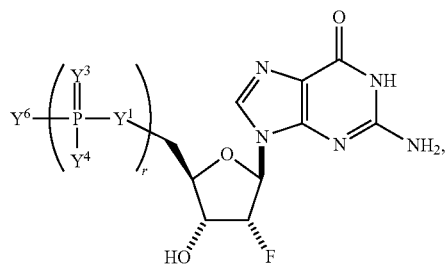
(BB-206)
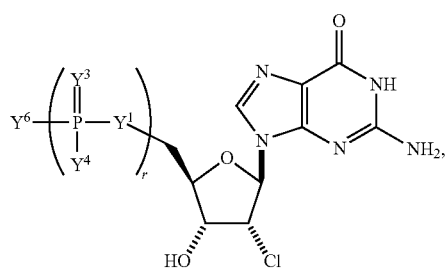
(BB-207)
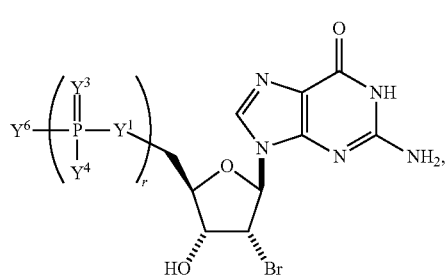
(BB-208)
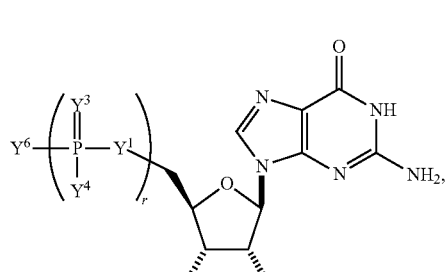
(BB-209)
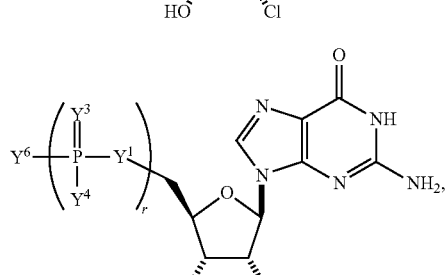
(BB-210)
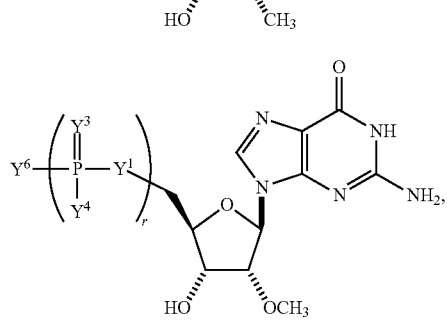
(BB-211)
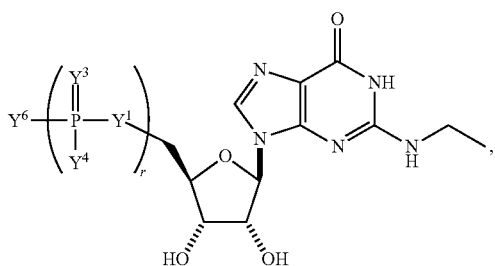
(BB-212)
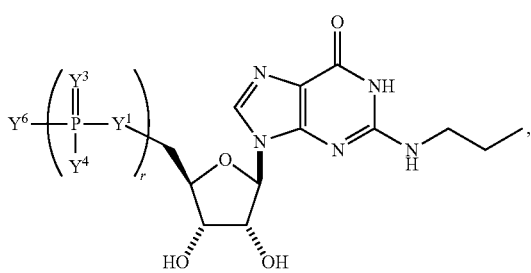
(BB-213)
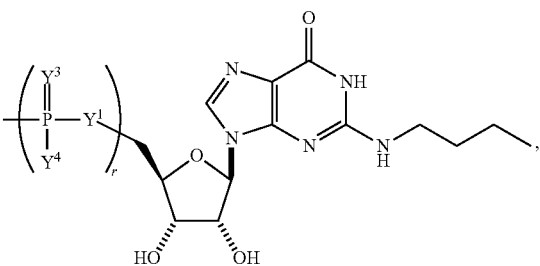
(BB-214)
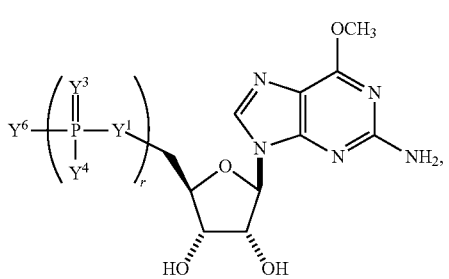
(BB-215)
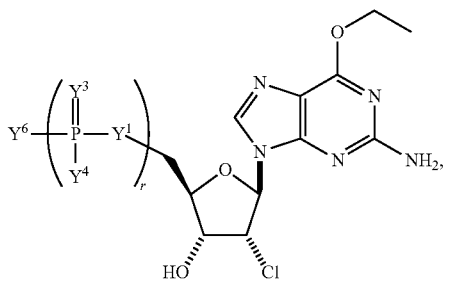

(BB-216)
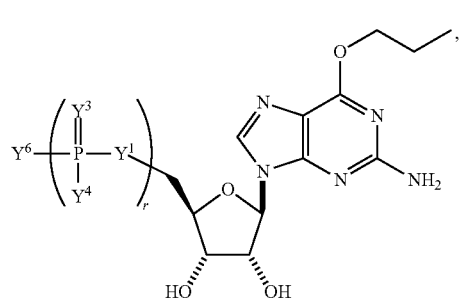
(BB-217)
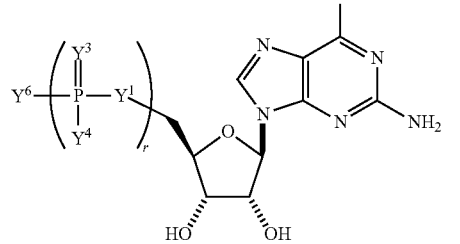
(BB-218)
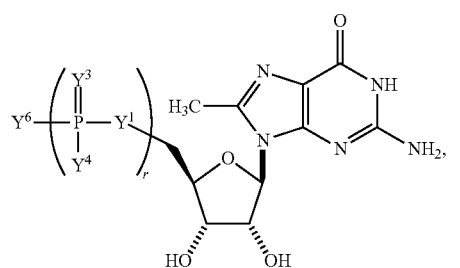
(BB-219)
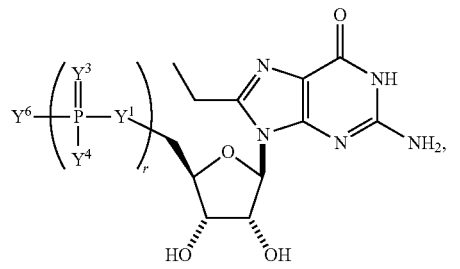
(BB-220)
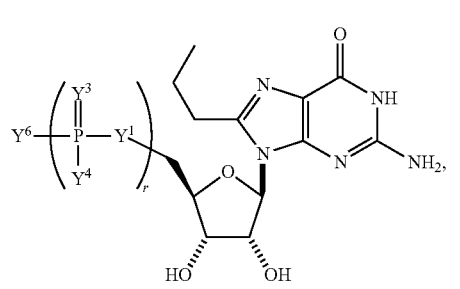
(BB-221)
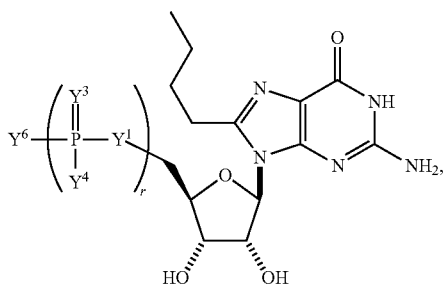
(BB-222)
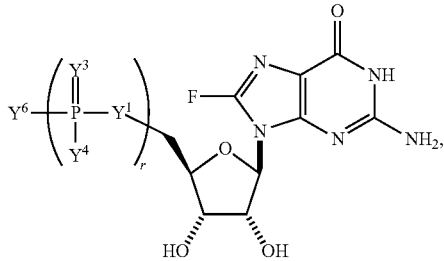
(BB-223)
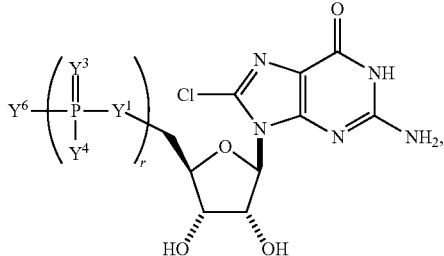
(BB-224)
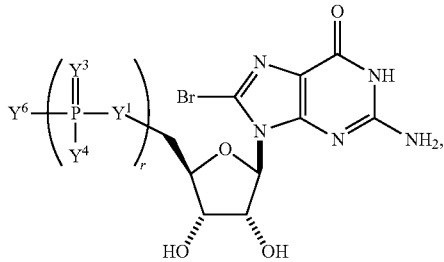
(BB-225)
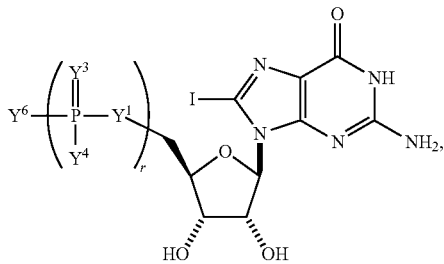
(BB-226)
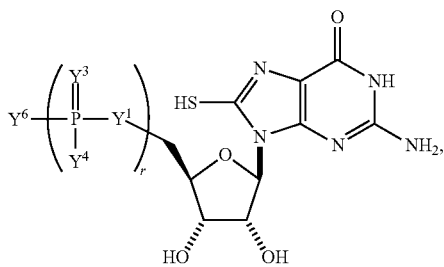

(BB-227)
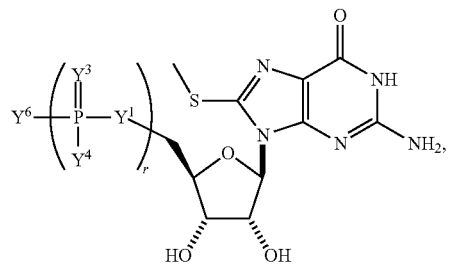
(BB-228)
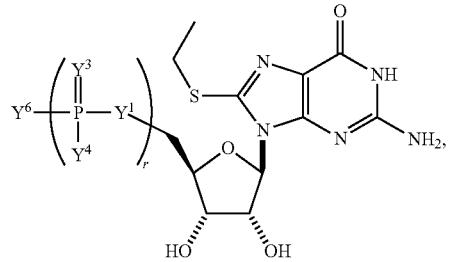
(BB-229)
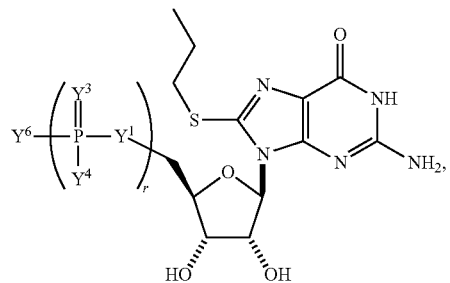
(BB-230)
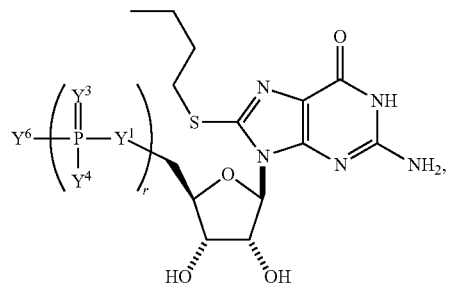
(BB-231)
(BB-232)
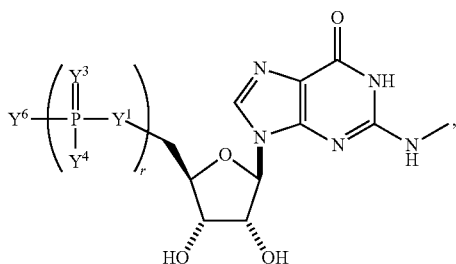
(BB-233)
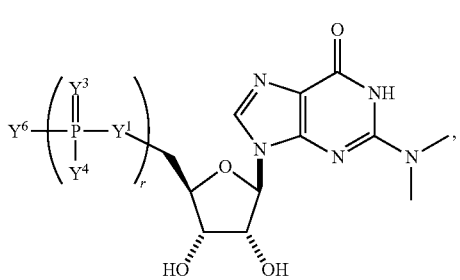
(BB-234)
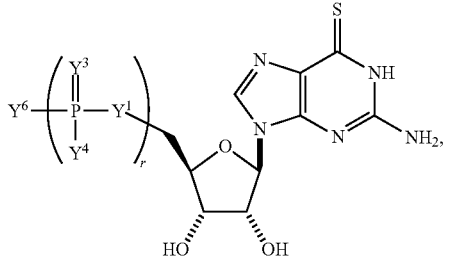
(BB-235)
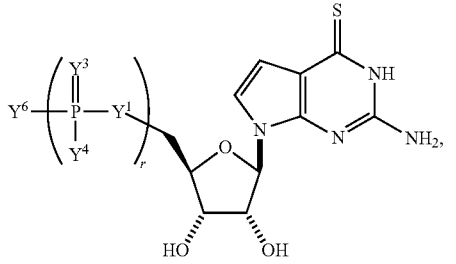
(BB-236)
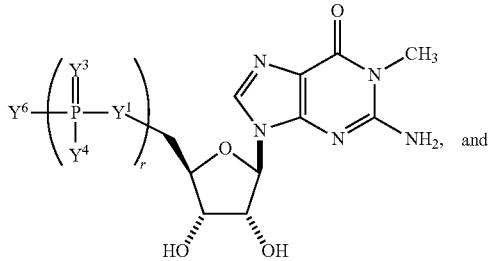
and (BB-237)

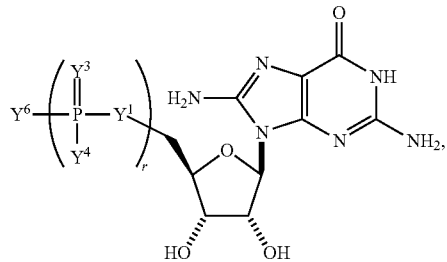

(BB-241)

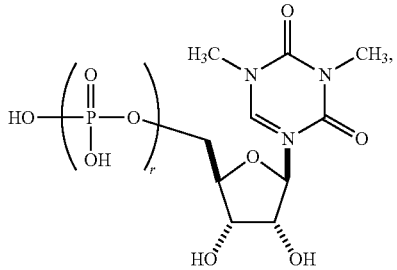

or a pharmaceutically acceptable salt or stereoisomer thereof, wherein $Y^1$, $Y^3$, $Y^4$, $Y^6$, and r are as described herein (e.g., each r is, independently, an integer from 0 to 5, such as from 0 to 3, from 1 to 3, or from 1 to 5)).

In some embodiments, the chemical alteration can include replacement of the C group at C-5 of the ring (e.g., for a pyrimidine nucleoside, such as cytosine or uracil) with N (e.g., replacement of the >CH group at C-5 with >NR$^{N1}$ group, wherein R$^{N1}$ is H or optionally substituted alkyl). For example, the building block molecule, which may be incorporated into a polynucleotide can be:

or a pharmaceutically acceptable salt or stereoisomer thereof, wherein each r is, independently, an integer from 0 to 5 (e.g., from 0 to 3, from 1 to 3, or from 1 to 5).

In another embodiment, the chemical alteration can include replacement of the hydrogen at C-5 of cytosine with halo (e.g., Br, Cl, F, or I) or optionally substituted alkyl (e.g., methyl). For example, the building block molecule, which may be incorporated into a polynucleotide can be:

(BB-238)

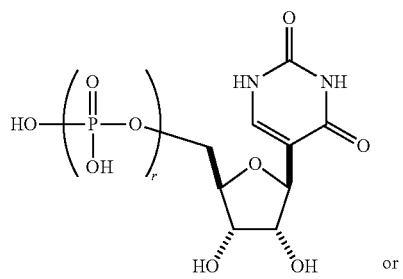

or (BB-242)

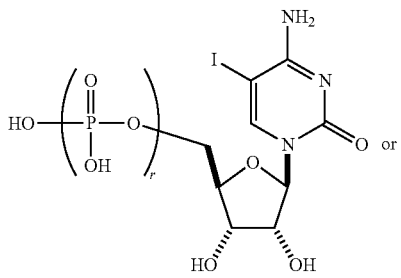

or (BB-239)

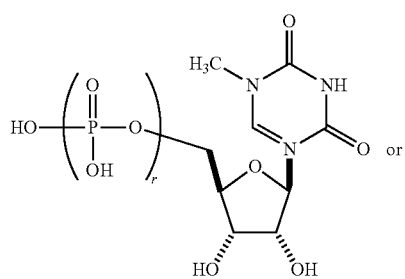

or (BB-243)

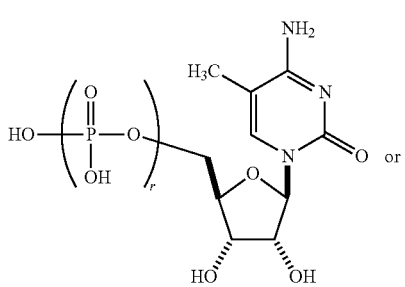

or (BB-240)

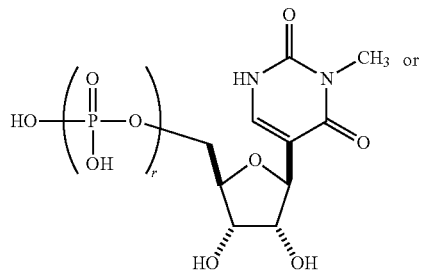

(BB-244)

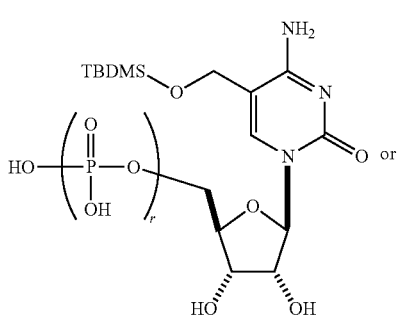

or

-continued

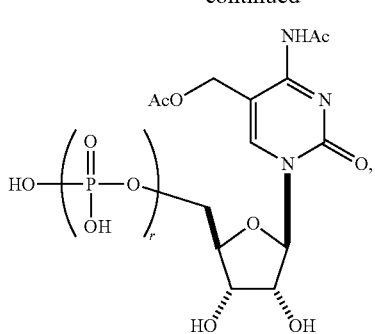

(BB-245)

or a pharmaceutically acceptable salt or stereoisomer thereof, wherein each r is, independently, an integer from 0 to 5 (e.g., from 0 to 3, from 1 to 3, or from 1 to 5).

In yet a further embodiment, the chemical alteration can include a fused ring that is formed by the $NH_2$ at the C-4 position and the carbon atom at the C-5 position. For example, the building block molecule, which may be incorporated into a polynucleotide can be:

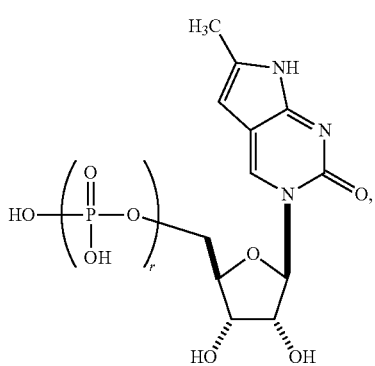

(BB-246)

or a pharmaceutically acceptable salt or stereoisomer thereof, wherein each r is, independently, an integer from 0 to 5 (e.g., from 0 to 3, from 1 to 3, or from 1 to 5).

Alterations on the Sugar

The alternative nucleosides and nucleotides (e.g., building block molecules), which may be incorporated into a polynucleotide (e.g., RNA or mRNA, as described herein), can be altered on the sugar of the ribonucleic acid. For example, the 2' hydroxyl group (OH) can be modified or replaced with a number of different substituents. Exemplary substitutions at the 2'-position include, but are not limited to, H, halo, optionally substituted $C_{1-6}$ alkyl; optionally substituted $C_{1-6}$ alkoxy; optionally substituted $C_{6-10}$ aryloxy; optionally substituted $C_{3-8}$ cycloalkyl; optionally substituted $C_{3-8}$ cycloalkoxy; optionally substituted $C_{6-10}$ aryloxy; optionally substituted $C_{6-10}$ aryl-$C_{1-6}$ alkoxy, optionally substituted $C_{1-12}$ (heterocyclyl)oxy; a sugar (e.g., ribose, pentose, or any described herein); a polyethyleneglycol (PEG), —O(CH$_2$CH$_2$O)$_n$CH$_2$CH$_2$OR, where R is H or optionally substituted alkyl, and n is an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20); "locked" nucleic acids (LNA) in which the 2'-hydroxyl is connected by a $C_{1-6}$ alkylene or $C_{1-6}$ heteroalkylene bridge to the 4'-carbon of the same ribose sugar, where exemplary bridges include methylene, propylene, ether, or amino bridges; aminoalkyl, as defined herein; aminoalkoxy, as defined herein; amino as defined herein; and amino acid, as defined herein Generally, RNA includes the sugar group ribose, which is a 5-membered ring having an oxygen. Exemplary, non-limiting alternative nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone); multicyclic forms (e.g., tricyclo; and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with α-L-threofuranosyl-(3'→2')), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide molecule can include nucleotides containing, e.g., arabinose, as the sugar.

Alterations on the Nucleobase

The present disclosure provides for alternative nucleosides and nucleotides. As described herein "nucleoside" is defined as a compound containing a sugar molecule (e.g., a pentose or ribose) or derivative thereof in combination with an organic base (e.g., a purine or pyrimidine) or a derivative thereof (also referred to herein as "nucleobase"). As described herein, "nucleotide" is defined as a nucleoside including a phosphate group.

Exemplary non-limiting alterations include an amino group, a thiol group, an alkyl group, a halo group, or any described herein. The alternative nucleotides may by synthesized by any useful method, as described herein (e.g., chemically, enzymatically, or recombinantly to include one or more alternative or non-natural nucleosides).

The alternative nucleotide base pairing encompasses not only the standard adenine-thymine, adenine-uracil, or guanine-cytosine base pairs, but also base pairs formed between nucleotides and/or alternative nucleotides comprising non-standard or alternative bases, wherein the arrangement of hydrogen bond donors and hydrogen bond acceptors permits hydrogen bonding between a non-standard base and a standard base or between two complementary non-standard base structures. One example of such non-standard base pairing is the base pairing between the alternative nucleotide inosine and adenosine, cytidine or uridine.

The alternative nucleosides and nucleotides can include an alternative nucleobase. Examples of nucleobases found in RNA include, but are not limited to, adenine, guanine, cytosine, and uracil. Examples of nucleobase found in DNA include, but are not limited to, adenine, guanine, cytosine, and thymine. These nucleobases can be altered or wholly replaced to provide polynucleotide molecules having enhanced properties, e.g., resistance to nucleases, stability, and these properties may manifest through disruption of the binding of a major groove binding partner.

Table 1 below identifies the chemical faces of each canonical nucleotide. Circles identify the atoms comprising the respective chemical regions.

TABLE 1
Chemical faces of each canonical nucleotide.
|  | Major Groove Face | Minor Groove Face | Watson-Crick Base-pairing Face |
|---|---|---|---|
| Pyrimidines Cytidine: | 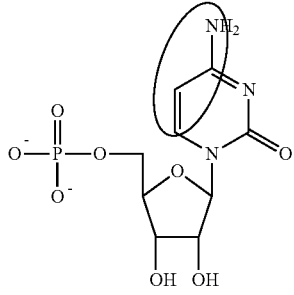 [SMILES: Nc1ccn(C2OC(COP(=O)(O)O)C(O)C2O)c(=O)n1] | 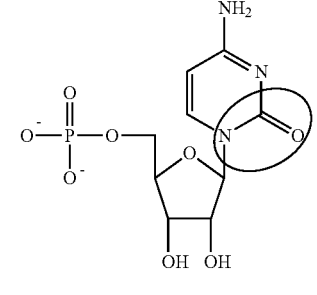 [SMILES: Nc1ccn(C2OC(COP(=O)(O)O)C(O)C2O)c(=O)n1] | 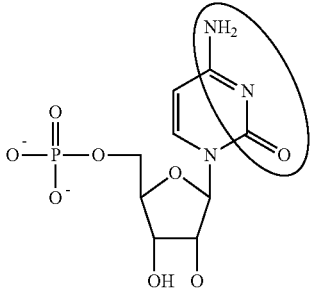 [SMILES: Nc1ccn(C2OC(COP(=O)(O)O)C(O)C2O)c(=O)n1] |
| Uridine: | 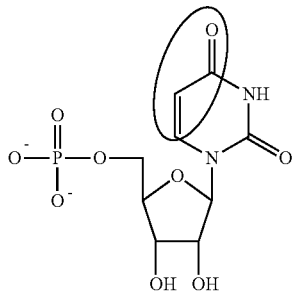 [SMILES: O=c1ccn(C2OC(COP(=O)(O)O)C(O)C2O)c(=O)[nH]1] | 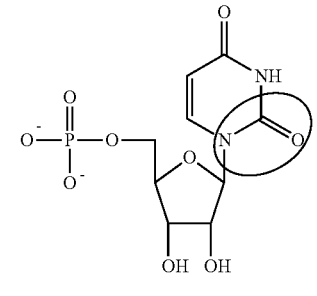 [SMILES: O=c1ccn(C2OC(COP(=O)(O)O)C(O)C2O)c(=O)[nH]1] | 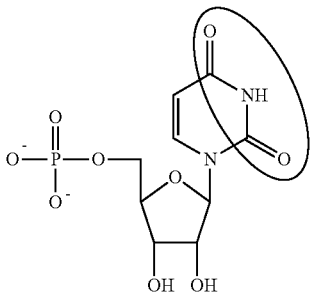 [SMILES: O=c1ccn(C2OC(COP(=O)(O)O)C(O)C2O)c(=O)[nH]1] |
| Purines Adenosine: | 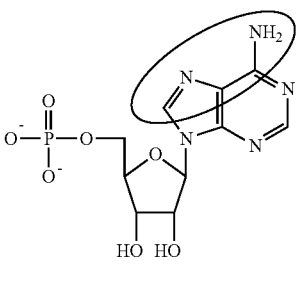 [SMILES: Nc1ncnc2c1ncn2C1OC(COP(=O)(O)O)C(O)C1O] | 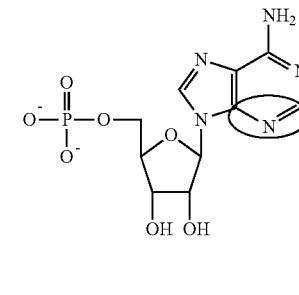 | 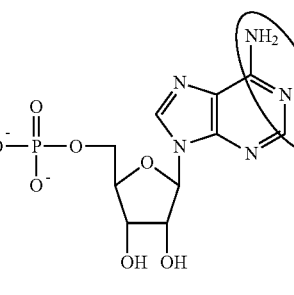 |
| Guanosine: | 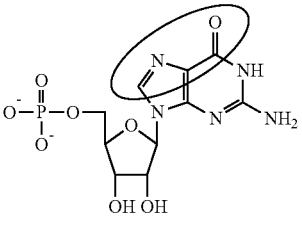 [SMILES: Nc1nc2c(ncn2C2OC(COP(=O)(O)O)C(O)C2O)c(=O)[nH]1] | 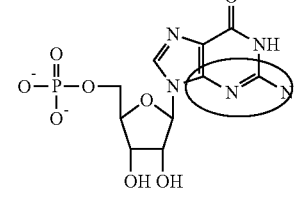 | 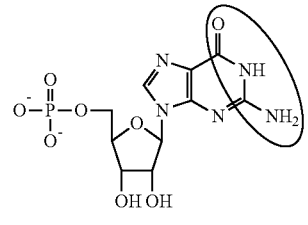 [SMILES: Nc1nc2c(ncn2C2OC(COP(=O)(O)O)C(O)C2O)c(=O)[nH]1] |

In some embodiments, B is an alternative uracil. Exemplary alternative uracils include those having Formula (b1)-(b5):

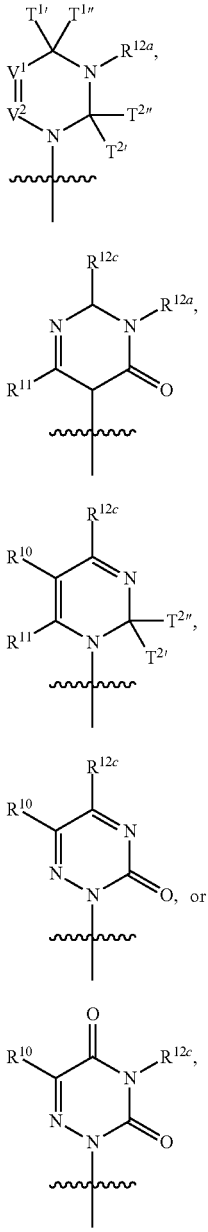

or a pharmaceutically acceptable salt or stereoisomer thereof, wherein

⇁ is a single or double bond;

each of $T^{1'}$, $T^{1''}$, $T^{2'}$, and $T^{2''}$ is, independently, H, optionally substituted alkyl, optionally substituted alkoxy, or optionally substituted thioalkoxy, or the combination of $T^{1'}$ and $T^{1''}$ or the combination of $T^{2'}$ and $T^{2''}$ join together (e.g., as in $T^2$) to form O (oxo), S (thio), or Se (seleno);

each of $V^1$ and $V^2$ is, independently, O, S, $N(R^{Vb})_{nv}$, or $C(R^{Vb})_{nv}$, wherein nv is an integer from 0 to 2 and each $R^{Vb}$ is, independently, H, halo, optionally substituted amino acid, optionally substituted alkyl, optionally substituted haloalkyl, optionally substituted alkenyl, optionally substituted alkynyl, optionally substituted alkoxy, optionally substituted alkenyloxy, optionally substituted alkynyloxy, optionally substituted hydroxyalkyl, optionally substituted hydroxyalkenyl, optionally substituted hydroxyalkynyl, optionally substituted aminoalkyl (e.g., substituted with an N-protecting group, such as any described herein, e.g., trifluoroacetyl), optionally substituted aminoalkenyl, optionally substituted aminoalkynyl, optionally substituted acylaminoalkyl (e.g., substituted with an N-protecting group, such as any described herein, e.g., trifluoroacetyl), optionally substituted alkoxycarbonylalkyl, optionally substituted alkoxycarbonylalkenyl, optionally substituted alkoxycarbonylalkynyl, or optionally substituted alkoxycarbonylalkoxy (e.g., optionally substituted with any substituent described herein, such as those selected from (1)-(21) for alkyl);

$R^{10}$ is H, halo, optionally substituted amino acid, hydroxyl, optionally substituted alkyl, optionally substituted alkenyl, optionally substituted alkynyl, optionally substituted aminoalkyl, optionally substituted hydroxyalkyl, optionally substituted hydroxyalkenyl, optionally substituted hydroxyalkynyl, optionally substituted aminoalkenyl, optionally substituted aminoalkynyl, optionally substituted alkoxy, optionally substituted alkoxycarbonylalkyl, optionally substituted alkoxycarbonylalkenyl, optionally substituted alkoxycarbonylalkynyl, optionally substituted alkoxycarbonylalkoxy, optionally substituted carboxyalkoxy, optionally substituted carboxyalkyl, or optionally substituted carbamoylalkyl;

$R^{11}$ is H or optionally substituted alkyl;

$R^{12a}$ is H, optionally substituted alkyl, optionally substituted hydroxyalkyl, optionally substituted hydroxyalkenyl, optionally substituted hydroxyalkynyl, optionally substituted aminoalkyl, optionally substituted aminoalkenyl, or optionally substituted aminoalkynyl, optionally substituted carboxyalkyl (e.g., optionally substituted with hydroxyl), optionally substituted carboxyalkoxy, optionally substituted carboxyaminoalkyl, or optionally substituted carbamoylalkyl; and $R^{12c}$ is H, halo, optionally substituted alkyl, optionally substituted alkoxy, optionally substituted thioalkoxy, optionally substituted amino, optionally substituted hydroxyalkyl, optionally substituted hydroxyalkenyl, optionally substituted hydroxyalkynyl, optionally substituted aminoalkyl, optionally substituted aminoalkenyl, or optionally substituted aminoalkynyl, or $R^{12c}$ combines with $R^{10}$ to form an optionally substituted $C_2$-$C_9$ heterocyclyl.

Other exemplary alternative uracils include those having Formula (b6)-(b9):

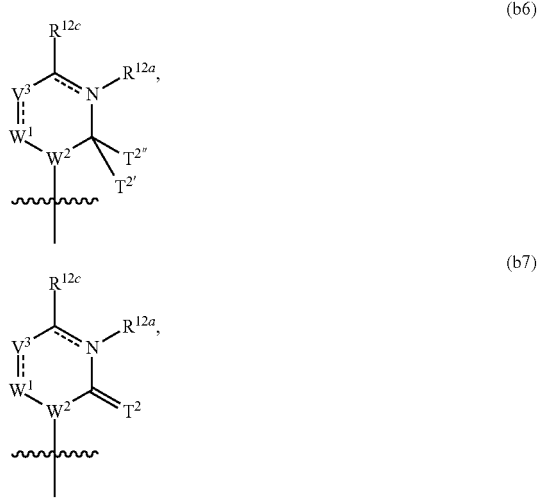

(b8)

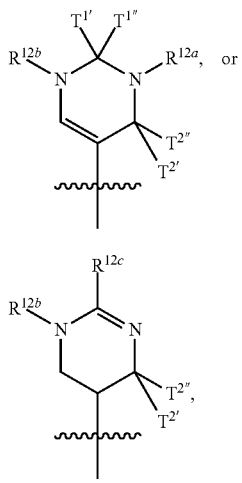

(b9)

or a pharmaceutically acceptable salt or stereoisomer thereof, wherein

⁓ is a single or double bond;

each of $T^{1'}$, $T^{1''}$, $T^{2'}$, and $T^{2''}$ is, independently, H, optionally substituted alkyl, optionally substituted alkoxy, or optionally substituted thioalkoxy, or the combination of $T^{1'}$ and $T^{1''}$ join together (acid. as in $T^1$) or the combination of $T^{2'}$ and $T^{2''}$ join together (e.g., as in $T^2$) to form O (oxo), S (thio), or Se (seleno), or each $T^1$ and $T^2$ is, independently, O (oxo), S (thio), or Se (seleno);

each of $W^1$ and $W^2$ is, independently, $N(R^{Wa})_{nw}$ or $C(R^{Wa})_{nw}$, wherein nw is an integer from 0 to 2 and each $R^{Wa}$ is, independently, H, optionally substituted alkyl, or optionally substituted alkoxy;

each $V^3$ is, independently, O, S, $N(R^{Va})_{nv}$, or $C(R^{Va})_{nv}$, wherein nv is an integer from 0 to 2 and each $R^{Va}$ is, independently, H, halo, optionally substituted amino acid, optionally substituted alkyl, optionally substituted hydroxyalkyl, optionally substituted hydroxyalkenyl, optionally substituted hydroxyalkynyl, optionally substituted alkenyl, optionally substituted alkynyl, optionally substituted heterocyclyl, optionally substituted alkheterocyclyl, optionally substituted alkoxy, optionally substituted alkenyloxy, or optionally substituted alkynyloxy, optionally substituted aminoalkyl (e.g., substituted with an N-protecting group, such as any described herein, e.g., trifluoroacetyl, or sulfoalkyl), optionally substituted aminoalkenyl, optionally substituted aminoalkynyl, optionally substituted acylaminoalkyl (e.g., substituted with an N-protecting group, such as any described herein, e.g., trifluoroacetyl), optionally substituted alkoxycarbonylalkyl, optionally substituted alkoxycarbonylalkenyl, optionally substituted alkoxycarbonylalkynyl, optionally substituted alkoxycarbonylacyl, optionally substituted alkoxycarbonylalkoxy, optionally substituted carboxyalkyl (e.g., optionally substituted with hydroxyl and/or an O-protecting group), optionally substituted carboxyalkoxy, optionally substituted carboxyaminoalkyl, or optionally substituted carbamoylalkyl (e.g., optionally substituted with any substituent described herein, such as those selected from (1)-(21) for alkyl), and wherein $R^{Va}$ and $R^{12c}$ taken together with the carbon atoms to which they are attached can form optionally substituted cycloalkyl, optionally substituted aryl, or optionally substituted heterocyclyl (e.g., a 5- or 6-membered ring);

$R^{12a}$ is H, optionally substituted alkyl, optionally substituted hydroxyalkyl, optionally substituted hydroxyalkenyl, optionally substituted hydroxyalkynyl, optionally substituted aminoalkyl, optionally substituted aminoalkenyl, optionally substituted aminoalkynyl, optionally substituted carboxyalkyl (e.g., optionally substituted with hydroxyl and/or an O-protecting group), optionally substituted carboxyalkoxy, optionally substituted carboxyaminoalkyl, optionally substituted carbamoylalkyl, or absent;

$R^{12b}$ is H, optionally substituted hydroxyl, optionally substituted amino, optionally substituted alkyl, optionally substituted alkenyl, optionally substituted alkynyl, optionally substituted hydroxyalkyl, optionally substituted hydroxyalkenyl, optionally substituted hydroxyalkynyl, optionally substituted aminoalkyl, optionally substituted aminoalkenyl, optionally substituted aminoalkynyl, optionally substituted alkaryl, optionally substituted heterocyclyl, optionally substituted alkheterocyclyl, optionally substituted amino acid, optionally substituted alkoxycarbonylacyl, optionally substituted alkoxycarbonylalkoxy, optionally substituted alkoxycarbonylalkyl, optionally substituted alkoxycarbonylalkenyl, optionally substituted alkoxycarbonylalkynyl, optionally substituted alkoxycarbonylalkoxy, optionally substituted carboxyalkyl (e.g., optionally substituted with hydroxyl and/or an O-protecting group), optionally substituted carboxyalkoxy, optionally substituted carboxyaminoalkyl, or optionally substituted carbamoylalkyl, wherein the combination of $R^{12b}$ and $T^{1'}$, the combination of $R^{12a}$ and $R^{12c}$, the combination of $R^{12a}$ and $T^{2'}$, or the combination of $R^{12b}$ and $R^{12c}$ can join together to form optionally substituted heterocyclyl (e.g., $C_{2-9}$); and $R^{12c}$ is H, halo, optionally substituted alkyl, optionally substituted alkoxy, optionally substituted thioalkoxy, optionally substituted amino, optionally substituted aminoalkyl, optionally substituted aminoalkenyl, or optionally substituted aminoalkynyl.

Further exemplary alternative uracils include those having Formula (b28)-(b31):

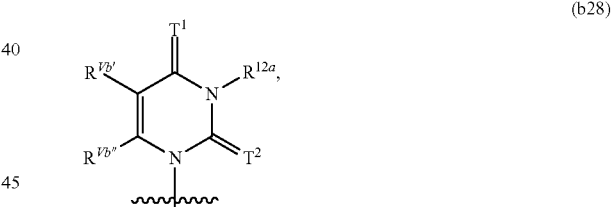

(b28)

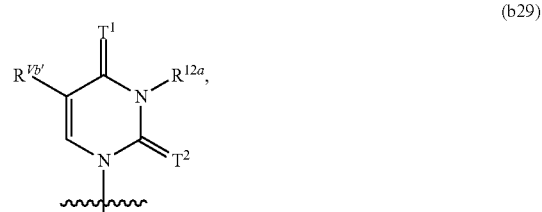

(b29)

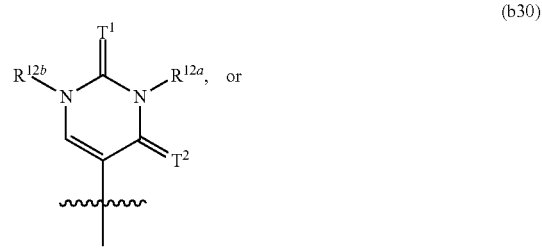

(b30)

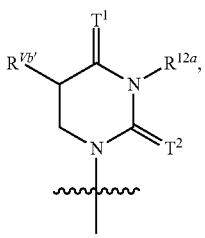

(b31)

or a pharmaceutically acceptable salt or stereoisomer thereof, wherein each of $T^1$ and $T^2$ is, independently, O (oxo), S (thio), or Se (seleno);

each $R^{Vb'}$ and $R^{Vb''}$ is, independently, H, halo, cyano, optionally substituted amino acid, optionally substituted alkyl, optionally substituted haloalkyl, optionally substituted hydroxyalkyl, optionally substituted hydroxyalkenyl, optionally substituted hydroxyalkynyl, optionally substituted alkenyl, optionally substituted alkynyl, optionally substituted alkoxyalkyl, optionally substituted aryl, optionally substituted heteroaryl, optionally substituted alkoxy, optionally substituted alkenyloxy, optionally substituted alkynyloxy, optionally substituted aminoalkyl (e.g., substituted with an N-protecting group, such as any described herein, e.g., trifluoroacetyl, or sulfoalkyl), optionally substituted aminoalkenyl, optionally substituted aminoalkynyl, optionally substituted acylaminoalkyl (e.g., substituted with an N-protecting group, such as any described herein, e.g., trifluoroacetyl), optionally substituted alkoxycarbonylalkyl, optionally substituted alkoxycarbonylalkenyl, optionally substituted alkoxycarbonylalkynyl, optionally substituted alkoxycarbonylacyl, optionally substituted alkoxycarbonylalkoxy, optionally substituted carboxyalkyl (e.g., optionally substituted with hydroxyl and/or an O-protecting group), optionally substituted carboxyalkoxy, optionally substituted carboxyaminoalkyl, or optionally substituted carbamoylalkyl (e.g., optionally substituted with any substituent described herein, such as those selected from (1)-(21) for alkyl) (e.g., $R^{Vb'}$ is optionally substituted alkyl, optionally substituted alkenyl, or optionally substituted aminoalkyl, e.g., substituted with an N-protecting group, such as any described herein, e.g., trifluoroacetyl, or sulfoalkyl);

$R^{12a}$ is H, optionally substituted alkyl, optionally substituted carboxyaminoalkyl, optionally substituted aminoalkyl (e.g., e.g., substituted with an N-protecting group, such as any described herein, e.g., trifluoroacetyl, or sulfoalkyl), optionally substituted aminoalkenyl, or optionally substituted aminoalkynyl; and $R^{12b}$ is H, optionally substituted hydroxyl, optionally substituted amino, optionally substituted alkyl, optionally substituted alkenyl, optionally substituted alkynyl, optionally substituted hydroxyalkyl, optionally substituted hydroxyalkenyl, optionally substituted hydroxyalkynyl, optionally substituted aminoalkyl, optionally substituted aminoalkenyl, optionally substituted aminoalkynyl (e.g., e.g., substituted with an N-protecting group, such as any described herein, e.g., trifluoroacetyl, or sulfoalkyl), optionally substituted alkoxycarbonylacyl, optionally substituted alkoxycarbonylalkoxy, optionally substituted alkoxycarbonylalkyl, optionally substituted alkoxycarbonylalkenyl, optionally substituted alkoxycarbonylalkynyl, optionally substituted alkoxycarbonylalkoxy, optionally substituted carboxyalkoxy, optionally substituted carboxyalkyl, or optionally substituted carbamoylalkyl.

In particular embodiments, $T^1$ is O (oxo), and $T^2$ is S (thio) or Se (seleno). In other embodiments, $T^1$ is S (thio), and $T^2$ is O (oxo) or Se (seleno). In some embodiments, $R^{Vb'}$ is H, optionally substituted alkyl, or optionally substituted alkoxy.

In other embodiments, each $R^{12a}$ and $R^{12b}$ is, independently, H, optionally substituted alkyl, optionally substituted alkenyl, optionally substituted alkynyl, or optionally substituted hydroxyalkyl. In particular embodiments, $R^{12a}$ is H. In other embodiments, both $R^{12a}$ and $R^{12b}$ are H.

In some embodiments, each $R^{Vb'}$ of $R^{12b}$ is, independently, optionally substituted aminoalkyl (e.g., substituted with an N-protecting group, such as any described herein, e.g., trifluoroacetyl, or sulfoalkyl), optionally substituted aminoalkenyl, optionally substituted aminoalkynyl, or optionally substituted acylaminoalkyl (e.g., substituted with an N-protecting group, such as any described herein, e.g., trifluoroacetyl). In some embodiments, the amino and/or alkyl of the optionally substituted aminoalkyl is substituted with one or more of optionally substituted alkyl, optionally substituted alkenyl, optionally substituted sulfoalkyl, optionally substituted carboxy (e.g., substituted with an O-protecting group), optionally substituted hydroxyl (e.g., substituted with an O-protecting group), optionally substituted carboxyalkyl (e.g., substituted with an O-protecting group), optionally substituted alkoxycarbonylalkyl (e.g., substituted with an O-protecting group), or N-protecting group.

In some embodiments, optionally substituted aminoalkyl is substituted with an optionally substituted sulfoalkyl or optionally substituted alkenyl. In particular embodiments, $R^{12a}$ and $R^{Vb'}$ are both H. In particular embodiments, $T^1$ is O (oxo), and $T^2$ is S (thio) or Se (seleno).

In some embodiments, $R^{Vb'}$ is optionally substituted alkoxycarbonylalkyl or optionally substituted carbamoylalkyl.

In particular embodiments, the optional substituent for $R^{12a}$, $R^{12b}$, $R^{12c}$, or $R^{Va}$ is a polyethylene glycol group (e.g., —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl); or an amino-polyethylene glycol group (e.g., —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl).

In some embodiments, B is an alternative cytosine. Exemplary alternative cytosines include compounds of Formula (b10)-(b14):

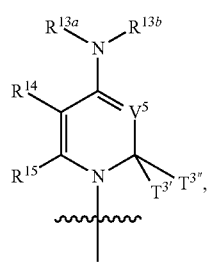

(b10)

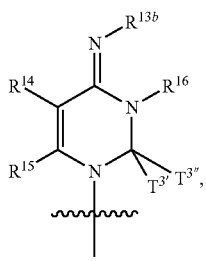
(b11)

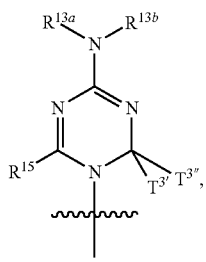
(b12)

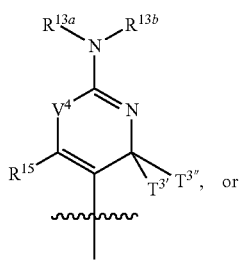
(b13)

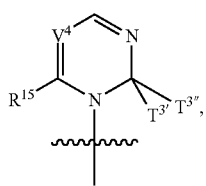
(b14)

or a pharmaceutically acceptable salt or stereoisomer thereof, wherein each of T$^{3'}$ and T$^{3'''}$ is, independently, H, optionally substituted alkyl, optionally substituted alkoxy, or optionally substituted thioalkoxy, or the combination of T$^{3'}$ and T$^{3''}$ join together (e.g., as in T$^3$) to form O (oxo), S (thio), or Se (seleno);

each V$^4$ is, independently, O, S, N(R$^{Vc}$)$_{nv}$, or C(R$^{Vc}$)$_{nv}$, wherein nv is an integer from 0 to 2 and each R$^{Vc}$ is, independently, H, halo, optionally substituted amino acid, optionally substituted alkyl, optionally substituted alkenyl, optionally substituted alkynyl, optionally substituted alkoxy, optionally substituted alkenyloxy, optionally substituted heterocyclyl, optionally substituted alkheterocyclyl, or optionally substituted alkynyloxy (e.g., optionally substituted with any substituent described herein, such as those selected from (1)-(21) for alkyl), wherein the combination of R$^{13b}$ and R$^{Vc}$ can be taken together to form optionally substituted heterocyclyl;

each V$^5$ is, independently, N(R$^{Vd}$)$_{nv}$, or C(R$^{Vd}$)$_{nv}$, wherein nv is an integer from 0 to 2 and each R$^{Vd}$ is, independently, H, halo, optionally substituted amino acid, optionally substituted alkyl, optionally substituted alkenyl, optionally substituted alkynyl, optionally substituted alkoxy, optionally substituted alkenyloxy, optionally substituted heterocyclyl, optionally substituted alkheterocyclyl, or optionally substituted alkynyloxy (e.g., optionally substituted with any substituent described herein, such as those selected from (1)-(21) for alkyl) (e.g., V$^5$ is —CH or N);

each of R$^{13a}$ and R$^{13b}$ is, independently, H, optionally substituted acyl, optionally substituted acyloxyalkyl, optionally substituted alkyl, or optionally substituted alkoxy, wherein the combination of R$^{13b}$ and R$^{14}$ can be taken together to form optionally substituted heterocyclyl;

each R$^{14}$ is, independently, H, halo, hydroxyl, thiol, optionally substituted acyl, optionally substituted amino acid, optionally substituted alkyl, optionally substituted haloalkyl, optionally substituted alkenyl, optionally substituted alkynyl, optionally substituted hydroxyalkyl (e.g., substituted with an O-protecting group), optionally substituted hydroxyalkenyl, optionally substituted hydroxyalkynyl, optionally substituted alkoxy, optionally substituted alkenyloxy, optionally substituted alkynyloxy, optionally substituted aminoalkoxy, optionally substituted alkoxyalkoxy, optionally substituted acyloxyalkyl, optionally substituted amino (e.g., —NHR, wherein R is H, alkyl, aryl, or phosphoryl), azido, optionally substituted aryl, optionally substituted heterocyclyl, optionally substituted alkheterocyclyl, optionally substituted aminoalkyl, optionally substituted aminoalkenyl, or optionally substituted aminoalkynyl; and each of R$^{15}$ and R$^{16}$ is, independently, H, optionally substituted alkyl, optionally substituted alkenyl, or optionally substituted alkynyl.

Further exemplary alternative cytosines include those having Formula (b32)-(b35):

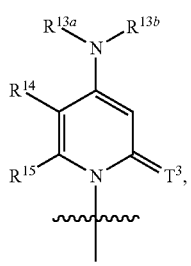
(b32)

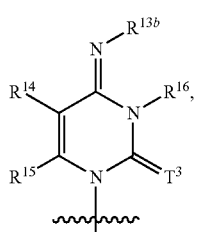
(b33)

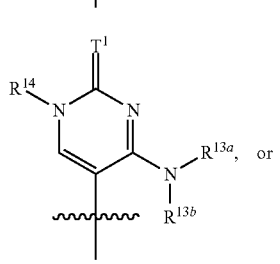
(b34)

-continued

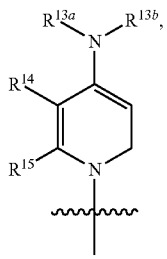
(b35)

or a pharmaceutically acceptable salt or stereoisomer thereof, wherein each of $T^1$ and $T^3$ is, independently, O (oxo), S (thio), or Se (seleno);

each of $R^{13a}$ and $R^{13b}$ is, independently, H, optionally substituted acyl, optionally substituted acyloxyalkyl, optionally substituted alkyl, or optionally substituted alkoxy, wherein the combination of $R^{13b}$ and $R^{14}$ can be taken together to form optionally substituted heterocyclyl;

each $R^{14}$ is, independently, H, halo, hydroxyl, thiol, optionally substituted acyl, optionally substituted amino acid, optionally substituted alkyl, optionally substituted haloalkyl, optionally substituted alkenyl, optionally substituted alkynyl, optionally substituted hydroxyalkyl (e.g., substituted with an O-protecting group), optionally substituted hydroxyalkenyl, optionally substituted hydroxyalkynyl, optionally substituted alkoxy, optionally substituted alkenyloxy, optionally substituted alkynyloxy, optionally substituted aminoalkoxy, optionally substituted alkoxyalkoxy, optionally substituted acyloxyalkyl, optionally substituted amino (e.g., —NHR, wherein R is H, alkyl, aryl, or phosphoryl), azido, optionally substituted aryl, optionally substituted cycloalkyl, optionally substituted heterocyclyl, optionally substituted alkheterocyclyl, optionally substituted aminoalkyl (e.g., hydroxyalkyl, alkyl, alkenyl, or alkynyl), optionally substituted aminoalkenyl, or optionally substituted aminoalkynyl; and each of $R^{15}$ and $R^{16}$ is, independently, H, optionally substituted alkyl, optionally substituted alkenyl, or optionally substituted alkynyl (e.g., $R^{15}$ is H, and $R^{16}$ is H or optionally substituted alkyl).

In some embodiments, $R^{15}$ is H, and $R^{16}$ is H or optionally substituted alkyl. In particular embodiments, $R^{14}$ is H, acyl, or hydroxyalkyl. In some embodiments, $R^{14}$ is halo. In some embodiments, both $R^{14}$ and $R^{15}$ are H. In some embodiments, both $R^{15}$ and $R^{16}$ are H. In some embodiments, each of $R^{14}$ and $R^{15}$ and $R^{16}$ is H. In further embodiments, each of $R^{13a}$ and $R^{13b}$ is independently, H or optionally substituted alkyl.

Further non-limiting examples of alternative cytosines include compounds of Formula (b36):

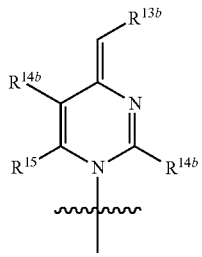
(b36)

or a pharmaceutically acceptable salt or stereoisomer thereof, wherein each $R^{13b}$ is, independently, H, optionally substituted acyl, optionally substituted acyloxyalkyl, optionally substituted alkyl, or optionally substituted alkoxy, wherein the combination of $R^{13b}$ and $R^{14b}$ can be taken together to form optionally substituted heterocyclyl;

each $R^{14a}$ and $R^{14b}$ is, independently, H, halo, hydroxyl, thiol, optionally substituted acyl, optionally substituted amino acid, optionally substituted alkyl, optionally substituted haloalkyl, optionally substituted alkenyl, optionally substituted alkynyl, optionally substituted hydroxyalkyl (e.g., substituted with an O-protecting group), optionally substituted hydroxyalkenyl, optionally substituted alkoxy, optionally substituted alkenyloxy, optionally substituted alkynyloxy, optionally substituted aminoalkoxy, optionally substituted alkoxyalkoxy, optionally substituted acyloxyalkyl, optionally substituted amino (e.g., —NHR, wherein R is H, alkyl, aryl, phosphoryl, optionally substituted aminoalkyl, or optionally substituted carboxyaminoalkyl), azido, optionally substituted aryl, optionally substituted heterocyclyl, optionally substituted alkheterocyclyl, optionally substituted aminoalkyl, optionally substituted aminoalkenyl, or optionally substituted aminoalkynyl; and each of $R^{15}$ is, independently, H, optionally substituted alkyl, optionally substituted alkenyl, or optionally substituted alkynyl.

In particular embodiments, $R^{14b}$ is an optionally substituted amino acid (e.g., optionally substituted lysine). In some embodiments, $R^{14a}$ is H.

In some embodiments, B is an alternative guanine. Exemplary alternative guanines include compounds of Formula (b15)-(b17):

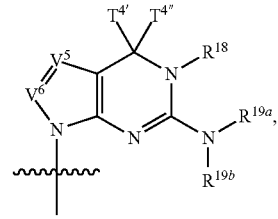
(b15)

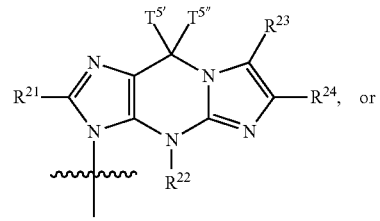
(b16)

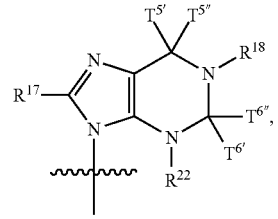
(b17)

or a pharmaceutically acceptable salt or stereoisomer thereof, wherein

Each of $T^{4'}$, $T^{4''}$, $T^{5'}$, $T^{5''}$, $T^{6'}$, and $T^{6''}$ is, independently, H, optionally substituted alkyl, or optionally substituted alkoxy, and wherein the combination of $T^{4'}$ and $T^{4''}$ (e.g., as in $T^4$)

or the combination of T⁵' and T⁵" (e.g., as in T⁵) or the combination of T⁶' and T⁶" join together (e.g., as in T⁶) form O (oxo), S (thio), or Se (seleno);

each of V⁵ and V⁶ is, independently, O, S, N(R$^{Vd}$)$_{nv}$, or C(R$^{Vd}$)$_{nv}$, wherein nv is an integer from 0 to 2 and each R$^{Vd}$ is, independently, H, halo, thiol, nitro, optionally substituted alkoxyalkyl, optionally substituted amino acid, cyano, amidine, optionally substituted aminoalkyl, optionally substituted aminoalkenyl, optionally substituted aminoalkynyl, optionally substituted alkyl, optionally substituted alkenyl, optionally substituted alkynyl, optionally substituted alkoxy, optionally substituted alkenyloxy, optionally substituted alkynyloxy (e.g., optionally substituted with any substituent described herein, such as those selected from (1)-(21) for alkyl), optionally substituted thioalkoxy, or optionally substituted amino; and each of R¹⁷, R¹⁸, R¹⁹ᵃ, R¹⁹ᵇ, R²¹, R²², R²³, and R²⁴ is, independently, H, halo, nitro, thiol, optionally substituted alkyl, optionally substituted alkenyl, optionally substituted alkynyl, optionally substituted thioalkoxy, optionally substituted amino, or optionally substituted amino acid.

Exemplary alternative guanosines include compounds of Formula (b37)-(b40):

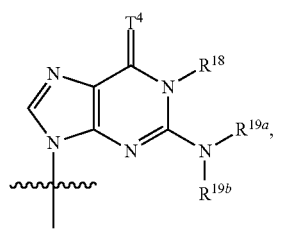
(b37)

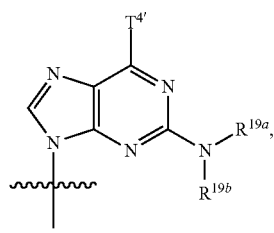
(b38)

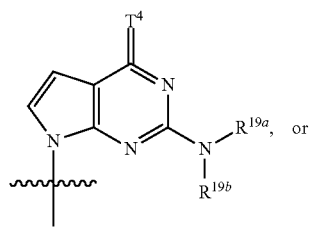
(b39)

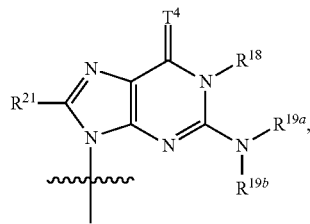
(b40)

or a pharmaceutically acceptable salt or stereoisomer thereof, wherein each of T⁴' is, independently, H, optionally substituted alkyl, or optionally substituted alkoxy, and each T⁴ is, independently, 0 (oxo), S (thio), or Se (seleno);

each of R¹⁸, R¹⁹ᵃ, R¹⁹ᵇ, and R²¹ is, independently, H, halo, thiol, optionally substituted alkyl, optionally substituted alkenyl, optionally substituted alkynyl, optionally substituted thioalkoxy, optionally substituted amino, or optionally substituted amino acid.

In some embodiments, R¹⁸ is H or optionally substituted alkyl. In further embodiments, T⁴ is oxo. In some embodiments, each of R¹⁹ᵃ and R¹⁹ᵇ is, independently, H or optionally substituted alkyl.

In some embodiments, B is an alternative adenine. Exemplary alternative adenines include compounds of Formula (b18)-(b20):

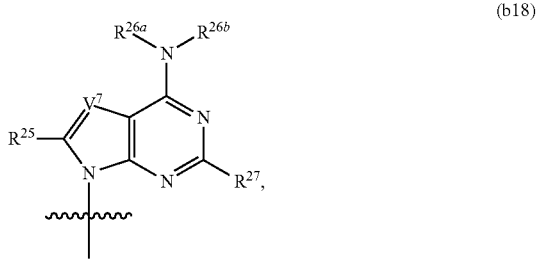
(b18)

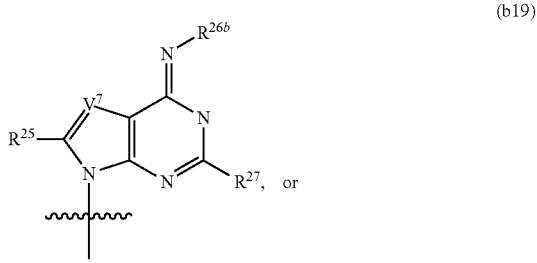
(b19)

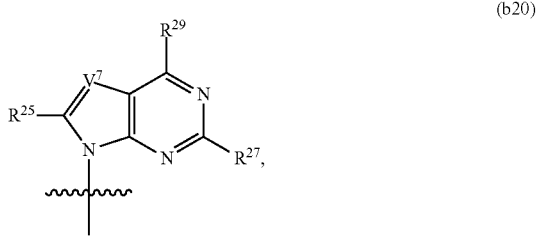
(b20)

or a pharmaceutically acceptable salt or stereoisomer thereof, wherein each V⁷ is, independently, O, S, N(R$^{Ve}$)$_{nv}$, or C(R$^{Ve}$)$_{nv}$, wherein nv is an integer from 0 to 2 and each R$^{Ve}$ is, independently, H, halo, optionally substituted amino acid, optionally substituted alkyl, optionally substituted alkenyl, optionally substituted alkynyl, optionally substituted alkoxy, optionally substituted alkenyloxy, or optionally substituted alkynyloxy (e.g., optionally substituted with any substituent described herein, such as those selected from (1)-(21) for alkyl);

each R²⁵ is, independently, H, halo, thiol, nitro, optionally substituted alkyl, optionally substituted alkenyl, optionally substituted alkynyl, optionally substituted thioalkoxy, or optionally substituted amino;

each of R²⁶ᵃ and R²⁶ᵇ is, independently, H, optionally substituted acyl, optionally substituted amino acid, optionally substituted carbamoylalkyl, optionally substituted alkyl, optionally substituted alkenyl, optionally substituted alkynyl, optionally substituted hydroxyalkyl, optionally substituted hydroxyalkenyl, optionally substituted hydroxyalkynyl, optionally substituted alkoxy, or polyethylene glycol group (e.g., —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl); or an amino-polyethylene glycol group (e.g., —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl);

each $R^{27}$ is, independently, H, optionally substituted alkyl, optionally substituted alkenyl, optionally substituted alkynyl, optionally substituted alkoxy, optionally substituted thioalkoxy, or optionally substituted amino;

each $R^{28}$ is, independently, H, optionally substituted alkyl, optionally substituted alkenyl, or optionally substituted alkynyl; and each $R^{29}$ is, independently, H, optionally substituted acyl, optionally substituted amino acid, optionally substituted carbamoylalkyl, optionally substituted alkyl, optionally substituted alkenyl, optionally substituted alkynyl, optionally substituted aryl, optionally substituted heteroaryl, optionally substituted hydroxyalkyl, optionally substituted hydroxyalkenyl, optionally substituted alkoxy, or optionally substituted amino.

Exemplary alternative adenines include compounds of Formula (b41)-(b43):

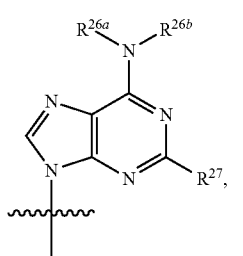

(b41)

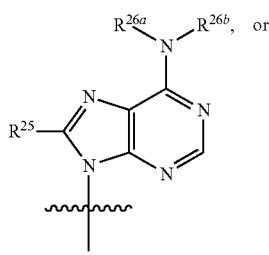

(b42)

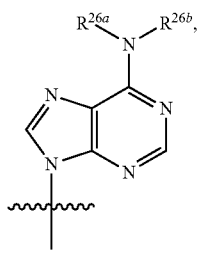

(b43)

or a pharmaceutically acceptable salt or stereoisomer thereof, wherein each $R^{25}$ is, independently, H, halo, thiol, optionally substituted alkyl, optionally substituted alkenyl, optionally substituted alkynyl, optionally substituted thioalkoxy, or optionally substituted amino;

each of $R^{26a}$ and $R^{26b}$ is, independently, H, optionally substituted acyl, optionally substituted amino acid, optionally substituted carbamoylalkyl, optionally substituted alkyl, optionally substituted alkenyl, optionally substituted alkynyl, optionally substituted hydroxyalkyl, optionally substituted hydroxyalkenyl, optionally substituted hydroxyalkynyl, optionally substituted alkoxy, or polyethylene glycol group (e.g., —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl); or an amino-polyethylene glycol group (e.g., —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl); and each $R^{27}$ is, independently, H, optionally substituted alkyl, optionally substituted alkenyl, optionally substituted alkynyl, optionally substituted alkoxy, optionally substituted thioalkoxy, or optionally substituted amino.

In some embodiments, $R^{26a}$ is H, and $R^{26b}$ is optionally substituted alkyl. In some embodiments, each of $R^{26a}$ and $R^{26b}$ is, independently, optionally substituted alkyl. In particular embodiments, $R^{27}$ is optionally substituted alkyl, optionally substituted alkoxy, or optionally substituted thioalkoxy. In other embodiments, $R^{25}$ is optionally substituted alkyl, optionally substituted alkoxy, or optionally substituted thioalkoxy.

In particular embodiments, the optional substituent for $R^{26a}$, $R^{26b}$, or $R^{29}$ is a polyethylene glycol group (e.g., —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl); or an amino-polyethylene glycol group (e.g., —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl).

In some embodiments, B may have Formula (b21):

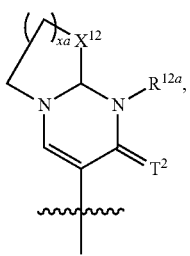

(b21)

wherein $X^{12}$ is, independently, O, S, optionally substituted alkylene (e.g., methylene), or optionally substituted heteroalkylene, xa is an integer from 0 to 3, and $R^{12a}$ and $T^2$ are as described herein.

In some embodiments, B may have Formula (b22):

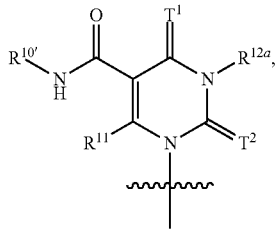

(b22)

wherein $R^{10'}$ is, independently, optionally substituted alkyl, optionally substituted alkenyl, optionally substituted alkynyl, optionally substituted aryl, optionally substituted heterocyclyl, optionally substituted aminoalkyl, optionally substituted aminoalkenyl, optionally substituted aminoalkynyl, optionally substituted alkoxy, optionally substituted alkoxycarbonylalkyl, optionally substituted alkoxycarbonylalkenyl, optionally substituted alkoxycarbonylalkynyl, optionally substituted alkoxycarbonylalkoxy, optionally substituted carboxyalkoxy, optionally substituted carboxyalkyl, or optionally substituted carbamoylalkyl, and $R^{11}$, $R^{12a}$, $T^1$, and $T^2$ are as described herein.

In some embodiments, B may have Formula (b23):

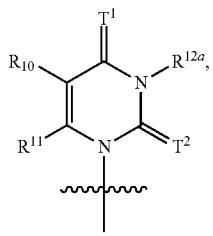

(b23)

wherein $R^{10}$ is optionally substituted heterocyclyl (e.g., optionally substituted furyl, optionally substituted thienyl, or optionally substituted pyrrolyl), optionally substituted aryl (e.g., optionally substituted phenyl or optionally substituted naphthyl), or any substituent described herein (e.g., for $R^{10}$); and wherein $R^{11}$ (e.g., H or any substituent described herein), $R^{12a}$ (e.g., H or any substituent described herein), $T^1$ (e.g., oxo or any substituent described herein), and $T^2$ (e.g., oxo or any substituent described herein) are as described herein.

In some embodiments, B may have Formula (b24):

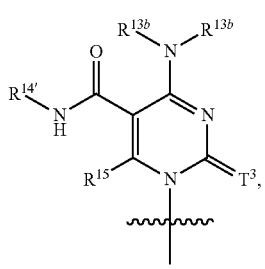

(b24)

wherein $R^{14'}$ is, independently, optionally substituted alkyl, optionally substituted alkenyl, optionally substituted alkynyl, optionally substituted aryl, optionally substituted heterocyclyl, optionally substituted alkaryl, optionally substituted alkheterocyclyl, optionally substituted aminoalkyl, optionally substituted aminoalkenyl, optionally substituted aminoalkynyl, optionally substituted alkoxy, optionally substituted alkoxycarbonylalkyl, optionally substituted alkoxycarbonylalkenyl, optionally substituted alkoxycarbonylalkynyl, optionally substituted alkoxycarbonylalkoxy, optionally substituted carboxyalkoxy, optionally substituted carboxyalkyl, or optionally substituted carbamoylalkyl, and $R^{13a}$, $R^{13b}$, $R^{15}$, and $T^3$ are as described herein.

In some embodiments, B may have Formula (b25):

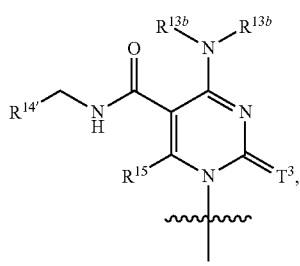

(b25)

wherein $R^{14'}$ is optionally substituted heterocyclyl (e.g., optionally substituted furyl, optionally substituted thienyl, or optionally substituted pyrrolyl), optionally substituted aryl (e.g., optionally substituted phenyl or optionally substituted naphthyl), or any substituent described herein (e.g., for $R^{14}$ or $R^{14'}$); and wherein $R^{13a}$ (e.g., H or any substituent described herein), $R^{13b}$ (e.g., H or any substituent described herein), $R^{15}$ (e.g., H or any substituent described herein), and $T^3$ (e.g., oxo or any substituent described herein) are as described herein.

In some embodiments, B is a nucleobase selected from the group consisting of cytosine, guanine, adenine, and uracil. In some embodiments, B may be:

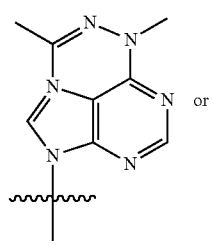

(b26)

or

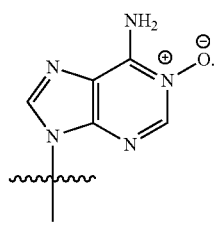

(b27)

In some embodiments, B may have the structure of Formula (b44):

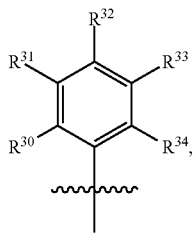
(b44)

wherein each of $R^{30}$, $R^{31}$, $R^{32}$, $R^{33}$, and $R^{34}$ is independently hydrogen, fluorine, or optionally substituted alkyl.

In some embodiments, B may have the structure of Formula (b45):

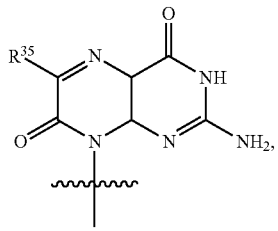
(b45)

wherein $R^{35}$ is hydrogen or optionally substituted alkyl.

In some embodiments, B may have the structure of Formula (b46):

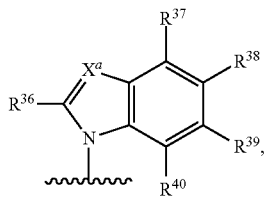
(b46)

wherein $X^a$ is N or $CR^{41}$; $R^{36}$ is hydrogen, halo, nitro, or optionally substituted alkyl; $R^{37}$, $R^{38}$, $R^{39}$, and $R^{40}$ are independently hydrogen or halo (e.g., fluorine); and $R^{41}$ is hydrogen or optionally substituted alkyl.

In some embodiments, B may have the structure of Formula (b47):

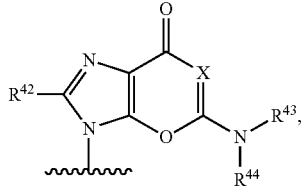
(b47)

wherein X is N or CH; $R^{42}$ is hydrogen, halo, nitro, or optionally substituted alkyl, and $R^{43}$ and $R^{44}$ are independently hydrogen or optionally substituted alkyl.

In some embodiments, the alternative nucleobase is an alternative uracil. Exemplary nucleobases and nucleosides having an alternative uracil include pseudouridine (ψ), pyridin-4-one ribonucleoside, 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridineor 5-bromo-uridine), 3-methyl-uridine ($m^3U$), 5-methoxy-uridine ($mo^5U$), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxycarbonylmethyl-2-thio-uridine ($mcm^5s^2U$), 5-aminomethyl-2-thio-uridine ($nm^5s^2U$), 5-methylaminomethyl-uridine ($mnm^5U$), 5-methylaminomethyl-2-thio-uridine ($mnm^5s^2U$), 5-methylaminomethyl-2-seleno-uridine ($mnm^5se^2U$), 5-carbamoylmethyl-uridine ($ncm^5U$), 5-carboxymethylaminomethyl-uridine ($cmnm^5U$), 5-carboxymethylaminomethyl-2-thio-uridine ($cmnm^5s^2U$), 5-propynyl-uridine, 1-propynyl-pseudouridine, 5-taurinomethyl-uridine ($Tm^5U$), 1-taurinomethyl-pseudouridine, 5-taurinomethyl-2-thio-uridine ($Tm^5s^2U$), 1-taurinomethyl-4-thio-pseudouridine, 5-methyl-uridine ($m^5U$, i.e., having the nucleobase deoxythymine), 1-methyl-pseudouridine ($m^1ψ$), 5-methyl-2-thio-uridine ($m^5s^2U$), 1-methyl-4-thio-pseudouridine ($m^1s^4ψ$), 4-thio-1-methyl-pseudouridine, 3-methyl-pseudouridine ($m^3ψ$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine ($acp^3U$), 1-methyl-3-(3-amino-3-carboxypropyl)pseudouridine ($acp^3ψ$), 5-(isopentenylaminomethyl)uridine ($inm^5U$), 5-(isopentenylaminomethyl)-2-thio-uridine ($inm^5s^2U$), α-thio-uridine, 2'-O-methyl-uridine (Um), 5,2'-O-dimethyl-uridine ($m^5Um$), 2'-O-methyl-pseudouridine (ψm), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), and 5-(isopentenylaminomethyl)-2'-O-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino) uridine.

In some embodiments, the alternative nucleobase is an alternative cytosine. Exemplary nucleobases and nucleosides having an alternative cytosine include 5-aza-cytidine, 6-aza-cytidine, pseudoisocytidine, 3-methyl-cytidine ($m^3C$), N4-acetyl-cytidine ($ac^4C$), 5-formyl-cytidine ($f^5C$), N4-methyl-cytidine ($m^4C$), 5-methyl-cytidine ($m^5C$), 5-halo-cytidine (e.g., 5-iodo-cytidine), 5-hydroxymethyl-cytidine ($hm^5C$), 1-methyl-pseudoisocytidine, pyrrolo-cytidine, pyrrolo-pseudoisocytidine, 2-thio-cytidine ($s^2C$), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine ($k_2C$), α-thio-cytidine, 2'-O-methyl-cytidine (Cm), 5,2'-O-dimethyl-cytidine ($m^5Cm$), N4-acetyl-2'-O-methyl-cytidine ($ac^4Cm$), N4,2'-O-dimethyl-cytidine ($m^4Cm$), 5-formyl-2'-

O-methyl-cytidine (f⁵Cm), N4,N4,2'-O-trimethyl-cytidine (m⁴₂Cm), 1-thio-cytidine, 2'-F-ara-cytidine, 2'-F-cytidine, and 2'-OH-ara-cytidine.

In some embodiments, the alternative nucleobase is an alternative adenine. Exemplary nucleobases and nucleosides having an alternative adenine include 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine (m¹A), 2-methyl-adenine (m²A), N6-methyl-adenosine (m⁶A), 2-methylthio-N6-methyl-adenosine (ms²m⁶A), N6-isopentenyl-adenosine (i⁶A), 2-methylthio-N6-isopentenyl-adenosine (ms²i⁶A), N6-(cis-hydroxyisopentenyl)adenosine (io⁶A), 2-methylthio-N6-(cis-hydroxyisopentenyl) adenosine (ms²io⁶A), N6-glycinylcarbamoyl-adenosine (g⁶A), N6-threonylcarbamoyl-adenosine (t⁶A), N6-methyl-N6-threonylcarbamoyl-adenosine (m⁶t⁶A), 2-methylthio-N6-threonylcarbamoyl-adenosine (ms²g⁶A), N6,N6-dimethyl-adenosine (m⁶₂A), N6-hydroxynorvalylcarbamoyl-adenosine (hn⁶A), 2-methylthio-N6-hydroxynorvalylcarbamoyl-adenosine (ms²hn⁶A), N6-acetyl-adenosine (ac⁶A), 7-methyl-adenine, 2-methylthio-adenine, 2-methoxy-adenine, α-thio-adenosine, 2'-O-methyl-adenosine (Am), N6,2'-O-dimethyl-adenosine (m⁶Am), N6,N6,2'-O-trimethyl-adenosine (m⁶₂Am), 1,2'-O-dimethyl-adenosine (m¹Am), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the alternative nucleobase is an alternative guanine. Exemplary nucleobases and nucleosides having an alternative guanine include inosine (I), 1-methyl-inosine (m¹), wyosine (imG), methylwyosine (mimG), 4-demethyl-wyosine (imG-14), isowyosine (imG2), wybutosine (yW), peroxywybutosine (o₂yW), hydroxywybutosine (OhyW), undermodified hydroxywybutosine (OhyW*), 7-deaza-guanosine, queuosine (Q), epoxyqueuosine (oQ), galactosyl-queuosine (galQ), mannosyl-queuosine (manQ), 7-cyano-7-deaza-guanosine (preQ₀), 7-aminomethyl-7-deaza-guanosine (preQ₁), archaeosine (G⁺), 7-deaza-8-aza-guanosine, 6-thio-guanosine, 6-thio-7-deaza-guanosine, 6-thio-7-deaza-8-aza-guanosine, 7-methyl-guanosine (m⁷G), 6-thio-7-methyl-guanosine, 7-methyl-inosine, 6-methoxy-guanosine, 1-methyl-guanosine (m¹G), N2-methyl-guanosine (m²G), N2,N2-dimethyl-guanosine (m²₂G), N2,7-dimethyl-guanosine (m²,⁷G), N2, N2,7-dimethyl-guanosine (m²,²,⁷G), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine (m²Gm), N2,N2-dimethyl-2'-O-methyl-guanosine (m²₂Gm), 1-methyl-2'-O-methyl-guanosine (m¹Gm), N2,7-dimethyl-2'-O-methyl-guanosine (m²,⁷Gm), 2'-O-methyl-inosine (Im), 1,2'-O-dimethyl-inosine (m¹Im), 2'-O-ribosylguanosine (phosphate) (Gr(p)), 1-thio-guanosine, O6-methyl-guanosine, 2'-F-ara-guanosine, and 2'-F-guanosine.

In some embodiments, the nucleotide can be altered. For example, such alterations include replacing hydrogen on C-5 of uracil or cytosine with alkyl (e.g., methyl) or halo.

The nucleobase of a nucleotide can be independently selected from a purine, a pyrimidine, a purine or pyrimidine analog. For example, the nucleobase can each be independently selected from adenine, cytosine, guanine, uracil, or hypoxanthine. In another embodiment, the nucleobase can also include, for example, naturally-occurring and synthetic derivatives of a base, including pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d] pyrimidines, pyrazin-2-ones, 1,2,4-triazine, pyridazine; and 1,3,5 triazine. When the nucleotides are depicted using the shorthand A, G, C, T or U, each letter refers to the representative base and/or derivatives thereof, e.g., A includes adenine or adenine analogs, e.g., 7-deaza adenine).

In some embodiments, the alternative nucleotide is a compound of Formula XI:

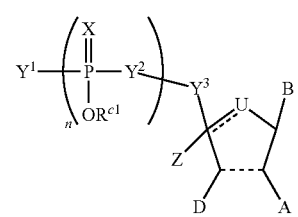

XI wherein:

⇌ denotes a single or a double bond;
--- denotes an optional single bond;

U is O, S, —NRᵃ—, or —CRᵃRᵇ— when ⇌ denotes a single bond, or U is —CRᵃ when ⇌ denotes a double bond;

Z is H, C₁₋₁₂ alkyl, or C₆₋₂₀ aryl, or Z is absent when ⇌ denotes a double bond; and Z can be —CRᵃRᵇ— and form a bond with A;

A is H, OH, NHR wherein R=alkyl or aryl or phosphoryl, sulfate, —NH₂, N₃, azido, —SH, N an amino acid, or a peptide comprising 1 to 12 amino acids;

D is H, OH, NHR wherein R=alkyl or aryl or phosphoryl, —NH₂, —SH, an amino acid, a peptide comprising 1 to 12 amino acids, or a group of Formula XII:

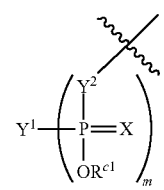

XII or A and D together with the carbon atoms to which they are attached form a 5-membered ring;

X is O or S;

each of $Y^1$ is independently selected from —$OR^{a1}$, —$NR^{a1}R^{b1}$, and —$SR^{a1}$;

each of $Y^2$ and $Y^3$ are independently selected from O, —$CR^aR^b$—, $NR^c$, S or a linker comprising one or more atoms selected from the group consisting of C, O, N, and S;

n is 0, 1, 2, or 3;

m is 0, 1, 2 or 3;

B is nucleobase;

$R^a$ and $R^b$ are each independently H, $C_{1-12}$ alkyl, $C_{2-12}$ alkenyl, $C_{2-12}$ alkynyl, or $C_{6-20}$ aryl;

$R^c$ is H, $C_{1-12}$ alkyl, $C_{2-12}$ alkenyl, phenyl, benzyl, a polyethylene glycol group, or an amino-polyethylene glycol group;

$R^{a1}$ and $R^{b1}$ are each independently H or a counterion; and

—$OR^{c1}$ is OH at a pH of about 1 or —$OR^{c1}$ is O⁻ at physiological pH;

provided that the ring encompassing the variables A, B, D, U, Z, $Y^2$ and $Y^3$ cannot be ribose.

In some embodiments, B is a nucleobase selected from the group consisting of cytosine, guanine, adenine, and uracil.

In some embodiments, the nucleobase is a pyrimidine or derivative thereof.

In some embodiments, the alternative nucleotides are a compound of Formula XI-a:

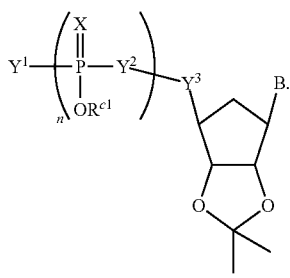

XI-a

In some embodiments, the alternative nucleotides are a compound of Formula XI-b:

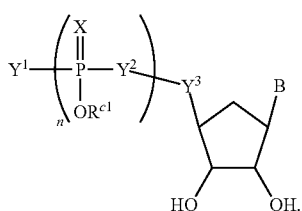

XI-b

In some embodiments, the alternative nucleotides are a compound of Formula XI-c1, XI-c2, or XI-c3:

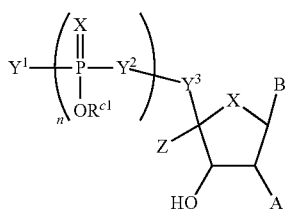

XI-c1

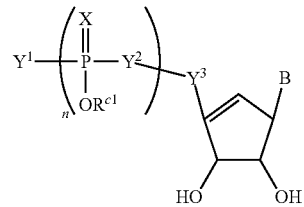

XI-c2

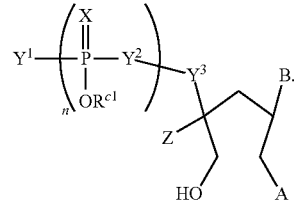

XI-c3

In some embodiments, the alternative nucleotides are a compound of Formula XI:

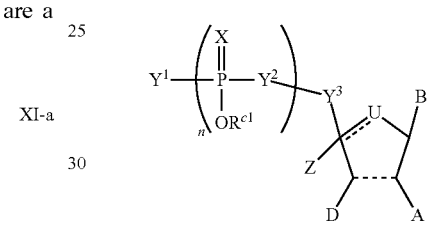

XI wherein

⤳ denotes a single or a double bond;

—— denotes an optional single bond;

U is O, S, —$NR^a$—, or —$CR^aR^b$— when ⤳ denotes a single bond, or U is —$CR^a$— when ⤳ denotes a double bond;

Z is H, $C_{1-12}$ alkyl, or $C_{6-20}$ aryl, or Z is absent when ⤳ denotes a double bond; and Z can be —$CR^aR^b$— and form a bond with A;

A is H, OH, sulfate, —$NH_2$, —SH, an amino acid, or a peptide comprising 1 to 12 amino acids;

D is H, OH, —$NH_2$, —SH, an amino acid, a peptide comprising 1 to 12 amino acids, or a group of Formula XII:

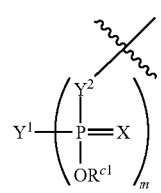

XII or A and D together with the carbon atoms to which they are attached form a 5-membered ring;

X is O or S;

each of $Y^1$ is independently selected from —$OR^{a1}$, —$NR^{a1}R^{b1}$, and —$SR^{a1}$;

each of $Y^2$ and $Y^3$ are independently selected from O, —$CR^aR^b$—, $NR^c$, S or a linker comprising one or more atoms selected from the group consisting of C, O, N, and S;

n is 0, 1, 2, or 3;
m is 0, 1, 2 or 3;
B is a nucleobase of Formula XIII:

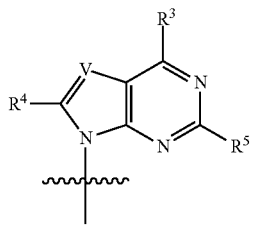

XIII wherein:
V is N or positively charged $NR^c$;
$R^3$ is $NR^cR^d$, $-OR^a$, or $-SR^a$;
$R^4$ is H or can optionally form a bond with $Y^3$
$R^5$ is H, $-NR^cR^d$, or $-OR^a$;
$R^a$ and $R^b$ are each independently H, $C_{1-12}$ alkyl, $C_{2-12}$ alkenyl, $C_{2-12}$ alkynyl, or $C_{6-20}$ aryl;
$R^c$ is H, $C_{1-12}$ alkyl, $C_{2-12}$ alkenyl, phenyl, benzyl, a polyethylene glycol group, or an amino-polyethylene glycol group;
$R^{a1}$ and $R^{b1}$ are each independently H or a counterion; and
$-OR^{c1}$ is OH at a pH of about 1 or $-OR^{c1}$ is $O^-$ at physiological pH.

In some embodiments, B is:

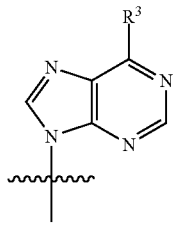

wherein $R^3$ is $-OH$, $-SH$, or

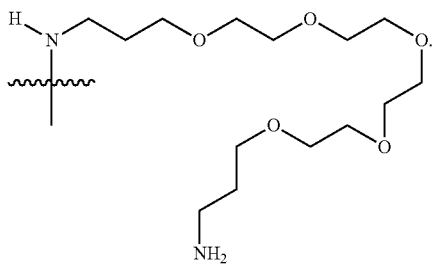 [SMILES: *NCCCOCCOCCOCCOCCOCCCN]

In some embodiments, B is:

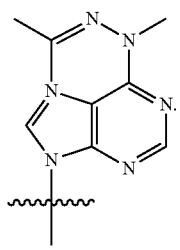

In some embodiments, B is:

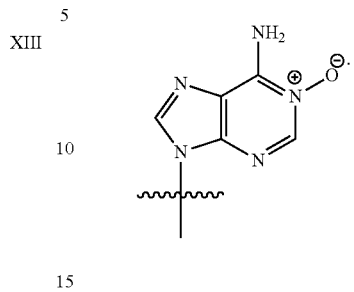

In some embodiments, the alternative nucleotides are a compound of Formula I-d:

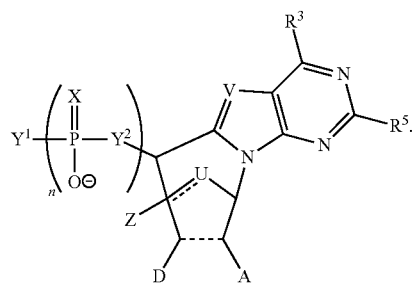

In some embodiments, the alternative nucleotides are a compound selected from the group consisting of:

(BB-247)

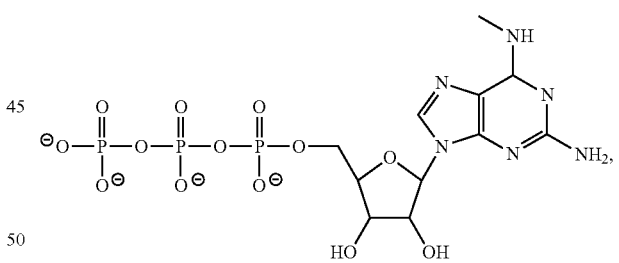

(BB-248)

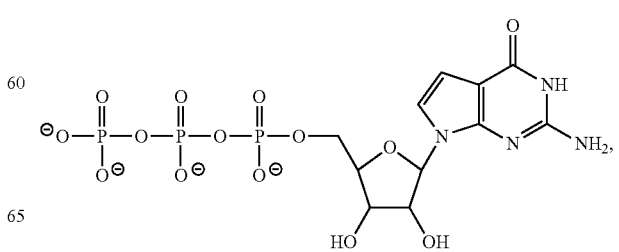

(BB-249)
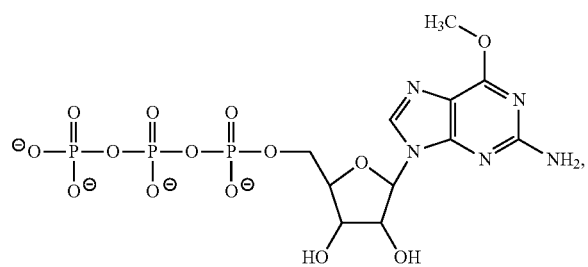
(BB-250)
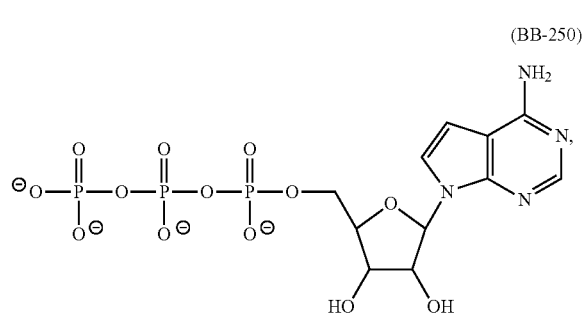
(BB-251)
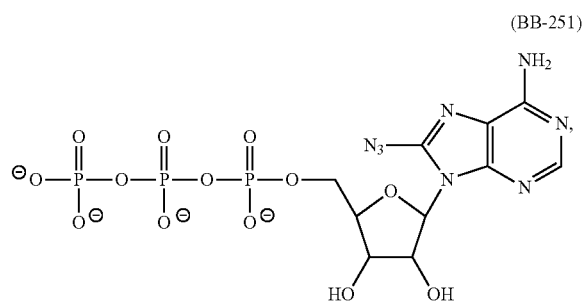
(BB-252)
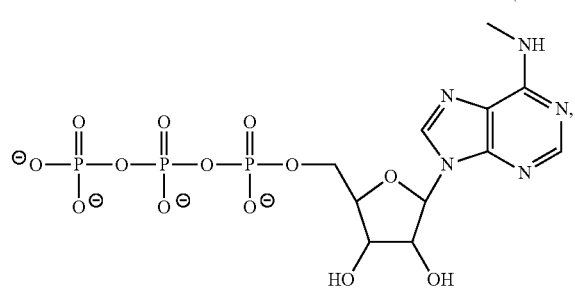
(BB-253)
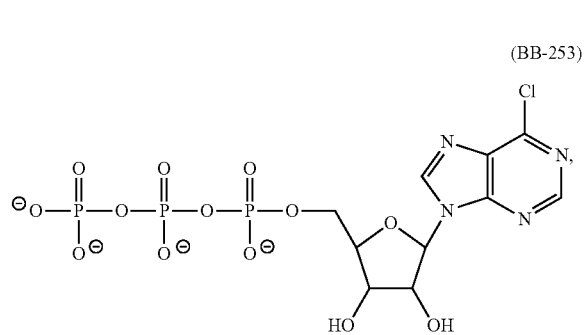
(BB-254)
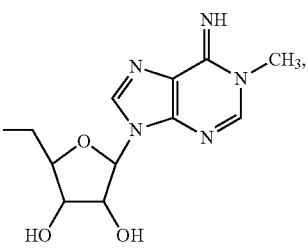
(BB-255)
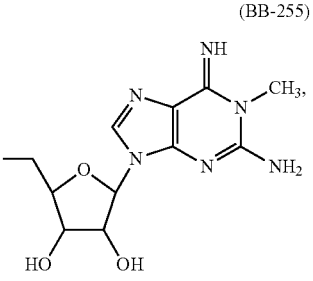
(BB-256)
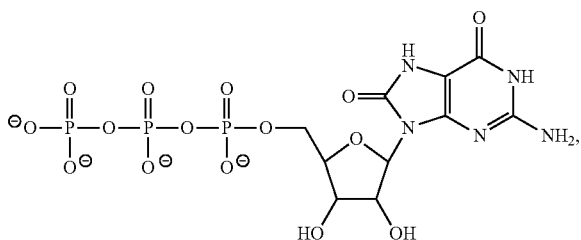
(BB-257)
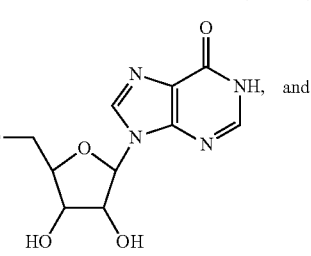
and
(BB-258)
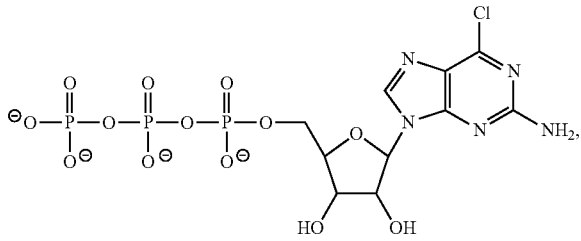
or a pharmaceutically acceptable salt thereof.
In some embodiments, the alternative nucleotides are a compound selected from the group consisting of:

(BB-259) 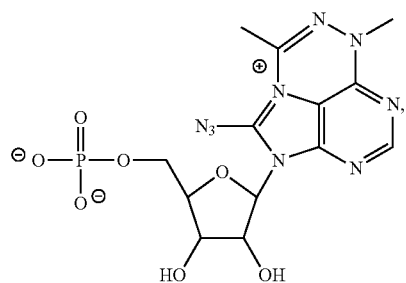
(BB-260) 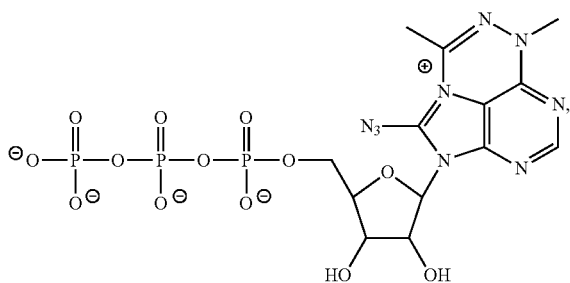
(BB-261) 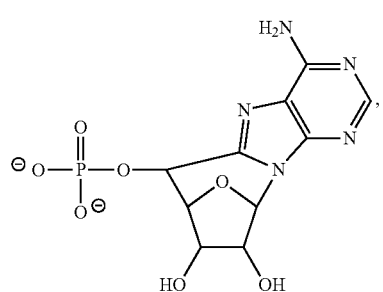
(BB-262) 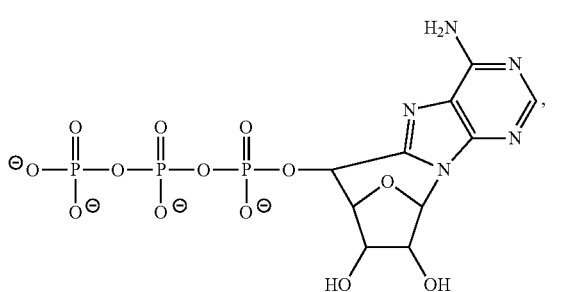
(BB-263) 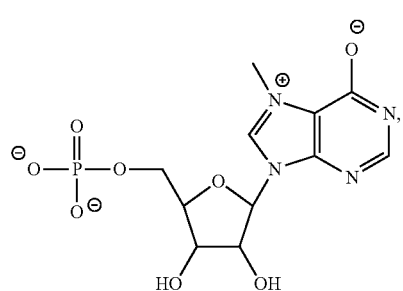
(BB-264) 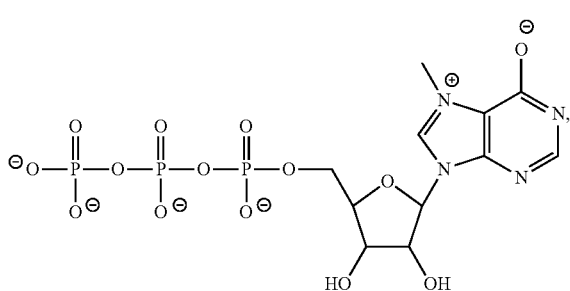
(BB-265) 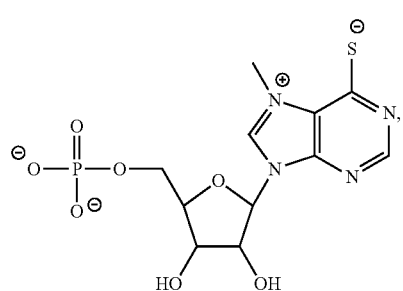
(BB-266) 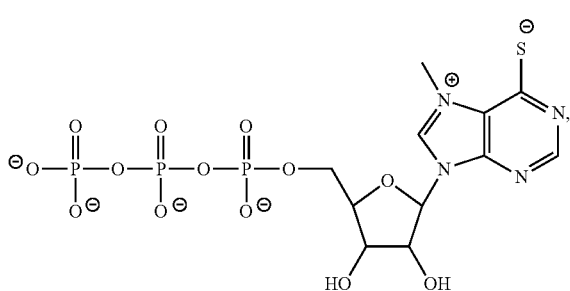
(BB-267) 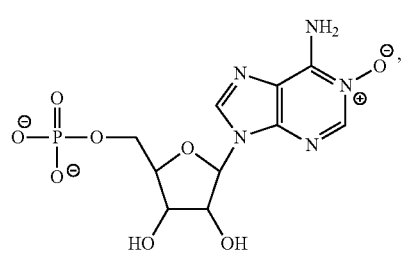
(BB-268) 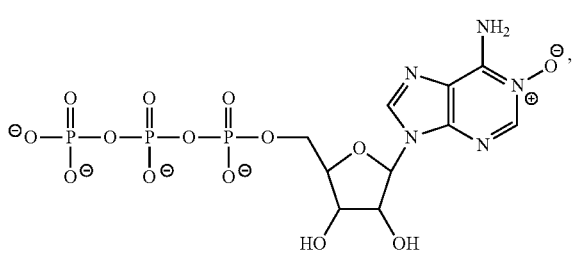

-continued
(BB-269)
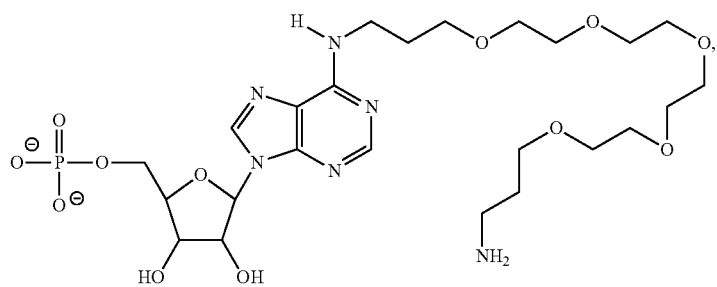
(BB-270)
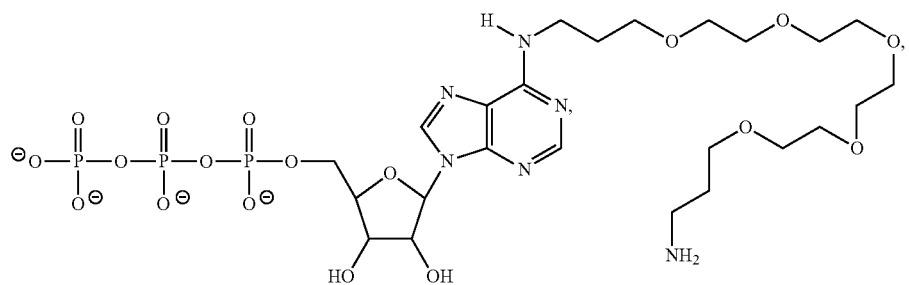
(BB-271)
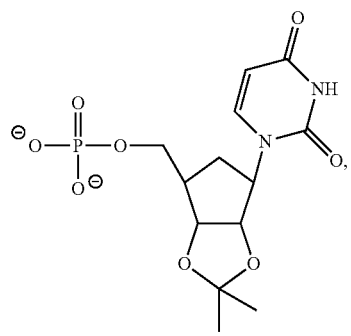
(BB-272)
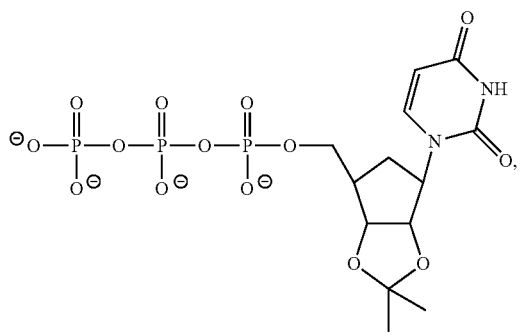
(BB-273)
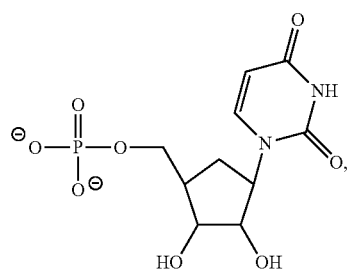
(BB-274)
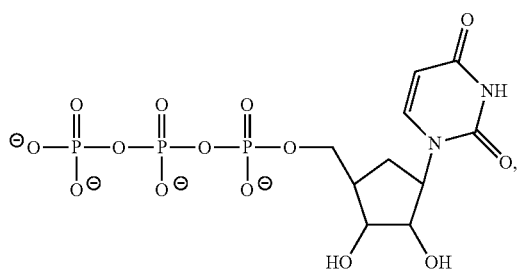
(BB-275)
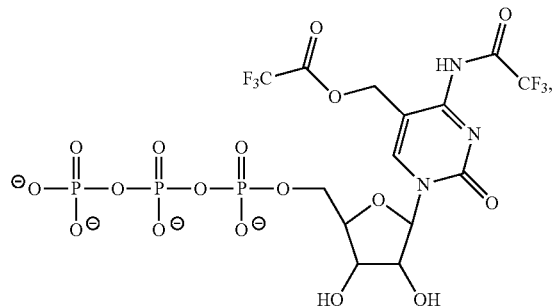
(BB-276)
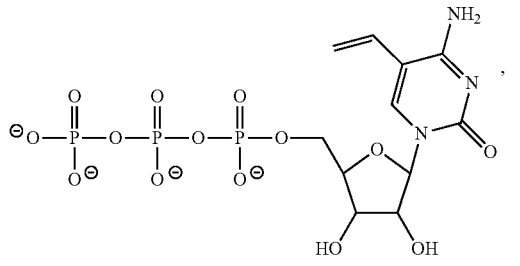

-continued
(BB-277)
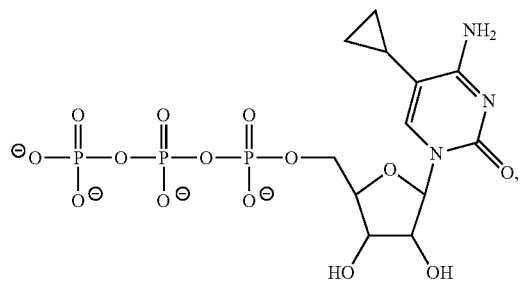
(BB-278)
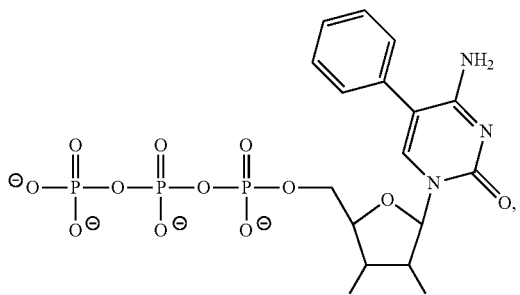
(BB-279)
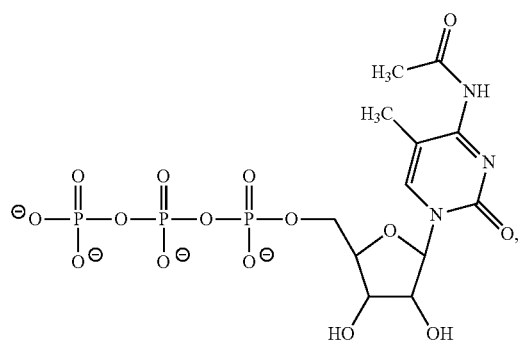
(BB-280)
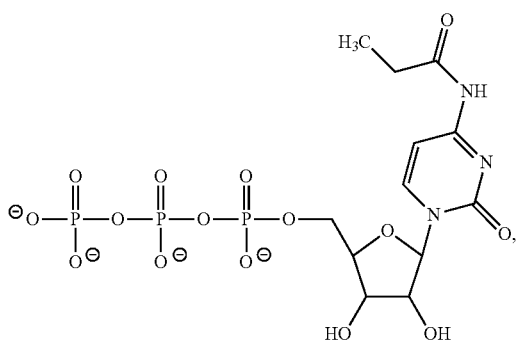
(BB-281)
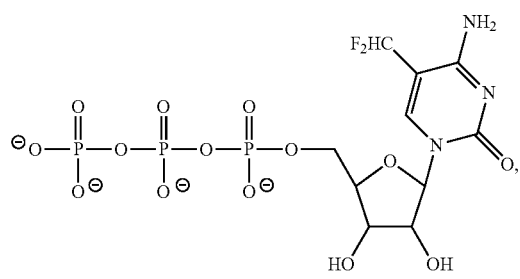
(BB-282)
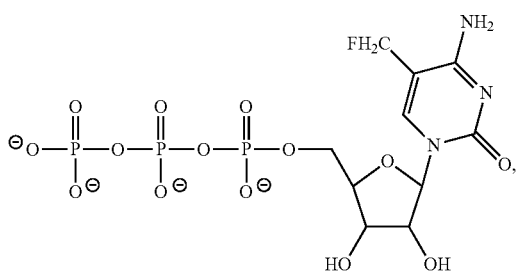
(BB-283)
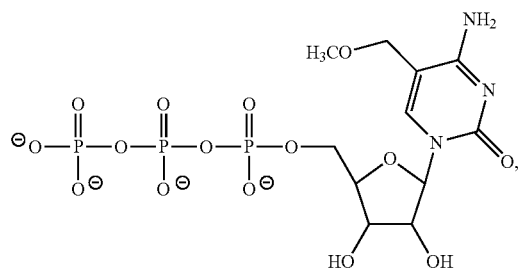
(BB-284)
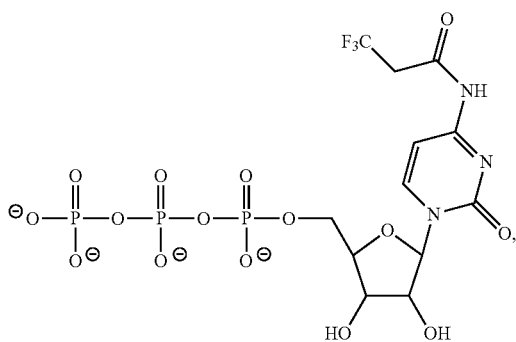
(BB-285)
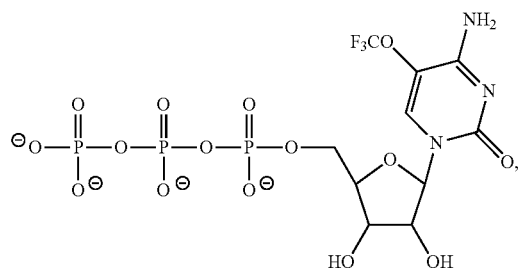
(BB-286)
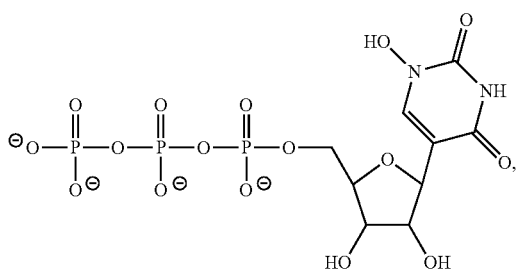

(BB-287)

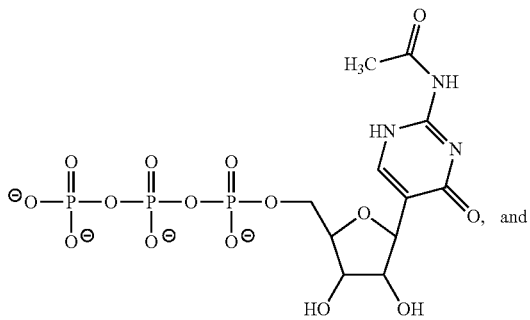

and (BB-288)

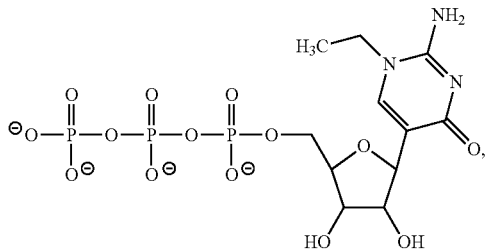

or a pharmaceutically acceptable salt thereof.

Alterations on the Internucleoside Linkage

The alternative nucleotides, which may be incorporated into a polynucleotide molecule, can be altered on the internucleoside linkage (e.g., phosphate backbone). Herein, in the context of the polynucleotide backbone, the phrases "phosphate" and "phosphodiester" are used interchangeably. Backbone phosphate groups can be altered by replacing one or more of the oxygen atoms with a different substituent.

The alternative nucleosides and nucleotides can include the wholesale replacement of an unaltered phosphate moiety with another internucleoside linkage as described herein. Examples of alternative phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be altered by the replacement of a linking oxygen with nitrogen (bridged phosphoramidates), sulfur (bridged phosphorothioates), and carbon (bridged methylene-phosphonates).

The alternative nucleosides and nucleotides can include the replacement of one or more of the non-bridging oxygens with a borane moiety ($BH_3$), sulfur (thio), methyl, ethyl and/or methoxy. As a non-limiting example, two non-bridging oxygens at the same position (e.g., the alpha (a), beta (p) or gamma (y) position) can be replaced with a sulfur (thio) and a methoxy.

The replacement of one or more of the oxygen atoms at the α position of the phosphate moiety (e.g., α-thio phosphate) is provided to confer stability (such as against exonucleases and endonucleases) to RNA and DNA through the unnatural phosphorothioate backbone linkages.

Phosphorothioate DNA and RNA have increased nuclease resistance and subsequently a longer half-life in a cellular environment. While not wishing to be bound by theory, phosphorothioate linked polynucleotide molecules are expected to also reduce the innate immune response through weaker binding/activation of cellular innate immune molecules.

In specific embodiments, an alternative nucleoside includes an alpha-thio-nucleoside (e.g., 5'-O-(1-thiophosphate)-adenosine, 5'-O-(1-thiophosphate)-cytidine (α-thio-cytidine), 5'-O-(1-thiophosphate)-guanosine, 5'-O-(1-thiophosphate)-uridine, or 5'-O-(1-thiophosphate)-pseudouridine).

Other internucleoside linkages that may be employed according to the present invention, including internucleoside linkages which do not contain a phosphorous atom, are described herein.

Combinations of Alternative Sugars, Nucleobases, and Internucleoside Linkages

The polynucleotides of the invention can include a combination of alterations to the sugar, the nucleobase, and/or the internucleoside linkage. These combinations can include any one or more alterations described herein. For examples, any of the nucleotides described herein in Formulas (Ia), (Ia-1)-(Ia-3), (Ib)-(If), (Iia)-(Iip), (Iib-1), (Iib-2), (Iic-1)-(Iic-2), (Iin-1), (Iin-2), (Iva)-(Ivl), and (Ixa)-(Ixr) can be combined with any of the nucleobases described herein (e.g., in Formulas (b1)-(b43) or any other described herein).

Synthesis of Polynucleotide Molecules

The polynucleotide molecules for use in accordance with the invention may be prepared according to any useful technique, as described herein. The alternative nucleosides and nucleotides used in the synthesis of polynucleotide molecules disclosed herein can be prepared from readily available starting materials using the following general methods and procedures. Where typical or preferred process conditions (e.g., reaction temperatures, times, mole ratios of reactants, solvents, and/or pressures) are provided, a skilled artisan would be able to optimize and develop additional process conditions. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

Preparation of polynucleotide molecules of the present invention can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis,* 2d. Ed., Wiley & Sons, 1991, which is incorporated herein by reference in its entirety.

The reactions of the processes described herein can be carried out in suitable solvents, which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of alternative polynucleotides or nucleic acids (e.g., polynucleotides or alternative mRNA molecules) can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

Alternative nucleosides and nucleotides (e.g., building block molecules) can be prepared according to the synthetic methods described in Ogata et al., J. Org. Chem. 74:2585-2588 (2009); Purmal et al., Nucl. Acids Res. 22(1): 72-78, (1994); Fukuhara et al., Biochemistry, 1(4): 563-568 (1962); and Xu et al., Tetrahedron, 48(9): 1729-1740 (1992), each of which are incorporated by reference in their entirety.

The polynucleotides of the invention may or may not be uniformly altered along the entire length of the molecule. For example, one or more or all types of nucleotide (e.g., purine or pyrimidine, or any one or more or all of A, G, U, C) may or may not be uniformly altered in a polynucleotide of the invention, or in a given predetermined sequence region thereof. In some embodiments, all nucleotides X in a polynucleotide of the invention (or in a given sequence region thereof) are altered, wherein X may any one of nucleotides A, G, U, C, or any one of the combinations A+G, A+U, A+C, G+U, G+C, U+C, A+G+U, A+G+C, G+U+C or A+G+C.

Different sugar alterations, nucleotide alterations, and/or internucleoside linkages (e.g., backbone structures) may exist at various positions in the polynucleotide. One of ordinary skill in the art will appreciate that the nucleotide analogs or other alteration(s) may be located at any position(s) of a polynucleotide such that the function of the polynucleotide is not substantially decreased. A alteration may also be a 5' or 3' terminal alteration. The polynucleotide may contain from about 1% to about 100% alternative nucleotides (either in relation to overall nucleotide content, or in relation to one or more types of nucleotide, i.e. any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100. In some embodiments, the remaining percentage is accounted for by the presence of A, G, U, or C.

In some embodiments, the polynucleotide includes an alternative pyrimidine (e.g., an alternative uracil/uridine/U or alternative cytosine/cytidine/C). In some embodiments, the uracil or uridine (generally: U) in the polynucleotide molecule may be replaced with from about 1% to about 100% of an alternative uracil or alternative uridine (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100% of an alternative uracil or alternative uridine). The alternative uracil or uridine can be replaced by a compound having a single unique structure or by a plurality of compounds having different structures (e.g., 2, 3, 4 or more unique structures, as described herein). In some embodiments, the cytosine or cytidine (generally: C) in the polynucleotide molecule may be replaced with from about 1% to about 100% of an alternative cytosine or alternative cytidine (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100% of an alternative cytosine or alternative cytidine). The alternative cytosine or cytidine can be replaced by a compound having a single unique structure or by a plurality of compounds having different structures (e.g., 2, 3, 4 or more unique structures, as described herein).

When referring to percentage incorporation by an alternative nucleoside (e.g., an alternative nucleoside containing an alternative uracil or cytosine or an alternative uridine or cytidine) in some embodiments the remaining percentage necessary to total 100% is accounted for by the corresponding natural nucleoside (e.g., uridine or cytidine) or natural nucleobase (e.g., uracil or cytosine). In other embodiments, the remaining percentage necessary to total 100% is accounted for by a second alternative nucleoside (e.g., an alternative nucleoside containing an alternative uracil or cytosine or an alternative uridine or cytidine). In some embodiments, the first alternative nucleoside is 5-methoxy-uridine or a nucleoside containing 5-methoxy-uracil and the second alternative nucleoside is 1-methyl-pseudouridine or a nucleoside containing 1-methyl-psuedouracil.

In some embodiments, the polynucleotide of the invention contains about 5% alternative uracil, e.g., alternative uracils described in Table 2, in combination with a percentage of alternative cytosine, e.g., alternative cytosines described in Table 3, according to columns 1 and 2 of Table A1. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

TABLE A1

| Column 1<br>Percentage of<br>alternative uracil | Column 2<br>Percentage of<br>alternative cytosine |
|---|---|
| 5 | 100 |
| 5 | 95 |
| 5 | 90 |
| 5 | 85 |
| 5 | 80 |
| 5 | 75 |
| 5 | 70 |
| 5 | 65 |
| 5 | 60 |
| 5 | 55 |
| 5 | 50 |
| 5 | 45 |
| 5 | 40 |
| 5 | 35 |
| 5 | 30 |
| 5 | 25 |
| 5 | 20 |
| 5 | 15 |
| 5 | 10 |
| 5 | 5 |

In some embodiments, the polynucleotide of the invention contains about 10% alternative uracil, e.g., alternative uracils described in Table 2, in combination with a percentage of alternative cytosine, e.g., alternative cytosines described in Table 3, according to columns 1 and 2 of Table A2. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

TABLE A2

| Column 1<br>Percentage of<br>alternative uracil | Column 2<br>Percentage of<br>alternative cytosine |
|---|---|
| 10 | 100 |
| 10 | 95 |
| 10 | 90 |
| 10 | 85 |
| 10 | 80 |
| 10 | 75 |
| 10 | 70 |
| 10 | 65 |
| 10 | 60 |
| 10 | 55 |
| 10 | 50 |
| 10 | 45 |
| 10 | 40 |
| 10 | 35 |
| 10 | 30 |
| 10 | 25 |
| 10 | 20 |
| 10 | 15 |
| 10 | 10 |
| 10 | 5 |

In some embodiments, the polynucleotide of the invention contains about 15% alternative uracil, e.g., alternative uracils described in Table 2, in combination with a percentage of alternative cytosine, e.g., alternative cytosines described in Table 3, according to columns 1 and 2 of Table A3. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

TABLE A3

| Column 1<br>Percentage of<br>alternative uracil | Column 2<br>Percentage of<br>alternative cytosine |
|---|---|
| 15 | 100 |
| 15 | 95 |
| 15 | 90 |
| 15 | 85 |
| 15 | 80 |
| 15 | 75 |
| 15 | 70 |
| 15 | 65 |
| 15 | 60 |
| 15 | 55 |
| 15 | 50 |
| 15 | 45 |
| 15 | 40 |
| 15 | 35 |
| 15 | 30 |
| 15 | 25 |
| 15 | 20 |
| 15 | 15 |
| 15 | 10 |
| 15 | 5 |

In some embodiments, the polynucleotide of the invention contains about 20% alternative uracil, e.g., alternative uracils described in Table 2, in combination with a percentage of alternative cytosine, e.g., alternative cytosines described in Table 3, according to columns 1 and 2 of Table A4. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

TABLE A4

| Column 1<br>Percentage of<br>alternative uracil | Column 2<br>Percentage of<br>alternative cytosine |
|---|---|
| 20 | 100 |
| 20 | 95 |
| 20 | 90 |
| 20 | 85 |
| 20 | 80 |
| 20 | 75 |
| 20 | 70 |
| 20 | 65 |
| 20 | 60 |
| 20 | 55 |
| 20 | 50 |
| 20 | 45 |
| 20 | 40 |
| 20 | 35 |
| 20 | 30 |
| 20 | 25 |
| 20 | 20 |
| 20 | 15 |
| 20 | 10 |
| 20 | 5 |

In some embodiments, the polynucleotide of the invention contains about 25% alternative uracil, e.g., alternative uracils described in Table 2, in combination with a percentage of alternative cytosine, e.g., alternative cytosines described in Table 3, according to columns 1 and 2 of Table A5. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

TABLE A5

| Column 1 Percentage of alternative uracil | Column 2 Percentage of alternative cytosine |
|---|---|
| 25 | 100 |
| 25 | 95 |
| 25 | 90 |
| 25 | 85 |
| 25 | 80 |
| 25 | 75 |
| 25 | 70 |
| 25 | 65 |
| 25 | 60 |
| 25 | 55 |
| 25 | 50 |
| 25 | 45 |
| 25 | 40 |
| 25 | 35 |
| 25 | 30 |
| 25 | 25 |
| 25 | 20 |
| 25 | 15 |
| 25 | 10 |
| 25 | 5 |

In some embodiments, the polynucleotide of the invention contains about 30% alternative uracil, e.g., alternative uracils described in Table 2, in combination with a percentage of alternative cytosine, e.g., alternative cytosines described in Table 3, according to columns 1 and 2 of Table A6. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

TABLE A6

| Column 1 Percentage of alternative uracil | Column 2 Percentage of alternative cytosine |
|---|---|
| 30 | 100 |
| 30 | 95 |
| 30 | 90 |
| 30 | 85 |
| 30 | 80 |
| 30 | 75 |
| 30 | 70 |
| 30 | 65 |
| 30 | 60 |
| 30 | 55 |
| 30 | 50 |
| 30 | 45 |
| 30 | 40 |
| 30 | 35 |
| 30 | 30 |
| 30 | 25 |
| 30 | 20 |
| 30 | 15 |
| 30 | 10 |
| 30 | 5 |

In some embodiments, the polynucleotide of the invention contains about 35% alternative uracil, e.g., alternative uracils described in Table 2, in combination with a percentage of alternative cytosine, e.g., alternative cytosines described in Table 3, according to columns 1 and 2 of Table A7. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

TABLE A7

| Column 1 Percentage of alternative uracil | Column 2 Percentage of alternative cytosine |
|---|---|
| 35 | 100 |
| 35 | 95 |
| 35 | 90 |
| 35 | 85 |
| 35 | 80 |
| 35 | 75 |
| 35 | 70 |
| 35 | 65 |
| 35 | 60 |
| 35 | 55 |
| 35 | 50 |
| 35 | 45 |
| 35 | 40 |
| 35 | 35 |
| 35 | 30 |
| 35 | 25 |
| 35 | 20 |
| 35 | 15 |
| 35 | 10 |
| 35 | 5 |

In some embodiments, the polynucleotide of the invention contains about 40% alternative uracil, e.g., alternative uracils described in Table 2, in combination with a percentage of alternative cytosine, e.g., alternative cytosines described in Table 3, according to columns 1 and 2 of Table A8. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

TABLE A8

| Column 1 Percentage of alternative uracil | Column 2 Percentage of alternative cytosine |
|---|---|
| 40 | 100 |
| 40 | 95 |
| 40 | 90 |
| 40 | 85 |
| 40 | 80 |
| 40 | 75 |
| 40 | 70 |
| 40 | 65 |
| 40 | 60 |
| 40 | 55 |
| 40 | 50 |
| 40 | 45 |
| 40 | 40 |
| 40 | 35 |
| 40 | 30 |
| 40 | 25 |
| 40 | 20 |
| 40 | 15 |
| 40 | 10 |
| 40 | 5 |

In some embodiments, the polynucleotide of the invention contains about 45% alternative uracil, e.g., alternative uracils described in Table 2, in combination with a percentage of alternative cytosine, e.g., alternative cytosines described in Table 3, according to columns 1 and 2 of Table A9. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

TABLE A9

| Column 1 Percentage of alternative uracil | Column 2 Percentage of alternative cytosine |
|---|---|
| 45 | 100 |
| 45 | 95 |
| 45 | 90 |
| 45 | 85 |
| 45 | 80 |
| 45 | 75 |
| 45 | 70 |
| 45 | 65 |
| 45 | 60 |
| 45 | 55 |
| 45 | 50 |
| 45 | 45 |
| 45 | 40 |
| 45 | 35 |
| 45 | 30 |
| 45 | 25 |
| 45 | 20 |
| 45 | 15 |
| 45 | 10 |
| 45 | 5 |

In some embodiments, the polynucleotide of the invention contains about 50% alternative uracil, e.g., alternative uracils described in Table 2, in combination with a percentage of alternative cytosine, e.g., alternative cytosines described in Table 3, according to columns 1 and 2 of Table A10. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

TABLE A10

| Column 1 Percentage of alternative uracil | Column 2 Percentage of alternative cytosine |
|---|---|
| 50 | 100 |
| 50 | 95 |
| 50 | 90 |
| 50 | 85 |
| 50 | 80 |
| 50 | 75 |
| 50 | 70 |
| 50 | 65 |
| 50 | 60 |
| 50 | 55 |
| 50 | 50 |
| 50 | 45 |
| 50 | 40 |
| 50 | 35 |
| 50 | 30 |
| 50 | 25 |
| 50 | 20 |
| 50 | 15 |
| 50 | 10 |
| 50 | 5 |

In some embodiments, the polynucleotide of the invention contains about 55% alternative uracil, e.g., alternative uracils described in Table 2, in combination with a percentage of alternative cytosine, e.g., alternative cytosines described in Table 3, according to columns 1 and 2 of Table A11. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

TABLE A11

| Column 1 Percentage of alternative uracil | Column 2 Percentage of alternative cytosine |
|---|---|
| 55 | 100 |
| 55 | 95 |
| 55 | 90 |
| 55 | 85 |
| 55 | 80 |
| 55 | 75 |
| 55 | 70 |
| 55 | 65 |
| 55 | 60 |
| 55 | 55 |
| 55 | 50 |
| 55 | 45 |
| 55 | 40 |
| 55 | 35 |
| 55 | 30 |
| 55 | 25 |
| 55 | 20 |
| 55 | 15 |
| 55 | 10 |
| 55 | 5 |

In some embodiments, the polynucleotide of the invention contains about 60% alternative uracil, e.g., alternative uracils described in Table 2, in combination with a percentage of alternative cytosine, e.g., alternative cytosines described in Table 3, according to columns 1 and 2 of Table A12. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

TABLE A12

| Column 1 Percentage of alternative uracil | Column 2 Percentage of alternative cytosine |
|---|---|
| 60 | 100 |
| 60 | 95 |
| 60 | 90 |
| 60 | 85 |
| 60 | 80 |
| 60 | 75 |
| 60 | 70 |
| 60 | 65 |
| 60 | 60 |
| 60 | 55 |
| 60 | 50 |
| 60 | 45 |
| 60 | 40 |
| 60 | 35 |
| 60 | 30 |
| 60 | 25 |
| 60 | 20 |
| 60 | 15 |
| 60 | 10 |
| 60 | 5 |

In some embodiments, the polynucleotide of the invention contains about 65% alternative uracil, e.g., alternative uracils described in Table 2, in combination with a percentage of alternative cytosine, e.g., alternative cytosines described in Table 3, according to columns 1 and 2 of Table A13. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

TABLE A13

| Column 1 Percentage of alternative uracil | Column 2 Percentage of alternative cytosine |
|---|---|
| 65 | 100 |
| 65 | 95 |
| 65 | 90 |
| 65 | 85 |
| 65 | 80 |
| 65 | 75 |
| 65 | 70 |
| 65 | 65 |
| 65 | 60 |
| 65 | 55 |
| 65 | 50 |
| 65 | 45 |
| 65 | 40 |
| 65 | 35 |
| 65 | 30 |
| 65 | 25 |
| 65 | 20 |
| 65 | 15 |
| 65 | 10 |
| 65 | 5 |

In some embodiments, the polynucleotide of the invention contains about 70% alternative uracil, e.g., alternative uracils described in Table 2, in combination with a percentage of alternative cytosine, e.g., alternative cytosines described in Table 3, according to columns 1 and 2 of Table A14. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

TABLE A14

| Column 1 Percentage of alternative uracil | Column 2 Percentage of alternative cytosine |
|---|---|
| 70 | 100 |
| 70 | 95 |
| 70 | 90 |
| 70 | 85 |
| 70 | 80 |
| 70 | 75 |
| 70 | 70 |
| 70 | 65 |
| 70 | 60 |
| 70 | 55 |
| 70 | 50 |
| 70 | 45 |
| 70 | 40 |
| 70 | 35 |
| 70 | 30 |
| 70 | 25 |
| 70 | 20 |
| 70 | 15 |

TABLE A14-continued

| Column 1 Percentage of alternative uracil | Column 2 Percentage of alternative cytosine |
|---|---|
| 70 | 10 |
| 70 | 5 |

In some embodiments, the polynucleotide of the invention contains about 75% alternative uracil, e.g., alternative uracils described in Table 2, in combination with a percentage of alternative cytosine, e.g., alternative cytosines described in Table 3, according to columns 1 and 2 of Table A15. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

TABLE A15

| Column 1 Percentage of alternative uracil | Column 2 Percentage of alternative cytosine |
|---|---|
| 75 | 100 |
| 75 | 95 |
| 75 | 90 |
| 75 | 85 |
| 75 | 80 |
| 75 | 75 |
| 75 | 70 |
| 75 | 65 |
| 75 | 60 |
| 75 | 55 |
| 75 | 50 |
| 75 | 45 |
| 75 | 40 |
| 75 | 35 |
| 75 | 30 |
| 75 | 25 |
| 75 | 20 |
| 75 | 15 |
| 75 | 10 |
| 75 | 5 |

In some embodiments, the polynucleotide of the invention contains about 80% alternative uracil, e.g., alternative uracils described in Table 2, in combination with a percentage of alternative cytosine, e.g., alternative cytosines described in Table 3, according to columns 1 and 2 of Table A16. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

TABLE A16

| Column 1 Percentage of alternative uracil | Column 2 Percentage of alternative cytosine |
|---|---|
| 80 | 100 |
| 80 | 95 |
| 80 | 90 |
| 80 | 85 |
| 80 | 80 |
| 80 | 75 |
| 80 | 70 |

TABLE A16-continued

| Column 1 Percentage of alternative uracil | Column 2 Percentage of alternative cytosine |
| --- | --- |
| 80 | 65 |
| 80 | 60 |
| 80 | 55 |
| 80 | 50 |
| 80 | 45 |
| 80 | 40 |
| 80 | 35 |
| 80 | 30 |
| 80 | 25 |
| 80 | 20 |
| 80 | 15 |
| 80 | 10 |
| 80 | 5 |

In some embodiments, the polynucleotide of the invention contains about 85% alternative uracil, e.g., alternative uracils described in Table 2, in combination with a percentage of alternative cytosine, e.g., alternative cytosines described in Table 3, according to columns 1 and 2 of Table A17. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

TABLE A17

| Column 1 Percentage of alternative uracil | Column 2 Percentage of alternative cytosine |
| --- | --- |
| 85 | 100 |
| 85 | 95 |
| 85 | 90 |
| 85 | 85 |
| 85 | 80 |
| 85 | 75 |
| 85 | 70 |
| 85 | 65 |
| 85 | 60 |
| 85 | 55 |
| 85 | 50 |
| 85 | 45 |
| 85 | 40 |
| 85 | 35 |
| 85 | 30 |
| 85 | 25 |
| 85 | 20 |
| 85 | 15 |
| 85 | 10 |
| 85 | 5 |

In some embodiments, the polynucleotide of the invention contains about 90% alternative uracil, e.g., alternative uracils described in Table 2, in combination with a percentage of alternative cytosine, e.g., alternative cytosines described in Table 3, according to columns 1 and 2 of Table A18. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

TABLE A18

| Column 1 Percentage of alternative uracil | Column 2 Percentage of alternative cytosine |
| --- | --- |
| 90 | 100 |
| 90 | 95 |
| 90 | 90 |
| 90 | 85 |
| 90 | 80 |
| 90 | 75 |
| 90 | 70 |
| 90 | 65 |
| 90 | 60 |
| 90 | 55 |
| 90 | 50 |
| 90 | 45 |
| 90 | 40 |
| 90 | 35 |
| 90 | 30 |
| 90 | 25 |
| 90 | 20 |
| 90 | 15 |
| 90 | 10 |
| 90 | 5 |

In some embodiments, the polynucleotide of the invention contains about 95% alternative uracil, e.g., alternative uracils described in Table 2, in combination with a percentage of alternative cytosine, e.g., alternative cytosines described in Table 3, according to columns 1 and 2 of Table A19. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

TABLE A19

| Column 1 Percentage of alternative uracil | Column 2 Percentage of alternative cytosine |
| --- | --- |
| 95 | 100 |
| 95 | 95 |
| 95 | 90 |
| 95 | 85 |
| 95 | 80 |
| 95 | 75 |
| 95 | 70 |
| 95 | 65 |
| 95 | 60 |
| 95 | 55 |
| 95 | 50 |
| 95 | 45 |
| 95 | 40 |
| 95 | 35 |
| 95 | 30 |
| 95 | 25 |
| 95 | 20 |
| 95 | 15 |
| 95 | 10 |
| 95 | 5 |

In some embodiments, the polynucleotide of the invention contains about 100% alternative uracil, e.g., alternative uracils described in Table 2, in combination with a percentage of alternative cytosine, e.g., alternative cytosines described in Table 3, according to columns 1 and 2 of Table A20. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

TABLE A20

| Column 1 Percentage of alternative uracil | Column 2 Percentage of alternative cytosine |
| --- | --- |
| 100 | 100 |
| 100 | 95 |
| 100 | 90 |
| 100 | 85 |
| 100 | 80 |
| 100 | 75 |
| 100 | 70 |
| 100 | 65 |
| 100 | 60 |
| 100 | 55 |
| 100 | 50 |
| 100 | 45 |
| 100 | 40 |
| 100 | 35 |
| 100 | 30 |
| 100 | 25 |
| 100 | 20 |
| 100 | 15 |
| 100 | 10 |
| 100 | 5 |

In some embodiments, the polynucleotide of the invention contains the percentage range of alternative uracil, e.g., alternative uracils described in Table 2, in row 1 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 1 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 1 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 2 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 2 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 2 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 3 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 3 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 3 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 4 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 4 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 4 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 5 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 5 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 5 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 6 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 6 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 6 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 7 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 7 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 7 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 8 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 8 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 8 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 9 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 9 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 9 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 10 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 10 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 10 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 11 of Table A21 and the percentage range of alternative cytosines, e.g., alternative cytosines as described in Table 3 , in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 11 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 11 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 12 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 12 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 12 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 13 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 13 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 13 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 14 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 14 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 14 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 15 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 15 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 15 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 16 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 16 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 16 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 17 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 17 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 17 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 18 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 18 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 18 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 19 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 19 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 19 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 20 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 20 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 20 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 21 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 21 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 21 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 22 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 22 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 22 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 23 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 23 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 23 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 24 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 24 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 24 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 25 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 25 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 25 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 26 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 26 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 26 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 27 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 27 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 27 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 28 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 28 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 28 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 29 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 29 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 29 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 30 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 30 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 30 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 31 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 31 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 31 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 32 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 32 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 32 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 33 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 33 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 33 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 34 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 34 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 34 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 35 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 35 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 35 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 36 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 36 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 36 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 37 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 37 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 37 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 38 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 38 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 38 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 39 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 39 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 39 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 40 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 40 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 40 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 41 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 41 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 41 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 42 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 42 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 42 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 43 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 43 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 43 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 44 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 44 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 44 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 45 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 45 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 45 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 46 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 46 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 46 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 47 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 47 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 47 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 48 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 48 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 48 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 49 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 49 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 49 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 50 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 50 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 50 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 51 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 51 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 51 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 52 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 52 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 52 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 53 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 53 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 53 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 54 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 54 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 54 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 55 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 55 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 55 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 56 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 56 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 56 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 57 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 57 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 57 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 58 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 58 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 58 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 59 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 59 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 59 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 60 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 60 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 60 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 61 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 61 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 61 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 62 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 62 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 62 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 63 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 63 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 63 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 64 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 64 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 64 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 65 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 65 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 65 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 66 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 66 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 66 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 67 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 67 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 67 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 68 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 68 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 68 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 69 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 69 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 69 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 70 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 70 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 70 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 71 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 71 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 71 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 72 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 72 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 72 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 73 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 73 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 73 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 74 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 74 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 74 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 75 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 75 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 75 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 76 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 76 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 76 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 77 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 77 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 77 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 78 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 78 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 78 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 79 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 79 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 79 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 80 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 80 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 80 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 81 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 81 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 81 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 82 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 82 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 82 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 83 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 83 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 83 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 84 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 84 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 84 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 85 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 85 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 85 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 86 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 86 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 86 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 87 of Table A21 and the percentage range of alternative cytosine, e.g., alternative cytosines as described in Table 3, in column 1 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 87 of Table A21 and the percentage range of alternative cytosine, e.g., alternative cytosines as described in Table 3, in column 2 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

In some embodiments, the polynucleotide of the invention contains the percentage range of alternative uracil, e.g., alternative uracils described in Table 2, in row 87 of Table A21 and the percentage range of alternative cytosine, e.g., alternative cytosines as described in Table 3, in column 3 of Table A21. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

TABLE A21

| Row | Percentage range of alternative uracil | Column 1 Percentage range of alternative cytosine | Column 2 Percentage range of alternative cytosine | Column 3 Percentage range of alternative cytosine |
| --- | --- | --- | --- | --- |
| 1 | 5 to 25 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |

TABLE A21-continued

| Row | Percentage range of alternative uracil | Column 1 Percentage range of alternative cytosine | Column 2 Percentage range of alternative cytosine | Column 3 Percentage range of alternative cytosine |
|---|---|---|---|---|
| 2 | 5 to 30 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 3 | 5 to 35 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 4 | 5 to 40 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 5 | 5 to 45 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 6 | 5 to 50 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |

TABLE A21-continued

| Row | Percentage range of alternative uracil | Column 1 Percentage range of alternative cytosine | Column 2 Percentage range of alternative cytosine | Column 3 Percentage range of alternative cytosine |
|---|---|---|---|---|
| 7 | 10 to 25 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 8 | 10 to 30 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 9 | 10 to 35 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 10 | 10 to 40 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 11 | 10 to 45 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |

TABLE A21-continued

| Row | Percentage range of alternative uracil | Column 1 Percentage range of alternative cytosine | Column 2 Percentage range of alternative cytosine | Column 3 Percentage range of alternative cytosine |
|---|---|---|---|---|
| 12 | 10 to 50 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 13 | 15 to 25 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 14 | 15 to 30 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 15 | 15 to 35 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 16 | 15 to 40 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |

TABLE A21-continued

| Row | Percentage range of alternative uracil | Column 1 Percentage range of alternative cytosine | Column 2 Percentage range of alternative cytosine | Column 3 Percentage range of alternative cytosine |
|---|---|---|---|---|
| 17 | 15 to 45 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 18 | 15 to 50 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 19 | 20 to 25 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 20 | 20 to 30 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 21 | 20 to 35 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |

TABLE A21-continued

| Row | Percentage range of alternative uracil | Column 1 Percentage range of alternative cytosine | Column 2 Percentage range of alternative cytosine | Column 3 Percentage range of alternative cytosine |
|---|---|---|---|---|
| 22 | 20 to 40 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 23 | 20 to 45 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 24 | 20 to 50 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 25 | 25 to 30 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 26 | 25 to 35 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |

TABLE A21-continued

| Row | Percentage range of alternative uracil | Column 1 Percentage range of alternative cytosine | Column 2 Percentage range of alternative cytosine | Column 3 Percentage range of alternative cytosine |
|---|---|---|---|---|
| 27 | 25 to 40 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 28 | 25 to 45 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 29 | 25 to 50 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 30 | 30 to 50 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 31 | 30 to 55 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |

TABLE A21-continued

| Row | Percentage range of alternative uracil | Column 1 Percentage range of alternative cytosine | Column 2 Percentage range of alternative cytosine | Column 3 Percentage range of alternative cytosine |
|---|---|---|---|---|
| 32 | 30 to 60 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 33 | 30 to 65 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 34 | 30 to 70 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 35 | 30 to 75 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 36 | 35 to 50 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |

TABLE A21-continued

| Row | Percentage range of alternative uracil | Column 1 Percentage range of alternative cytosine | Column 2 Percentage range of alternative cytosine | Column 3 Percentage range of alternative cytosine |
|---|---|---|---|---|
| 37 | 35 to 55 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 38 | 35 to 60 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 39 | 35 to 65 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 40 | 35 to 70 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 41 | 35 to 75 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |

TABLE A21-continued

| Row | Percentage range of alternative uracil | Column 1 Percentage range of alternative cytosine | Column 2 Percentage range of alternative cytosine | Column 3 Percentage range of alternative cytosine |
|---|---|---|---|---|
| 42 | 40 to 50 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 43 | 40 to 55 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 44 | 40 to 60 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 45 | 40 to 65 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 46 | 40 to 70 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |

TABLE A21-continued

| Row | Percentage range of alternative uracil | Column 1 Percentage range of alternative cytosine | Column 2 Percentage range of alternative cytosine | Column 3 Percentage range of alternative cytosine |
|---|---|---|---|---|
| 47 | 40 to 75 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 48 | 45 to 50 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 49 | 45 to 55 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 50 | 45 to 60 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 51 | 45 to 65 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |

TABLE A21-continued

| Row | Percentage range of alternative uracil | Column 1 Percentage range of alternative cytosine | Column 2 Percentage range of alternative cytosine | Column 3 Percentage range of alternative cytosine |
|---|---|---|---|---|
| 52 | 45 to 70 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 53 | 45 to 75 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 54 | 50 to 55 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 55 | 50 to 60 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 56 | 50 to 65 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |

TABLE A21-continued

| Row | Percentage range of alternative uracil | Column 1 Percentage range of alternative cytosine | Column 2 Percentage range of alternative cytosine | Column 3 Percentage range of alternative cytosine |
|---|---|---|---|---|
| 57 | 50 to 70 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 58 | 50 to 75 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 59 | 55 to 75 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 60 | 55 to 80 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 61 | 55 to 85 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |

TABLE A21-continued

| Row | Percentage range of alternative uracil | Column 1 Percentage range of alternative cytosine | Column 2 Percentage range of alternative cytosine | Column 3 Percentage range of alternative cytosine |
|---|---|---|---|---|
| 62 | 55 to 90 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 63 | 55 to 95 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 64 | 55 to 100 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 65 | 60 to 75 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 66 | 60 to 80 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |

TABLE A21-continued

| Row | Percentage range of alternative uracil | Column 1 Percentage range of alternative cytosine | Column 2 Percentage range of alternative cytosine | Column 3 Percentage range of alternative cytosine |
|---|---|---|---|---|
| 67 | 60 to 85 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 68 | 60 to 90 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 69 | 60 to 95 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 70 | 60 to 100 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 71 | 65 to 75 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |

TABLE A21-continued

| Row | Percentage range of alternative uracil | Column 1 Percentage range of alternative cytosine | Column 2 Percentage range of alternative cytosine | Column 3 Percentage range of alternative cytosine |
|---|---|---|---|---|
| 72 | 65 to 80 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 73 | 65 to 85 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 74 | 65 to 90 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 75 | 65 to 95 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 76 | 65 to 100 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |

TABLE A21-continued

| Row | Percentage range of alternative uracil | Column 1 Percentage range of alternative cytosine | Column 2 Percentage range of alternative cytosine | Column 3 Percentage range of alternative cytosine |
|---|---|---|---|---|
| 77 | 70 to 75 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 78 | 70 to 80 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 79 | 70 to 85 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 80 | 70 to 90 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 81 | 70 to 95 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |

TABLE A21-continued

| Row | Percentage range of alternative uracil | Column 1 Percentage range of alternative cytosine | Column 2 Percentage range of alternative cytosine | Column 3 Percentage range of alternative cytosine |
| --- | --- | --- | --- | --- |
| 82 | 70 to 100 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 83 | 75 to 80 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 84 | 75 to 85 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 85 | 75 to 90 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 86 | 75 to 95 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |

TABLE A21-continued

| Row | Percentage range of alternative uracil | Column 1 Percentage range of alternative cytosine | Column 2 Percentage range of alternative cytosine | Column 3 Percentage range of alternative cytosine |
|---|---|---|---|---|
| 87 | 75 to 100 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |

Preferably, in some embodiments, the polynucleotide of the invention contains the percentage of alternative uracil, e.g., alternative uracils described in Table 2, in row 1 of Table A22 and the percentages of alternative cytosine, e.g., alternative cytosines described in Table 3, in column 1 of Table A22. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

Preferably, in some embodiments, the polynucleotide of the invention contains the percentage of alternative uracil, e.g., alternative uracils described in Table 2, in row 2 of Table A22 and the percentages of alternative cytosine, e.g., alternative cytosines described in Table 3, in column 1 of Table A22. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

Preferably, in some embodiments, the polynucleotide of the invention contains the percentage of alternative uracil, e.g., alternative uracils described in Table 2, in row 3 of Table A22 and the percentages of alternative cytosine, e.g., alternative cytosines described in Table 3, in column 1 of Table A22. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

Preferably, in some embodiments, the polynucleotide of the invention contains the percentage of alternative uracil, e.g., alternative uracils described in Table 2, in row 4 of Table A22 and the percentages of alternative cytosine, e.g., alternative cytosines described in Table 3, in column 1 of Table A22. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

Preferably, in some embodiments, the polynucleotide of the invention contains the percentage of alternative uracil, e.g., alternative uracils described in Table 2, in row 5 of Table A22 and the percentages of alternative cytosine, e.g., alternative cytosines described in Table 3, in column 1 of Table A22. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

Preferably, in some embodiments, the polynucleotide of the invention contains the percentage of alternative uracil, e.g., alternative uracils described in Table 2, in row 6 of Table A22 and the percentages of alternative cytosine, e.g., alternative cytosines described in Table 3, in column 1 of Table A22. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

Preferably, in some embodiments, the polynucleotide of the invention contains the percentage of alternative uracil, e.g., alternative uracils described in Table 2, in row 7 of Table A22 and the percentages of alternative cytosine, e.g., alternative cytosines described in Table 3, in column 1 of Table A22. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

Preferably, in some embodiments, the polynucleotide of the invention contains the percentage of alternative uracil, e.g., alternative uracils described in Table 2, in row 8 of Table A22 and the percentages of alternative cytosine, e.g., alternative cytosines described in Table 3, in column 1 of Table A22. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

Preferably, in some embodiments, the polynucleotide of the invention contains the percentage of alternative uracil, e.g., alternative uracils described in Table 2, in row 9 of Table A22 and the percentages of alternative cytosine, e.g., alternative cytosines described in Table 3, in column 1 of Table A22. In some embodiments, the polynucleotide of the invention contains 5-methoxy-uracil, uracil, 5-methyl-cytosine, and cytosine as the only uracils and cytosines. In further embodiments, the polynucleotide does not include an alternative adenine or guanine.

TABLE A22

| Row | Percentage range of alternative uracil | Column 1 Percentage range of alternative cytosine |
|---|---|---|
| 1 | 10 | 50 |
|  |  | 55 |
|  |  | 60 |
|  |  | 65 |
|  |  | 70 |

TABLE A22-continued

| Row | Percentage range of alternative uracil | Column 1 Percentage range of alternative cytosine |
|---|---|---|
|   |   | 75 |
|   |   | 80 |
|   |   | 85 |
|   |   | 90 |
|   |   | 95 |
|   |   | 100 |
| 2 | 15 | 50 |
|   |   | 55 |
|   |   | 60 |
|   |   | 65 |
|   |   | 70 |
|   |   | 75 |
|   |   | 80 |
|   |   | 85 |
|   |   | 90 |
|   |   | 95 |
|   |   | 100 |
| 3 | 20 | 50 |
|   |   | 55 |
|   |   | 60 |
|   |   | 65 |
|   |   | 70 |
|   |   | 75 |
|   |   | 80 |
|   |   | 85 |
|   |   | 90 |
|   |   | 95 |
|   |   | 100 |
| 4 | 25 | 50 |
|   |   | 55 |
|   |   | 60 |
|   |   | 65 |
|   |   | 70 |
|   |   | 75 |
|   |   | 80 |
|   |   | 85 |
|   |   | 90 |
|   |   | 95 |
|   |   | 100 |
| 5 | 30 | 50 |
|   |   | 55 |
|   |   | 60 |
|   |   | 65 |
|   |   | 70 |
|   |   | 75 |
|   |   | 80 |
|   |   | 85 |
|   |   | 90 |
|   |   | 95 |
|   |   | 100 |
| 6 | 35 | 50 |
|   |   | 55 |
|   |   | 60 |
|   |   | 65 |
|   |   | 70 |
|   |   | 75 |
|   |   | 80 |
|   |   | 85 |
|   |   | 90 |
|   |   | 95 |
|   |   | 100 |
| 7 | 40 | 50 |
|   |   | 55 |
|   |   | 60 |
|   |   | 65 |
|   |   | 70 |
|   |   | 75 |
|   |   | 80 |
|   |   | 85 |
|   |   | 90 |
|   |   | 95 |
|   |   | 100 |
| 8 | 45 | 50 |
|   |   | 55 |
|   |   | 60 |
|   |   | 65 |
|   |   | 70 |
|   |   | 75 |
|   |   | 80 |
|   |   | 85 |
|   |   | 90 |
|   |   | 95 |
|   |   | 100 |
| 9 | 50 | 50 |
|   |   | 55 |
|   |   | 60 |
|   |   | 65 |
|   |   | 70 |
|   |   | 75 |
|   |   | 80 |
|   |   | 85 |
|   |   | 90 |
|   |   | 95 |
|   |   | 100 |

In some embodiments, the polynucleotide of the invention contains about 5% alternative uridine, e.g., alternative uridines as described in Table 2, in combination with a percentage of alternative cytidine, e.g., alternative cytidines described in Table 3, according to columns 1 and 2 of Table B1. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

TABLE B1

| Column 1 Percentage of alternative uridine | Column 2 Percentage of alternative cytidine |
|---|---|
| 5 | 100 |
| 5 | 95 |
| 5 | 90 |
| 5 | 85 |
| 5 | 80 |
| 5 | 75 |
| 5 | 70 |
| 5 | 65 |
| 5 | 60 |
| 5 | 55 |
| 5 | 50 |
| 5 | 45 |
| 5 | 40 |
| 5 | 35 |
| 5 | 30 |
| 5 | 25 |
| 5 | 20 |
| 5 | 15 |
| 5 | 10 |
| 5 | 5 |

In some embodiments, the polynucleotide of the invention contains about 10% alternative uridine, e.g., alternative uridines as described in Table 2, in combination with a percentage of alternative cytidine, e.g., alternative cytidines described in Table 3, according to columns 1 and 2 of Table B2. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

TABLE B2

| Column 1 Percentage of alternative uridine | Column 2 Percentage of alternative cytidine |
|---|---|
| 10 | 100 |
| 10 | 95 |
| 10 | 90 |
| 10 | 85 |
| 10 | 80 |
| 10 | 75 |
| 10 | 70 |
| 10 | 65 |
| 10 | 60 |
| 10 | 55 |
| 10 | 50 |
| 10 | 45 |
| 10 | 40 |
| 10 | 35 |
| 10 | 30 |
| 10 | 25 |
| 10 | 20 |
| 10 | 15 |
| 10 | 10 |
| 10 | 5 |

In some embodiments, the polynucleotide of the invention contains about 15% alternative uridine, e.g., alternative uridines as described in Table 2, in combination with a percentage of alternative cytidine, e.g., alternative cytidines described in Table 3, according to columns 1 and 2 of Table B3. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

TABLE B3

| Column 1 Percentage of alternative uridine | Column 2 Percentage of alternative cytidine |
|---|---|
| 15 | 100 |
| 15 | 95 |
| 15 | 90 |
| 15 | 85 |
| 15 | 80 |
| 15 | 75 |
| 15 | 70 |
| 15 | 65 |
| 15 | 60 |
| 15 | 55 |
| 15 | 50 |
| 15 | 45 |
| 15 | 40 |
| 15 | 35 |
| 15 | 30 |
| 15 | 25 |
| 15 | 20 |
| 15 | 15 |
| 15 | 10 |
| 15 | 5 |

In some embodiments, the polynucleotide of the invention contains about 20% alternative uridine, e.g., alternative uridines as described in Table 2, in combination with a percentage of alternative cytidine, e.g., alternative cytidines described in Table 3, according to columns 1 and 2 of Table B4. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

TABLE B4

| Column 1 Percentage of alternative uridine | Column 2 Percentage of alternative cytidine |
|---|---|
| 20 | 100 |
| 20 | 95 |
| 20 | 90 |
| 20 | 85 |
| 20 | 80 |
| 20 | 75 |
| 20 | 70 |
| 20 | 65 |
| 20 | 60 |
| 20 | 55 |
| 20 | 50 |
| 20 | 45 |
| 20 | 40 |
| 20 | 35 |
| 20 | 30 |
| 20 | 25 |
| 20 | 20 |
| 20 | 15 |
| 20 | 10 |
| 20 | 5 |

In some embodiments, the polynucleotide of the invention contains about 25% alternative uridine, e.g., alternative uridines as described in Table 2, in combination with a percentage of alternative cytidine, e.g., alternative cytidines described in Table 3, according to columns 1 and 2 of Table B5. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

TABLE B5

| Column 1 Percentage of alternative uridine | Column 2 Percentage of alternative cytidine |
|---|---|
| 25 | 100 |
| 25 | 95 |
| 25 | 90 |
| 25 | 85 |
| 25 | 80 |
| 25 | 75 |
| 25 | 70 |
| 25 | 65 |
| 25 | 60 |
| 25 | 55 |
| 25 | 50 |
| 25 | 45 |
| 25 | 40 |
| 25 | 35 |
| 25 | 30 |
| 25 | 25 |
| 25 | 20 |
| 25 | 15 |
| 25 | 10 |
| 25 | 5 |

In some embodiments, the polynucleotide of the invention contains about 30% alternative uridine, e.g., alternative uridines as described in Table 2, in combination with a percentage of alternative cytidine, e.g., alternative cytidines described in Table 3, according to columns 1 and 2 of Table B6. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

TABLE B6

| Column 1 Percentage of alternative uridine | Column 2 Percentage of alternative cytidine |
| --- | --- |
| 30 | 100 |
| 30 | 95 |
| 30 | 90 |
| 30 | 85 |
| 30 | 80 |
| 30 | 75 |
| 30 | 70 |
| 30 | 65 |
| 30 | 60 |
| 30 | 55 |
| 30 | 50 |
| 30 | 45 |
| 30 | 40 |
| 30 | 35 |
| 30 | 30 |
| 30 | 25 |
| 30 | 20 |
| 30 | 15 |
| 30 | 10 |
| 30 | 5 |

In some embodiments, the polynucleotide of the invention contains about 35% alternative uridine, e.g., alternative uridines as described in Table 2, in combination with a percentage of alternative cytidine, e.g., alternative cytidines described in Table 3, according to columns 1 and 2 of Table B7. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

TABLE B7

| Column 1 Percentage of alternative uridine | Column 2 Percentage of alternative cytidine |
| --- | --- |
| 35 | 100 |
| 35 | 95 |
| 35 | 90 |
| 35 | 85 |
| 35 | 80 |
| 35 | 75 |
| 35 | 70 |
| 35 | 65 |
| 35 | 60 |
| 35 | 55 |
| 35 | 50 |
| 35 | 45 |
| 35 | 40 |
| 35 | 35 |
| 35 | 30 |
| 35 | 25 |
| 35 | 20 |
| 35 | 15 |
| 35 | 10 |
| 35 | 5 |

In some embodiments, the polynucleotide of the invention contains about 40% alternative uridine, e.g., alternative uridines as described in Table 2, in combination with a percentage of alternative cytidine, e.g., alternative cytidines described in Table 3, according to columns 1 and 2 of Table B8. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

TABLE B8

| Column 1 Percentage of alternative uridine | Column 2 Percentage of alternative cytidine |
| --- | --- |
| 40 | 100 |
| 40 | 95 |
| 40 | 90 |
| 40 | 85 |
| 40 | 80 |
| 40 | 75 |
| 40 | 70 |
| 40 | 65 |
| 40 | 60 |
| 40 | 55 |
| 40 | 50 |
| 40 | 45 |
| 40 | 40 |
| 40 | 35 |
| 40 | 30 |
| 40 | 25 |
| 40 | 20 |
| 40 | 15 |
| 40 | 10 |
| 40 | 5 |

In some embodiments, the polynucleotide of the invention contains about 45% alternative uridine, e.g., alternative uridines as described in Table 2, in combination with a percentage of alternative cytidine, e.g., alternative cytidines described in Table 3, according to columns 1 and 2 of Table B9. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

TABLE B9

| Column 1 Percentage of alternative uridine | Column 2 Percentage of alternative cytidine |
| --- | --- |
| 45 | 100 |
| 45 | 95 |
| 45 | 90 |
| 45 | 85 |
| 45 | 80 |
| 45 | 75 |
| 45 | 70 |
| 45 | 65 |
| 45 | 60 |
| 45 | 55 |
| 45 | 50 |
| 45 | 45 |
| 45 | 40 |
| 45 | 35 |
| 45 | 30 |
| 45 | 25 |
| 45 | 20 |
| 45 | 15 |
| 45 | 10 |
| 45 | 5 |

In some embodiments, the polynucleotide of the invention contains about 50% alternative uridine, e.g., alternative uridines as described in Table 2, in combination with a percentage of alternative cytidine, e.g., alternative cytidines described in Table 3, according to columns 1 and 2 of Table B10. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

TABLE B10

| Column 1 Percentage of alternative uridine | Column 2 Percentage of alternative cytidine |
|---|---|
| 50 | 100 |
| 50 | 95 |
| 50 | 90 |
| 50 | 85 |
| 50 | 80 |
| 50 | 75 |
| 50 | 70 |
| 50 | 65 |
| 50 | 60 |
| 50 | 55 |
| 50 | 50 |
| 50 | 45 |
| 50 | 40 |
| 50 | 35 |
| 50 | 30 |
| 50 | 25 |
| 50 | 20 |
| 50 | 15 |
| 50 | 10 |
| 50 | 5 |

In some embodiments, the polynucleotide of the invention contains about 55% alternative uridine, e.g., alternative uridines as described in Table 2, in combination with a percentage of alternative cytidine, e.g., alternative cytidines described in Table 3, according to columns 1 and 2 of Table B11. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

TABLE B11

| Column 1 Percentage of alternative uridine | Column 2 Percentage of alternative cytidine |
|---|---|
| 55 | 100 |
| 55 | 95 |
| 55 | 90 |
| 55 | 85 |
| 55 | 80 |
| 55 | 75 |
| 55 | 70 |
| 55 | 65 |
| 55 | 60 |
| 55 | 55 |
| 55 | 50 |
| 55 | 45 |
| 55 | 40 |
| 55 | 35 |
| 55 | 30 |
| 55 | 25 |
| 55 | 20 |
| 55 | 15 |
| 55 | 10 |
| 55 | 5 |

In some embodiments, the polynucleotide of the invention contains about 60% alternative uridine, e.g., alternative uridines as described in Table 2, in combination with a percentage of alternative cytidine, e.g., alternative cytidines described in Table 3, according to columns 1 and 2 of Table B12. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

TABLE B12

| Column 1 Percentage of alternative uridine | Column 2 Percentage of alternative cytidine |
|---|---|
| 60 | 100 |
| 60 | 95 |
| 60 | 90 |
| 60 | 85 |
| 60 | 80 |
| 60 | 75 |
| 60 | 70 |
| 60 | 65 |
| 60 | 60 |
| 60 | 55 |
| 60 | 50 |
| 60 | 45 |
| 60 | 40 |
| 60 | 35 |
| 60 | 30 |
| 60 | 25 |
| 60 | 20 |
| 60 | 15 |
| 60 | 10 |
| 60 | 5 |

In some embodiments, the polynucleotide of the invention contains about 65% alternative uridine, e.g., alternative uridines as described in Table 2, in combination with a percentage of alternative cytidine, e.g., alternative cytidines described in Table 3, according to columns 1 and 2 of Table B13. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

TABLE B13

| Column 1 Percentage of alternative uridine | Column 2 Percentage of alternative cytidine |
|---|---|
| 65 | 100 |
| 65 | 95 |
| 65 | 90 |
| 65 | 85 |
| 65 | 80 |
| 65 | 75 |
| 65 | 70 |
| 65 | 65 |
| 65 | 60 |
| 65 | 55 |
| 65 | 50 |
| 65 | 45 |
| 65 | 40 |
| 65 | 35 |
| 65 | 30 |
| 65 | 25 |
| 65 | 20 |
| 65 | 15 |
| 65 | 10 |
| 65 | 5 |

In some embodiments, the polynucleotide of the invention contains about 70% alternative uridine, e.g., alternative uridines as described in Table 2, in combination with a percentage of alternative cytidine, e.g., alternative cytidines described in Table 3, according to columns 1 and 2 of Table B14. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

TABLE B14

| Column 1 Percentage of alternative uridine | Column 2 Percentage of alternative cytidine |
|---|---|
| 70 | 100 |
| 70 | 95 |
| 70 | 90 |
| 70 | 85 |
| 70 | 80 |
| 70 | 75 |
| 70 | 70 |
| 70 | 65 |
| 70 | 60 |
| 70 | 55 |
| 70 | 50 |
| 70 | 45 |
| 70 | 40 |
| 70 | 35 |
| 70 | 30 |
| 70 | 25 |
| 70 | 20 |
| 70 | 15 |
| 70 | 10 |
| 70 | 5 |

In some embodiments, the polynucleotide of the invention contains about 75% alternative uridine, e.g., alternative uridines as described in Table 2, in combination with a percentage of alternative cytidine, e.g., alternative cytidines described in Table 3, according to columns 1 and 2 of Table B15. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

TABLE B15

| Column 1 Percentage of alternative uridine | Column 2 Percentage of alternative cytidine |
|---|---|
| 75 | 100 |
| 75 | 95 |
| 75 | 90 |
| 75 | 85 |
| 75 | 80 |
| 75 | 75 |
| 75 | 70 |
| 75 | 65 |
| 75 | 60 |
| 75 | 55 |
| 75 | 50 |
| 75 | 45 |
| 75 | 40 |
| 75 | 35 |
| 75 | 30 |
| 75 | 25 |
| 75 | 20 |
| 75 | 15 |
| 75 | 10 |
| 75 | 5 |

In some embodiments, the polynucleotide of the invention contains about 80% alternative uridine, e.g., alternative uridines as described in Table 2, in combination with a percentage of alternative cytidine, e.g., alternative cytidines described in Table 3, according to columns 1 and 2 of Table B16. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

TABLE B16

| Column 1 Percentage of alternative uridine | Column 2 Percentage of alternative cytidine |
|---|---|
| 80 | 100 |
| 80 | 95 |
| 80 | 90 |
| 80 | 85 |
| 80 | 80 |
| 80 | 75 |
| 80 | 70 |
| 80 | 65 |
| 80 | 60 |
| 80 | 55 |
| 80 | 50 |
| 80 | 45 |
| 80 | 40 |
| 80 | 35 |
| 80 | 30 |
| 80 | 25 |
| 80 | 20 |
| 80 | 15 |
| 80 | 10 |
| 80 | 5 |

In some embodiments, the polynucleotide of the invention contains about 85% alternative uridine, e.g., alternative uridines as described in Table 2, in combination with a percentage of alternative cytidine, e.g., alternative cytidines described in Table 3, according to columns 1 and 2 of Table B17. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

TABLE B17

| Column 1 Percentage of alternative uridine | Column 2 Percentage of alternative cytidine |
|---|---|
| 85 | 100 |
| 85 | 95 |
| 85 | 90 |
| 85 | 85 |
| 85 | 80 |
| 85 | 75 |
| 85 | 70 |
| 85 | 65 |
| 85 | 60 |
| 85 | 55 |
| 85 | 50 |
| 85 | 45 |
| 85 | 40 |
| 85 | 35 |
| 85 | 30 |
| 85 | 25 |
| 85 | 20 |
| 85 | 15 |
| 85 | 10 |
| 85 | 5 |

In some embodiments, the polynucleotide of the invention contains about 90% alternative uridine, e.g., alternative uridines as described in Table 2, in combination with a percentage of alternative cytidine, e.g., alternative cytidines described in Table 3, according to columns 1 and 2 of Table B18. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

TABLE B18

| Column 1 Percentage of alternative uridine | Column 2 Percentage of alternative cytidine |
|---|---|
| 90 | 100 |
| 90 | 95 |
| 90 | 90 |
| 90 | 85 |
| 90 | 80 |
| 90 | 75 |
| 90 | 70 |
| 90 | 65 |
| 90 | 60 |
| 90 | 55 |
| 90 | 50 |
| 90 | 45 |
| 90 | 40 |
| 90 | 35 |
| 90 | 30 |
| 90 | 25 |
| 90 | 20 |
| 90 | 15 |
| 90 | 10 |
| 90 | 5 |

In some embodiments, the polynucleotide of the invention contains about 95% alternative uridine, e.g., alternative uridines as described in Table 2, in combination with a percentage of alternative cytidine, e.g., alternative cytidines described in Table 3, according to columns 1 and 2 of Table B19. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

TABLE B19

| Column 1 Percentage of alternative uridine | Column 2 Percentage of alternative cytidine |
|---|---|
| 95 | 100 |
| 95 | 95 |
| 95 | 90 |
| 95 | 85 |
| 95 | 80 |
| 95 | 75 |
| 95 | 70 |
| 95 | 65 |
| 95 | 60 |
| 95 | 55 |
| 95 | 50 |
| 95 | 45 |
| 95 | 40 |
| 95 | 35 |
| 95 | 30 |
| 95 | 25 |
| 95 | 20 |
| 95 | 15 |
| 95 | 10 |
| 95 | 5 |

In some embodiments, the polynucleotide of the invention contains about 100% alternative uridine, e.g., alternative uridines as described in Table 2, in combination with a percentage of alternative cytidine, e.g., alternative cytidines described in Table 3, according to columns 1 and 2 of Table B20. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

TABLE B20

| Column 1 Percentage of alternative uridine | Column 2 Percentage of alternative cytidine |
|---|---|
| 100 | 100 |
| 100 | 95 |
| 100 | 90 |
| 100 | 85 |
| 100 | 80 |
| 100 | 75 |
| 100 | 70 |
| 100 | 65 |
| 100 | 60 |
| 100 | 55 |
| 100 | 50 |
| 100 | 45 |
| 100 | 40 |
| 100 | 35 |
| 100 | 30 |
| 100 | 25 |
| 100 | 20 |
| 100 | 15 |
| 100 | 10 |
| 100 | 5 |

In some embodiments, the polynucleotide of the invention contains the percentage range of alternative uridine, e.g., alternative uridines as described in Table 2, in row 1 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 1 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 1 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 2 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 2 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 2 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 3 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 3 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 3 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 4 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 4 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 4 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 5 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 5 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 5 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 6 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 6 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 6 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methylcytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 7 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 7 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 7 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 8 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 8 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 8 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 9 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 9 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 9 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 10 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 10 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 10 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 11 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 11 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 11 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 12 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 12 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 12 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 13 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 13 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 13 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 14 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 14 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 14 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 15 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 15 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 15 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 16 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 16 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 16 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 17 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 17 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 17 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 18 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 18 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 18 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 19 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 19 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 19 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 20 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 20 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 20 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 21 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 21 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 21 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 22 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 22 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 22 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 23 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 23 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 23 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 24 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 24 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 24 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 25 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 25 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 25 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 26 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 26 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 26 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 27 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 27 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 27 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 28 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 28 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 28 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 29 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 29 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 29 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 30 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 30 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 30 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 31 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 31 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 31 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 32 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 32 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 32 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 33 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 33 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 33 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 34 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 34 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 34 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 35 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 35 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 35 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 36 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 36 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 36 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 37 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 37 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 37 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 38 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 38 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 38 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 39 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 39 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 39 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 40 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 40 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 40 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 41 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 41 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 41 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 42 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 42 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 42 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 43 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 43 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 43 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 44 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 44 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 44 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 45 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 45 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 45 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 46 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 46 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 46 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 47 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 47 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 47 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 48 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 48 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 48 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 49 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 49 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 49 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 50 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 50 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 50 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 51 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 51 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 51 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 52 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 52 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 52 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 53 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 53 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 53 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 54 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 54 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 54 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 55 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 55 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 55 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 56 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 56 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 56 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 57 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 57 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 57 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 58 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 58 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 58 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 59 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 59 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 59 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 60 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 60 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 60 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 61 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 61 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 61 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 62 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 62 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 62 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 63 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 63 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 63 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 64 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 64 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 64 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 65 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 65 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 65 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 66 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 66 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 66 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 67 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 67 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 67 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 68 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 68 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 68 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 69 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 69 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 69 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 70 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 70 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 70 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 71 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 71 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 71 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 72 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 72 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 72 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 73 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 73 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 73 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 74 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 74 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 74 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 75 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 75 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 75 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 76 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 76 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 76 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 77 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 77 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 77 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 78 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 78 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 78 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 79 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 79 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 79 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 80 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 80 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 80 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 81 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 81 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 81 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 82 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 82 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 82 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 83 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 83 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 83 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 84 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 84 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 84 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 85 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 85 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 85 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 86 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 86 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 86 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 87 of Table B21 and the percentage range of alternative cytidine, e.g., alternative cytidines as described in Table 3, in column 1 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 87 of Table B21 and the percentage range of alternative cytidine, e.g., alternative cytidines as described in Table 3, in column 2 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

In some embodiments, the polynucleotide of the invention contains the percentage range of alternative uridine, e.g., alternative uridines as described in Table 2, in row 87 of Table B21 and the percentage range of alternative cytidine, e.g., alternative cytidines as described in Table 3, in column 3 of Table B21. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

TABLE B21

| Row | Percentage range of alternative uridine | Column 1 Percentage range of alternative cytidine | Column 2 Percentage range of alternative cytidine | Column 3 Percentage range of alternative cytidine |
|---|---|---|---|---|
| 1 | 5 to 25 | 5 to 25 | 30 to 50 | 55 to 75 |
|   |         | 5 to 30 | 30 to 55 | 55 to 80 |
|   |         | 5 to 35 | 30 to 60 | 55 to 85 |
|   |         | 5 to 40 | 30 to 65 | 55 to 90 |
|   |         | 5 to 45 | 30 to 70 | 55 to 95 |
|   |         | 5 to 50 | 30 to 75 | 55 to 100 |
|   |         | 10 to 25 | 35 to 50 | 60 to 75 |
|   |         | 10 to 30 | 35 to 55 | 60 to 80 |
|   |         | 10 to 35 | 35 to 60 | 60 to 85 |
|   |         | 10 to 40 | 35 to 65 | 60 to 90 |
|   |         | 10 to 45 | 35 to 70 | 60 to 95 |
|   |         | 10 to 50 | 35 to 75 | 60 to 100 |
|   |         | 15 to 25 | 40 to 50 | 65 to 75 |
|   |         | 15 to 30 | 40 to 55 | 65 to 80 |
|   |         | 15 to 35 | 40 to 60 | 65 to 85 |
|   |         | 15 to 40 | 40 to 65 | 65 to 90 |
|   |         | 15 to 45 | 40 to 70 | 65 to 95 |
|   |         | 15 to 50 | 40 to 75 | 65 to 100 |
|   |         | 20 to 25 | 45 to 50 | 70 to 75 |
|   |         | 20 to 30 | 45 to 55 | 70 to 80 |
|   |         | 20 to 35 | 45 to 60 | 70 to 85 |
|   |         | 20 to 40 | 45 to 65 | 70 to 90 |
|   |         | 20 to 45 | 45 to 70 | 70 to 95 |
|   |         | 20 to 50 | 45 to 75 | 70 to 100 |
|   |         | 25 to 30 | 50 to 55 | 75 to 80 |
|   |         | 25 to 35 | 50 to 60 | 75 to 85 |
|   |         | 25 to 40 | 50 to 65 | 75 to 90 |
|   |         | 25 to 45 | 50 to 70 | 75 to 95 |
|   |         | 25 to 50 | 50 to 75 | 75 to 100 |
| 2 | 5 to 30 | 5 to 25 | 30 to 50 | 55 to 75 |
|   |         | 5 to 30 | 30 to 55 | 55 to 80 |
|   |         | 5 to 35 | 30 to 60 | 55 to 85 |
|   |         | 5 to 40 | 30 to 65 | 55 to 90 |
|   |         | 5 to 45 | 30 to 70 | 55 to 95 |
|   |         | 5 to 50 | 30 to 75 | 55 to 100 |
|   |         | 10 to 25 | 35 to 50 | 60 to 75 |
|   |         | 10 to 30 | 35 to 55 | 60 to 80 |
|   |         | 10 to 35 | 35 to 60 | 60 to 85 |
|   |         | 10 to 40 | 35 to 65 | 60 to 90 |
|   |         | 10 to 45 | 35 to 70 | 60 to 95 |
|   |         | 10 to 50 | 35 to 75 | 60 to 100 |
|   |         | 15 to 25 | 40 to 50 | 65 to 75 |
|   |         | 15 to 30 | 40 to 55 | 65 to 80 |
|   |         | 15 to 35 | 40 to 60 | 65 to 85 |
|   |         | 15 to 40 | 40 to 65 | 65 to 90 |
|   |         | 15 to 45 | 40 to 70 | 65 to 95 |
|   |         | 15 to 50 | 40 to 75 | 65 to 100 |
|   |         | 20 to 25 | 45 to 50 | 70 to 75 |
|   |         | 20 to 30 | 45 to 55 | 70 to 80 |
|   |         | 20 to 35 | 45 to 60 | 70 to 85 |
|   |         | 20 to 40 | 45 to 65 | 70 to 90 |
|   |         | 20 to 45 | 45 to 70 | 70 to 95 |
|   |         | 20 to 50 | 45 to 75 | 70 to 100 |
|   |         | 25 to 30 | 50 to 55 | 75 to 80 |
|   |         | 25 to 35 | 50 to 60 | 75 to 85 |
|   |         | 25 to 40 | 50 to 65 | 75 to 90 |
|   |         | 25 to 45 | 50 to 70 | 75 to 95 |
|   |         | 25 to 50 | 50 to 75 | 75 to 100 |
| 3 | 5 to 35 | 5 to 25 | 30 to 50 | 55 to 75 |
|   |         | 5 to 30 | 30 to 55 | 55 to 80 |
|   |         | 5 to 35 | 30 to 60 | 55 to 85 |
|   |         | 5 to 40 | 30 to 65 | 55 to 90 |
|   |         | 5 to 45 | 30 to 70 | 55 to 95 |
|   |         | 5 to 50 | 30 to 75 | 55 to 100 |
|   |         | 10 to 25 | 35 to 50 | 60 to 75 |
|   |         | 10 to 30 | 35 to 55 | 60 to 80 |
|   |         | 10 to 35 | 35 to 60 | 60 to 85 |
|   |         | 10 to 40 | 35 to 65 | 60 to 90 |
|   |         | 10 to 45 | 35 to 70 | 60 to 95 |
|   |         | 10 to 50 | 35 to 75 | 60 to 100 |
|   |         | 15 to 25 | 40 to 50 | 65 to 75 |
|   |         | 15 to 30 | 40 to 55 | 65 to 80 |
|   |         | 15 to 35 | 40 to 60 | 65 to 85 |
|   |         | 15 to 40 | 40 to 65 | 65 to 90 |
|   |         | 15 to 45 | 40 to 70 | 65 to 95 |
|   |         | 15 to 50 | 40 to 75 | 65 to 100 |
|   |         | 20 to 25 | 45 to 50 | 70 to 75 |
|   |         | 20 to 30 | 45 to 55 | 70 to 80 |
|   |         | 20 to 35 | 45 to 60 | 70 to 85 |
|   |         | 20 to 40 | 45 to 65 | 70 to 90 |
|   |         | 20 to 45 | 45 to 70 | 70 to 95 |
|   |         | 20 to 50 | 45 to 75 | 70 to 100 |
|   |         | 25 to 30 | 50 to 55 | 75 to 80 |
|   |         | 25 to 35 | 50 to 60 | 75 to 85 |
|   |         | 25 to 40 | 50 to 65 | 75 to 90 |
|   |         | 25 to 45 | 50 to 70 | 75 to 95 |
|   |         | 25 to 50 | 50 to 75 | 75 to 100 |
| 4 | 5 to 40 | 5 to 25 | 30 to 50 | 55 to 75 |
|   |         | 5 to 30 | 30 to 55 | 55 to 80 |
|   |         | 5 to 35 | 30 to 60 | 55 to 85 |
|   |         | 5 to 40 | 30 to 65 | 55 to 90 |
|   |         | 5 to 45 | 30 to 70 | 55 to 95 |
|   |         | 5 to 50 | 30 to 75 | 55 to 100 |
|   |         | 10 to 25 | 35 to 50 | 60 to 75 |
|   |         | 10 to 30 | 35 to 55 | 60 to 80 |
|   |         | 10 to 35 | 35 to 60 | 60 to 85 |
|   |         | 10 to 40 | 35 to 65 | 60 to 90 |
|   |         | 10 to 45 | 35 to 70 | 60 to 95 |
|   |         | 10 to 50 | 35 to 75 | 60 to 100 |
|   |         | 15 to 25 | 40 to 50 | 65 to 75 |
|   |         | 15 to 30 | 40 to 55 | 65 to 80 |
|   |         | 15 to 35 | 40 to 60 | 65 to 85 |
|   |         | 15 to 40 | 40 to 65 | 65 to 90 |

TABLE B21-continued

| Row | Percentage range of alternative uridine | Column 1 Percentage range of alternative cytidine | Column 2 Percentage range of alternative cytidine | Column 3 Percentage range of alternative cytidine |
|---|---|---|---|---|
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 5 | 5 to 45 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 6 | 5 to 50 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 7 | 10 to 25 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 8 | 10 to 30 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 9 | 10 to 35 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |

TABLE B21-continued

| Row | Percentage range of alternative uridine | Column 1 Percentage range of alternative cytidine | Column 2 Percentage range of alternative cytidine | Column 3 Percentage range of alternative cytidine |
|---|---|---|---|---|
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 10 | 10 to 40 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 11 | 10 to 45 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 12 | 10 to 50 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 13 | 15 to 25 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 14 | 15 to 30 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |

TABLE B21-continued

| Row | Percentage range of alternative uridine | Column 1 Percentage range of alternative cytidine | Column 2 Percentage range of alternative cytidine | Column 3 Percentage range of alternative cytidine |
|---|---|---|---|---|
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 15 | 15 to 35 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 16 | 15 to 40 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 17 | 15 to 45 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 18 | 15 to 50 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 19 | 20 to 25 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |

TABLE B21-continued

| Row | Percentage range of alternative uridine | Column 1 Percentage range of alternative cytidine | Column 2 Percentage range of alternative cytidine | Column 3 Percentage range of alternative cytidine |
|---|---|---|---|---|
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 20 | 20 to 30 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 21 | 20 to 35 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 22 | 20 to 40 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 23 | 20 to 45 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 24 | 20 to 50 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |

TABLE B21-continued

| Row | Percentage range of alternative uridine | Column 1 Percentage range of alternative cytidine | Column 2 Percentage range of alternative cytidine | Column 3 Percentage range of alternative cytidine |
|---|---|---|---|---|
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 25 | 25 to 30 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 26 | 25 to 35 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 27 | 25 to 40 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 28 | 25 to 45 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 29 | 25 to 50 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |

TABLE B21-continued

| Row | Percentage range of alternative uridine | Column 1 Percentage range of alternative cytidine | Column 2 Percentage range of alternative cytidine | Column 3 Percentage range of alternative cytidine |
|---|---|---|---|---|
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 30 | 30 to 50 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 31 | 30 to 55 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 32 | 30 to 60 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 33 | 30 to 65 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 34 | 30 to 70 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |

TABLE B21-continued

| Row | Column 1 Percentage range of alternative uridine | Percentage range of alternative cytidine | Column 2 Percentage range of alternative cytidine | Column 3 Percentage range of alternative cytidine |
|---|---|---|---|---|
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 35 | 30 to 75 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 36 | 35 to 50 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 37 | 35 to 55 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 38 | 35 to 60 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 39 | 35 to 65 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |

TABLE B21-continued

| Row | Percentage range of alternative uridine | Column 1 Percentage range of alternative cytidine | Column 2 Percentage range of alternative cytidine | Column 3 Percentage range of alternative cytidine |
|---|---|---|---|---|
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 40 | 35 to 70 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 41 | 35 to 75 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 42 | 40 to 50 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 43 | 40 to 55 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 44 | 40 to 60 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |

TABLE B21-continued

| Row | Percentage range of alternative uridine | Column 1 Percentage range of alternative cytidine | Column 2 Percentage range of alternative cytidine | Column 3 Percentage range of alternative cytidine |
|---|---|---|---|---|
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 45 | 40 to 65 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 46 | 40 to 70 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 47 | 40 to 75 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 48 | 45 to 50 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 49 | 45 to 55 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |

TABLE B21-continued

| Row | Percentage range of alternative uridine | Column 1 Percentage range of alternative cytidine | Column 2 Percentage range of alternative cytidine | Column 3 Percentage range of alternative cytidine |
|---|---|---|---|---|
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 50 | 45 to 60 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 51 | 45 to 65 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 52 | 45 to 70 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 53 | 45 to 75 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 54 | 50 to 55 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |

TABLE B21-continued

| Row | Percentage range of alternative uridine | Column 1 Percentage range of alternative cytidine | Column 2 Percentage range of alternative cytidine | Column 3 Percentage range of alternative cytidine |
|---|---|---|---|---|
|    |          | 15 to 45 | 40 to 70 | 65 to 95 |
|    |          | 15 to 50 | 40 to 75 | 65 to 100 |
|    |          | 20 to 25 | 45 to 50 | 70 to 75 |
|    |          | 20 to 30 | 45 to 55 | 70 to 80 |
|    |          | 20 to 35 | 45 to 60 | 70 to 85 |
|    |          | 20 to 40 | 45 to 65 | 70 to 90 |
|    |          | 20 to 45 | 45 to 70 | 70 to 95 |
|    |          | 20 to 50 | 45 to 75 | 70 to 100 |
|    |          | 25 to 30 | 50 to 55 | 75 to 80 |
|    |          | 25 to 35 | 50 to 60 | 75 to 85 |
|    |          | 25 to 40 | 50 to 65 | 75 to 90 |
|    |          | 25 to 45 | 50 to 70 | 75 to 95 |
|    |          | 25 to 50 | 50 to 75 | 75 to 100 |
| 55 | 50 to 60 | 5 to 25  | 30 to 50 | 55 to 75 |
|    |          | 5 to 30  | 30 to 55 | 55 to 80 |
|    |          | 5 to 35  | 30 to 60 | 55 to 85 |
|    |          | 5 to 40  | 30 to 65 | 55 to 90 |
|    |          | 5 to 45  | 30 to 70 | 55 to 95 |
|    |          | 5 to 50  | 30 to 75 | 55 to 100 |
|    |          | 10 to 25 | 35 to 50 | 60 to 75 |
|    |          | 10 to 30 | 35 to 55 | 60 to 80 |
|    |          | 10 to 35 | 35 to 60 | 60 to 85 |
|    |          | 10 to 40 | 35 to 65 | 60 to 90 |
|    |          | 10 to 45 | 35 to 70 | 60 to 95 |
|    |          | 10 to 50 | 35 to 75 | 60 to 100 |
|    |          | 15 to 25 | 40 to 50 | 65 to 75 |
|    |          | 15 to 30 | 40 to 55 | 65 to 80 |
|    |          | 15 to 35 | 40 to 60 | 65 to 85 |
|    |          | 15 to 40 | 40 to 65 | 65 to 90 |
|    |          | 15 to 45 | 40 to 70 | 65 to 95 |
|    |          | 15 to 50 | 40 to 75 | 65 to 100 |
|    |          | 20 to 25 | 45 to 50 | 70 to 75 |
|    |          | 20 to 30 | 45 to 55 | 70 to 80 |
|    |          | 20 to 35 | 45 to 60 | 70 to 85 |
|    |          | 20 to 40 | 45 to 65 | 70 to 90 |
|    |          | 20 to 45 | 45 to 70 | 70 to 95 |
|    |          | 20 to 50 | 45 to 75 | 70 to 100 |
|    |          | 25 to 30 | 50 to 55 | 75 to 80 |
|    |          | 25 to 35 | 50 to 60 | 75 to 85 |
|    |          | 25 to 40 | 50 to 65 | 75 to 90 |
|    |          | 25 to 45 | 50 to 70 | 75 to 95 |
|    |          | 25 to 50 | 50 to 75 | 75 to 100 |
| 56 | 50 to 65 | 5 to 25  | 30 to 50 | 55 to 75 |
|    |          | 5 to 30  | 30 to 55 | 55 to 80 |
|    |          | 5 to 35  | 30 to 60 | 55 to 85 |
|    |          | 5 to 40  | 30 to 65 | 55 to 90 |
|    |          | 5 to 45  | 30 to 70 | 55 to 95 |
|    |          | 5 to 50  | 30 to 75 | 55 to 100 |
|    |          | 10 to 25 | 35 to 50 | 60 to 75 |
|    |          | 10 to 30 | 35 to 55 | 60 to 80 |
|    |          | 10 to 35 | 35 to 60 | 60 to 85 |
|    |          | 10 to 40 | 35 to 65 | 60 to 90 |
|    |          | 10 to 45 | 35 to 70 | 60 to 95 |
|    |          | 10 to 50 | 35 to 75 | 60 to 100 |
|    |          | 15 to 25 | 40 to 50 | 65 to 75 |
|    |          | 15 to 30 | 40 to 55 | 65 to 80 |
|    |          | 15 to 35 | 40 to 60 | 65 to 85 |
|    |          | 15 to 40 | 40 to 65 | 65 to 90 |
|    |          | 15 to 45 | 40 to 70 | 65 to 95 |
|    |          | 15 to 50 | 40 to 75 | 65 to 100 |
|    |          | 20 to 25 | 45 to 50 | 70 to 75 |
|    |          | 20 to 30 | 45 to 55 | 70 to 80 |
|    |          | 20 to 35 | 45 to 60 | 70 to 85 |
|    |          | 20 to 40 | 45 to 65 | 70 to 90 |
|    |          | 20 to 45 | 45 to 70 | 70 to 95 |
|    |          | 20 to 50 | 45 to 75 | 70 to 100 |
|    |          | 25 to 30 | 50 to 55 | 75 to 80 |
|    |          | 25 to 35 | 50 to 60 | 75 to 85 |
|    |          | 25 to 40 | 50 to 65 | 75 to 90 |
|    |          | 25 to 45 | 50 to 70 | 75 to 95 |
|    |          | 25 to 50 | 50 to 75 | 75 to 100 |
| 57 | 50 to 70 | 5 to 25  | 30 to 50 | 55 to 75 |
|    |          | 5 to 30  | 30 to 55 | 55 to 80 |
|    |          | 5 to 35  | 30 to 60 | 55 to 85 |
|    |          | 5 to 40  | 30 to 65 | 55 to 90 |
|    |          | 5 to 45  | 30 to 70 | 55 to 95 |
|    |          | 5 to 50  | 30 to 75 | 55 to 100 |
|    |          | 10 to 25 | 35 to 50 | 60 to 75 |
|    |          | 10 to 30 | 35 to 55 | 60 to 80 |
|    |          | 10 to 35 | 35 to 60 | 60 to 85 |
|    |          | 10 to 40 | 35 to 65 | 60 to 90 |
|    |          | 10 to 45 | 35 to 70 | 60 to 95 |
|    |          | 10 to 50 | 35 to 75 | 60 to 100 |
|    |          | 15 to 25 | 40 to 50 | 65 to 75 |
|    |          | 15 to 30 | 40 to 55 | 65 to 80 |
|    |          | 15 to 35 | 40 to 60 | 65 to 85 |
|    |          | 15 to 40 | 40 to 65 | 65 to 90 |
|    |          | 15 to 45 | 40 to 70 | 65 to 95 |
|    |          | 15 to 50 | 40 to 75 | 65 to 100 |
|    |          | 20 to 25 | 45 to 50 | 70 to 75 |
|    |          | 20 to 30 | 45 to 55 | 70 to 80 |
|    |          | 20 to 35 | 45 to 60 | 70 to 85 |
|    |          | 20 to 40 | 45 to 65 | 70 to 90 |
|    |          | 20 to 45 | 45 to 70 | 70 to 95 |
|    |          | 20 to 50 | 45 to 75 | 70 to 100 |
|    |          | 25 to 30 | 50 to 55 | 75 to 80 |
|    |          | 25 to 35 | 50 to 60 | 75 to 85 |
|    |          | 25 to 40 | 50 to 65 | 75 to 90 |
|    |          | 25 to 45 | 50 to 70 | 75 to 95 |
|    |          | 25 to 50 | 50 to 75 | 75 to 100 |
| 58 | 50 to 75 | 5 to 25  | 30 to 50 | 55 to 75 |
|    |          | 5 to 30  | 30 to 55 | 55 to 80 |
|    |          | 5 to 35  | 30 to 60 | 55 to 85 |
|    |          | 5 to 40  | 30 to 65 | 55 to 90 |
|    |          | 5 to 45  | 30 to 70 | 55 to 95 |
|    |          | 5 to 50  | 30 to 75 | 55 to 100 |
|    |          | 10 to 25 | 35 to 50 | 60 to 75 |
|    |          | 10 to 30 | 35 to 55 | 60 to 80 |
|    |          | 10 to 35 | 35 to 60 | 60 to 85 |
|    |          | 10 to 40 | 35 to 65 | 60 to 90 |
|    |          | 10 to 45 | 35 to 70 | 60 to 95 |
|    |          | 10 to 50 | 35 to 75 | 60 to 100 |
|    |          | 15 to 25 | 40 to 50 | 65 to 75 |
|    |          | 15 to 30 | 40 to 55 | 65 to 80 |
|    |          | 15 to 35 | 40 to 60 | 65 to 85 |
|    |          | 15 to 40 | 40 to 65 | 65 to 90 |
|    |          | 15 to 45 | 40 to 70 | 65 to 95 |
|    |          | 15 to 50 | 40 to 75 | 65 to 100 |
|    |          | 20 to 25 | 45 to 50 | 70 to 75 |
|    |          | 20 to 30 | 45 to 55 | 70 to 80 |
|    |          | 20 to 35 | 45 to 60 | 70 to 85 |
|    |          | 20 to 40 | 45 to 65 | 70 to 90 |
|    |          | 20 to 45 | 45 to 70 | 70 to 95 |
|    |          | 20 to 50 | 45 to 75 | 70 to 100 |
|    |          | 25 to 30 | 50 to 55 | 75 to 80 |
|    |          | 25 to 35 | 50 to 60 | 75 to 85 |
|    |          | 25 to 40 | 50 to 65 | 75 to 90 |
|    |          | 25 to 45 | 50 to 70 | 75 to 95 |
|    |          | 25 to 50 | 50 to 75 | 75 to 100 |
| 59 | 55 to 75 | 5 to 25  | 30 to 50 | 55 to 75 |
|    |          | 5 to 30  | 30 to 55 | 55 to 80 |
|    |          | 5 to 35  | 30 to 60 | 55 to 85 |
|    |          | 5 to 40  | 30 to 65 | 55 to 90 |
|    |          | 5 to 45  | 30 to 70 | 55 to 95 |
|    |          | 5 to 50  | 30 to 75 | 55 to 100 |
|    |          | 10 to 25 | 35 to 50 | 60 to 75 |
|    |          | 10 to 30 | 35 to 55 | 60 to 80 |
|    |          | 10 to 35 | 35 to 60 | 60 to 85 |
|    |          | 10 to 40 | 35 to 65 | 60 to 90 |
|    |          | 10 to 45 | 35 to 70 | 60 to 95 |
|    |          | 10 to 50 | 35 to 75 | 60 to 100 |
|    |          | 15 to 25 | 40 to 50 | 65 to 75 |
|    |          | 15 to 30 | 40 to 55 | 65 to 80 |
|    |          | 15 to 35 | 40 to 60 | 65 to 85 |
|    |          | 15 to 40 | 40 to 65 | 65 to 90 |

TABLE B21-continued

| Row | Column 1 Percentage range of alternative uridine | Percentage range of alternative cytidine | Column 2 Percentage range of alternative cytidine | Column 3 Percentage range of alternative cytidine |
|---|---|---|---|---|
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 60 | 55 to 80 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 61 | 55 to 85 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 62 | 55 to 90 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 63 | 55 to 95 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 64 | 55 to 100 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |

TABLE B21-continued

| Row | Percentage range of alternative uridine | Column 1 Percentage range of alternative cytidine | Column 2 Percentage range of alternative cytidine | Column 3 Percentage range of alternative cytidine |
|---|---|---|---|---|
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 65 | 60 to 75 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 66 | 60 to 80 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 67 | 60 to 85 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 68 | 60 to 90 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 69 | 60 to 95 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |

TABLE B21-continued

| Row | Percentage range of alternative uridine | Column 1 Percentage range of alternative cytidine | Column 2 Percentage range of alternative cytidine | Column 3 Percentage range of alternative cytidine |
|---|---|---|---|---|
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 70 | 60 to 100 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 71 | 65 to 75 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 72 | 65 to 80 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 73 | 65 to 85 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |
|  |  | 15 to 45 | 40 to 70 | 65 to 95 |
|  |  | 15 to 50 | 40 to 75 | 65 to 100 |
|  |  | 20 to 25 | 45 to 50 | 70 to 75 |
|  |  | 20 to 30 | 45 to 55 | 70 to 80 |
|  |  | 20 to 35 | 45 to 60 | 70 to 85 |
|  |  | 20 to 40 | 45 to 65 | 70 to 90 |
|  |  | 20 to 45 | 45 to 70 | 70 to 95 |
|  |  | 20 to 50 | 45 to 75 | 70 to 100 |
|  |  | 25 to 30 | 50 to 55 | 75 to 80 |
|  |  | 25 to 35 | 50 to 60 | 75 to 85 |
|  |  | 25 to 40 | 50 to 65 | 75 to 90 |
|  |  | 25 to 45 | 50 to 70 | 75 to 95 |
|  |  | 25 to 50 | 50 to 75 | 75 to 100 |
| 74 | 65 to 90 | 5 to 25 | 30 to 50 | 55 to 75 |
|  |  | 5 to 30 | 30 to 55 | 55 to 80 |
|  |  | 5 to 35 | 30 to 60 | 55 to 85 |
|  |  | 5 to 40 | 30 to 65 | 55 to 90 |
|  |  | 5 to 45 | 30 to 70 | 55 to 95 |
|  |  | 5 to 50 | 30 to 75 | 55 to 100 |
|  |  | 10 to 25 | 35 to 50 | 60 to 75 |
|  |  | 10 to 30 | 35 to 55 | 60 to 80 |
|  |  | 10 to 35 | 35 to 60 | 60 to 85 |
|  |  | 10 to 40 | 35 to 65 | 60 to 90 |
|  |  | 10 to 45 | 35 to 70 | 60 to 95 |
|  |  | 10 to 50 | 35 to 75 | 60 to 100 |
|  |  | 15 to 25 | 40 to 50 | 65 to 75 |
|  |  | 15 to 30 | 40 to 55 | 65 to 80 |
|  |  | 15 to 35 | 40 to 60 | 65 to 85 |
|  |  | 15 to 40 | 40 to 65 | 65 to 90 |

TABLE B21-continued

| Row | Percentage range of alternative uridine | Column 1 Percentage range of alternative cytidine | Column 2 Percentage range of alternative cytidine | Column 3 Percentage range of alternative cytidine |
|---|---|---|---|---|
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 75 | 65 to 95 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 76 | 65 to 100 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 77 | 70 to 75 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 78 | 70 to 80 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 79 | 70 to 85 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |

TABLE B21-continued

| Row | Percentage range of alternative uridine | Column 1 Percentage range of alternative cytidine | Column 2 Percentage range of alternative cytidine | Column 3 Percentage range of alternative cytidine |
|---|---|---|---|---|
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 80 | 70 to 90 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 81 | 70 to 95 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 82 | 70 to 100 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 83 | 75 to 80 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 84 | 75 to 85 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |

TABLE B21-continued

| Row | Percentage range of alternative uridine | Column 1 Percentage range of alternative cytidine | Column 2 Percentage range of alternative cytidine | Column 3 Percentage range of alternative cytidine |
|---|---|---|---|---|
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 85 | 75 to 90 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 86 | 75 to 95 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |
| 87 | 75 to 100 | 5 to 25 | 30 to 50 | 55 to 75 |
| | | 5 to 30 | 30 to 55 | 55 to 80 |
| | | 5 to 35 | 30 to 60 | 55 to 85 |
| | | 5 to 40 | 30 to 65 | 55 to 90 |
| | | 5 to 45 | 30 to 70 | 55 to 95 |
| | | 5 to 50 | 30 to 75 | 55 to 100 |
| | | 10 to 25 | 35 to 50 | 60 to 75 |
| | | 10 to 30 | 35 to 55 | 60 to 80 |
| | | 10 to 35 | 35 to 60 | 60 to 85 |
| | | 10 to 40 | 35 to 65 | 60 to 90 |
| | | 10 to 45 | 35 to 70 | 60 to 95 |
| | | 10 to 50 | 35 to 75 | 60 to 100 |
| | | 15 to 25 | 40 to 50 | 65 to 75 |
| | | 15 to 30 | 40 to 55 | 65 to 80 |
| | | 15 to 35 | 40 to 60 | 65 to 85 |
| | | 15 to 40 | 40 to 65 | 65 to 90 |
| | | 15 to 45 | 40 to 70 | 65 to 95 |
| | | 15 to 50 | 40 to 75 | 65 to 100 |
| | | 20 to 25 | 45 to 50 | 70 to 75 |
| | | 20 to 30 | 45 to 55 | 70 to 80 |
| | | 20 to 35 | 45 to 60 | 70 to 85 |
| | | 20 to 40 | 45 to 65 | 70 to 90 |
| | | 20 to 45 | 45 to 70 | 70 to 95 |
| | | 20 to 50 | 45 to 75 | 70 to 100 |
| | | 25 to 30 | 50 to 55 | 75 to 80 |
| | | 25 to 35 | 50 to 60 | 75 to 85 |
| | | 25 to 40 | 50 to 65 | 75 to 90 |
| | | 25 to 45 | 50 to 70 | 75 to 95 |
| | | 25 to 50 | 50 to 75 | 75 to 100 |

Preferably, in some embodiments, the polynucleotide of the invention contains the percentage of alternative uridine, e.g., alternative uridines as described in Table 2, in row 1 of Table B22 and the percentages of alternative cytidine, e.g., alternative cytidines as described in Table 3, in column 1 of Table B22. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

Preferably, in some embodiments, the polynucleotide of the invention contains the percentage of alternative uridine, e.g., alternative uridines as described in Table 2, in row 2 of Table B22 and the percentages of alternative cytidine, e.g., alternative cytidines as described in Table 3, in column 1 of Table B22. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

Preferably, in some embodiments, the polynucleotide of the invention contains the percentage of alternative uridine, e.g., alternative uridines as described in Table 2, in row 3 of Table B22 and the percentages of alternative cytidine, e.g., alternative cytidines as described in Table 3, in column 1 of Table B22. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

Preferably, in some embodiments, the polynucleotide of the invention contains the percentage of alternative uridine, e.g., alternative uridines as described in Table 2, in row 4 of Table B22 and the percentages of alternative cytidine, e.g., alternative cytidines as described in Table 3, in column 1 of Table B22. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

Preferably, in some embodiments, the polynucleotide of the invention contains the percentage of alternative uridine, e.g., alternative uridines as described in Table 2, in row 5 of Table B22 and the percentages of alternative cytidine, e.g., alternative cytidines as described in Table 3, in column 1 of Table B22. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

Preferably, in some embodiments, the polynucleotide of the invention contains the percentage of alternative uridine, e.g., alternative uridines as described in Table 2, in row 6 of Table B22 and the percentages of alternative cytidine, e.g., alternative cytidines as described in Table 3, in column 1 of Table B22. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

Preferably, in some embodiments, the polynucleotide of the invention contains the percentage of alternative uridine, e.g., alternative uridines as described in Table 2, in row 7 of Table B22 and the percentages of alternative cytidine, e.g., alternative cytidines as described in Table 3, in column 1 of Table B22. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

Preferably, in some embodiments, the polynucleotide of the invention contains the percentage of alternative uridine, e.g., alternative uridines as described in Table 2, in row 8 of Table B22 and the percentages of alternative cytidine, e.g., alternative cytidines as described in Table 3, in column 1 of Table B22. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

Preferably, in some embodiments, the polynucleotide of the invention contains the percentage of alternative uridine, e.g., alternative uridines as described in Table 2, in row 9 of Table B22 and the percentages of alternative cytidine, e.g., alternative cytidines as described in Table 3, in column 1 of Table B22. In some embodiments, the polynucleotide of the invention contains 5-methoxy-uridine, uridine, 5-methyl-cytidine, and cytidine as the only uridines and cytidines. In further embodiments, the polynucleotide does not include an alternative adenosine or guanosine.

TABLE B22

| Row | Percentage range of alternative uridine | Column 1 Percentage range of alternative cytidine |
|---|---|---|
| 1 | 10 | 50 |
|   |   | 55 |
|   |   | 60 |
|   |   | 65 |
|   |   | 70 |
|   |   | 75 |
|   |   | 80 |
|   |   | 85 |
|   |   | 90 |
|   |   | 95 |
|   |   | 100 |
| 2 | 15 | 50 |
|   |   | 55 |
|   |   | 60 |
|   |   | 65 |
|   |   | 70 |
|   |   | 75 |
|   |   | 80 |
|   |   | 85 |
|   |   | 90 |
|   |   | 95 |
|   |   | 100 |
| 3 | 20 | 50 |
|   |   | 55 |
|   |   | 60 |
|   |   | 65 |
|   |   | 70 |
|   |   | 75 |
|   |   | 80 |
|   |   | 85 |
|   |   | 90 |
|   |   | 95 |
|   |   | 100 |
| 4 | 25 | 50 |
|   |   | 55 |
|   |   | 60 |
|   |   | 65 |
|   |   | 70 |
|   |   | 75 |
|   |   | 80 |
|   |   | 85 |
|   |   | 90 |
|   |   | 95 |
|   |   | 100 |
| 5 | 30 | 50 |
|   |   | 55 |
|   |   | 60 |
|   |   | 65 |
|   |   | 70 |
|   |   | 75 |
|   |   | 80 |
|   |   | 85 |
|   |   | 90 |
|   |   | 95 |
|   |   | 100 |
| 6 | 35 | 50 |
|   |   | 55 |
|   |   | 60 |
|   |   | 65 |
|   |   | 70 |
|   |   | 75 |
|   |   | 80 |
|   |   | 85 |
|   |   | 90 |
|   |   | 95 |
|   |   | 100 |
| 7 | 40 | 50 |
|   |   | 55 |
|   |   | 60 |
|   |   | 65 |
|   |   | 70 |
|   |   | 75 |
|   |   | 80 |
|   |   | 85 |
|   |   | 90 |
|   |   | 95 |
|   |   | 100 |
| 8 | 45 | 50 |
|   |   | 55 |
|   |   | 60 |
|   |   | 65 |
|   |   | 70 |

TABLE B22-continued

| Row | Column 1 Percentage range of alternative uridine | Percentage range of alternative cytidine |
|---|---|---|
|   |   | 75 |
|   |   | 80 |
|   |   | 85 |
|   |   | 90 |
|   |   | 95 |
|   |   | 100 |
| 9 | 50 | 50 |
|   |   | 55 |
|   |   | 60 |
|   |   | 65 |
|   |   | 70 |
|   |   | 75 |
|   |   | 80 |
|   |   | 85 |
|   |   | 90 |
|   |   | 95 |
|   |   | 100 |

In some embodiments, the polynucleotides of the invention contain 5-methoxy-uracil, uracil, 5-methyl-cytosine, and cytosine as the only uracils and cytosines. In some embodiments, the polynucleotides of the invention contain 5-methoxy-uracil, uracil, 5-trifluoromethyl-cytosine, and cytosine as the only uracils and cytosines. In some embodiments, the polynucleotides of the invention contain 5-methoxy-uracil, uracil, 5-hydroxymethyl-cytosine, and cytosine as the only uracils and cytosines. In some embodiments, the polynucleotides of the invention contain 5-methoxy-uracil, uracil, 5-bromo-cytosine, and cytosine as the only uracils and cytosines. In some embodiments, the polynucleotides of the invention contain 5-methoxy-uracil, uracil, 5-iodo-cytosine, and cytosine as the only uracils and cytosines. In some embodiments, the polynucleotides of the invention contain 5-methoxy-uracil, uracil, 5-methoxy-cytosine, and cytosine as the only uracils and cytosines. In some embodiments, the polynucleotides of the invention contain 5-methoxy-uracil, uracil, 5-ethyl-cytosine, and cytosine as the only uracils and cytosines. In some embodiments, the polynucleotides of the invention contain 5-methoxy-uracil, uracil, 5-phenyl-cytosine, and cytosine as the only uracils and cytosines. In some embodiments, the polynucleotides of the invention contain 5-methoxy-uracil, uracil, 5-ethnyl-cytosine, and cytosine as the only uracils and cytosines. In some embodiments, the polynucleotides of the invention contain 5-methoxy-uracil, uracil, N4-methyl-cytosine, and cytosine as the only uracils and cytosines. In some embodiments, the polynucleotides of the invention contain 5-methoxy-uracil, uracil, 5-fluoro-cytosine, and cytosine as the only uracils and cytosines. In some embodiments, the polynucleotides of the invention contain 5-methoxy-uracil, uracil, N4-acetyl-cytosine, and cytosine as the only uracils and cytosines. In some embodiments, the polynucleotides of the invention contain 5-methoxy-uracil, uracil, pseudoisocytosine, and cytosine as the only uracils and cytosines. In some embodiments, the polynucleotides of the invention contain 5-methoxy-uracil, uracil, 5-formyl-cytosine, and cytosine as the only uracils and cytosines. In some embodiments, the polynucleotides of the invention contain 5-methoxy-uracil, uracil, 5-aminoallyl-cytosine, and cytosine as the only uracils and cytosines. In some embodiments, the polynucleotides of the invention contain 5-methoxy-uracil, uracil, 5-carboxy-cytosine, and cytosine as the only uracils and cytosines.

In some embodiments, the polynucleotides of the invention contain 1-methyl-pseudouracil, uracil, 5-methyl-cytosine, and cytosine as the only uracils and cytosines. In some embodiments, the polynucleotides of the invention contain 1-methyl-pseudouracil, uracil, 5-trifluoromethyl-cytosine, and cytosine as the only uracils and cytosines. In some embodiments, the polynucleotides of the invention contain 1-methyl-pseudouracil, uracil, 5-hydroxymethyl-cytosine, and cytosine as the only uracils and cytosines. In some embodiments, the polynucleotides of the invention contain 1-methyl-pseudouracil, uracil, 5-bromo-cytosine, and cytosine as the only uracils and cytosines. In some embodiments, the polynucleotides of the invention contain 1-methyl-pseudouracil, uracil, 5-iodo-cytosine, and cytosine as the only uracils and cytosines. In some embodiments, the polynucleotides of the invention contain 1-methyl-pseudouracil, uracil, 5-methoxy-cytosine, and cytosine as the only uracils and cytosines. In some embodiments, the polynucleotides of the invention contain 1-methyl-pseudouracil, uracil, 5-ethyl-cytosine, and cytosine as the only uracils and cytosines. In some embodiments, the polynucleotides of the invention contain 1-methyl-pseudouracil, uracil, 5-phenyl-cytosine, and cytosine as the only uracils and cytosines. In some embodiments, the polynucleotides of the invention contain 1-methyl-pseudouracil, uracil, 5-ethnyl-cytosine, and cytosine as the only uracils and cytosines. In some embodiments, the polynucleotides of the invention contain 1-methyl-pseudouracil, uracil, N4-methyl-cytosine, and cytosine as the only uracils and cytosines. In some embodiments, the polynucleotides of the invention contain 1-methyl-pseudouracil, uracil, 5-fluoro-cytosine, and cytosine as the only uracils and cytosines. In some embodiments, the polynucleotides of the invention contain 1-methyl-pseudouracil, uracil, N4-acetyl-cytosine, and cytosine as the only uracils and cytosines. In some embodiments, the polynucleotides of the invention contain 1-methyl-pseudouracil, uracil, pseudoisocytosine, and cytosine as the only uracils and cytosines. In some embodiments, the polynucleotides of the invention contain 1-methyl-pseudouracil, uracil, 5-formyl-cytosine, and cytosine as the only uracils and cytosines. In some embodiments, the polynucleotides of the invention contain 1-methyl-pseudouracil, uracil, 5-aminoallyl-cytosine, and cytosine as the only uracils and cytosines. In some embodiments, the polynucleotides of the invention contain 1-methyl-pseudouracil, uracil, 5-carboxy-cytosine, and cytosine as the only uracils and cytosines.

In some embodiments, the polynucleotides of the invention contain 5-methoxy-uridine, uridine, 5-methyl-cytidine, and cytidine as the only uridines and cytidines. In some embodiments, the polynucleotides of the invention contain 5-methoxy-uridine, uridine, 5-trifluoromethyl-cytidine, and cytidine as the only uridines and cytidines. In some embodiments, the polynucleotides of the invention contain 5-methoxy-uridine, uridine, 5-hydroxymethyl-cytidine, and cytidine as the only uridines and cytidines. In some embodiments, the polynucleotides of the invention contain 5-methoxy-uridine, uridine, 5-bromo-cytidine, and cytidine as the only uridines and cytidines. In some embodiments, the polynucleotides of the invention contain 5-methoxy-uridine, uridine, 5-iodo-cytidine, and cytidine as the only uridines and cytidines. In some embodiments, the polynucleotides of the invention contain 5-methoxy-uridine, uridine, 5-methoxy-cytidine, and cytidine as the only uridines and cytidines. In some embodiments, the polynucleotides of the invention contain 5-methoxy-uridine, uridine, 5-ethyl-cytidine, and cytidine as the only uridines and cytidines. In some embodiments, the polynucleotides of the invention contain 5-methoxy-uridine, uridine, 5-phenyl-cytidine, and cytidine as the only uridines and cytidines. In some embodiments, the polynucleotides of the invention contain 5-methoxy-uridine, uridine, 5-ethnyl-cytidine, and cytidine as the only uridines and cytidines. In some embodiments, the polynucleotides of the invention contain 5-methoxy-uridine, uridine, N4-methyl-cytidine, and cytidine as the only uridines and cytidines. In some embodiments, the polynucleotides of the invention contain 5-methoxy-uridine, uridine, 5-fluoro-cytidine, and cytidine as the only uridines and cytidines. In some embodiments, the polynucleotides of the invention contain 5-methoxy-uridine, uridine, N4-acetyl-cytidine, and cytidine as the only uridines and cytidines. In some embodiments, the polynucleotides of the invention contain 5-methoxy-uridine, uridine, pseudoisocytidine, and cytidine as the only uridines and cytidines. In some embodiments, the polynucleotides of the invention contain 5-methoxy-uridine, uridine, 5-formyl-cytidine, and cytidine as the only uridines and cytidines. In some embodiments, the polynucleotides of the invention contain 5-methoxy-uridine, uridine, 5-aminoallyl-cytidine, and cytidine as the only uridines and cytidines. In some embodiments, the polynucleotides of the invention contain 5-methoxy-uridine, uridine, 5-carboxy-cytidine, and cytidine as the only uridines and cytidines.

In some embodiments, the polynucleotides of the invention contain 1-methyl-pseudouridine, uridine, 5-methyl-cytidine, and cytidine as the only uridines and cytidines. In some embodiments, the polynucleotides of the invention contain 1-methyl-pseudouridine, uridine, 5-trifluoromethyl-cytidine, and cytidine as the only uridines and cytidines. In some embodiments, the polynucleotides of the invention contain 1-methyl-pseudouridine, uridine, 5-hydroxymethyl-cytidine, and cytidine as the only uridines and cytidines. In some embodiments, the polynucleotides of the invention contain 1-methyl-pseudouridine, uridine, 5-bromo-cytidine, and cytidine as the only uridines and cytidines. In some embodiments, the polynucleotides of the invention contain 1-methyl-pseudouridine, uridine, 5-iodo-cytidine, and cytidine as the only uridines and cytidines. In some embodiments, the polynucleotides of the invention contain 1-methyl-pseudouridine, uridine, 5-methoxy-cytidine, and cytidine as the only uridines and cytidines. In some embodiments, the polynucleotides of the invention contain 1-methyl-pseudouridine, uridine, 5-ethyl-cytidine, and cytidine as the only uridines and cytidines. In some embodiments, the polynucleotides of the invention contain 1-methyl-pseudouridine, uridine, 5-phenyl-cytidine, and cytidine as the only uridines and cytidines. In some embodiments, the polynucleotides of the invention contain 1-methyl-pseudouridine, uridine, 5-ethnyl-cytidine, and cytidine as the only uridines and cytidines. In some embodiments, the polynucleotides of the invention contain 1-methyl-pseudouridine, uridine, N4-methyl-cytidine, and cytidine as the only uridines and cytidines. In some embodiments, the polynucleotides of the invention contain 1-methyl-pseudouridine, uridine, 5-fluoro-cytidine, and cytidine as the only uridines and cytidines. In some embodiments, the polynucleotides of the invention contain 1-methyl-pseudouridine, uridine, N4-acetyl-cytidine, and cytidine as the only uridines and cytidines. In some embodiments, the polynucleotides of the invention contain 1-methyl-pseudouridine, uridine, pseudoisocytidine, and cytidine as the only uridines and cytidines. In some embodiments, the polynucleotides of the invention contain 1-methyl-pseudouridine, uridine, 5-formyl-cytidine, and cytidine as the only uridines and cytidines. In some embodiments, the polynucleotides of the invention contain 1-methyl-pseudouridine, uridine, 5-aminoallyl-cytidine, and cytidine as the only uridines and cytidines. In some embodiments, the polynucleotides of the invention contain 1-methyl-pseudouridine, uridine, 5-carboxy-cytidine, and cytidine as the only uridines and cytidines.

In some embodiments, the polynucleotides of the invention contain the uracil of one of the nucleosides of Table 2 and uracil as the only uracils. In other embodiments, the polynucleotides of the invention contain a uridine of Table 2 and uridine as the only uridines.

TABLE 2

Exemplary uracil containing nucleosides
Nucleoside Name 5-methoxy-uridine
1-Methyl-pseudo-uridine
pseudouridine
5-methyl-uridine
5-bromo-uridine
2-thio-uridine
4-thiouridine
2'-O-methyluridine
5-methyl-2-thiouridine
5,2'-O-dimethyluridine
5-aminomethyl-2-thiouridine
5-(1-Propynyl)ara-uridine
2'-O-Methyl-5-(1-propynyl)uridine
5-Vinylarauridine
(Z)-5-(2-Bromo-vinyl)ara-uridine
(E)-5-(2-Bromo-vinyl)ara-uridine
(Z)-5-(2-Bromo-vinyl)uridine
(E)-5-(2-Bromo-vinyl)uridine
5-Cyanouridine
5-Formyluridine
5-Dimethylaminouridine
5-Trideuteromethyl-6-deuterouridine
5-(2-Furanyl)uridine
5-Phenylethynyluridine
4'-Carbocyclic uridine
4'-Ethynyluridine
4'-Azidouridine
2'-Deoxy-2',2'-difluorouridine
2'-Deoxy-2'-b-fluorouridine
2'-Deoxy-2'-b-chlorouridine
2'-Deoxy-2'-b-bromouridine
2'-Deoxy-2'-b-iodouridine
5'-Homo-uridine
2'-Deoxy-2'-a-mercaptouridine
2'-Deoxy-2'-a-thiomethoxyuridine
2'-Deoxy-2'-a-azidouridine
2'-Deoxy-2'-a-aminouridine
2'-Deoxy-2'-b-mercaptouridine
2'-Deoxy-2'-b-thiomethoxyuridine
2'-Deoxy-2'-b-azidouridine
2'-Deoxy-2'-b-aminouridine
2'-b-Trifluoromethyluridine
2'-a-Trifluoromethyluridine
2'-b-Ethynyluridine
2'-a-Ethynyluridine
1-ethyl-pseudo-uridine
1-propyl-pseudo-uridine
1-iso-propyl-pseudo-uridine
1-(2,2,2-trifluoroethyl)-pseudo-uridine
1-cyclopropyl-pseudo-uridine
1-cyclopropylmethyl-pseudo-uridine
1-phenyl-pseudo-uridine
1-benzyl-pseudo-uridine
1-aminomethyl-pseudo-uridine
pseudo-uridine-1-2-ethanoic acid
1-(3-amino-3-carboxypropyl)pseudo-uridine
1-methyl-3-(3-amino-3-carboxypropyl)pseudo-uridine
6-methyl-pseudo-uridine
6-trifluoromethyl-pseudo-uridine
6-methoxy-pseudo-uridine
6-phenyl-pseudo-uridine
6-iodo-pseudo-uridine
6-bromo-pseudo-uridine
6-chloro-pseudo-uridine
6-fluoro-pseudo-uridine
4-Thio-pseudo-uridine
2-Thio-pseudo-uridine
Alpha-thio-pseudo-uridine
1-Me-alpha-thio-pseudo-uridine
1-butyl-pseudo-uridine
1-tert-butyl-pseudo-uridine
1-pentyl-pseudo-uridine TABLE 2-continued Exemplary uracil containing nucleosides
Nucleoside Name 1-hexyl-pseudo-uridine
1-trifluoromethyl-pseudo-uridine
1-cyclobutyl-pseudo-uridine
1-cyclopentyl-pseudo-uridine
1-cyclohexyl-pseudo-uridine
1-cycloheptyl-pseudo-uridine
1-cyclooctyl-pseudo-uridine
1-cyclobutylmethyl-pseudo-uridine
1-cyclopentylmethyl-pseudo-uridine
1-cyclohexylmethyl-pseudo-uridine
1-cycloheptylmethyl-pseudo-uridine
1-cyclooctylmethyl-pseudo-uridine
1-p-tolyl-pseudo-uridine
1-(2,4,6-trimethyl-phenyl)pseudo-uridine
1-(4-methoxy-phenyl)pseudo-uridine
1-(4-amino-phenyl)pseudo-uridine
1(4-nitro-phenyl)pseudo-uridine
pseudo-uridine-N1-p-benzoic acid
1-(4-methyl-benzyl)pseudo-uridine
1-(2,4,6-trimethyl-benzyl)pseudo-uridine
1-(4-methoxy-benzyl)pseudo-uridine
1-(4-amino-benzyl)pseudo-uridine
1-(4-nitro-benzyl)pseudo-uridine
pseudo-uridine-N1-methyl-p-benzoic acid
1-(2-amino-ethyl)pseudo-uridine
1-(3-amino-propyl)pseudo-uridine
1-(4-amino-butyl)pseudo-uridine
1-(5-amino-pentyl)pseudo-uridine
1-(6-amino-hexyl)pseudo-uridine
pseudo-uridine-N1-3-propionic acid
pseudo-uridine-N1-4-butanoic acid
pseudo-uridine-N1-5-pentanoic acid
pseudo-uridine-N1-6-hexanoic acid
pseudo-uridine-N1-7-heptanoic acid
1-(2-amino-2-carboxyethyl)pseudo-uridine
1-(4-amino-4-carboxybutyl)pseudo-uridine
3-alkyl-pseudo-uridine
6-ethyl-pseudo-uridine
6-propyl-pseudo-uridine
6-iso-propyl-pseudo-uridine
6-butyl-pseudo-uridine
6-tert-butyl-pseudo-uridine
6-(2,2,2-trifluoroethyl)-pseudo-uridine
6-ethoxy-pseudo-uridine
6-trifluoromethoxy-pseudo-uridine
6-phenyl-pseudo-uridine
6-(substituted-phenyl)-pseudo-uridine
6-cyano-pseudo-uridine
6-azido-pseudo-uridine
6-amino-pseudo-uridine
6-ethylcarboxylate-pseudo-uridine
6-hydroxy-pseudo-uridine
6-methylamino-pseudo-uridine
6-dimethylamino-pseudo-uridine
6-hydroxyamino-pseudo-uridine
6-formyl-pseudo-uridine
6-(4-morpholino)-pseudo-uridine
6-(4-thiomorpholino)-pseudo-uridine
1-me-4-thio-pseudo-uridine
1-me-2-thio-pseudo-uridine
1,6-dimethyl-pseudo-uridine
1-methyl-6-trifluoromethyl-pseudo-uridine
1-methyl-6-ethyl-pseudo-uridine
1-methyl-6-propyl-pseudo-uridine
1-methyl-6-iso-propyl-pseudo-uridine
1-methyl-6-butyl-pseudo-uridine
1-methyl-6-tert-butyl-pseudo-uridine
1-methyl-6-(2,2,2-trifluoroethyl)pseudo-uridine
1-methyl-6-iodo-pseudo-uridine
1-methyl-6-bromo-pseudo-uridine
1-methyl-6-chloro-pseudo-uridine
1-methyl-6-fluoro-pseudo-uridine
1-methyl-6-methoxy-pseudo-uridine
1-methyl-6-ethoxy-pseudo-uridine
1-methyl-6-trifluoromethoxy-pseudo-uridine
1-methyl-6-phenyl-pseudo-uridine
1-methyl-6-(substituted phenyl)pseudo-uridine
1-methyl-6-cyano-pseudo-uridine
1-methyl-6-azido-pseudo-uridine
1-methyl-6-amino-pseudo-uridine
1-methyl-6-ethylcarboxylate-pseudo-uridine
1-methyl-6-hydroxy-pseudo-uridine
1-methyl-6-methylamino-pseudo-uridine
1-methyl-6-dimethylamino-pseudo-uridine
1-methyl-6-hydroxyamino-pseudo-uridine
1-methyl-6-formyl-pseudo-uridine
1-methyl-6-(4-morpholino)-pseudo-uridine
1-methyl-6-(4-thiomorpholino)-pseudo-uridine
1-alkyl-6-vinyl-pseudo-uridine
1-alkyl-6-allyl-pseudo-uridine
1-alkyl-6-homoallyl-pseudo-uridine
1-alkyl-6-ethynyl-pseudo-uridine
1-alkyl-6-(2-propynyl)-pseudo-uridine
1-alkyl-6-(1-propynyl)-pseudo-uridine
1-Hydroxymethylpseudouridine
1-(2-Hydroxyethyl)pseudouridine
1-Methoxymethylpseudouridine
1-(2-Methoxyethyl)pseudouridine
1-(2,2-Diethoxyethyl)pseudouridine
(±)1-(2-Hydroxypropyl)pseudouridine
(2R)-1-(2-Hydroxypropyl)pseudouridine
(2S)-1-(2-Hydroxypropyl)pseudouridine
1-Cyanomethylpseudouridine
1-Morpholinomethylpseudouridine
1-Thiomorpholinomethylpseudouridine
1-Benzyloxymethylpseudouridine
1-(2,2,3,3,3-Pentafluoropropyl)pseudouridine
1-Thiomethoxymethylpseudouridine
1-Methanesulfonylmethylpseudouridine
1-Vinylpseudouridine
1-Allylpseudouridine
1-Homoallylpseudouridine
1-Propargylpseudouridine
1-(4-Fluorobenzyl)pseudouridine
1-(4-Chlorobenzyl)pseudouridine
1-(4-Bromobenzyl)pseudouridine
1-(4-Iodobenzyl)pseudouridine
1-(4-Methylbenzyl)pseudouridine
1-(4-Trifluoromethylbenzyl)pseudouridine
1-(4-Methoxybenzyl)pseudouridine
1-(4-Trifluoromethoxybenzyl)pseudouridine
1-(4-Thiomethoxybenzyl)pseudouridine
1-(4-Methanesulfonylbenzyl)pseudouridine
Pseudouridine 1-(4-methylbenzoic acid)
Pseudouridine 1-(4-methylbenzenesulfonic acid)
1-(2,4,6-Trimethylbenzyl)pseudouridine
1-(4-Nitrobenzyl)pseudouridine
1-(4-Azidobenzyl)pseudouridine
1-(3,4-Dimethoxybenzyl)pseudouridine
1-(3,4-Bis-trifluoromethoxybenzyl)pseudouridine
1-Acetylpseudouridine
1-Trifluoroacetylpseudouridine
1-Benzoylpseudouridine
1-Pivaloylpseudouridine
1-(3-Cyclopropyl-prop-2-ynyl)pseudouridine
Pseudouridine 1-methylphosphonic acid diethyl ester
Pseudouridine 1-methylphosphonic acid
Pseudouridine 1-[3-(2-ethoxy)]propionic acid
Pseudouridine 1-[3-{2-(2-ethoxy)-ethoxy}] propionic acid
Pseudouridine TP 1-[3-{2-(2-[2-ethoxy]-ethoxy)-ethoxy}]propionic acid
Pseudouridine 1-[3-{2-(2-[2-(2-ethoxy)-ethoxy]-ethoxy)-ethoxy}]propionic acid
Pseudouridine 1-[3-{2-(2-[2-{2(2-ethoxy)-ethoxy}-ethoxy]-ethoxy}]propionic acid
1-{3-[2-(2-Aminoethoxy)-ethoxy]-propionyl} pseudouridine
1-[3-(2-{2-[2-(2-Aminoethoxy)-ethoxy]-ethoxy}-ethoxy)-propionyl]pseudouridine
1-Biotinylpseudouridine
1-Biotinyl-PEG2-pseudouridine
5-Oxyacetic acid-methyl ester-uridine
3-Methyl-pseudo-uridine
5-trifluoromethyl-uridine
5-methyl-amino-methyl-uridine
5-carboxy-methyl-amino-methyl-uridine

TABLE 2-continued

Exemplary uracil containing nucleosides
Nucleoside Name 5-carboxymethylaminomethyl-2'-OMe-uridine
5-carboxymethylaminomethyl-2-thio-uridine
5-methylaminomethyl-2-thio-uridine
5-methoxy-carbonyl-methyl-uridine
5-methoxy-carbonyl-methyl-2'-OMe-uridine
5-oxyacetic acid-uridine
3-(3-amino-3-carboxypropyl)-uridine
5-(carboxyhydroxymethyl)uridine methyl ester
5-(carboxyhydroxymethyl)uridine
2'-OMe-pseudo-uridine
2'-Azido-2'-deoxy-uridine
2'-Amino-2'-deoxy-uridine
2'-F-5-Methyl-2'-deoxy-uridine
5-iodo-2'-fluoro-deoxyuridine
2'-bromo-deoxyuridine
2,2'-anhydro-uridine
2'-Azido-deoxyuridine
5-Methoxycarbonylmethyl-2-thiouridine
5-Methylaminomethyl-2-thiouridine
5-Carbamoylmethyluridine
5-Carbamoylmethyl-2'-O-methyluridine
1-Methyl-3-(3-amino-3-carboxypropyl) pseudouridine
5-Methylaminomethyl-2-selenouridine
5-Carboxymethyluridine
5-Methyldihydrouridine
5-Taurinomethyluridine
5-Taurinomethyl-2-thiouridine
5-(iso-Pentenylaminomethyl)uridine
5-(iso-Pentenylaminomethyl)-2-thiouridine
5-(iso-Pentenylaminomethyl)-2'-O-methyluridine
2'-O-Methylpseudouridine
2-Thio-2'-O-methyluridine
3,2'-O-Dimethyluridine
5-Methoxy-carbonylmethyl-uridine
5-hydroxy-uridine
5-Isopentenyl-aminomethyl-uridine In some embodiments, the polynucleotides of the invention contain the cytosine of one of the nucleosides of Table 3 and cytosine as the only cytosines. In other embodiments, the polynucleotides of the invention contain a cytidine of Table 3 and cytidine as the only cytidines.

TABLE 3

Exemplary cytosine containing nucleosides
Nucleoside Name

α-thio-cytidine
pseudoisocytidine
pyrrolo-cytidine
5-methyl-cytidine
N4-acetyl-cytidine
5-Bromo-cytidine
5-Trifluoromethyl-cytidine
5-Hydroxymethyl-cytidine
5-Iodo-cytidine
5-Ethyl-cytidine
5-Methoxy-cytidine
5-Ethynyl-cytidine
5-Fluoro-cytidine
5-Phenyl-cytidine
N4-Bz-cytidine
N4-Methyl-cytidine
5-Pseudo-iso-cytidine
5-Formyl-cytidine
5-Aminoallyl-cytidine
2'-O-methylcytidine
2'-O-Methyl-5-(1-propynyl)cytidine
5-(1-Propynyl)ara-cytidine
5-Ethynylara-cytidine
5-Ethynylcytidine
5-Cyanocytidine
5-(2-Chloro-phenyl)-2-thiocytidine

TABLE 3-continued

Exemplary cytosine containing nucleosides
Nucleoside Name 5-(4-Amino-phenyl)-2-thiocytidine
N4,2'-O-Dimethylcytidine
3'-Ethynylcytidine
4'-Carbocyclic cytidine
4'-Ethynylcytidine
4'-Azidocytidine
2'-Deoxy-2',2'-difluorocytidine
2'-Deoxy-2'-b-fluorocytidine
2'-Deoxy-2'-b-chlorocytidine
2'-Deoxy-2'-b-bromocytidine
2'-Deoxy-2'-b-iodocytidine
5'-Homo-cytidine
2'-Deoxy-2'-a-mercaptocytidine
2'-Deoxy-2'-a-thiomethoxycytidine
2'-Deoxy-2'-a-azidocytidine
2'-Deoxy-2'-a-aminocytidine
2'-Deoxy-2'-b-mercaptocytidine
2'-Deoxy-2'-b-thiomethoxycytidine
2'-Deoxy-2'-b-azidocytidine
2'-Deoxy-2'-b-aminocytidine
2'-b-Trifluoromethylcytidine
2'-a-Trifluoromethylcytidine
2'-b-Ethynylcytidine
2'-a-Ethynylcytidine
(E)-5-(2-Bromo-vinyl)cytidine
2'-Azido-2'-deoxy-cytidine
2'-Amino-2'-deoxy-cytidine
5-aminoallyl-cytidine
2,2'-anhydro-cytidine
N4-amino-cytidine
2'-O-Methyl-N4-acetyl-cytidine
2'-fluoro-N4-acetyl-cytidine
2'-fluor-N4-Bz-cytidine
2'-O-methyl-N4-Bz-cytidine
N4,2'-O-Dimethylcytidine
5-Formyl-2'-O-methylcytidine In some embodiments, the present disclosure provides methods of synthesizing a polynucleotide (e.g., the first region, first flanking region, or second flanking region) including n number of linked nucleosides having Formula (Ia-1):

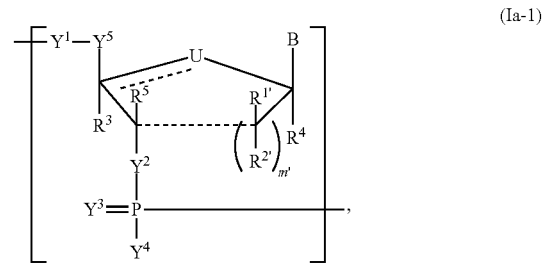

(Ia-1)

comprising:
a) reacting a nucleotide of Formula V-1):

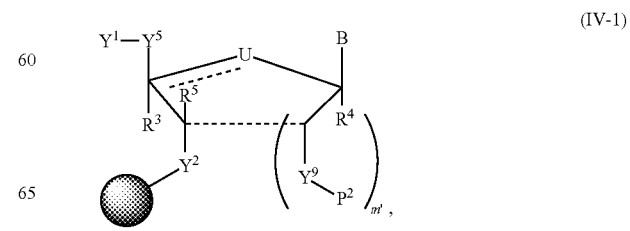

(IV-1)

with a phosphoramidite compound of Formula (V-1):

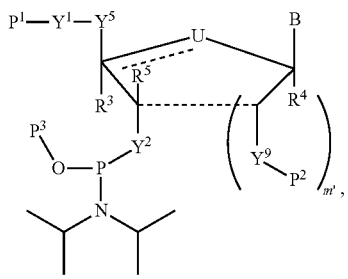
(V-1)

wherein $Y^9$ is H, hydroxyl, phosphoryl, pyrophosphate, sulfate, amino, thiol, optionally substituted amino acid, or a peptide (e.g., including from 2 to 12 amino acids); and each $P^1$, $P^2$, and $P^3$ is, independently, a suitable protecting group; and

denotes a solid support;
to provide a polynucleotide of Formula (VI-1):

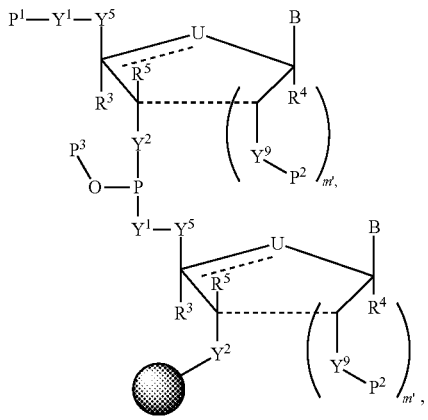
(VI-1)

and
b) oxidizing or sulfurizing the polynucleotide of Formula (V) to yield a polynucleotide of Formula (VII-1):

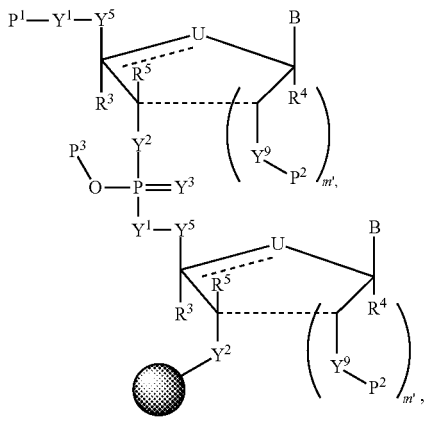
(VII-1)

and
c) removing the protecting groups to yield the polynucleotide of Formula (Ia).

In some embodiments, steps a) and b) are repeated from 1 to about 10,000 times. In some embodiments, the methods further comprise a nucleotide selected from the group consisting of adenosine, cytosine, guanosine, and uracil. In some embodiments, the nucleobase may be a pyrimidine or derivative thereof. In some embodiments, the polynucleotide is translatable.

Other components of polynucleotides are optional, and are beneficial in some embodiments. For example, a 5' untranslated region (UTR) and/or a 3'UTR are provided, wherein either or both may independently contain one or more different nucleotide alterations. In such embodiments, nucleotide alterations may also be present in the translatable region. Also provided are polynucleotides containing a Kozak sequence.

Combinations of Nucleotides

Further examples of alternative nucleotides and alternative nucleotide combinations are provided below in Table 4. These combinations of alternative nucleotides can be used to form the polynucleotides of the invention. Unless otherwise noted, the alternative nucleotides may be completely substituted for the natural nucleotides of the polynucleotides of the invention. As a non-limiting example, the natural nucleotide uridine may be substituted with an alternative nucleoside described herein. In another non-limiting example, the natural nucleotide uridine may be partially substituted (e.g., about 0.1%, 1%, 5%, 10%, 15%, 20%, 25%, 30%, 35%, 40%, 45%, 50%, 55%, 60%, 65%, 70%, 75%, 80%, 85%, 90%, 95% or 99.9%) with at least one of the alternative nucleoside disclosed herein.

TABLE 4

Examples of alternative nucleotides and alternative nucleotide combinations.

| Alternative Nucleotide | Alternative Nucleotide Combination |
|---|---|
| α-thio-cytidine | α-thio-cytidine/5-iodo-uridine |
| | α-thio-cytidine/N1-methyl-pseudo-uridine |
| | α-thio-cytidine/α-thio-uridine |
| | α-thio-cytidine/5-methyl-uridine |
| | α-thio-cytidine/pseudo-uridine |
| | about 50% of the cytosines are α-thio-cytidine |
| pseudoisocytidine | pseudoisocytidine/5-iodo-uridine |
| | pseudoisocytidine/N1-methyl-pseudouridine |
| | pseudoisocytidine/α-thio-uridine |
| | pseudoisocytidine/5-methyl-uridine |
| | pseudoisocytidine/pseudouridine |

TABLE 4-continued

Examples of alternative nucleotides and alternative nucleotide combinations.

| Alternative Nucleotide | Alternative Nucleotide Combination |
|---|---|
| | about 25% of cytosines are pseudoisocytidine pseudoisocytidine/about 50% of uridines are N1-methyl-pseudouridine and about 50% of uridines are pseudouridine pseudoisocytidine/about 25% of uridines are N1-methyl-pseudouridine and about 25% of uridines are pseudouridine (e.g., 25% N1-methyl-pseudouridine/75% pseudouridine) |
| pyrrolo-cytidine | pyrrolo-cytidine/5-iodo-uridine pyrrolo-cytidine/N1-methyl-pseudouridine pyrrolo-cytidine/α-thio-uridine pyrrolo-cytidine/5-methyl-uridine pyrrolo-cytidine/pseudouridine about 50% of the cytosines are pyrrolo-cytidine |
| 5-methyl-cytidine | 5-methyl-cytidine/5-iodo-uridine 5-methyl-cytidine/N1-methyl-pseudouridine 5-methyl-cytidine/α-thio-uridine 5-methyl-cytidine/5-methyl-uridine 5-methyl-cytidine/pseudouridine about 25% of cytosines are 5-methyl-cytidine about 50% of cytosines are 5-methyl-cytidine 5-methyl-cytidine/5-methoxy-uridine 5-methyl-cytidine/5-bromo-uridine 5-methyl-cytidine/2-thio-uridine 5-methyl-cytidine/about 50% of uridines are 2-thio-uridine about 50% of uridines are 5-methyl-cytidine/about 50% of uridines are 2-thio-uridine |
| N4-acetyl-cytidine | N4-acetyl-cytidine/5-iodo-uridine N4-acetyl-cytidine/N1-methyl-pseudouridine N4-acetyl-cytidine/α-thio-uridine N4-acetyl-cytidine/5-methyl-uridine N4-acetyl-cytidine/pseudouridine about 50% of cytosines are N4-acetyl-cytidine about 25% of cytosines are N4-acetyl-cytidine N4-acetyl-cytidine/5-methoxy-uridine N4-acetyl-cytidine/5-bromo-uridine N4-acetyl-cytidine/2-thio-uridine about 50% of cytosines are N4-acetyl-cytidine/about 50% of uridines are 2-thio-uridine |
| 5-methoxy-uridine | 5-methoxy-uridine/cytidine 5-methoxy-uridine/5-methyl-cytidine 5-methoxy-uridine/5-trifluoromethyl-cytidine 5-methoxy-uridine/5-hydroxymethyl-cytidine 5-methoxy-uridine/5-bromo-cytidine 5-methoxy-uridine/α-thio-cytidine 5-methoxy-uridine/N4-acetyl-cytidine 5-methoxy-uridine/pseudoisocytidine about 100% of uridines are 5-methoxy-uridine about 75% of uridines are 5-methoxy-uridine about 50% of uridines are 5-methoxy-uridine about 25% of uridines are 5-methoxy-uridine |

TABLE 5

Examples of alternative nucleotides and alternative nucleotide combinations.

| Uracil | Cytosine | Adenine | Guanine |
|---|---|---|---|
| 5-methoxy-UTP | CTP | ATP | GTP |
| 5-Methoxy-UTP | N4Ac-CTP | ATP | GTP |
| 5-Methoxy-UTP | 5-Methyl-CTP | ATP | GTP |
| 5-Methoxy-UTP | 5-Trifluoromethyl-CTP | ATP | GTP |
| 5-Methoxy-UTP | 5-Hydroxymethyl-CTP | ATP | GTP |
| 5-Methoxy-UTP | 5-Bromo-CTP | ATP | GTP |
| 5-Methoxy-UTP | N4Ac-CTP | ATP | GTP |
| 5-Methoxy-UTP | CTP | ATP | GTP |
| 5-Methoxy-UTP | 5-Methyl-CTP | ATP | GTP |
| 5-Methoxy-UTP | 5-Trifluoromethyl-CTP | ATP | GTP |
| 5-Methoxy-UTP | 5-Hydroxymethyl-CTP | ATP | GTP |
| 5-Methoxy-UTP | 5-Bromo-CTP | ATP | GTP |
| 5-Methoxy-UTP | N4-Ac-CTP | ATP | GTP |
| 5-Methoxy-UTP | 5-Iodo-CTP | ATP | GTP |
| 5-Methoxy-UTP | 5-Bromo-CTP | ATP | GTP |
| 5-Methoxy-UTP | CTP | ATP | GTP |
| 5-Methoxy-UTP | 5-Methyl-CTP | ATP | GTP |

TABLE 5-continued

Examples of alternative nucleotides and alternative nucleotide combinations.

| Uracil | Cytosine | Adenine | Guanine |
|---|---|---|---|
| 75% 5-Methoxy-UTP + 25% UTP | 5-Methyl-CTP | ATP | GTP |
| 50% 5-Methoxy-UTP + 50% UTP | 5-Methyl-CTP | ATP | GTP |
| 25% 5-Methoxy-UTP + 75% UTP | 5-Methyl-CTP | ATP | GTP |
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 75% 5-Methoxy-UTP + 25% UTP | 50% 5-Methyl-CTP + 50% CTP | ATP | GTP |
| 75% 5-Methoxy-UTP + 25% UTP | 25% 5-Methyl-CTP + 75% CTP | ATP | GTP |
| 50% 5-Methoxy-UTP + 50% UTP | 75% 5-Methyl-CTP + 25% CTP | ATP | GTP |
| 50% 5-Methoxy-UTP + 50% UTP | 50% 5-Methyl-CTP + 50% CTP | ATP | GTP |
| 50% 5-Methoxy-UTP + 50% UTP | 25% 5-Methyl-CTP + 75% CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | CTP | ATP | GTP |
| 50% 5-Methoxy-UTP + 50% UTP | CTP | ATP | GTP |
| 25% 5-Methoxy-UTP + 75% UTP | CTP | ATP | GTP |
| 5-Methoxy-UTP | CTP | ATP | GTP |
| 5-Methoxy-UTP | CTP | ATP | GTP |
| 5-Methoxy-UTP | CTP | ATP | GTP |
| 5-Methoxy-UTP | 5-Methyl-CTP | ATP | GTP |
| 5-Methoxy-UTP | 5-Methyl-CTP | ATP | GTP |
| 5-Methoxy-UTP | 5-Methyl-CTP | ATP | GTP |
| 5-Methoxy-UTP | CTP | Alpha-thio-ATP | GTP |
| 5-Methoxy-UTP | 5-Methyl-CTP | Alpha-thio-ATP | GTP |
| 5-Methoxy-UTP | CTP | ATP | Alpha-thio-GTP |
| 5-Methoxy-UTP | 5-Methyl-CTP | ATP | Alpha-thio-GTP |
| 5-Methoxy-UTP | CTP | N6-Me-ATP | GTP |
| 5-Methoxy-UTP | 5-Methyl-CTP | N6-Me-ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% UTP | 5-Methyl-CTP | ATP | GTP |
| 50% 5-Methoxy-UTP + 50% UTP | 5-Methyl-CTP | ATP | GTP |
| 25% 5-Methoxy-UTP + 75% UTP | 5-Methyl-CTP | ATP | GTP |
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 75% 5-Methoxy-UTP + 25% UTP | 50% 5-Methyl-CTP + 50% CTP | ATP | GTP |
| 75% 5-Methoxy-UTP + 25% UTP | 25% 5-Methyl-CTP + 75% CTP | ATP | GTP |
| 50% 5-Methoxy-UTP + 50% UTP | 75% 5-Methyl-CTP + 25% CTP | ATP | GTP |
| 50% 5-Methoxy-UTP + 50% UTP | 50% 5-Methyl-CTP + 50% CTP | ATP | GTP |
| 50% 5-Methoxy-UTP + 50% UTP | 25% 5-Methyl-CTP + 75% CTP | ATP | GTP |
| 25% 5-Methoxy-UTP + 75% UTP | 75% 5-Methyl-CTP + 25% CTP | ATP | GTP |

TABLE 5-continued

Examples of alternative nucleotides and alternative nucleotide combinations.

| Uracil | Cytosine | Adenine | Guanine |
|---|---|---|---|
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | CTP | ATP | GTP |
| 50% 5-Methoxy-UTP + 50% UTP | CTP | ATP | GTP |
| 25% 5-Methoxy-UTP + 75% UTP | CTP | ATP | GTP |
| 5-Methoxy-UTP | 5-Ethyl-CTP | ATP | GTP |
| 5-Methoxy-UTP | 5-Methoxy-CTP | ATP | GTP |
| 5-Methoxy-UTP | 5-Ethynyl-CTP | ATP | GTP |
| 5-Methoxy-UTP | CTP | ATP | GTP |
| 5-Methoxy-UTP | 5-Methyl-CTP | ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% 1-Methyl-pseudo-UTP | 5-Methyl-CTP | ATP | GTP |
| 50% 5-Methoxy-UTP + 50% 1-Methyl-pseudo-UTP | 5-Methyl-CTP | ATP | GTP |
| 25% 5-Methoxy-UTP + 75% 1-Methyl-pseudo-UTP | 5-Methyl-CTP | ATP | GTP |
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% 1-Methyl-pseudo-UTP | 75% 5-Methyl-CTP + 25% CTP | ATP | GTP |
| 75% 5-Methoxy-UTP + 25% 1-Methyl-pseudo-UTP | 50% 5-Methyl-CTP + 50% CTP | ATP | GTP |
| 75% 5-Methoxy-UTP + 25% 1-Methyl-pseudo-UTP | 25% 5-Methyl-CTP + 75% CTP | ATP | GTP |
| 50% 5-Methoxy-UTP + 50% 1-Methyl-pseudo-UTP | 75% 5-Methyl-CTP + 25% CTP | ATP | GTP |
| 50% 5-Methoxy-UTP + 50% 1-Methyl-pseudo-UTP | 50% 5-Methyl-CTP + 50% CTP | ATP | GTP |
| 50% 5-Methoxy-UTP + 50% 1-Methyl-pseudo-UTP | 25% 5-Methyl-CTP + 75% CTP | ATP | GTP |
| 25% 5-Methoxy-UTP + 75% 1-Methyl-pseudo-UTP | 75% 5-Methyl-CTP + 25% CTP | ATP | GTP |
| 25% 5-Methoxy-UTP + 75% 1-Methyl-pseudo-UTP | 50% 5-Methyl-CTP + 50% CTP | ATP | GTP |
| 25% 5-Methoxy-UTP + 75% 1-Methyl-pseudo-UTP | 25% 5-Methyl-CTP + 75% CTP | ATP | GTP |
| 75% 5-Methoxy-UTP + 25% 1-Methyl-pseudo-UTP | CTP | ATP | GTP |
| 50% 5-Methoxy-UTP + 50% 1-Methyl-pseudo-UTP | CTP | ATP | GTP |
| 25% 5-Methoxy-UTP + 75% 1-Methyl-pseudo-UTP | CTP | ATP | GTP |
| 5-methoxy-UTP | CTP | ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% UTP | 5-Methyl-CTP | ATP | GTP |
| 50% 5-Methoxy-UTP + 50% UTP | 5-Methyl-CTP | ATP | GTP |

TABLE 5-continued

Examples of alternative nucleotides and alternative nucleotide combinations.

| Uracil | Cytosine | Adenine | Guanine |
|---|---|---|---|
| 25% 5-Methoxy-UTP + 75% UTP | 5-Methyl-CTP | ATP | GTP |
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 75% 5-Methoxy-UTP + 25% UTP | 50% 5-Methyl-CTP + 50% CTP | ATP | GTP |
| 75% 5-Methoxy-UTP + 25% UTP | 25% 5-Methyl-CTP + 75% CTP | ATP | GTP |
| 50% 5-Methoxy-UTP + 50% UTP | 75% 5-Methyl-CTP + 25% CTP | ATP | GTP |
| 50% 5-Methoxy-UTP + 50% UTP | 50% 5-Methyl-CTP + 50% CTP | ATP | GTP |
| 50% 5-Methoxy-UTP + 50% UTP | 25% 5-Methyl-CTP + 75% CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | CTP | ATP | GTP |
| 50% 5-Methoxy-UTP + 50% UTP | CTP | ATP | GTP |
| 25% 5-Methoxy-UTP + 75% UTP | CTP | ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% UTP | 5-Methyl-CTP | ATP | GTP |
| 50% 5-Methoxy-UTP + 50% UTP | 5-Methyl-CTP | ATP | GTP |
| 25% 5-Methoxy-UTP + 75% UTP | 5-Methyl-CTP | ATP | GTP |
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 75% 5-Methoxy-UTP + 25% UTP | 50% 5-Methyl-CTP + 50% CTP | ATP | GTP |
| 75% 5-Methoxy-UTP + 25% UTP | 25% 5-Methyl-CTP + 75% CTP | ATP | GTP |
| 50% 5-Methoxy-UTP + 50% UTP | 75% 5-Methyl-CTP + 25% CTP | ATP | GTP |
| 50% 5-Methoxy-UTP + 50% UTP | 50% 5-Methyl-CTP + 50% CTP | ATP | GTP |
| 50% 5-Methoxy-UTP + 50% UTP | 25% 5-Methyl-CTP + 75% CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | CTP | ATP | GTP |
| 50% 5-Methoxy-UTP + 50% UTP | CTP | ATP | GTP |
| 25% 5-Methoxy-UTP + 75% UTP | CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |

TABLE 5-continued

Examples of alternative nucleotides and alternative nucleotide combinations.

| Uracil | Cytosine | Adenine | Guanine |
|---|---|---|---|
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | 5-Fluoro-CTP | ATP | GTP |
| 5-Methoxy-UTP | 5-Phenyl-CTP | ATP | GTP |
| 5-Methoxy-UTP | N4-Bz-CTP | ATP | GTP |
| 5-Methoxy-UTP | CTP | N6-Isopentenyl-ATP | GTP |
| 5-Methoxy-UTP | N4-Ac-CTP | ATP | GTP |
| 25% 5-Methoxy-UTP + 75% UTP | 25% N4-Ac-CTP + 75% CTP | ATP | GTP |
| 25% 5-Methoxy-UTP + 75% UTP | 75% N4-Ac-CTP + 25% CTP | ATP | GTP |
| 75% 5-Methoxy-UTP + 25% UTP | 25% N4-Ac-CTP + 75% CTP | ATP | GTP |
| 75% 5-Methoxy-UTP + 25% UTP | 75% N4-Ac-CTP + 25% CTP | ATP | GTP |
| 5-Methoxy-UTP | 5-Hydroxymethyl-CTP | ATP | GTP |
| 25% 5-Methoxy-UTP + 75% UTP | 25% 5-Hydroxymethyl-CTP + 75% CTP | ATP | GTP |

TABLE 5-continued

Examples of alternative nucleotides and alternative nucleotide combinations.

| Uracil | Cytosine | Adenine | Guanine |
|---|---|---|---|
| 25% 5-Methoxy-UTP + 75% UTP | 75% 5-Hydroxymethyl-CTP + 25% CTP | ATP | GTP |
| 75% 5-Methoxy-UTP + 25% UTP | 25% 5-Hydroxymethyl-CTP + 75% CTP | ATP | GTP |
| 75% 5-Methoxy-UTP + 25% UTP | 75% 5-Hydroxymethyl-CTP + 25% CTP | ATP | GTP |
| 5-Methoxy-UTP | N4-Methyl CTP | ATP | GTP |
| 25% 5-Methoxy-UTP + 75% UTP | 25% N4-Methyl CTP + 75% CTP | ATP | GTP |
| 25% 5-Methoxy-UTP + 75% UTP | 75% N4-Methyl CTP + 25% CTP | ATP | GTP |
| 75% 5-Methoxy-UTP + 25% UTP | 25% N4-Methyl CTP + 75% CTP | ATP | GTP |
| 75% 5-Methoxy-UTP + 25% UTP | 75% N4-Methyl CTP + 25% CTP | ATP | GTP |
| 5-Methoxy-UTP | 5-Trifluoromethyl-CTP | ATP | GTP |
| 25% 5-Methoxy-UTP + 75% UTP | 25% 5-Trifluoromethyl-CTP + 75% CTP | ATP | GTP |
| 25% 5-Methoxy-UTP + 75% UTP | 75% 5-Trifluoromethyl-CTP + 25% CTP | ATP | GTP |
| 75% 5-Methoxy-UTP + 25% UTP | 25% 5-Trifluoromethyl-CTP + 75% CTP | ATP | GTP |
| 75% 5-Methoxy-UTP + 25% UTP | 75% 5-Trifluoromethyl-CTP + 25% CTP | ATP | GTP |
| 5-Methoxy-UTP | 5-Bromo-CTP | ATP | GTP |
| 25% 5-Methoxy-UTP + 75% UTP | 25% 5-Bromo-CTP + 75% CTP | ATP | GTP |
| 25% 5-Methoxy-UTP + 75% UTP | 75% 5-Bromo-CTP + 25% CTP | ATP | GTP |
| 75% 5-Methoxy-UTP + 25% UTP | 25% 5-Bromo-CTP + 75% CTP | ATP | GTP |
| 75% 5-Methoxy-UTP + 25% UTP | 75% 5-Bromo-CTP + 25% CTP | ATP | GTP |
| 5-Methoxy-UTP | 5-Iodo-CTP | ATP | GTP |
| 25% 5-Methoxy-UTP + 75% UTP | 25% 5-Iodo-CTP + 75% CTP | ATP | GTP |
| 25% 5-Methoxy-UTP + 75% UTP | 75% 5-Iodo-CTP + 25% CTP | ATP | GTP |
| 75% 5-Methoxy-UTP + 25% UTP | 25% 5-Iodo-CTP + 75% CTP | ATP | GTP |
| 75% 5-Methoxy-UTP + 25% UTP | 75% 5-Iodo-CTP + 25% CTP | ATP | GTP |
| 5-Methoxy-UTP | 5-Ethyl-CTP | ATP | GTP |
| 25% 5-Methoxy-UTP + 75% UTP | 25% 5-Ethyl-CTP + 75% CTP | ATP | GTP |
| 25% 5-Methoxy-UTP + 75% UTP | 75% 5-Ethyl-CTP + 25% CTP | ATP | GTP |
| 75% 5-Methoxy-UTP + 25% UTP | 25% 5-Ethyl-CTP + 75% CTP | ATP | GTP |
| 75% 5-Methoxy-UTP + 25% UTP | 75% 5-Ethyl-CTP + 25% CTP | ATP | GTP |
| 5-Methoxy-UTP | 5-Methoxy-CTP | ATP | GTP |
| 25% 5-Methoxy-UTP + 75% UTP | 25% 5-Methoxy-CTP + 75% CTP | ATP | GTP |
| 25% 5-Methoxy-UTP + 75% UTP | 75% 5-Methoxy-CTP + 25% CTP | ATP | GTP |
| 75% 5-Methoxy-UTP + 25% UTP | 25% 5-Methoxy-CTP + 75% CTP | ATP | GTP |
| 75% 5-Methoxy-UTP + 25% UTP | 75% 5-Methoxy-CTP + 25% CTP | ATP | GTP |
| 5-Methoxy-UTP | 5-Ethynyl-CTP | ATP | GTP |
| 25% 5-Methoxy-UTP + 75% UTP | 25% 5-Ethynyl-CTP + 75% CTP | ATP | GTP |
| 25% 5-Methoxy-UTP + 75% UTP | 75% 5-Ethynyl-CTP + 25% CTP | ATP | GTP |
| 75% 5-Methoxy-UTP + 25% UTP | 25% 5-Ethynyl-CTP + 75% CTP | ATP | GTP |
| 75% 5-Methoxy-UTP + 25% UTP | 75% 5-Ethynyl-CTP + 25% CTP | ATP | GTP |
| 5-Methoxy-UTP | 5-Pseudo-iso-CTP | ATP | GTP |
| 25% 5-Methoxy-UTP + 75% UTP | 25% 5-Pseudo-iso-CTP + 75% CTP | ATP | GTP |
| 25% 5-Methoxy-UTP + 75% UTP | 75% 5-Pseudo-iso-CTP + 25% CTP | ATP | GTP |

TABLE 5-continued

Examples of alternative nucleotides and alternative nucleotide combinations.

| Uracil | Cytosine | Adenine | Guanine |
|---|---|---|---|
| 75% 5-Methoxy-UTP + 25% UTP | 25% 5-Pseudo-iso-CTP + 75% CTP | ATP | GTP |
| 75% 5-Methoxy-UTP + 25% UTP | 75% 5-Pseudo-iso-CTP + 25% CTP | ATP | GTP |
| 5-Methoxy-UTP | 5-Formyl-CTP | ATP | GTP |
| 25% 5-Methoxy-UTP + 75% UTP | 25% 5-Formyl-CTP + 75% CTP | ATP | GTP |
| 25% 5-Methoxy-UTP + 75% UTP | 75% 5-Formyl-CTP + 25% CTP | ATP | GTP |
| 75% 5-Methoxy-UTP + 25% UTP | 25% 5-Formyl-CTP + 75% CTP | ATP | GTP |
| 75% 5-Methoxy-UTP + 25% UTP | 75% 5-Formyl-CTP + 25% CTP | ATP | GTP |
| 5-Methoxy-UTP | 5-Aminoallyl-CTP | ATP | GTP |
| 25% 5-Methoxy-UTP + 75% UTP | 25% 5-Aminoallyl-CTP + 75% CTP | ATP | GTP |
| 25% 5-Methoxy-UTP + 75% UTP | 75% 5-Aminoallyl-CTP + 25% CTP | ATP | GTP |
| 75% 5-Methoxy-UTP + 25% UTP | 25% 5-Aminoallyl-CTP + 75% CTP | ATP | GTP |
| 75% 5-Methoxy-UTP + 25% UTP | 75% 5-Aminoallyl-CTP + 25% CTP | ATP | GTP |

Certain alternative nucleotides and nucleotide combinations have been explored by the current inventors. These findings are described in U.S. Provisional Application No. 61/404,413, U.S. patent application Ser. No. 13/251,840, U.S. Patent Publication No US 2013/0102034, International Patent Publication No WO2012045075, U.S. Patent Publication No US20120237975, and International Patent Publication No WO2012045082, each of which is incorporated by reference in its entirety.

Further examples of alternative nucleotide combinations are provided below in Table 6. These combinations of alternative nucleotides can be used to form the polynucleotides of the invention.

TABLE 6

Examples of alternative nucleotide combinations.

| Alternative Nucleotide | Alternative Nucleotide Combination |
|---|---|
| alternative cytidine having one or more nucleobases of Formula (b10) | alternative cytidine with (b10)/pseudouridine |
| | alternative cytidine with (b10)/N1-methyl-pseudouridine |
| | alternative cytidine with (b10)/5-methoxy-uridine |
| | alternative cytidine with (b10)/5-methyl-uridine |
| | alternative cytidine with (b10)/5-bromo-uridine |
| | alternative cytidine with (b10)/2-thio-uridine |
| | about 50% of cytidine substituted with alternative cytidine (b10)/about 50% of uridines are 2-thio-uridine |
| alternative cytidine having one or more nucleobases of Formula (b32) | alternative cytidine with (b32)/pseudouridine |
| | alternative cytidine with (b32)/N1-methyl-pseudouridine |
| | alternative cytidine with (b32)/5-methoxy-uridine |
| | alternative cytidine with (b32)/5-methyl-uridine |
| | alternative cytidine with (b32)/5-bromo-uridine |
| | alternative cytidine with (b32)/2-thio-uridine |
| | about 50% of cytidine substituted with alternative cytidine (b32)/about 50% of uridines are 2-thio-uridine |
| alternative uridine having one or more nucleobases of Formula (b1) | alternative uridine with (b1)/N4-acetyl-cytidine |
| | alternative uridine with (b1)/5-methyl-cytidine |
| alternative uridine having one or more nucleobases of Formula (b8) | alternative uridine with (b8)/N4-acetyl-cytidine |
| | alternative uridine with (b8)/5-methyl-cytidine |
| alternative uridine having one or more nucleobases of Formula (b28) | alternative uridine with (b28)/N4-acetyl-cytidine |
| | alternative uridine with (b28)/5-methyl-cytidine |
| alternative uridine having one or more nucleobases of Formula (b29) | alternative uridine with (b29)/N4-acetyl-cytidine |
| | alternative uridine with (b29)/5-methyl-cytidine |
| alternative uridine having one or more nucleobases of Formula (b30) | alternative uridine with (b30)/N4-acetyl-cytidine |
| | alternative uridine with (b30)/5-methyl-cytidine |

In some embodiments, at least 25% of the cytosines are replaced by a compound of Formula (b10)-(b14), (b24), (b25), or (b32)-(b35) (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of, e.g., a compound of Formula (b10) or (b32)).

In some embodiments, at least 25% of the uracils are replaced by a compound of Formula (b1)-(b9), (b21)-(b23), or (b28)-(b31) (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of, e.g., a compound of Formula (b1), (b8), (b28), (b29), or (b30)).

In some embodiments, at least 25% of the cytosines are replaced by a compound of Formula (b10)-(b14), (b24), (b25), or (b32)-(b35) (e.g. Formula (b10) or (b32)), and at least 25% of the uracils are replaced by a compound of Formula (b1)-(b9), (b21)-(b23), or (b28)-(b31) (e.g. Formula (b1), (b8), (b28), (b29), or (b30)) (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

Alterations including Linker and a Payload

The nucleobase of the nucleotide can be covalently linked at any chemically appropriate position to a payload, e.g., detectable agent or therapeutic agent. For example, the nucleobase can be deaza-adenine or deaza-guanine and the linker can be attached at the C-7 or C-8 positions of the deaza-adenine or deaza-guanine. In other embodiments, the nucleobase can be cytosine or uracil and the linker can be attached to the N-3 or C-5 positions of cytosine or uracil. Scheme 1 below depicts an exemplary alternative nucleotide wherein the nucleobase, adenine, is attached to a linker at the C-7 carbon of 7-deaza adenine. In addition, Scheme 1 depicts the alternative nucleotide with the linker and payload, e.g., a detectable agent, incorporated onto the 3' end of the mRNA. Disulfide cleavage and 1,2-addition of the thiol group onto the propargyl ester releases the detectable agent. The remaining structure (depicted, for example, as pApC5Parg in Scheme 1) is the inhibitor. The rationale for the structure of the alternative nucleotides is that the tethered inhibitor sterically interferes with the ability of the polymerase to incorporate a second base. Thus, it is critical that the tether be long enough to affect this function and that the inhibitor be in a stereochemical orientation that inhibits or prohibits second and follow on nucleotides into the growing polynucleotide strand.

Scheme 1

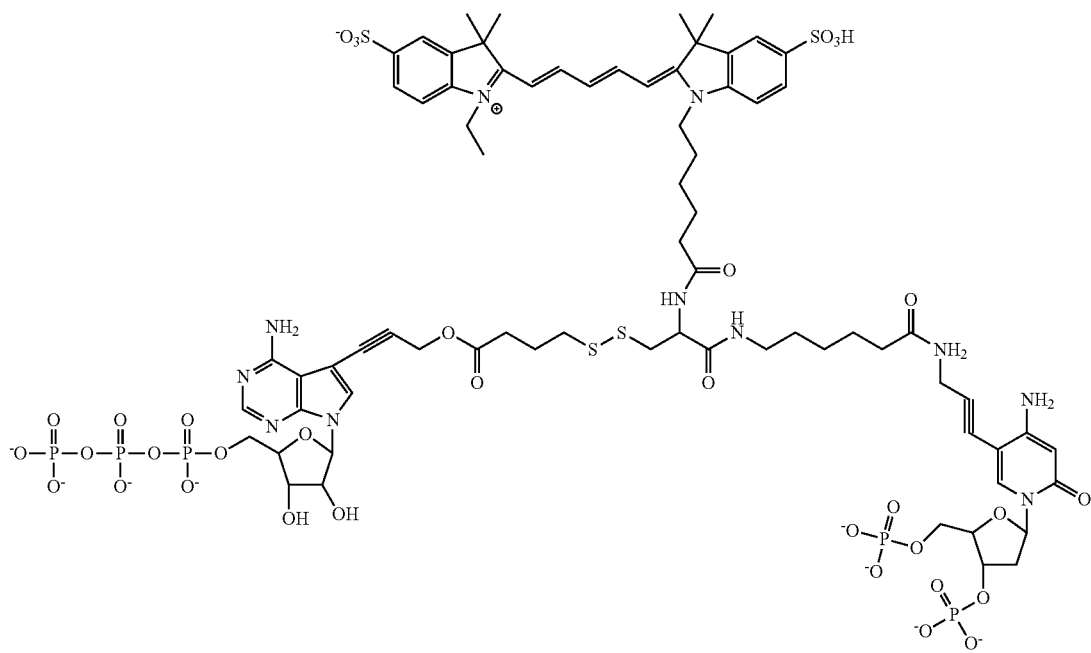

A Capless pCpC5 Parg incorporation

-continued

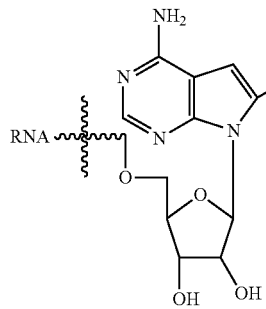
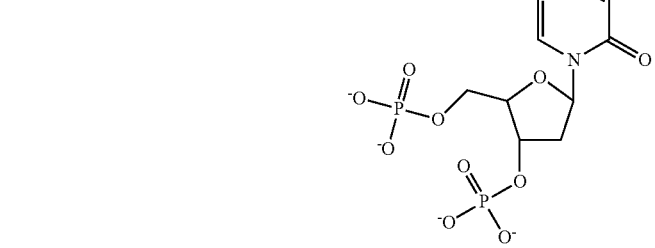
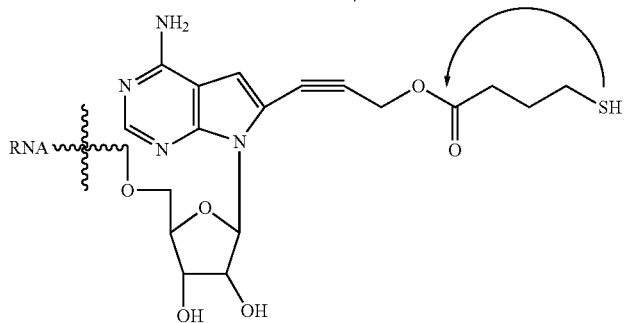
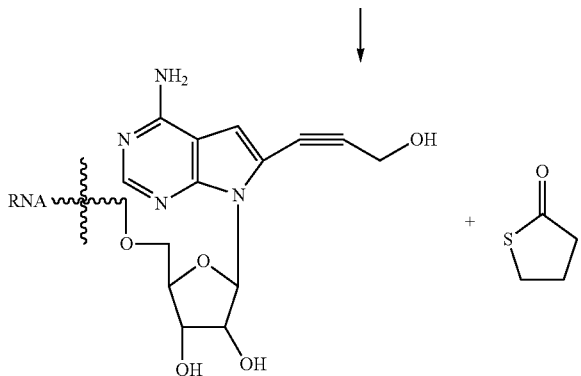

Linker

The term "linker" as used herein refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to an alternative nucleoside or nucleotide on the nucleobase or sugar moiety at a first end, and to a payload, e.g., detectable or therapeutic agent, at a second end. The linker is of sufficient length as to not interfere with incorporation into a nucleic acid sequence.

Examples of chemical groups that can be incorporated into the linker include, but are not limited to, an alkyl, alkene, an alkyne, an amido, an ether, a thioether, an or an ester group. The linker chain can also comprise part of a saturated, unsaturated or aromatic ring, including polycyclic and heteroaromatic rings wherein the heteroaromatic ring is an aryl group containing from one to four heteroatoms, N, O or S. Specific examples of linkers include, but are not limited to, unsaturated alkanes, polyethylene glycols, and dextran polymers.

For example, the linker can include ethylene or propylene glycol monomeric units, e.g., diethylene glycol, dipropylene glycol, triethylene glycol, tripropylene glycol, tetraethylene glycol, or tetraethylene glycol. In some embodiments, the linker can include a divalent alkyl, alkenyl, and/or alkynyl moiety. The linker can include an ester, amide, or ether moiety.

Other examples include cleavable moieties within the linker, such as, for example, a disulfide bond (—S—S—) or an azo bond (—N=N—), which can be cleaved using a reducing agent or photolysis. A cleavable bond incorporated into the linker and attached to an alternative nucleotide, when cleaved, results in, for example, a short "scar" or chemical alteration on the nucleotide. For example, after cleaving, the resulting scar on a nucleotide base, which formed part of the alternative nucleotide, and is incorporated into a polynucleotide strand, is unreactive and does not need to be chemically neutralized. This increases the ease with which a subsequent nucleotide can be incorporated during sequencing of a nucleic acid polymer template. For example, conditions include the use of tris(2-carboxyethyl)phosphine (TCEP), dithiothreitol (DTT) and/or other reducing agents for cleavage of a disulfide bond. A selectively severable bond that includes an amido bond can be cleaved for example by the use of TCEP or other reducing agents, and/or photolysis. A selectively severable bond that includes an ester bond can be cleaved for example by acidic or basic hydrolysis.

Payload

The methods and compositions described herein are useful for delivering a payload to a biological target. The payload can be used, e.g., for labeling (e.g., a detectable agent such as a fluorophore), or for therapeutic purposes (e.g., a cytotoxin or other therapeutic agent).

Payload: Therapeutic Agents

In some embodiments the payload is a therapeutic agent such as a cytotoxin, radioactive ion, chemotherapeutic, or other therapeutic agent. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846, 545) and analogs or homologs thereof. Radioactive ions include, but are not limited to iodine (e.g., iodine 125 or iodine 131), strontium 89, phosphorous, palladium, cesium, iridium, phosphate, cobalt, yttrium 90, Samarium 153 and praseodymium. Other therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

Payload: Detectable Agents

Examples of detectable substances include various organic small molecules, inorganic compounds, nanoparticles, enzymes or enzyme substrates, fluorescent materials, luminescent materials, bioluminescent materials, chemiluminescent materials, radioactive materials, and contrast agents. Such optically-detectable labels include for example, without limitation, 4-acetamido-4'-isothiocyanatostilbene-2, 2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl] naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]-naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodarnine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N tetramethyl-6-carboxyrhodamine (TAMRA); tetramethyl rhodamine; tetramethyl rhodamine isothiocyanate (TRITC); riboflavin; rosolic acid; terbium chelate derivatives; Cyanine-3 (Cy3); Cyanine-5 (Cy5); Cyanine-5.5 (Cy5.5), Cyanine-7 (Cy7); IRD 700; IRD 800; Alexa 647; La Jolta Blue; phthalo cyanine; and naphthalo cyanine. In some embodiments, the detectable label is a fluorescent dye, such as Cy5 and Cy3.

Examples luminescent material includes luminol; examples of bioluminescent materials include luciferase, luciferin, and aequorin.

Examples of suitable radioactive material include $^{18}F$, $^{67}Ga$, $^{81m}Kr$, $^{82}Rb$, $^{111}In$, $^{123}I$, $^{133}Xe$, $^{201}Tl$, $^{125}I$, $^{35}S$, $^{14}C$, or $^{3}H$, $^{99m}Tc$ (e.g., as pertechnetate (technetate(VII), $TcO_4$) either directly or indirectly, or other radioisotope detectable by direct counting of radioemission or by scintillation counting.

In addition, contrast agents, e.g., contrast agents for MRI or NMR, for X-ray CT, Raman imaging, optical coherence tomography, absorption imaging, ultrasound imaging, or thermal imaging can be used. Exemplary contrast agents include gold (e.g., gold nanoparticles), gadolinium (e.g., chelated Gd), iron oxides (e.g., superparamagnetic iron oxide (SPIO), monocrystalline iron oxide nanoparticles (MI-ONs), and ultrasmall superparamagnetic iron oxide (US-PIO)), manganese chelates (e.g., Mn-DPDP), barium sulfate, iodinated contrast media (iohexol), microbubbles, or perfluorocarbons can also be used.

In some embodiments, the detectable agent is a non-detectable pre-cursor that becomes detectable upon activation. Examples include fluorogenic tetrazine-fluorophore constructs (e.g., tetrazine-BODIPY FL, tetrazine-Oregon Green 488, or tetrazine-BODIPY TMR-X) or enzyme activatable fluorogenic agents (e.g., PROSENSE (VisEn Medical)).

When the compounds are enzymatically labeled with, for example, horseradish peroxidase, alkaline phosphatase, or luciferase, the enzymatic label is detected by determination of conversion of an appropriate substrate to product.

In vitro assays in which these compositions can be used include enzyme linked immunosorbent assays (ELISAs), immunoprecipitations, immunofluorescence, enzyme immunoassay (EIA), radioimmunoassay (RIA), and Western blot analysis.

Labels other than those described herein are contemplated by the present disclosure, including other optically-detectable labels. Labels can be attached to the alternative nucleotide of the present disclosure at any position using standard chemistries such that the label can be removed from the incorporated base upon cleavage of the cleavable linker.

Payload: Cell Penetrating Payloads

In some embodiments, the alternative nucleotides and alternative nucleic acids can also include a payload that can be a cell penetrating moiety or agent that enhances intracellular delivery of the compositions. For example, the compositions can include a cell-penetrating peptide sequence that facilitates delivery to the intracellular space, e.g., HIV-derived TAT peptide, penetratins, transportans, or hCT derived cell-penetrating peptides, see, e.g., Caron et al., (2001) Mol Ther. 3(3):310-8; Langel, Cell-Penetrating Peptides: Processes and Applications (CRC Press, Boca Raton Fla. 2002); El-Andaloussi et al., (2005) Curr Pharm Des. 11(28):3597-611; and Deshayes et al., (2005) Cell Mol Life Sci. 62(16):1839-49. The compositions can also be formulated to include a cell penetrating agent, e.g., liposomes, which enhance delivery of the compositions to the intracellular space.

Payload: Biological Targets

The alternative nucleotides and alternative nucleic acids described herein can be used to deliver a payload to any biological target for which a specific ligand exists or can be generated. The ligand can bind to the biological target either covalently or non-covalently.

Exemplary biological targets include biopolymers, e.g., antibodies, nucleic acids such as RNA and DNA, proteins, enzymes; exemplary proteins include enzymes, receptors, and ion channels. In some embodiments the target is a tissue- or cell-type specific marker, e.g., a protein that is expressed specifically on a selected tissue or cell type. In some embodiments, the target is a receptor, such as, but not limited to, plasma membrane receptors and nuclear receptors; more specific examples include G-protein-coupled receptors, cell pore proteins, transporter proteins, surface-expressed antibodies, HLA proteins, MHC proteins and growth factor receptors.

Synthesis of Alternative Nucleotides

The alternative nucleosides and nucleotides disclosed herein can be prepared from readily available starting materials using the following general methods and procedures. It is understood that where typical or preferred process conditions (i.e., reaction temperatures, times, mole ratios of reactants, solvents, pressures) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Preparation of alternative nucleosides and nucleotides can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 2d. Ed., Wiley & Sons, 1991, which is incorporated herein by reference in its entirety.

The reactions of the processes described herein can be carried out in suitable solvents, which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of alternative nucleosides and nucleotides can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

Alternative Nucleic Acids

The present disclosure provides nucleic acids (or polynucleotides), including RNAs such as mRNAs that contain one or more alternative nucleosides (termed "alternative nucleic acids") or nucleotides as described herein, which have useful properties including the lack of a substantial induction of the innate immune response of a cell into which the mRNA is introduced. Because these alternative nucleic acids enhance the efficiency of protein production, intracellular retention of nucleic acids, and viability of contacted cells, as well as possess reduced immunogenicity, these nucleic acids having these properties are also termed "enhanced nucleic acids" herein.

The term "nucleic acid," in its broadest sense, includes any compound and/or substance that is or can be incorporated into an oligonucleotide chain. In this context, the term nucleic acid is used synonymously with polynucleotide. Exemplary nucleic acids for use in accordance with the present disclosure include, but are not limited to, one or more of DNA, RNA including messenger mRNA (mRNA), hybrids thereof, RNAi-inducing agents, RNAi agents, siRNAs, shRNAs, miRNAs, antisense RNAs, ribozymes, catalytic DNA, RNAs that induce triple helix formation, aptamers, vectors, described in detail herein.

Provided are alternative nucleic acids containing a translatable region and one, two, or more than two different nucleoside alterations. In some embodiments, the alternative nucleic acid exhibits reduced degradation in a cell into which the nucleic acid is introduced, relative to a corresponding unaltered nucleic acid. Exemplary nucleic acids include ribonucleic acids (RNAs), deoxyribonucleic acids (DNAs), threose nucleic acids (TNAs), glycol nucleic acids (GNAs), or a hybrid thereof. In preferred embodiments, the alternative nucleic acid includes messenger RNAs (mRNAs). As described herein, the nucleic acids of the present disclosure do not substantially induce an innate immune response of a cell into which the mRNA is introduced.

In certain embodiments, it is desirable to intracellularly degrade an alternative nucleic acid introduced into the cell, for example if precise timing of protein production is desired. Thus, the present disclosure provides an alternative nucleic acid containing a degradation domain, which is capable of being acted on in a directed manner within a cell.

Other components of nucleic acid are optional, and are beneficial in some embodiments. For example, a 5' untranslated region (UTR) and/or a 3' UTR are provided, wherein either or both may independently contain one or more different nucleoside alterations. In such embodiments, nucleoside alterations may also be present in the translatable region. Also provided are nucleic acids containing a Kozak sequence.

Additionally, provided are nucleic acids containing one or more intronic nucleotide sequences capable of being excised from the nucleic acid.

Further, provided are nucleic acids containing an internal ribosome entry site (IRES). An IRES may act as the sole ribosome binding site, or may serve as one of multiple ribosome binding sites of an mRNA. An mRNA containing more than one functional ribosome binding site may encode several peptides or polypeptides that are translated independently by the ribosomes ("multicistronic mRNA"). When nucleic acids are provided with an IRES, further optionally provided is a second translatable region. Examples of IRES sequences that can be used according to the present disclosure include without limitation, those from picornaviruses (e.g. FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV).

In some embodiments, the nucleic acid is a compound of Formula XI-a:

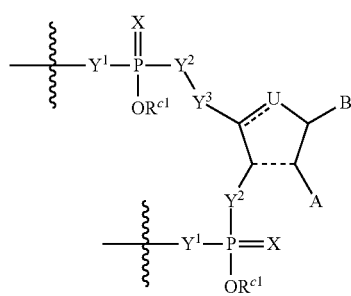

XI-a wherein

↷ denotes an optional double bond;

――― denotes an optional single bond;

U is O, S, —NR$^a$—, or —CR$^a$R$^b$— when ↷ denotes a single bond, or U is —CR$^a$— when ↷ denotes a double bond;

A is H, OH, phosphoryl, pyrophosphate, sulfate, —NH$_2$, —SH, an amino acid, a peptide comprising 2 to 12 amino acids;

X is O or S;

each of $Y^1$ is independently selected from —OR$^{a1}$, —NR$^{a1}$R$^{b1}$, and —SR$^{a1}$;

each of $Y^2$ and $Y^3$ are independently selected from O, —CR$^a$R$^b$—, NR$^c$, S or a linker comprising one or more atoms selected from the group consisting of C, O, N, and S;

R$^a$ and R$^b$ are each independently H, C$_{1-12}$ alkyl, C$_{2-12}$ alkenyl, C$_{2-12}$ alkynyl, or C$_{6-20}$ aryl;

R$^c$ is H, C$_{1-12}$ alkyl, C$_{2-12}$ alkenyl, phenyl, benzyl, a polyethylene glycol group, or an amino-polyethylene glycol group;

R$^{a1}$ and R$^{b1}$ are each independently H or a counterion;

—OR$^{c1}$ is OH at a pH of about 1 or —OR$^{c1}$ is O$^-$ at physiological pH; and B is nucleobase;

provided that the ring encompassing the variables A, B, D, U, Z, $Y^2$ and $Y^3$ cannot be ribose.

In some embodiments, B is a nucleobase of Formula XII-a, XII-b, or XII-c:

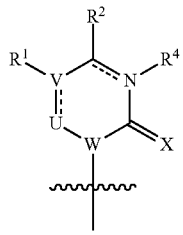

XII-a

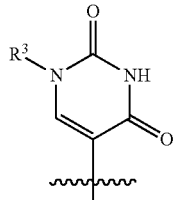

XII-b

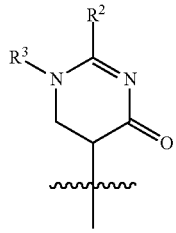

XII-c wherein:

↷ denotes a single or double bond;

X is O or S;

U and W are each independently C or N;

V is O, S, C or N;

wherein when V is C then R$^1$ is H, C$_{1-6}$ alkyl, C$_{1-6}$ alkenyl, C$_{1-6}$ alkynyl, halo, or —OR$^c$, wherein C$_{1-20}$ alkyl, C$_{2-20}$ alkenyl, C$_{2-20}$ alkynyl are each optionally substituted with —OH, —NR$^a$R$^b$, —SH, —C(O)R$^c$, —C(O)OR$^c$, —NHC(O)R$^c$, or —NHC(O)OR$^c$;

and wherein when V is O, S, or N then R$^1$ is absent;

R$^2$ is H, —OR$^c$, —SR$^c$, —NR$^a$R$^b$, or halo;

or when V is C then $R^1$ and $R^2$ together with the carbon atoms to which they are attached can form a 5- or 6-membered ring optionally substituted with 1-4 substituents selected from halo, —OH, —SH, —$NR^aR^b$, $C_{1-20}$ alkyl, $C_{2-20}$ alkenyl, $C_{2-20}$ alkynyl, $C_{1-20}$ alkoxy, or $C_{1-20}$ thioalkyl;

$R^3$ is H or $C_{1-20}$ alkyl;

$R^4$ is H or $C_{1-20}$ alkyl; wherein when ⇝ denotes a double bond then $R^4$ is absent, or N—$R^4$, taken together, forms a positively charged N substituted with $C_{1-20}$ alkyl;

$R^a$ and $R^b$ are each independently H, $C_{1-20}$ alkyl, $C_{2-20}$ alkenyl, $C_{2-20}$ alkynyl, or $C_{6-20}$ aryl; and $R^c$ is H, $C_{1-20}$ alkyl, $C_{2-20}$ alkenyl, phenyl, benzyl, a polyethylene glycol group, or an amino-polyethylene glycol group.

In some embodiments, B is a nucleobase of Formula XII-a1, XII-a2, XII-a X-a4, or XII-a5:

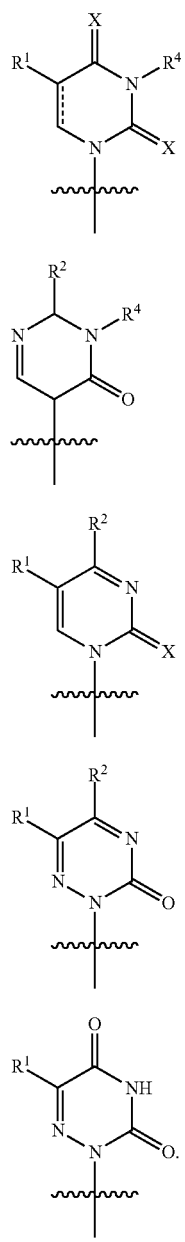

In some embodiments, the nucleobase is a pyrimidine or derivative thereof.

In some embodiments, the nucleic acid contains a plurality of structurally unique compounds of Formula XI-a.

In some embodiments, at least 25% of the cytosines are replaced by a compound of Formula XI-a (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

In some embodiments, at least 25% of the uracils are replaced by a compound of Formula XI-a (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

In some embodiments, at least 25% of the cytosines and 25% of the uracils are replaced by a compound of Formula XI-a (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

In some embodiments, the nucleic acid is translatable.

In some embodiments, when the nucleic acid includes a nucleotide altered with a linker and payload, for example, as described herein, the nucleotide altered with a linker and payload is on the 3' end of the nucleic acid.

Major Groove Interacting Partners

As described herein, the phrase "major groove interacting partner" refers RNA recognition receptors that detect and respond to RNA ligands through interactions, e.g. binding, with the major groove face of a nucleotide or nucleic acid. As such, RNA ligands comprising alternative nucleotides or nucleic acids as described herein decrease interactions with major groove binding partners, and therefore decrease an innate immune response, or expression and secretion of pro-inflammatory cytokines, or both.

Example major groove interacting, e.g. binding, partners include, but are not limited to the following nucleases and helicases. Within membranes, TLRs (Toll-like Receptors) 3, 7, and 8 can respond to single- and double-stranded RNAs. Within the cytoplasm, members of the superfamily 2 class of DEX(D/H) helicases and ATPases can sense RNAs to initiate antiviral responses. These helicases include the RIG-I (retinoic acid-inducible gene I) and MDA5 (melanoma differentiation-associated gene 5). Other examples include laboratory of genetics and physiology 2 (LGP2), HIN-200 domain containing proteins, or Helicase-domain containing proteins.

Prevention or Reduction of Innate Cellular Immune Response

The term "innate immune response" includes a cellular response to exogenous single stranded nucleic acids, generally of viral or bacterial origin, which involves the induction of cytokine expression and release, particularly the interferons, and cell death. Protein synthesis is also reduced during the innate cellular immune response. While it is advantageous to eliminate the innate immune response in a cell which is triggered by introduction of exogenous nucleic acids, the present disclosure provides alternative nucleic acids such as mRNAs that substantially reduce the immune response, including interferon signaling, without entirely eliminating such a response. In some embodiments, the immune response is reduced by 10%, 20%, 30%, 40%, 50%, 60%, 70%, 80%, 90%, 95%, 99%, 99.9%, or greater than 99.9% as compared to the immune response induced by a corresponding unaltered nucleic acid. Such a reduction can be measured by expression or activity level of Type 1 interferons or the expression of interferon-regulated genes such as the toll-like receptors (e.g., TLR7 and TLR8). Reduction or lack of induction of innate immune response can also be measured by decreased cell death following one or more administrations of alternative RNAs to a cell population; e.g., cell death is 10%, 25%, 50%, 75%, 85%, 90%, 95%, or over 95% less than the cell death frequency observed with a corresponding unaltered nucleic acid. Moreover, cell death may affect fewer than 50%, 40%, 30%, 20%, 10%, 5%, 1%, 0.1%, 0.01% or fewer than 0.01% of cells contacted with the alternative nucleic acids.

In some embodiments, the alternative nucleic acids, including polynucleotides and/or mRNA molecules are alternative in such a way as to not induce, or induce only minimally, an immune response by the recipient cell or organism. Such evasion or avoidance of an immune response trigger or activation is a novel feature of the alternative polynucleotides of the present invention.

The present disclosure provides for the repeated introduction (e.g., transfection) of alternative nucleic acids into a target cell population, e.g., in vitro, ex vivo, or in vivo. The step of contacting the cell population may be repeated one or more times (such as two, three, four, five or more than five times). In some embodiments, the step of contacting the cell population with the alternative nucleic acids is repeated a number of times sufficient such that a predetermined efficiency of protein translation in the cell population is achieved. Given the reduced cytotoxicity of the target cell population provided by the nucleic acid alterations, such repeated transfections are achievable in a diverse array of cell types in vitro and/or in vivo.

Polypeptide Variants

Provided are nucleic acids that encode variant polypeptides, which have a certain identity with a reference polypeptide sequence. The term "identity" as known in the art, refers to a relationship between the sequences of two or more peptides, as determined by comparing the sequences. In the art, "identity" also means the degree of sequence relatedness between peptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related peptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

In some embodiments, the polypeptide variant has the same or a similar activity as the reference polypeptide. Alternatively, the variant has an altered activity (e.g., increased or decreased) relative to a reference polypeptide. Generally, variants of a particular polynucleotide or polypeptide of the present disclosure will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular reference polynucleotide or polypeptide as determined by sequence alignment programs and parameters described herein and known to those skilled in the art.

As recognized by those skilled in the art, protein fragments, functional protein domains, and homologous proteins are also considered to be within the scope of this present disclosure. For example, provided herein is any protein fragment of a reference protein (meaning a polypeptide sequence at least one amino acid residue shorter than a reference polypeptide sequence but otherwise identical) 10, 20, 30, 40, 50, 60, 70, 80, 90, 100 or greater than 100 amino acids in length In another example, any protein that includes a stretch of about 20, about 30, about 40, about 50, or about 100 amino acids which are about 40%, about 50%, about 60%, about 70%, about 80%, about 90%, about 95%, or about 100% identical to any of the sequences described herein can be utilized in accordance with the present disclosure. In certain embodiments, a protein sequence to be utilized in accordance with the present disclosure includes 2, 3, 4, 5, 6, 7, 8, 9, 10, or more mutations as shown in any of the sequences provided or referenced herein.

Erythropoietin (EPO) and granulocyte colony-stimulating factor (GCSF) are exemplary polypeptides of interest.

Polynucleotide Libraries

Also provided are polynucleotide libraries containing nucleoside alterations, wherein the polynucleotides individually contain a first nucleic acid sequence encoding a polypeptide, such as an antibody, protein binding partner, scaffold protein, and other polypeptides known in the art. Preferably, the polynucleotides are mRNA in a form suitable for direct introduction into a target cell host, which in turn synthesizes the encoded polypeptide.

In certain embodiments, multiple variants of a protein, each with different amino acid alteration(s), are produced and tested to determine the best variant in terms of pharmacokinetics, stability, biocompatibility, and/or biological activity, or a biophysical property such as expression level. Such a library may contain 10, $10^2$, $10^3$, $10^4$, $10^5$, $10^6$, $10^7$, $10^8$, $10^9$, or over $10^9$ possible variants (including substitutions, deletions of one or more residues, and insertion of one or more residues).

Polypeptide-nucleic Acid Complexes

Proper protein translation involves the physical aggregation of a number of polypeptides and nucleic acids associated with the mRNA. Provided by the present disclosure are protein-nucleic acid complexes, containing a translatable mRNA having one or more nucleoside alterations (e.g., at least two different nucleoside alterations) and one or more polypeptides bound to the mRNA. Generally, the proteins are provided in an amount effective to prevent or reduce an innate immune response of a cell into which the complex is introduced.

Untranslatable Alternative Nucleic Acids

As described herein, provided are mRNAs having sequences that are substantially not translatable. Such mRNA is effective as a vaccine when administered to a mammalian subject.

Also provided are alternative nucleic acids that contain one or more noncoding regions. Such alternative nucleic acids are generally not translated, but are capable of binding to and sequestering one or more translational machinery component such as a ribosomal protein or a transfer RNA (tRNA), thereby effectively reducing protein expression in the cell. The alternative nucleic acid may contain a small nucleolar RNA (sno-RNA), micro RNA (miRNA), small interfering RNA (siRNA) or Piwi-interacting RNA (piRNA).

Synthesis of Alternative Nucleic Acids

Nucleic acids for use in accordance with the present disclosure may be prepared according to any available technique including, but not limited to chemical synthesis, enzymatic synthesis, which is generally termed in vitro transcription, enzymatic or chemical cleavage of a longer precursor. Methods of synthesizing RNAs are known in the art (see, e.g., Gait, M. J. (ed.) Oligonucleotide synthesis: a practical approach, Oxford [Oxfordshire], Washington, D.C.: IRL Press, 1984; and Herdewijn, P. (ed.) Oligonucleotide synthesis: methods and applications, Methods in Molecular Biology, v. 288 (Clifton, N.J.) Totowa, N.J.: Humana Press, 2005; both of which are incorporated herein by reference).

In certain embodiments, a method for producing an mRNA encoding a polypeptide of interest comprises contacting a cDNA that encodes the protein of interest with an RNA polymerase in the presence of a nucleotide triphosphate mix, wherein from 10% to 50% of the uridine triphosphate comprises 5-methoxy-uracil and 50% to 100% of the cytidine triphosphate comprises 5-methyl-cytosine. The invention also provides mRNA produced by such methods. The methods may include additional steps, such as capping (e.g. the addition of a 5' cap structure), addition of a poly-A tail and/or formulation into a pharmaceutical composition. The RNA polymerase may be T7 RNA polymerase. The in vitro transcription reaction mixture may include a transcription buffer (such as 400 mM Tris-HCl pH 8.0, or an equivalent) and may include $MgCl_2$, DTT, Spermidine (or equivalents). An RNase inhibitor may be included. The remaining reaction volume is generally made up with $dH_2O$. The reaction may be incubated at approximately 37° C. (such as between 30 and 40° C.) and may be incubated for 3 hr-5 hrs (such as 3½ hr-4½ hr, or about 4 hr). The RNA may then be cleaned using DNase and a purification kit.

Alternative nucleic acids need not be uniformly present along the entire length of the molecule. Different nucleotide alterations and/or backbone structures may exist at various positions in the nucleic acid. One of ordinary skill in the art will appreciate that the nucleotide analogs or other alteration(s) may be located at any position(s) of a nucleic acid such that the function of the nucleic acid is not substantially decreased. An alteration may also be a 5' or 3' terminal alteration. The nucleic acids may contain at a minimum one and at maximum 100% alternative nucleotides, or any intervening percentage, such as at least 5% alternative nucleotides, at least 10% alternative nucleotides, at least 25% alternative nucleotides, at least 50% alternative nucleotides, at least 80% alternative nucleotides, or at least 90% alternative nucleotides. For example, the nucleic acids may contain an alternative pyrimidine such as uracil or cytosine. In some embodiments, at least 5%, at least 10%, at least 25%, at least 50%, at least 80%, at least 90% or 100% of the uracil in the nucleic acid is replaced with an alternative uracil. The alternative uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the nucleic acid is replaced with an alternative cytosine. The alternative cytosine can be replaced by a compound having a single unique structure, or can be replaced by a plurality of compounds having different structures (e.g., 2, 3, 4 or more unique structures).

Generally, the shortest length of an alternative mRNA of the present disclosure can be the length of an mRNA sequence that is sufficient to encode for a dipeptide. In another embodiment, the length of the mRNA sequence is sufficient to encode for a tripeptide. In another embodiment, the length of an mRNA sequence is sufficient to encode for a tetrapeptide. In another embodiment, the length of an mRNA sequence is sufficient to encode for a pentapeptide. In another embodiment, the length of an mRNA sequence is sufficient to encode for a hexapeptide. In another embodiment, the length of an mRNA sequence is sufficient to encode for a heptapeptide. In another embodiment, the length of an mRNA sequence is sufficient to encode for an octapeptide. In another embodiment, the length of an mRNA sequence is sufficient to encode for a nonapeptide. In another embodiment, the length of an mRNA sequence is sufficient to encode for a decapeptide.

Examples of dipeptides that the alternative nucleic acid sequences can encode for include, but are not limited to, carnosine and anserine.

In a further embodiment, the mRNA is greater than 30 nucleotides in length. In another embodiment, the RNA molecule is greater than 35 nucleotides in length. In another embodiment, the length is at least 40 nucleotides. In another embodiment, the length is at least 45 nucleotides. In another embodiment, the length is at least 55 nucleotides. In another embodiment, the length is at least 60 nucleotides. In another embodiment, the length is at least 60 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1800 nucleotides. In another embodiment, the length is at least 2000 nucleotides. In another embodiment, the length is at least 2500 nucleotides. In another embodiment, the length is at least 3000 nucleotides. In another embodiment, the length is at least 4000 nucleotides. In another embodiment, the length is at least 5000 nucleotides, or greater than 5000 nucleotides.

For example, the alternative nucleic acids described herein can be prepared using methods that are known to those skilled in the art of nucleic acid synthesis.

In some embodiments, the present disclosure provides methods, e.g., enzymatic, of preparing a nucleic acid sequence comprising a nucleotide, wherein the nucleic acid sequence comprises a compound of Formula XI-a:

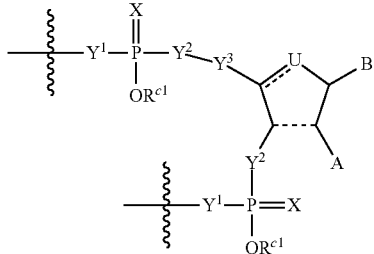

XI-a wherein:
the nucleotide has decreased binding affinity;

⇌ denotes an optional double bond;

——— denotes an optional single bond;

U is O, S, —NR$^a$—, or —CR$^a$R$^b$— when ⇌ denotes a single bond, or U is —CR$^a$— when ⇌ denotes a double bond;

A is H, OH, phosphoryl, pyrophosphate, sulfate, —NH$_2$, —SH, an amino acid, a peptide comprising 2 to 12 amino acids;

X is O or S;

each of Y$^1$ is independently selected from —OR$^{a1}$, —NR$^{a1}$R$^{b1}$, and —SR$^{a1}$;

each of Y$^2$ and Y$^3$ are independently selected from O, —CR$^a$R$^b$—, NR$^c$, S or a linker comprising one or more atoms selected from the group consisting of C, O, N, and S;

R$^a$ and R$^b$ are each independently H, C$_{1-12}$ alkyl, C$_{2-12}$ alkenyl, C$_{2-12}$ alkynyl, or C$_{6-20}$ aryl;

R$^c$ is H, C$_{1-12}$ alkyl, C$_{2-12}$ alkenyl, phenyl, benzyl, a polyethylene glycol group, or an amino-polyethylene glycol group;

R$^{a1}$ and R$^{b1}$ are each independently H or a counterion;

—OR$^{c1}$ is OH at a pH of about 1 or —OR$^{c1}$ is O$^-$ at physiological pH; and B is nucleobase;

provided that the ring encompassing the variables A, B, D, U, Z, Y$^2$ and Y$^3$ cannot be ribose the method comprising reacting a compound of Formula XIII:

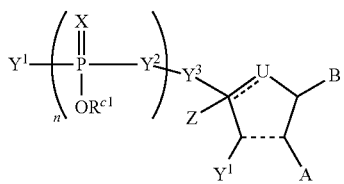

XIII with an RNA polymerase, and a cDNA template.

In some embodiments, the reaction is repeated from 1 to about 7,000 times.

In some embodiments, B is a nucleobase of Formula XII-a, XII-b, or XII-c:

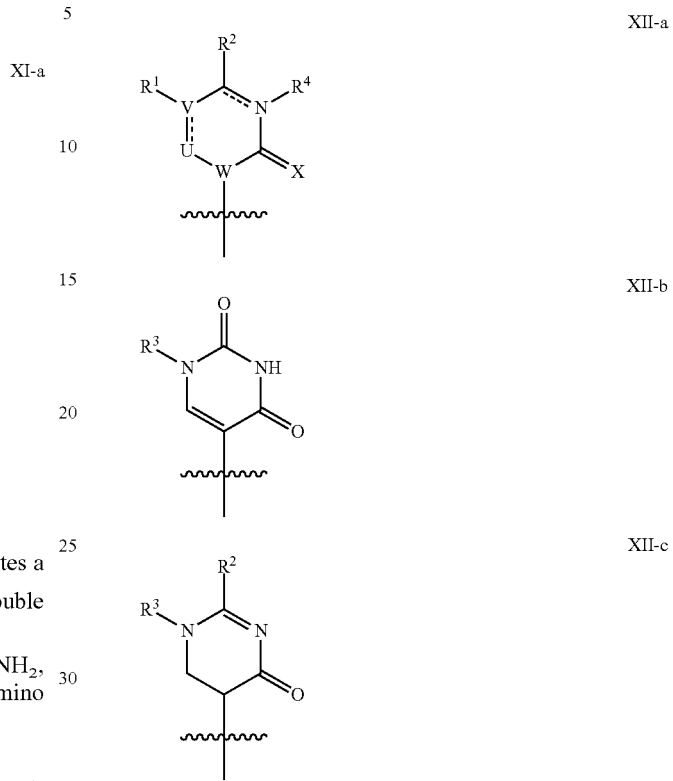

wherein

⇌ denotes a single or double bond;

X is O or S;

U and W are each independently C or N;

V is O, S, C or N;

wherein when V is C then R$^1$ is H, C$_{1-6}$ alkyl, C$_{1-6}$ alkenyl, C$_{1-6}$ alkynyl, halo, or —OR$^c$, wherein C$_{1-20}$ alkyl, C$_{2-20}$ alkenyl, C$_{2-20}$ alkynyl are each optionally substituted with —OH, —NR$^a$R$^b$, —SH, —C(O)R$^c$, —C(O)OR$^c$, —NHC(O)R$^c$, or —NHC(O)OR$^c$;

and wherein when V is O, S, or N then R$^1$ is absent;

R$^2$ is H, —OR$^c$, —SR$^c$, —NR$^a$R$^b$, or halo;

or when V is C then R$^1$ and R$^2$ together with the carbon atoms to which they are attached can form a 5- or 6-membered ring optionally substituted with 1-4 substituents selected from halo, —OH, —SH, —NR$^a$R$^b$, C$_{1-20}$ alkyl, C$_{2-20}$ alkenyl, C$_{2-20}$ alkynyl, C$_{1-20}$ alkoxy, or C$_{1-20}$ thioalkyl;

R$^3$ is H or C$_{1-20}$ alkyl;

R$^4$ is H or C$_{1-20}$ alkyl; wherein when ⇌ denotes a double bond then R$^4$ is absent, or N—R$^4$ taken together, forms a positively charged N substituted with C$_{1-20}$ alkyl;

R$^a$ and R$^b$ are each independently H, C$_{1-20}$ alkyl, C$_{2-20}$ alkenyl, C$_{2-20}$ alkynyl, or C$_{6-20}$ aryl; and R$^c$ is H, C$_{1-20}$ alkyl, C$_{2-20}$ alkenyl, phenyl, benzyl, a polyethylene glycol group, or an amino-polyethylene glycol group.

In some embodiments, B is a nucleobase of Formula XII-a1, XII-a2, XII-a3, XII-a4, or XII-a5:

XII-a1
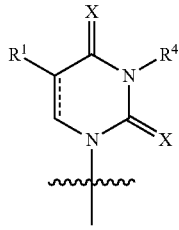

XII-a2
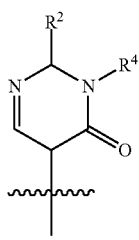

XII-a3
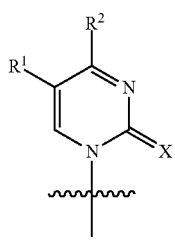

XII-a4
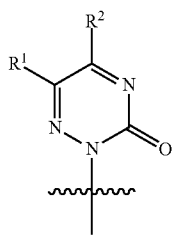

XII-a5
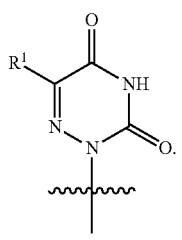

In some embodiments, the methods further comprise a nucleotide selected from the group consisting of adenosine, cytidine, guanosine, and uridine.

In some embodiments, the nucleobase is a pyrimidine or derivative thereof.

In another aspect, the present disclosure provides for methods of amplifying a nucleic acid sequence, the method comprising:

reacting a compound of Formula XI-d:

XI-d
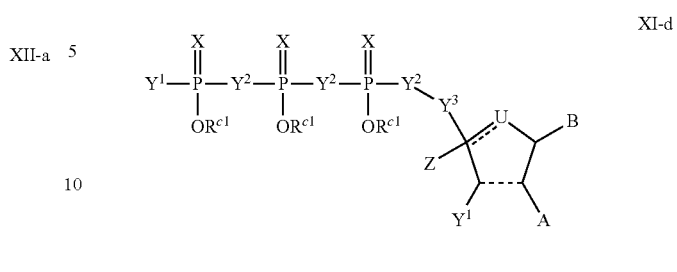

wherein

⇝ denotes a single or a double bond;

⸺ denotes an optional single bond;

U is O, S, —$NR^a$—, or —$CR^aR^b$— when ⇝ denotes a single bond, or U is —$CR^a$— when ⇝ denotes a double bond;

Z is H, $C_{1-12}$ alkyl, or $C_{6-20}$ aryl, or Z is absent when ⇝ denotes a double bond; and Z can be —$CR^aR^b$— and form a bond with A;

A is H, OH, phosphoryl, pyrophosphate, sulfate, —$NH_2$, —SH, an amino acid, or a peptide comprising 1 to 12 amino acids;

X is O or S;

each of $Y^1$ is independently selected from —$OR^{a'}$, —$NR^{a1}R^{b1}$, and —$SR^{a1}$;

each of $Y^2$ and $Y^3$ are independently selected from O, —$CR^aR^b$—, $NR^c$, S or a linker comprising one or more atoms selected from the group consisting of C, O, N, and S;

n is 0, 1, 2, or 3;

m is 0, 1, 2 or 3;

B is nucleobase;

$R^a$ and $R^b$ are each independently H, $C_{1-12}$ alkyl, $C_{2-12}$ alkenyl, $C_{2-12}$ alkynyl, or $C_{6-20}$ aryl;

$R^c$ is H, $C_{1-12}$ alkyl, $C_{2-12}$ alkenyl, phenyl, benzyl, a polyethylene glycol group, or an amino-polyethylene glycol group;

$R^{a1}$ and $R^{b1}$ are each independently H or a counterion; and

—$OR^{c1}$ is OH at a pH of about 1 or —$OR^{c1}$ is O⁻ at physiological pH;

provided that the ring encompassing the variables A, B, D, U, Z, $Y^2$ and $Y^3$ cannot be ribose with a primer, a cDNA template, and an RNA polymerase.

In some embodiments, B is a nucleobase of Formula XII-a, XII-b, or XII-c:

XII-a
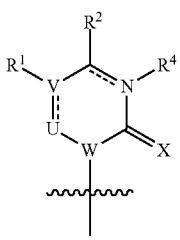

-continued

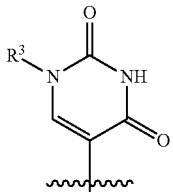
XII-b

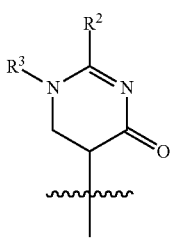
XII-c wherein:

⁀ denotes a single or double bond;

X is O or S;

U and W are each independently C or N;

V is O, S, C or N;

wherein when V is C then $R^1$ is H, $C_{1-6}$ alkyl, $C_{1-6}$ alkenyl, $C_{1-6}$ alkynyl, halo, or —$OR^c$, wherein $C_{1-20}$ alkyl, $C_{2-20}$ alkenyl, $C_{2-20}$ alkynyl are each optionally substituted with —OH, —$NR^aR^b$, —SH, —$C(O)R^c$, —$C(O)OR^c$, —$NHC(O)R^c$, or —$NHC(O)OR^c$;

and wherein when V is O, S, or N then $R^1$ is absent;

$R^2$ is H, —$OR^c$, —$SR^c$, —$NR^aR^b$, or halo;

or when V is C then $R^1$ and $R^2$ together with the carbon atoms to which they are attached can form a 5- or 6-membered ring optionally substituted with 1-4 substituents selected from halo, —OH, —SH, —$NR^aR^b$, $C_{1-20}$ alkyl, $C_{2-20}$ alkenyl, $C_{2-20}$ alkynyl, $C_{1-20}$ alkoxy, or $C_{1-20}$ thioalkyl;

$R^3$ is H or $C_{1-20}$ alkyl;

$R^4$ is H or $C_{1-20}$ alkyl; wherein when ⁀ denotes a double bond then $R^4$ is absent, or N—$R^4$, taken together, forms a positively charged N substituted with $C_{1-20}$ alkyl;

$R^a$ and $R^b$ are each independently H, $C_{1-20}$ alkyl, $C_{2-20}$ alkenyl, $C_{2-20}$ alkynyl, or $C_{6-20}$ aryl; and $R^c$ is H, $C_{1-20}$ alkyl, $C_{2-20}$ alkenyl, phenyl, benzyl, a polyethylene glycol group, or an amino-polyethylene glycol group.

In some embodiments, B is a nucleobase of Formula XII-a1, XII-a2, XII-a3, XII-a4, or XII-a5:

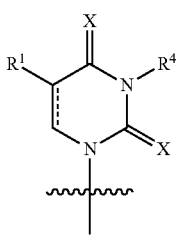
XII-a1

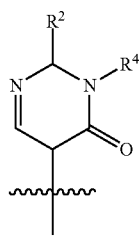
XII-a2

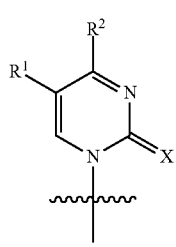
XII-a3

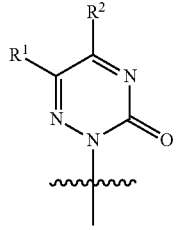
XII-a4

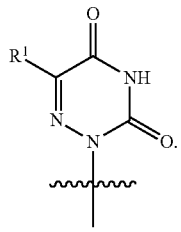
XII-a5

In some embodiments, the methods further comprise a nucleotide selected from the group consisting of adenosine, cytidine, guanosine, and uridine.

In some embodiments, the nucleobase is a pyrimidine or derivative thereof.

In some embodiments, the present disclosure provides for methods of synthesizing a pharmaceutical nucleic acid, comprising the steps of:

a) providing a complementary deoxyribonucleic acid (cDNA) that encodes a pharmaceutical protein of interest;

b) selecting a nucleotide and c) contacting the provided cDNA and the selected nucleotide with an RNA polymerase, under conditions such that the pharmaceutical nucleic acid is synthesized.

In further embodiments, the pharmaceutical nucleic acid is a ribonucleic acid (RNA).

In still a further aspect of the present disclosure, the alternative nucleic acids can be prepared using solid phase synthesis methods.

In some embodiments, the present disclosure provides methods of synthesizing a nucleic acid comprising a compound of Formula XI-a:

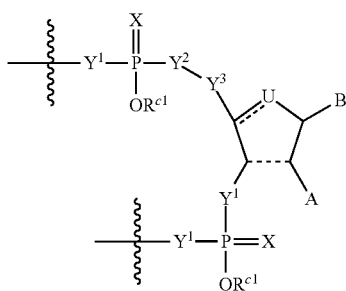

XI-a wherein

⁀⁀ denotes an optional double bond;

--- denotes an optional single bond;

U is O, S, —NR$^a$—, or —CR$^a$R$^b$— when ⁀⁀ denotes a single bond, or U is —CR$^a$— when ⁀⁀ denotes a double bond;

A is H, OH, phosphoryl, pyrophosphate, sulfate, —NH$_2$, —SH, an amino acid, a peptide comprising 2 to 12 amino acids;

X is O or S;

each of Y$^1$ is independently selected from —OR$^{a1}$, —NR$^{a1}$R$^{b1}$, and —SR$^{a1}$;

each of Y$^2$ and Y$^3$ are independently selected from O, —CR$^a$R$^b$—, NR$^c$, S or a linker comprising one or more atoms selected from the group consisting of C, O, N, and S;

R$^a$ and R$^b$ are each independently H, C$_{1-12}$ alkyl, C$_{2-12}$ alkenyl, C$_{2-12}$ alkynyl, or C$_{6-20}$ aryl;

R$^c$ is H, C$_{1-12}$ alkyl, C$_{2-12}$ alkenyl, phenyl, benzyl, a polyethylene glycol group, or an amino-polyethylene glycol group;

R$^{a1}$ and R$^{b1}$ are each independently H or a counterion;

—OR$^{c1}$ is OH at a pH of about 1 or —OR$^{c1}$ is O$^−$ at physiological pH; and B is nucleobase;

provided that the ring encompassing the variables A, B, U, Z, Y$^2$ and Y$^3$ cannot be ribose;

comprising:

a) reacting a nucleotide of Formula XIII-a:

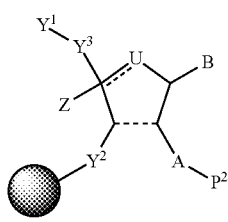

XIII-a with a phosphoramidite compound of Formula XIII-b:

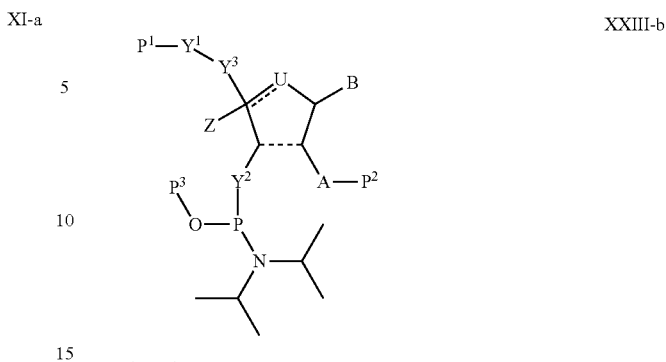

XXIII-b wherein:

denotes a solid support; and

P$^1$, P$^2$ and P$^3$ are each independently suitable protecting groups;

to provide a nucleic acid of Formula XIV-a:

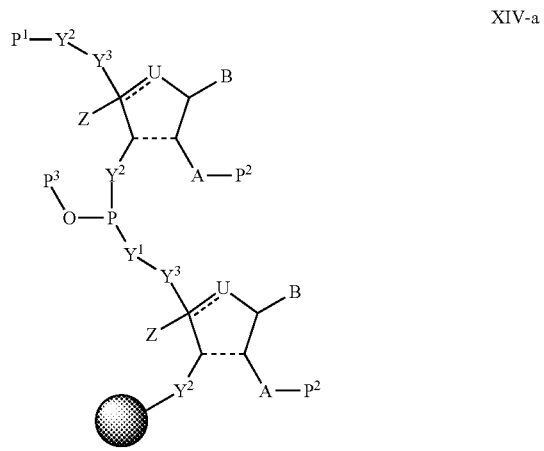

XIV-a and b) oxidizing or sulfurizing the nucleic acid of Formula XIV-a to yield a nucleic acid of Formula XIVb:

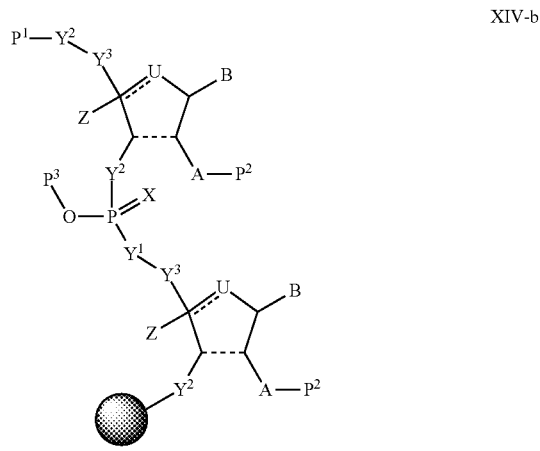

XIV-b and c) removing the protecting groups to yield the nucleic acid of Formula XI-a.

In some embodiments, the methods further comprise a nucleotide selected from the group consisting of adenosine, cytidine, guanosine, and uridine.

In some embodiments, B is a nucleobase of Formula XIII:

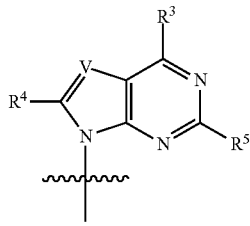

XIII wherein:
V is N or positively charged $NR^c$;
$R^3$ is $NR^cR^d$, —$OR^a$, or —$SR^a$;
$R^4$ is H or can optionally form a bond with $Y^3$;
$R^5$ is H, —$NR^cR^d$, or —$OR^a$;
$R^a$ and $R^b$ are each independently H, $C_{1-12}$ alkyl, $C_{2-12}$ alkenyl, $C_{2-12}$ alkynyl, or $C_{6-20}$ aryl; and
$R^c$ is H, $C_{1-12}$ alkyl, $C_{2-12}$ alkenyl, phenyl, benzyl, a polyethylene glycol group, or an amino-polyethylene glycol group.

In some embodiments, steps a) and b) are repeated from 1 to about 10,000 times.

5' Capping

The 5' cap structure of an mRNA is involved in nuclear export, increasing mRNA stability and binds the mRNA Cap Binding Protein (CBP), which is responsible for mRNA stability in the cell and translation competency through the association of CBP with poly(A) binding protein to form the mature cyclic mRNA species. The cap further assists the removal of 5' proximal introns removal during mRNA splicing.

Endogenous mRNA molecules may be 5'-end capped generating a 5'-ppp-5'-triphosphate linkage between a terminal guanosine cap residue and the 5'-terminal transcribed sense nucleotide of the mRNA. This 5'-guanylate cap may then be methylated to generate an N7-methyl-guanylate residue. The ribose sugars of the terminal and/or anteterminal transcribed nucleotides of the 5' end of the mRNA may optionally also be 2'-O-methylated. 5'-decapping through hydrolysis and cleavage of the guanylate cap structure may target a nucleic acid molecule, such as an mRNA molecule, for degradation.

Alterations to the nucleic acids of the present invention may generate a non-hydrolyzable cap structure preventing decapping and thus increasing mRNA half-life. Because cap structure hydrolysis requires cleavage of 5'-ppp-5' phosphorodiester linkages, alternative nucleotides may be used during the capping reaction. For example, a Vaccinia Capping Enzyme from New England Biolabs (Ipswich, Mass.) may be used with α-thio-guanosine nucleotides according to the manufacturer's instructions to create a phosphorothioate linkage in the 5'-ppp-5' cap. Additional alternative guanosine nucleotides may be used such as α-methyl-phosphonate and seleno-phosphate nucleotides.

Additional alterations include, but are not limited to, 2'-O-methylation of the ribose sugars of 5'-terminal and/or 5'-anteterminal nucleotides of the mRNA (as mentioned above) on the 2'-hydroxyl group of the sugar ring. Multiple distinct 5'-cap structures can be used to generate the 5'-cap of a nucleic acid molecule, such as an mRNA molecule. 5' Cap structures include those described in International Patent Publication Nos. WO2008127688, WO 2008016473, and WO 2011015347, each of which is incorporated herein by reference in its entirety.

Cap analogs, which herein are also referred to as synthetic cap analogs, chemical caps, chemical cap analogs, or structural or functional cap analogs, differ from natural (i.e. endogenous, wild-type or physiological) 5'-caps in their chemical structure, while retaining cap function. Cap analogs may be chemically (i.e. non-enzymatically) or enzymatically synthesized and/linked to a nucleic acid molecule.

For example, the Anti-Reverse Cap Analog (ARCA) cap contains two guanosines linked by a 5'-5'-triphosphate group, wherein one guanosine contains an N7 methyl group as well as a 3'-O-methyl group (i.e., N7,3'-O-dimethyl-guanosine-5'-triphosphate-5'-guanosine ($m^7$G-3'mppp-G; which may equivalently be designated 3' O-Me-$m^7$G(5')ppp (5')G). The 3'-O atom of the other, unaltered, guanosine becomes linked to the 5'-terminal nucleotide of the capped nucleic acid molecule (e.g. an mRNA or mRNA). The N7- and 3'-O-methylated guanosine provides the terminal moiety of the capped nucleic acid molecule (e.g. mRNA or mRNA).

Another exemplary cap is mCAP, which is similar to ARCA but has a 2'-O-methyl group on guanosine (i.e., N7,2'-O-dimethyl-guanosine-5'-triphosphate-5'-guanosine, $m^7$Gm-ppp-G).

In one embodiment, the cap is a dinucleotide cap analog. As a non-limiting example, the dinucleotide cap analog may be altered at different phosphate positions with a boranophosphate group or a phophoroselenoate group such as the dinucleotide cap analogs described in U.S. Pat. No. 8,519,110, the contents of which are herein incorporated by reference in its entirety.

In another embodiment, the cap analog is a N7-(4-chlorophenoxyethyl) substituted dicnucleotide form of a cap analog known in the art and/or described herein. Non-limiting examples of a N7-(4-chlorophenoxyethyl) substituted dinucleotide form of a cap analog include a N7-(4-chlorophenoxyethyl)-G(5')ppp(5')G and a N7-(4-chlorophenoxyethyl)-$m^{3'-O}$G(5')ppp(5')G cap analog (See e.g., the various cap analogs and the methods of synthesizing cap analogs described in Kore et al. Bioorganic & Medicinal Chemistry 2013 21:4570-4574; the contents of which are herein incorporated by reference in its entirety). In another embodiment, a cap analog of the present invention is a 4-chloro/bromophenoxyethyl analog.

While cap analogs allow for the concomitant capping of a nucleic acid molecule in an in vitro transcription reaction, up to 20% of transcripts remain uncapped. This, as well as the structural differences of a cap analog from endogenous 5'-cap structures of nucleic acids produced by the endogenous, cellular transcription machinery, may lead to reduced translational competency and reduced cellular stability.

Alternative nucleic acids of the invention may also be capped post-transcriptionally, using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function and/or structure as compared to synthetic features or analogs, of the prior art, or which outperforms the corresponding endogenous, wild-type, natural or physiological feature in one or more respects. Non-limiting examples of more authentic 5'-cap structures of the present invention are those which, among other things, have enhanced binding of cap binding proteins, increased half life, reduced susceptibility to 5' endonucleases and/or reduced 5' decapping, as compared to synthetic 5'-cap structures known in the art (or to a wild-type, natural or physiological 5'-cap structure). For example, recombinant Vaccinia Virus Capping Enzyme and recombinant 2'-O-methyltransferase enzyme can create a canonical 5'-5'-triphosphate linkage between the 5'-terminal nucleotide of an mRNA and a guanosine cap nucleotide wherein the cap guanosine contains an N7 methylation and the 5'-terminal nucleotide of the mRNA contains a 2'-O-methyl. Such a structure is termed the Cap1 structure. This cap results in a higher translational-competency and cellular stability and a reduced activation of cellular pro-inflammatory cytokines, as compared, e.g., to other 5'cap analog structures known in the art. Cap structures include 7mG(5')ppp(5')N,pN2p (cap 0), 7mG(5')ppp(5')NlmpNp (cap 1), 7mG(5')-ppp(5') NlmpN2mp (cap 2) and m(7)Gpppm(3)(6,6,2')Apm(2')Apm (2')Cpm(2)(3,2')Up (cap 4).

Because the alternative nucleic acids may be capped post-transcriptionally, and because this process is more efficient, nearly 100% of the alternative nucleic acids may be capped. This is in contrast to ~80% when a cap analog is linked to an mRNA in the course of an in vitro transcription reaction.

According to the present invention, 5' terminal caps may include endogenous caps or cap analogs. According to the present invention, a 5' terminal cap may comprise a guanosine analog. Useful guanosine analogs include inosine, N1-methyl-guanosine, 2'fluoro-guanosine, 7-deaza-guanosine, 8-oxo-guanosine, 2-amino-guanosine, LNA-guanosine, and 2-azido-guanosine.

In one embodiment, the nucleic acids described herein may contain a modified 5'-cap. A modification on the 5'-cap may increase the stability of mRNA, increase the half-life of the mRNA, and could increase the mRNA translational efficiency. The modified 5'-cap may include, but is not limited to, one or more of the following modifications: modification at the 2' and/or 3' position of a capped guanosine triphosphate (GTP), a replacement of the sugar ring oxygen (that produced the carbocyclic ring) with a methylene moiety ($CH_2$), a modification at the triphosphate bridge moiety of the cap structure, or a modification at the nucleobase (G) moiety.

The 5'-cap structure that may be modified includes, but is not limited to, the caps described herein such as Cap0 having the substrate structure for cap dependent translation of:

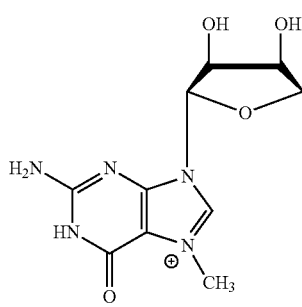
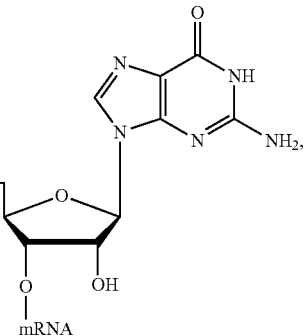

(CAP-001)

or Cap1 having the substrate structure for cap dependent translation of:

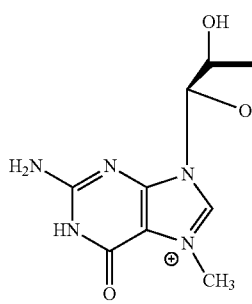
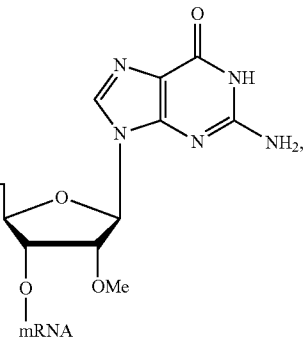

(CAP-002)

As a non-limiting example, the modified 5'-cap may have the substrate structure for cap dependent translation of:

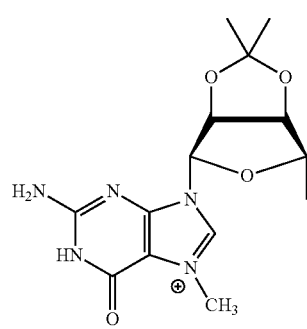
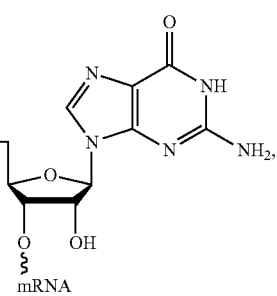

(CAP-003)

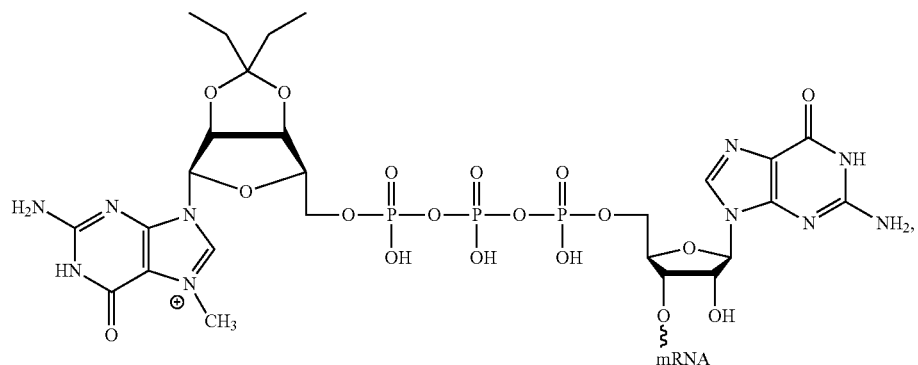
(CAP-004)
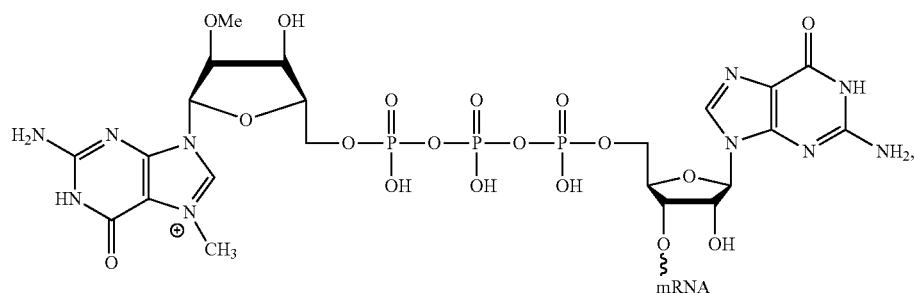
(CAP-005)
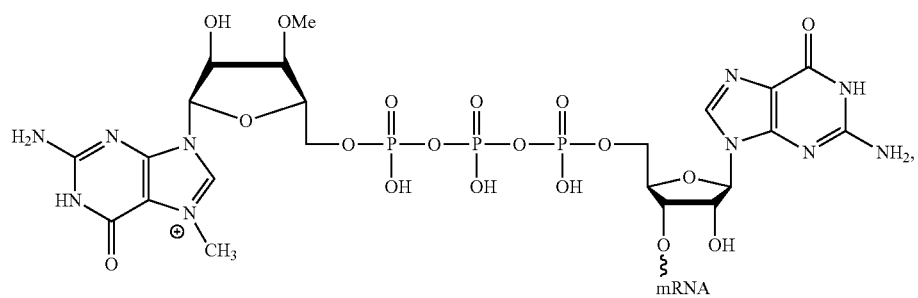
(CAP-006)
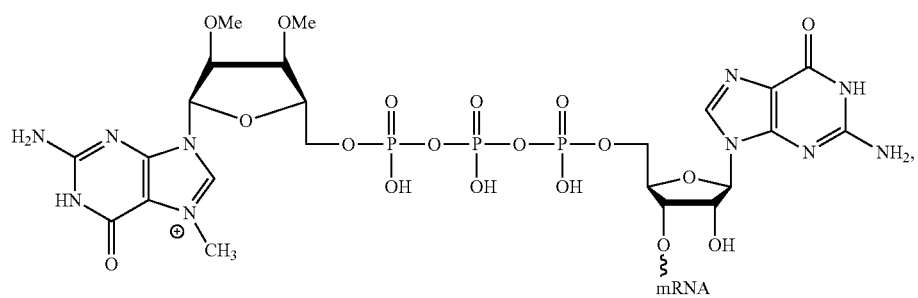
(CAP-007)
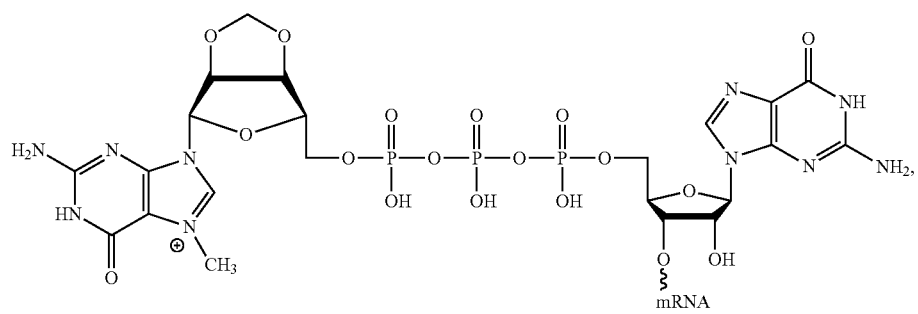
(CAP-008)

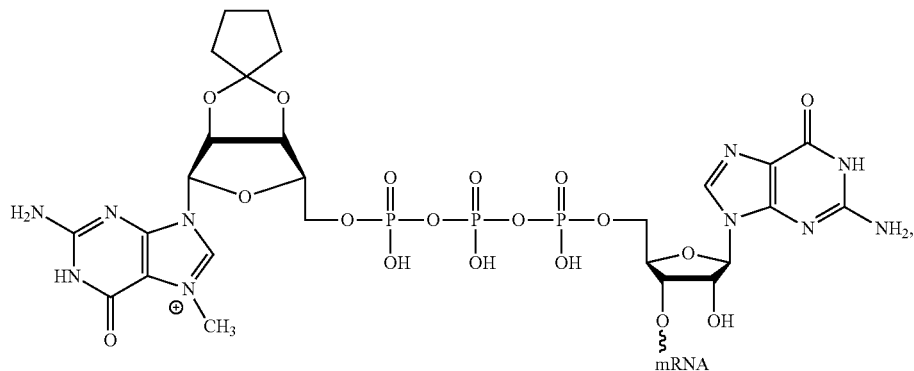
(CAP-009)
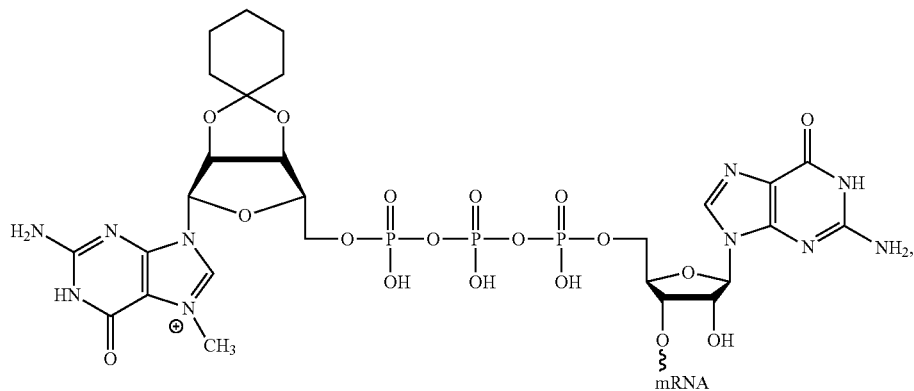
(CAP-010)
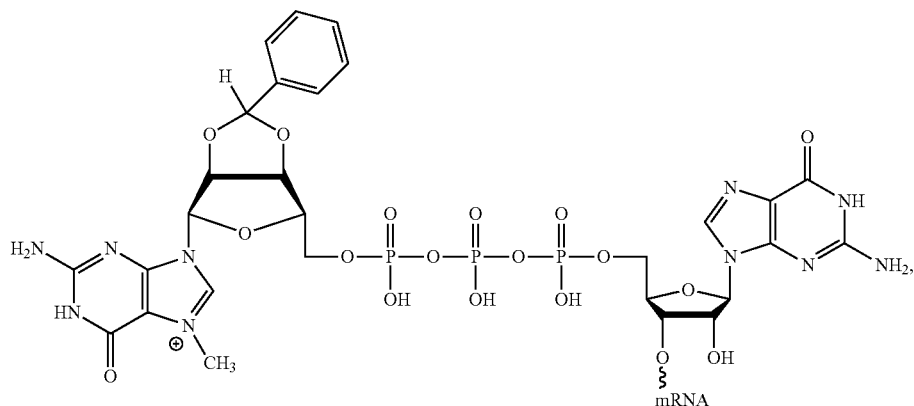
(CAP-011)
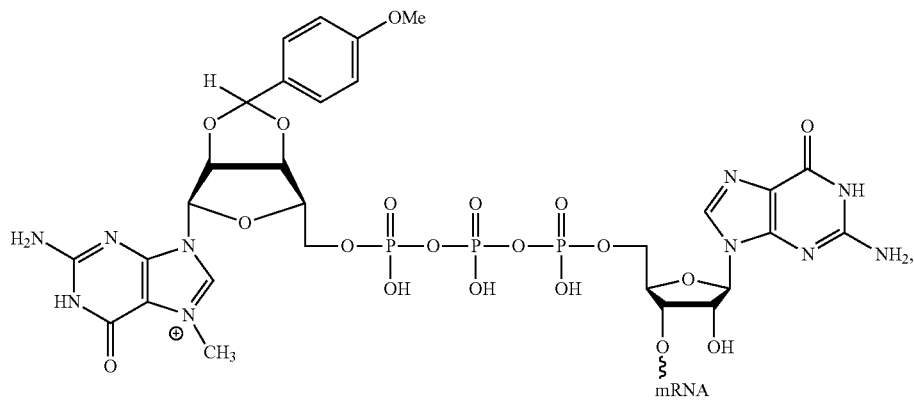
(CAP-012)

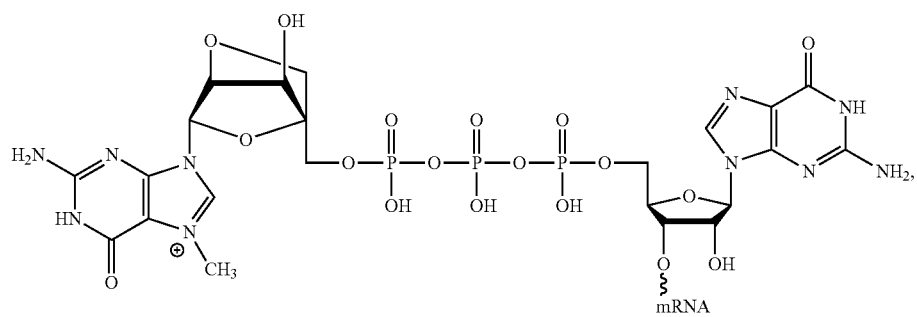
(CAP-013)
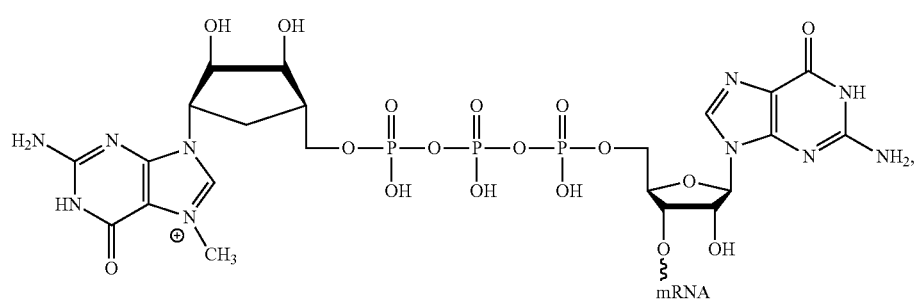
(CAP-014)
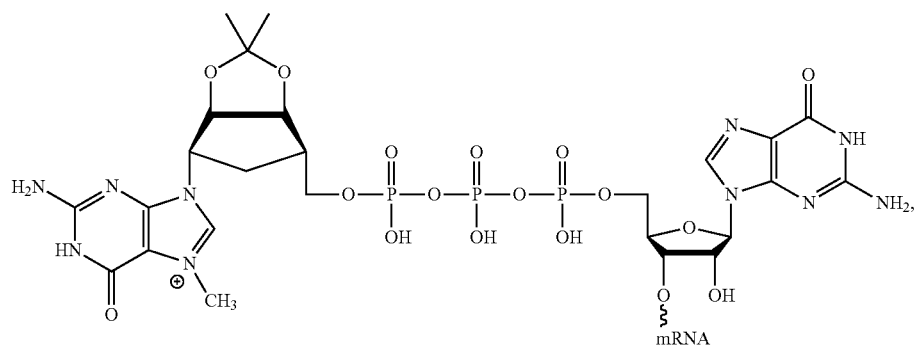
(CAP-015)
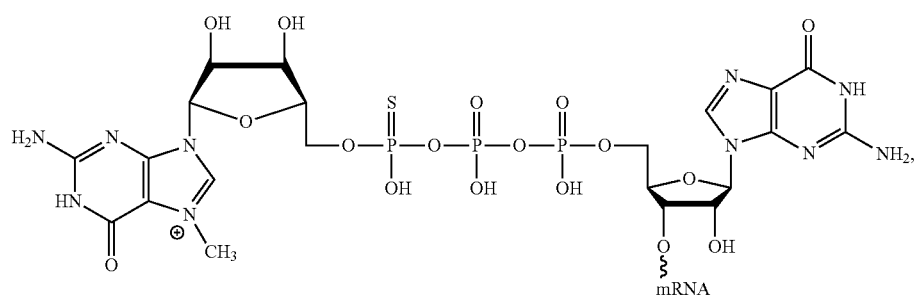
(CAP-016)
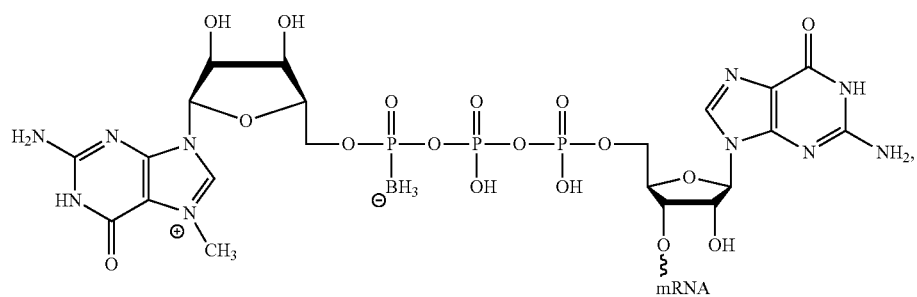
(CAP-017)

-continued
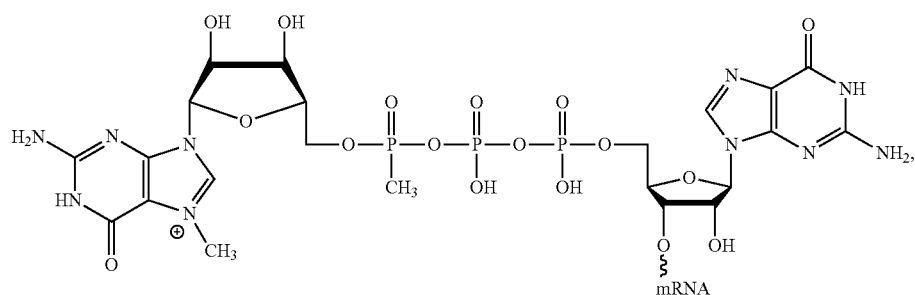
(CAP-018)
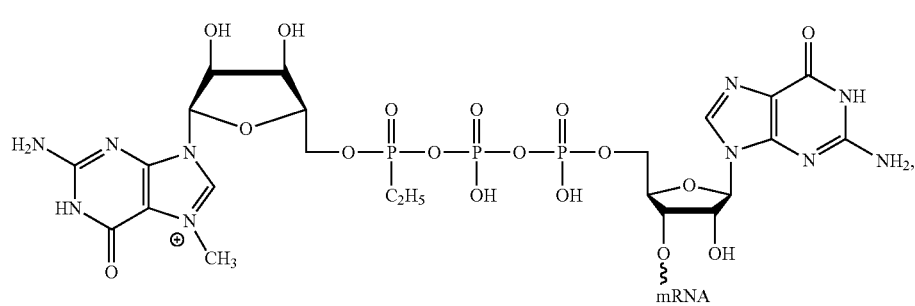
(CAP-019)
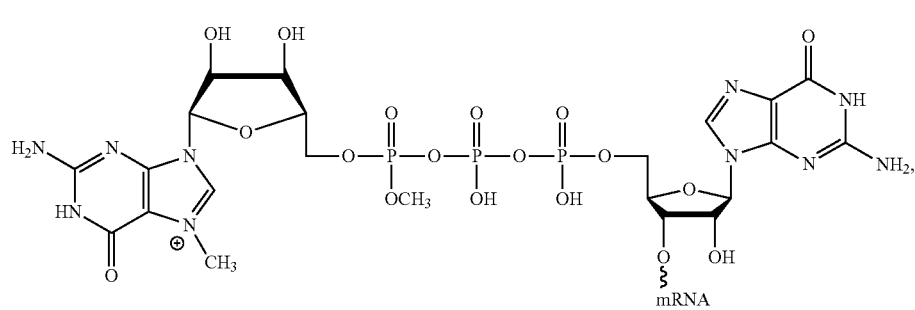
(CAP-020)
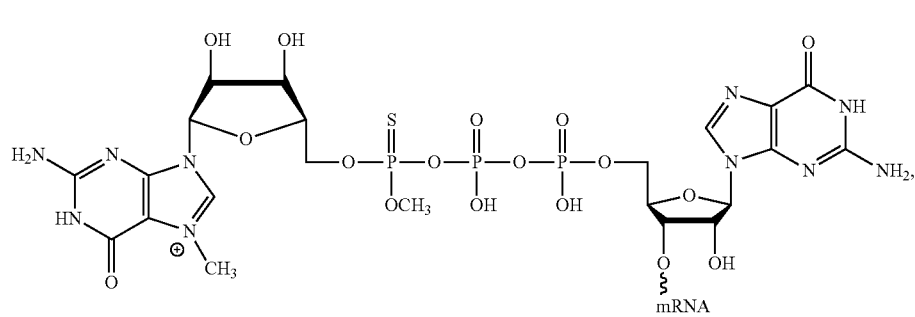
(CAP-021)
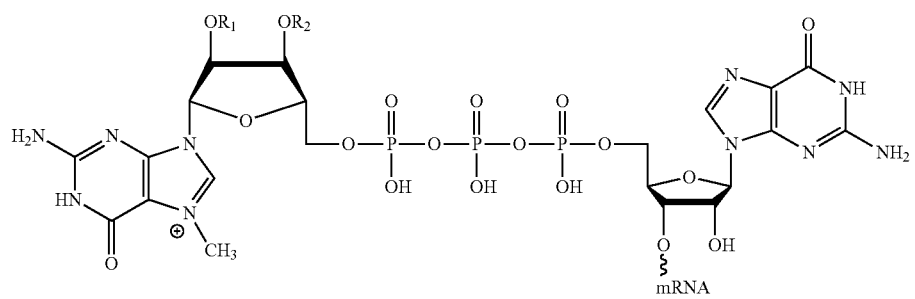

where $R_1$ and $R_2$ are defined in Table 7:

TABLE 7

$R_1$ and $R_2$ groups for CAP-022 to CAP096.

| Cap Structure Number | $R_1$ | $R_2$ |
|---|---|---|
| CAP-022 | $C_2H_5$ (Ethyl) | H |
| CAP-023 | H | $C_2H_5$ (Ethyl) |
| CAP-024 | $C_2H_5$ (Ethyl) | $C_2H_5$ (Ethyl) |
| CAP-025 | $C_3H_7$ (Propyl) | H |
| CAP-026 | H | $C_3H_7$ (Propyl) |
| CAP-027 | $C_3H_7$ (Propyl) | $C_3H_7$ (Propyl) |
| CAP-028 | $C_4H_9$ (Butyl) | H |
| CAP-029 | H | $C_4H_9$ (Butyl) |
| CAP-030 | $C_4H_9$ (Butyl) | $C_4H_9$ (Butyl) |
| CAP-031 | $C_5H_{11}$ (Pentyl) | H |
| CAP-032 | H | $C_5H_{11}$ (Pentyl) |
| CAP-033 | $C_5H_{11}$ (Pentyl) | $C_5H_{11}$ (Pentyl) |
| CAP-034 | $H_2C-C\equiv CH$ (Propargyl) | H |
| CAP-035 | H | $H_2C-C\equiv CH$ (Propargyl) |
| CAP-036 | $H_2C-C\equiv CH$ (Propargyl) | $H_2C-C\equiv CH$ (Propargyl) |
| CAP-037 | $CH_2CH=CH_2$ (Allyl) | H |
| CAP-038 | H | $CH_2CH=CH_2$ (Allyl) |
| CAP-039 | $CH_2CH=CH_2$ (Allyl) | $CH_2CH=CH_2$ (Allyl) |
| CAP-040 | $CH_2OCH_3$ (MOM) | H |
| CAP-041 | H | $CH_2OCH_3$ (MOM) |
| CAP-042 | $CH_2OCH_3$ (MOM) | $CH_2OCH_3$ (MOM) |
| CAP-043 | $CH_2OCH_2CH_2OCH_3$ (MEM) | H |
| CAP-044 | H | $CH_2OCH_2CH_2OCH_3$ (MEM) |
| CAP-045 | $CH_2OCH_2CH_2OCH_3$ (MEM) | $CH_2OCH_2CH_2OCH_3$ (MEM) |
| CAP-046 | $CH_2SCH_3$ (MTM) | H |
| CAP-047 | H | $CH_2SCH_3$ (MTM) |
| CAP-048 | $CH_2SCH_3$ (MTM) | $CH_2SCH_3$ (MTM) |
| CAP-049 | $CH_2C_6H_5$ (Benzyl) | H |
| CAP-050 | H | $CH_2C_6H_5$ (Benzyl) |
| CAP-051 | $CH_2C_6H_5$ (Benzyl) | $CH_2C_6H_5$ (Benzyl) |
| CAP-052 | $CH_2OCH_2C_6H_5$ (BOM) | H |
| CAP-053 | H | $CH_2OCH_2C_6H_5$ (BOM) |
| CAP-054 | $CH_2OCH_2C_6H_5$ (BOM) | $CH_2OCH_2C_6H_5$ (BOM) |
| CAP-055 | $CH_2C_6H_4$—OMe (p-Methoxybenzyl) | H |
| CAP-056 | H | $CH_2C_6H_4$—OMe (p-Methoxybenzyl) |
| CAP-057 | $CH_2C_6H_4$—OMe (p-Methoxybenzyl) | $CH_2C_6H_4$—OMe (p-Methoxybenzyl) |
| CAP-058 | $CH_2C_6H_4$—$NO_2$ (p-Nitrobenzyl) | H |
| CAP-059 | H | $CH_2C_6H_4$—$NO_2$ (p-Nitrobenzyl) |
| CAP-060 | $CH_2C_6H_4$—$NO_2$ (p-Nitrobenzyl) | $CH_2C_6H_4$—$NO_2$ (p-Nitrobenzyl) |
| CAP-061 | $CH_2C_6H_4$—X (p-Halobenzyl) where X = F, Cl, Br or I | H |
| CAP-062 | H | $CH_2C_6H_4$—X (p-Halobenzyl) where X = F, Cl, Br or I |
| CAP-063 | $CH_2C_6H_4$—X (p-Halobenzyl) where X = F, Cl, Br or I | $CH_2C_6H_4$—X (p-Halobenzyl) where X = F, Cl, Br or I |
| CAP-064 | $CH_2C_6H_4$—$N_3$ (p-Azidobenzyl) | H |
| CAP-065 | H | $CH_2C_6H_4$—$N_3$ (p-Azidobenzyl) |
| CAP-066 | $CH_2C_6H_4$—$N_3$ (p-Azidobenzyl) | $CH_2C_6H_4$—$N_3$ (p-Azidobenzyl) |
| CAP-067 | $CH_2C_6H_4$—$CF_3$ (p-Trifluoromethylbenzyl) | H |
| CAP-068 | H | $CH_2C_6H_4$—$CF_3$ (p-Trifluoromethylbenzyl) |
| CAP-069 | $CH_2C_6H_4$—$CF_3$ (p-Trifluoromethylbenzyl) | $CH_2C_6H_4$—$CF_3$ (p-Trifluoromethylbenzyl) |
| CAP-070 | $CH_2C_6H_4$—$OCF_3$ (p-Trifluoromethoxylbenzyl) | H |
| CAP-071 | H | $CH_2C_6H_4$—$OCF_3$ (p-Trifluoromethoxylbenzyl) |
| CAP-072 | $CH_2C_6H_4$—$OCF_3$ (p-Trifluoromethoxylbenzyl) | $CH_2C_6H_4$—$OCF_3$ (p-Trifluoromethoxylbenzyl) |
| CAP-073 | $CH_2C_6H_3$—$(CF_3)_2$ [2,4-bis(Trifluoromethyl)benzyl] | H |
| CAP-074 | H | $CH_2C_6H_3$—$(CF_3)_2$ [2,4-bis(Trifluoromethyl)benzyl] |
| CAP-075 | $CH_2C_6H_3$—$(CF_3)_2$ [2,4-bis(Trifluoromethyl)benzyl] | $CH_2C_6H_3$—$(CF_3)_2$ [2,4-bis(Trifluoromethyl)benzyl] |
| CAP-076 | $Si(C_6H_5)_2C_4H_9$ (t-Butyldiphenylsilyl) | H |
| CAP-077 | H | $Si(C_6H_5)_2C_4H_9$ (t-Butyldiphenylsilyl) |
| CAP-078 | $Si(C_6H_5)_2C_4H_9$ (t-Butyldiphenylsilyl) | $Si(C_6H_5)_2C_4H_9$ (t-Butyldiphenylsilyl) |

TABLE 7-continued

R₁ and R₂ groups for CAP-022 to CAP096.

| Cap Structure Number | R₁ | R₂ |
|---|---|---|
| CAP-079 | CH₂CH₂CH=CH₂ (Homoallyl) | H |
| CAP-080 | H | CH₂CH₂CH=CH₂ (Homoallyl) |
| CAP-081 | CH₂CH₂CH=CH₂ (Homoallyl) | CH₂CH₂CH=CH₂ (Homoallyl) |
| CAP-082 | P(O)(OH)₂ (MP) | H |
| CAP-083 | H | P(O)(OH)₂ (MP) |
| CAP-084 | P(O)(OH)₂ (MP) | P(O)(OH)₂ (MP) |
| CAP-085 | P(S)(OH)₂ (Thio-MP) | H |
| CAP-086 | H | P(S)(OH)₂ (Thio-MP) |
| CAP-087 | P(S)(OH)₂ (Thio-MP) | P(S)(OH)₂ (Thio-MP) |
| CAP-088 | P(O)(CH₃)(OH) (Methylphophonate) | H |
| CAP-089 | H | P(O)(CH₃)(OH) (Methylphophonate) |
| CAP-090 | P(O)(CH₃)(OH) (Methylphophonate) | P(O)(CH₃)(OH) (Methylphophonate) |
| CAP-091 | PN(ⁱPr)₂(OCH₂CH₂CN) (Phosporamidite) | H |
| CAP-092 | H | PN(ⁱPr)₂(OCH₂CH₂CN) (Phosporamidite) |
| CAP-093 | PN(ⁱPr)₂(OCH₂CH₂CN) (Phosporamidite) | PN(ⁱPr)₂(OCH₂CH₂CN) (Phosporamidite) |
| CAP-094 | SO₂CH₃ (Methanesulfonic acid) | H |
| CAP-095 | H | SO₂CH₃ (Methanesulfonic acid) |
| CAP-096 | SO₂CH₃ (Methanesulfonic acid) | SO₂CH₃ (Methanesulfonic acid) | or,

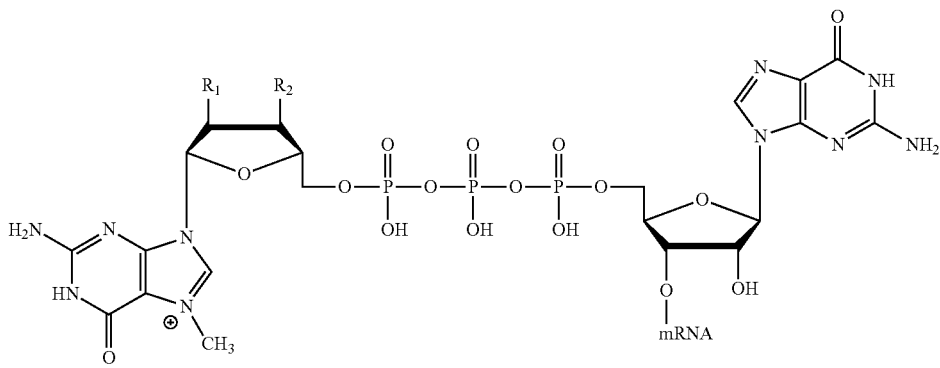

where R₁ and R₂ are defined in Table 8:

TABLE 8

R₁ and R₂ groups for CAP-097 to CAP111.

| Cap Structure Number | R₁ | R₂ |
|---|---|---|
| CAP-097 | NH₂ (amino) | H |
| CAP-098 | H | NH₂ (amino) |
| CAP-099 | NH₂ (amino) | NH₂ (amino) |
| CAP-100 | N₃ (Azido) | H |
| CAP-101 | H | N₃ (Azido) |
| CAP-102 | N₃ (Azido) | N₃ (Azido) |
| CAP-103 | X (Halo: F, Cl, Br, I) | H |
| CAP-104 | H | X (Halo: F, Cl, Br, I) |
| CAP-105 | X (Halo: F, Cl, Br, I) | X (Halo: F, Cl, Br, I) |
| CAP-106 | SH (Thiol) | H |
| CAP-107 | H | SH (Thiol) |
| CAP-108 | SH (Thiol) | SH (Thiol) |
| CAP-109 | SCH₃ (Thiomethyl) | H |

TABLE 8-continued

R₁ and R₂ groups for CAP-097 to CAP111.

| Cap Structure Number | R₁ | R₂ |
|---|---|---|
| CAP-110 | H | SCH₃ (Thiomethyl) |
| CAP-111 | SCH₃ (Thiomethyl) | SCH₃ (Thiomethyl) |

In Table 7, "MOM" stands for methoxymethyl, "MEM" stands for methoxyethoxymethyl, "MTM" stands for methylthiomethyl, "BOM" stands for benzyloxymethyl and "MP" stands for monophosphonate.

In a non-limiting example, the modified 5' cap may have the substrate structure for vaccinia mRNA capping enzyme of:

(CAP-112)
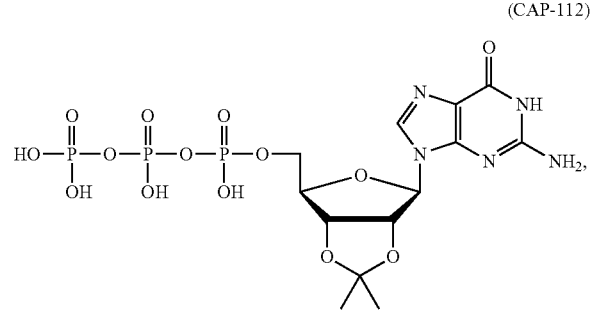
(CAP-113)
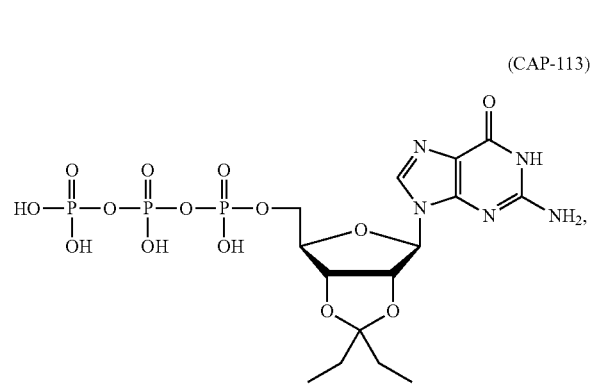
(CAP-114)
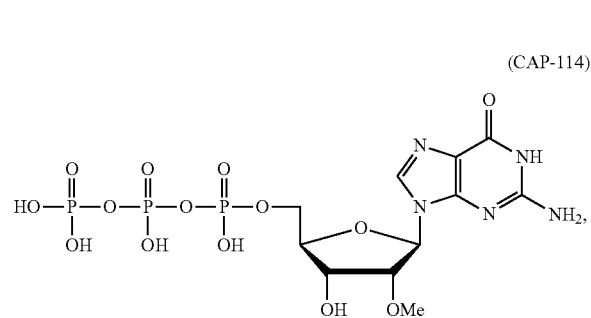
(CAP-115)
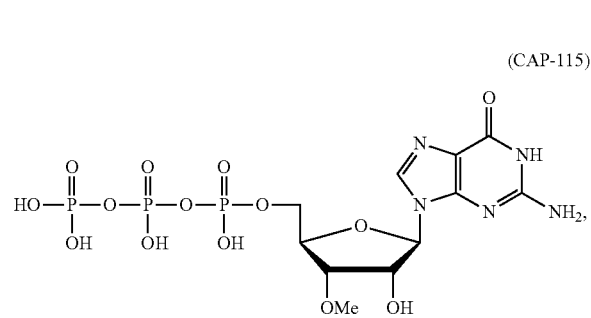
(CAP-116)
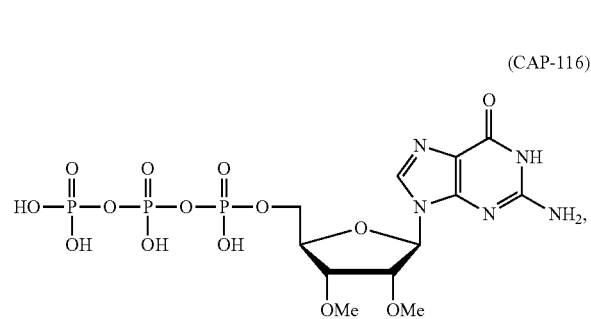
(CAP-117)
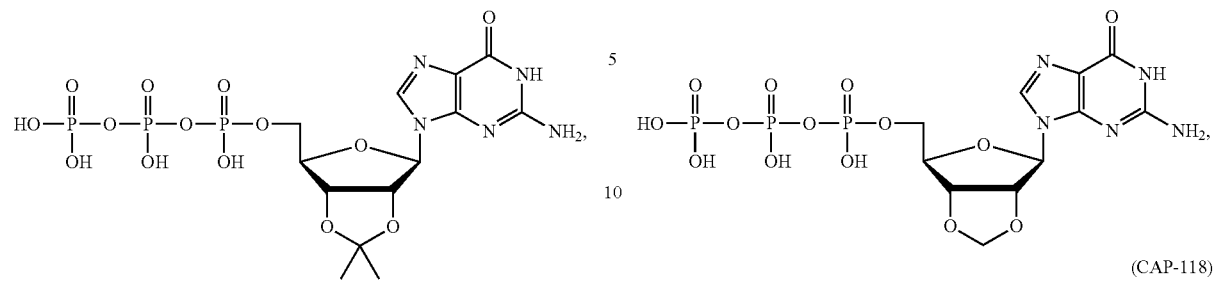
(CAP-118)
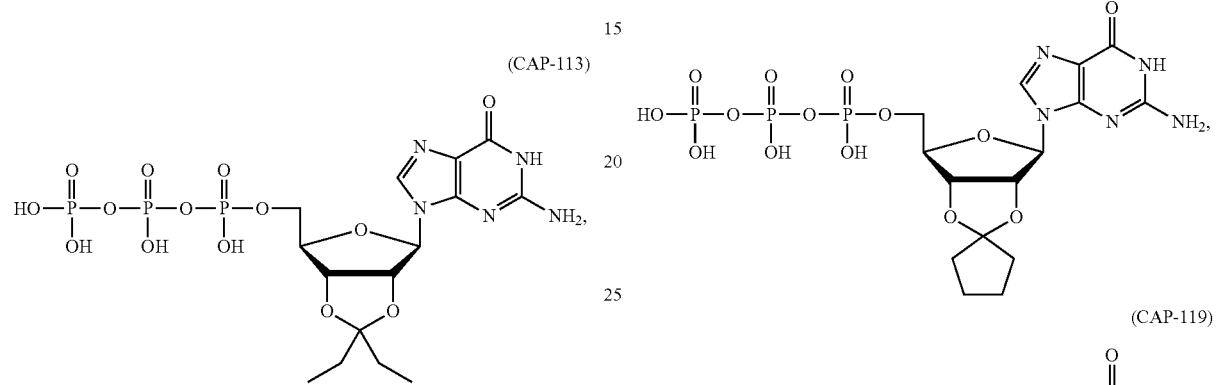
(CAP-119)
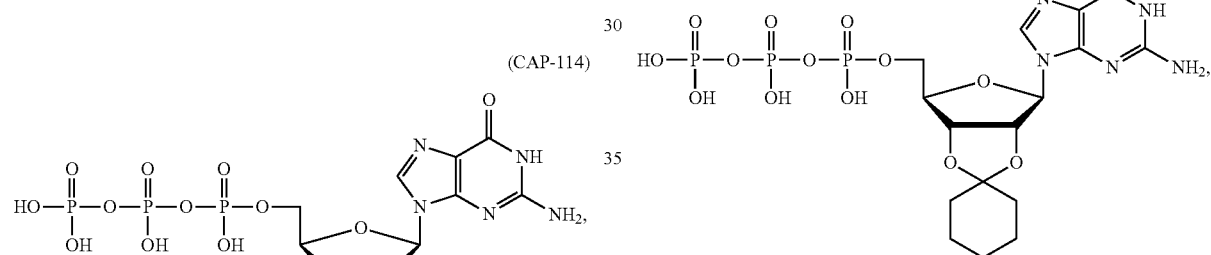
(CAP-120)
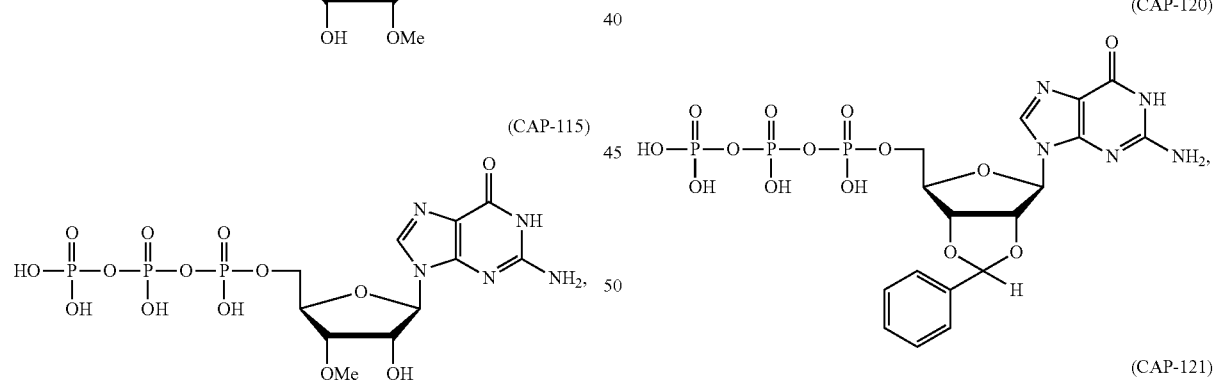
(CAP-121)
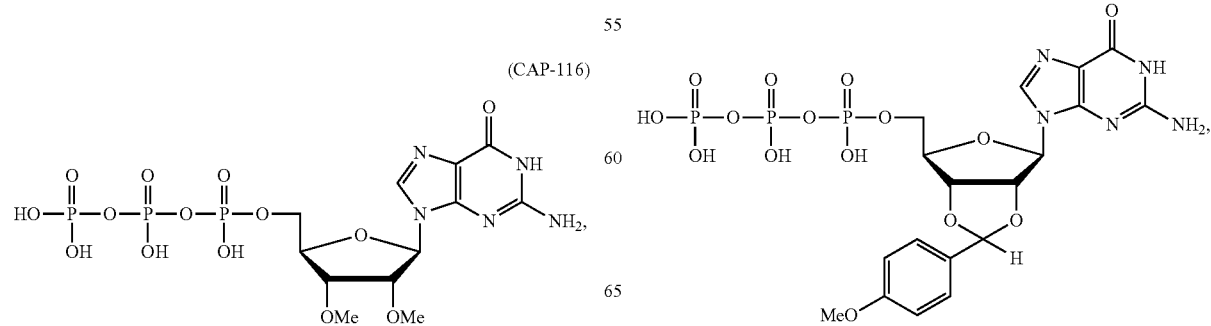

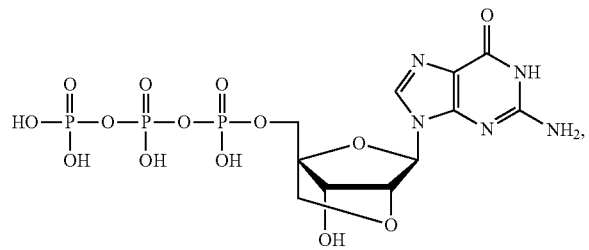
(CAP-122)
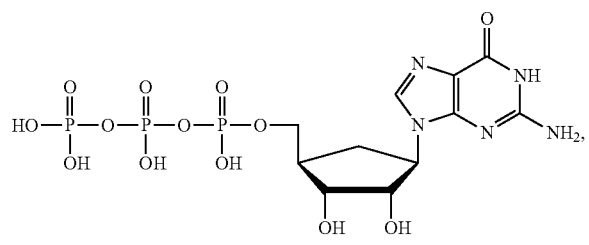
(CAP-123)
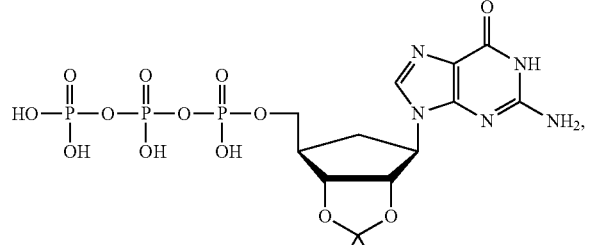
(CAP-124)
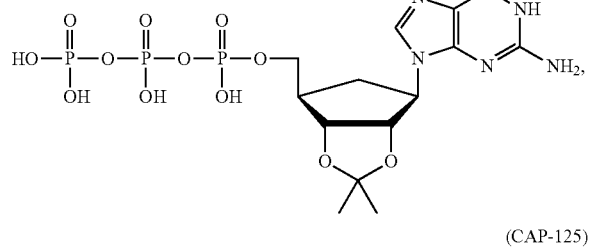
(CAP-125)
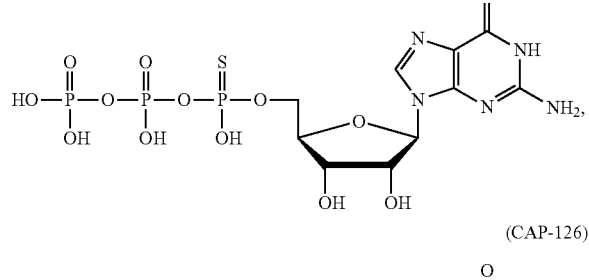
(CAP-126)
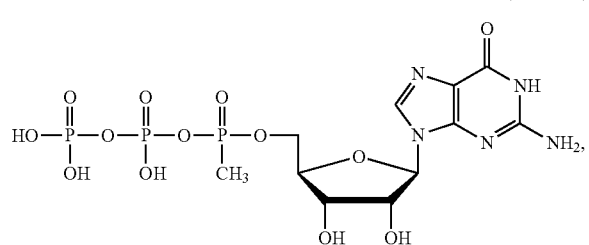
(CAP-127)
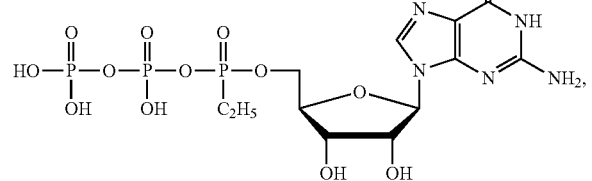
(CAP-128)
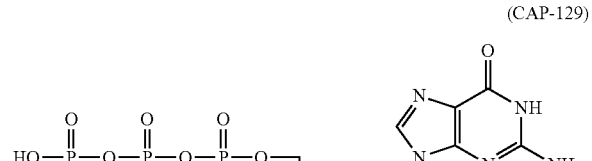
(CAP-129)
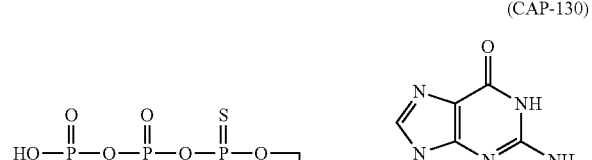
(CAP-130)
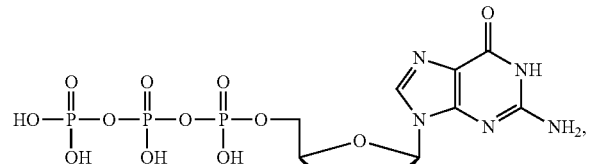
(CAP-131)
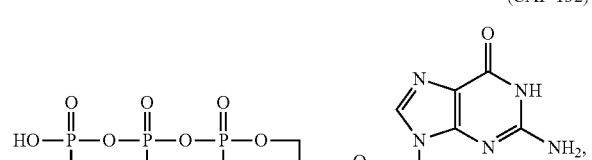
(CAP-132)

(CAP-133)

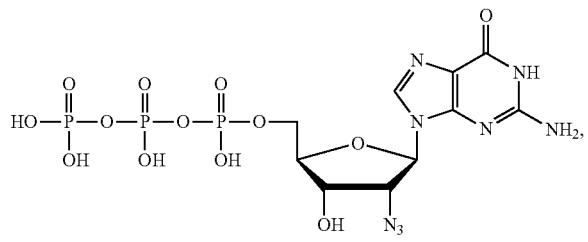

(CAP-134)

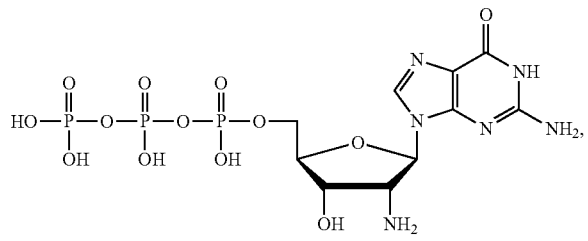

(CAP-135)

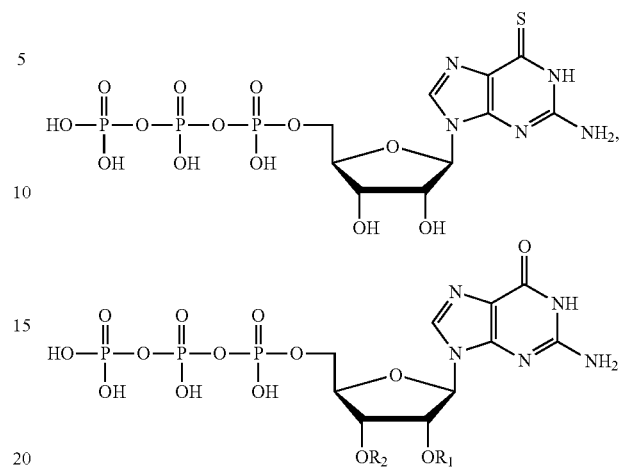

where R₁ and R₂ are defined in Table 9:

TABLE 9

R₁ and R₂ groups for CAP-136 to CAP-210.

| Cap Structure Number | R₁ | R₂ |
|---|---|---|
| CAP-136 | C₂H₅ (Ethyl) | H |
| CAP-137 | H | C₂H₅ (Ethyl) |
| CAP-138 | C₂H₅ (Ethyl) | C₂H₅ (Ethyl) |
| CAP-139 | C₃H₇ (Propyl) | H |
| CAP-140 | H | C₃H₇ (Propyl) |
| CAP-141 | C₃H₇ (Propyl) | C₃H₇ (Propyl) |
| CAP-142 | C₄H₉ (Butyl) | H |
| CAP-143 | H | C₄H₉ (Butyl) |
| CAP-144 | C₄H₉ (Butyl) | C₄H₉ (Butyl) |
| CAP-145 | C₅H₁₁ (Pentyl) | H |
| CAP-146 | H | C₅H₁₁ (Pentyl) |
| CAP-147 | C₅H₁₁ (Pentyl) | C₅H₁₁ (Pentyl) |
| CAP-148 | H₂C—C≡CH (Propargyl) | H |
| CAP-149 | H | H₂C—C≡CH (Propargyl) |
| CAP-150 | H₂C—C≡CH (Propargyl) | H₂C—C≡CH (Propargyl) |
| CAP-151 | CH₂CH=CH₂ (Allyl) | H |
| CAP-152 | H | CH₂CH=CH₂ (Allyl) |
| CAP-153 | CH₂CH=CH₂ (Allyl) | CH₂CH=CH₂ (Allyl) |
| CAP-154 | CH₂OCH₃ (MOM) | H |
| CAP-155 | H | CH₂OCH₃ (MOM) |
| CAP-156 | CH₂OCH₃ (MOM) | CH₂OCH₃ (MOM) |
| CAP-157 | CH₂OCH₂CH₂OCH₃ (MEM) | H |
| CAP-158 | H | CH₂OCH₂CH₂OCH₃ (MEM) |
| CAP-159 | CH₂OCH₂CH₂OCH₃ (MEM) | CH₂OCH₂CH₂OCH₃ (MEM) |
| CAP-160 | CH₂SCH₃ (MTM) | H |
| CAP-161 | H | CH₂SCH₃ (MTM) |
| CAP-162 | CH₂SCH₃ (MTM) | CH₂SCH₃ (MTM) |
| CAP-163 | CH₂C₆H₅ (Benzyl) | H |
| CAP-164 | H | CH₂C₆H₅ (Benzyl) |
| CAP-165 | CH₂C₆H₅ (Benzyl) | CH₂C₆H₅ (Benzyl) |
| CAP-166 | CH₂OCH₂C₆H₅ (BOM) | H |
| CAP-167 | H | CH₂OCH₂C₆H₅ (BOM) |
| CAP-168 | CH₂OCH₂C₆H₅ (BOM) | CH₂OCH₂C₆H₅ (BOM) |
| CAP-169 | CH₂C₆H₄—OMe (p-Methoxybenzyl) | H |
| CAP-170 | H | CH₂C₆H₄—OMe (p-Methoxybenzyl) |
| CAP-171 | CH₂C₆H₄—OMe (p-Methoxybenzyl) | CH₂C₆H₄—OMe (p-Methoxybenzyl) |
| CAP-172 | CH₂C₆H₄—NO₂ (p-Nitrobenzyl) | H |
| CAP-173 | H | CH₂C₆H₄—NO₂ (p-Nitrobenzyl) |
| CAP-174 | CH₂C₆H₄—NO₂ (p-Nitrobenzyl) | CH₂C₆H₄—NO₂ (p-Nitrobenzyl) |
| CAP-175 | CH₂C₆H₄—X (p-Halobenzyl) where X = F, Cl, Br or I | H |

TABLE 9-continued

R₁ and R₂ groups for CAP-136 to CAP-210.

| Cap Structure Number | R₁ | R₂ |
| --- | --- | --- |
| CAP-176 | H | CH₂C₆H₄—X (p-Halobenzyl) where X = F, Cl, Br or I |
| CAP-177 | CH₂C₆H₄—X (p-Halobenzyl) where X = F, Cl, Br or I | CH₂C₆H₄—X (p-Halobenzyl) where X = F, Cl, Br or I |
| CAP-178 | CH₂C₆H₄—N₃ (p-Azidobenzyl) | H |
| CAP-179 | H | CH₂C₆H₄—N₃ (p-Azidobenzyl) |
| CAP-180 | CH₂C₆H₄—N₃ (p-Azidobenzyl) | CH₂C₆H₄—N₃ (p-Azidobenzyl) |
| CAP-181 | CH₂C₆H₄—CF₃ (p-Trifluoromethylbenzyl) | H |
| CAP-182 | H | CH₂C₆H₄—CF₃ (p-Trifluoromethylbenzyl) |
| CAP-183 | CH₂C₆H₄—CF₃ (p-Trifluoromethylbenzyl) | CH₂C₆H₄—CF₃ (p-Trifluoromethylbenzyl) |
| CAP-184 | CH₂C₆H₄—OCF₃ (p-Trifluoromethoxylbenzyl) | H |
| CAP-185 | H | CH₂C₆H₄—OCF₃ (p-Trifluoromethoxylbenzyl) |
| CAP-186 | CH₂C₆H₄—OCF₃ (p-Trifluoromethoxylbenzyl) | CH₂C₆H₄—OCF₃ (p-Trifluoromethoxylbenzyl) |
| CAP-187 | CH₂C₆H₃—(CF₃)₂ [2,4-bis(Trifluoromethyl)benzyl] | H |
| CAP-188 | H | CH₂C₆H₃—(CF₃)₂ [2,4-bis(Trifluoromethyl)benzyl] |
| CAP-189 | CH₂C₆H₃—(CF₃)₂ [2,4-bis(Trifluoromethyl)benzyl] | CH₂C₆H₃—(CF₃)₂ [2,4-bis(Trifluoromethyl)benzyl] |
| CAP-190 | Si(C₆H₅)₂C₄H₉ (t-Butyldiphenylsilyl) | H |
| CAP-191 | H | Si(C₆H₅)₂C₄H₉ (t-Butyldiphenylsilyl) |
| CAP-192 | Si(C₆H₅)₂C₄H₉ (t-Butyldiphenylsilyl) | Si(C₆H₅)₂C₄H₉ (t-Butyldiphenylsilyl) |
| CAP-193 | CH₂CH₂CH=CH₂ (Homoallyl) | H |
| CAP-194 | H | CH₂CH₂CH=CH₂ (Homoallyl) |
| CAP-195 | CH₂CH₂CH=CH₂ (Homoallyl) | CH₂CH₂CH=CH₂ (Homoallyl) |
| CAP-196 | P(O)(OH)₂ (MP) | H |
| CAP-197 | H | P(O)(OH)₂ (MP) |
| CAP-198 | P(O)(OH)₂ (MP) | P(O)(OH)₂ (MP) |
| CAP-199 | P(S)(OH)₂ (Thio-MP) | H |
| CAP-200 | H | P(S)(OH)₂ (Thio-MP) |
| CAP-201 | P(S)(OH)₂ (Thio-MP) | P(S)(OH)₂ (Thio-MP) |
| CAP-202 | P(O)(CH₃)(OH) (Methylphophonate) | H |
| CAP-203 | H | P(O)(CH₃)(OH) (Methylphophonate) |
| CAP-204 | P(O)(CH₃)(OH) (Methylphophonate) | P(O)(CH₃)(OH) (Methylphophonate) |
| CAP-205 | PN(ⁱPr)₂(OCH₂CH₂CN) (Phosporamidite) | H |
| CAP-206 | H | PN(ⁱPr)₂(OCH₂CH₂CN) (Phosporamidite) |
| CAP-207 | PN(ⁱPr)₂(OCH₂CH₂CN) (Phosporamidite) | PN(ⁱPr)₂(OCH₂CH₂CN) (Phosporamidite) |
| CAP-208 | SO₂CH₃ (Methanesulfonic acid) | H |
| CAP-209 | H | SO₂CH₃ (Methanesulfonic acid) |
| CAP-210 | SO₂CH₃ (Methanesulfonic acid) | SO₂CH₃ (Methanesulfonic acid) | or

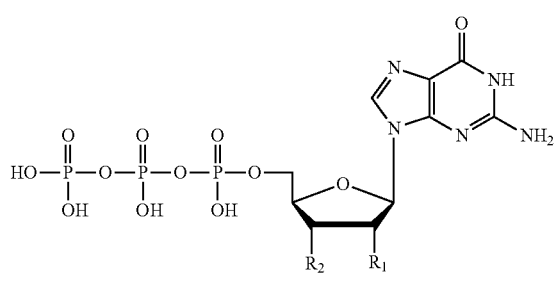

where R₁ and R₂ are defined in Table 10:

TABLE 10

R₁ and R₂ groups for CAP-211 to 225.

| Cap Structure Number | R₁ | R₂ |
| --- | --- | --- |
| CAP-211 | NH₂ (amino) | H |
| CAP-212 | H | NH₂ (amino) |
| CAP-213 | NH₂ (amino) | NH₂ (amino) |
| CAP-214 | N₃ (Azido) | H |
| CAP-215 | H | N₃ (Azido) |
| CAP-216 | N₃ (Azido) | N₃ (Azido) |
| CAP-217 | X (Halo: F, Cl, Br, I) | H |

TABLE 10-continued

R₁ and R₂ groups for CAP-211 to 225.

| Cap Structure Number | R₁ | R₂ |
|---|---|---|
| CAP-218 | H | X (Halo: F, Cl, Br, I) |
| CAP-219 | X (Halo: F, Cl, Br, I) | X (Halo: F, Cl, Br, I) |
| CAP-220 | SH (Thiol) | H |
| CAP-221 | H | SH (Thiol) |
| CAP-222 | SH (Thiol) | SH (Thiol) |
| CAP-223 | SCH₃ (Thiomethyl) | H |
| CAP-224 | H | SCH₃ (Thiomethyl) |
| CAP-225 | SCH₃ (Thiomethyl) | SCH₃ (Thiomethyl) |

In Table 9, "MOM" stands for methoxymethyl, "MEM" stands for methoxyethoxymethyl, "MTM" stands for methylthiomethyl, "BOM" stands for benzyloxymethyl and "MP" stands for monophosphonate.

In another non-limiting example, of the modified capping structure substrates CAP-112-CAP-225 could be added in the presence of vaccinia capping enzyme with a component to create enzymatic activity such as, but not limited to, S-adenosylmethionine (AdoMet), to form a modified cap for mRNA.

In one embodiment, the replacement of the sugar ring oxygen (that produced the carbocyclic ring) with a methylene moiety ($CH_2$) could create greater stability to the C—N bond against phosphorylases as the C—N bond is resistant to acid or enzymatic hydrolysis. The methylene moiety may also increase the stability of the triphosphate bridge moiety and thus increasing the stability of the mRNA. As a non-limiting example, the cap substrate structure for cap dependent translation may have the structure such as, but not limited to, CAP-014 and CAP-015 and/or the cap substrate structure for vaccinia mRNA capping enzyme such as, but not limited to, CAP-123 and CAP-124. In another example, CAP-112-CAP-122 and/or CAP-125-CAP-225, can be modified by replacing the sugar ring oxygen (that produced the carbocyclic ring) with a methylene moiety ($CH_2$).

In another embodiment, the triphosphate bridge may be modified by the replacement of at least one oxygen with sulfur (thio), a borane ($BH_3$) moiety, a methyl group, an ethyl group, a methoxy group and/or combinations thereof. This modification could increase the stability of the mRNA towards decapping enzymes. As a non-limiting example, the cap substrate structure for cap dependent translation may have the structure such as, but not limited to, CAP-016-CAP-021 and/or the cap substrate structure for vaccinia mRNA capping enzyme such as, but not limited to, CAP-125-CAP-130. In another example, CAP-003-CAP-015, CAP-022-CAP-124 and/or CAP-131-CAP-225, can be modified on the triphosphate bridge by replacing at least one of the triphosphate bridge oxygens with sulfur (thio), a borane ($BH_3$) moiety, a methyl group, an ethyl group, a methoxy group and/or combinations thereof.

In one embodiment, CAP-001-134 and/or CAP-136-CAP-225 may be modified to be a thioguanosine analog similar to CAP-135. The thioguanosine analog may comprise additional modifications such as, but not limited to, a modification at the triphosphate moiety (e.g., thio, $BH_3$, $CH_3$, $C_2H_5$, $OCH_3$, S and S with $OCH_3$), a modification at the 2' and/or 3' positions of 6-thio guanosine as described herein and/or a replacement of the sugar ring oxygen (that produced the carbocyclic ring) as described herein.

In one embodiment, CAP-001-121 and/or CAP-123-CAP-225 may be altered to be an alternative 5' cap similar to CAP-122. The alternative 5' cap may comprise additional alterations such as, but not limited to, an alteration at the triphosphate moiety (e.g., thio, $BH_3$, $CH_3$, $C_2H_5$, $OCH_3$, S and S with $OCH_3$), an alteration at the 2' and/or 3' positions of 6-thio guanosine as described herein and/or a replacement of the sugar ring oxygen (that produced the carbocyclic ring) as described herein.

In one embodiment, the 5' cap modification may be the attachment of biotin or conjugation at the 2' or 3' position of a GTP.

In another embodiment, the 5' cap modification may include a $CF_2$ modified triphosphate moiety.

In another embodiment, the triphosphate bridge of any of the cap structures described herein may be replaced with a tetraphosphate or pentaphosphate bridge. Examples of tetraphosphate and pentaphosphate containing bridges and other cap modifications are described in Jemielity, J. et al. RNA 2003 9:1108-1122; Grudzien-Nogalska, E. et al. Methods Mol. Biol. 2013 969:55-72; and Grudzien, E. et al. RNA, 2004 10:1479-1487, each of which is incorporated herein by reference in its entirety.

Terminal Architecture Alterations: Stem Loop

In one embodiment, the nucleic acids of the present invention may include a stem loop such as, but not limited to, a histone stem loop. The stem loop may be a nucleotide sequence that is about 25 or about 26 nucleotides in length such as, but not limited to, SEQ ID NOs: 7-17 as described in International Patent Publication No. WO2013103659, incorporated herein by reference in its entirety. The histone stem loop may be located 3' relative to the coding region (e.g., at the 3' terminus of the coding region). As a non-limiting example, the stem loop may be located at the 3' end of a nucleic acid described herein.

In one embodiment, the stem loop may be located in the second terminal region. As a non-limiting example, the stem loop may be located within an untranslated region (e.g., 3' UTR) in the second terminal region.

In one embodiment, the nucleic acid such as, but not limited to mRNA, which comprises the histone stem loop may be stabilized by the addition of at least one chain terminating nucleoside. Not wishing to be bound by theory, the addition of at least one chain terminating nucleoside may slow the degradation of a nucleic acid and thus can increase the half-life of the nucleic acid.

In one embodiment, the chain terminating nucleoside may be, but is not limited to, those described in International Patent Publication No. WO2013103659, incorporated herein by reference in its entirety. In another embodiment, the chain terminating nucleosides which may be used with the present invention includes, but is not limited to, 3'-deoxyadenosine (cordycepin), 3'-deoxyuridine, 3'-deoxycytidine, 3'-deoxyguanosine, 3'-deoxythymidine, 2',3'-dideoxynucleosides, such as 2',3'-dideoxyadenosine, 2',3'-dideoxyuridine, 2',3'-dideoxycytidine, 2',3'-dideoxyguanosine, 2',3'-dideoxythymidine, a 2'-deoxynucleoside, or a —O— methylnucleoside.

In another embodiment, the nucleic acid such as, but not limited to mRNA, which comprises the histone stem loop may be stabilized by an alteration to the 3' region of the nucleic acid that can prevent and/or inhibit the addition of oligio(U) (see e.g., International Patent Publication No. WO2013103659, incorporated herein by reference in its entirety).

In yet another embodiment, the nucleic acid such as, but not limited to mRNA, which comprises the histone stem loop may be stabilized by the addition of an oligonucleotide that terminates in a 3'-deoxynucleoside, 2',3'-dideoxynucleoside 3'-O-methylnucleosides, 3'-O-ethylnucleosides, 3'-arabinosides, and other alternative nucleosides known in the art and/or described herein.

In one embodiment, the nucleic acids of the present invention may include a histone stem loop, a polyA tail sequence and/or a 5' cap structure. The histone stem loop may be before and/or after the polyA tail sequence. The nucleic acids comprising the histone stem loop and a polyA tail sequence may include a chain terminating nucleoside described herein.

In another embodiment, the nucleic acids of the present invention may include a histone stem loop and a 5' cap structure. The 5' cap structure may include, but is not limited to, those described herein and/or known in the art.

In one embodiment, the conserved stem loop region may comprise a miR sequence described herein. As a non-limiting example, the stem loop region may comprise the seed sequence of a miR sequence described herein. In another non-limiting example, the stem loop region may comprise a miR-122 seed sequence.

In another embodiment, the conserved stem loop region may comprise a miR sequence described herein and may also include a TEE sequence.

In one embodiment, the incorporation of a miR sequence and/or a TEE sequence changes the shape of the stem loop region which may increase and/or decrease translation. (see e.g, Kedde et al. A *Pumilio*-induced RNA structure switch in p27-3' UTR controls miR-221 and miR-22 accessibility. Nature Cell Biology. 2010, herein incorporated by reference in its entirety).

In one embodiment, the alternative nucleic acids described herein may comprise at least one histone stem-loop and a polyA sequence or polyadenylation signal. Non-limiting examples of nucleic acid sequences encoding for at least one histone stem-loop and a polyA sequence or a polyadenylation signal are described in International Patent Publication Nos. WO2013120497, WO2013120629, WO2013120500, WO2013120627, WO2013120498, WO2013120626, WO2013120499 and WO2013120628, the contents of each of which are incorporated herein by reference in their entirety. In one embodiment, the nucleic acid encoding for a histone stem loop and a polyA sequence or a polyadenylation signal may code for a pathogen antigen or fragment thereof such as the nucleic acid sequences described in International Patent Publication Nos. WO2013120499 and WO2013120628, the contents of both of which are incorporated herein by reference in their entirety. In another embodiment, the nucleic acid encoding for a histone stem loop and a polyA sequence or a polyadenylation signal may code for a therapeutic protein such as the nucleic acid sequences described in International Patent Publication Nos. WO2013120497 and WO2013120629, the contents of both of which are incorporated herein by reference in their entirety. In one embodiment, the nucleic acid encoding for a histone stem loop and a polyA sequence or a polyadenylation signal may code for a tumor antigen or fragment thereof such as the nucleic acid sequences described in International Patent Publication Nos. WO2013120500 and WO2013120627, the contents of both of which are incorporated herein by reference in their entirety. In another embodiment, the nucleic acid encoding for a histone stem loop and a polyA sequence or a polyadenylation signal may code for a allergenic antigen or an autoimmune self-antigen such as the nucleic acid sequences described in International Patent Publication Nos. WO2013120498 and WO2013120626, the contents of both of which are incorporated herein by reference in their entirety.

Terminal Architecture Alterations: 3' UTR and Triple Helices

In one embodiment, nucleic acids of the present invention may include a triple helix on the 3' end of the alternative nucleic acid, enhanced alternative RNA or ribonucleic acid. The 3' end of the nucleic acids of the present invention may include a triple helix alone or in combination with a Poly-A tail.

In one embodiment, the nucleic acid of the present invention may comprise at least a first and a second U-rich region, a conserved stem loop region between the first and second region and an A-rich region. The first and second U-rich region and the A-rich region may associate to form a triple helix on the 3' end of the nucleic acid. This triple helix may stabilize the nucleic acid, enhance the translational efficiency of the nucleic acid and/or protect the 3' end from degradation. Exemplary triple helices include, but are not limited to, the triple helix sequence of metastasis-associated lung adenocarcinoma transcript 1 (MALAT1), MEN-β and polyadenylated nuclear (PAN) RNA (See Wilusz et al., Genes & Development 2012 26:2392-2407; herein incorporated by reference in its entirety). In one embodiment, the 3' end of the alternative nucleic acid, enhanced alternative RNA or ribonucleic acids of the present invention comprises a first U-rich region comprising TTTTTCTTTT (SEQ ID NO: 11), a second U-rich region comprising TTTT-GCTTTTT (SEQ ID NO: 12) or TTTTGCTTTT (SEQ ID NO: 13), an A-rich region comprising AAAAAGCAAAA (SEQ ID NO: 14). In another embodiment, the 3' end of the nucleic acids of the present invention comprises a triple helix formation structure comprising a first U-rich region, a conserved region, a second U-rich region and an A-rich region.

In one embodiment, the triple helix may be formed from the cleavage of a MALAT1 sequence prior to the cloverleaf structure. While not meaning to be bound by theory, MALAT1 is a long non-coding RNA which, when cleaved, forms a triple helix and a tRNA-like cloverleaf structure. The MALAT1 transcript then localizes to nuclear speckles and the tRNA-like cloverleaf localizes to the cytoplasm (Wilusz et al. Cell 2008 135(5): 919-932; incorporated herein by reference in its entirety).

As a non-limiting example, the terminal end of the nucleic acid of the present invention comprising the MALAT1 sequence can then form a triple helix structure, after RNaseP cleavage from the cloverleaf structure, which stabilizes the nucleic acid (Peart et al. Non-mRNA 3' end formation: how the other half lives; WIREs RNA 2013; incorporated herein by reference in its entirety).

In one embodiment, the nucleic acids or mRNA described herein comprise a MALAT1 sequence. In another embodiment, the nucleic acids or mRNA may be polyadenylated. In yet another embodiment, the nucleic acids or mRNA is not polyadenylated but has an increased resistance to degradation compared to unaltered nucleic acids or mRNA.

In one embodiment, the nucleic acids of the present invention may comprise a MALAT1 sequence in the second flanking region (e.g., the 3' UTR). As a non-limiting example, the MALAT1 sequence may be human or mouse.

In another embodiment, the cloverleaf structure of the MALAT1 sequence may also undergo processing by RNaseZ and CCA adding enzyme to form a tRNA-like structure called mascRNA (MALAT1-associated small cytoplasmic RNA). As a non-limiting example, the mascRNA may encode a protein or a fragment thereof and/or may comprise a microRNA sequence. The mascRNA may comprise at least one chemical alteration described herein.

Terminal Architecture Alterations: Poly-A Tails

During RNA processing, a long chain of adenosine nucleotides (poly-A tail) is normally added to a messenger RNA (mRNA) molecules to increase the stability of the molecule. Immediately after transcription, the 3' end of the transcript is cleaved to free a 3' hydroxyl. Then poly-A polymerase adds a chain of adenosine nucleotides to the RNA. The process, called polyadenylation, adds a poly-A tail that is between 100 and 250 residues long.

Methods for the stabilization of RNA by incorporation of chain-terminating nucleosides at the 3'-terminus include those described in International Patent Publication No. WO2013103659, incorporated herein in its entirety.

Unique poly-A tail lengths may provide certain advantages to the alternative RNAs of the present invention.

Generally, the length of a poly-A tail of the present invention is greater than 30 nucleotides in length. In another embodiment, the poly-A tail is greater than 35 nucleotides in length. In another embodiment, the length is at least 40 nucleotides. In another embodiment, the length is at least 45 nucleotides. In another embodiment, the length is at least 55 nucleotides. In another embodiment, the length is at least 60 nucleotides. In another embodiment, the length is at least 60 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1700 nucleotides. In another embodiment, the length is at least 1800 nucleotides. In another embodiment, the length is at least 1900 nucleotides. In another embodiment, the length is at least 2000 nucleotides. In another embodiment, the length is at least 2500 nucleotides. In another embodiment, the length is at least 3000 nucleotides.

In some embodiments, the nucleic acid or mRNA includes from about 30 to about 3,000 nucleotides (e.g., from 30 to 50, from 30 to 100, from 30 to 250, from 30 to 500, from 30 to 750, from 30 to 1,000, from 30 to 1,500, from 30 to 2,000, from 30 to 2,500, from 50 to 100, from 50 to 250, from 50 to 500, from 50 to 750, from 50 to 1,000, from 50 to 1,500, from 50 to 2,000, from 50 to 2,500, from 50 to 3,000, from 100 to 500, from 100 to 750, from 100 to 1,000, from 100 to 1,500, from 100 to 2,000, from 100 to 2,500, from 100 to 3,000, from 500 to 750, from 500 to 1,000, from 500 to 1,500, from 500 to 2,000, from 500 to 2,500, from 500 to 3,000, from 1,000 to 1,500, from 1,000 to 2,000, from 1,000 to 2,500, from 1,000 to 3,000, from 1,500 to 2,000, from 1,500 to 2,500, from 1,500 to 3,000, from 2,000 to 3,000, from 2,000 to 2,500, and from 2,500 to 3,000).

In one embodiment, the poly-A tail may be 80 nucleotides, 120 nucleotides, 160 nucleotides in length on an alternative RNA molecule described herein.

In another embodiment, the poly-A tail may be 20, 40, 80, 100, 120, 140 or 160 nucleotides in length on an alternative RNA molecule described herein.

In one embodiment, the poly-A tail is designed relative to the length of the overall alternative RNA molecule. This design may be based on the length of the coding region of the alternative RNA, the length of a particular feature or region of the alternative RNA (such as the mRNA), or based on the length of the ultimate product expressed from the alternative RNA. When relative to any additional feature of the alternative RNA (e.g., other than the mRNA portion which includes the poly-A tail) the poly-A tail may be 10, 20, 30, 40, 50, 60, 70, 80, 90 or 100% greater in length than the additional feature. The poly-A tail may also be designed as a fraction of the alternative RNA to which it belongs. In this context, the poly-A tail may be 10, 20, 30, 40, 50, 60, 70, 80, or 90% or more of the total length of the construct or the total length of the construct minus the poly-A tail.

In one embodiment, engineered binding sites and/or the conjugation of nucleic acids or mRNA for Poly-A binding protein (PABP) may be used to enhance expression. The engineered binding sites may be sensor sequences which can operate as binding sites for ligands of the local microenvironment of the nucleic acids and/or mRNA. As a non-limiting example, the nucleic acids and/or mRNA may comprise at least one engineered binding site to alter the binding affinity of PABP and analogs thereof. The incorporation of at least one engineered binding site may increase the binding affinity of the PABP and analogs thereof.

Additionally, multiple distinct nucleic acids or mRNA may be linked together to the PABP through the 3'-end using alternative nucleotides at the 3'-terminus of the poly-A tail. Transfection experiments can be conducted in relevant cell lines at and protein production can be assayed by ELISA at 12 hr, 24 hr, 48 hr, 72 hr and day 7 post-transfection. As a non-limiting example, the transfection experiments may be used to evaluate the effect on PABP or analogs thereof binding affinity as a result of the addition of at least one engineered binding site.

In one embodiment, a polyA tail may be used to modulate translation initiation. While not wishing to be bound by theory, the polyA tail recruits PABP which in turn can interact with translation initiation complex and thus may be essential for protein synthesis.

In another embodiment, a polyA tail may also be used in the present invention to protect against 3'-5' exonuclease digestion.

In one embodiment, the nucleic acids or mRNA of the present invention are designed to include a polyA-G Quartet. The G-quartet is a cyclic hydrogen bonded array of four guanosine nucleotides that can be formed by G-rich sequences in both DNA and RNA. In this embodiment, the G-quartet is incorporated at the end of the poly-A tail. The resultant nucleic acid or mRNA may be assayed for stability, protein production and other parameters including half-life at various time points. It has been discovered that the polyA-G quartet results in protein production equivalent to at least 75% of that seen using a poly-A tail of 120 nucleotides alone.

In one embodiment, the nucleic acids or mRNA of the present invention may comprise a polyA tail and may be stabilized by the addition of a chain terminating nucleoside. The nucleic acids and/or mRNA with a polyA tail may further comprise a 5' cap structure.

In another embodiment, the nucleic acids or mRNA of the present invention may comprise a polyA-G Quartet. The nucleic acids and/or mRNA with a polyA-G Quartet may further comprise a 5' cap structure.

In one embodiment, the chain terminating nucleoside which may be used to stabilize the nucleic acid or mRNA comprising a polyA tail or polyA-G Quartet may be, but is not limited to, those described in International Patent Publication No. WO2013103659, incorporated herein by reference in its entirety. In another embodiment, the chain terminating nucleosides which may be used with the present invention includes, but is not limited to, 3'-deoxyadenosine (cordycepin), 3'-deoxyuridine, 3'-deoxycytidine, 3'-deoxyguanosine, 3'-deoxythymidine, 2',3'-dideoxynucleosides, such as 2',3'-dideoxyadenosine, 2',3'-dideoxyuridine, 2',3'-dideoxycytidine, 2',3'-dideoxyguanosine, 2',3'-dideoxythymidine, a 2'-deoxynucleoside, or a —O— methylnucleoside.

In another embodiment, the nucleic acid such as, but not limited to mRNA, which comprise a polyA tail or a polyA-G Quartet may be stabilized by an alteration to the 3' region of the nucleic acid that can prevent and/or inhibit the addition of oligio(U) (see e.g., International Patent Publication No. WO2013103659, incorporated herein by reference in its entirety).

In yet another embodiment, the nucleic acid such as, but not limited to mRNA, which comprise a polyA tail or a polyA-G Quartet may be stabilized by the addition of an oligonucleotide that terminates in a 3'-deoxynucleoside, 2',3'-dideoxynucleoside 3'-O-methylnucleosides, 3'-O-ethylnucleosides, 3'-arabinosides, and other alternative nucleosides known in the art and/or described herein.

5' UTR, 3' UTR and Translation Enhancer Elements (TEEs)

In one embodiment, the 5' UTR of the polynucleotides, primary constructs, alternative nucleic acids and/or mRNA may include at least one translational enhancer polynucleotide, translation enhancer element, translational enhancer elements (collectively referred to as "TEE"s). As a non-limiting example, the TEE may be located between the transcription promoter and the start codon. The polynucleotides, primary constructs, alternative nucleic acids and/or mmRNA with at least one TEE in the 5' UTR may include a cap at the 5' UTR. Further, at least one TEE may be located in the 5' UTR of polynucleotides, primary constructs, alternative nucleic acids and/or mRNA undergoing cap-dependent or cap-independent translation.

The term "translational enhancer element" or "translation enhancer element" (herein collectively referred to as "TEE") refers to sequences that increase the amount of polypeptide or protein produced from an mRNA.

In one aspect, TEEs are conserved elements in the UTR which can promote translational activity of a nucleic acid such as, but not limited to, cap-dependent or cap-independent translation. The conservation of these sequences has been previously shown by Panek et al (Nucleic Acids Research, 2013, 1-10; incorporated herein by reference in its entirety) across 14 species including humans.

In one non-limiting example, the TEEs known may be in the 5'-leader of the Gtx homeodomain protein (Chappell et al., Proc. Natl. Acad. Sci. USA 101:9590-9594, 2004, incorporated herein by reference in its entirety).

In another non-limiting example, TEEs are disclosed as SEQ ID NOs: 1-35 in US Patent Publication No. 20090226470, SEQ ID NOs: 1-35 in US Patent Publication No. 20130177581, SEQ ID NOs: 1-35 in International Patent Publication No. WO2009075886, SEQ ID NOs: 1-5, and 7-645 in International Patent Publication No. WO2012009644, SEQ ID NO: 1 in International Patent Publication No. WO1999024595, SEQ ID NO: 1 in U.S. Pat. No. 6,310,197, and SEQ ID NO: 1 in U.S. Pat. No. 6,849,405, each of which is incorporated herein by reference in its entirety.

In yet another non-limiting example, the TEE may be an internal ribosome entry site (IRES), HCV-IRES or an IRES element such as, but not limited to, those described in U.S. Pat. No. 7,468,275, US Patent Publication Nos. 20070048776 and 20110124100 and International Patent Publication Nos. WO2007025008 and WO2001055369, each of which is incorporated herein by reference in its entirety. The IRES elements may include, but are not limited to, the Gtx sequences (e.g., Gtx9-nt, Gtx8-nt, Gtx7-nt) described by Chappell et al. (Proc. Natl. Acad. Sci. USA 101:9590-9594, 2004) and Zhou et al. (PNAS 102:6273-6278, 2005) and in US Patent Publication Nos. 20070048776 and 20110124100 and International Patent Publication No. WO2007025008, each of which is incorporated herein by reference in its entirety.

"Translational enhancer polynucleotides" or "translation enhancer polynucleotide sequences" are polynucleotides which include one or more of the specific TEE exemplified herein and/or disclosed in the art (see e.g., U.S. Pat. Nos. 6,310,197, 6,849,405, 7,456,273, 7,183,395, US Patent Publication Nos. 20090226470, 20070048776, 20110124100, 20090093049, 20130177581, International Patent Publication Nos. WO2009075886, WO2007025008, WO2012009644, WO2001055371 WO1999024595, and European Patent Publication Nos. 2610341A1 and 2610340A1; each of which is incorporated herein by reference in its entirety) or their variants, homologs or functional derivatives. One or multiple copies of a specific TEE can be present in the polynucleotides, primary constructs, alternative nucleic acids and/or mRNA. The TEEs in the translational enhancer polynucleotides can be organized in one or more sequence segments. A sequence segment can harbor one or more of the specific TEEs exemplified herein, with each TEE being present in one or more copies. When multiple sequence segments are present in a translational enhancer polynucleotide, they can be homogenous or heterogeneous. Thus, the multiple sequence segments in a translational enhancer polynucleotide can harbor identical or different types of the specific TEEs exemplified herein, identical or different number of copies of each of the specific TEEs, and/or identical or different organization of the TEEs within each sequence segment.

In one embodiment, the polynucleotides, primary constructs, alternative nucleic acids and/or mmRNA may include at least one TEE that is described in International Patent Publication Nos. WO1999024595, WO2012009644, WO2009075886, WO2007025008, WO1999024595, European Patent Publication Nos. 2610341A1 and 2610340A1, U.S. Pat. Nos. 6,310,197, 6,849,405, 7,456,273, 7,183,395, US Patent Publication Nos. 20090226470, 20110124100, 20070048776, 20090093049, and 20130177581 each of which is incorporated herein by reference in its entirety. The TEE may be located in the 5'UTR of the polynucleotides, primary constructs, alternative nucleic acids and/or mRNA.

In another embodiment, the polynucleotides, primary constructs, alternative nucleic acids and/or mmRNA may include at least one TEE that has at least 50%, at least 55%, at least 60%, at least 65%, at least 70%, at least 75%, at least 80%, at least 85%, at least 90%, at least 95% or at least 99% identity with the TEEs described in US Patent Publication Nos. 20090226470, 20070048776, 20130177581 and 20110124100, International Patent Publication Nos. WO1999024595, WO2012009644, WO2009075886 and WO2007025008, European Patent Publication Nos. 2610341A1 and 2610340A1, U.S. Pat. Nos. 6,310,197, 6,849,405, 7,456,273, 7,183,395, each of which is incorporated herein by reference in its entirety.

In one embodiment, the 5' UTR of the polynucleotides, primary constructs, alternative nucleic acids and/or mRNA may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. The TEE sequences in the 5' UTR of the polynucleotides, primary constructs, alternative nucleic acids and/or mRNA of the present invention may be the same or different TEE sequences. The TEE sequences may be in a pattern such as ABABAB or AABBAABBAABB or ABCABCABC or variants thereof repeated once, twice, or more than three times. In these patterns, each letter, A, B, or C represent a different TEE sequence at the nucleotide level.

In one embodiment, the 5' UTR may include a spacer to separate two TEE sequences. As a non-limiting example, the spacer may be a 15 nucleotide spacer and/or other spacers known in the art. As another non-limiting example, the 5' UTR may include a TEE sequence-spacer module repeated at least once, at least twice, at least 3 times, at least 4 times, at least 5 times, at least 6 times, at least 7 times, at least 8 times and at least 9 times or more than 9 times in the 5' UTR.

In another embodiment, the spacer separating two TEE sequences may include other sequences known in the art which may regulate the translation of the polynucleotides, primary constructs, alternative nucleic acids and/or mRNA of the present invention such as, but not limited to, miR sequences described herein (e.g., miR binding sites and miR seeds). As a non-limiting example, each spacer used to separate two TEE sequences may include a different miR sequence or component of a miR sequence (e.g., miR seed sequence).

In one embodiment, the TEE in the 5' UTR of the polynucleotides, primary constructs, alternative nucleic acids and/or mRNA of the present invention may include at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or more than 99% of the TEE sequences disclosed in US Patent Publication Nos. 20090226470, 20070048776, 20130177581 and 20110124100, International Patent Publication Nos. WO1999024595, WO2012009644, WO2009075886 and WO2007025008, European Patent Publication Nos. 2610341A1 and 2610340A1, U.S. Pat. Nos. 6,310,197, 6,849,405, 7,456,273, and 7,183,395 each of which is incorporated herein by reference in its entirety. In another embodiment, the TEE in the 5' UTR of the polynucleotides, primary constructs, alternative nucleic acids and/or mRNA of the present invention may include a 5-30 nucleotide fragment, a 5-25 nucleotide fragment, a 5-20 nucleotide fragment, a 5-15 nucleotide fragment, a 5-10 nucleotide fragment of the TEE sequences disclosed in US Patent Publication Nos. 20090226470, 20070048776, 20130177581 and 20110124100, International Patent Publication Nos. WO1999024595, WO2012009644, WO2009075886 and WO2007025008, European Patent Publication Nos. 2610341A1 and 2610340A1, U.S. Pat. Nos. 6,310,197, 6,849,405, 7,456,273, and 7,183,395; each of which is incorporated herein by reference in its entirety.

In one embodiment, the TEE in the 5' UTR of the polynucleotides, primary constructs, alternative nucleic acids and/or mmRNA of the present invention may include at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or more than 99% of the TEE sequences disclosed in Chappell et al. (Proc. Natl. Acad. Sci. USA 101:9590-9594, 2004) and Zhou et al. (PNAS 102: 6273-6278, 2005), in Supplemental Table 1 and in Supplemental Table 2 disclosed by Wellensiek et al (Genome-wide profiling of human cap-independent translation-enhancing elements, Nature Methods, 2013; DOI:10.1038/NMETH.2522); each of which is herein incorporated by reference in its entirety. In another embodiment, the TEE in the 5' UTR of the polynucleotides, primary constructs, alternative nucleic acids and/or mRNA of the present invention may include a 5-30 nucleotide fragment, a 5-25 nucleotide fragment, a 5-20 nucleotide fragment, a 5-15 nucleotide fragment, a 5-10 nucleotide fragment of the TEE sequences disclosed in Chappell et al. (Proc. Natl. Acad. Sci. USA 101:9590-9594, 2004) and Zhou et al. (PNAS 102:6273-6278, 2005), in Supplemental Table 1 and in Supplemental Table 2 disclosed by Wellensiek et al (Genome-wide profiling of human cap-independent translation-enhancing elements, Nature Methods, 2013; DOI:10.1038/NMETH.2522); each of which is incorporated herein by reference in its entirety.

In one embodiment, the TEE used in the 5' UTR of the polynucleotides, primary constructs, alternative nucleic acids and/or mRNA of the present invention is an IRES sequence such as, but not limited to, those described in U.S. Pat. No. 7,468,275 and International Patent Publication No. WO2001055369, each of which is incorporated herein by reference in its entirety.

In one embodiment, the TEEs used in the 5' UTR of the polynucleotides, primary constructs, alternative nucleic acids and/or mRNA of the present invention may be identified by the methods described in US Patent Publication No. 20070048776 and 20110124100 and International Patent Publication Nos. WO2007025008 and WO2012009644, each of which is incorporated herein by reference in its entirety.

In another embodiment, the TEEs used in the 5' UTR of the polynucleotides, primary constructs, alternative nucleic acids and/or mRNA of the present invention may be a transcription regulatory element described in U.S. Pat. Nos. 7,456,273 and 7,183,395, US Patent Publication No. 20090093049, and International Publication No. WO2001055371, each of which is incorporated herein by reference in its entirety. The transcription regulatory elements may be identified by methods known in the art, such as, but not limited to, the methods described in U.S. Pat. Nos. 7,456,273 and 7,183,395, US Patent Publication No. 20090093049, and International Publication No. WO2001055371, each of which is incorporated herein by reference in its entirety.

In yet another embodiment, the TEE used in the 5' UTR of the polynucleotides, primary constructs, alternative nucleic acids and/or mRNA of the present invention is an oligonucleotide or portion thereof as described in U.S. Pat.

Nos. 7,456,273 and 7,183,395, US Patent Publication No. 20090093049, and International Publication No. WO2001055371, each of which is incorporated herein by reference in its entirety.

The 5' UTR comprising at least one TEE described herein may be incorporated in a monocistronic sequence such as, but not limited to, a vector system or a nucleic acid vector. As a non-limiting example, the vector systems and nucleic acid vectors may include those described in U.S. Pat. Nos. 7,456,273 and 7,183,395, US Patent Publication Nos. 20070048776, 20090093049 and 20110124100 and International Patent Publication Nos. WO2007025008 and WO2001055371, each of which is incorporated herein by reference in its entirety.

In one embodiment, the TEEs described herein may be located in the 5' UTR and/or the 3' UTR of the polynucleotides, primary constructs, alternative nucleic acids and/or mRNA. The TEEs located in the 3' UTR may be the same and/or different than the TEEs located in and/or described for incorporation in the 5' UTR.

In one embodiment, the 3' UTR of the polynucleotides, primary constructs, alternative nucleic acids and/or mRNA may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. The TEE sequences in the 3' UTR of the polynucleotides, primary constructs, alternative nucleic acids and/or mRNA of the present invention may be the same or different TEE sequences. The TEE sequences may be in a pattern such as ABABAB or AABBAABBAABB or ABCABCABC or variants thereof repeated once, twice, or more than three times. In these patterns, each letter, A, B, or C represent a different TEE sequence at the nucleotide level.

In one embodiment, the 3' UTR may include a spacer to separate two TEE sequences. As a non-limiting example, the spacer may be a 15 nucleotide spacer and/or other spacers known in the art. As another non-limiting example, the 3' UTR may include a TEE sequence-spacer module repeated at least once, at least twice, at least 3 times, at least 4 times, at least 5 times, at least 6 times, at least 7 times, at least 8 times and at least 9 times or more than 9 times in the 3' UTR.

In another embodiment, the spacer separating two TEE sequences may include other sequences known in the art which may regulate the translation of the polynucleotides, primary constructs, alternative nucleic acids and/or mRNA of the present invention such as, but not limited to, miR sequences described herein (e.g., miR binding sites and miR seeds). As a non-limiting example, each spacer used to separate two TEE sequences may include a different miR sequence or component of a miR sequence (e.g., miR seed sequence).

In one embodiment, the incorporation of a miR sequence and/or a TEE sequence changes the shape of the stem loop region which may increase and/or decrease translation. (see e.g, Kedde et al. A Pumilio-induced RNA structure switch in p27-3'UTR controls miR-221 and miR-22 accessibility. Nature Cell Biology. 2010, herein incorporated by reference in its entirety).

Heterologous 5' UTRs

A 5' UTR may be provided as a flanking region to the alternative nucleic acids (mRNA), enhanced alternative RNA or ribonucleic acids of the invention. 5' UTR may be homologous or heterologous to the coding region found in the alternative nucleic acids (mRNA), enhanced alternative RNA or ribonucleic acids of the invention. Multiple 5' UTRs may be included in the flanking region and may be the same or of different sequences. Any portion of the flanking regions, including none, may be codon optimized and any may independently contain one or more different structural or chemical alterations, before and/or after codon optimization.

Shown in Lengthy Table 21 in U.S. Provisional Application No. 61/775,509, and in Lengthy Table 21 and in Table 22 in U.S. Provisional Application No. 61/829,372, the contents of each of which are incorporated herein by reference in their entirety, is a listing of the start and stop site of the alternative nucleic acids (mRNA), enhanced alternative RNA or ribonucleic acids of the invention. In Table 21 each 5' UTR (5' UTR-005 to 5' UTR 68511) is identified by its start and stop site relative to its native or wild type (homologous) transcript (ENST; the identifier used in the ENSEMBL database).

To alter one or more properties of the polynucleotides, primary constructs or mRNA of the invention, 5' UTRs which are heterologous to the coding region of the alternative nucleic acids (mRNA), enhanced alternative RNA or ribonucleic acids of the invention are engineered into compounds of the invention. The alternative nucleic acids (mRNA), enhanced alternative RNA or ribonucleic acids are then administered to cells, tissue or organisms and outcomes such as protein level, localization and/or half-life are measured to evaluate the beneficial effects the heterologous 5' UTR may have on the alternative nucleic acids (mRNA), enhanced alternative RNA or ribonucleic acids of the invention. Variants of the 5' UTRs may be utilized wherein one or more nucleotides are added or removed to the termini, including A, T, C or G. 5' UTRs may also be codon-optimized or altered in any manner described herein.

Incorporating microRNA Binding Sites

In one embodiment, alternative nucleic acids (mRNA), enhanced alternative RNA or ribonucleic acids of the invention would not only encode a polypeptide but also a sensor sequence. Sensor sequences include, for example, microRNA binding sites, transcription factor binding sites, structured mRNA sequences and/or motifs, artificial binding sites engineered to act as pseudo-receptors for endogenous nucleic acid binding molecules. Non-limiting examples, of polynucleotides comprising at least one sensor sequence are described in co-pending and co-owned U.S. Provisional Patent Application No. 61/753,661, filed Jan. 17, 2013, U.S. Provisional Patent Application No. 61/754,159, filed Jan. 18, 2013, U.S. Provisional Patent Application No. 61/781,097, filed Mar. 14, 2013, U.S. Provisional Patent Application No. 61/829,334, filed May 31, 2013, U.S. Provisional Patent Application No. 61/839,893, filed Jun. 27, 2013, U.S. Provisional Patent Application No. 61/842,733, filed Jul. 3, 2013, and U.S. Provisional Patent Application No. 61/857,304, filed Jul. 23, 2013, the contents of each of which are incorporated herein by reference in their entirety.

In one embodiment, microRNA (miRNA) profiling of the target cells or tissues is conducted to determine the presence or absence of miRNA in the cells or tissues.

microRNAs (or miRNA) are 19-25 nucleotide long non-coding RNAs that bind to the 3'UTR of nucleic acid molecules and down-regulate gene expression either by reducing nucleic acid molecule stability or by inhibiting translation. The alternative nucleic acids (mRNA), enhanced alternative RNA or ribonucleic acids of the invention may comprise one or more microRNA target sequences, microRNA sequences, or microRNA seeds. Such sequences may correspond to any known microRNA such as those taught in US Patent Publication Nos. 2005/0261218 and 2005/0059005, the contents of which are incorporated herein by reference in their entirety.

A microRNA sequence comprises a "seed" region, i.e., a sequence in the region of positions 2-8 of the mature microRNA, which sequence has perfect Watson-Crick complementarity to the miRNA target sequence. A microRNA seed may comprise positions 2-8 or 2-7 of the mature microRNA. In some embodiments, a microRNA seed may comprise 7 nucleotides (e.g., nucleotides 2-8 of the mature microRNA), wherein the seed-complementary site in the corresponding miRNA target is flanked by an adenosine (A) opposed to microRNA position 1. In some embodiments, a microRNA seed may comprise 6 nucleotides (e.g., nucleotides 2-7 of the mature microRNA), wherein the seed-complementary site in the corresponding miRNA target is flanked by an adenosine (A) opposed to microRNA position 1. See for example, Grimson A, Farh K K, Johnston W K, Garrett-Engele P, Lim L P, Bartel D P; Mol Cell. 2007 Jul. 6; 27(1):91-105. The bases of the microRNA seed have complete complementarity with the target sequence. By engineering microRNA target sequences into the 3'UTR of nucleic acids or mRNA of the invention one can target the molecule for degradation or reduced translation, provided the microRNA in question is available. This process will reduce the hazard of off target effects upon nucleic acid molecule delivery. Identification of microRNA, microRNA target regions, and their expression patterns and role in biology have been reported (Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/leu.2011.356); Bartel Cell 2009 136:215-233; Landgraf et al, Cell, 2007 129:1401-1414; Gentner and Naldini, Tissue Antigens. 2012 80:393-403 and all references therein; each of which is incorporated herein by reference in its entirety).

For example, if the mRNA is not intended to be delivered to the liver but ends up there, then miR-122, a microRNA abundant in liver, can inhibit the expression of the gene of interest if one or multiple target sites of miR-122 are engineered into the 3'UTR of the alternative nucleic acids, enhanced alternative RNA or ribonucleic acids. Introduction of one or multiple binding sites for different microRNA can be engineered to further decrease the longevity, stability, and protein translation of an alternative nucleic acids, enhanced alternative RNA or ribonucleic acids. As used herein, the term "microRNA site" refers to a microRNA target site or a microRNA recognition site, or any nucleotide sequence to which a microRNA binds or associates. It should be understood that "binding" may follow traditional Watson-Crick hybridization rules or may reflect any stable association of the microRNA with the target sequence at or adjacent to the microRNA site.

Conversely, for the purposes of the alternative nucleic acids, enhanced alternative RNA or ribonucleic acids of the present invention, microRNA binding sites can be engineered out of (i.e. removed from) sequences in which they naturally occur in order to increase protein expression in specific tissues. For example, miR-122 binding sites may be removed to improve protein expression in the liver.

In one embodiment, the alternative nucleic acids, enhanced alternative RNA or ribonucleic acids of the present invention may include at least one miRNA-binding site in the 3' UTR in order to direct cytotoxic or cytoprotective mRNA therapeutics to specific cells such as, but not limited to, normal and/or cancerous cells (e.g., HEP3B or SNU449).

In another embodiment, the alternative nucleic acids, enhanced alternative RNA or ribonucleic acids of the present invention may include three miRNA-binding sites in the 3' UTR in order to direct cytotoxic or cytoprotective mRNA therapeutics to specific cells such as, but not limited to, normal and/or cancerous cells (e.g., HEP3B or SNU449).

Regulation of expression in multiple tissues can be accomplished through introduction or removal or one or several microRNA binding sites. The decision of removal or insertion of microRNA binding sites, or any combination, is dependent on microRNA expression patterns and their profilings in diseases.

Examples of tissues where microRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-1d, miR-149), kidney (miR-192, miR-194, miR-204), and lung epithelial cells (let-7, miR-133, miR-126).

Specifically, microRNAs are known to be differentially expressed in immune cells (also called hematopoietic cells), such as antigen presenting cells (APCs) (e.g. dendritic cells and macrophages), macrophages, monocytes, B lymphocytes, T lymphocytes, granuocytes, natural killer cells. Immune cell specific microRNAs are involved in immunogenicity, autoimmunity, the immune-response to infection, inflammation, as well as unwanted immune response after gene therapy and tissue/organ transplantation. Immune cells specific microRNAs also regulate many aspects of development, proliferation, differentiation and apoptosis of hematopoietic cells (immune cells). For example, miR-142 and miR-146 are exclusively expressed in the immune cells, particularly abundant in myeloid dendritic cells. It was demonstrated in the art that the immune response to exogenous nucleic acid molecules was shut-off by adding miR-142 binding sites to the 3' UTR of the delivered gene construct, enabling more stable gene transfer in tissues and cells. miR-142 efficiently degrades the exogenous mRNA in antigen presenting cells and suppresses cytotoxic elimination of transduced cells (Annoni A et al., blood, 2009, 114, 5152-5161; Brown B D, et al., Nat med. 2006, 12(5), 585-591; Brown B D, et al., blood, 2007, 110(13): 4144-4152, each of which is incorporated herein by reference in its entirety).

An antigen-mediated immune response can refer to an immune response triggered by foreign antigens, which, when entering an organism, are processed by the antigen presenting cells and displayed on the surface of the antigen presenting cells. T cells can recognize the presented antigen and induce a cytotoxic elimination of cells that express the antigen.

Introducing the miR-142 binding site into the 3' UTR of a polypeptide of the present invention can selectively repress the gene expression in the antigen presenting cells through miR-142 mediated mRNA degradation, limiting antigen presentation in APCs (e.g. dendritic cells) and thereby preventing antigen-mediated immune response after the delivery of the polynucleotides. The polynucleotides are therefore stably expressed in target tissues or cells without triggering cytotoxic elimination.

In one embodiment, microRNAs binding sites that are known to be expressed in immune cells, in particular, the antigen presenting cells, can be engineered into the polynucleotide to suppress the expression of the sensor-signal polynucleotide in APCs through microRNA mediated RNA degradation, subduing the antigen-mediated immune response, while the expression of the polynucleotide is maintained in non-immune cells where the immune cell specific microRNAs are not expressed. For example, to prevent the immunogenic reaction caused by a liver specific protein expression, the miR-122 binding site can be removed and the miR-142 (and/or mirR-146) binding sites can be engineered into the 3-UTR of the polynucleotide.

To further drive the selective degradation and suppression of mRNA in APCs and macrophage, the polynucleotide may include another negative regulatory element in the 3-UTR, either alone or in combination with mir-142 and/or mir-146 binding sites. As a non-limiting example, one regulatory element is the Constitutive Decay Elements (CDEs).

Immune cells specific microRNAs include, but are not limited to, hsa-let-7a-2-3p, hsa-let-7a-3p, hsa-7a-5p, hsa-let-7c, hsa-let-7e-3p, hsa-let-7e-5p, hsa-let-7g-3p, hsa-let-7g-5p, hsa-let-7i-3p, hsa-let-7i-5p, miR-10a-3p, miR-10a-5p, miR-1184, hsa-let-7f-1-3p, hsa-let-7f-2-5p, hsa-let-7f-5p, miR-125b-1-3p, miR-125b-2-3p, miR-125b-5p, miR-1279, miR-130a-3p, miR-130a-5p, miR-132-3p, miR-132-5p, miR-142-3p, miR-142-5p, miR-143-3p, miR-143-5p, miR-146a-3p, miR-146a-5p, miR-146b-3p, miR-146b-5p, miR-147a, miR-147b, miR-148a-5p, miR-148a-3p, miR-150-3p, miR-150-5p, miR-151b, miR-155-3p, miR-155-5p, miR-15a-3p, miR-15a-5p, miR-15b-5p, miR-15b-3p, miR-16-1-3p, miR-16-2-3p, miR-16-5p, miR-17-5p, miR-181a-3p, miR-181a-5p, miR-181a-2-3p, miR-182-3p, miR-182-5p, miR-197-3p, miR-197-5p, miR-21-5p, miR-21-3p, miR-214-3p, miR-214-5p, miR-223-3p, miR-223-5p, miR-221-3p, miR-221-5p, miR-23b-3p, miR-23b-5p, miR-24-1-5p, miR-24-2-5p, miR-24-3p, miR-26a-1-3p, miR-26a-2-3p, miR-26a-5p, miR-26b-3p, miR-26b-5p, miR-27a-3p, miR-27a-5p, miR-27b-3p, miR-27b-5p, miR-28-3p, miR-28-5p, miR-2909, miR-29a-3p, miR-29a-5p, miR-29b-1-5p, miR-29b-2-5p, miR-29c-3p, miR-29c-5p, miR-30e-3p, miR-30e-5p, miR-331-5p, miR-339-3p, miR-339-5p, miR-345-3p, miR-345-5p, miR-346, miR-34a-3p, miR-34a-5p, miR-363-3p, miR-363-5p, miR-372, miR-377-3p, miR-377-5p, miR-493-3p, miR-493-5p, miR-542, miR-548b-5p, miR548c-5p, miR-548i, miR-548j, miR-548n, miR-574-3p, miR-598, miR-718, miR-935, miR-99a-3p, miR-99a-5p, miR-99b-3p and miR-99b-5p. Furthermore, novel miroRNAs are discovered in the immune cells in the art through micro-array hybridization and microtome analysis (Jima D D et al, Blood, 2010, 116:e118-e127; Vaz C et al., BMC Genomics, 2010, 11,288, the content of each of which is incorporated herein by reference in its entirety.)

MicroRNAs that are known to be expressed in the liver include, but are not limited to, miR-107, miR-122-3p, miR-122-5p, miR-1228-3p, miR-1228-5p, miR-1249, miR-129-5p, miR-1303, miR-151a-3p, miR-151a-5p, miR-152, miR-194-3p, miR-194-5p, miR-199a-3p, miR-199a-5p, miR-199b-3p, miR-199b-5p, miR-296-5p, miR-557, miR-581, miR-939-3p, miR-939-5p. MicroRNA binding sites from any liver specific microRNA can be introduced to or removed from the polynucleotides to regulate the expression of the polynucleotides in the liver. Liver specific microRNAs binding sites can be engineered alone or further in combination with immune cells (e.g. APCs) microRNA binding sites in order to prevent immune reaction against protein expression in the liver.

MicroRNAs that are known to be expressed in the lung include, but are not limited to, let-7a-2-3p, let-7a-3p, let-7a-5p, miR-126-3p, miR-126-5p, miR-127-3p, miR-127-5p, miR-130a-3p, miR-130a-5p, miR-130b-3p, miR-130b-5p, miR-133a, miR-133b, miR-134, miR-18a-3p, miR-18a-5p, miR-18b-3p, miR-18b-5p, miR-24-1-5p, miR-24-2-5p, miR-24-3p, miR-296-3p, miR-296-5p, miR-32-3p, miR-337-3p, miR-337-5p, miR-381-3p, miR-381-5p. MicroRNA binding sites from any lung specific microRNA can be introduced to or removed from the polynucleotide to regulate the expression of the polynucleotide in the lung. Lung specific microRNAs binding sites can be engineered alone or further in combination with immune cells (e.g. APCs) microRNA binding sites in order to prevent an immune reaction against protein expression in the lung.

MicroRNAs that are known to be expressed in the heart include, but are not limited to, miR-1, miR-133a, miR-133b, miR-149-3p, miR-149-5p, miR-186-3p, miR-186-5p, miR-208a, miR-208b, miR-210, miR-296-3p, miR-320, miR-451a, miR-451 b, miR-499a-3p, miR-499a-5p, miR-499b-3p, miR-499b-5p, miR-744-3p, miR-744-5p, miR-92b-3p and miR-92b-5p. MicroRNA binding sites from any heart specific microRNA can be introduced to or removed from the polynucleotides to regulate the expression of the polynucleotides in the heart. Heart specific microRNAs binding sites can be engineered alone or further in combination with immune cells (e.g. APCs) microRNA binding sites to prevent an immune reaction against protein expression in the heart.

MicroRNAs that are known to be expressed in the nervous system include, but are not limited to, miR-124-5p, miR-125a-3p, miR-125a-5p, miR-125b-1-3p, miR-125b-2-3p, miR-125b-5p, miR-1271-3p, miR-1271-5p, miR-128, miR-132-5p, miR-135a-3p, miR-135a-5p, miR-135b-3p, miR-135b-5p, miR-137, miR-139-5p, miR-139-3p, miR-149-3p, miR-149-5p, miR-153, miR-181c-3p, miR-181c-5p, miR-183-3p, miR-183-5p, miR-190a, miR-190b, miR-212-3p, miR-212-5p, miR-219-1-3p, miR-219-2-3p, miR-23a-3p, miR-23a-5p, miR-30a-5p, miR-30b-3p, miR-30b-5p, miR-30c-1-3p, miR-30c-2-3p, miR-30c-5p, miR-30d-3p, miR-30d-5p, miR-329, miR-342-3p, miR-3665, miR-3666, miR-380-3p, miR-380-5p, miR-383, miR-410, miR-425-3p, miR-425-5p, miR-454-3p, miR-454-5p, miR-483, miR-510, miR-516a-3p, miR-548b-5p, miR-548c-5p, miR-571, miR-7-1-3p, miR-7-2-3p, miR-7-5p, miR-802, miR-922, miR-9-3p and miR-9-5p. MicroRNAs enriched in the nervous system further include those specifically expressed in neurons, including, but not limited to, miR-132-3p, miR-132-3p, miR-148b-3p, miR-148b-5p, miR-151a-3p, miR-151a-5p, miR-212-3p, miR-212-5p, miR-320b, miR-320e, miR-323a-3p, miR-323a-5p, miR-324-5p, miR-325, miR-326, miR-328, miR-922 and those specifically expressed in glial cells, including, but not limited to, miR-1250, miR-219-1-3p, miR-219-2-3p, miR-219-5p, miR-23a-3p, miR-23a-5p, miR-3065-3p, miR-3065-5p, miR-30e-3p, miR-30e-5p, miR-32-5p, miR-338-5p, miR-657. MicroRNA binding sites from any CNS specific microRNA can be introduced to or removed from the polynucleotides to regulate the expression of the polynucleotide in the nervous system. Nervous system specific microRNAs binding sites can be engineered alone or further in combination with immune cells (e.g. APCs) microRNA binding sites in order to prevent immune reaction against protein expression in the nervous system.

MicroRNAs that are known to be expressed in the pancreas include, but are not limited to, miR-105-3p, miR-105-5p, miR-184, miR-195-3p, miR-195-5p, miR-196a-3p, miR-196a-5p, miR-214-3p, miR-214-5p, miR-216a-3p, miR-216a-5p, miR-30a-3p, miR-33a-3p, miR-33a-5p, miR-375, miR-7-1-3p, miR-7-2-3p, miR-493-3p, miR-493-5p and miR-944. MicroRNA binding sites from any pancreas specific microRNA can be introduced to or removed from the polynucleotide to regulate the expression of the polynucleotide in the pancreas. Pancreas specific microRNAs binding sites can be engineered alone or further in combination with immune cells (e.g. APCs) microRNA binding sites in order to prevent an immune reaction against protein expression in the pancreas.

MicroRNAs that are known to be expressed in the kidney further include, but are not limited to, miR-122-3p, miR-145-5p, miR-17-5p, miR-192-3p, miR-192-5p, miR-194-3p, miR-194-5p, miR-20a-3p, miR-20a-5p, miR-204-3p, miR-204-5p, miR-210, miR-216a-3p, miR-216a-5p, miR-296-3p, miR-30a-3p, miR-30a-5p, miR-30b-3p, miR-30b-5p, miR-30c-1-3p, miR-30c-2-3p, miR30c-5p, miR-324-3p, miR-335-3p, miR-335-5p, miR-363-3p, miR-363-5p and miR-562. MicroRNA binding sites from any kidney specific microRNA can be introduced to or removed from the polynucleotide to regulate the expression of the polynucleotide in the kidney. Kidney specific microRNAs binding sites can be engineered alone or further in combination with immune cells (e.g. APCs) microRNA binding sites to prevent an immune reaction against protein expression in the kidney.

MicroRNAs that are known to be expressed in the muscle further include, but are not limited to, let-7g-3p, let-7g-5p, miR-1, miR-1286, miR-133a, miR-133b, miR-140-3p, miR-143-3p, miR-143-5p, miR-145-3p, miR-145-5p, miR-188-3p, miR-188-5p, miR-206, miR-208a, miR-208b, miR-25-3p and miR-25-5p. MicroRNA binding sites from any muscle specific microRNA can be introduced to or removed from the polynucleotide to regulate the expression of the polynucleotide in the muscle. Muscle specific microRNAs binding sites can be engineered alone or further in combination with immune cells (e.g. APCs) microRNA binding sites to prevent an immune reaction against protein expression in the muscle.

MicroRNAs are differentially expressed in different types of cells, such as endothelial cells, epithelial cells and adipocytes. For example, microRNAs that are expressed in endothelial cells include, but are not limited to, let-7b-3p, let-7b-5p, miR-100-3p, miR-100-5p, miR-101-3p, miR-101-5p, miR-126-3p, miR-126-5p, miR-1236-3p, miR-1236-5p, miR-130a-3p, miR-130a-5p, miR-17-5p, miR-17-3p, miR-18a-3p, miR-18a-5p, miR-19a-3p, miR-19a-5p, miR-19b-1-5p, miR-19b-2-5p, miR-19b-3p, miR-20a-3p, miR-20a-5p, miR-217, miR-210, miR-21-3p, miR-21-5p, miR-221-3p, miR-221-5p, miR-222-3p, miR-222-5p, miR-23a-3p, miR-23a-5p, miR-296-5p, miR-361-3p, miR-361-5p, miR-421, miR-424-3p, miR-424-5p, miR-513a-5p, miR-92a-1-5p, miR-92a-2-5p, miR-92a-3p, miR-92b-3p and miR-92b-5p. Many novel microRNAs are discovered in endothelial cells from deep-sequencing analysis (Voellenkle C et al., RNA, 2012, 18, 472-484, herein incorporated by reference in its entirety) microRNA binding sites from any endothelial cell specific microRNA can be introduced to or removed from the polynucleotide to modulate the expression of the polynucleotide in the endothelial cells in various conditions.

For further example, microRNAs that are expressed in epithelial cells include, but are not limited to, let-7b-3p, let-7b-5p, miR-1246, miR-200a-3p, miR-200a-5p, miR-200b-3p, miR-200b-5p, miR-200c-3p, miR-200c-5p, miR-338-3p, miR-429, miR-451a, miR-451b, miR-494, miR-802 and miR-34a, miR-34b-5p, miR-34c-5p, miR-449a, miR-449b-3p, miR-449b-5p specific in respiratory ciliated epithelial cells; let-7 family, miR-133a, miR-133b, miR-126 specific in lung epithelial cells; miR-382-3p, miR-382-5p specific in renal epithelial cells and miR-762 specific in corneal epithelial cells. MicroRNA binding sites from any epithelial cell specific MicroRNA can be introduced to or removed from the polynucleotide to modulate the expression of the polynucleotide in the epithelial cells in various conditions.

In addition, a large group of microRNAs are enriched in embryonic stem cells, controlling stem cell self-renewal as well as the development and/or differentiation of various cell lineages, such as neural cells, cardiac, hematopoietic cells, skin cells, osteogenic cells and muscle cells (Kuppusamy K T et al., Curr. Mol Med, 2013, 13(5), 757-764; Vidigal J A and Ventura A, Semin Cancer Biol. 2012, 22(5-6), 428-436; Goff L A et al., PLoS One, 2009, 4:e7192; Morin R D et al., Genome Res, 2008, 18, 610-621; Yoo J K et al., Stem Cells Dev. 2012, 21(11), 2049-2057, each of which is herein incorporated by reference in its entirety). MicroRNAs abundant in embryonic stem cells include, but are not limited to, let-7a-2-3p, let-a-3p, let-7a-5p, let7d-3p, let-7d-5p, miR-103a-2-3p, miR-103a-5p, miR-106b-3p, miR-106b-5p, miR-1246, miR-1275, miR-138-1-3p, miR-138-2-3p, miR-138-5p, miR-154-3p, miR-154-5p, miR-200c-3p, miR-200c-5p, miR-290, miR-301a-3p, miR-301a-5p, miR-302a-3p, miR-302a-5p, miR-302b-3p, miR-302b-5p, miR-302c-3p, miR-302c-5p, miR-302d-3p, miR-302d-5p, miR-302e, miR-367-3p, miR-367-5p, miR-369-3p, miR-369-5p, miR-370, miR-371, miR-373, miR-380-5p, miR-423-3p, miR-423-5p, miR-486-5p, miR-520c-3p, miR-548e, miR-548f, miR-548g-3p, miR-548g-5p, miR-548i, miR-548k, miR-548l, miR-548m, miR-548n, miR-548o-3p, miR-548o-5p, miR-548p, miR-664a-3p, miR-664a-5p, miR-664b-3p, miR-664b-5p, miR-766-3p, miR-766-5p, miR-885-3p, miR-885-5p, miR-93-3p, miR-93-5p, miR-941, miR-96-3p, miR-96-5p, miR-99b-3p and miR-99b-5p. Many predicted novel microRNAs are discovered by deep sequencing in human embryonic stem cells (Morin R D et al., Genome Res, 2008, 18, 610-621; Goff L A et al., PLoS One, 2009, 4:e7192; Bar M et al., Stem cells, 2008, 26, 2496-2505, the content of each of which is incorporated herein by references in its entirety).

In one embodiment, the binding sites of embryonic stem cell specific microRNAs can be included in or removed from the 3-UTR of the polynucleotide to modulate the development and/or differentiation of embryonic stem cells, to inhibit the senescence of stem cells in a degenerative condition (e.g. degenerative diseases), or to stimulate the senescence and apoptosis of stem cells in a disease condition (e.g. cancer stem cells).

Many microRNA expression studies are conducted in the art to profile the differential expression of microRNAs in various cancer cells/tissues and other diseases. Some microRNAs are abnormally over-expressed in certain cancer cells and others are under-expressed. For example, microRNAs are differentially expressed in cancer cells (WO2008/154098, US2013/0059015, US2013/0042333, WO2011/157294); cancer stem cells (US2012/0053224); pancreatic cancers and diseases (US2009/0131348, US2011/0171646, US2010/0286232, U.S. Pat. No. 8,389,210); asthma and inflammation (U.S. Pat. No. 8,415,096); prostate cancer (US2013/0053264); hepatocellular carcinoma (WO2012/151212, US2012/0329672, WO2008/054828, U.S. Pat. No. 8,252,538); lung cancer cells (WO2011/076143, WO2013/033640, WO2009/070653, US2010/0323357); cutaneous T cell lymphoma (WO2013/011378); colorectal cancer cells (WO2011/0281756, WO2011/076142); cancer positive lymph nodes (WO2009/100430, US2009/0263803); nasopharyngeal carcinoma (EP2112235); chronic obstructive pulmonary disease (US2012/0264626, US2013/0053263); thyroid cancer (WO2013/066678); ovarian cancer cells (US2012/0309645, WO2011/095623); breast cancer cells (WO2008/154098, WO2007/081740, US2012/0214699), leukemia and lymphoma (WO2008/073915, US2009/0092974, US2012/0316081, US2012/0283310, WO2010/018563, the content of each of which is incorporated herein by reference in its entirety.)

As a non-limiting example, microRNA sites that are over-expressed in certain cancer and/or tumor cells can be removed from the 3-UTR of the polynucleotide encoding the polypeptide of interest, restoring the expression suppressed by the over-expressed microRNAs in cancer cells, thus ameliorating the corresponsive biological function, for instance, transcription stimulation and/or repression, cell cycle arrest, apoptosis and cell death. Normal cells and tissues, wherein microRNAs expression is not up-regulated, will remain unaffected.

MicroRNA can also regulate complex biological processes such as angiogenesis (miR-132) (Anand and Cheresh Curr Opin Hematol 2011 18:171-176). In the alternative nucleic acids, enhanced alternative RNA or ribonucleic acids of the invention, binding sites for microRNAs that are involved in such processes may be removed or introduced, in order to tailor the expression of the alternative nucleic acids, enhanced alternative RNA or ribonucleic acids expression to biologically relevant cell types or to the context of relevant biological processes. In this context, the mRNA are defined as auxotrophic mRNA.

MicroRNA gene regulation may be influenced by the sequence surrounding the microRNA such as, but not limited to, the species of the surrounding sequence, the type of sequence (e.g., heterologous, homologous and artificial), regulatory elements in the surrounding sequence and/or structural elements in the surrounding sequence. The microRNA may be influenced by the 5' UTR and/or the 3' UTR. As a non-limiting example, a non-human 3' UTR may increase the regulatory effect of the microRNA sequence on the expression of a polypeptide of interest compared to a human 3' UTR of the same sequence type.

In one embodiment, other regulatory elements and/or structural elements of the 5' UTR can influence microRNA mediated gene regulation. One example of a regulatory element and/or structural element is a structured IRES (Internal Ribosome Entry Site) in the 5' UTR, which is necessary for the binding of translational elongation factors to initiate protein translation. EIF4A2 binding to this secondarily structured element in the 5' UTR is necessary for microRNA mediated gene expression (Meijer H A et al., Science, 2013, 340, 82-85, herein incorporated by reference in its entirety). The alternative nucleic acids, enhanced alternative RNA or ribonucleic acids of the invention can further be alternative to include this structured 5' UTR in order to enhance microRNA mediated gene regulation.

At least one microRNA site can be engineered into the 3' UTR of the alternative nucleic acids, enhanced alternative RNA or ribonucleic acids of the present invention. In this context, at least two, at least three, at least four, at least five, at least six, at least seven, at least eight, at least nine, at least ten or more microRNA sites may be engineered into the 3' UTR of the ribonucleic acids of the present invention. In one embodiment, the microRNA sites incorporated into the alternative nucleic acids, enhanced alternative RNA or ribonucleic acids may be the same or may be different microRNA sites. In another embodiment, the microRNA sites incorporated into the alternative nucleic acids, enhanced alternative RNA or ribonucleic acids may target the same or different tissues in the body. As a non-limiting example, through the introduction of tissue-, cell-type-, or disease-specific microRNA binding sites in the 3' UTR of an alternative nucleic acid mRNA, the degree of expression in specific cell types (e.g. hepatocytes, myeloid cells, endothelial cells, cancer cells) can be reduced.

In one embodiment, a microRNA site can be engineered near the 5' terminus of the 3' UTR, about halfway between the 5' terminus and 3' terminus of the 3' UTR and/or near the 3' terminus of the 3' UTR. As a non-limiting example, a microRNA site may be engineered near the 5' terminus of the 3' UTR and about halfway between the 5' terminus and 3' terminus of the 3' UTR. As another non-limiting example, a microRNA site may be engineered near the 3' terminus of the 3' UTR and about halfway between the 5' terminus and 3' terminus of the 3' UTR. As yet another non-limiting example, a microRNA site may be engineered near the 5' terminus of the 3' UTR and near the 3' terminus of the 3' UTR.

In another embodiment, a 3' UTR can comprise 4 microRNA sites. The microRNA sites may be complete microRNA binding sites, microRNA seed sequences and/or microRNA binding site sequences without the seed sequence.

In one embodiment, a nucleic acid of the invention may be engineered to include at least one microRNA in order to dampen the antigen presentation by antigen presenting cells. The microRNA may be the complete microRNA sequence, the microRNA seed sequence, the microRNA sequence without the seed or a combination thereof. As a non-limiting example, the microRNA incorporated into the nucleic acid may be specific to the hematopoietic system. As another non-limiting example, the microRNA incorporated into the nucleic acid of the invention to dampen antigen presentation is miR-142-3p.

In one embodiment, a nucleic acid may be engineered to include microRNA sites which are expressed in different tissues of a subject. As a non-limiting example, an alternative nucleic acid, enhanced alternative RNA or ribonucleic acid of the present invention may be engineered to include miR-192 and miR-122 to regulate expression of the alternative nucleic acid, enhanced alternative RNA or ribonucleic acid in the liver and kidneys of a subject. In another embodiment, an alternative nucleic acid, enhanced alternative RNA or ribonucleic acid may be engineered to include more than one microRNA sites for the same tissue. For example, an alternative nucleic acid, enhanced alternative RNA or ribonucleic acid of the present invention may be engineered to include miR-17-92 and miR-126 to regulate expression of the alternative nucleic acid, enhanced alternative RNA or ribonucleic acid in endothelial cells of a subject.

In one embodiment, the therapeutic window and or differential expression associated with the target polypeptide encoded by the alternative nucleic acid, enhanced alternative RNA or ribonucleic acid encoding a signal (also referred to herein as a polynucleotide) of the invention may be altered. For example, polynucleotides may be designed whereby a death signal is more highly expressed in cancer cells (or a survival signal in a normal cell) by virtue of the miRNA signature of those cells. Where a cancer cell expresses a lower level of a particular miRNA, the polynucleotide encoding the binding site for that miRNA (or miRNAs) would be more highly expressed. Hence, the target polypeptide encoded by the polynucleotide is selected as a protein which triggers or induces cell death. Neighboring noncancer cells, harboring a higher expression of the same miRNA would be less affected by the encoded death signal as the polynucleotide would be expressed at a lower level due to the effects of the miRNA binding to the binding site or "sensor" encoded in the 3' UTR. Conversely, cell survival or cytoprotective signals may be delivered to tissues containing cancer and non-cancerous cells where a miRNA has a higher expression in the cancer cells—the result being a lower survival signal to the cancer cell and a larger survival signature to the normal cell. Multiple polynucleotides may be designed and administered having different signals according to the previous paradigm.

In one embodiment, the expression of a nucleic acid may be controlled by incorporating at least one sensor sequence in the nucleic acid and formulating the nucleic acid. As a non-limiting example, a nucleic acid may be targeted to an orthotopic tumor by having a nucleic acid incorporating a miR-122 binding site and formulated in a lipid nanoparticle comprising the cationic lipid DLin-KC2-DMA.

According to the present invention, the polynucleotides may be altered as to avoid the deficiencies of other polypeptide-encoding molecules of the art. Hence, in this embodiment the polynucleotides are referred to as alternative polynucleotides.

Through an understanding of the expression patterns of microRNA in different cell types, alternative nucleic acids, enhanced alternative RNA or ribonucleic acids such as polynucleotides can be engineered for more targeted expression in specific cell types or only under specific biological conditions. Through introduction of tissue-specific microRNA binding sites, alternative nucleic acids, enhanced alternative RNA or ribonucleic acids, could be designed that would be optimal for protein expression in a tissue or in the context of a biological condition.

Transfection experiments can be conducted in relevant cell lines, using engineered alternative nucleic acids, enhanced alternative RNA or ribonucleic acids and protein production can be assayed at various time points post-transfection. For example, cells can be transfected with different microRNA binding site-engineering nucleic acids or mRNA and by using an ELISA kit to the relevant protein and assaying protein produced at 6 hr, 12 hr, 24 hr, 48 hr, 72 hr and 7 days post-transfection. In vivo experiments can also be conducted using microRNA-binding site-engineered molecules to examine changes in tissue-specific expression of formulated alternative nucleic acids, enhanced alternative RNA or ribonucleic acids.

Non-limiting examples of cell lines which may be useful in these investigations include those from ATCC (Manassas, Va.) including MRC-5, A549, T84, NCI-H2126 [H2126], NCI-H1688 [H1688], WI-38, WI-38 VA-13 subline 2RA, WI-26 VA4, C3A [HepG2/C3A, derivative of Hep G2 (ATCC HB-8065)], THLE-3, H69AR, NCI-H292 [H292], CFPAC-1, NTERA-2 cl.D1 [NT2/D1], DMS 79, DMS 53, DMS 153, DMS 114, MSTO-211H, SW 1573 [SW-1573, SW1573], SW 1271 [SW-1271, SW1271], SHP-77, SNU-398, SNU-449, SNU-182, SNU-475, SNU-387, SNU-423, NL20, NL20-TA [NL20T-A], THLE-2, HBE135-E6E7, HCC827, HCC4006, NCI-H23 [H23], NCI-H1299, NCI-H187 [H187], NCI-H358 [H-358, H358], NCI-H378 [H378], NCI-H522 [H522], NCI-H526 [H526], NCI-H727 [H727], NCI-H810 [H810], NCI-H889 [H889], NCI-H1155 [H1155], NCI-H1404 [H1404], NCI-N87 [N87], NCI-H196 [H196], NCI-H211 [H211], NCI-H220 [H220], NCI-H250 [H250], NCI-H524 [H524], NCI-H647 [H647], NCI-H650 [H650], NCI-H711 [H711], NCI-H719 [H719], NCI-H740 [H740], NCI-H748 [H748], NCI-H774 [H774], NCI-H838 [H838], NCI-H841 [H841], NCI-H847 [H847], NCI-H865 [H865], NCI-H920 [H920], NCI-H1048 [H1048], NCI-H1092 [H1092], NCI-H1105 [H1105], NCI-H1184 [H1184], NCI-H1238 [H1238], NCI-H1341 [H1341], NCI-H1385 [H1385], NCI-H1417 [H1417], NCI-H1435 [H1435], NCI-H1436 [H1436], NCI-H1437 [H1437], NCI-H1522 [H1522], NCI-H1563 [H1563], NCI-H1568 [H1568], NCI-H1573 [H1573], NCI-H1581 [H1581], NCI-H1618 [H1618], NCI-H1623 [H1623], NCI-H1650 [H-1650, H1650], NCI-H1651 [H1651], NCI-H1666 [H-1666, H1666], NCI-H1672 [H1672], NCI-H1693 [H1693], NCI-H1694 [H1694], NCI-H1703 [H1703], NCI-H1734 [H-1734, H1734], NCI-H1755 [H1755], NCI-H1755 [H1755], NCI-H1770 [H1770], NCI-H1793 [H1793], NCI-H1836 [H1836], NCI-H1838 [H1838], NCI-H1869 [H1869], NCI-H1876 [H1876], NCI-H1882 [H1882], NCI-H1915 [H1915], NCI-H1930 [H1930], NCI-H1944 [H1944], NCI-H1975 [H-1975, H1975], NCI-H1993 [H1993], NCI-H2023 [H2023], NCI-H2029 [H2029], NCI-H2030 [H2030], NCI-H2066 [H2066], NCI-H2073 [H2073], NCI-H2081 [H2081], NCI-H2085 [H2085], NCI-H2087 [H2087], NCI-H2106 [H2106], NCI-H2110 [H2110], NCI-H2135 [H2135], NCI-H2141 [H2141], NCI-H2171 [H2171], NCI-H2172 [H2172], NCI-H2195 [H2195], NCI-H2196 [H2196], NCI-H2198 [H2198], NCI-H2227 [H2227], NCI-H2228 [H2228], NCI-H2286 [H2286], NCI-H2291 [H2291], NCI-H2330 [H2330], NCI-H2342 [H2342], NCI-H2347 [H2347], NCI-H2405 [H2405], NCI-H2444 [H2444], UMC-11, NCI-H64 [H64], NCI-H735 [H735], NCI-H735 [H735], NCI-H1963 [H1963], NCI-H2107 [H2107], NCI-H2108 [H2108], NCI-H2122 [H2122], Hs 573.T, Hs 573.Lu, PLC/PRF/5, BEAS-2B, Hep G2, Tera-1, Tera-2, NCI-H69 [H69], NCI-H128 [H128], ChaGo-K-1, NCI-H446 [H446], NCI-H209 [H209], NCI-H146 [H146], NCI-H441 [H441], NCI-H82 [H82], NCI-H460 [H460], NCI-H596 [H596], NCI-H676B [H676B], NCI-H345 [H345], NCI-H820 [H820], NCI-H520 [H520], NCI-H661 [H661], NCI-H510A [H510A, NCI-H510], SK-HEP-1, A-427, Calu-1, Calu-3, Calu-6, SK-LU-1, SK-MES-1, SW 900 [SW-900, SW900], Malme-3M, and Capan-1.

In some embodiments, alternative messenger RNA can be designed to incorporate microRNA binding region sites that either have 100% identity to known seed sequences or have less than 100% identity to seed sequences. The seed sequence can be partially mutated to decrease microRNA binding affinity and as such result in reduced downmodulation of that mRNA transcript. In essence, the degree of match or mismatch between the target mRNA and the microRNA seed can act as a rheostat to more finely tune the ability of the microRNA to modulate protein expression. In addition, mutation in the non-seed region of a microRNA binding site may also impact the ability of a microRNA to modulate protein expression.

In one embodiment, a miR sequence may be incorporated into the loop of a stem loop.

In another embodiment, a miR seed sequence may be incorporated in the loop of a stem loop and a miR binding site may be incorporated into the 5' or 3' stem of the stem loop.

In one embodiment, a TEE may be incorporated on the 5' end of the stem of a stem loop and a miR seed may be incorporated into the stem of the stem loop. In another embodiment, a TEE may be incorporated on the 5' end of the stem of a stem loop, a miR seed may be incorporated into the stem of the stem loop and a miR binding site may be incorporated into the 3' end of the stem or the sequence after the stem loop. The miR seed and the miR binding site may be for the same and/or different miR sequences.

In one embodiment, the incorporation of a miR sequence and/or a TEE sequence changes the shape of the stem loop region which may increase and/or decrease translation. (see e.g, Kedde et al. A Pumilio-induced RNA structure switch in p27-3' UTR controls miR-221 and miR-22 accessibility. Nature Cell Biology. 2010, incorporated herein by reference in its entirety).

In one embodiment, the incorporation of a miR sequence and/or a TEE sequence changes the shape of the stem loop region which may increase and/or decrease translation. (see e.g, Kedde et al. A Pumilio-induced RNA structure switch in p27-3' UTR controls miR-221 and miR-22 accessibility. Nature Cell Biology. 2010, incorporated herein by reference in its entirety).

In one embodiment, the 5' UTR may comprise at least one microRNA sequence. The microRNA sequence may be, but is not limited to, a 19 or 22 nucleotide sequence and/or a microRNA sequence without the seed.

In one embodiment the microRNA sequence in the 5' UTR may be used to stabilize the nucleic acid and/or mRNA described herein.

In another embodiment, a microRNA sequence in the 5' UTR may be used to decrease the accessibility of the site of translation initiation such as, but not limited to a start codon. Matsuda et al (PLoS One. 2010 11(5):e15057; incorporated herein by reference in its entirety) used antisense locked nucleic acid (LNA) oligonucleotides and exon-junction complexes (EJCs) around a start codon (−4 to +37 where the A of the AUG codons is +1) in order to decrease the accessibility to the first start codon (AUG). Matsuda showed that altering the sequence around the start codon with an LNA or EJC the efficiency, length and structural stability of the nucleic acid or mRNA is affected. The nucleic acids or mRNA of the present invention may comprise a microRNA sequence, instead of the LNA or EJC sequence described by Matsuda et al, near the site of translation initiation in order to decrease the accessibility to the site of translation initiation. The site of translation initiation may be prior to, after or within the microRNA sequence. As a non-limiting example, the site of translation initiation may be located within a microRNA sequence such as a seed sequence or binding site. As another non-limiting example, the site of translation initiation may be located within a miR-122 sequence such as the seed sequence or the mir-122 binding site.

In one embodiment, the nucleic acids or mRNA of the present invention may include at least one microRNA in order to dampen the antigen presentation by antigen presenting cells. The microRNA may be the complete microRNA sequence, the microRNA seed sequence, the microRNA sequence without the seed or a combination thereof. As a non-limiting example, the microRNA incorporated into the nucleic acids or mRNA of the present invention may be specific to the hematopoietic system. As another non-limiting example, the microRNA incorporated into the nucleic acids or mRNA of the present invention to dampen antigen presentation is miR-142-3p.

In one embodiment, the nucleic acids or mRNA of the present invention may include at least one microRNA in order to dampen expression of the encoded polypeptide in a cell of interest. As a non-limiting example, the nucleic acids or mRNA of the present invention may include at least one miR-122 binding site in order to dampen expression of an encoded polypeptide of interest in the liver. As another non-limiting example, the nucleic acids or mRNA of the present invention may include at least one miR-142-3p binding site, miR-142-3p seed sequence, miR-142-3p binding site without the seed, miR-142-5p binding site, miR-142-5p seed sequence, miR-142-5p binding site without the seed, miR-146 binding site, miR-146 seed sequence and/or miR-146 binding site without the seed sequence.

In one embodiment, the nucleic acids or mRNA of the present invention may comprise at least one microRNA binding site in the 3' UTR in order to selectively degrade mRNA therapeutics in the immune cells to subdue unwanted immunogenic reactions caused by therapeutic delivery. As a non-limiting example, the microRNA binding site may be the alternative nucleic acids more unstable in antigen presenting cells. Non-limiting examples of these microRNA include mir-142-5p, mir-142-3p, mir-146a-5p and mir-146-3p.

In one embodiment, the nucleic acids or mRNA of the present invention comprises at least one microRNA sequence in a region of the nucleic acid or mRNA which may interact with a RNA binding protein.

RNA Motifs for RNA Binding Proteins (RBPs)

RNA binding proteins (RBPs) can regulate numerous aspects of co- and post-transcription gene expression such as, but not limited to, RNA splicing, localization, translation, turnover, polyadenylation, capping, alteration, export and localization. RNA-binding domains (RBDs), such as, but not limited to, RNA recognition motif (RR) and hnRNP K-homology (KH) domains, typically regulate the sequence association between RBPs and their RNA targets (Ray et al. Nature 2013. 499:172-177; incorporated herein by reference in its entirety). In one embodiment, the canonical RBDs can bind short RNA sequences. In another embodiment, the canonical RBDs can recognize structure RNAs.

In one embodiment, to increase the stability of the mRNA of interest, an mRNA encoding HuR can be co-transfected or co-injected along with the mRNA of interest into the cells or into the tissue. These proteins can also be tethered to the mRNA of interest in vitro and then administered to the cells together. Poly A tail binding protein, PABP interacts with eukaryotic translation initiation factor eIF4G to stimulate translational initiation. Co-administration of mRNAs encoding these RBPs along with the mRNA drug and/or tethering these proteins to the mRNA drug in vitro and administering the protein-bound mRNA into the cells can increase the translational efficiency of the mRNA. The same concept can be extended to co-administration of mRNA along with mRNAs encoding various translation factors and facilitators as well as with the proteins themselves to influence RNA stability and/or translational efficiency.

In one embodiment, the nucleic acids and/or mRNA may comprise at least one RNA-binding motif such as, but not limited to a RNA-binding domain (RBD).

In one embodiment, the RBD may be any of the RBDs, fragments or variants thereof descried by Ray et al. (Nature 2013. 499:172-177; incorporated herein by reference in its entirety).

In one embodiment, the nucleic acids or mRNA of the present invention may comprise a sequence for at least one RNA-binding domain (RBDs). When the nucleic acids or mRNA of the present invention comprise more than one RBD, the RBDs do not need to be from the same species or even the same structural class.

In one embodiment, at least one flanking region (e.g., the 5' UTR and/or the 3' UTR) may comprise at least one RBD. In another embodiment, the first flanking region and the second flanking region may both comprise at least one RBD. The RBD may be the same or each of the RBDs may have at least 60% sequence identity to the other RBD. As a non-limiting example, at least on RBD may be located before, after and/or within the 3' UTR of the nucleic acid or mRNA of the present invention. As another non-limiting example, at least one RBD may be located before or within the first 300 nucleosides of the 3' UTR.

In another embodiment, the nucleic acids and/or mRNA of the present invention may comprise at least one RBD in the first region of linked nucleosides. The RBD may be located before, after or within a coding region (e.g., the ORF).

In yet another embodiment, the first region of linked nucleosides and/or at least one flanking region may comprise at least on RBD. As a non-limiting example, the first region of linked nucleosides may comprise a RBD related to splicing factors and at least one flanking region may comprise a RBD for stability and/or translation factors.

In one embodiment, the nucleic acids and/or mRNA of the present invention may comprise at least one RBD located in a coding and/or non-coding region of the nucleic acids and/or mRNA.

In one embodiment, at least one RBD may be incorporated into at least one flanking region to increase the stability of the nucleic acid and/or mRNA of the present invention.

In one embodiment, a microRNA sequence in a RNA binding protein motif may be used to decrease the accessibility of the site of translation initiation such as, but not limited to a start codon. The nucleic acids or mRNA of the present invention may comprise a microRNA sequence, instead of the LNA or EJC sequence described by Matsuda et al, near the site of translation initiation in order to decrease the accessibility to the site of translation initiation. The site of translation initiation may be prior to, after or within the microRNA sequence. As a non-limiting example, the site of translation initiation may be located within a microRNA sequence such as a seed sequence or binding site. As another non-limiting example, the site of translation initiation may be located within a miR-122 sequence such as the seed sequence or the mir-122 binding site.

In another embodiment, an antisense locked nucleic acid (LNA) oligonucleotides and exon-junction complexes (EJCs) may be used in the RNA binding protein motif. The LNA and EJCs may be used around a start codon (−4 to +37 where the A of the AUG codons is +1) in order to decrease the accessibility to the first start codon (AUG).

Codon Optimization

The polynucleotides of the invention, their regions or parts or subregions may be codon optimized. Codon optimization methods are known in the art and may be useful in efforts to achieve one or more of several goals. These goals include to match codon frequencies in target and host organisms to ensure proper folding, bias GC content to increase mRNA stability or reduce secondary structures, minimize tandem repeat codons or base runs that may impair gene construction or expression, customize transcriptional and translational control regions, insert or remove protein trafficking sequences, remove/add post translation modification sites in encoded protein (e.g., glycosylation sites), add, remove or shuffle protein domains, insert or delete restriction sites, modify ribosome binding sites and mRNA degradation sites, to adjust translational rates to allow the various domains of the protein to fold properly, or to reduce or eliminate problem secondary structures within the polynucleotide. Codon optimization tools, algorithms and services are known in the art, non-limiting examples include services from GeneArt (Life Technologies), DNA2.0 (Menlo Park Calif.) and/or proprietary methods. In one embodiment, the ORF sequence is optimized using optimization algorithms. Codon options for each amino acid are given in Table 11.

TABLE 11

Codon Options.

| Amino Acid | Single Letter Code | Codon Options |
|---|---|---|
| Isoleucine | I | ATT, ATC, ATA |
| Leucine | L | CTT, CTC, CTA, CTG, TTA, TTG |
| Valine | V | GTT, GTC, GTA, GTG |
| Phenylalanine | F | TTT, TTC |
| Methionine | M | ATG |
| Cysteine | C | TGT, TGC |
| Alanine | A | GCT, GCC, GCA, GCG |
| Glycine | G | GGT, GGC, GGA, GGG |
| Proline | P | CCT, CCC, CCA, CCG |
| Threonine | T | ACT, ACC, ACA, ACG |
| Serine | S | TCT, TCC, TCA, TCG, AGT, AGC |
| Tyrosine | Y | TAT, TAC |
| Tryptophan | W | TGG |
| Glutamine | Q | CAA, CAG |
| Asparagine | N | AAT, AAC |
| Histidine | H | CAT, CAC |
| Glutamic acid | E | GAA, GAG |
| Aspartic acid | D | GAT, GAC |
| Lysine | K | AAA, AAG |
| Arginine | R | CGT, CGC, CGA, CGG, AGA, AGG |
| Selenocysteine | Sec | UGA in mRNA in presence of Selenocystein insertion element (SECIS) |
| Stop codons | Stop | TAA, TAG, TGA |

"Codon optimized" refers to the modification of a starting nucleotide sequence by replacing at least one codon of the starting nucleotide sequence with a codon that is more frequently used in the group of abundant polypeptides of the host organism. Table 12 contains the codon usage frequency for humans (Codon usage database: [[www.]]kazusa.or.jp/codon/cgi-bin/showcodon.cgi?species=9606&aa=1&style=N).

Codon optimization may be used to increase the expression of polypeptides by the replacement of at least one, at least two, at least three, at least four, at least five, at least six, at least seven, at least eight, at least nine, at least ten or at least 1%, at least 2%, at least 4%, at least 6%, at least 8%, at least 10%, at least 20%, at least 40%, at least 60%, at least 80%, at least 90% or at least 95%, or all codons of the starting nucleotide sequence with more frequently or the most frequently used codons for the respective amino acid as determined for the group of abundant proteins.

In one embodiment of the invention, the alternative nucleotide sequences contain for each amino acid the most frequently used codons of the abundant proteins of the respective host cell.

After optimization (if desired), the polynucleotides components are reconstituted and transformed into a vector such as, but not limited to, plasmids, viruses, cosmids, and artificial chromosomes. For example, the optimized poly-

TABLE 12

Codon usage frequency table for humans.

| Codon | Amino Acid | % | Codon | Amino Acid | % | Codon | Amino Acid | % | Codon | Amino Acid | % |
|---|---|---|---|---|---|---|---|---|---|---|---|
| UUU | F | 46 | UCU | S | 19 | UAU | Y | 44 | UGU | C | 46 |
| UUC | F | 54 | UCC | S | 22 | UAC | Y | 56 | UGC | C | 54 |
| UUA | L | 8 | UCA | S | 15 | UAA | * | 30 | UGA | * | 47 |
| UUG | L | 13 | UCG | S | 5 | UAG | * | 24 | UGG | W | 100 |
| CUU | L | 13 | CCU | P | 29 | CAU | H | 42 | CGU | R | 8 |
| CUC | L | 20 | CCC | P | 32 | CAC | H | 58 | CGC | R | 18 |
| CUA | L | 7 | CCA | P | 28 | CAA | Q | 27 | CGA | R | 11 |
| CUG | L | 40 | CCG | P | 11 | CAG | Q | 73 | CGG | R | 20 |
| AUU | I | 36 | ACU | T | 25 | AAU | N | 47 | AGU | S | 15 |
| AUC | I | 47 | ACC | T | 36 | AAC | N | 53 | AGC | S | 24 |
| AUA | I | 17 | ACA | T | 28 | AAA | K | 43 | AGA | R | 21 |
| AUG | M | 100 | ACG | T | 11 | AAG | K | 57 | AGG | R | 21 |
| GUU | V | 18 | GCU | A | 27 | GAU | D | 46 | GGU | G | 16 |
| GUC | V | 24 | GCC | A | 40 | GAC | D | 54 | GGC | G | 34 |
| GUA | V | 12 | GCA | A | 23 | GAA | E | 42 | GGA | G | 25 |
| GUG | V | 46 | GCG | A | 11 | GAG | E | 58 | GGG | G | 25 |

In one embodiment, after a nucleotide sequence has been codon optimized it may be further evaluated for regions containing restriction sites. At least one nucleotide within the restriction site regions may be replaced with another nucleotide in order to remove the restriction site from the sequence but the replacement of nucleotides does alter the amino acid sequence which is encoded by the codon optimized nucleotide sequence.

Features, which may be considered beneficial in some embodiments of the present invention, may be encoded by regions of the polynucleotide and such regions may be upstream (5') or downstream (3') to a region which encodes a polypeptide. These regions may be incorporated into the polynucleotide before and/or after codon optimization of the protein encoding region or open reading frame (ORF). It is not required that a polynucleotide contain both a 5' and 3' flanking region. Examples of such features include, but are not limited to, untranslated regions (UTRs), Kozak sequences, an oligo(dT) sequence, and detectable tags and may include multiple cloning sites which may have XbaI recognition.

In some embodiments, a 5' UTR and/or a 3' UTR region may be provided as flanking regions. Multiple 5' or 3' UTRs may be included in the flanking regions and may be the same or of different sequences. Any portion of the flanking regions, including none, may be codon optimized and any may independently contain one or more different structural or chemical alterations, before and/or after codon optimization.

nucleotide may be reconstituted and transformed into chemically competent E. coli, yeast, neurospora, maize, drosophila where high copy plasmid-like or chromosome structures occur by methods described herein.

Uses of Alternative Nucleic Acids

Therapeutic Agents

The alternative nucleic acids described herein can be used as therapeutic agents. For example, an alternative nucleic acid described herein can be administered to an animal or subject, wherein the alternative nucleic acid is translated in vivo to produce a therapeutic peptide in the animal or subject. Accordingly, provided herein are mRNA, compositions (such as pharmaceutical compositions), methods, kits, and reagents for treatment or prevention of disease or conditions in humans and other mammals. The active therapeutic agents of the present disclosure include alternative nucleic acids, cells containing alternative nucleic acids or polypeptides translated from the alternative nucleic acids, polypeptides translated from alternative nucleic acids, cells contacted with cells containing alternative nucleic acids or polypeptides translated from the alternative nucleic acids, tissues containing cells containing alternative nucleic acids and organs containing tissues containing cells containing alternative nucleic acids.

Provided are methods of inducing translation of a synthetic or recombinant polynucleotide to produce a polypeptide in a cell population using the alternative nucleic acids described herein. Such translation can be in vivo, ex vivo, in culture, or in vitro. The cell population is contacted with an effective amount of a composition containing a nucleic acid that has at least one nucleoside alteration, and a translatable region encoding the polypeptide. The population is contacted under conditions such that the nucleic acid is localized into one or more cells of the cell population and the recombinant polypeptide is translated in the cell from the nucleic acid.

An effective amount of the composition is provided based, at least in part, on the target tissue, target cell type, means of administration, physical characteristics of the nucleic acid (e.g., size, and extent of alternative nucleosides), and other determinants. In general, an effective amount of the composition provides efficient protein production in the cell, preferably more efficient than a composition containing a corresponding unaltered nucleic acid. Increased efficiency may be demonstrated by increased cell transfection (i.e., the percentage of cells transfected with the nucleic acid), increased protein translation from the nucleic acid, decreased nucleic acid degradation (as demonstrated, e.g., by increased duration of protein translation from a modified nucleic acid), or reduced innate immune response of the host cell or improve therapeutic utility.

Aspects of the present disclosure are directed to methods of inducing in vivo translation of a recombinant polypeptide in a mammalian subject in need thereof. Therein, an effective amount of a composition containing a nucleic acid that has at least one nucleoside alteration and a translatable region encoding the polypeptide is administered to the subject using the delivery methods described herein. The nucleic acid is provided in an amount and under other conditions such that the nucleic acid is localized into a cell or cells of the subject and the recombinant polypeptide is translated in the cell from the nucleic acid. The cell in which the nucleic acid is localized, or the tissue in which the cell is present, may be targeted with one or more than one rounds of nucleic acid administration.

Other aspects of the present disclosure relate to transplantation of cells containing alternative nucleic acids to a mammalian subject. Administration of cells to mammalian subjects is known to those of ordinary skill in the art, such as local implantation (e.g., topical or subcutaneous administration), organ delivery or systemic injection (e.g., intravenous injection or inhalation), as is the formulation of cells in pharmaceutically acceptable carrier. Compositions containing alternative nucleic acids are formulated for administration intramuscularly, transarterially, intraperitoneally, intravenously, intranasally, subcutaneously, endoscopically, transdermally, or intrathecally. In some embodiments, the composition is formulated for extended release.

The subject to whom the therapeutic agent is administered suffers from or is at risk of developing a disease, disorder, or deleterious condition. Provided are methods of identifying, diagnosing, and classifying subjects on these bases, which may include clinical diagnosis, biomarker levels, genome-wide association studies (GWAS), and other methods known in the art.

In certain embodiments, the administered alternative nucleic acid directs production of one or more recombinant polypeptides that provide a functional activity which is substantially absent in the cell in which the recombinant polypeptide is translated. For example, the missing functional activity may be enzymatic, structural, or gene regulatory in nature.

In other embodiments, the administered alternative nucleic acid directs production of one or more recombinant polypeptides that replace a polypeptide (or multiple polypeptides) that is substantially absent in the cell in which the recombinant polypeptide is translated. Such absence may be due to genetic mutation of the encoding gene or regulatory pathway thereof. In other embodiments, the administered alternative nucleic acid directs production of one or more recombinant polypeptides to supplement the amount of polypeptide (or multiple polypeptides) that is present in the cell in which the recombinant polypeptide is translated. Alternatively, the recombinant polypeptide functions to antagonize the activity of an endogenous protein present in, on the surface of, or secreted from the cell. Usually, the activity of the endogenous protein is deleterious to the subject, for example, due to mutation of the endogenous protein resulting in altered activity or localization. Additionally, the recombinant polypeptide antagonizes, directly or indirectly, the activity of a biological moiety present in, on the surface of, or secreted from the cell. Examples of antagonized biological moieties include lipids (e.g., cholesterol), a lipoprotein (e.g., low density lipoprotein), a nucleic acid, a carbohydrate, or a small molecule toxin.

The recombinant proteins described herein are engineered for localization within the cell, potentially within a specific compartment such as the nucleus, or are engineered for secretion from the cell or translocation to the plasma membrane of the cell.

As described herein, a useful feature of the alternative nucleic acids of the present disclosure is the capacity to reduce, evade, avoid or eliminate the innate immune response of a cell to an exogenous nucleic acid. Provided are methods for performing the titration, reduction or elimination of the immune response in a cell or a population of cells. In some embodiments, the cell is contacted with a first composition that contains a first dose of a first exogenous nucleic acid including a translatable region and at least one nucleoside alteration, and the level of the innate immune response of the cell to the first exogenous nucleic acid is determined. Subsequently, the cell is contacted with a second composition, which includes a second dose of the first exogenous nucleic acid, the second dose containing a lesser amount of the first exogenous nucleic acid as compared to the first dose. Alternatively, the cell is contacted with a first dose of a second exogenous nucleic acid.

The second exogenous nucleic acid may contain one or more alternative nucleosides, which may be the same or different from the first exogenous nucleic acid or, alternatively, the second exogenous nucleic acid may not contain alternative nucleosides. The steps of contacting the cell with the first composition and/or the second composition may be repeated one or more times. Additionally, efficiency of protein production (e.g., protein translation) in the cell is optionally determined, and the cell may be re-transfected with the first and/or second composition repeatedly until a target protein production efficiency is achieved.

Therapeutics for Diseases and Conditions

Provided are methods for treating or preventing a symptom of diseases characterized by missing or aberrant protein activity, by replacing the missing protein activity or overcoming the aberrant protein activity. Because of the rapid initiation of protein production following introduction of alternative mRNAs, as compared to viral DNA vectors, the compounds of the present disclosure are particularly advantageous in treating acute diseases such as sepsis, stroke, and myocardial infarction. Moreover, the lack of transcriptional regulation of the alternative mRNAs of the present disclosure is advantageous in that accurate titration of protein production is achievable. Multiple diseases are characterized by missing (or substantially diminished such that proper protein function does not occur) protein activity. Such proteins may not be present, are present in very low quantities or are essentially non-functional. The present disclosure provides a method for treating such conditions or diseases in a subject by introducing nucleic acid or cell-based therapeutics containing the alternative nucleic acids provided herein, wherein the alternative nucleic acids encode for a protein that replaces the protein activity missing from the target cells of the subject.

Diseases characterized by dysfunctional or aberrant protein activity include, but not limited to, cancer and proliferative diseases, genetic diseases (e.g., cystic fibrosis), autoimmune diseases, diabetes, neurodegenerative diseases, cardiovascular diseases, and metabolic diseases. The present disclosure provides a method for treating such conditions or diseases in a subject by introducing nucleic acid or cell-based therapeutics containing the alternative nucleic acids provided herein, wherein the alternative nucleic acids encode for a protein that antagonizes or otherwise overcomes the aberrant protein activity present in the cell of the subject.

Specific examples of a dysfunctional protein are the missense or nonsense mutation variants of the cystic fibrosis transmembrane conductance regulator (CFTR) gene, which produce a dysfunctional or nonfunctional, respectively, protein variant of CFTR protein, which causes cystic fibrosis.

Thus, provided are methods of treating cystic fibrosis in a mammalian subject by contacting a cell of the subject with an alternative nucleic acid having a translatable region that encodes a functional CFTR polypeptide, under conditions such that an effective amount of the CTFR polypeptide is present in the cell. Preferred target cells are epithelial cells, such as the lung, and methods of administration are determined in view of the target tissue; i.e., for lung delivery, the RNA molecules are formulated for administration by inhalation. Therefore, in certain embodiments, the polypeptide of interest encoded by the mRNA of the invention is the CTFR polypeptide and the mRNA or pharmaceutical composition of the invention is for use in treating cystic fibrosis.

In another embodiment, the present disclosure provides a method for treating hyperlipidemia in a subject, by introducing into a cell population of the subject with an alternative mRNA molecule encoding Sortilin, a protein recently characterized by genomic studies, thereby ameliorating the hyperlipidemia in a subject. The SORT1 gene encodes a trans-Golgi network (TGN) transmembrane protein called Sortilin. Genetic studies have shown that one of five individuals has a single nucleotide polymorphism, rs12740374, in the 1p13 locus of the SORT1 gene that predisposes them to having low levels of low-density lipoprotein (LDL) and very-low-density lipoprotein (VLDL). Each copy of the minor allele, present in about 30% of people, alters LDL cholesterol by 8 mg/dL, while two copies of the minor allele, present in about 5% of the population, lowers LDL cholesterol 16 mg/dL. Carriers of the minor allele have also been shown to have a 40% decreased risk of myocardial infarction. Functional in vivo studies in mice describes that overexpression of SORT1 in mouse liver tissue led to significantly lower LDL-cholesterol levels, as much as 80% lower, and that silencing SORT1 increased LDL cholesterol approximately 200% (Musunuru K et al. From noncoding variant to phenotype via SORT1 at the 1p13 cholesterol locus. Nature 2010; 466: 714-721). Therefore, in certain embodiments, the polypeptide of interest encoded by the mRNA of the invention is Sortilin and the mRNA or pharmaceutical composition of the invention is for use in treating hyperlipidemia.

In certain embodiments, the polypeptide of interest encoded by the mRNA of the invention is granulocyte colony-stimulating factor (GCSF), and the mRNA or pharmaceutical composition of the invention is for use in treating a neurological disease such as cerebral ischemia, or treating neutropenia, or for use in increasing the number of hematopoietic stem cells in the blood (e.g. before collection by leukapheresis for use in hematopoietic stem cell transplantation).

In certain embodiments, the polypeptide of interest encoded by the mRNA of the invention is erythropoietin (EPO), and the mRNA or pharmaceutical composition of the invention is for use in treating anemia, inflammatory bowel disease (such as Crohn's disease and/or ulcer colitis) or myelodysplasia.

Methods of Cellular Nucleic Acid Delivery

Methods of the present disclosure enhance nucleic acid delivery into a cell population, in vivo, ex vivo, or in culture. For example, a cell culture containing a plurality of host cells (e.g., eukaryotic cells such as yeast or mammalian cells) is contacted with a composition that contains an enhanced nucleic acid having at least one nucleoside alteration and, optionally, a translatable region. The composition also generally contains a transfection reagent or other compound that increases the efficiency of enhanced nucleic acid uptake into the host cells. The enhanced nucleic acid exhibits enhanced retention in the cell population, relative to a corresponding unaltered nucleic acid. The retention of the enhanced nucleic acid is greater than the retention of the unaltered nucleic acid. In some embodiments, it is at least about 50%, 75%, 90%, 95%, 100%, 150%, 200% or more than 200% greater than the retention of the unaltered nucleic acid. Such retention advantage may be achieved by one round of transfection with the enhanced nucleic acid, or may be obtained following repeated rounds of transfection.

In some embodiments, the enhanced nucleic acid is delivered to a target cell population with one or more additional nucleic acids. Such delivery may be at the same time, or the enhanced nucleic acid is delivered prior to delivery of the one or more additional nucleic acids. The additional one or more nucleic acids may be alternative nucleic acids or unaltered nucleic acids. It is understood that the initial presence of the enhanced nucleic acids does not substantially induce an innate immune response of the cell population and, moreover, that the innate immune response will not be activated by the later presence of the unaltered nucleic acids. In this regard, the enhanced nucleic acid may not itself contain a translatable region, if the protein desired to be present in the target cell population is translated from the unaltered nucleic acids.

Targeting Moieties

In embodiments of the present disclosure, alternative nucleic acids are provided to express a protein-binding partner or a receptor on the surface of the cell, which functions to target the cell to a specific tissue space or to interact with a specific moiety, either in vivo or in vitro. Suitable protein-binding partners include antibodies and functional fragments thereof, scaffold proteins, or peptides. Additionally, alternative nucleic acids can be employed to direct the synthesis and extracellular localization of lipids, carbohydrates, or other biological moieties.

Permanent Gene Expression Silencing

A method for epigenetically silencing gene expression in a mammalian subject, comprising a nucleic acid where the translatable region encodes a polypeptide or polypeptides capable of directing sequence-specific histone H3 methylation to initiate heterochromatin formation and reduce gene transcription around specific genes for the purpose of silencing the gene. For example, a gain-of-function mutation in the Janus Kinase 2 gene is responsible for the family of Myeloproliferative Diseases.

Delivery of a Detectable or Therapeutic Agent to a Biological Target

The alternative nucleosides, alternative nucleotides, and alternative nucleic acids described herein can be used in a number of different scenarios in which delivery of a substance (the "payload") to a biological target is desired, for example delivery of detectable substances for detection of the target, or delivery of a therapeutic agent. Detection methods can include both imaging in vitro and in vivo imaging methods, e.g., immunohistochemistry, bioluminescence imaging (BLI), Magnetic Resonance Imaging (MRI), positron emission tomography (PET), electron microscopy, X-ray computed tomography, Raman imaging, optical coherence tomography, absorption imaging, thermal imaging, fluorescence reflectance imaging, fluorescence microscopy, fluorescence molecular tomographic imaging, nuclear magnetic resonance imaging, X-ray imaging, ultrasound imaging, photoacoustic imaging, lab assays, or in any situation where tagging/staining/imaging is required.

For example, the alternative nucleosides, alternative nucleotides, and alternative nucleic acids described herein can be used in reprogramming induced pluripotent stem cells (iPS cells), which can then be used to directly track cells that are transfected compared to total cells in the cluster. In another example, a drug that is attached to the alternative nucleic acid via a linker and is fluorescently labeled can be used to track the drug in vivo, e.g. intracellularly. Other examples include the use of an alternative nucleic acid in reversible drug delivery into cells.

The alternative nucleosides, alternative nucleotides, and alternative nucleic acids described herein can be used in intracellular targeting of a payload, e.g., detectable or therapeutic agent, to specific organelle. Exemplary intracellular targets can include the nuclear localization for advanced mRNA processing, or a nuclear localization sequence (NLS) linked to the mRNA containing an inhibitor.

In addition, the alternative nucleosides, alternative nucleotides, and alternative nucleic acids described herein can be used to deliver therapeutic agents to cells or tissues, e.g., in living animals. For example, the alternative nucleosides, alternative nucleotides, and alternative nucleic acids described herein can be used to deliver highly polar chemotherapeutics agents to kill cancer cells. The alternative nucleic acids attached to the therapeutic agent through a linker can facilitate member permeation allowing the therapeutic agent to travel into a cell to reach an intracellular target.

In another example, the alternative nucleosides, alternative nucleotides, and alternative nucleic acids can be attached to a viral inhibitory peptide (VIP) through a cleavable linker. The cleavable linker will release the VIP and dye into the cell. In another example, the alternative nucleosides, alternative nucleotides, and alternative nucleic acids can be attached through the linker to a ADP-ribosylate, which is responsible for the actions of some bacterial toxins, such as cholera toxin, diphtheria toxin, and pertussis toxin. These toxin proteins are ADP-ribosyltransferases that modify target proteins in human cells. For example, cholera toxin ADP-ribosylates G proteins, causing massive fluid secretion from the lining of the small intestine, resulting in life-threatening diarrhea.

Pharmaceutical Compositions

The present disclosure provides proteins generated from alternative mRNAs. Pharmaceutical compositions may optionally comprise one or more additional therapeutically active substances. In accordance with some embodiments, a method of administering pharmaceutical compositions comprising an alternative nucleic acid encoding one or more proteins to be delivered to a subject in need thereof is provided. In some embodiments, compositions are administered to humans. For the purposes of the present disclosure, the phrase "active ingredient" generally refers to a protein, protein encoding or protein-containing complex as described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, shaping and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure will vary, depending upon the identity, size, and/or condition of the subject treated and further depending upon the route by which the composition is to be administered. By way of example, the composition may comprise between 0.1% and 100% (w/w) active ingredient.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, and lubricants, as suited to the particular dosage form desired. Remington's The Science and Practice of Pharmacy, $21^{st}$ Edition, A. R. Gennaro (Lippincott, Williams & Wilkins, Baltimore, Md., 2006; incorporated herein by reference)

discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this present disclosure.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. Excipients such as cocoa butter and suppository waxes, coloring agents, coating agents, sweetening, flavoring, and/or perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween®20], polyoxyethylene sorbitan [Tween®60], polyoxyethylene sorbitan monooleate [Tween®80], sorbitan monopalmitate [Span®40], sorbitan monostearate [Span®60], sorbitan tristearate [Span®65], glyceryl monooleate, sorbitan monooleate [Span®80]), polyoxyethylene esters (e.g. polyoxyethylene monostearate [Myrj®45], polyoxyethylene hydrogenated castor oil, polyethoxylated castor oil, polyoxymethylene stearate, and Solutol®), sucrose fatty acid esters, polyethylene glycol fatty acid esters (e.g. Cremophor®), polyoxyethylene ethers, (e.g. polyoxyethylene lauryl ether [Brij®30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F 68, Poloxamer®188, cetrimonium bromide, cetylpyridinium chloride, benzalkonium chloride, docusate sodium, and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan); alginates; polyethylene oxide; polyethylene glycol; inorganic calcium salts; silicic acid; polymethacrylates; waxes; water; alcohol; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus®, Phenonip®, methylparaben, Germall®115, Germaben®II, Neolone™, Kathon™, and/or Euxyl®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, d-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as Cremophor®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions which are compatible with body tissues.

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, an active ingredient is mixed with at least one inert, pharmaceutically acceptable excipient such as sodium citrate or dicalcium phosphate and/or fillers or extenders (e.g. starches, lactose, sucrose, glucose, mannitol, and silicic acid), binders (e.g. carboxymethylcellulose, alginates, gelatin, polyvinylpyrrolidinone, sucrose, and acacia), humectants (e.g. glycerol), disintegrating agents (e.g. agar, calcium carbonate, potato or tapioca starch, alginic acid, certain silicates, and sodium carbonate), solution retarding agents (e.g. paraffin), absorption accelerators (e.g. quaternary ammonium compounds), wetting agents (e.g. cetyl alcohol and glycerol monostearate), absorbents (e.g. kaolin and bentonite clay), and lubricants (e.g. talc, calcium stearate, magnesium stearate, solid polyethylene glycols, sodium lauryl sulfate), and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols. Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols.

Dosage forms for topical and/or transdermal administration of a composition may include ointments, pastes, creams, lotions, gels, powders, solutions, sprays, inhalants and/or patches. Generally, an active ingredient is admixed under sterile conditions with a pharmaceutically acceptable excipient and/or any needed preservatives and/or buffers as may be required. Additionally, the present disclosure contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in International Patent Publication No. WO 99/34850 and functional equivalents thereof. Jet injection devices which deliver liquid compositions to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and International Patent Publication No. WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of active ingredient may be as high as the solubility limit of the active ingredient in the solvent. Formulations for topical administration may further comprise one or more of the additional ingredients described herein.

A pharmaceutical composition may be prepared, packaged, and/or sold in a formulation suitable for pulmonary administration via the buccal cavity. Such a formulation may comprise dry particles which comprise the active ingredient and which have a diameter in the range from about 0.5 nm to about 7 nm or from about 1 nm to about 6 nm. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nm and at least 95% of the particles by number have a diameter less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (w/w) of the composition, and active ingredient may constitute 0.1% to 20% (w/w) of the composition. A propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, comprising active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 0.1 nm to about 200 nm.

Formulations described herein as being useful for pulmonary delivery are useful for intranasal delivery of a pharmaceutical composition. Another formulation suitable for intranasal administration is a coarse powder comprising the active ingredient and having an average particle from about 0.2 µm to 500 µm. Such a formulation is administered in the manner in which snuff is taken, i.e. by rapid inhalation through the nasal passage from a container of the powder held close to the nose.

Formulations suitable for nasal administration mayinclude from about as little as 0.1% (w/w) and as much as 100% (w/w) of active ingredient, and may include one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance including an orally dissolvable and/or degradable composition and, optionally, one or more of the additional ingredients described herein. Alternately, formulations suitable for buccal administration may include a powder and/or an aerosolized and/or atomized solution and/or suspension including active ingredient. Such powdered, aerosolized, and/or aerosolized formulations, when dispersed, may have an average particle and/or droplet size in the range from about 0.1 nm to about 200 nm, and may further include one or more of any additional ingredients described herein.

A pharmaceutical composition may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid excipient. Such drops may further comprise buffering agents, salts, and/or one or more other of any additional ingredients described herein. Other opthalmically-administrable formulations which are useful include those which comprise the active ingredient in microcrystalline form and/or in a liposomal preparation. Ear drops and/or eye drops are contemplated as being within the scope of this present disclosure.

General considerations in the formulation and/or manufacture of pharmaceutical agents may be found, for example, in Remington: *The Science and Practice of Pharmacy* 21$^{st}$ ed., Lippincott Williams & Wilkins, 2005 (incorporated herein by reference).

Administration

The present disclosure provides methods comprising administering proteins or complexes in accordance with the present disclosure to a subject in need thereof. Proteins or complexes, or pharmaceutical, imaging, diagnostic, or prophylactic compositions thereof, may be administered to a subject using any amount and any route of administration effective for preventing, treating, diagnosing, or imaging a disease, disorder, and/or condition (e.g., a disease, disorder, and/or condition relating to working memory deficits). The exact amount required will vary from subject to subject, depending on the species, age, and general condition of the subject, the severity of the disease, the particular composition, its mode of administration, and its mode of activity. Compositions in accordance with the present disclosure are typically formulated in dosage unit form for ease of administration and uniformity of dosage. It will be understood, however, that the total daily usage of the compositions of the present disclosure will be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Proteins to be delivered and/or pharmaceutical, prophylactic, diagnostic, or imaging compositions thereof may be administered to animals, such as mammals (e.g., humans, domesticated animals, cats, dogs, mice, rats). In some embodiments, pharmaceutical, prophylactic, diagnostic, or imaging compositions thereof are administered to humans.

Proteins to be delivered and/or pharmaceutical, prophylactic, diagnostic, or imaging compositions thereof in accordance with the present disclosure may be administered by any route. In some embodiments, proteins and/or pharmaceutical, prophylactic, diagnostic, or imaging compositions thereof, are administered by one or more of a variety of routes, including oral, intravenous, intramuscular, intraarterial, intramedullary, intrathecal, subcutaneous, intraventricular, transdermal, interdermal, rectal, intravaginal, intraperitoneal, topical (e.g. by powders, ointments, creams, gels, lotions, and/or drops), mucosal, nasal, buccal, enteral, vitreal, intratumoral, sublingual; by intratracheal instillation, bronchial instillation, and/or inhalation; as an oral spray, nasal spray, and/or aerosol, and/or through a portal vein catheter. In some embodiments, proteins or complexes, and/or pharmaceutical, prophylactic, diagnostic, or imaging compositions thereof, are administered by systemic intravenous injection. In specific embodiments, proteins or complexes and/or pharmaceutical, prophylactic, diagnostic, or imaging compositions thereof may be administered intravenously and/or orally. In specific embodiments, proteins or complexes, and/or pharmaceutical, prophylactic, diagnostic, or imaging compositions thereof, may be administered in a way which allows the protein or complex to cross the blood-brain barrier, vascular barrier, or other epithelial barrier.

However, the present disclosure encompasses the delivery of proteins or complexes, and/or pharmaceutical, prophylactic, diagnostic, or imaging compositions thereof, by any appropriate route taking into consideration likely advances in the sciences of drug delivery.

In general the most appropriate route of administration will depend upon a variety of factors including the nature of the protein or complex comprising proteins associated with at least one agent to be delivered (e.g., its stability in the environment of the gastrointestinal tract, bloodstream), the condition of the patient (e.g., whether the patient is able to tolerate particular routes of administration).

The present disclosure encompasses the delivery of the pharmaceutical, prophylactic, diagnostic, or imaging compositions by any appropriate route taking into consideration likely advances in the sciences of drug delivery.

In certain embodiments, compositions in accordance with the present disclosure may be administered at dosage levels sufficient to deliver from about 0.0001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

Proteins or complexes may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, diagnostic, or imaging compositions in combination with agents that improve their bioavailability, reduce and/or modify their metabolism, inhibit their excretion, and/or modify their distribution within the body.

It will further be appreciated that therapeutically, prophylactically, diagnostically, or imaging active agents utilized in combination may be administered together in a single composition or administered separately in different compositions. In general, it is expected that agents utilized in combination with be utilized at levels that do not exceed the levels at which they are utilized individually. In some embodiments, the levels utilized in combination will be lower than those utilized individually.

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a composition useful for treating cancer in accordance with the present disclosure may be administered concurrently with a chemotherapeutic agent), or they may achieve different effects (e.g., control of any adverse effects).

Kits

The present disclosure provides a variety of kits for conveniently and/or effectively carrying out methods of the present disclosure. Typically kits will comprise sufficient amounts and/or numbers of components to allow a user to perform multiple treatments of a subject(s) and/or to perform multiple experiments.

In one aspect, the disclosure provides kits for protein production, comprising a first isolated nucleic acid comprising a translatable region and a nucleic acid alteration, wherein the nucleic acid is capable of evading or avoiding induction of an innate immune response of a cell into which the first isolated nucleic acid is introduced, and packaging and instructions.

In one aspect, the disclosure provides kits for protein production, comprising: a first isolated alternative nucleic acid comprising a translatable region, provided in an amount effective to produce a desired amount of a protein encoded by the translatable region when introduced into a target cell; a second nucleic acid comprising an inhibitory nucleic acid, provided in an amount effective to substantially inhibit the innate immune response of the cell; and packaging and instructions.

In one aspect, the disclosure provides kits for protein production, comprising a first isolated nucleic acid comprising a translatable region and a nucleoside alteration, wherein the nucleic acid exhibits reduced degradation by a cellular nuclease, and packaging and instructions.

In one aspect, the disclosure provides kits for protein production, comprising a first isolated nucleic acid comprising a translatable region and at least two different nucleoside alterations, wherein the nucleic acid exhibits reduced degradation by a cellular nuclease, and packaging and instructions.

In one aspect, the disclosure provides kits for protein production, comprising a first isolated nucleic acid comprising a translatable region and at least one nucleoside alteration, wherein the nucleic acid exhibits reduced degradation by a cellular nuclease; a second nucleic acid comprising an inhibitory nucleic acid; and packaging and instructions.

In some embodiments, the first isolated nucleic acid comprises messenger RNA (mRNA). In some embodiments the mRNA comprises at least one nucleoside selected from the group consisting of 5-methoxy uridine, pyridin-4-one ribonucleoside, 5-aza-uridine, 2-thio-5-aza-uridine, 2-thio-uridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine or any disclosed herein.

In some embodiments, the mRNA comprises at least one nucleoside selected from the group consisting of 5-methyl-cytidine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine or any disclosed herein.

In some embodiments, the mRNA comprises at least one nucleoside selected from the group consisting of 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine or any disclosed herein.

In some embodiments, the mRNA comprises at least one nucleoside selected from the group consisting of inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, N2,N2-dimethyl-6-thio-guanosine or any disclosed herein.

In another aspect, the disclosure provides compositions for protein production, comprising a first isolated nucleic acid comprising a translatable region and a nucleoside alteration, wherein the nucleic acid exhibits reduced degradation by a cellular nuclease, and a mammalian cell suitable for translation of the translatable region of the first nucleic acid.

Definitions

At various places in the present specification, substituents of compounds of the present disclosure are disclosed in groups or in ranges. It is specifically intended that the present disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

About: As used herein, the term "about" when used in the context of the amount of an alternative nucleobase or nucleoside in a polynucleic acid means +/−2.5% of the recited value. For example, a polynucleotide containing about 25% of an alternative uracil includes between 22.5-27.5% of the alternative uracil.

Administered in combination: As used herein, the term "administered in combination" or "combined administration" means that two or more agents are administered to a subject at the same time or within an interval such that there may be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Antigens of interest or desired antigens: As used herein, the terms "antigens of interest" or "desired antigens" include those proteins and other biomolecules provided herein that are immunospecifically bound by the antibodies and fragments, mutants, variants, and alterations thereof described herein. Examples of antigens of interest include, but are not limited to, insulin, insulin-like growth factor, hGH, tPA, cytokines, such as interleukins (IL), e.g., IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosis factor (TNF), such as TNF alpha and TNF beta, TNF gamma, TRAIL; G-CSF, GM-CSF, M-CSF, MCP-1 and VEGF.

Approximately: As used herein, the term "approximately" or "about," as applied to one or more values of interest other than the amount of an alternative nucleobase or nucleoside in a polynucleic acid, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, a polynucleotide of the present invention may be considered biologically active if even a portion of the polynucleotide is biologically active or mimics an activity considered biologically relevant.

Chemical terms: The following provides the definition of various chemical terms from "acyl" to "thiol."

The term "acyl," as used herein, represents a hydrogen or an alkyl group (e.g., a haloalkyl group), as defined herein, that is attached to the parent molecular group through a carbonyl group, as defined herein, and is exemplified by formyl (i.e., a carboxyaldehyde group), acetyl, trifluoroacetyl, propionyl, butanoyl and the like. Exemplary unsubstituted acyl groups include from 1 to 7, from 1 to 11, or from 1 to 21 carbons. In some embodiments, the alkyl group is further substituted with 1, 2, 3, or 4 substituents as described herein.

The term "acylamino," as used herein, represents an acyl group, as defined herein, attached to the parent molecular group though an amino group, as defined herein (i.e., —N($R^{N1}$)—C(O)—R, where R is H or an optionally substituted $C_{1-6}$, $C_{1-10}$, or $C_{1-20}$ alkyl group (e.g., haloalkyl) and $R^{N1}$ is as defined herein). Exemplary unsubstituted acylamino groups include from 1 to 41 carbons (e.g., from 1 to 7, from 1 to 13, from 1 to 21, from 2 to 7, from 2 to 13, from 2 to 21, or from 2 to 41 carbons). In some embodiments, the alkyl group is further substituted with 1, 2, 3, or 4 substituents as described herein, and/or the amino group is —$NH_2$ or —$NHR^{N1}$, wherein $R^{N1}$ is, independently, OH, $NO_2$, $NH_2$, $NR^{N2}_2$, $SO_2OR^{N2}$, $SO_2R^{N2}$, $SOR^{N2}$, alkyl, aryl, acyl (e.g., acetyl, trifluoroacetyl, or others described herein), or alkoxycarbonylalkyl, and each $R^{N2}$ can be H, alkyl, or aryl.

The term "acylaminoalkyl," as used herein, represents an acyl group, as defined herein, attached to an amino group that is in turn attached to the parent molecular group though an alkyl group, as defined herein (i.e., -alkyl-N($R^{N1}$)—C(O)—R, where R is H or an optionally substituted $C_{1-6}$, $C_{1-10}$, or $C_{1-20}$ alkyl group (e.g., haloalkyl) and $R^{N1}$ is as defined herein). Exemplary unsubstituted acylamino groups include from 1 to 41 carbons (e.g., from 1 to 7, from 1 to 13, from 1 to 21, from 2 to 7, from 2 to 13, from 2 to 21, or from 2 to 41 carbons). In some embodiments, the alkyl group is further substituted with 1, 2, 3, or 4 substituents as described herein, and/or the amino group is —$NH_2$ or —$NHR^{N1}$, wherein $R^{N1}$ is, independently, OH, $NO_2$, $NH_2$, $NR^{N2}_2$, $SO_2OR^{N2}$, $SO_2R^{N2}$, $SOR^{N2}$, alkyl, aryl, acyl (e.g., acetyl, trifluoroacetyl, or others described herein), or alkoxycarbonylalkyl, and each $R^{N2}$ can be H, alkyl, or aryl.

The term "acyloxy," as used herein, represents an acyl group, as defined herein, attached to the parent molecular group though an oxygen atom (i.e., —O—C(O)—R, where R is H or an optionally substituted $C_{1-6}$, $C_{1-10}$, or $C_{1-20}$ alkyl group). Exemplary unsubstituted acyloxy groups include from 1 to 21 carbons (e.g., from 1 to 7 or from 1 to 11 carbons). In some embodiments, the alkyl group is further substituted with 1, 2, 3, or 4 substituents as described herein.

The term "acyloxyalkyl," as used herein, represents an acyl group, as defined herein, attached to an oxygen atom that in turn is attached to the parent molecular group though an alkyl group (i.e., -alkyl-O—C(O)—R, where R is H or an optionally substituted $C_{1-6}$, $C_{1-10}$, or $C_{1-20}$ alkyl group). Exemplary unsubstituted acyloxyalkyl groups include from 1 to 21 carbons (e.g., from 1 to 7 or from 1 to 11 carbons). In some embodiments, the alkyl group is, independently, further substituted with 1, 2, 3, or 4 substituents as described herein.

The term "alkaryl," as used herein, represents an aryl group, as defined herein, attached to the parent molecular group through an alkylene group, as defined herein. Exemplary unsubstituted alkaryl groups are from 7 to 30 carbons (e.g., from 7 to 16 or from 7 to 20 carbons, such as $C_{6-10}$ aryl $C_{1-6}$ alkyl, $C_{6-10}$ aryl $C_{1-10}$ alkyl, or $C_{6-10}$ aryl $C_{1-20}$ alkyl). In some embodiments, the alkylene and the aryl each can be further substituted with 1, 2, 3, or 4 substituent groups as defined herein for the respective groups.

The term "alkcycloalkyl" represents a cycloalkyl group, as defined herein, attached to the parent molecular group through an alkylene group, as defined herein (e.g., an alkylene group of from 1 to 4, from 1 to 6, from 1 to 10, or form 1 to 20 carbons). In some embodiments, the alkylene and the cycloalkyl each can be further substituted with 1, 2, 3, or 4 substituent groups as defined herein for the respective group.

The term "alkenyl," as used herein, represents monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, 2-butenyl, and the like. Alkenyls include both cis and trans isomers. Alkenyl groups may be optionally substituted with 1, 2, 3, or 4 substituent groups that are selected, independently, from amino, aryl, cycloalkyl, or heterocyclyl (e.g., heteroaryl), as defined herein, or any of the exemplary alkyl substituent groups described herein.

The term "alkenyloxy" represents a chemical substituent of formula —OR, where R is a $C_{2-20}$ alkenyl group (e.g., $C_{2-6}$ or $C_{2-10}$ alkenyl), unless otherwise specified. Exemplary alkenyloxy groups include ethenyloxy, propenyloxy, and the like. In some embodiments, the alkenyl group can be further substituted with 1, 2, 3, or 4 substituent groups as defined herein (e.g., a hydroxy group).

The term "alkheteroaryl" refers to a heteroaryl group, as defined herein, attached to the parent molecular group through an alkylene group, as defined herein. Exemplary unsubstituted alkheteroaryl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-12}$ heteroaryl $C_{1-6}$ alkyl, $C_{1-12}$ heteroaryl $C_{1-10}$ alkyl, or $C_{1-12}$ heteroaryl $C_{1-20}$ alkyl). In some embodiments, the alkylene and the heteroaryl each can be further substituted with 1, 2, 3, or 4 substituent groups as defined herein for the respective group. Alkheteroaryl groups are a subset of alkheterocyclyl groups.

The term "alkheterocyclyl" represents a heterocyclyl group, as defined herein, attached to the parent molecular group through an alkylene group, as defined herein. Exemplary unsubstituted alkheterocyclyl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-12}$ heterocyclyl $C_{1-6}$ alkyl, $C_{1-12}$ heterocyclyl $C_{1-10}$ alkyl, or $C_{1-12}$ heterocyclyl $C_{1-20}$ alkyl). In some embodiments, the alkylene and the heterocyclyl each can be further substituted with 1, 2, 3, or 4 substituent groups as defined herein for the respective group.

The term "alkoxy" represents a chemical substituent of formula —OR, where R is a $C_{1-20}$ alkyl group (e.g., $C_{1-6}$ or $C_{1-10}$ alkyl), unless otherwise specified. Exemplary alkoxy groups include methoxy, ethoxy, propoxy (e.g., n-propoxy and isopropoxy), t-butoxy, and the like. In some embodiments, the alkyl group can be further substituted with 1, 2, 3, or 4 substituent groups as defined herein (e.g., hydroxy or alkoxy).

The term "alkoxyalkoxy" represents an alkoxy group that is substituted with an alkoxy group. Exemplary unsubstituted alkoxyalkoxy groups include between 2 to 40 carbons (e.g., from 2 to 12 or from 2 to 20 carbons, such as $C_{1-6}$ alkoxy-$C_{1-6}$ alkoxy, $C_{1-10}$ alkoxy-$C_{1-10}$ alkoxy, or $C_{1-20}$ alkoxy-$C_{1-20}$ alkoxy). In some embodiments, the each alkoxy group can be further substituted with 1, 2, 3, or 4 substituent groups as defined herein.

The term "alkoxyalkyl" represents an alkyl group that is substituted with an alkoxy group. Exemplary unsubstituted alkoxyalkyl groups include between 2 to 40 carbons (e.g., from 2 to 12 or from 2 to 20 carbons, such as $C_{1-6}$ alkoxy-$C_{1-6}$ alkyl, $C_{1-10}$ alkoxy-$C_{1-10}$ alkyl, or $C_{1-20}$ alkoxy-$C_{1-20}$ alkyl). In some embodiments, the alkyl and the alkoxy each can be further substituted with 1, 2, 3, or 4 substituent groups as defined herein for the respective group.

The term "alkoxycarbonyl," as used herein, represents an alkoxy, as defined herein, attached to the parent molecular group through a carbonyl atom (e.g., —C(O)—OR, where R is H or an optionally substituted $C_{1-6}$, $C_{1-10}$, or $C_{1-20}$ alkyl group). Exemplary unsubstituted alkoxycarbonyl include from 1 to 21 carbons (e.g., from 1 to 11 or from 1 to 7 carbons). In some embodiments, the alkoxy group is further substituted with 1, 2, 3, or 4 substituents as described herein.

The term "alkoxycarbonylacyl," as used herein, represents an acyl group, as defined herein, that is substituted with an alkoxycarbonyl group, as defined herein (e.g., —C(O)-alkyl-C(O)—OR, where R is an optionally substituted $C_{1-6}$, $C_{1-10}$, or $C_{1-20}$ alkyl group). Exemplary unsubstituted alkoxycarbonylacyl include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ acyl, $C_{1-10}$ alkoxycarbonyl-$C_{1-10}$ acyl, or $C_{1-20}$ alkoxycarbonyl-$C_{1-20}$ acyl). In some embodiments, each alkoxy and alkyl group is further independently substituted with 1, 2, 3, or 4 substituents, as described herein (e.g., a hydroxy group) for each group.

The term "alkoxycarbonylalkoxy," as used herein, represents an alkoxy group, as defined herein, that is substituted with an alkoxycarbonyl group, as defined herein (e.g., —O-alkyl-C(O)—OR, where R is an optionally substituted $C_{1-6}$, $C_{1-10}$, or $C_{1-20}$ alkyl group). Exemplary unsubstituted alkoxycarbonylalkoxy include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ alkoxy, $C_{1-10}$ alkoxycarbonyl-$C_{1-10}$ alkoxy, or $C_{1-20}$ alkoxycarbonyl-$C_{1-20}$ alkoxy). In some embodiments, each alkoxy group is further independently substituted with 1, 2, 3, or 4 substituents, as described herein (e.g., a hydroxy group).

The term "alkoxycarbonylalkyl," as used herein, represents an alkyl group, as defined herein, that is substituted with an alkoxycarbonyl group, as defined herein (e.g., -alkyl-C(O)—OR, where R is an optionally substituted $C_{1-20}$, $C_{1-10}$, or $C_{1-6}$ alkyl group). Exemplary unsubstituted alkoxycarbonylalkyl include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ alkyl, $C_{1-10}$ alkoxycarbonyl-$C_{1-10}$ alkyl, or $C_{1-20}$ alkoxycarbonyl-$C_{1-20}$ alkyl). In some embodiments, each alkyl and alkoxy group is further independently substituted with 1, 2, 3, or 4 substituents as described herein (e.g., a hydroxy group).

The term "alkoxycarbonylalkenyl," as used herein, represents an alkenyl group, as defined herein, that is substituted with an alkoxycarbonyl group, as defined herein (e.g., -alkenyl-C(O)—OR, where R is an optionally substituted $C_{1-20}$, $C_{1-10}$, or $C_{1-6}$ alkyl group). Exemplary unsubstituted alkoxycarbonylalkenyl include from 4 to 41 carbons (e.g., from 4 to 10, from 4 to 13, from 4 to 17, from 4 to 21, or from 4 to 31 carbons, such as $C_{1-6}$ alkoxycarbonyl-$C_{2-6}$ alkenyl, $C_{1-10}$ alkoxycarbonyl-$C_{2-10}$ alkenyl, or $C_{1-20}$ alkoxycarbonyl-$C_{2-20}$ alkenyl). In some embodiments, each alkyl, alkenyl, and alkoxy group is further independently substituted with 1, 2, 3, or 4 substituents as described herein (e.g., a hydroxy group).

The term "alkoxycarbonylalkynyl," as used herein, represents an alkynyl group, as defined herein, that is substituted with an alkoxycarbonyl group, as defined herein (e.g., -alkynyl-C(O)—OR, where R is an optionally substituted $C_{1-20}$, $C_{1-10}$, or $C_{1-6}$ alkyl group). Exemplary unsubstituted alkoxycarbonylalkynyl include from 4 to 41 carbons (e.g., from 4 to 10, from 4 to 13, from 4 to 17, from 4 to 21, or from 4 to 31 carbons, such as $C_{1-6}$ alkoxycarbonyl-$C_{2-6}$ alkynyl, $C_{1-10}$ alkoxycarbonyl-$C_{2-10}$ alkynyl, or $C_{1-20}$ alkoxycarbonyl-$C_{2-20}$ alkynyl). In some embodiments, each alkyl, alkynyl, and alkoxy group is further independently substituted with 1, 2, 3, or 4 substituents as described herein (e.g., a hydroxy group).

The term "alkyl," as used herein, is inclusive of both straight chain and branched chain saturated groups from 1 to 20 carbons (e.g., from 1 to 10 or from 1 to 6), unless otherwise specified. Alkyl groups are exemplified by methyl, ethyl, n- and iso-propyl, n-, sec-, iso- and tert-butyl, neopentyl, and the like, and may be optionally substituted with one, two, three, or, in the case of alkyl groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., —NH$_2$) or a substituted amino (i.e., —N(R$^{N1}$)$_2$, where R$^{N1}$ is as defined for amino); (4) $C_{6-10}$ aryl-$C_{1-6}$ alkoxy; (5) azido; (6) halo; (7) ($C_{2-9}$ heterocyclyl)oxy; (8) hydroxy, optionally substituted with an O-protecting group; (9) nitro; (10) oxo (e.g., carboxyaldehyde or acyl); (11) $C_{1-7}$ spirocyclyl; (12) thioalkoxy; (13) thiol; (14) —CO$_2$R$^{A'}$, optionally substituted with an O-protecting group and where R$^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{6-10}$ aryl $C_{1-6}$ alkyl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; (15) —C(O)NR$^{B'}$R$^{C'}$, where each of R$^{B'}$ and R$^{C'}$ is, independently, selected from the group consisting of (a) hydrogen, (b) $C_{1-6}$ alkyl, (c) $C_{6-10}$ aryl, and (d) $C_{6-10}$ aryl $C_{1-6}$ alkyl; (16) —SO$_2$R$^{D'}$, where R$^{D'}$ is selected from the group consisting of (a) $C_{1-6}$ alkyl, (b) $C_{6-10}$ aryl, (c) $C_{6-10}$ aryl $C_{1-6}$ alkyl, and (d) hydroxy; (17) —SO$_2$NR$^{E'}$R$^{F'}$, where each of R$^{E'}$ and R$^{F'}$ is, independently, selected from the group consisting of (a) hydrogen, (b) $C_{1-6}$ alkyl, (c) $C_{6-10}$ aryl and (d) $C_{6-10}$ aryl $C_{1-6}$ alkyl; (18) —C(O)R$^{G'}$, where R$^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{6-10}$ aryl $C_{1-6}$ alkyl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; (19) —NR$^{H'}$C(O)R$^{I'}$, wherein R$^{H'}$ is selected from the group consisting of (a1) hydrogen and (b1) $C_{1-6}$ alkyl, and R$^{I'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{6-10}$ aryl $C_{1-6}$ alkyl, (f2) amino-$C_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; (20) —NR$^{J'}$C(O)OR$^{K'}$, wherein R$^{J'}$ is selected from the group consisting of (a1) hydrogen and (b1) $C_{1-6}$ alkyl, and R$^{K'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{6-10}$ aryl $C_{1-6}$ alkyl, (f2) amino-$C_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; and (21) amidine. In some embodiments, each of these groups can be further substituted as described herein. For example, the alkylene group of a $C_1$-alkaryl can be further substituted with an oxo group to afford the respective aryloyl substituent.

The term "alkylene" as used herein, represent a saturated divalent hydrocarbon group derived from a straight or branched chain saturated hydrocarbon by the removal of two hydrogen atoms, and is exemplified by methylene, ethylene, isopropylene, and the like. The term "$C_{x-y}$ alkylene" represent alkylene groups having between x and y carbons. Exemplary values for x are 1, 2, 3, 4, 5, and 6, and exemplary values for y are 2, 3, 4, 5, 6, 7, 8, 9, 10, 12, 14, 16, 18, or 20 (e.g., $C_{1-6}$, $C_{1-10}$, $C_{2-20}$, $C_{2-6}$, $C_{2-10}$, or $C_{2-20}$ alkylene). In some embodiments, the alkylene can be further substituted with 1, 2, 3, or 4 substituent groups as defined herein for an alkyl group.

The term "alkylsulfinyl," as used herein, represents an alkyl group attached to the parent molecular group through an —S(O)— group. Exemplary unsubstituted alkylsulfinyl groups are from 1 to 6, from 1 to 10, or from 1 to 20 carbons. In some embodiments, the alkyl group can be further substituted with 1, 2, 3, or 4 substituent groups as defined herein.

The term "alkylsulfinylalkyl," as used herein, represents an alkyl group, as defined herein, substituted by an alkylsulfinyl group. Exemplary unsubstituted alkylsulfinylalkyl groups are from 2 to 12, from 2 to 20, or from 2 to 40 carbons. In some embodiments, each alkyl group can be further substituted with 1, 2, 3, or 4 substituent groups as defined herein.

The term "alkynyl," as used herein, represents monovalent straight or branched chain groups from 2 to 20 carbon atoms (e.g., from 2 to 4, from 2 to 6, or from 2 to 10 carbons) containing a carbon-carbon triple bond and is exemplified by ethynyl, 1-propynyl, and the like. Alkynyl groups may be optionally substituted with 1, 2, 3, or 4 substituent groups that are selected, independently, from aryl, cycloalkyl, or heterocyclyl (e.g., heteroaryl), as defined herein, or any of the exemplary alkyl substituent groups described herein.

The term "alkynyloxy" represents a chemical substituent of formula —OR, where R is a $C_{2-20}$ alkynyl group (e.g., $C_{2-6}$ or $C_{2-10}$ alkynyl), unless otherwise specified. Exemplary alkynyloxy groups include ethynyloxy, propynyloxy, and the like. In some embodiments, the alkynyl group can be further substituted with 1, 2, 3, or 4 substituent groups as defined herein (e.g., a hydroxy group).

The term "amidine," as used herein, represents a —C(=NH)NH$_2$ group.

The term "amino," as used herein, represents —N(R$^{N1}$)$_2$, wherein each R$^{N1}$ is, independently, H, OH, NO$_2$, N(R$^{N2}$)$_2$, SO$_2$OR$^{N2}$, SO$_2$R$^{N2}$, SOR$^{N2}$, an N-protecting group, alkyl, alkenyl, alkynyl, alkoxy, aryl, alkaryl, cycloalkyl, alkcycloalkyl, carboxyalkyl (e.g., optionally substituted with an O-protecting group, such as optionally substituted arylalkoxycarbonyl groups or any described herein), sulfoalkyl, acyl (e.g., acetyl, trifluoroacetyl, or others described herein), alkoxycarbonylalkyl (e.g., optionally substituted with an O-protecting group, such as optionally substituted arylalkoxycarbonyl groups or any described herein), heterocyclyl (e.g., heteroaryl), or alkheterocyclyl (e.g., alkheteroaryl), wherein each of these recited R$^{N1}$ groups can be optionally substituted, as defined herein for each group; or two R$^{N1}$ combine to form a heterocyclyl or an N-protecting group, and wherein each R$^{N2}$ is, independently, H, alkyl, or aryl. The amino groups of the invention can be an unsubstituted amino (i.e., —NH$_2$) or a substituted amino (i.e., —N(R$^{N1}$)$_2$). In a preferred embodiment, amino is —NH$_2$ or —NHR, wherein R$^{N1}$ is, independently, OH, NO$_2$, NH$_2$, NR$^{N2}$$_2$, SO$_2$OR$^{N2}$, SO$_2$R$^{N2}$, SOR$^{N2}$, alkyl, carboxyalkyl, sulfoalkyl, acyl (e.g., acetyl, trifluoroacetyl, or others described herein), alkoxycarbonylalkyl (e.g., t-butoxycarbonylalkyl) or aryl, and each R$^{N2}$ can be H, $C_{1-20}$ alkyl (e.g., $C_{1-6}$ alkyl), or $C_{6-10}$ aryl.

The term "amino acid," as described herein, refers to a molecule having a side chain, an amino group, and an acid group (e.g., a carboxy group of —CO$_2$H or a sulfo group of —SO$_3$H), wherein the amino acid is attached to the parent molecular group by the side chain, amino group, or acid group (e.g., the side chain). In some embodiments, the amino acid is attached to the parent molecular group by a carbonyl group, where the side chain or amino group is attached to the carbonyl group. Exemplary side chains include an optionally substituted alkyl, aryl, heterocyclyl, alkaryl, alkheterocyclyl, aminoalkyl, carbamoylalkyl, and carboxyalkyl. Exemplary amino acids include alanine, arginine, asparagine, aspartic acid, cysteine, glutamic acid, glutamine, glycine, histidine, hydroxynorvaline, isoleucine, leucine, lysine, methionine, norvaline, ornithine, phenylalanine, proline, pyrrolysine, selenocysteine, serine, taurine, threonine, tryptophan, tyrosine, and valine. Amino acid groups may be optionally substituted with one, two, three, or, in the case of amino acid groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., —NH$_2$) or a substituted amino (i.e., —N(R$^{N1}$)$_2$, where R$^{N1}$ is as defined for amino); (4) $C_{6-10}$ aryl-$C_{1-6}$ alkoxy; (5) azido; (6) halo; (7) ($C_{2-9}$ heterocyclyl)oxy; (8) hydroxy; (9) nitro; (10) oxo (e.g., carboxyaldehyde or acyl); (11) $C_{1-7}$ spirocyclyl; (12) thioalkoxy; (13) thiol; (14) —CO$_2$R$^{A'}$, where R$^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{6-10}$ aryl $C_{1-6}$ alkyl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; (15) —C(O)NR$^{B'}$R$^{C'}$, where each of R$^{B'}$ and R$^{C'}$ is, independently, selected from the group consisting of (a) hydrogen, (b) $C_{1-6}$ alkyl, (c) $C_{6-10}$ aryl, and (d) $C_{6-10}$ aryl $C_{1-6}$ alkyl; (16) —SO$_2$R$^{D'}$, where R$^{D'}$ is selected from the group consisting of (a) $C_{1-6}$ alkyl, (b) $C_{6-10}$ aryl, (c) $C_{6-10}$ aryl $C_{1-6}$ alkyl, and (d) hydroxy; (17) —SO$_2$NR$^{E'}$R$^{F'}$, where each of R$^{E'}$ and R$^{F'}$ is, independently, selected from the group consisting of (a) hydrogen, (b) $C_{1-6}$ alkyl, (c) $C_{6-10}$ aryl and (d) $C_{6-10}$ aryl $C_{1-6}$ alkyl; (18) —C(O)R$^{G'}$, where R$^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{6-10}$ aryl $C_{1-6}$ alkyl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted $C_{1-6}$ alkyl; (19) —NR$^{H'}$C(O)R$^{I'}$, wherein R$^{H'}$ is selected from the group consisting of (a1) hydrogen and (b1) $C_{1-6}$ alkyl, and R$^{I'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{6-10}$ aryl $C_{1-6}$ alkyl, (f2) amino-$C_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (20) —$NR^{J'}C(O)OR^{K'}$, wherein $R^{U'}$ is selected from the group consisting of (a1) hydrogen and (b1) $C_{1-6}$ alkyl, and $R^{K'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_6$-10 aryl, (d2) hydrogen, (e2) $C_6$-10 aryl $C_{1-6}$ alkyl, (f2) amino-$C_{1-20}$ alkyl, (g2) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; and (21) amidine. In some embodiments, each of these groups can be further substituted as described herein.

The term "aminoalkoxy," as used herein, represents an alkoxy group, as defined herein, substituted by an amino group, as defined herein. The alkyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{6-10}$ aryl $C_{1-6}$ alkyl, e.g., carboxy).

The term "aminoalkyl," as used herein, represents an alkyl group, as defined herein, substituted by an amino group, as defined herein. The alkyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{6-10}$ aryl $C_{1-6}$ alkyl, e.g., carboxy, and/or an N-protecting group).

The term "aminoalkenyl," as used herein, represents an alkenyl group, as defined herein, substituted by an amino group, as defined herein. The alkenyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{6-10}$ aryl $C_{1-6}$ alkyl, e.g., carboxy, and/or an N-protecting group).

The term "aminoalkynyl," as used herein, represents an alkynyl group, as defined herein, substituted by an amino group, as defined herein. The alkynyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{6-10}$ aryl $C_{1-6}$ alkyl, e.g., carboxy, and/or an N-protecting group).

The term "aryl," as used herein, represents a mono-, bicyclic, or multicyclic carbocyclic ring system having one or two aromatic rings and is exemplified by phenyl, naphthyl, 1,2-dihydronaphthyl, 1,2,3,4-tetrahydronaphthyl, anthracenyl, phenanthrenyl, fluorenyl, indanyl, indenyl, and the like, and may be optionally substituted with 1, 2, 3, 4, or 5 substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{6-10}$ aryl $C_{1-6}$ alkyl; (8) azido; (9) $C_{3-8}$ cycloalkyl; (10) $C_{3-8}$ cycloalkyl $C_{1-6}$ alkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{6-10}$ aryl $C_{1-6}$ alkyl; (18) —$(CH_2)_qCONR^{B'}R^{C'}$, where q is an integer from zero to four and where $R^{B'}$ and $R^{C'}$ are independently selected from the group consisting of (a) hydrogen, (b) $C_{1-6}$ alkyl, (c) $C_{6-10}$ aryl, and (d) $C_{6-10}$ aryl $C_{1-6}$ alkyl; (19) —$(CH_2)_qSO_2R^{D'}$, where q is an integer from zero to four and where $R^{D'}$ is selected from the group consisting of (a) alkyl, (b) $C_{6-10}$ aryl, and (c) $C_{6-10}$ aryl alkyl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{1-6}$ alkyl, (c) $C_{6-10}$ aryl, and (d) $C_{6-10}$ aryl $C_{1-6}$ alkyl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-12}$ heterocyclyl $C_{1-6}$ alkyl (e.g., $C_{1-12}$ heteroaryl $C_{1-6}$ alkyl); (26) $C_{2-20}$ alkenyl; and (27) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "arylalkoxy," as used herein, represents an alkaryl group, as defined herein, attached to the parent molecular group through an oxygen atom. Exemplary unsubstituted arylalkoxy groups include from 7 to 30 carbons (e.g., from 7 to 16 or from 7 to 20 carbons, such as $C_{6-10}$ aryl-$C_{1-6}$ alkoxy, $C_{6-10}$ aryl-$C_{10}$ alkoxy, or $C_{6-10}$ aryl-$C_{1-20}$ alkoxy). In some embodiments, the arylalkoxy group can be substituted with 1, 2, 3, or 4 substituents as defined herein The term "arylalkoxycarbonyl," as used herein, represents an arylalkoxy group, as defined herein, attached to the parent molecular group through a carbonyl (e.g., —C(O)—O-alkyl-aryl). Exemplary unsubstituted arylalkoxy groups include from 8 to 31 carbons (e.g., from 8 to 17 or from 8 to 21 carbons, such as $C_{6-10}$ aryl-$C_{1-6}$ alkoxy-carbonyl, $C_{6-10}$ aryl-$C_{1-10}$ alkoxy-carbonyl, or $C_{6-10}$ aryl-$C_{1-20}$ alkoxy-carbonyl). In some embodiments, the arylalkoxycarbonyl group can be substituted with 1, 2, 3, or 4 substituents as defined herein.

The term "aryloxy" represents a chemical substituent of formula —OR', where R' is an aryl group of 6 to 18 carbons, unless otherwise specified. In some embodiments, the aryl group can be substituted with 1, 2, 3, or 4 substituents as defined herein.

The term "aryloyl," as used herein, represents an aryl group, as defined herein, that is attached to the parent molecular group through a carbonyl group. Exemplary unsubstituted aryloyl groups are of 7 to 11 carbons. In some embodiments, the aryl group can be substituted with 1, 2, 3, or 4 substituents as defined herein.

The term "azido" represents an —$N_3$ group, which can also be represented as —N=N=N.

The term "bicyclic," as used herein, refer to a structure having two rings, which may be aromatic or non-aromatic. Bicyclic structures include spirocyclyl groups, as defined herein, and two rings that share one or more bridges, where such bridges can include one atom or a chain including two, three, or more atoms. Exemplary bicyclic groups include a bicyclic carbocyclyl group, where the first and second rings are carbocyclyl groups, as defined herein; a bicyclic aryl groups, where the first and second rings are aryl groups, as defined herein; bicyclic heterocyclyl groups, where the first ring is a heterocyclyl group and the second ring is a carbocyclyl (e.g., aryl) or heterocyclyl (e.g., heteroaryl) group; and bicyclic heteroaryl groups, where the first ring is a heteroaryl group and the second ring is a carbocyclyl (e.g., aryl) or heterocyclyl (e.g., heteroaryl) group. In some embodiments, the bicyclic group can be substituted with 1, 2, 3, or 4 substituents as defined herein for cycloalkyl, heterocyclyl, and aryl groups.

The term "boranyl," as used herein, represents —B($R^{B1}$)$_3$, where each $R^{B1}$ is, independently, selected from the group consisting of H and optionally substituted alkyl. In some embodiments, the boranyl group can be substituted with 1, 2, 3, or 4 substituents as defined herein for alkyl.

The terms "carbocyclic" and "carbocyclyl," as used herein, refer to an optionally substituted $C_{3-12}$ monocyclic, bicyclic, or tricyclic structure in which the rings, which may be aromatic or non-aromatic, are formed by carbon atoms. Carbocyclic structures include cycloalkyl, cycloalkenyl, and aryl groups.

The term "carbamoyl," as used herein, represents —C(O)—N($R^{N1}$)$_2$, where the meaning of each $R^{N1}$ is found in the definition of "amino" provided herein.

The term "carbamoylalkyl," as used herein, represents an alkyl group, as defined herein, substituted by a carbamoyl group, as defined herein. The alkyl group can be further substituted with 1, 2, 3, or 4 substituent groups as described herein.

The term "carbamyl," as used herein, refers to a carbamate group having the structure —N$R^{N1}$C(=O)OR or —OC(=O)N($R^{N1}$)$_2$, where the meaning of each $R^{N1}$ is found in the definition of "amino" provided herein, and R is alkyl, cycloalkyl, alkcycloalkyl, aryl, alkaryl, heterocyclyl (e.g., heteroaryl), or alkheterocyclyl (e.g., alkheteroaryl), as defined herein.

The term "carbonyl," as used herein, represents a C(O) group, which can also be represented as C=O.

The term "carboxyaldehyde" represents an acyl group having the structure —CHO.

The term "carboxy," as used herein, means —CO$_2$H.

The term "carboxyalkoxy," as used herein, represents an alkoxy group, as defined herein, substituted by a carboxy group, as defined herein. The alkoxy group can be further substituted with 1, 2, 3, or 4 substituent groups as described herein for the alkyl group, and the carboxy group can be optionally substituted with one or more O-protecting groups.

The term "carboxyalkyl," as used herein, represents an alkyl group, as defined herein, substituted by a carboxy group, as defined herein. The alkyl group can be further substituted with 1, 2, 3, or 4 substituent groups as described herein, and the carboxy group can be optionally substituted with one or more O-protecting groups.

The term "carboxyaminoalkyl," as used herein, represents an aminoalkyl group, as defined herein, substituted by a carboxy, as defined herein. The carboxy, alkyl, and amino each can be further substituted with 1, 2, 3, or 4 substituent groups as described herein for the respective group (e.g., CO$_2$$R^{A'}$, where $R^{A'}$ is selected from the group consisting of (a) $C_{1-6}$ alkyl, (b) $C_{6-10}$ aryl, (c) hydrogen, and (d) $C_{6-10}$ aryl $C_{1-6}$ alkyl, e.g., carboxy, and/or an N-protecting group, and/or an O-protecting group).

The term "cyano," as used herein, represents an —CN group.

The term "cycloalkoxy" represents a chemical substituent of formula —OR, where R is a $C_{3-8}$ cycloalkyl group, as defined herein, unless otherwise specified. The cycloalkyl group can be further substituted with 1, 2, 3, or 4 substituent groups as described herein. Exemplary unsubstituted cycloalkoxy groups are from 3 to 8 carbons. In some embodiment, the cycloalkyl group can be further substituted with 1, 2, 3, or 4 substituent groups as described herein.

The term "cycloalkyl," as used herein represents a monovalent saturated or unsaturated non-aromatic cyclic hydrocarbon group from three to eight carbons, unless otherwise specified, and is exemplified by cyclopropyl, cyclobutyl, cyclopentyl, cyclohexyl, cycloheptyl, bicycle heptyl, and the like. When the cycloalkyl group includes one carbon-carbon double bond, the cycloalkyl group can be referred to as a "cycloalkenyl" group. Exemplary cycloalkenyl groups include cyclopentenyl, cyclohexenyl, and the like. The cycloalkyl groups of this invention can be optionally substituted with: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{6-10}$ aryl $C_{1-6}$ alkyl; (8) azido; (9) $C_{3-8}$ cycloalkyl; (10) $C_{3-8}$ cycloalkyl $C_{1-6}$ alkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —(CH$_2$)$_q$CO$_2$$R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{6-10}$ aryl $C_{1-6}$ alkyl; (18) —(CH$_2$)$_q$CONR$^{B'}$R$^{C'}$, where q is an integer from zero to four and where $R^{B'}$ and $R^{C'}$ are independently selected from the group consisting of (a) hydrogen, (b) $C_{6-10}$ alkyl, (c) $C_{6-10}$ aryl, and (d) $C_{6-10}$ aryl $C_{1-6}$ alkyl; (19) —(CH$_2$)$_q$SO$_2$$R^{D'}$, where q is an integer from zero to four and where $R^{D'}$ is selected from the group consisting of (a) $C_{6-10}$ alkyl, (b) $C_{6-10}$ aryl, and (c) $C_{6-10}$ aryl $C_{1-6}$ alkyl; (20) —(CH$_2$)$_q$SO$_2$NR$^{E'}$R$^{F'}$, where q is an integer from zero to four and where each of $R^{E'}$ and $R^{F'}$ is, independently, selected from the group consisting of (a) hydrogen, (b) $C_{6-10}$ alkyl, (c) $C_{6-10}$ aryl, and (d) $C_{6-10}$ aryl $C_{1-6}$ alkyl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-12}$ heterocyclyl $C_{1-6}$ alkyl (e.g., $C_{1-12}$ heteroaryl $C_{1-6}$ alkyl); (26) oxo; (27) $C_{2-20}$ alkenyl; and (28) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "diastereomer," as used herein means stereoisomers that are not mirror images of one another and are non-superimposable on one another.

The term "effective amount" of an agent, as used herein, is that amount sufficient to effect beneficial or desired results, for example, clinical results, and, as such, an "effective amount" depends upon the context in which it is being applied. For example, in the context of administering an agent that treats cancer, an effective amount of an agent is, for example, an amount sufficient to achieve treatment, as defined herein, of cancer, as compared to the response obtained without administration of the agent.

The term "enantiomer," as used herein, means each individual optically active form of a compound of the invention, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "halo," as used herein, represents a halogen selected from bromine, chlorine, iodine, or fluorine.

The term "haloalkoxy," as used herein, represents an alkoxy group, as defined herein, substituted by a halogen group (i.e., F, Cl, Br, or I). A haloalkoxy may be substituted with one, two, three, or, in the case of alkyl groups of two carbons or more, four halogens. Haloalkoxy groups include perfluoroalkoxys (e.g., —$OCF_3$), —$OCHF_2$, —$OCH_2F$, —$OCCl_3$, —$OCH_2CH_2Br$, —$OCH_2CH(CH_2CH_2Br)CH_3$, and —$OCHICH_3$. In some embodiments, the haloalkoxy group can be further substituted with 1, 2, 3, or 4 substituent groups as described herein for alkyl groups.

The term "haloalkyl," as used herein, represents an alkyl group, as defined herein, substituted by a halogen group (i.e., F, Cl, Br, or I). A haloalkyl may be substituted with one, two, three, or, in the case of alkyl groups of two carbons or more, four halogens. Haloalkyl groups include perfluoroalkyls (e.g., —$CF_3$), —$CHF_2$, —$CH_2F$, —$CCl_3$, —$CH_2CH_2Br$, —$CH_2CH(CH_2CH_2Br)CH_3$, and —$CHICH_3$. In some embodiments, the haloalkyl group can be further substituted with 1, 2, 3, or 4 substituent groups as described herein for alkyl groups.

The term "heteroalkylene," as used herein, refers to an alkylene group, as defined herein, in which one or two of the constituent carbon atoms have each been replaced by nitrogen, oxygen, or sulfur. In some embodiments, the heteroalkylene group can be further substituted with 1, 2, 3, or 4 substituent groups as described herein for alkylene groups.

The term "heteroaryl," as used herein, represents that subset of heterocyclyls, as defined herein, which are aromatic: i.e., they contain 4n+2 pi electrons within the mono- or multicyclic ring system. Exemplary unsubstituted heteroaryl groups are of 1 to 12 (e.g., 1 to 11, 1 to 10, 1 to 9, 2 to 12, 2 to 11, 2 to 10, or 2 to 9) carbons. In some embodiment, the heteroaryl is substituted with 1, 2, 3, or 4 substituents groups as defined for a heterocyclyl group.

The term "heterocyclyl," as used herein represents a 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocyclyl groups are of 1 to 12 (e.g., 1 to 11, 1 to 10, 1 to 9, 2 to 12, 2 to 11, 2 to 10, or 2 to 9) carbons. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, indazolyl, quinolyl, isoquinolyl, quinoxalinyl, dihydroquinoxalinyl, quinazolinyl, cinnolinyl, phthalazinyl, benzimidazolyl, benzothiazolyl, benzoxazolyl, benzothiadiazolyl, furyl, thienyl, thiazolidinyl, isothiazolyl, triazolyl, tetrazolyl, oxadiazolyl (e.g., 1,2,3-oxadiazolyl), purinyl, thiadiazolyl (e.g., 1,2,3-thiadiazolyl), tetrahydrofuranyl, dihydrofuranyl, tetrahydrothienyl, dihydrothienyl, dihydroindolyl, dihydroquinolyl, tetrahydroquinolyl, tetrahydroisoquinolyl, dihydroisoquinolyl, pyranyl, dihydropyranyl, dithiazolyl, benzofuranyl, isobenzofuranyl, benzothienyl, and the like, including dihydro and tetrahydro forms thereof, where one or more double bonds are reduced and replaced with hydrogens. Still other exemplary heterocyclyls include: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl (e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxo-pyridazinyl (e.g., 1,6-dihydro-6-oxo-3-ethylpyridazinyl); 1,6-dihydro-6-oxo-1,2,4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo, 4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H-purinyl); 1,2,3,6-tetrahydro-2,6-dioxo-1H-purinyl (e.g., 1,2,3,6-tetrahydro-3,7-dimethyl-2,6-dioxo-1H-purinyl); 2-oxobenz[c,d]indolyl; 1,1-dioxo-2H-naphth[1,8-c,d]isothiazolyl; and 1,8-naphthylenedicarboxamido. Additional heterocyclics include 3,3a,4,5,6,6a-hexahydro-pyrrolo[3,4-b]pyrrol-(2H)-yl, and 2,5-diazabicyclo[2.2.1]heptan-2-yl, homopiperazinyl (or diazepanyl), tetrahydropyranyl, dithiazolyl, benzofuranyl, benzothienyl, oxepanyl, thiepanyl, azocanyl, oxecanyl, and thiocanyl. Heterocyclic groups also include groups of the formula

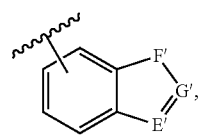

where

E' is selected from the group consisting of —N— and —CH—; F' is selected from the group consisting of —N=CH—, —NH—$CH_2$—, —NH—C(O)—, —NH—, —CH=N—, —$CH_2$—NH—, —C(O)—NH—, —CH=CH—, —$CH_2$—, —$CH_2CH_2$—, —$CH_2O$—, —OCH$_2$—, —O—, and —S—; and G' is selected from the group consisting of —CH— and —N—. Any of the heterocyclyl groups mentioned herein may be optionally substituted with one, two, three, four or five substituents independently selected from the group consisting of: (1) C$_{1-7}$ acyl (e.g., carboxyaldehyde); (2) C$_{1-20}$ alkyl (e.g., C$_{1-6}$ alkyl, C$_{1-6}$ alkoxy-C$_{1-6}$ alkyl, C$_{1-6}$ alkylsulfinyl-C$_{1-6}$ alkyl, amino-C$_{1-6}$ alkyl, azido-C$_{1-6}$ alkyl, (carboxyaldehyde)-C$_{1-6}$ alkyl, halo-C$_{1-6}$ alkyl (e.g., perfluoroalkyl), hydroxy-C$_{1-6}$ alkyl, nitro-C$_{1-6}$ alkyl, or C$_{1-6}$ thioalkoxy-C$_{1-6}$ alkyl); (3) C$_{1-20}$ alkoxy (e.g., C$_{1-6}$ alkoxy, such as perfluoroalkoxy); (4) C$_{1-6}$ alkylsulfinyl; (5) C$_{6-10}$ aryl; (6) amino; (7) C$_{6-10}$ aryl C$_{1-6}$ alkyl; (8) azido; (9) C$_{3-8}$ cycloalkyl; (10) C$_{3-8}$ cycloalkyl C$_{1-6}$ alkyl; (11) halo; (12) C$_{1-12}$ heterocyclyl (e.g., C$_{2-12}$ heteroaryl); (13) (C$_{1-12}$ heterocyclyl)oxy; (14) hydroxy; (15) nitro; (16) C$_{1-20}$ thioalkoxy (e.g., C$_{1-6}$ thioalkoxy); (17) —(CH$_2$)$_q$CO$_2$R$^{A'}$, where q is an integer from zero to four, and R$^{A'}$ is selected from the group consisting of (a) C$_{1-6}$ alkyl, (b) C$_{6-10}$ aryl, (c) hydrogen, and (d) C$_{6-10}$ aryl C$_{1-6}$ alkyl; (18) —(CH$_2$)$_q$CONR$^{B'}$R$^{C'}$, where q is an integer from zero to four and where R$^{B'}$ and R$^{C'}$ are independently selected from the group consisting of (a) hydrogen, (b) C$_{1-6}$ alkyl, (c) C$_{6-10}$ aryl, and (d) C$_{6-10}$ aryl C$_{1-6}$ alkyl; (19) —(CH$_2$)$_q$SO$_2$R$^{D'}$ where q is an integer from zero to four and where R$^{D'}$ is selected from the group consisting of (a) C$_{1-6}$ alkyl, (b) C$_{6-10}$ aryl, and (c) C$_{6-10}$ aryl C$_{1-6}$ alkyl; (20) —(CH$_2$)$_q$SO$_2$NR$^{E'}$R$^{F'}$, where q is an integer from zero to four and where each of R$^{E'}$ and R$^{F'}$ is, independently, selected from the group consisting of (a) hydrogen, (b) C$_{1-6}$ alkyl, (c) C$_{6-10}$ aryl, and (d) C$_{6-10}$ aryl C$_{1-6}$ alkyl; (21) thiol; (22) C$_{6-10}$ aryloxy; (23) C$_{3-8}$ cycloalkoxy; (24) arylalkoxy; (25) C$_{1-12}$ heterocyclyl C$_{1-6}$ alkyl (e.g., C$_{1-12}$ heteroaryl C$_{1-6}$ alkyl); (26) oxo; (27) (C$_{1-12}$ heterocyclyl)imino; (28) C$_{2-20}$ alkenyl; and (29) C$_{2-20}$ alkynyl. In some embodiments, each of these groups can be further substituted as described herein. For example, the alkylene group of a C$_1$-alkaryl or a C$_1$-alkheterocyclyl can be further substituted with an oxo group to afford the respective aryloyl and (heterocyclyl)oyl substituent group.

The term "(heterocyclyl) imino," as used herein, represents a heterocyclyl group, as defined herein, attached to the parent molecular group through an imino group. In some embodiments, the heterocyclyl group can be substituted with 1, 2, 3, or 4 substituent groups as defined herein.

The term "(heterocyclyl)oxy," as used herein, represents a heterocyclyl group, as defined herein, attached to the parent molecular group through an oxygen atom. In some embodiments, the heterocyclyl group can be substituted with 1, 2, 3, or 4 substituent groups as defined herein.

The term "(heterocyclyl)oyl," as used herein, represents a heterocyclyl group, as defined herein, attached to the parent molecular group through a carbonyl group. In some embodiments, the heterocyclyl group can be substituted with 1, 2, 3, or 4 substituent groups as defined herein.

The term "hydrocarbon," as used herein, represents a group consisting only of carbon and hydrogen atoms.

The term "hydroxy," as used herein, represents an —OH group. In some embodiments, the hydroxy group can be substituted with 1, 2, 3, or 4 substituent groups (e.g., O-protecting groups) as defined herein for an alkyl.

The term "hydroxyalkenyl," as used herein, represents an alkenyl group, as defined herein, substituted by one to three hydroxy groups, with the proviso that no more than one hydroxy group may be attached to a single carbon atom of the alkyl group, and is exemplified by dihydroxypropenyl, hydroxyisopentenyl, and the like. In some embodiments, the hydroxyalkenyl group can be substituted with 1, 2, 3, or 4 substituent groups (e.g., O-protecting groups) as defined herein for an alkyl.

The term "hydroxyalkyl," as used herein, represents an alkyl group, as defined herein, substituted by one to three hydroxy groups, with the proviso that no more than one hydroxy group may be attached to a single carbon atom of the alkyl group, and is exemplified by hydroxymethyl, dihydroxypropyl, and the like. In some embodiments, the hydroxyalkyl group can be substituted with 1, 2, 3, or 4 substituent groups (e.g., O-protecting groups) as defined herein for an alkyl.

The term "hydroxyalkynyl," as used herein, represents an alkynyl group, as defined herein, substituted by one to three hydroxy groups, with the proviso that no more than one hydroxy group may be attached to a single carbon atom of the alkyl group. In some embodiments, the hydroxyalkynyl group can be substituted with 1, 2, 3, or 4 substituent groups (e.g., O-protecting groups) as defined herein for an alkyl.

The term "isomer," as used herein, means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

The term "N-protected amino," as used herein, refers to an amino group, as defined herein, to which is attached one or two N-protecting groups, as defined herein.

The term "N-protecting group," as used herein, represents those groups intended to protect an amino group against undesirable reactions during synthetic procedures. Commonly used N-protecting groups are disclosed in Greene, "Protective Groups in Organic Synthesis," 3$^{rd}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5- trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, alkaryl groups such as benzyl, triphenylmethyl, benzyloxymethyl, and the like and silyl groups, such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —$NO_2$ group.

The term "O-protecting group," as used herein, represents those groups intended to protect an oxygen containing (e.g., phenol, hydroxyl, or carbonyl) group against undesirable reactions during synthetic procedures. Commonly used O-protecting groups are disclosed in Greene, "Protective Groups in Organic Synthesis," $3^{rd}$ Edition (John Wiley & Sons, New York, 1999), which is incorporated herein by reference. Exemplary O-protecting groups include acyl, aryloyl, or carbamyl groups, such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl; alkylcarbonyl groups, such as acyl, acetyl, propionyl, pivaloyl, and the like; optionally substituted arylcarbonyl groups, such as benzoyl; silyl groups, such as trimethylsilyl (TMS), tert-butyldimethylsilyl (TBDMS), tri-iso-propylsilyloxymethyl (TOM), triisopropylsilyl (TIPS), and the like; ether-forming groups with the hydroxyl, such methyl, methoxymethyl, tetrahydropyranyl, benzyl, p-methoxybenzyl, trityl, and the like; alkoxycarbonyls, such as methoxycarbonyl, ethoxycarbonyl, isopropoxycarbonyl, n-isopropoxycarbonyl, n-butyloxycarbonyl, isobutyloxycarbonyl, sec-butyloxycarbonyl, t-butyloxycarbonyl, 2-ethylhexyloxycarbonyl, cyclohexyloxycarbonyl, methyloxycarbonyl, and the like; alkoxyalkoxycarbonyl groups, such as methoxymethoxycarbonyl, ethoxymethoxycarbonyl, 2-methoxyethoxycarbonyl, 2-ethoxyethoxycarbonyl, 2-butoxyethoxycarbonyl, 2-methoxyethoxymethoxycarbonyl, allyloxycarbonyl, propargyloxycarbonyl, 2-butenoxycarbonyl, 3-methyl-2-butenoxycarbonyl, and the like; haloalkoxycarbonyls, such as 2-chloroethoxycarbonyl, 2-chloroethoxycarbonyl, 2,2,2-trichloroethoxycarbonyl, and the like; optionally substituted arylalkoxycarbonyl groups, such as benzyloxycarbonyl, p-methylbenzyloxycarbonyl, p-methoxybenzyloxycarbonyl, p-nitrobenzyloxycarbonyl, 2,4-dinitrobenzyloxycarbonyl, 3,5-dimethylbenzyloxycarbonyl, p-chlorobenzyloxycarbonyl, p-bromobenzyloxycarbonyl, fluorenylmethyloxycarbonyl, and the like; and optionally substituted aryloxycarbonyl groups, such as phenoxycarbonyl, p-nitrophenoxycarbonyl, o-nitrophenoxycarbonyl, 2,4-dinitrophenoxycarbonyl, p-methyl-phenoxycarbonyl, m-methylphenoxycarbonyl, o-bromophenoxycarbonyl, 3,5-dimethylphenoxycarbonyl, p-chlorophenoxycarbonyl, 2-chloro-4-nitrophenoxy-carbonyl, and the like); substituted alkyl, aryl, and alkaryl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl)ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenylmethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl); carbonyl-protecting groups (e.g., acetal and ketal groups, such as dimethyl acetal, 1,3-dioxolane, and the like; acylal groups; and dithiane groups, such as 1,3-dithianes, 1,3-dithiolane, and the like); carboxylic acid-protecting groups (e.g., ester groups, such as methyl ester, benzyl ester, t-butyl ester, orthoesters, and the like; and oxazoline groups.

The term "oxo" as used herein, represents =O.

The term "perfluoroalkyl," as used herein, represents an alkyl group, as defined herein, where each hydrogen radical bound to the alkyl group has been replaced by a fluoride radical. Perfluoroalkyl groups are exemplified by trifluoromethyl, pentafluoroethyl, and the like.

The term "perfluoroalkoxy," as used herein, represents an alkoxy group, as defined herein, where each hydrogen radical bound to the alkoxy group has been replaced by a fluoride radical. Perfluoroalkoxy groups are exemplified by trifluoromethoxy, pentafluoroethoxy, and the like.

The term "spirocyclyl," as used herein, represents a $C_{2-7}$ alkylene diradical, both ends of which are bonded to the same carbon atom of the parent group to form a spirocyclic group, and also a $C_{1-6}$ heteroalkylene diradical, both ends of which are bonded to the same atom. The heteroalkylene radical forming the spirocyclyl group can containing one, two, three, or four heteroatoms independently selected from the group consisting of nitrogen, oxygen, and sulfur. In some embodiments, the spirocyclyl group includes one to seven carbons, excluding the carbon atom to which the diradical is attached. The spirocyclyl groups of the invention may be optionally substituted with 1, 2, 3, or 4 substituents provided herein as optional substituents for cycloalkyl and/or heterocyclyl groups.

The term "stereoisomer," as used herein, refers to all possible different isomeric as well as conformational forms which a compound may possess (e.g., a compound of any formula described herein), in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

The term "sulfoalkyl," as used herein, represents an alkyl group, as defined herein, substituted by a sulfo group of —$SO_3H$. In some embodiments, the alkyl group can be further substituted with 1, 2, 3, or 4 substituent groups as described herein, and the sulfo group can be further substituted with one or more O-protecting groups (e.g., as described herein).

The term "sulfonyl," as used herein, represents an —$S(O)_2$— group.

The term "thioalkaryl," as used herein, represents a chemical substituent of formula —SR, where R is an alkaryl group. In some embodiments, the alkaryl group can be further substituted with 1, 2, 3, or 4 substituent groups as described herein.

The term "thioalkheterocyclyl," as used herein, represents a chemical substituent of formula —SR, where R is an alkheterocyclyl group. In some embodiments, the alkheterocyclyl group can be further substituted with 1, 2, 3, or 4 substituent groups as described herein.

The term "thioalkoxy," as used herein, represents a chemical substituent of formula —SR, where R is an alkyl group, as defined herein. In some embodiments, the alkyl group can be further substituted with 1, 2, 3, or 4 substituent groups as described herein.

Compound: As used herein, the term "compound," is meant to include all stereoisomers, geometric isomers, tautomers, and isotopes of the structures depicted.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of an oligonucleotide or polypeptide or may apply to a portion, region or feature thereof.

Cyclic or Cyclized: As used herein, the term "cyclic" refers to the presence of a continuous loop. Cyclic molecules need not be circular, only joined to form an unbroken chain of subunits. Cyclic molecules such as the mRNA of the present invention may be single units or multimers or comprise one or more components of a complex or higher order structure.

Cytostatic: As used herein, "cytostatic" refers to inhibiting, reducing, suppressing the growth, division, or multiplication of a cell (e.g., a mammalian cell (e.g., a human cell)), bacterium, virus, fungus, protozoan, parasite, prion, or a combination thereof.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivery: As used herein, "delivery" refers to the act or manner of delivering a compound, substance, entity, moiety, cargo or payload.

Delivery Agent: As used herein, "delivery agent" refers to any substance which facilitates, at least in part, the in vivo delivery of a polynucleotide to targeted cells.

Destabilized: As used herein, the term "destable," "destabilize," or "destabilizing region" means a region or molecule that is less stable than a starting, wild-type or native form of the same region or molecule.

Detectable label: As used herein, "detectable label" refers to one or more markers, signals, or moieties which are attached, incorporated or associated with another entity that is readily detected by methods known in the art including radiography, fluorescence, chemiluminescence, enzymatic activity, and absorbance. Detectable labels include radioisotopes, fluorophores, chromophores, enzymes, dyes, metal ions, ligands such as biotin, avidin, streptavidin and haptens, and quantum dots. Detectable labels may be located at any position in the peptides or proteins disclosed herein. They may be within the amino acids, the peptides, or proteins, or located at the N- or C-termini.

Digest: As used herein, the term "digest" means to break apart into smaller pieces or components. When referring to polypeptides or proteins, digestion results in the production of peptides.

Distal: As used herein, the term "distal" means situated away from the center or away from a point or region of interest.

Encoded protein cleavage signal: As used herein, "encoded protein cleavage signal" refers to the nucleotide sequence which encodes a protein cleavage signal.

Engineered: As used herein, embodiments of the invention are "engineered" when they are designed to have a feature or property, whether structural or chemical, that varies from a starting point, wild type or native molecule.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Feature: As used herein, a "feature" refers to a characteristic, a property, or a distinctive element.

Formulation: As used herein, a "formulation" includes at least a polynucleotide and a delivery agent.

Fragment: A "fragment," as used herein, refers to a portion. For example, fragments of proteins may comprise polypeptides obtained by digesting full-length protein isolated from cultured cells.

Functional: As used herein, a "functional" biological molecule is a biological molecule in a form in which it exhibits a property and/or activity by which it is characterized.

Homology: As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the invention, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the invention, two protein sequences are considered to be homologous if the proteins are at least about 50%, 60%, 70%, 80%, or 90% identical for at least one stretch of at least about 20 amino acids.

Identity: As used herein, the term "identity" refers to the overall relatedness between polymeric molecules, e.g., between oligonucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., Nucleic Acids Research, 12(1), 387 (1984)), BLASTP, BLASTN, and FASTAn altschul, S. F. et al., J. Molec. Biol., 215, 403 (1990)).

Inhibit expression of a gene: As used herein, the phrase "inhibit expression of a gene" means to cause a reduction in the amount of an expression product of the gene. The expression product can be an RNA transcribed from the gene (e.g., an mRNA) or a polypeptide translated from an mRNA transcribed from the gene. Typically a reduction in the level of an mRNA results in a reduction in the level of a polypeptide translated therefrom. The level of expression may be determined using standard techniques for measuring mRNA or protein.

In vitro: As used herein, the term "in vitro" refers to events that occur in an artificial environment, e.g., in a test tube or reaction vessel, in cell culture, or in a Petri dish, rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art.

Linker: As used herein, a linker refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to an alternative nucleoside or nucleotide on the nucleobase or sugar moiety at a first end, and to a payload, e.g., a detectable or therapeutic agent, at a second end. The linker may be of sufficient length as to not interfere with incorporation into a nucleic acid sequence. The linker can be used for any useful purpose, such as to form multimers (e.g., through linkage of two or more polynucleotides) or conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers, Other examples include, but are not limited to, cleavable moieties within the linker, such as, for example, a disulfide bond (—S—S—) or an azo bond (—N=N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

Altered: As used herein "altered" refers to a changed state or structure of a molecule of the invention. Molecules may be altered in many ways including chemically, structurally, and functionally. In one embodiment, the mRNA molecules of the present invention are altered by the introduction of non-natural nucleosides and/or nucleotides, e.g., as it relates to the natural ribonucleotides A, U, G, and C. Noncanonical nucleotides such as the cap structures are not considered "altered" although they differ from the chemical structure of the A, C, G, U ribonucleotides.

Naturally occurring: As used herein, "naturally occurring" means existing in nature without artificial aid.

Non-human vertebrate: As used herein, a "non human vertebrate" includes all vertebrates except *Homo sapiens*, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Off-target: As used herein, "off target" refers to any unintended effect on any one or more target, gene, or cellular transcript.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Paratope: As used herein, a "paratope" refers to the antigen-binding site of an antibody.

Patient: As used herein, "patient" refers to a subject who may seek or be in need of treatment, requires treatment, is receiving treatment, will receive treatment, or a subject who is under care by a trained professional for a particular disease or condition.

Optionally substituted: Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g. alkyl) per se is optional.

Peptide: As used herein, "peptide" is less than or equal to 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is altered by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's *Pharmaceutical Sciences*, 17$^{th}$ ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., *Journal of Pharmaceutical Science*, 66, 1-19 (1977), each of which is incorporated herein by reference in its entirety.

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Pharmaceutically acceptable solvate: The term "pharmaceutically acceptable solvate," as used herein, means a compound of the invention wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, and benzyl benzoate. When water is the solvent, the solvate is referred to as a "hydrate."

Physicochemical: As used herein, "physicochemical" means of or relating to a physical and/or chemical property.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Prodrug: The present disclosure also includes prodrugs of the compounds described herein. As used herein, "prodrugs" refer to any substance, molecule or entity which is in a form predicate for that substance, molecule or entity to act as a therapeutic upon chemical or physical alteration. Prodrugs may by covalently bonded or sequestered in some way and which release or are converted into the active drug moiety prior to, upon or after administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Preparation and use of prodrugs is discussed in T. Higuchi and V. Stella, "Prodrugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Protein cleavage site: As used herein, "protein cleavage site" refers to a site where controlled cleavage of the amino acid chain can be accomplished by chemical, enzymatic or photochemical means.

Protein cleavage signal: As used herein "protein cleavage signal" refers to at least one amino acid that flags or marks a polypeptide for cleavage.

Protein of interest: As used herein, the terms "proteins of interest" or "desired proteins" include those provided herein and fragments, mutants, variants, and alterations thereof.

Proximal: As used herein, the term "proximal" means situated nearer to the center or to a point or region of interest.

Purified: As used herein, "purify," "purified," "purification" means to make substantially pure or clear from unwanted components, material defilement, admixture or imperfection.

Sample: As used herein, the term "sample" or "biological sample" refers to a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

Signal Sequences: As used herein, the phrase "signal sequences" refers to a sequence which can direct the transport or localization of a protein.

Significant or Significantly: As used herein, the terms "significant" or "significantly" are used synonymously with the term "substantially."

Single unit dose: As used herein, a "single unit dose" is a dose of any therapeutic administered in one dose/at one time/single route/single point of contact, i.e., single administration event.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Split dose: As used herein, a "split dose" is the division of single unit dose or total daily dose into two or more doses.

Stable: As used herein "stable" refers to a compound that is sufficiently robust to survive isolation to a useful degree of purity from a reaction mixture, and preferably capable of formulation into an efficacious therapeutic agent.

Stabilized: As used herein, the term "stabilize", "stabilized," "stabilized region" means to make or become stable.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially equal: As used herein as it relates to time differences between doses, the term means plus/minus 2%.

Substantially simultaneously: As used herein and as it relates to plurality of doses, the term means within 2 seconds.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Synthetic: The term "synthetic" means produced, prepared, and/or manufactured by the hand of man. Synthesis of polynucleotides or polypeptides or other molecules of the present invention may be chemical or enzymatic.

Targeted Cells: As used herein, "targeted cells" refers to any one or more cells of interest. The cells may be found in vitro, in vivo, in situ or in the tissue or organ of an organism. The organism may be an animal, preferably a mammal, more preferably a human and most preferably a patient.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hr period. It may be administered as a single unit dose.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unaltered: As used herein, "unaltered" refers to any substance, compound or molecule prior to being changed in any way. Unaltered may, but does not always, refer to the wild type or native form of a biomolecule. Molecules may undergo a series of alterations whereby each alternative molecule may serve as the "unaltered" starting molecule for a subsequent alteration.

Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

EXAMPLES

The present disclosure is further described in the following examples, which do not limit the scope of the disclosure described in the claims.

Example 1

PCR for cDNA Production

PCR procedures for the preparation of cDNA are performed using 2×KAPA HIFI™ HotStart ReadyMix by Kapa Biosystems (Woburn, Mass.). This system includes 2×KAPA ReadyMix12.5 µl; Forward Primer (10 µM) 0.75 µl; Reverse Primer (10 µM) 0.75 µl; Template cDNA 100 ng; and dH$_2$0 diluted to 25.0 µl. The reaction conditions are at 95° C. for 5 min. and 25 cycles of 98° C. for 20 sec, then 58° C. for 15 sec, then 72° C. for 45 sec, then 72° C. for 5 min. then 4° C. to termination.

The reverse primer of the instant invention incorporates a poly-T$_{120}$ for a poly-A$_{120}$ in the mRNA. Other reverse primers with longer or shorter poly-T tracts can be used to adjust the length of the poly-A tail in the mRNA.

The reaction is cleaned up using Invitrogen's PURELINK™ PCR Micro Kit (Carlsbad, Calif.) per manufacturer's instructions (up to 5 µg). Larger reactions will require a cleanup using a product with a larger capacity. Following the cleanup, the cDNA is quantified using the NanoDrop and analyzed by agarose gel electrophoresis to confirm the cDNA is the expected size. The cDNA is then submitted for sequencing analysis before proceeding to the in vitro transcription reaction.

Example 2

In Vitro Transcription (IVT)

A. Materials and Methods

Alternative mRNAs according to the invention are made using standard laboratory methods and materials for in vitro transcription with the exception that the nucleotide mix contains alternative nucleotides. The open reading frame (ORF) of the gene of interest may be flanked by a 5' untranslated region (UTR) containing a strong Kozak translational initiation signal and an alpha-globin 3' UTR terminating with an oligo(dT) sequence for templated addition of a polyA tail for mRNAs not incorporating adenosine analogs. Adenosine-containing mRNAs are synthesized without an oligo (dT) sequence to allow for post-transcription poly (A) polymerase poly-(A) tailing.

The ORF may also include various upstream or downstream additions (such as, but not limited to, β-globin, tags) may be ordered from an optimization service such as, but limited to, DNA2.0 (Menlo Park, Calif.) and may contain multiple cloning sites which may have XbaI recognition. Upon receipt of the construct, it may be reconstituted and transformed into chemically competent *E. coli*.

For the present invention, NEB DH5-alpha Competent *E. coli* may be used. Transformations are performed according to NEB instructions using 100 ng of plasmid. The protocol is as follows:

Thaw a tube of NEB 5-alpha Competent *E. coli* cells on ice for 10 minutes.

Add 1-5 µl containing 1 pg-100 ng of plasmid DNA to the cell mixture. Carefully flick the tube 4-5 times to mix cells and DNA. Do not vortex.

Place the mixture on ice for 30 minutes. Do not mix.
Heat shock at 42° C. for exactly 30 seconds. Do not mix.
Place on ice for 5 minutes. Do not mix.
Pipette 950 µl of room temperature SOC into the mixture.
Place at 37° C. for 60 minutes. Shake vigorously (250 rpm) or rotate.
Warm selection plates to 37° C.
Mix the cells thoroughly by flicking the tube and inverting.
Spread 50-100 µl of each dilution onto a selection plate and incubate overnight at 37° C.
Alternatively, incubate at 30° C. for 24-36 hours or 25° C. for 48 hours.
A single colony is then used to inoculate 5 ml of LB growth media using the appropriate antibiotic and then allowed to grow (250 RPM, 37° C.) for 5 hours. This is then used to inoculate a 200 ml culture medium and allowed to grow overnight under the same conditions.
To isolate the plasmid (up to 850 µg), a maxi prep is performed using the Invitrogen PURELINK™ HiPure Maxiprep Kit (Carlsbad, Calif.), following the manufacturer's instructions.
In order to generate cDNA for In Vitro Transcription (IVT), the plasmid is first linearized using a restriction enzyme such as XbaI. A typical restriction digest with XbaI will comprise the following: Plasmid 1.0 µg; 10× Buffer 1.0 µl; XbaI 1.5 µl; $dH_2O$ up to 10 µl; incubated at 37° C. for 1 hr. If performing at lab scale (<5µg), the reaction is cleaned up using Invitrogen's PURELINK™ PCR Micro Kit (Carlsbad, Calif.) per manufacturer's instructions. Larger scale purifications may need to be done with a product that has a larger load capacity such as Invitrogen's standard PURELINK™ PCR Kit (Carlsbad, Calif.). Following the cleanup, the linearized vector is quantified using the NanoDrop and analyzed to confirm linearization using agarose gel electrophoresis.

IVT Reaction

The in vitro transcription reaction generates mRNA containing alternative nucleotides or alternative RNA. The input nucleotide triphosphate (NTP) mix is made in-house using natural and un-natural NTPs.

A typical in vitro transcription reaction includes the following:

| | |
|---|---|
| Template cDNA | 1.0 µg |
| 10x transcription buffer (400 mM Tris-HCl pH 8.0, 190 mM MgCl2, 50 mM DTT, 10 mM Spermidine) | 2.0 µl |
| Custom NTPs (25 mM each) | 7.2 µl |
| RNase Inhibitor | 20 U |
| T7 RNA polymerase | 3000 U |
| $dH_2O$ | up to 20.0 µl |

Incubation at 37° C. for 3 hr-5 hrs.

The crude IVT mix may be stored at 4° C. overnight for cleanup the next day. 1 U of RNase-free DNase is then used to digest the original template. After 15 minutes of incubation at 37° C., the mRNA is purified using Ambion's MEGACLEAR™ Kit (Austin, Tex.) following the manufacturer's instructions. This kit can purify up to 500 µg of RNA. Following the cleanup, the RNA is quantified using the NanoDrop and analyzed by agarose gel electrophoresis to confirm the RNA is the proper size and that no degradation of the RNA has occurred.

The T7 RNA polymerase may be selected from, T7 RNA polymerase, T3 RNA polymerase and mutant polymerases such as, but not limited to, the novel polymerases able to incorporate alternative NTPs as well as those polymerases described by Liu (Esvelt et al. (Nature (2011) 472(7344): 499-503 and U.S. Publication No. 20110177495) which recognize alternate promoters, Ellington (Chelliserrykattil and Ellington, Nature Biotechnology (2004) 22(9):1155-1160) describing a T7 RNA polymerase variant to transcribe 2'-O-methyl RNA and Sousa (Padilla and Sousa, Nucleic Acids Research (2002) 30(24): e128) describing a T7 RNA polymerase double mutant; herein incorporated by reference in their entireties.

B. Agarose Gel Electrophoresis of Alternative mRNA

Individual alternative mRNAs (200-400 ng in a 20 µl volume) are loaded into a well on a non-denaturing 1.2% Agarose E-Gel (Invitrogen, Carlsbad, Calif.) and run for 12-15 minutes according to the manufacturer protocol.

C. Agarose Gel Electrophoresis of RT-PCR Products

Individual reverse transcribed-PCR products (200-400 ng) are loaded into a well of a non-denaturing 1.2% Agarose E-Gel (Invitrogen, Carlsbad, Calif.) and run for 12-15 minutes according to the manufacturer protocol.

D. Nanodrop Alternative mRNA Quantification and UV Spectral Data

Alternative mRNAs in TE buffer (1 µl) are used for Nanodrop UV absorbance readings to quantitate the yield of each alternative mRNA from an in vitro transcription reaction (UV absorbance traces are not shown).

Example 3

Enzymatic Capping of mRNA

Capping of the mRNA is performed as follows where the mixture includes: IVT RNA 60 µg-180 µg and $dH_2O$ up to 72 µl. The mixture is incubated at 65° C. for 5 minutes to denature RNA, and then is transferred immediately to ice.

The protocol then involves the mixing of 10× Capping Buffer (0.5 M Tris-HCl (pH 8.0), 60 mM KCl, 12.5 mM $MgCl_2$) (10.0 µl); 20 mM GTP (5.0 µl); 20 mM S-Adenosyl Methionine (2.5 µl); RNase Inhibitor (100 U); 2'-O-Methyltransferase (400U); Vaccinia capping enzyme (Guanylyl transferase) (40 U); $dH_2O$ (Up to 28 µl); and incubation at 37° C. for 30 minutes for 60 µg RNA or up to 2 hours for 180 µg of RNA.

The mRNA is then purified using Ambion's MEGACLEAR™ Kit (Austin, Tex.) following the manufacturer's instructions. Following the cleanup, the RNA is quantified using the NANODROP™ (ThermoFisher, Waltham, Mass.) and analyzed by agarose gel electrophoresis to confirm the RNA is the proper size and that no degradation of the RNA has occurred. The RNA product may also be sequenced by running a reverse-transcription-PCR to generate the cDNA for sequencing.

Example 4

5'-Guanosine Capping

A. Materials and Methods

The cloning, gene synthesis and vector sequencing may be performed by DNA2.0 Inc. (Menlo Park, Calif.). The ORF is restriction digested using XbaI and used for cDNA synthesis using tailed- or tail-less-PCR. The tailed-PCR cDNA product is used as the template for the alternative mRNA synthesis reaction using 25 mM each alternative nucleotide mix (all alternative nucleotides may be custom synthesized or purchased from TriLink Biotech, San Diego, Calif. except pyrrolo-C triphosphate which may be purchased from Glen Research, Sterling Va.; unmodifed nucleotides are purchased from Epicenter Biotechnologies, Madison, Wis.) and CellScript MEGASCRIPT™ (Epicenter Biotechnologies, Madison, Wis.) complete mRNA synthesis kit.

The in vitro transcription reaction is run for 4 hours at 37° C. Alternative mRNAs incorporating adenosine analogs are poly (A) tailed using yeast Poly (A) Polymerase (Affymetrix, Santa Clara, Calif.). The PCR reaction uses HiFi PCR 2× MASTER MIX™ (Kapa Biosystems, Woburn, Mass.). Alternative mRNAs are post-transcriptionally capped using recombinant Vaccinia Virus Capping Enzyme (New England BioLabs, Ipswich, Mass.) and a recombinant 2'-O-methyltransferase (Epicenter Biotechnologies, Madison, Wis.) to generate the 5'-guanosine Cap1 structure. Cap 2 structure and Cap 2 structures may be generated using additional 2'-O-methyltransferases. The In vitro transcribed mRNA product is run on an agarose gel and visualized. Alternative mRNA may be purified with Ambion/Applied Biosystems (Austin, Tex.) MEGAClear RNA™ purification kit. The PCR uses PURELINK™ PCR purification kit (Invitrogen, Carlsbad, Calif.). The product is quantified on NANO-DROP™ UV Absorbance (ThermoFisher, Waltham, Mass.). Quality, UV absorbance quality and visualization of the product was performed on an 1.2% agarose gel. The product is resuspended in TE buffer.

B. 5' Capping Alternative Nucleic Acid (mRNA) Structure

5'-capping of alternative mRNA may be completed concomitantly during the in vitro-transcription reaction using the following chemical RNA cap analogs to generate the 5'-guanosine cap structure according to manufacturer protocols: 3'-O-Me-m$^7$G(5')ppp(5')G (the ARCA cap); G(5')ppp(5')A; G(5')ppp(5')G; m$^7$G(5')ppp(5')A; m$^7$G(5')ppp(5')G (New England BioLabs, Ipswich, Mass.). 5'-capping of alternative mRNA may be completed post-transcriptionally using a Vaccinia Virus Capping Enzyme to generate the "Cap 0" structure: m$^7$G(5')ppp(5')G (New England BioLabs, Ipswich, Mass.). Cap 1 structure may be generated using both Vaccinia Virus Capping Enzyme and a 2'-O methyltransferase to generate: m7G(5')ppp(5')G-2'-O-methyl. Cap 2 structure may be generated from the Cap 1 structure followed by the 2'-o-methylation of the 5'-antepenultimate nucleotide using a 2'-O methyl-transferase. Cap 3 structure may be generated from the Cap 2 structure followed by the 2'-o-methylation of the 5'-preantepenultimate nucleotide using a 2'-O methyl-transferase. Enzymes are preferably derived from a recombinant source.

When transfected into mammalian cells, the alternative mRNAs have a stability of 12-18 hours or more than 18 hours, e.g., 24, 36, 48, 60, 72 or greater than 72 hours.

Example 5

PolyA Tailing Reaction

Without a poly-T in the cDNA, a poly-A tailing reaction must be performed before cleaning the final product. This is done by mixing Capped IVT RNA (100 µl); RNase Inhibitor (20 U); 10× Tailing Buffer (0.5 M Tris-HCl (pH 8.0), 2.5 M NaCl, 100 mM MgCl$_2$)(12.0 µl); 20 mM ATP (6.0 µl); Poly-A Polymerase (20 U); dH$_2$O up to 123.5 µl and incubation at 37° C. for 30 min. If the poly-A tail is already in the transcript, then the tailing reaction may be skipped and proceed directly to cleanup with Ambion's MEGA-CLEAR™ kit (Austin, Tex.) (up to 500 µg). Poly-A Polymerase is preferably a recombinant enzyme expressed in yeast.

For studies performed and described herein, the poly-A tail is encoded in the IVT template to comprise 160 nucleotides in length. However, it should be understood that the processivity or integrity of the poly-A tailing reaction may not always result in exactly 160 nucleotides. Hence poly-A tails of approximately 160 nucleotides, acid about 150-165, 155, 156, 157, 158, 159, 160, 161, 162, 163, 164 or 165 are within the scope of the invention.

Example 6

Method of Screening for Protein Expression

A. Electrospray Ionization

A biological sample which may contain proteins encoded by alternative RNA administered to the subject is prepared and analyzed according to the manufacturer protocol for electrospray ionization (ESI) using 1, 2, 3 or 4 mass analyzers. A biologic sample may also be analyzed using a tandem ESI mass spectrometry system.

Patterns of protein fragments, or whole proteins, are compared to known controls for a given protein and identity is determined by comparison.

B. Matrix-Assisted Laser Desorption/Ionization

A biological sample which may contain proteins encoded by alternative RNA administered to the subject is prepared and analyzed according to the manufacturer protocol for matrix-assisted laser desorption/ionization (MALDI).

Patterns of protein fragments, or whole proteins, are compared to known controls for a given protein and identity is determined by comparison.

C. Liquid Chromatography-Mass Spectrometry-Mass Spectrometry

A biological sample, which may contain proteins encoded by alternative RNA, may be treated with a trypsin enzyme to digest the proteins contained within. The resulting peptides are analyzed by liquid chromatography-mass spectrometry-mass spectrometry (LC/MS/MS). The peptides are fragmented in the mass spectrometer to yield diagnostic patterns that can be matched to protein sequence databases via computer algorithms. The digested sample may be diluted to achieve 1 ng or less starting material for a given protein. Biological samples containing a simple buffer background (e.g. water or volatile salts) are amenable to direct in-solution digest; more complex backgrounds (e.g. detergent, non-volatile salts, glycerol) require an additional clean-up step to facilitate the sample analysis.

Patterns of protein fragments, or whole proteins, are compared to known controls for a given protein and identity is determined by comparison.

Example 7

Transfection

A. Reverse Transfection

For experiments performed in a 24-well collagen-coated tissue culture plate, Keratinocytes or other cells are seeded at a cell density of 1×10$^5$. For experiments performed in a 96-well collagen-coated tissue culture plate, Keratinocytes are seeded at a cell density of 0.5×10$^5$. For each alternative mRNA to be transfected, alternative mRNA: RNAIMAX™ are prepared as described and mixed with the cells in the multi-well plate within 6 hours of cell seeding before cells had adhered to the tissue culture plate.

B. Forward Transfection

In a 24-well collagen-coated tissue culture plate, Cells are seeded at a cell density of $0.7 \times 10^5$. For experiments performed in a 96-well collagen-coated tissue culture plate, Keratinocytes, if used, are seeded at a cell density of $0.3 \times 10^5$. Cells are then grown to a confluency of >70% for over 24 hours. For each alternative mRNA to be transfected, alternative mRNA: RNAIMAX™ are prepared as described and transfected onto the cells in the multi-well plate over 24 hours after cell seeding and adherence to the tissue culture plate.

C. Translation Screen: ELISA

Cells are grown in EpiLife medium with Supplement S7 from Invitrogen at a confluence of >70%. Cells are reverse transfected with 300 ng of the indicated chemically alternative mRNA complexed with RNAIMAX™ from Invitrogen. Alternatively, cells are forward transfected with 300 ng alternative mRNA complexed with RNAIMAX™ from Invitrogen. The RNA: RNAIMAX™ complex is formed by first incubating the RNA with Supplement-free EPILIFE® media in a 5× volumetric dilution for 10 minutes at room temperature.

In a second vial, RNAIMAX™ reagent is incubated with Supplement-free EPILIFE® Media in a 10× volumetric dilution for 10 minutes at room temperature. The RNA vial is then mixed with the RNAIMAX™ vial and incubated for 20-30 at room temperature before being added to the cells in a drop-wise fashion. Secreted polypeptide concentration in the culture medium is measured at 18 hours post-transfection for each of the alternative mRNAs in triplicate. Secretion of the polypeptide of interest from transfected human cells is quantified using an ELISA kit from Invitrogen or R&D Systems (Minneapolis, Minn.) following the manufacturers recommended instructions.

D. Dose and Duration: ELISA

Cells are grown in EPILIFE® medium with Supplement S7 from Invitrogen at a confluence of >70%. Cells are reverse transfected with 0 ng, 46.875 ng, 93.75 ng, 187.5 ng, 375 ng, 750 ng, or 1500 ng alternative mRNA complexed with RNAIMAX™ from Invitrogen. The alternative mRNA: RNAIMAX™ complex is formed as described. Secreted polypeptide concentration in the culture medium is measured at 0, 6, 12, 24, and 48 hours post-transfection for each concentration of each alternative mRNA in triplicate. Secretion of the polypeptide of interest from transfected human cells is quantified using an ELISA kit from Invitrogen or R&D Systems following the manufacturers recommended instructions.

Example 8

Cellular Innate Immune Response: IFN-beta ELISA and TNF-alpha ELISA

An enzyme-linked immunosorbent assay (ELISA) for Human Tumor Necrosis Factor-α (TNF-α), Human Interferon-β (IFN-β) and Human Granulocyte-Colony Stimulating Factor (G-CSF) secreted from in vitro-transfected Human Keratinocyte cells is tested for the detection of a cellular innate immune response.

Cells are grown in EPILIFE® medium with Human Growth Supplement in the absence of hydrocortisone from Invitrogen at a confluence of >70%. Cells are reverse transfected with 0 ng, 93.75 ng, 187.5 ng, 375 ng, 750 ng, 1500 ng or 3000 ng of the indicated alternative mRNA complexed with RNAIMAX™ from Invitrogen as described in triplicate. Secreted TNF-α in the culture medium is measured 24 hours post-transfection for each of the alternative mRNAs using an ELISA kit from Invitrogen according to the manufacturer protocols.

Secreted IFN-β is measured 24 hours post-transfection for each of the alternative mRNAs using an ELISA kit from Invitrogen according to the manufacturer protocols. Secreted hu-G-CSF concentration is measured at 24 hours post-transfection for each of the alternative mRNAs. Secretion of the polypeptide of interest from transfected human cells is quantified using an ELISA kit from Invitrogen or R&D Systems (Minneapolis, Minn.) following the manufacturers recommended instructions. These data indicate which alternative mRNA are capable eliciting a reduced cellular innate immune response in comparison to natural and other alternative polynucleotides or reference compounds by measuring exemplary type 1 cytokines such as TNF-alpha and IFN-beta.

Example 9

Cytotoxicity and Apoptosis

This experiment demonstrates cellular viability, cytotoxicity and apoptosis for distinct alternative mRNA-in vitro transfected Human Keratinocyte cells. Keratinocytes are grown in EPILIFE® medium with Human Keratinocyte Growth Supplement in the absence of hydrocortisone from Invitrogen at a confluence of >70%. Keratinocytes are reverse transfected with 0 ng, 46.875 ng, 93.75 ng, 187.5 ng, 375 ng, 750 ng, 1500 ng, 3000 ng, or 6000 ng of alternative mRNA complexed with RNAIMAX™ from Invitrogen. The alternative mRNA: RNAIMAX™ complex is formed. Secreted huG-CSF concentration in the culture medium is measured at 0, 6, 12, 24, and 48 hours post-transfection for each concentration of each alternative mRNA in triplicate. Secretion of the polypeptide of interest from transfected human keratinocytes is quantified using an ELISA kit from Invitrogen or R&D Systems following the manufacturers recommended instructions. Cellular viability, cytotoxicity and apoptosis is measured at 0, 12, 48, 96, and 192 hours post-transfection using the APOTOX-GLO™ kit from Promega (Madison, Wis.) according to manufacturer instructions.

Example 10

Incorporation of Naturally and Non-naturally Occurring Nucleosides

Naturally and non-naturally occurring nucleosides are incorporated into mRNA encoding a polypeptide of interest. Examples of these are given in Tables 4 and 5. Certain commercially available nucleoside triphosphates (NTPs) are investigated in the polynucleotides of the invention. A selection of these is given in Table 13. The resultant mRNAs are then examined for their ability to produce protein, induce cytokines, and/or produce a therapeutic outcome.

TABLE 13

Naturally occurring nucleotides.

| Chemistry Alteration | Compound # | Naturally occuring |
|---|---|---|
| 2'-O-methylcytidine TP | 00901074001 | Y |
| 4-thiouridine TP | 00901013011 | Y |
| 2'-O-methyluridine TP | 00901073001 | Y |
| 5-methyl-2-thiouridine TP | 00901013003 | Y |
| 5,2'-O-dimethyluridine TP | 03601073014 | Y |
| 5-aminomethyl-2-thiouridine TP | 00901013015 | Y |
| 5,2'-O-dimethylcytidine TP | 00901074002 | Y |
| 2-methylthio-N6-isopentenyladenosine TP | 00901011015 | Y |
| 2'-O-methyladenosine TP | 00901071001 | Y |
| 2'-O-methylguanosine TP | 00901072001 | Y |
| N6-methyl-N6-threonylcarbamoyladenosine TP | 03601011016 | Y |
| N6-hydroxynorvalylcarbamoyladenosine TP | 00901011017 | Y |
| 2-methylthio-N6-hydroxynorvalyl carbamoyladenosine TP | 00901011018 | Y |
| 2'-O-ribosyladenosine (phosphate) TP | 00901461001 | Y |
| N6,2'-O-dimethyladenosine TP | 00901071006 | Y |
| N6,N6,2'-O-trimethyladenosine TP | 00901071012 | Y |
| 1,2'-O-dimethyladenosine TP | 00901071008 | Y |
| N6-acetyladenosine TP | 00901011013 | Y |
| 2-methyladenosine TP | 00901011014 | Y |
| 2-methylthio-N6-methyladenosine TP | 00901011019 | Y |
| N2,2'-O-dimethylguanosine TP | 03601072014 | Y |
| N2,N2,2'-O-trimethylguanosine TP | 03601072015 | Y |
| 7-cyano-7-deazaguanosine TP | 03601012016 | Y |
| 7-aminomethyl-7-deazaguanosine TP | 03601012017 | Y |
| 2'-O-ribosylguanosine (phosphate) TP | 00901462001 | Y |
| N2,7-dimethylguanosine TP | 00901012018 | Y |
| N2,N2,7-trimethylguanosine TP | 03601012019 | Y |
| 1,2'-O-dimethylguanosine TP | 03601072008 | Y |
| Peroxywybutosine TP | 00901012023 | Y |
| Hydroxywybutosine TP | 00901012024 | Y |
| undermodified hydroxywybutosine TP | 00901012025 | Y |
| Methylwyosine TP | 00901012026 | Y |
| N2,7,2'-O-trimethylguanosine TP | 00901072018 | Y |
| 1,2'-O-dimethylinosine TP | 00901072027 | Y |
| 2'-O-methylinosine TP | 00901072028 | Y |
| 4-demethylwyosine TP | 00901012029 | Y |
| Isowyosine TP | 00901012030 | Y |
| Queuosine TP | 00901012031 | Y |
| Epoxyqueuosine TP | 00901012032 | Y |
| galactosyl-queuosine TP | 00901012033 | Y |
| mannosyl-queuosine TP | 00901012034 | Y |
| Archaeosine TP | 00901012035 | Y |

Non-natural nucleotides of the present invention may also include those listed below in Table 14.

TABLE 14

Non-naturally occurring nucleotides.

| Chemistry Alteration | Compound # | Naturally occurring |
|---|---|---|
| 5-(1-Propynyl)ara-uridine TP | 036012293016 | N |
| 2'-O-Methyl-5-(1-propynyl)uridine TP | 03601073016 | N |
| 2'-O-Methyl-5-(1-propynyl)cytidine TP | 03601074012 | N |
| 5-(1-Propynyl)ara-cytidine TP | 03601294012 | N |
| 5-Ethynylara-cytidine TP | 03601294011 | N |
| 5-Ethynylcytidine TP | 03601014011 | N |
| 5-Vinylarauridine TP | 03601013017 | N |
| (Z)-5-(2-Bromo-vinyl)ara-uridine TP | 03601293018 | N |
| (E)-5-(2-Bromo-vinyl)ara-uridine TP | 03601293019 | N |
| (Z)-5-(2-Bromo-vinyl)uridine TP | 03601013018 | N |
| (E)-5-(2-Bromo-vinyl)uridine TP | 03601013019 | N |
| 5-Methoxycytidine TP | 03601014030 | N |
| 5-Formyluridine TP | 03601013020 | N |
| 5-Cyanouridine TP | 03601013021 | N |
| 5-Dimethylaminouridine TP | 03601013022 | N |
| 5-Trideuteromethyl-6-deuterouridine TP | 03601013023 | N |
| 5-Cyanocytidine TP | 03601014031 | N |
| 5-(2-Chloro-phenyl)-2-thiocytidine TP | 03601014032 | N |
| 5-(4-Amino-phenyl)-2-thiocytidine TP | 03601014033 | N |

TABLE 14-continued

Non-naturally occurring nucleotides.

| Chemistry Alteration | Compound # | Naturally occurring |
|---|---|---|
| 5-(2-Furanyl)uridine TP | 03601013024 | N |
| 5-Phenylethynyluridine TP | 03601013025 | N |
| N4,2'-O-Dimethylcytidine TP | 00901074004 | N |
| 3'-Ethynylcytidine TP | 00901304001 | N |
| 4'-Carbocyclic adenosine TP | 00901171001 | N |
| 4'-Carbocyclic cytidine TP | 00901174001 | N |
| 4'-Carbocyclic guanosine TP | 00901172001 | N |
| 4'-Carbocyclic uridine TP | 00901173001 | N |
| 4'-Ethynyladenosine TP | 00901311001 | N |
| 4'-Ethynyluridine TP | 00901313001 | N |
| 4'-Ethynylcytidine TP | 00901314001 | N |
| 4'-Ethynylguanosine TP | 00901312001 | N |
| 4'-Azidouridine TP | 00901323001 | N |
| 4'-Azidocytidine TP | 00901324001 | N |
| 4'-Azidoadenosine TP | 0090132001 | N |
| 4'-Azidoguanosine TP | 00901322001 | N |
| 2'-Deoxy-2',2'-difluorocytidine TP | 00901334001 | N |
| 2'-Deoxy-2',2'-difluorouridine TP | 00901333001 | N |
| 2'-Deoxy-2',2'-difluoroadenosine TP | 00901331001 | N |
| 2'-Deoxy-2',2'-difluoroguanosine TP | 00901332001 | N |
| 2'-Deoxy-2'-b-fluorocytidine TP | 00901024001 | N |
| 2'-Deoxy-2'-b-fluorouridine TP | 00901023001 | N |

TABLE 14-continued

Non-naturally occurring nucleotides.

| Chemistry Alteration | Compound # | Naturally occurring |
|---|---|---|
| 2'-Deoxy-2'-b-fluoroadenosine TP | 00901021001 | N |
| 2'-Deoxy-2'-b-fluoroguanosine TP | 00901022001 | N |
| 8-Trifluoromethyladenosine TP | 03601011020 | N |
| 2'-Deoxy-2'-b-chlorouridine TP | 00901033001 | N |
| 2'-Deoxy-2'-b-bromouridine TP | 00901043001 | N |
| 2'-Deoxy-2'-b-iodouridine TP | 00901053001 | N |
| 2'-Deoxy-2'-b-chlorocytidine TP | 00901034001 | N |
| 2'-Deoxy-2'-b-bromocytidine TP | 00901044001 | N |
| 2'-Deoxy-2'-b-iodocytidine TP | 00901054001 | N |
| 2'-Deoxy-2'-b-chloroadenosine TP | 00901031001 | N |
| 2'-Deoxy-2'-b-bromoadenosine TP | 00901041001 | N |
| 2'-Deoxy-2'-b-iodoadenosine TP | 00901051001 | N |
| 2'-Deoxy-2'-b-chloroguanosine TP | 00901032001 | N |
| 2'-Deoxy-2'-b-bromoguanosine TP | 00901042001 | N |
| 2'-Deoxy-2'-b-iodoguanosine TP | 00901052001 | N |
| 5'-Homo-cytidine TP | 00901344001 | N |
| 5'-Homo-adenosine TP | 00901341001 | N |
| 5'-Homo-uridine TP | 00901343001 | N |
| 5'-Homo-guanosine TP | 00901342001 | N |
| 2'-Deoxy-2'-a-mercaptouridine TP | 00901353001 | N |
| 2'-Deoxy-2'-a-thiomethoxyuridine TP | 00901363001 | N |
| 2'-Deoxy-2'-a-azidouridine TP | 00901373001 | N |
| 2'-Deoxy-2'-a-aminouridine TP | 00901383001 | N |
| 2'-Deoxy-2'-a-mercaptocytidine TP | 00901354001 | N |
| 2'-Deoxy-2'-a-thiomethoxycytidine TP | 00901364001 | N |
| 2'-Deoxy-2'-a-azidocytidine TP | 00901374001 | N |
| 2'-Deoxy-2'-a-aminocytidine TP | 00901384001 | N |
| 2'-Deoxy-2'-a-mercaptoadenosine TP | 00901351001 | N |
| 2'-Deoxy-2'-a-thiomethoxyadenosine TP | 00901361001 | N |
| 2'-Deoxy-2'-a-azidoadenosine TP | 00901371001 | N |
| 2'-Deoxy-2'-a-aminoadenosine TP | 00901381001 | N |
| 2'-Deoxy-2'-a-mercaptoguanosine TP | 00901352001 | N |
| 2'-Deoxy-2'-a-thiomethoxyguanosine TP | 00901362001 | N |
| 2'-Deoxy-2'-a-azidoguanosine TP | 00901372001 | N |
| 2'-Deoxy-2'-a-aminoguanosine TP | 00901382001 | N |
| 2'-Deoxy-2'-b-mercaptouridine TP | 00901393001 | N |
| 2'-Deoxy-2'-b-thiomethoxyuridine TP | 00901403001 | N |
| 2'-Deoxy-2'-b-azidouridine TP | 00901413001 | N |
| 2'-Deoxy-2'-b-aminouridine TP | 00901423001 | N |
| 2'-Deoxy-2'-b-mercaptocytidine TP | 00901394001 | N |
| 2'-Deoxy-2'-b-thiomethoxycytidine TP | 00901404001 | N |
| 2'-Deoxy-2'-b-azidocytidine TP | 00901414001 | N |
| 2'-Deoxy-2'-b-aminocytidine TP | 00901424001 | N |
| 2'-Deoxy-2'-b-mercaptoadenosine TP | 00901391001 | N |
| 2'-Deoxy-2'-b-thiomethoxyadenosine TP | 00901401001 | N |
| 2'-Deoxy-2'-b-azidoadenosine TP | 00901411001 | N |
| 2'-Deoxy-2'-b-aminoadenosine TP | 00901421001 | N |
| 2'-Deoxy-2'-b-mercaptoguanosine TP | 00901392001 | N |
| 2'-Deoxy-2'-b-thiomethoxyguanosine TP | 00901402001 | N |
| 2'-Deoxy-2'-b-azidoguanosine TP | 00901412001 | N |
| 2'-Deoxy-2'-b-aminoguanosine TP | 00901422001 | N |
| 2'-b-Trifluoromethyladenosine TP | 00901431001 | N |
| 2'-b-Trifluoromethylcytidine TP | 00901434001 | N |
| 2'-b-Trifluoromethylguanosine TP | 00901432001 | N |
| 2'-b-Trifluoromethyluridine TP | 00901433001 | N |
| 2'-a-Trifluoromethyladenosine TP | 00901441001 | N |
| 2'-a-Trifluoromethylcytidine TP | 00901444001 | N |
| 2'-a-Trifluoromethylguanosine TP | 00901442001 | N |
| 2'-a-Trifluoromethyluridine TP | 00901443001 | N |
| 2'-b-Ethynyladenosine TP | 00901441001 | N |
| 2'-b-Ethynylcytidine TP | 00901444001 | N |
| 2'-b-Ethynylguanosine TP | 00901442001 | N |
| 2'-b-Ethynyluridine TP | 00901443001 | N |
| 2'-a-Ethynyladenosine TP | 00901451001 | N |
| 2'-a-Ethynylcytidine TP | 00901454001 | N |
| 2'-a-Ethynylguanosine TP | 00901452001 | N |
| 2'-a-Ethynyluridine TP | 00901453001 | N |
| (E)-5-(2-Bromo-vinyl)cytidine TP | 03601014034 | N |
| 2-Trifluoromethyladenosine TP | 03601011021 | N |
| 2-Mercaptoadenosine TP | 03601011022 | N |
| 2-Aminoadenosine TP | 03601011002 | N |
| 2-Azidoadenosine TP | 03601011023 | N |
| 2-Fluoroadenosine TP | 03601011024 | N |
| 2-Chloroadenosine TP | 03601011025 | N |
| 2-Bromoadenosine TP | 03601011026 | N |
| 2-Iodoadenosine TP | 03601011027 | N |
| Formycin A TP | 03601011038 | N |
| Formycin B TP | 03601011039 | N |
| Oxoformycin TP | 03601011040 | N |
| Pyrrolosine TP | 03601011037 | N |
| 9-Deazaadenosine TP | 03601011028 | N |
| 9-Deazaguanosine TP | 03601012020 | N |
| 3-Deazaadenosine TP | 03601011029 | N |
| 3-Deaza-3-fluoroadenosine TP | 03601011030 | N |
| 3-Deaza-3-chloroadenosine TP | 03601011031 | N |
| 3-Deaza-3-bromoadenosine TP | 03601011032 | N |
| 3-Deaza-3-iodoadenosine TP | 03601011033 | N |
| 1-Deazaadenosine TP | 03601011034 | N |

Example 11

Directed SAR of Pseudouridine and N1-methyl PseudoUridine

With the recent focus on the pyrimidine nucleoside pseudouridine, a series of structure-activity studies were designed to investigate mRNA containing alterations to pseudouridine or N1-methyl-pseudourdine.

The study was designed to explore the effect of chain length, increased lipophilicity, presence of ring structures, and alteration of hydrophobic or hydrophilic interactions when alterations were made at the N1 position, C6 position, the 2-position, the 4-position and on the phosphate backbone. Stability is also investigated.

To this end, alterations involving alkylation, cycloalkylation, alkyl-cycloalkylation, arylation, alkyl-arylation, alkylation moieties with amino groups, alkylation moieties with carboxylic acid groups, and alkylation moieties containing amino acid charged moieties are investigated. The degree of alkylation is generally $C_1$-$C_6$. Examples of the chemistry alterations include those listed in Tables 15, 16 and 17.

TABLE 15

Pseudouridine and N1-methyl Pseudo Uridine SAR.

| Chemistry Alteration | Compound # | Naturally occuring |
|---|---|---|
| N1-Alterations | | |
| 1-Ethyl-pseudo-UTP | 03601015003 | N |
| 1-Propyl-pseudo-UTP | 03601015004 | N |
| 1-iso-propyl-pseudo-UTP | 03601015028 | N |
| 1-(2,2,2-Trifluoroethyl)-pseudo-UTP | 03601015005 | N |
| 1-Cyclopropyl-pseudo-UTP | 03601015029 | N |
| 1-Cyclopropylmethyl-pseudo-UTP | 03601015030 | N |
| 1-Phenyl-pseudo-UTP | 03601015031 | N |
| 1-Benzyl-pseudo-UTP | 03601015032 | N |
| 1-Aminomethyl-pseudo-UTP | 03601015033 | N |
| Pseudo-UTP-1-2-ethanoic acid | 03601015034 | N |
| 1-(3-Amino-3-carboxypropyl)pseudo-UTP | 03601015035 | N |
| 1-Methyl-3-(3-amino-3-carboxypropyl)pseudo-UTP | 03601015036 | Y |
| C-6 Alterations | | |
| 6-Methyl-pseudo-UTP | 03601015037 | N |
| 6-Trifluoromethyl-pseudo-UTP | 03601015038 | N |
| 6-Methoxy-pseudo-UTP | 03601015039 | N |
| 6-Phenyl-pseudo-UTP | 03601015040 | N |
| 6-Iodo-pseudo-UTP | 03601015041 | N |
| 6-Bromo-pseudo-UTP | 03601015042 | N |

TABLE 15-continued

Pseudouridine and N1-methyl Pseudo Uridine SAR.

| Chemistry Alteration | Compound # | Naturally occuring |
|---|---|---|
| 6-Chloro-pseudo-UTP | 03601015043 | N |
| 6-Fluoro-pseudo-UTP | 03601015044 | N |
| 2-or 4-position Alterations | | |
| 4-Thio-pseudo-UTP | 00901015022 | N |
| 2-Thio-pseudo-UTP | 00901015006 | N |
| Phosphate backbone Alterations | | |
| Alpha-thio-pseudo-UTP | 00902015001 | N |
| 1-Me-alpha-thio-pseudo-UTP | 00902015002 | N |

TABLE 16

Pseudouridine and N1-methyl Pseudo Uridine SAR.

| Chemistry Alteration | Compound # | Naturally occuring |
|---|---|---|
| 1-Methyl-pseudo-UTP | 00901015002 | Y |
| 1-Butyl-pseudo-UTP | 03601015045 | N |
| 1-tert-Butyl-pseudo-UTP | 03601015046 | N |
| 1-Pentyl-pseudo-UTP | 03601015047 | N |
| 1-Hexyl-pseudo-UTP | 03601015048 | N |
| 1-Trifluoromethyl-pseudo-UTP | 03601015049 | Y |
| 1-Cyclobutyl-pseudo-UTP | 03601015050 | N |
| 1-Cyclopentyl-pseudo-UTP | 03601015051 | N |
| 1-Cyclohexyl-pseudo-UTP | 03601015052 | N |
| 1-Cycloheptyl-pseudo-UTP | 03601015053 | N |
| 1-Cyclooctyl-pseudo-UTP | 03601015054 | N |
| 1-Cyclobutylmethyl-pseudo-UTP | 03601015055 | N |
| 1-Cyclopentylmethyl-pseudo-UTP | 03601015056 | N |
| 1-Cyclohexylmethyl-pseudo-UTP | 03601015057 | N |
| 1-Cycloheptylmethyl-pseudo-UTP | 03601015058 | N |
| 1-Cyclooctylmethyl-pseudo-UTP | 03601015059 | N |
| 1-p-tolyl-pseudo-UTP | 03601015060 | N |
| 1-(2,4,6-Trimethyl-phenyl)pseudo-UTP | 03601015061 | N |
| 1-(4-Methoxy-phenyl)pseudo-UTP | 03601015062 | N |
| 1-(4-Amino-phenyl)pseudo-UTP | 03601015063 | N |
| 1(4-Nitro-phenyl)pseudo-UTP | 03601015064 | N |
| Pseudo-UTP-N1-p-benzoic acid | 03601015065 | N |
| 1-(4-Methyl-benzyl)pseudo-UTP | 03601015066 | N |
| 1-(2,4,6-Trimethyl-benzyl)pseudo-UTP | 03601015067 | N |
| 1-(4-Methoxy-benzyl)pseudo-UTP | 03601015068 | N |
| 1-(4-Amino-benzyl)pseudo-UTP | 03601015069 | N |
| 1-(4-Nitro-benzyl)pseudo-UTP | 03601015070 | N |
| Pseudo-UTP-N1-methyl-p-benzoic acid | 03601015071 | N |
| 1-(2-Amino-ethyl)pseudo-UTP | 03601015072 | N |
| 1-(3-Amino-propyl)pseudo-UTP | 03601015073 | N |
| 1-(4-Amino-butyl)pseudo-UTP | 03601015074 | N |
| 1-(5-Amino-pentyl)pseudo-UTP | 03601015075 | N |
| 1-(6-Amino-hexyl)pseudo-UTP | 03601015076 | N |
| Pseudo-UTP-N1-3-propionic acid | 03601015077 | N |
| Pseudo-UTP-N1-4-butanoic acid | 03601015078 | N |
| Pseudo-UTP-N1-5-pentanoic acid | 03601015079 | N |
| Pseudo-UTP-N1-6-hexanoic acid | 03601015080 | N |
| Pseudo-UTP-N1-7-heptanoic acid | 03601015081 | N |
| 1-(2-Amino-2-carboxyethyl)pseudo-UTP | 03601015082 | N |
| 1-(4-Amino-4-carboxybutyl)pseudo-UTP | 03601015083 | N |
| 3-Alkyl-pseudo-UTP | 00901015187 | N |
| 6-Ethyl-pseudo-UTP | 03601015084 | N |

TABLE 16-continued

Pseudouridine and N1-methyl Pseudo Uridine SAR.

| Chemistry Alteration | Compound # | Naturally occuring |
|---|---|---|
| 6-Propyl-pseudo-UTP | 03601015085 | N |
| 6-iso-Propyl-pseudo-UTP | 03601015086 | N |
| 6-Butyl-pseudo-UTP | 03601015087 | N |
| 6-tert-Butyl-pseudo-UTP | 03601015088 | N |
| 6-(2,2,2-Trifluoroethyl)-pseudo-UTP | 03601015089 | N |
| 6-Ethoxy-pseudo-UTP | 03601015090 | N |
| 6-Trifluoromethoxy-pseudo-UTP | 03601015091 | N |
| 6-Phenyl-pseudo-UTP | 03601015092 | N |
| 6-(Substituted-Phenyl)-pseudo-UTP | 03601015093 | N |
| 6-Cyano-pseudo-UTP | 03601015094 | N |
| 6-Azido-pseudo-UTP | 03601015095 | N |
| 6-Amino-pseudo-UTP | 03601015096 | N |
| 6-Ethylcarboxylate-pseudo-UTP | 03601015097 | N |
| 6-Hydroxy-pseudo-UTP | 03601015098 | N |
| 6-Methylamino-pseudo-UTP | 03601015099 | N |
| 6-Dimethylamino-pseudo-UTP | 03601015100 | N |
| 6-Hydroxyamino-pseudo-UTP | 03601015101 | N |
| 6-Formyl-pseudo-UTP | 03601015102 | N |
| 6-(4-Morpholino)-pseudo-UTP | 03601015103 | N |
| 6-(4-Thiomorpholino)-pseudo-UTP | 03601015104 | N |
| 1-Me-4-thio-pseudo-UTP | 03601015105 | N |
| 1-Me-2-thio-pseudo-UTP | 03601015106 | N |
| 1,6-Dimethyl-pseudo-UTP | 03601015107 | N |
| 1-Methyl-6-trifluoromethyl-pseudo-UTP | 03601015108 | N |
| 1-Methyl-6-ethyl-pseudo-UTP | 03601015109 | N |
| 1-Methyl-6-propyl-pseudo-UTP | 03601015110 | N |
| 1-Methyl-6-iso-propyl-pseudo-UTP | 03601015111 0 | N |
| 1-Methyl-6-butyl-pseudo-UTP | 03601015112 | N |
| 1-Methyl-6-tert-butyl-pseudo-UTP | 03601015113 | N |
| 1-Methyl-6-(2,2,2-Trifluoroethyl)pseudo-UTP | 03601015114 | N |
| 1-Methyl-6-iodo-pseudo-UTP | 03601015115 | N |
| 1-Methyl-6-bromo-pseudo-UTP | 03601015116 | N |
| 1-Methyl-6-chloro-pseudo-UTP | 03601015117 | N |
| 1-Methyl-6-fluoro-pseudo-UTP | 03601015118 | N |
| 1-Methyl-6-methoxy-pseudo-UTP | 03601015119 | N |
| 1-Methyl-6-ethoxy-pseudo-UTP | 03601015120 | N |
| 1-Methyl-6-trifluoromethoxy-pseudo-UTP | 03601015121 | N |
| 1-Methyl-6-phenyl-pseudo-UTP | 03601015122 | N |
| 1-Methyl-6-(substituted phenyl)pseudo-UTP | 03601015123 | N |
| 1-Methyl-6-cyano-pseudo-UTP | 03601015124 | N |
| 1-Methyl-6-azido-pseudo-UTP | 03601015125 | N |
| 1-Methyl-6-amino-pseudo-UTP | 03601015126 | N |
| 1-Methyl-6-ethylcarboxylate-pseudo-UTP | 03601015127 | N |
| 1-Methyl-6-hydroxy-pseudo-UTP | 03601015128 | N |
| 1-Methyl-6-methylamino-pseudo-UTP | 03601015129 | N |
| 1-Methyl-6-dimethylamino-pseudo-UTP | 03601015130 | N |
| 1-Methyl-6-hydroxyamino-pseudo-UTP | 03601015131 | N |
| 1-Methyl-6-formyl-pseudo-UTP | 03601015132 | N |
| 1-Methyl-6-(4-morpholino)-pseudo-UTP | 03601015133 | N |
| 1-Methyl-6-(4-thiomorpholino)-pseudo-UTP | 03601015134 | N |
| 1-Alkyl-6-vinyl-pseudo-UTP | 03601015188 | N |
| 1-Alkyl-6-allyl-pseudo-UTP | 03601015189 | N |
| 1-Alkyl-6-homoallyl-pseudo-UTP | 03601015190 | N |
| 1-Alkyl-6-ethynyl-pseudo-UTP | 03601015191 | N |
| 1-Alkyl-6-(2-propynyl)-pseudo-UTP | 03601015192 | N |
| 1-Alkyl-6-(1-propynyl)-pseudo-UTP | 03601015193 | N |

Additional non-naturally occurring compounds were designed for structure activity relationship around 1-methylpseudouridine. These compounds include those listed in Table 17.

TABLE 17

Non-naturally occurring nucleotides designed using SAR around 1-methypseudouridine.

| Chemistry Alteration | Compound # | Naturally occuring |
|---|---|---|
| 1-Hydroxymethylpseudouridine TP | 03601015135 | N |
| 1-(2-Hydroxyethyl)pseudouridine TP | 03601015136 | N |

TABLE 17-continued

Non-naturally occurring nucleotides designed using SAR around 1-methypseudouridine.

| Chemistry Alteration | Compound # | Naturally occuring |
|---|---|---|
| 1-Methoxymethylpseudouridine TP | 03601015137 | N |
| 1-(2-Methoxyethyl)pseudouridine TP | 03601015138 | N |
| 1-(2,2-Diethoxyethyl)pseudouridine TP | 03601015139 | N |
| (±)1-(2-Hydroxypropyl)pseudouridine TP | 03601015140 | N |
| (2R)-1-(2-Hydroxypropyl)pseudouridine TP | 03601015141 | N |
| (2S)-1-(2-Hydroxypropyl)pseudouridine TP | 03601015142 | N |
| 1-Cyanomethylpseudouridine TP | 03601015143 | N |
| 1-Morpholinomethylpseudouridine TP | 03601015144 | N |
| 1-Thiomorpholinomethylpseudouridine TP | 03601015145 | N |
| 1-Benzyloxymethylpseudouridine TP | 03601015146 | N |
| 1-(2,2,3,3,3-Pentafluoropropyl)pseudouridine TP | 03601015147 | N |
| 1-Thiomethoxymethylpseudouridine TP | 03601015148 | N |
| 1-Methanesulfonylmethylpseudouridine TP | 03601015149 | N |
| 1-Vinylpseudouridine TP | 03601015150 | N |
| 1-Allylpseudouridine TP | 03601015151 | N |
| 1-Homoallylpseudouridine TP | 03601015152 | N |
| 1-Propargylpseudouridine TP | 03601015153 | N |
| 1-(4-Fluorobenzyl)pseudouridine TP | 03601015154 | N |
| 1-(4-Chlorobenzyl)pseudouridine TP | 03601015155 | N |
| 1-(4-Bromobenzyl)pseudouridine TP | 03601015156 | N |
| 1-(4-Iodobenzyl)pseudouridine TP | 03601015157 | N |
| 1-(4-Methylbenzyl)pseudouridine TP | 03601015158 | N |
| 1-(4-Trifluoromethylbenzyl)pseudouridine TP | 03601015159 | N |
| 1-(4-Methoxybenzyl)pseudouridine TP | 03601015160 | N |
| 1-(4-Trifluoromethoxybenzyl)pseudouridine TP | 03601015161 | N |
| 1-(4-Thiomethoxybenzyl)pseudouridine TP | 03601015162 | N |
| 1-(4-Methanesulfonylbenzyl)pseudouridine TP | 03601015163 | N |
| Pseudouridine 1-(4-methylbenzoic acid) TP | 03601015164 | N |
| Pseudouridine 1-(4-methylbenzenesulfonic acid) TP | 03601015165 | N |
| 1-(2,4,6-Trimethylbenzyl)pseudouridine TP | 03601015166 | N |
| 1-(4-Nitrobenzyl)pseudouridine TP | 03601015167 | N |
| 1-(4-Azidobenzyl)pseudouridine TP | 03601015168 | N |
| 1-(3,4-Dimethoxybenzyl)pseudouridine TP | 03601015169 | N |
| 1-(3,4-Bis-trifluoromethoxybenzyl)pseudouridine TP | 03601015170 | N |
| 1-Acetylpseudouridine TP | 03601015171 | N |
| 1-Trifluoroacetylpseudouridine TP | 03601015172 | N |
| 1-Benzoylpseudouridine TP | 03601015173 | N |
| 1-Pivaloylpseudouridine TP | 03601015174 | N |
| 1-(3-Cyclopropyl-prop-2-ynyl)pseudouridine TP | 03601015175 | N |
| Pseudouridine TP 1-methylphosphonic acid diethyl ester | 03601015176 | N |
| Pseudouridine TP 1-methylphosphonic acid | 03601015177 | N |
| Pseudouridine TP 1-[3-(2-ethoxy)]propionic acid | 03601015178 | N |
| Pseudouridine TP 1[3-{2-(2-ethoxy)-ethoxy}] propionic acid | 03601015179 | N |
| Pseudouridine TP 1-[3-{2-(2-[2-ethoxy]-ethoxy)-ethoxy}]propionic acid | 03601015180 | N |
| Pseudouridine TP 1-[3-{2-(2-[2-(2-ethoxy)-ethoxy]-ethoxy)-ethoxy}]propionic acid | 03601015181 | N |
| Pseudouridine TP 1-[3-{2-(2-[2-{2(2-ethoxy)-ethoxy}-ethoxy]-ethoxy)-ethoxy}]propionic acid | 03601015182 | N |
| 1-{3-[2-(2-Aminoethoxy)-ethoxy]-propionyl}pseudouridine TP | 03601015183 | N |
| 1-[3-(2-{2-[2-(2-Aminoethoxy)-ethoxy]-ethoxy}-ethoxy)-propionyl]pseudouridine TP | 03601015184 | N |
| 1-Biotinylpseudouridine TP | 03601015185 | N |
| 1-Biotinyl-PEG2-pseudouridine TP | 03601015186 | N |

Example 12

Incorporation of Naturally and Non-naturally Occurring Nucleosides

Naturally and non-naturally occurring nucleosides are incorporated into mRNA encoding a polypeptide of interest. Examples of these are given in Tables 18, 19, and 20. Certain commercially available nucleoside triphosphates (NTPs) are investigated in the polynucleotides of the invention. A selection of these are given in Table 19. The resultant mRNA are then examined for their ability to produce protein, induce cytokines, and/or produce a therapeutic outcome.

TABLE 18

Naturally and non-naturally occurring nucleosides.

| Chemistry Alteration | Compound # | Naturally occuring |
|---|---|---|
| N4-Methyl-Cytidine TP | 00901014004 | Y |
| N4,N4-Dimethyl-2'-OMe-Cytidine TP | 03601014029 | Y |
| 5-Oxyacetic acid-methyl ester-Uridine TP | 00901013004 | Y |
| 3-Methyl-pseudo-Uridine TP | 00901015007 | Y |
| 5-Hydroxymethyl-Cytidine TP | 00901014005 | Y |
| 5-Trifluoromethyl-Cytidine TP | 00901014003 | N |
| 5-Trifluoromethyl-Uridine TP | 00901013002 | N |
| 5-Methyl-amino-methyl-Uridine TP | 00901013006 | Y |
| 5-Carboxy-methyl-amino-methyl-Uridine TP | 00901013026 | Y |
| 5-Carboxymethylaminomethyl-2'-OMe-Uridine TP | 00901023026 | Y |

TABLE 18-continued

Naturally and non-naturally occurring nucleosides.

| Chemistry Alteration | Compound # | Naturally occuring |
|---|---|---|
| 5-Carboxymethylaminomethyl-2-thio-Uridine TP | 00901013027 | Y |
| 5-Methylaminomethyl-2-thio-Uridine TP | 00901013028 | Y |
| 5-Methoxy-carbonyl-methyl-Uridine TP | 00901013005 | Y |
| 5-Methoxy-carbonyl-methyl-2'-OMe-Uridine TP | 00901023005 | Y |
| 5-Oxyacetic acid-Uridine TP | 00901013029 | Y |
| 3-(3-Amino-3-carboxypropyl)-Uridine TP | 00901013030 | Y |
| 5-(carboxyhydroxymethyl)uridine methyl ester TP | 00901013031 | Y |
| 5-(carboxyhydroxymethyl)uridine TP | 00901013032 | Y |

TABLE 19

Non-naturally occurring nucleoside triphosphates.

| Chemistry Alteration | Compound # | Naturally occuring |
|---|---|---|
| 1-Me-GTP | 00901012008 | N |
| 2'-OMe-2-Amino-ATP | 00901071002 | N |
| 2'-OMe-pseudo-UTP | 00901075001 | Y |
| 2'-OMe-6-Me-UTP | 03601073033 | N |
| 2'-Azido-2'-deoxy-ATP | 00901371001 | N |
| 2'-Azido-2'-deoxy-GTP | 00901372001 | N |
| 2'-Azido-2'-deoxy-UTP | 00901373001 | N |
| 2'-Azido-2'-deoxy-CTP | 00901374001 | N |
| 2'-Amino-2'-deoxy-ATP | 00901381001 | N |
| 2'-Amino-2'-deoxy-GTP | 00901382001 | N |
| 2'-Amino-2'-deoxy-UTP | 00901383001 | N |
| 2'-Amino-2'-deoxy-CTP | 00901384001 | N |
| 2-Amino-ATP | 00901011002 | N |
| 8-Aza-ATP | 00901011003 | N |
| Xanthosine-5'-TP | 00901012003 | N |
| 5-Bromo-CTP | 03601014008 | N |
| 2'-F-5-Methyl-2'-deoxy-UTP | 03601023014 | N |
| 5-Aminoallyl-CTP | 03601014009 | N |
| 2-Amino-riboside-TP | 03601012004 | N |

TABLE 20

Combinations of naturally occurring and non-naturally occurring nucleotides in mRNA

| Uracil | Cytosine | Adenine | Guanine |
|---|---|---|---|
| 5-methoxy-UTP | CTP | ATP | GTP |
| 5-Methoxy-UTP | N4Ac-CTP | ATP | GTP |
| 5-Methoxy-UTP | 5-Methyl-CTP | ATP | GTP |
| 5-Methoxy-UTP | 5-Trifluoromethyl-CTP | ATP | GTP |
| 5-Methoxy-UTP | 5-Hydroxymethyl-CTP | ATP | GTP |
| 5-Methoxy-UTP | 5-Bromo-CTP | ATP | GTP |
| 5-Methoxy-UTP | N4Ac-CTP | ATP | GTP |
| 5-Methoxy-UTP | CTP | ATP | GTP |
| 5-Methoxy-UTP | 5-Methyl-CTP | ATP | GTP |
| 5-Methoxy-UTP | 5-Trifluoromethyl-CTP | ATP | GTP |
| 5-Methoxy-UTP | 5-Hydroxymethyl-CTP | ATP | GTP |
| 5-Methoxy-UTP | 5-Bromo-CTP | ATP | GTP |
| 5-Methoxy-UTP | N4-Ac-CTP | ATP | GTP |
| 5-Methoxy-UTP | 5-Iodo-CTP | ATP | GTP |
| 5-Methoxy-UTP | 5-Bromo-CTP | ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% UTP | 5-Methyl-CTP | ATP | GTP |
| 50% 5-Methoxy-UTP + 50% UTP | 5-Methyl-CTP | ATP | GTP |
| 25% 5-Methoxy-UTP + 75% UTP | 5-Methyl-CTP | ATP | GTP |
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 75% 5-Methoxy-UTP + 25% UTP | 50% 5-Methyl-CTP + 50% CTP | ATP | GTP |
| 75% 5-Methoxy-UTP + 25% UTP | 25% 5-Methyl-CTP + 75% CTP | ATP | GTP |
| 50% 5-Methoxy-UTP + 50% UTP | 75% 5-Methyl-CTP + 25% CTP | ATP | GTP |
| 50% 5-Methoxy-UTP + 50% UTP | 50% 5-Methyl-CTP + 50% CTP | ATP | GTP |
| 50% 5-Methoxy-UTP + 50% UTP | 25% 5-Methyl-CTP + 75% CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |

TABLE 20-continued

Combinations of naturally occurring and non-naturally occurring nucleotides in mRNA

| Uracil | Cytosine | Adenine | Guanine |
|---|---|---|---|
| 25% 5-Methoxy-UTP + 75% UTP | 25% 5-Methyl-CTP + 75% CTP | ATP | GTP |
| 75% 5-Methoxy-UTP + 25% UTP | CTP | ATP | GTP |
| 50% 5-Methoxy-UTP + 50% UTP | CTP | ATP | GTP |
| 25% 5-Methoxy-UTP + 75% UTP | CTP | ATP | GTP |
| 5-Methoxy-UTP | CTP | ATP | GTP |
| 5-Methoxy-UTP | CTP | ATP | GTP |
| 5-Methoxy-UTP | CTP | ATP | GTP |
| 5-Methoxy-UTP | 5-Methyl-CTP | ATP | GTP |
| 5-Methoxy-UTP | 5-Methyl-CTP | ATP | GTP |
| 5-Methoxy-UTP | 5-Methyl-CTP | ATP | GTP |
| 5-Methoxy-UTP | CTP | Alpha-thio-ATP | GTP |
| 5-Methoxy-UTP | 5-Methyl-CTP | Alpha-thio-ATP | GTP |
| 5-Methoxy-UTP | CTP | ATP | Alpha-thio-GTP |
| 5-Methoxy-UTP | 5-Methyl-CTP | ATP | Alpha-thio-GTP |
| 5-Methoxy-UTP | CTP | N6-Me-ATP | GTP |
| 5-Methoxy-UTP | 5-Methyl-CTP | N6-Me-ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% UTP | 5-Methyl-CTP | ATP | GTP |
| 50% 5-Methoxy-UTP + 50% UTP | 5-Methyl-CTP | ATP | GTP |
| 25% 5-Methoxy-UTP + 75% UTP | 5-Methyl-CTP | ATP | GTP |
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 75% 5-Methoxy-UTP + 25% UTP | 50% 5-Methyl-CTP + 50% CTP | ATP | GTP |
| 75% 5-Methoxy-UTP + 25% UTP | 25% 5-Methyl-CTP + 75% CTP | ATP | GTP |
| 50% 5-Methoxy-UTP + 50% UTP | 75% 5-Methyl-CTP + 25% CTP | ATP | GTP |
| 50% 5-Methoxy-UTP + 50% UTP | 50% 5-Methyl-CTP + 50% CTP | ATP | GTP |
| 50% 5-Methoxy-UTP + 50% UTP | 25% 5-Methyl-CTP + 75% CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | CTP | ATP | GTP |
| 50% 5-Methoxy-UTP + 50% UTP | CTP | ATP | GTP |
| 25% 5-Methoxy-UTP + 75% UTP | CTP | ATP | GTP |
| 5-Methoxy-UTP | 5-Ethyl-CTP | ATP | GTP |
| 5-Methoxy-UTP | 5-Methoxy-CTP | ATP | GTP |
| 5-Methoxy-UTP | 5-Ethynyl-CTP | ATP | GTP |
| 5-Methoxy-UTP | CTP | ATP | GTP |
| 5-Methoxy-UTP | 5-Methyl-CTP | ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% 1-Methyl-pseudo-UTP | 5-Methyl-CTP | ATP | GTP |
| 50% 5-Methoxy-UTP + 50% 1-Methyl-pseudo-UTP | 5-Methyl-CTP | ATP | GTP |
| 25% 5-Methoxy-UTP + 75% 1-Methyl-pseudo-UTP | 5-Methyl-CTP | ATP | GTP |
| 5-Methoxy-UTP | 75% 5-Methyl-CTP + 25% CTP | ATP | GTP |

TABLE 20-continued

Combinations of naturally occurring and non-naturally occurring nucleotides in mRNA

| Uracil | Cytosine | Adenine | Guanine |
|---|---|---|---|
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% 1-Methyl-pseudo-UTP | 75% 5-Methyl-CTP + 25% CTP | ATP | GTP |
| 75% 5-Methoxy-UTP + 25% 1-Methyl-pseudo-UTP | 50% 5-Methyl-CTP + 50% CTP | ATP | GTP |
| 75% 5-Methoxy-UTP + 25% 1-Methyl-pseudo-UTP | 25% 5-Methyl-CTP + 75% CTP | ATP | GTP |
| 50% 5-Methoxy-UTP + 50% 1-Methyl-pseudo-UTP | 75% 5-Methyl-CTP + 25% CTP | ATP | GTP |
| 50% 5-Methoxy-UTP + 50% 1-Methyl-pseudo-UTP | 50% 5-Methyl-CTP + 50% CTP | ATP | GTP |
| 50% 5-Methoxy-UTP + 50% 1-Methyl-pseudo-UTP | 25% 5-Methyl-CTP + 75% CTP | ATP | GTP |
| 25% 5-Methoxy-UTP + 75% 1-Methyl-pseudo-UTP | 75% 5-Methyl-CTP + 25% CTP | ATP | GTP |
| 25% 5-Methoxy-UTP + 75% 1-Methyl-pseudo-UTP | 50% 5-Methyl-CTP + 50% CTP | ATP | GTP |
| 25% 5-Methoxy-UTP + 75% 1-Methyl-pseudo-UTP | 25% 5-Methyl-CTP + 75% CTP | ATP | GTP |
| 75% 5-Methoxy-UTP + 25% 1-Methyl-pseudo-UTP | CTP | ATP | GTP |
| 50% 5-Methoxy-UTP + 50% 1-Methyl-pseudo-UTP | CTP | ATP | GTP |
| 25% 5-Methoxy-UTP + 75% 1-Methyl-pseudo-UTP | CTP | ATP | GTP |
| 5-methoxy-UTP (In House) | CTP | ATP | GTP |
| 5-methoxy-UTP (Hongene) | CTP | ATP | GTP |
| 5-methoxy-UTP (Hongene) | 5-Methyl-CTP | ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% UTP | 5-Methyl-CTP | ATP | GTP |
| 50% 5-Methoxy-UTP + 50% UTP | 5-Methyl-CTP | ATP | GTP |
| 25% 5-Methoxy-UTP + 75% UTP | 5-Methyl-CTP | ATP | GTP |
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 75% 5-Methoxy-UTP + 25% UTP | 50% 5-Methyl-CTP + 50% CTP | ATP | GTP |
| 75% 5-Methoxy-UTP + 25% UTP | 25% 5-Methyl-CTP + 75% CTP | ATP | GTP |
| 50% 5-Methoxy-UTP + 50% UTP | 75% 5-Methyl-CTP + 25% CTP | ATP | GTP |
| 50% 5-Methoxy-UTP + 50% UTP | 50% 5-Methyl-CTP + 50% CTP | ATP | GTP |
| 50% 5-Methoxy-UTP + 50% UTP | 25% 5-Methyl-CTP + 75% CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | CTP | ATP | GTP |
| 50% 5-Methoxy-UTP + 50% UTP | CTP | ATP | GTP |
| 25% 5-Methoxy-UTP + 75% UTP | CTP | ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% UTP | 5-Methyl-CTP | ATP | GTP |
| 50% 5-Methoxy-UTP + 50% UTP | 5-Methyl-CTP | ATP | GTP |

TABLE 20-continued

Combinations of naturally occurring and non-naturally occurring nucleotides in mRNA

| Uracil | Cytosine | Adenine | Guanine |
|---|---|---|---|
| 25% 5-Methoxy-UTP + 75% UTP | 5-Methyl-CTP | ATP | GTP |
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 75% 5-Methoxy-UTP + 25% UTP | 50% 5-Methyl-CTP + 50% CTP | ATP | GTP |
| 75% 5-Methoxy-UTP + 25% UTP | 25% 5-Methyl-CTP + 75% CTP | ATP | GTP |
| 50% 5-Methoxy-UTP + 50% UTP | 75% 5-Methyl-CTP + 25% CTP | ATP | GTP |
| 50% 5-Methoxy-UTP + 50% UTP | 50% 5-Methyl-CTP + 50% CTP | ATP | GTP |
| 50% 5-Methoxy-UTP + 50% UTP | 25% 5-Methyl-CTP + 75% CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | CTP | ATP | GTP |
| 50% 5-Methoxy-UTP + 50% UTP | CTP | ATP | GTP |
| 25% 5-Methoxy-UTP + 75% UTP | CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |

TABLE 20-continued

Combinations of naturally occurring and non-naturally occurring nucleotides in mRNA

| Uracil | Cytosine | Adenine | Guanine |
|---|---|---|---|
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | 5-Fluoro-CTP | ATP | GTP |
| 5-Methoxy-UTP | 5-Phenyl-CTP | ATP | GTP |
| 5-Methoxy-UTP | N4-Bz-CTP | ATP | GTP |
| 5-Methoxy-UTP | CTP | N6-Isopentenyl-ATP | GTP |
| 5-Methoxy-UTP | N4-Ac-CTP | ATP | GTP |
| 25% 5-Methoxy-UTP + 75% UTP | 25% N4-Ac-CTP + 75% CTP | ATP | GTP |
| 25% 5-Methoxy-UTP + 75% UTP | 75% N4-Ac-CTP + 25% CTP | ATP | GTP |
| 75% 5-Methoxy-UTP + 25% UTP | 25% N4-Ac-CTP + 75% CTP | ATP | GTP |
| 75% 5-Methoxy-UTP + 25% UTP | 75% N4-Ac-CTP + 25% CTP | ATP | GTP |
| 5-Methoxy-UTP | 5-Hydroxymethyl-CTP | ATP | GTP |
| 25% 5-Methoxy-UTP + 75% UTP | 25% 5-Hydroxymethyl-CTP + 75% CTP | ATP | GTP |
| 25% 5-Methoxy-UTP + 75% UTP | 75% 5-Hydroxymethyl-CTP + 25% CTP | ATP | GTP |
| 75% 5-Methoxy-UTP + 25% UTP | 25% 5-Hydroxymethyl-CTP + 75% CTP | ATP | GTP |
| 75% 5-Methoxy-UTP + 25% UTP | 75% 5-Hydroxymethyl-CTP +25% CTP | ATP | GTP |
| 5-Methoxy-UTP | N4-Methyl CTP | ATP | GTP |
| 25% 5-Methoxy-UTP + 75% UTP | 25% N4-Methyl CTP + 75% CTP | ATP | GTP |
| 25% 5-Methoxy-UTP + 75% UTP | 75% N4-Methyl CTP + 25% CTP | ATP | GTP |
| 75% 5-Methoxy-UTP + 25% UTP | 25% N4-Methyl CTP + 75% CTP | ATP | GTP |
| 75% 5-Methoxy-UTP + 25% UTP | 75% N4-Methyl CTP + 25% CTP | ATP | GTP |
| 5-Methoxy-UTP | 5-Trifluoromethyl-CTP | ATP | GTP |
| 25% 5-Methoxy-UTP + 75% UTP | 25% 5-Trifluoromethyl-CTP + 75% CTP | ATP | GTP |
| 25% 5-Methoxy-UTP + 75% UTP | 75% 5-Trifluoromethyl-CTP + 25% CTP | ATP | GTP |
| 75% 5-Methoxy-UTP + 25% UTP | 25% 5-Trifluoromethyl-CTP + 75% CTP | ATP | GTP |
| 75% 5-Methoxy-UTP + 25% UTP | 75% 5-Trifluoromethyl-CTP + 25% CTP | ATP | GTP |
| 5-Methoxy-UTP | 5-Bromo-CTP | ATP | GTP |
| 25% 5-Methoxy-UTP + 75% UTP | 25% 5-Bromo-CTP + 75% CTP | ATP | GTP |
| 25% 5-Methoxy-UTP + 75% UTP | 75% 5-Bromo-CTP + 25% CTP | ATP | GTP |
| 75% 5-Methoxy-UTP + 25% UTP | 25% 5-Bromo-CTP + 75% CTP | ATP | GTP |
| 75% 5-Methoxy-UTP + 25% UTP | 75% 5-Bromo-CTP + 25% CTP | ATP | GTP |
| 5-Methoxy-UTP | 5-Iodo-CTP | ATP | GTP |
| 25% 5-Methoxy-UTP + 75% UTP | 25% 5-Iodo-CTP + 75% CTP | ATP | GTP |
| 25% 5-Methoxy-UTP + 75% UTP | 75% 5-Iodo-CTP + 25% CTP | ATP | GTP |

TABLE 20-continued

Combinations of naturally occurring and non-naturally occurring nucleotides in mRNA

| Uracil | Cytosine | Adenine | Guanine |
|---|---|---|---|
| 75% 5-Methoxy-UTP + 25% UTP | 25% 5-Iodo-CTP + 75% CTP | ATP | GTP |
| 75% 5-Methoxy-UTP + 25% UTP | 75% 5-Iodo-CTP + 25% CTP | ATP | GTP |
| 5-Methoxy-UTP | 5-Ethyl-CTP | ATP | GTP |
| 25% 5-Methoxy-UTP + 75% UTP | 25% 5-Ethyl-CTP + 75% CTP | ATP | GTP |
| 25% 5-Methoxy-UTP + 75% UTP | 75% 5-Ethyl-CTP + 25% CTP | ATP | GTP |
| 75% 5-Methoxy-UTP + 25% UTP | 25% 5-Ethyl-CTP + 75% CTP | ATP | GTP |
| 75% 5-Methoxy-UTP + 25% UTP | 75% 5-Ethyl-CTP + 25% CTP | ATP | GTP |
| 5-Methoxy-UTP | 5-Methoxy-CTP | ATP | GTP |
| 25% 5-Methoxy-UTP + 75% UTP | 25% 5-Methoxy-CTP + 75% CTP | ATP | GTP |
| 25% 5-Methoxy-UTP + 75% UTP | 75% 5-Methoxy-CTP + 25% CTP | ATP | GTP |
| 75% 5-Methoxy-UTP + 25% UTP | 25% 5-Methoxy-CTP + 75% CTP | ATP | GTP |
| 75% 5-Methoxy-UTP + 25% UTP | 75% 5-Methoxy-CTP + 25% CTP | ATP | GTP |
| 5-Methoxy-UTP | 5-Ethynyl-CTP | ATP | GTP |
| 25% 5-Methoxy-UTP + 75% UTP | 25% 5-Ethynyl-CTP + 75% CTP | ATP | GTP |
| 25% 5-Methoxy-UTP + 75% UTP | 75% 5-Ethynyl-CTP + 25% CTP | ATP | GTP |
| 75% 5-Methoxy-UTP + 25% UTP | 25% 5-Ethynyl-CTP + 75% CTP | ATP | GTP |
| 75% 5-Methoxy-UTP + 25% UTP | 75% 5-Ethynyl-CTP + 25% CTP | ATP | GTP |
| 5-Methoxy-UTP | 5-Pseudo-iso-CTP | ATP | GTP |
| 25% 5-Methoxy-UTP + 75% UTP | 25% 5-Pseudo-iso-CTP + 75% CTP | ATP | GTP |
| 25% 5-Methoxy-UTP + 75% UTP | 75% 5-Pseudo-iso-CTP + 25% CTP | ATP | GTP |
| 75% 5-Methoxy-UTP + 25% UTP | 25% 5-Pseudo-iso-CTP + 75% CTP | ATP | GTP |
| 75% 5-Methoxy-UTP + 25% UTP | 75% 5-Pseudo-iso-CTP + 25% CTP | ATP | GTP |
| 5-Methoxy-UTP | 5-Formyl-CTP | ATP | GTP |
| 25% 5-Methoxy-UTP + 75% UTP | 25% 5-Formyl-CTP + 75% CTP | ATP | GTP |
| 25% 5-Methoxy-UTP + 75% UTP | 75% 5-Formyl-CTP + 25% CTP | ATP | GTP |
| 75% 5-Methoxy-UTP + 25% UTP | 25% 5-Formyl-CTP + 75% CTP | ATP | GTP |
| 75% 5-Methoxy-UTP + 25% UTP | 75% 5-Formyl-CTP + 25% CTP | ATP | GTP |
| 5-Methoxy-UTP | 5-Aminoallyl-CTP | ATP | GTP |
| 25% 5-Methoxy-UTP + 75% UTP | 25% 5-Aminoallyl-CTP + 75% CTP | ATP | GTP |
| 25% 5-Methoxy-UTP + 75% UTP | 75% 5-Aminoallyl-CTP + 25% CTP | ATP | GTP |
| 75% 5-Methoxy-UTP + 25% UTP | 25% 5-Aminoallyl-CTP + 75% CTP | ATP | GTP |
| 75% 5-Methoxy-UTP + 25% UTP | 75% 5-Aminoallyl-CTP + 25% CTP | ATP | GTP |

Example 13

Incorporation of Alterations to the Nucleobase and Carbohydrate (Sugar)

Naturally and non-naturally occurring nucleosides are incorporated into mRNA encoding a polypeptide of interest. Commercially available nucleosides and NTPs having alterations to both the nucleobase and carbohydrate (sugar) are examined for their ability to be incorporated into mRNA and to produce protein, induce cytokines, and/or produce a therapeutic outcome. Examples of these nucleosides are given in Tables 21 and 22.

TABLE 21

Combination alterations.

| Chemistry Alteration | Compound # |
|---|---|
| 5-iodo-2'-fluoro-deoxyuridine TP | 03601023034 |
| 5-iodo-cytidine TP | 00901014035 |
| 2'-bromo-deoxyuridine TP | 00901043001 |
| 8-bromo-adenosine TP | 03601011035 |
| 8-bromo-guanosine TP | 03601012021 |
| 2,2'-anhydro-cytidine TP hydrochloride | 00901144001 |
| 2,2'-anhydro-uridine TP | 00901143001 |
| 2'-Azido-deoxyuridine TP | 00901373001 |

TABLE 21-continued

Combination alterations.

| Chemistry Alteration | Compound # |
|---|---|
| 2-amino-adenosine TP | 03601011002 |
| N4-Benzoyl-cytidine TP | 03601014013 |
| N4-Amino-cytidine TP | 03601014037 |
| 2'-O-Methyl-N4-Acetyl-cytidine TP | 00901074007 |
| 2'Fluoro-N4-Acetyl-cytidine TP | 00901024007 |
| 2'Fluor-N4-Bz-cytidine TP | 03601024013 |
| 2'O-methyl-N4-Bz-cytidine TP | 03601074013 |
| 2'O-methyl-N6-Bz-deoxyadenosine TP | 03601071036 |
| 2'Fluoro-N6-Bz-deoxyadenosine TP | 03601021036 |
| N2-isobutyl-guanosine TP | 03601012022 |
| 2'Fluro-N2-isobutyl-guanosine TP | 03601022022 |
| 2'O-methyl-N2-isobutyl-guanosine TP | 03601072022 |

TABLE 22

Naturally occuring combinations.

| Name | Compound # | Naturally occurring |
|---|---|---|
| 5-Methoxycarbonylmethyl-2-thiouridine TP | 00901013035 | Y |
| 5-Methylaminomethyl-2-thiouridine TP | 00901013028 | Y |
| 5-Carbamoylmethyluridine TP | 00901013036 | Y |
| 5-Carbamoylmethyl-2'-O-methyluridine TP | 00901073036 | Y |
| 1-Methyl-3-(3-amino-3-carboxypropyl) pseudouridine TP | 00901015036 | Y |
| 5-Methylaminomethyl-2-selenouridine TP | 00901013037 | Y |
| 5-Carboxymethyluridine TP | 00901013038 | Y |
| 5-Methyldihydrouridine TP | 03601013039 | Y |

TABLE 22-continued

Naturally occuring combinations.

| Name | Compound # | Naturally occurring |
|---|---|---|
| lysidine TP | 00901014038 | Y |
| 5-Taurinomethyluridine TP | 00901013040 | Y |
| 5-Taurinomethyl-2-thiouridine TP | 00901013041 | Y |
| 5-(iso-Pentenylaminomethyl)uridine TP | 00901013042 | Y |
| 5-(iso-Pentenylaminomethyl)-2-thiouridine TP | 00901013043 | Y |
| 5-(iso-Pentenylaminomethyl)-2'-O-methyluridine TP | 00901013044 | Y |
| N4-Acetyl-2'-O-methylcytidine TP | 00901074007 | Y |
| N4,2'-O-Dimethylcytidine TP | 00901074004 | Y |
| 5-Formyl-2'-O-methylcytidine TP | 03601074036 | Y |
| 2'-O-Methylpseudouridine TP | 00901073001 | Y |
| 2-Thio-2'-O-methyluridine TP | 00901073008 | Y |
| 3,2'-O-Dimethyluridine TP | 00901073045 | Y |

In the tables "UTP" stands for uridine triphosphate, "GTP" stands for guanosine triphosphate, "ATP" stands for adenosine triphosphate, "CTP" stands for cytosine triphosphate, "TP" stands for triphosphate and "Bz" stands for benzoyl.

The non-naturally occurring nucleobases of the invention, e.g., as indicated in Tables 5-10, can be provided as the 5'-mono-, di-, or triphosphate and/or the 3'-phosphoramidite (e.g., the 2-cyanoethyl-N,N-diisopropylphosphoramidite).

Example 14

Synthesis of Pseudo-U-alpha-thio-TP (00902015001)

Scheme 2

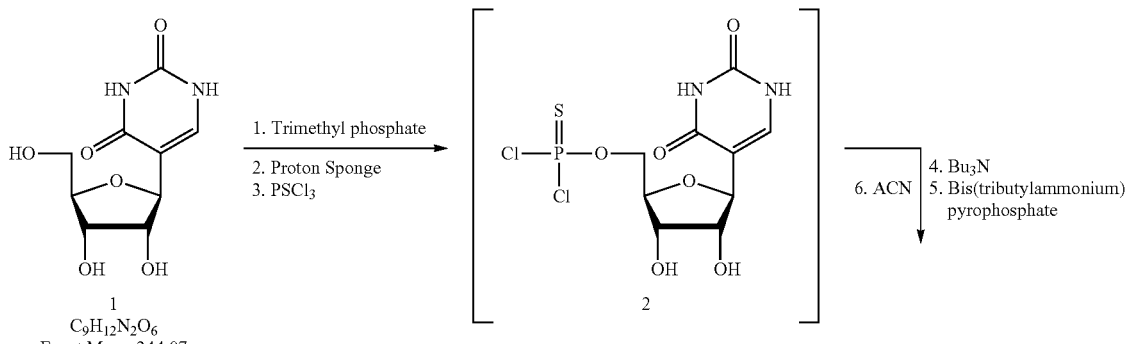

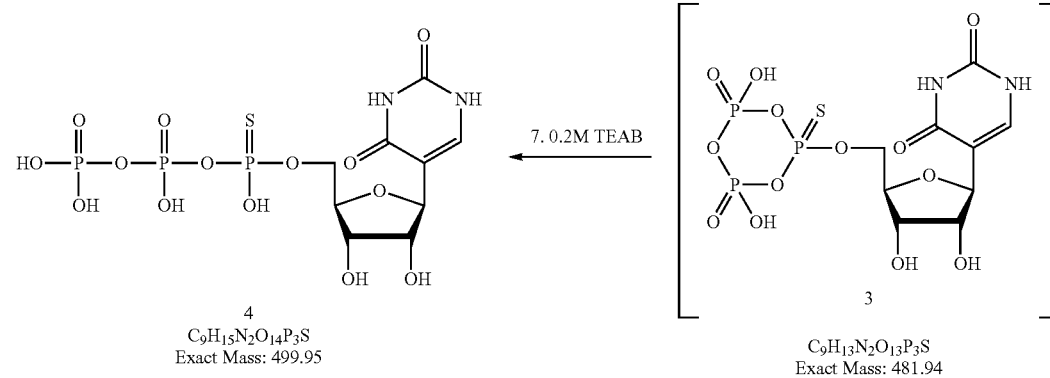

A solution of pseudouridine 1 (130.0 mg, 0.53 mmol; applied heat to make it soluble) and proton sponge (170.4 mg, 0.8 mmol, 1.5 equiv.) in trimethyl phosphate (0.8 mL) was stirred for 10.0 minutes at 0° C. Thiophosphoryl chloride (107.5 µL, 1.06 mmol, 2.0 equiv.) was added dropwise to the solution and it was then kept stirring for 2.0 hours under $N_2$ atmosphere. A mixture of tributylamine (514.84 µL, 2.13 mmol, 4.0 equiv.) and bis(tributylammonium) pyrophosphate (872.4 mg, 1.59 mmol, 3.0 equiv.) in acetonitrile (2.5 mL) was added at once. After ~25 minutes, the reaction was quenched with 24.5 mL of water and the clear solution was stirred vigorously for about an hour at room temperature. The pH of the solution was adjusted to 6.75 by adding 4.5 mL of 1.0 M TEAB buffer along with vigorous stirring for about 3.0 hours. LCMS analysis indicated the formation of the corresponding triphosphate. The reaction mixture was then lyophilized overnight. The crude reaction mixture was HPLC purified (Shimadzu, Phenomenex C18 preparative column, 250×30.0 mm, 5.0 micron; gradient (1%): 100% A for 3.0 min, then 1% B/min, A=100 mM TEAB buffer, B=ACN; flow rate: 20.0 mL/min; retention time: 16.57-18.15 min). Fractions containing the desired were pooled and lyophilized to yield the Pseudo-U-alpha-thio-TP as a tetrakis(triethylammonium salt) (62.73 mg, 24.5%, based on $\alpha_{265}$=7,546). UVmax=265 nm; MS: m/e 498.70 (M−H).

Example 15

Synthesis of 1-methyl-pseudo-U-alpha-thio-TP (00902015002)

A solution of 1-methyl-pseudouridine 5 (130.0 mg, 0.5 mmol; applied heat to make it soluble) and proton sponge (160.7 mg, 0.75 mmol, 1.5 equiv.) in trimethyl phosphate (0.8 mL) was stirred for 10.0 minutes at 0° C. Thiophosphoryl chloride (101.43 µL, 1.00 mmol, 2.0 equiv.) was added dropwise to the solution and it was then kept stirring for 2.0 hours under $N_2$ atmosphere. A mixture of tributylamine (485.7 µL, 2.00 mmol, 4.0 equiv.) and bis(tributylammonium) pyrophosphate (823.0 mg, 1.5 mmol, 3.0 equiv.) in acetonitrile (2.5 mL) was added at once. After ~25 minutes, the reaction was quenched with 24.0 mL of water and the clear solution was stirred vigorously for about an hour at room temperature. The pH of the solution was adjusted to 6.85 by adding about 3.5 mL of 1.0 M TEAB buffer along with vigorous stirring for about 3.0 hours. LCMS analysis indicated the formation of the corresponding triphosphate. The reaction mixture was then lyophilized overnight. The crude reaction mixture was HPLC purified (Shimadzu, Phenomenex C18 preparative column, 250×30.0 mm, 5.0 micron; gradient (1%): 100% A for 3.0 min, then 1% B/min, A=100 mM TEAB buffer, B=ACN; flow rate: 20.0 mL/min; retention time: 17.34-18.72 min). Fractions containing the desired were pooled and lyophilized to yield the 1-Methyl-Pseudo-U-alpha-thio-TP as a tetrakis(triethylammonium salt) (72.37 mg, 28.0%, based on $\alpha_{271}$=8,500). UVmax=271 nm; MS: m/e 512.66 (M−H).

Scheme 3

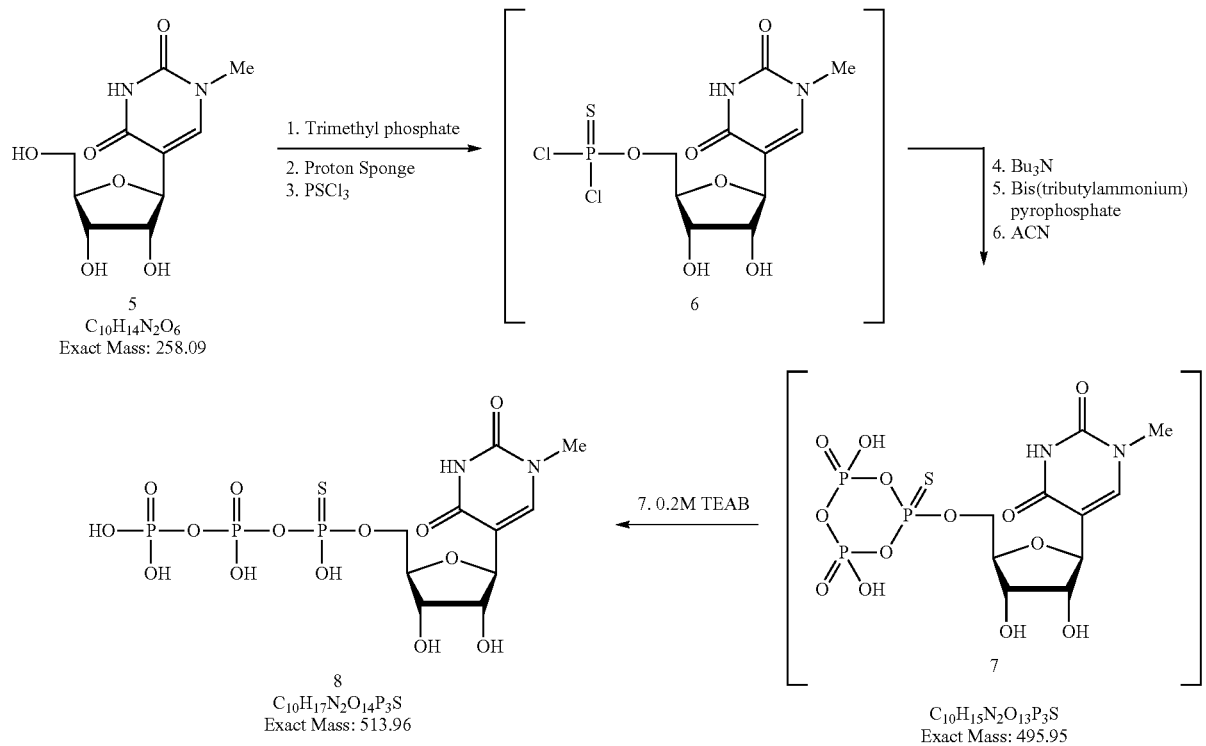

Example 16

Synthesis of 1-ethyl-pseudo-UTP (03601015003)

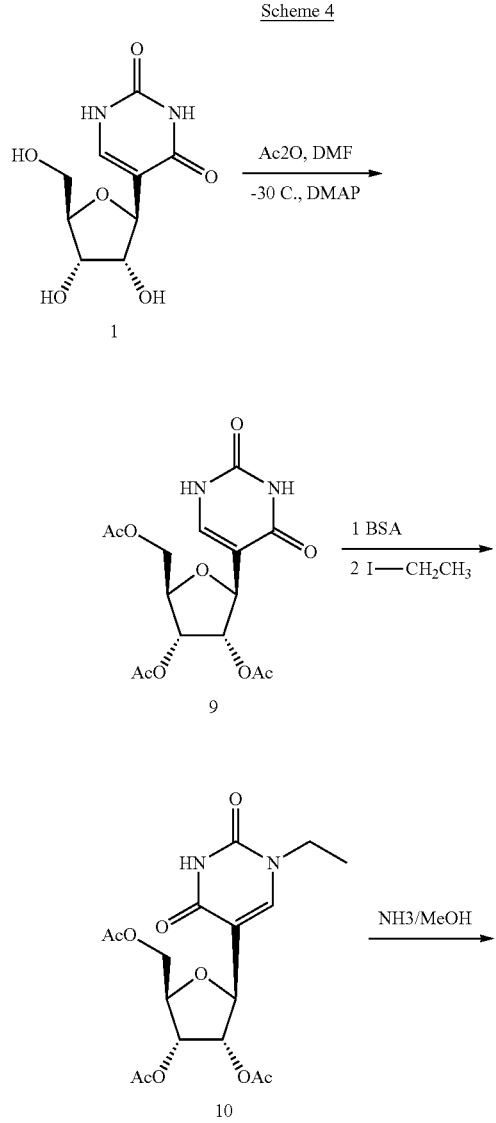

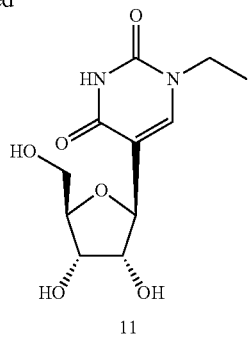

Compound 9: To a solution of pseudouridine (1, 2.4 g, 9.8 mmol) in anhydrous N,N-dimethylformamide (30 mL) at −30° C. was added 4-dimethylaminopyridine (DMAP, 1.1 g, 9.8 mmol), followed by acetic anhydride (10 mL) portion wise over a period of 15 min. The reaction mixture was stirred at −30° C. for 3 h, and then the temperature was raised to room temperature. The reaction mixture was quenched with MeOH (10 mL), and concentrated to dryness under reduced pressure. The residue was dissolved in $CH_2Cl_2$ (100 mL), and washed with $H_2O$ (50 mL). The organic phase was dried ($Na_2SO_4$) and concentrated. Then the crude compound 9 was dried overnight in a vacuum oven with $P_2O_5$ and used without further purification.

Compound 10: To a solution of 2',3',5'-tri-O-acetyl-pseudo uridine (9) (0.8 g, 2.2 mmol) in dry $CH_3CN$ (20 mL) was added N,O-bis(trimethylsilyl)acetamide (BSA) (3.0 mL), and the reaction mixture was reflux for 2 h. The reaction mixture was then cooled to room temperature. $CH_3CH_2I$ (0.5 g, 3.3 mmol) was added, and the reaction mixture was stirred at 62° C. overnight. Then $CH_3CH_2I$ (0.5 g, 3.3 mmol) was added, and the reaction mixture was stirred at 62° C. for four days. The reaction mixture was evaporated under reduced pressure. The residue was dissolved in $CH_2Cl_2$ (100 mL), washed with 1% $NaHCO_3$ solution (50 mL), dried ($Na_2SO_4$) and evaporated to dryness. The residual was purified by silica gel column using PE: EA (5:1 to 1:1) as the eluent to give 0.56 g of desired product 10.

1-Ethyl-pseudouridine 11: A solution of compound 10 (0.56 g) in ammonia saturated methanol (50 mL) was stirred at room temperature overnight. The volatiles were removed under reduced pressure. Then the residue was purified by silica gel column chromatography, eluted with 5-10% methanol in dichloromethane to give 230 mg compound 11 as a light yellow solid with 95.95% HPLC purity. $^1$H-NMR (DMSO-d6, 300 MHz, ppm) δ 11.32 (br, 1H), 7.81 (s, 1H), 5.01 (d, J=3.00 Hz, 1H), 4.98 (t, J=3.00 Hz, 1H), 4.75 (dd, J=1.5, 2.7 Hz, 1H), 4.46 (d, J=3.00 Hz, 1H), 3.88-3.95 (m, 2H), 3.69-3.70 (m, 4H), 3.45-3.48 (m, 1H), 1.17 (t, J=5.10 Hz, 1H).

Scheme 5

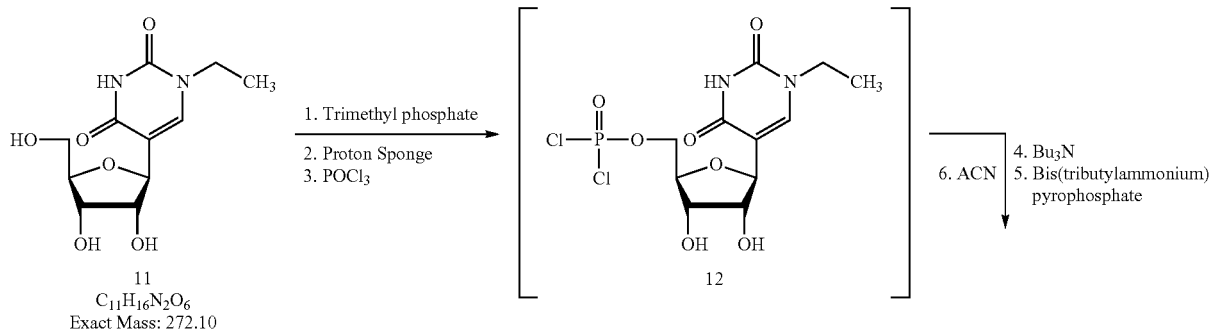

507

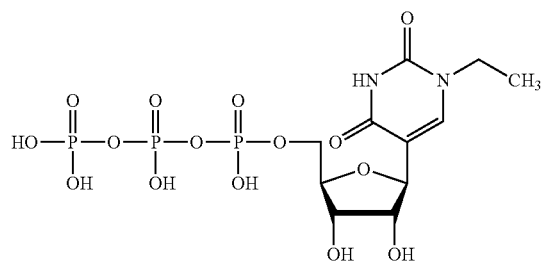

14
C₁₁H₁₉N₂O₁₅P₃
Exact Mass: 512.00

508

-continued

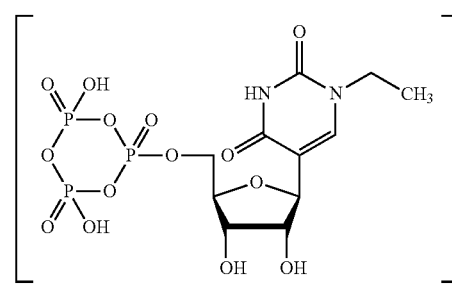

7. 0.2M TEAB

13
C₁₁H₁₇N₂O₁₄P₃
Exact Mass: 493.99

1-Ethyl-pseudo-UTP: A solution of 1-ethyl-pseudouridine 11 (124.0 mg, 0.46 mmol; applied heat to make it soluble) and proton sponge (147.87 mg, 0.69 mmol, 1.5 equiv.) in trimethyl phosphate (0.8 mL) was stirred for 10.0 minutes at 0° C. Phosphorus oxychloride (85.9 µL, 0.92 mmol, 2.0 equiv.) was added dropwise to the solution and it was then kept stirring for 2.0 hours under $N_2$ atmosphere. A mixture of tributylamine (446.5 µL, 1.8 mmol, 4.0 equiv.) and bis(tributylammonium) pyrophosphate (757.2 mg, 1.38 mmol, 3.0 equiv.) in acetonitrile (2.5 mL) was added at once. After ~25 minutes, the reaction was quenched with 25.0 mL of water and the clear solution was stirred vigorously for about an hour at room temperature. The pH of the solution was adjusted to 6.50 by adding about 3.5 mL of 1.0 M TEAB buffer along with vigorous stirring for about 3.0 hours. LCMS analysis indicated the formation of the corresponding triphosphate. The reaction mixture was then lyophilized overnight. The crude reaction mixture was HPLC purified (Shimadzu, Phenomenex C18 preparative column, 250×30.0 mm, 5.0 micron; gradient (1%): 100% A for 3.0 min, then 1% B/min, A=100 mM TEAB buffer, B=ACN; flow rate: 20.0 mL/min; retention time: 17.87-18.68 min). Fractions containing the desired were pooled and lyophilized to yield the 1-Ethyl-pseudo-UTP as a tetrakis(triethylammonium salt) (47.7 mg, 20.2%, based on $α_{271}$=8,500). UVmax=271 nm; MS: m/e 510.70 (M−H).

Example 17

Synthesis of 1-propyl-pseudo-UTP (03601015004)

Scheme 6

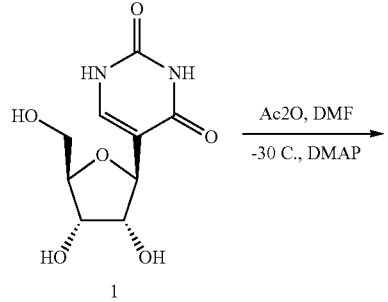

1

Ac2O, DMF
-30 C., DMAP

-continued

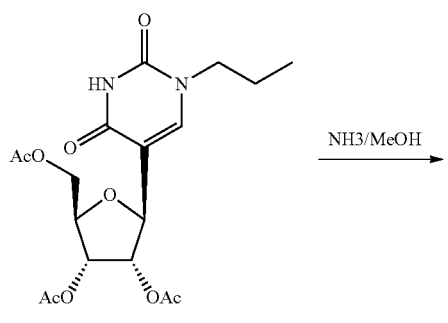

9

I—CH₂CH₂CH₃
DBU

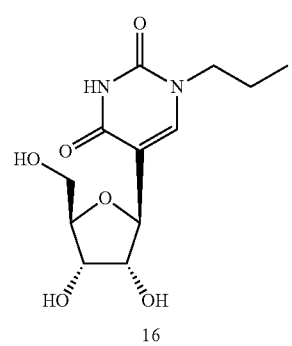

15

NH3/MeOH

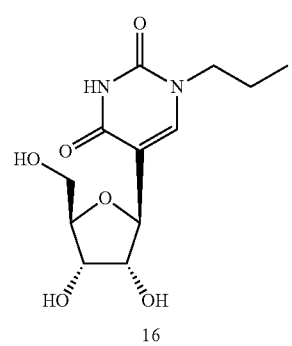

16

Compound 15: To a solution of 2′,3′,5′-tri-O-acetyl pseudouridine 9 (1.0 g, 2.7 mmol) in dry pyridine (20 mL)

was added DBU (0.6 g, 4.1 mmol), and the reaction mixture was stirred at room temperature for 0.5 h. To this mixture, CH$_3$CH$_2$CH$_2$I (0.69 g, 4.0 mmol) was added and stirred at room temperature for 2~3 h. The reaction mixture was dissolved in CH$_2$Cl$_2$ (100 mL), washed with brine (3×50 mL), dried (Na$_2$SO$_4$) and evaporated to dryness. The residual was purified with silica gel column using PE:EA-10:1 to 3:1 as the eluent to afford 0.5 g desired compound 15.

1-Propyl-pseudo-U (16): A solution of compound 15 (0.5 g) in ammonia saturated methanol (50 mL) was stirred at room temperature overnight. The volatiles were removed under reduced pressure. The residue was purified by silica gel column chromatography, eluted with 5-10% methanol in dichloromethane to give 260 mg compound 16 as off-white solid with 96.59% HPLC purity. Analytical data for 1-Propyl-pseudo-U (16): $^1$H-NMR (DMSO-d6, 300 MHz, ppm) δ 11.29 (br, 1H), 7.79 (s, 1H), 4.96 (d, J=1.80 Hz, 1H), 4.83 (t, J=3.90 Hz, 1H), 4.73 (d, J=3.90 Hz, 1H), 4.44 (d, J=3.00 Hz, 1H), 3.85-3.92 (m, 2H), 3.43-3.69 (m, 5H), 1.56 (q, J=5.40 Hz, 2H), 8.38 (t, J=5.40 Hz, 3H).

soluble) and proton sponge (144.66 mg, 0.67 mmol, 1.5 equiv.) in trimethyl phosphate (0.8 mL) was stirred for 10.0 minutes at 0° C. Phosphorus oxychloride (84.0 µL, 0.90 mmol, 2.0 equiv.) was added dropwise to the solution and it was then kept stirring for 2.0 hours under N$_2$ atmosphere. A mixture of tributylamine (436.75 µL, 1.8 mmol, 4.0 equiv.) and bis(tributylammonium) pyrophosphate (740.7 mg, 1.35 mmol, 3.0 equiv.) in acetonitrile (2.5 mL) was added at once. After ~25 minutes, the reaction was quenched with 25.0 mL of water and the clear solution was stirred vigorously for about an hour at room temperature. The pH of the solution was adjusted to 6.50 by adding about 3.5 mL of 1.0 M TEAB buffer along with vigorous stirring for about 3.0 hours. LCMS analysis indicated the formation of the corresponding triphosphate. The reaction mixture was then lyophilized overnight. The crude reaction mixture was HPLC purified (Shimadzu, Phenomenex C18 preparative column, 250×30.0 mm, 5.0 micron; gradient (1%): 100% A for 3.0 min, then 1% B/min, A=100 mM TEAB buffer, B=ACN; flow rate: 20.0 mL/min; retention time: 18.66-19.45 min). Fractions containing the desired were pooled and lyophilized to yield the 1-Propyl-pseudo-UTP as a tetrakis(triethylammonium

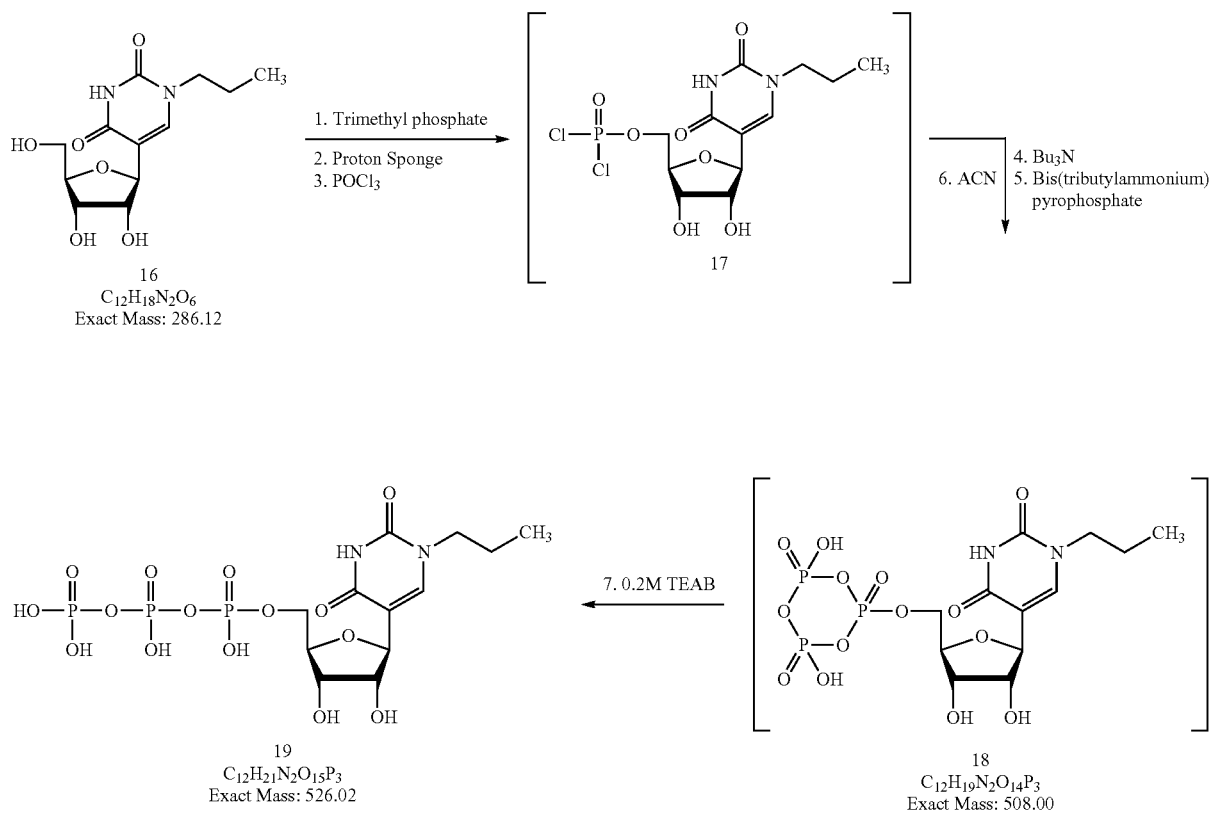

1-Propyl-pseudo-UTP: A solution of 1-propyl-pseudouridine 16 (130.0 mg, 0.45 mmol; applied heat to make it salt) (63.33 mg, 26.66%, based on ε$_{271}$=8,500). UVmax=271 nm; MS: m/e 524.70 (M−H).

Example 18

Synthesis of 1-(2,2,2-trifluoroethyl)pseudo-UTP (03601015005)

Scheme 8

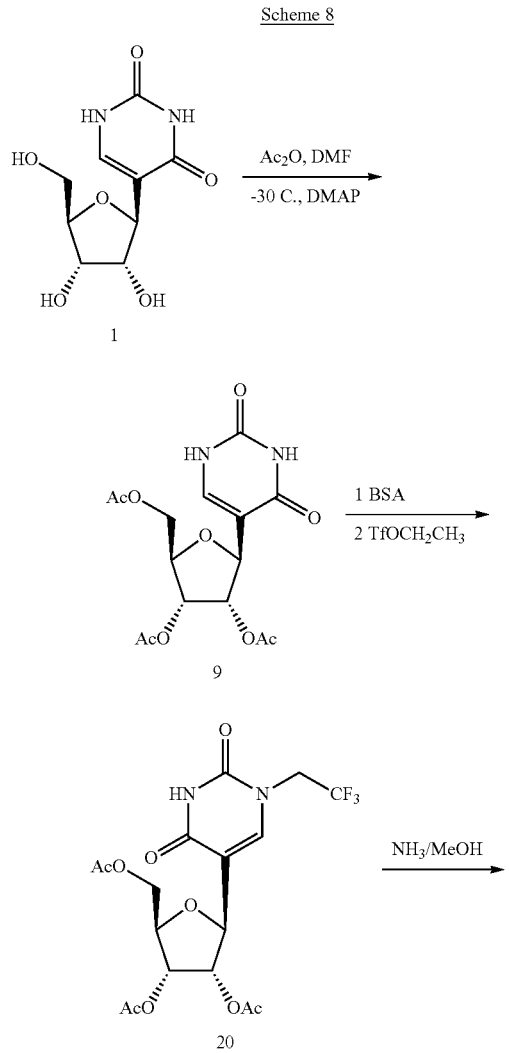

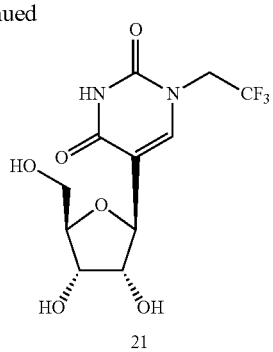

Synthesis of Compound 20: To a solution of 2′,3′,5′-tri-O-acetyl pseudouridine 9 (0.8 g, 2.2 mmol) in dry $CH_3CN$ (20 mL) was added N,O-bis(trimethylsilyl)acetamide (BSA) (3.0 mL), and the reaction mixture was reflux for 2 h. The reaction mixture was then cooled to room temperature. To this mixture, $CF_3CH_2OTf$ (0.75 g, 3.3 mmol) was added, and the reaction mixture was stirred at 60° C. overnight. More $CF_3CH_2OTf$ (0.75 g, 3.3 mmol) was then added, and the reaction mixture was stirred at 60° C. overnight. The reaction mixture was concentrated under reduced pressure. The residue was dissolved in $CH_2Cl_2$ (100 mL), washed with 1% $NaHCO_3$ solution (3×50 mL), dried ($Na_2SO_4$) and evaporated to dryness. The residual was purified by silica gel column using PE: EA (5:1 to 1:1) as the eluent to give 0.7 g (72%) of product 20.

1-(2, 2, 2-Trifluoroethyl)pseudo-U (21): A solution of compound 20 (0.7 g) in ammonia saturated methanol (50 mL) was stirred at room temperature overnight. The volatiles were removed under reduced pressure. The residue was purified by silica gel column chromatography, eluted with 5-10% methanol in dichloromethane to give 260 mg compound 21 as pale yellow foam with 98.66% HPLC purity. $^1$H-NMR (DMSO-d6, 300 MHz, ppm) δ 11.62 (br, 1H), 7.79 (s, 1H), 5.01 (d, J=3.60 Hz, 1H), 4.80 (d, J=4.20 Hz, 1H), 4.75 (t, J=3.70 Hz, 1H), 4.61 (q, J=6.60 Hz, 1H), 4.48 (d, J=2.70 Hz, 1H), 3.83-3.93 (m, 2H), 3.71 (d, J=2.40 Hz, 1H), 3.61-3.65 (m, 1H), 3.43-3.49 (m, 1H). The structure was also verified by HMBC NMR.

Scheme 9

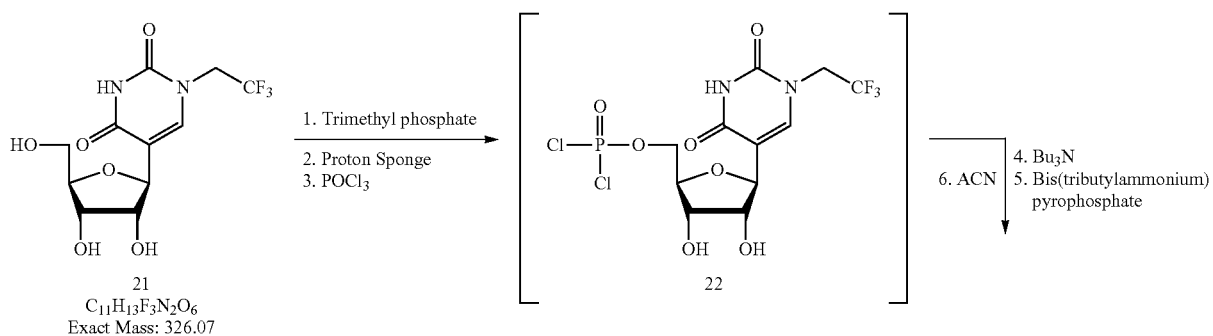

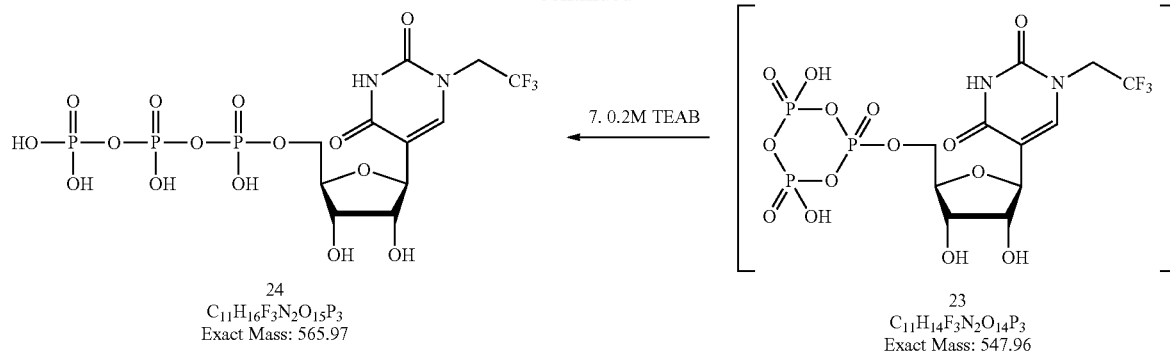

1-(2,2,2-Trifluoroethyl)pseudo-UTP: A solution of 1-(2,2,2-trifluoroethyl)pseudouridine 21 (135.6 mg, 0.42 mmol; applied heat to make it soluble) and proton sponge (135.01 mg, 0.63 mmol, 1.5 equiv.) in trimethyl phosphate (0.8 mL) was stirred for 10.0 minutes at 0° C. Phosphorus oxychloride (78.4.0 µL, 0.84 mmol, 2.0 equiv.) was added dropwise to the solution and it was then kept stirring for 2.0 hours under $N_2$ atmosphere. A mixture of tributylamine (407.63 µL, 1.68 mmol, 4.0 equiv.) and bis(tributylammonium) pyrophosphate (691.32 mg, 1.26 mmol, 3.0 equiv.) in acetonitrile (2.5 mL) was added at once. After ~25 minutes, the reaction was quenched with 25.0 mL of water, and the clear solution was stirred vigorously for about an hour at room temperature. The pH of the solution was adjusted to 6.53 by adding about 3.6 mL of 1.0 M TEAB buffer along with vigorous stirring for about 3.0 hours. LCMS analysis indicated the formation of the corresponding triphosphate. The reaction mixture was then lyophilized overnight. The crude reaction mixture was HPLC purified (Shimadzu, Phenomenex C18 preparative column, 250×30.0 mm, 5.0 micron; gradient (1%): 100% A for 3.0 min, then 1% B/min, A=100 mM TEAB buffer, B=ACN; flow rate: 20.0 mL/min; retention time: 19.33-20.74 min). Fractions containing the desired were pooled and lyophilized to yield the 1-(2,2,2-Trifluoroethyl)pseudo-UTP as a tetrakis(triethylammonium salt) (93.88 mg, 39.52%, based on $\varepsilon_{271}$=9,000). UVmax=262 nm; MS: m/e 564.65 (M−H).

Example 19

Synthesis of 2-thio-pseudo-UTP (00901015006)

Scheme 10

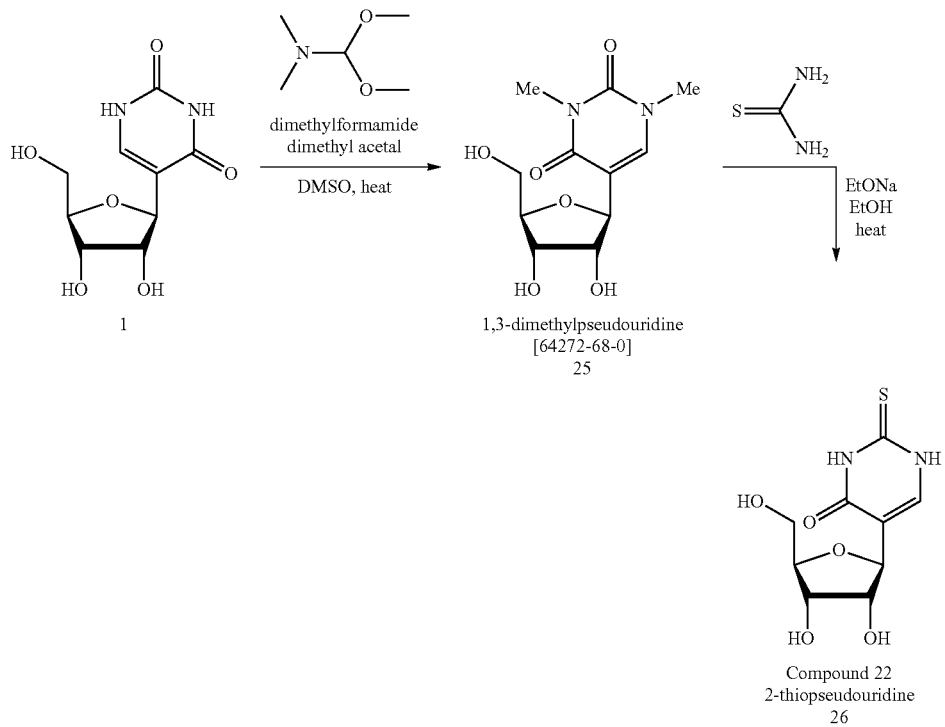

Synthesis of N1,N3-Dimethylpseudouridine (25): A suspension of pseudouridine (1) (1.0 g, 4.1 mmol) in N,N-dimethylformamide dimethyl acetal (10 mL) was refluxed at 110° C. for 1 h until a clear solution was obtained. TLC (DCM-MeOH=9:1) indicated the reaction was almost completed. The solution was concentrated in vacuo to give syrup which was triturated with a small amount of methanol to give 640 mg solid product. The filtrate was concentrated and then further purified by flash chromatography on a silica gel column using DCM-MeOH 30:1 to 10:1 gradient eluent to give additional 200 mg product resulting in the total yield of 75.4%.

2-Thio-pseudo-U (26): A mixture of compound 25 (680 mg, 2.5 mmol) and thiourea (950 mg, 12.5 mmol) in 1 M ethanolic sodium ethoxide (25 mL) was refluxed with stirring for 2 h. TLC (DCM-MeOH=9:1) indicated completion of the reaction. After cooling, 3M hydrochloric acid was added to adjust the pH to neutral, and the mercapto compound smell was noticed. It was then adjusted to week basic with ammonium hydroxide. It was purified by flash chromatography on a silica gel column using DCM-MeOH 20:1 to 10:1 to 5:1 gradient eluent giving 310 mg product in 47.7% yield. This material contained 69% beta-anomer and 28% alpha-anomer. It was then further purified by preparative TLC to give 230 mg pure beta-anomer product 26. The second preparative TLC purification generated 183 mg final product with 94.23% HPLC purity. It was characterized by NMR and MS spectral analysis.

2-Thio-pseudo-UTP: A solution of 2-Thiopseudouridine 26 (100.5 mg, 0.39 mmol; applied heat to make it soluble) and proton sponge (125.37 mg, 0.59 mmol, 1.5 equiv.) in trimethyl phosphate (0.8 mL) was stirred for 10.0 minutes at 0° C. Phosphorus oxychloride (72.8 µL, 0.78 mmol, 2.0 equiv.) was added dropwise to the solution and it was then kept stirring for 2.0 hours under $N_2$ atmosphere. A mixture of tributylamine (378.52 µL, 1.56 mmol, 4.0 equiv.) and bis(tributylammonium) pyrophosphate (641.94 mg, 1.17 mmol, 3.0 equiv.) in acetonitrile (2.5 mL) was added at once. After ~25 minutes, the reaction was quenched with 25.0 mL of water, and the clear solution was stirred vigorously for about an hour at room temperature. The pH of the solution was adjusted to 6.75 by adding about 3.5 mL of 1.0 M TEAB buffer along with vigorous stirring for about 3.0 hours. LCMS analysis indicated the formation of the corresponding triphosphate. The reaction mixture was then lyophilized overnight. The crude reaction mixture was HPLC purified (Shimadzu, Phenomenex C18 preparative column, 250×30.0 mm, 5.0 micron; gradient (1%): 100% A for 3.0 min, then 1% B/min, A=100 mM TEAB buffer, B=ACN; flow rate: 20.0 mL/min; retention time: 17.06-18.18 min). Fractions containing the desired were pooled and lyophilized to yield the 2-Thio-pseudo-UTP as a tetrakis(triethylammonium) salt) (67.13 mg, 34.36%, based on $\alpha_{269}$=10,000). UVmax=269 nm; MS: m/e 498.75 (M−H).

Scheme 11

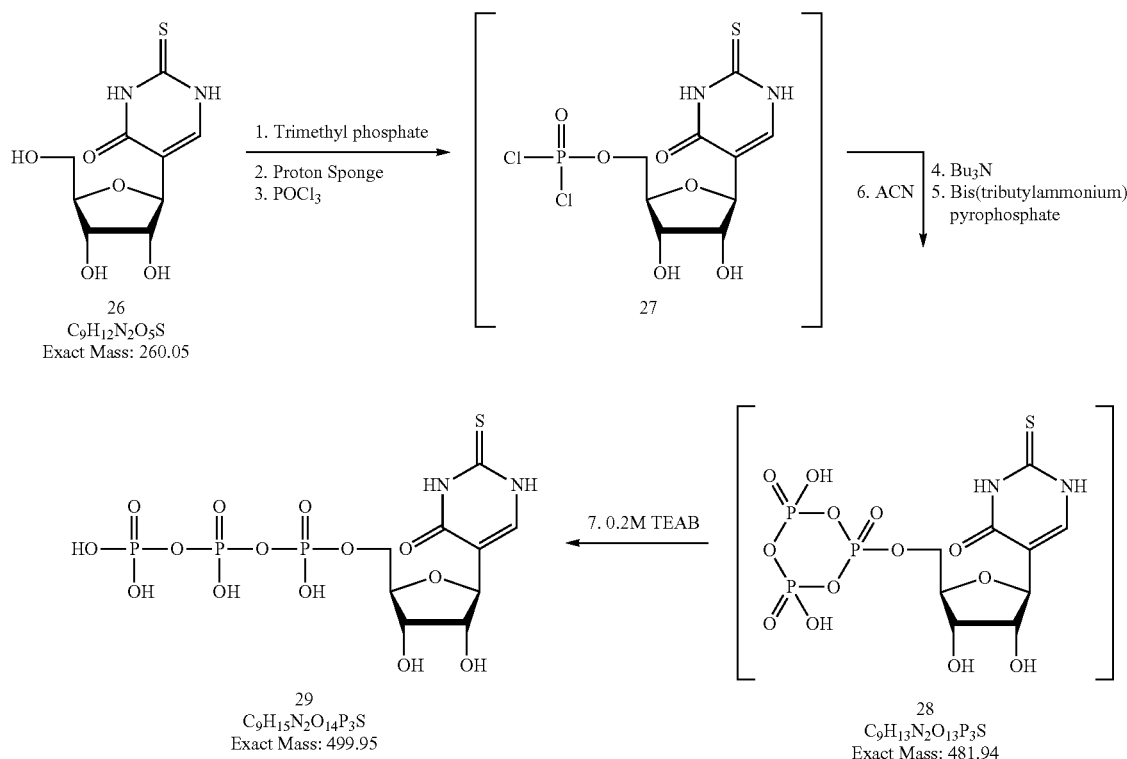

Example 20

Synthesis of 5-trifluoromethyl-UTP (00901013002)

Scheme 12

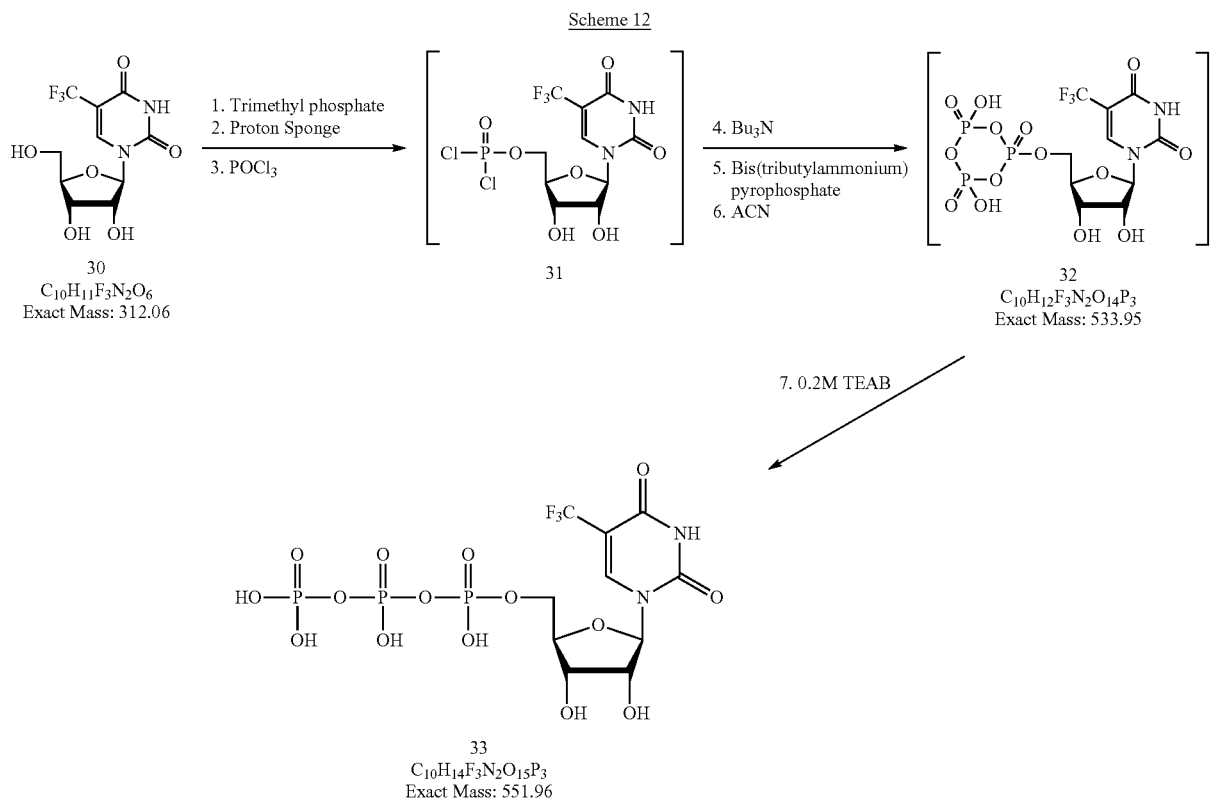

5-Trifluoromethyl-UTP: A solution of 5-Trifluoromethyluridine 30 (101 mg, 0.32 mmol; applied heat to make it soluble) and proton sponge (102.86 mg, 0.48 mmol, 1.5 equiv.) in trimethyl phosphate (0.8 mL) was stirred for 10.0 minutes at 0° C. Phosphorus oxychloride (59.73 µL, 0.64 mmol, 2.0 equiv.) was added dropwise to the solution and it was then kept stirring for 2.0 hours under $N_2$ atmosphere. A mixture of tributylamine (310.85 µL, 1.56 mmol, 4.0 equiv.) and bis(tributylammonium) pyrophosphate (526.72 mg, 0.96 mmol, 3.0 equiv.) in acetonitrile (2.5 mL) was added at once. After ~25 minutes, the reaction was quenched with 0.2 M TEAB buffer (13.7 mL) and the clear solution was stirred at room temperature for an hour. LCMS analysis indicated the formation of the corresponding triphosphate. The reaction mixture was then lyophilized overnight. The crude reaction mixture was HPLC purified (Shimadzu, Phenomenex C18 preparative column, 250×30.0 mm, 5.0 micron; gradient (1%): 100% A for 3.0 min, then 1% B/min, A=100 mM TEAB buffer, B=ACN; flow rate: 20.0 mL/min; retention time: 26.69-27.87 min). Fractions containing the desired were pooled and lyophilized to yield the 5-Trifluoromethyl-UTP as a tetrakis(triethylammonium salt) (34.11 mg, 19.30%, based on $\alpha_{260}$=10,000). UVmax=258 nm; MS: m/e 550.65 (M–H).

Example 21

Synthesis of 5-trifluoromethyl-CTP (00901014003)

Scheme 13

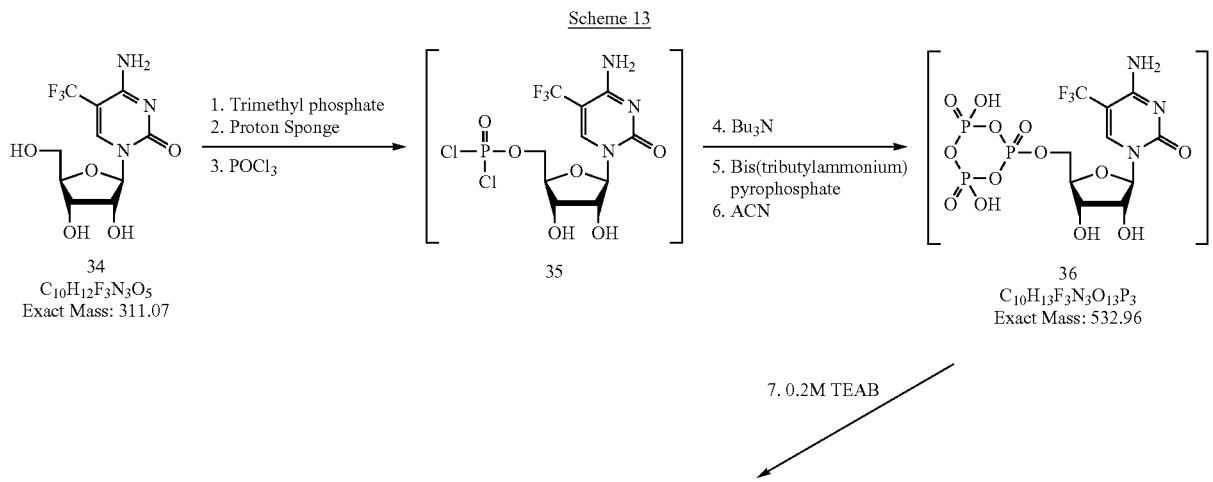

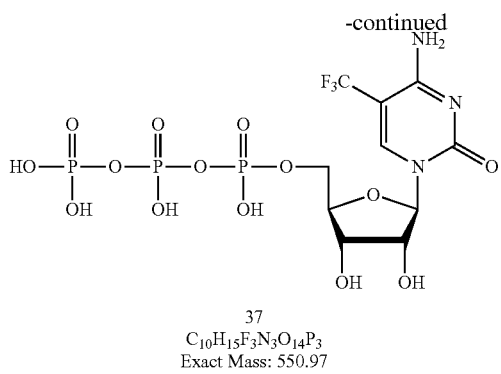

37
C₁₀H₁₅F₃N₃O₁₄P₃
Exact Mass: 550.97

5-Trifluoromethyl-CTP: A solution of 5-Trifluoromethyl-cytidine 34 (109 mg, 0.35 mmol; applied heat to make it soluble) and proton sponge (112.5 mg, 0.52 mmol, 1.5 equiv.) in trimethyl phosphate (0.8 mL) was stirred for 10.0 minutes at 0° C. Phosphorus oxychloride (65.34 µL, 0.70 mmol, 2.0 equiv.) was added dropwise to the solution and it was then kept stirring for 2.0 hours under N₂ atmosphere. A mixture of tributylamine (340.00 µL, 1.40 mmol, 4.0 equiv.) and bis(tributylammonium) pyrophosphate (576.10 mg, 1.05 mmol, 3.0 equiv.) in acetonitrile (2.5 mL) was added at once. After ~25 minutes, the reaction was quenched with 0.2 M TEAB buffer (16.5 mL) and the clear solution was stirred at room temperature for an hour. LCMS analysis indicated the formation of the corresponding triphosphate. The reaction mixture was then lyophilized overnight. The crude reaction mixture was HPLC purified (Shimadzu, Phenomenex C18 preparative column, 250×30.0 mm, 5.0 micron; gradient (1%): 100% A for 3.0 min, then 1% B/min, A=100 mM TEAB buffer, B=ACN; flow rate: 20.0 mL/min; retention time: 17.77-18.63 min). Fractions containing the desired were pooled and lyophilized to yield the 5-Trifluoromethyl-CTP as a tetrakis(triethylammonium salt) (50.75 mg, 26.28%, based on α₂₆₉=9,000). UVmax=269 nm; MS: m/e 549.65 (M−H).

Example 22

Synthesis of 3-methyl-pseudo-UTP (00901015187)

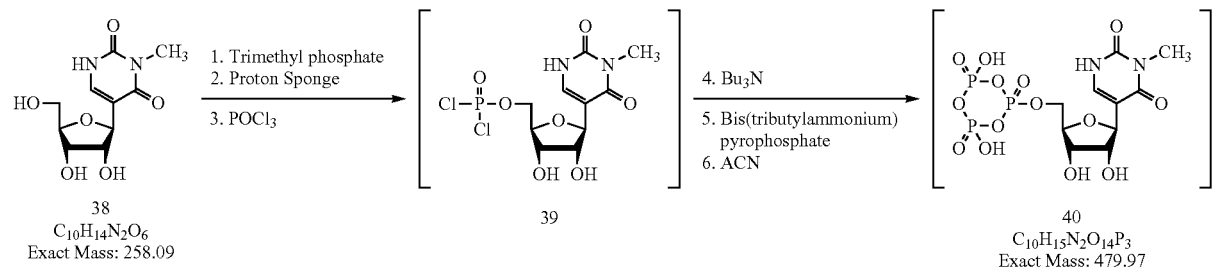

Scheme 14

38
C₁₀H₁₄N₂O₆
Exact Mass: 258.09

40
C₁₀H₁₅N₂O₁₄P₃
Exact Mass: 479.97

7. 0.2M TEAB

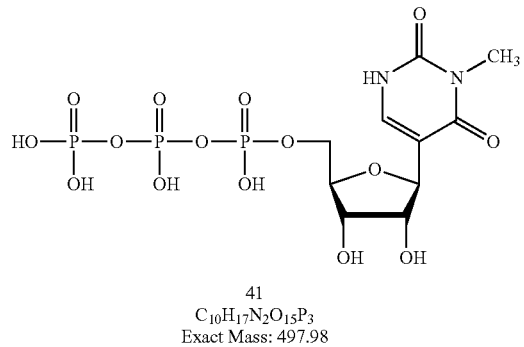

41
C₁₀H₁₇N₂O₁₅P₃
Exact Mass: 497.98

3-Methyl-pseudo-UTP: A solution of 3-Methylpseudouridine 38 (104 mg, 0.4 mmol; applied heat to make it soluble) and proton sponge (128.58 mg, 0.6 mmol, 1.5 equiv.) in trimethyl phosphate (0.8 mL) was stirred for 10.0 minutes at 0° C. Phosphorus oxychloride (74.70 µL, 0.80 mmol, 2.0 equiv.) was added dropwise to the solution, and it was then kept stirring for 2.0 hours under $N_2$ atmosphere. A mixture of tributylamine (388.56 µL, 1.60 mmol, 4.0 equiv.) and bis(tributylammonium) pyrophosphate (658.40 mg, 1.05 mmol, 3.0 equiv.) in acetonitrile (2.5 mL) was added at once. After ~25 minutes, the reaction was quenched with 0.2 M TEAB buffer (17.0 mL) and the clear solution was stirred at room temperature for an hour. LCMS analysis indicated the formation of the corresponding triphosphate. The reaction mixture was then lyophilized overnight. The crude reaction mixture was HPLC purified (Shimadzu, Phenomenex C18 preparative column, 250×30.0 mm, 5.0 micron; gradient (1%): 100% A for 3.0 min, then 1% B/min, A=100 mM TEAB buffer, B=ACN; flow rate: 20.0 mL/min; retention time: 15.61-17.21 min). Fractions containing the desired were pooled and lyophilized to yield the 3-Methyl-pseudo-UTP as a tetrakis-(triethylammonium salt) (52.38 mg, 26.25%, based on $\alpha_{264}$=8,000). UVmax=264 nm; MS: m/e 496.75 (M−H).

Example 23

Synthesis of 5-methyl-2-thio-UTP (00901013003)

5-Methyl-2-thio-UTP: A solution of 5-Methyl-2-thiouridine 42 (55 mg, 0.2 mmol; applied heat to make it soluble) and proton sponge (64.30 mg, 0.3 mmol, 1.5 equiv.) in trimethyl phosphate (0.8 mL) was stirred for 10.0 minutes at 0° C. Phosphorus oxychloride (37.35 µL, 0.40 mmol, 2.0 equiv.) was added dropwise to the solution and it was then kept stirring for 2.0 hours under $N_2$ atmosphere. A mixture of tributylamine (194.28 µL, 0.8 mmol, 4.0 equiv.), and bis(tributylammonium) pyrophosphate (329.20 mg, 0.6 mmol, 3.0 equiv.) in acetonitrile (2.5 mL) was added at once. After ~25 minutes, the reaction was quenched with 0.2 M TEAB buffer (8.5 mL) and the clear solution was stirred at room temperature for an hour. LCMS analysis indicated the formation of the corresponding triphosphate. The reaction mixture was then lyophilized overnight. The crude reaction mixture was HPLC purified (Shimadzu, Phenomenex C18 preparative column, 250×30.0 mm, 5.0 micron; gradient (1%): 100% A for 3.0 min, then 1% B/min, A=100 mM TEAB buffer, B=ACN; flow rate: 20.0 mL/min; retention time: 18.21-18.92 min). Fractions containing the desired were pooled and lyophilized to yield the 5-Methyl-2-thio-UTP as a tetrakis(triethylammonium salt) (62.44 mg, 60.00%, based on $\alpha_{276}$=13,120). UVmax=276 nm; MS: m/e 512.70 (M−H).

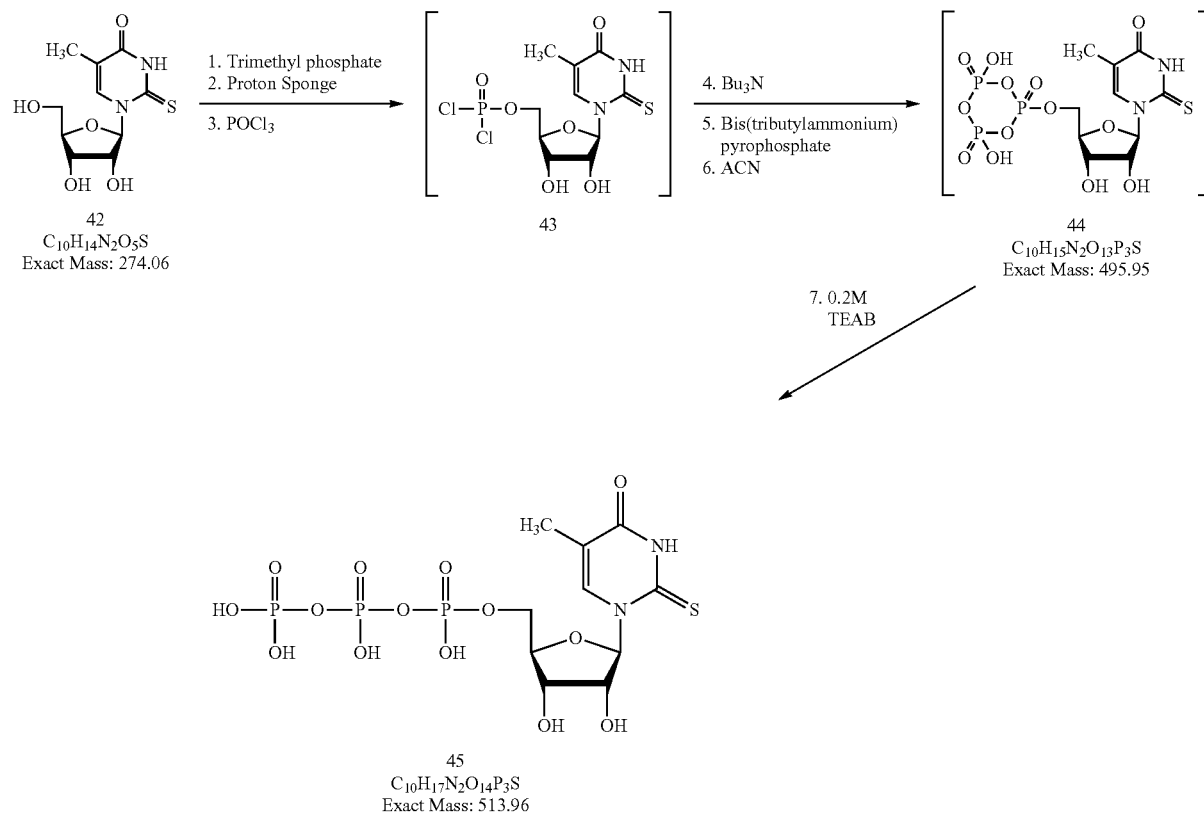

Example 24

Synthesis of N4-methyl-CTP (00901014004)

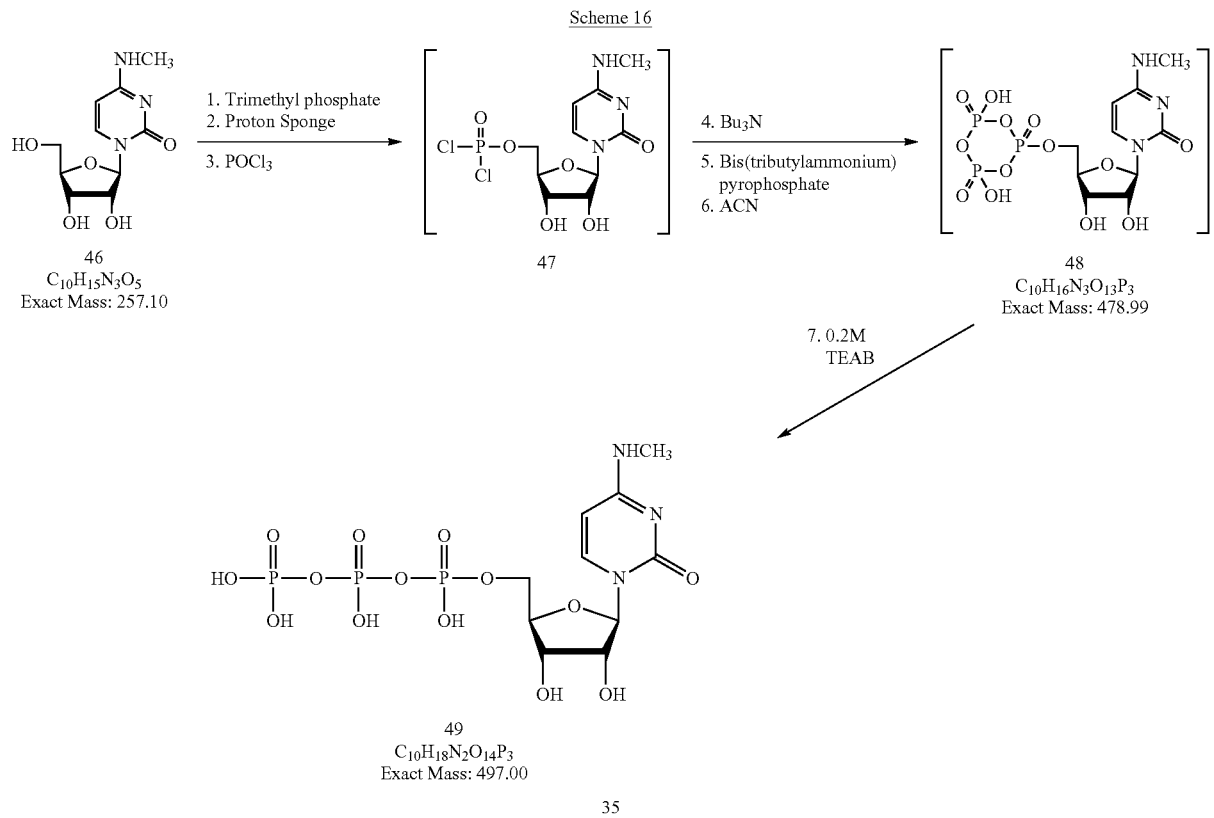

N4-Methyl-CTP: A solution of N4-Methyl-cytidine 46 (100.7 mg, 0.39 mmol; applied heat to make it soluble) and proton sponge (126.44 mg, 0.59 mmol, 1.5 equiv.) in trimethyl phosphate (0.8 mL) was stirred for 10.0 minutes at 0° C. Phosphorus oxychloride (72.8 µL, 0.78 mmol, 2.0 equiv.) was added dropwise to the solution, and it was then kept stirring for 2.0 hours under $N_2$ atmosphere. A mixture of tributylamine (378.85 µL, 1.56 mmol, 4.0 equiv.) and bis(tributylammonium) pyrophosphate (642.0 mg, 1.17 mmol, 3.0 equiv.) in acetonitrile (2.5 mL) was added at once. After ~25 minutes, the reaction was quenched with 0.2 M TEAB buffer (17.0 mL) and the clear solution was stirred at room temperature for an hour. LCMS analysis indicated the formation of the corresponding triphosphate. The reaction mixture was then lyophilized overnight. The crude reaction mixture was HPLC purified (Shimadzu, Phenomenex C18 preparative column, 250×30.0 mm, 5.0 micron; gradient (1%): 100% A for 3.0 min, then 1% B/min, A=100 mM TEAB buffer, B=ACN; flow rate: 20.0 mL/min; retention time: 17.05-17.80 min). Fractions containing the desired were pooled and lyophilized to yield the N4-Methyl-CTP as a tetrakis(triethylammonium salt) (35.05 mg, 17.94%, based on $\alpha_{270}$=11,000). UVmax=270 nm; MS: m/e 495.70 (M−H).

Example 25

Synthesis of 5-hydroxymethyl-CTP (00901014005)

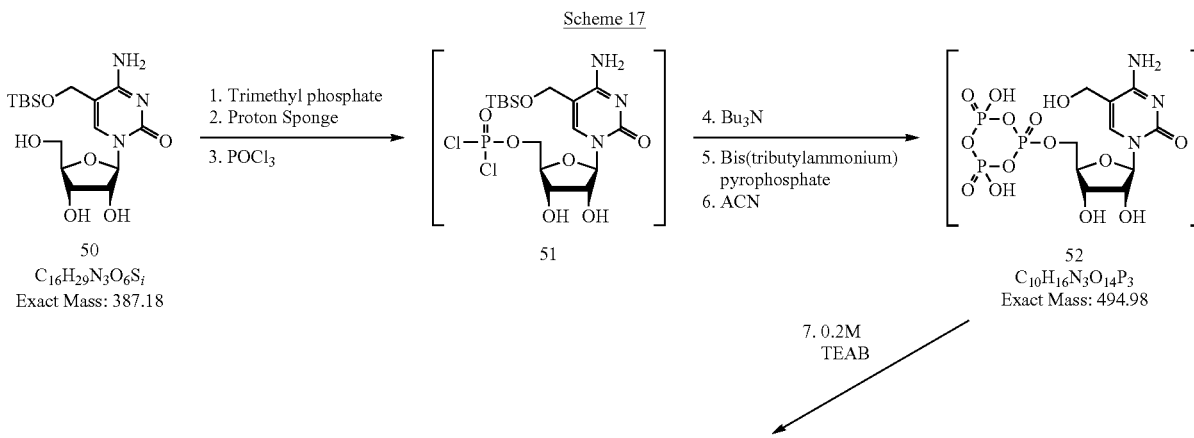

-continued

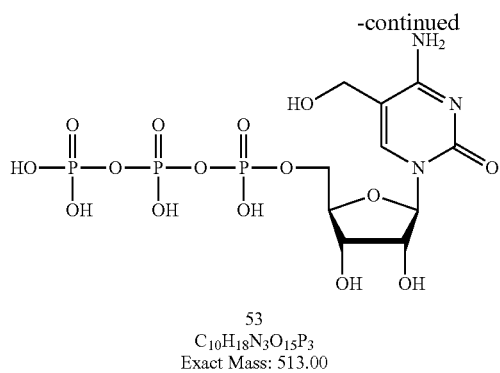

53
C₁₀H₁₈N₃O₁₅P₃
Exact Mass: 513.00

5-Hydroxymethyl-CTP: A solution of 5-OTBS-CH$_2$-cytidine 50 (126.0 mg, 0.33 mmol; applied heat to make it soluble) and proton sponge (107.2 mg, 0.5 mmol, 1.5 equiv.) in trimethyl phosphate (0.8 mL) was stirred for 10.0 minutes at 0° C. Phosphorus oxychloride (61.6 μL, 0.66 mmol, 2.0 equiv.) was added dropwise to the solution, and it was then kept stirring for 2.0 hours under N$_2$ atmosphere. The TBS group had been removed during POCl$_3$ reaction and corresponding monophosphate (without TBS) was detected by LCMS. A mixture of tributylamine (320.28 μL, 1.32 mmol, 4.0 equiv.) and bis(tributylammonium) pyrophosphate (543.2 mg, 0.99 mmol, 3.0 equiv.) in acetonitrile (2.3 mL) was added at once. After ~25 minutes, the reaction was quenched with 0.2 M TEAB buffer (13.0 mL) and the clear solution was stirred at room temperature for an hour. LCMS analysis indicated the formation of corresponding triphosphate (without TBS). The reaction mixture was then lyophilized overnight. The crude reaction mixture was HPLC purified (Shimadzu, Phenomenex C18 preparative column, 250×30.0 mm, 5.0 micron; gradient (1%): 100% A for 3.0 min, then 1% B/min, A=100 mM TEAB buffer, B=ACN; flow rate: 20.0 mL/min; retention time: 16.48-17.36 min). Fractions containing the desired were pooled and lyophilized to yield the 5-Hydroxymethyl-CTP as a tetrakis(triethylammonium salt) (16.72 mg, 9.75% for two steps, based on $\alpha_{276}$=9,000). UVmax=276 nm; MS: m/e 511.70 (M−H).

Example 26

Synthesis of 3-methyl-CTP (00901014006)

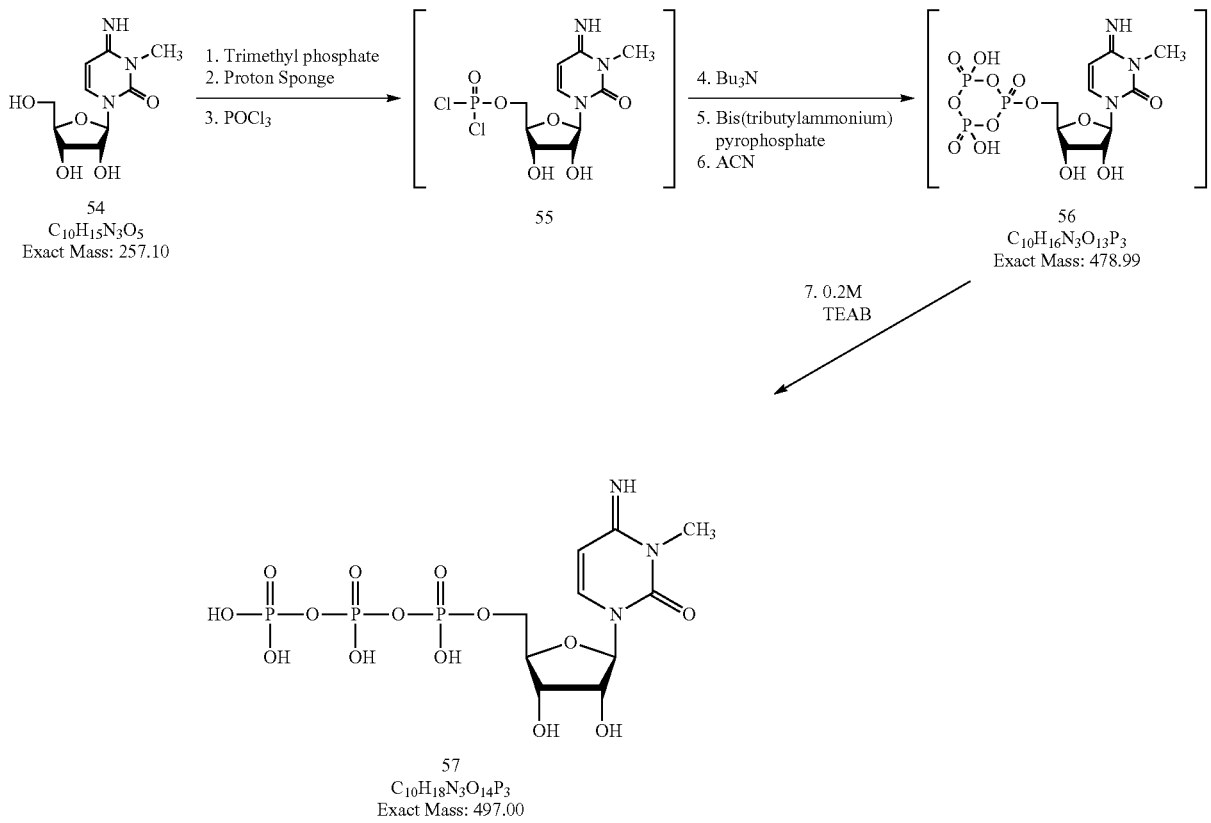

3-Methyl-CTP: A solution of 3-Methyl-cytidine 54 (93.0 mg, 0.36 mmol; applied heat to make it soluble) and proton sponge (115.7 mg, 0.54 mmol, 1.5 equiv.) in trimethyl phosphate (0.8 mL) was stirred for 10.0 minutes at 0° C. Phosphorus oxychloride (67.2 µL, 0.72 mmol, 2.0 equiv.) was added dropwise to the solution, and it was then kept stirring for 2.0 hours under $N_2$ atmosphere. A mixture of tributylamine (349.4 µL, 1.44 mmol, 4.0 equiv.) and bis(tributylammonium) pyrophosphate (592.6 mg, 1.08 mmol, 3.0 equiv.) in acetonitrile (2.5 mL) was added at once. After ~25 minutes, the reaction was quenched with 0.2 M TEAB buffer (17.0 mL), and the clear solution was stirred at room temperature for an hour. LCMS analysis indicated the formation of the corresponding triphosphate. The reaction mixture was then lyophilized overnight. The crude reaction mixture was HPLC purified (Shimadzu, Phenomenex C18 preparative column, 250×30.0 mm, 5.0 micron; gradient (1%): 100% A for 3.0 min, then 1% B/min, A=100 mM TEAB buffer, B=ACN; flow rate: 20.0 mL/min; retention time: 16.15-16.67 min). Fractions containing the desired were pooled and lyophilized to yield the 3-Methyl-CTP as a tetrakis(triethylammonium salt) (20.4 mg, 11.4%, based on $\alpha_{277}$=9,000). UVmax=277 nm; MS: m/e 495.75 (M−H).

Example 27

Synthesis of UTP-oxyacetic acid Me ester (00901013004))

UTP-5-oxyacetic acid Me ester: A solution of Uridine-5-oxyacetic acid Me ester 58 (100.3 mg, 0.3 mmol; applied heat to make it soluble) and proton sponge (96.44 mg, 0.45 mmol, 1.5 equiv.) in trimethyl phosphate (0.8 mL) was stirred for 10.0 minutes at 0° C. Phosphorus oxychloride (56.0 µL, 0.6 mmol, 2.0 equiv.) was added dropwise to the solution and it was then kept stirring for 2.0 hours under $N_2$ atmosphere. A mixture of tributylamine (291.2 µL, 1.2 mmol, 4.0 equiv.) and bis(tributylammonium) pyrophosphate (493.8 mg, 0.9 mmol, 3.0 equiv.) in acetonitrile (2.5 mL) was added at once. After ~25 minutes, the reaction was quenched with 0.2 M TEAB buffer (14.2 mL) and the clear solution was stirred at room temperature for an hour. LCMS analysis indicated the formation of the corresponding triphosphate. The reaction mixture was then lyophilized overnight. The crude reaction mixture was HPLC purified (Shimadzu, Phenomenex C18 preparative column, 250×30.0 mm, 5.0 micron; gradient (1%): 100% A for 3.0 min, then 1% B/min, A=100 mM TEAB buffer, B=ACN; flow rate: 20.0 mL/min; retention time: 18.52-19.06 min). Fractions containing the desired were pooled and lyophilized to yield the UTP-5-oxyacetic acid Me ester as a tetrakis(triethylammonium salt) (20.04 mg, 11.67%, based on $\alpha_{275}$=10,000). UVmax=275 nm; MS: m/e 570.65 (M−H).

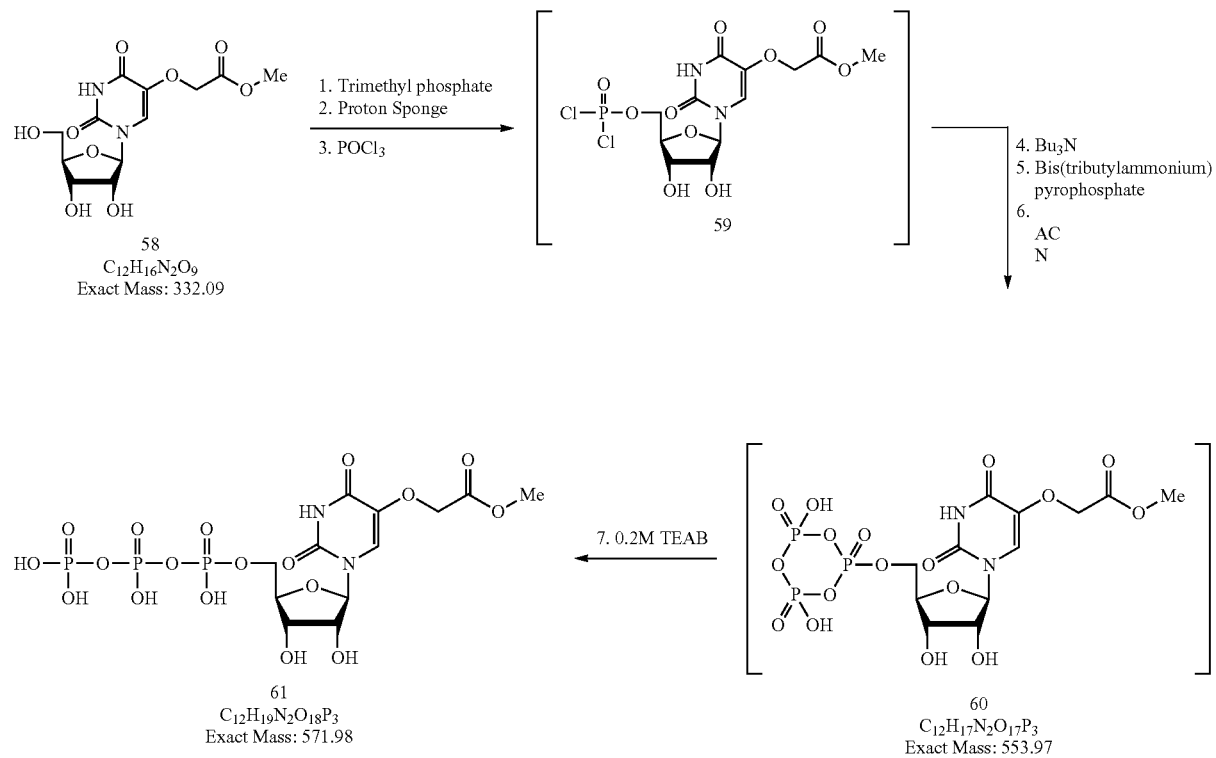

Scheme 19

Example 28

Synthesis of 5-methoxycarbonylmethyl-UTP (00901013005)

Scheme 20

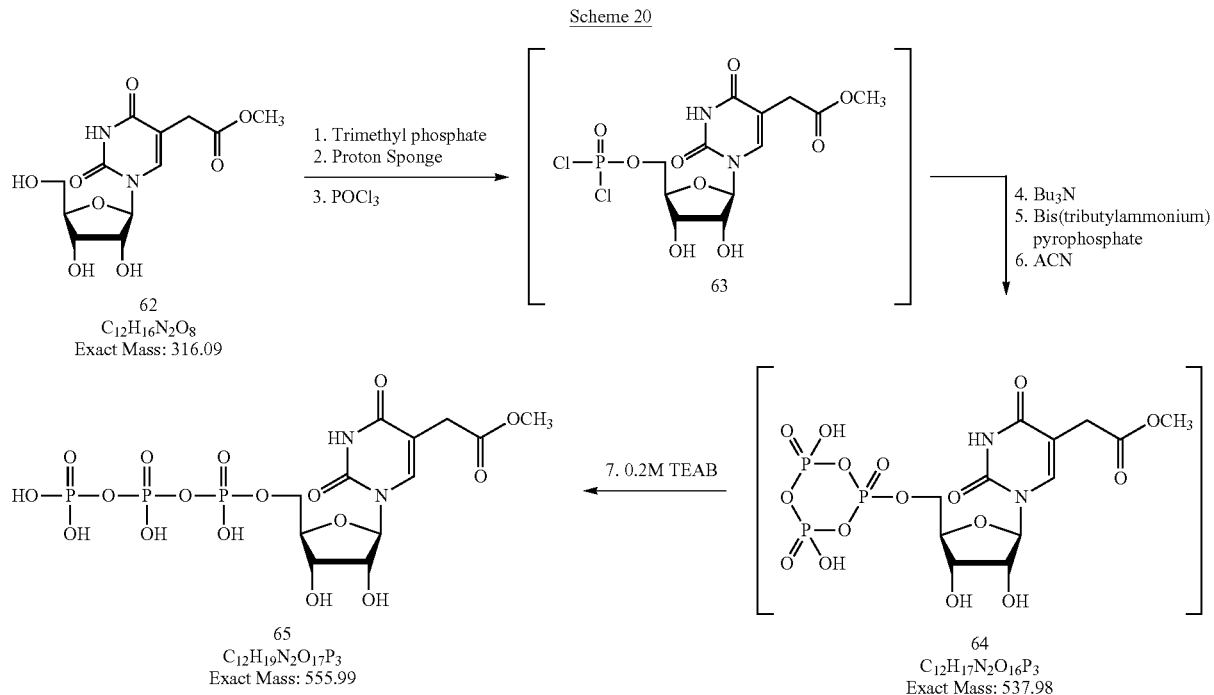

5-Methoxycarbonylmethyl-UTP: A solution of 5-Methoxycarbonylmethyl-uridine 62 (101.0 mg, 0.32 mmol; applied heat to make it soluble) and proton sponge (102.86 mg, 0.48 mmol, 1.5 equiv.) in trimethyl phosphate (0.8 mL) was stirred for 10.0 minutes at 0° C. Phosphorus oxychloride (59.73 µL, 0.64 mmol, 2.0 equiv.) was added dropwise to the solution and it was then kept stirring for 2.0 hours under $N_2$ atmosphere. A mixture of tributylamine (310.58 µL, 1.28 mmol, 4.0 equiv.) and bis(tributylammonium) pyrophosphate (526.72 mg, 0.9 mmol, 3.0 equiv.) in acetonitrile (2.5 mL) was added at once. After ~25 minutes, the reaction was quenched with 0.2 M TEAB buffer (15.1 mL) and the clear solution was stirred at room temperature for an hour. LCMS analysis indicated the formation of the corresponding triphosphate. The reaction mixture was then lyophilized overnight. The crude reaction mixture was HPLC purified (Shimadzu, Phenomenex C18 preparative column, 250×30.0 mm, 5.0 micron; gradient (1%): 100% A for 3.0 min, then 1% B/min, A=100 mM TEAB buffer, B=ACN; flow rate: 20.0 mL/min; retention time: 17.15-18.38 min). Fractions containing the desired were pooled and lyophilized to yield the 5-Methoxycarbonylmethyl-UTP as a tetrakis(triethylammonium salt) (49.88 mg, 28.12%, based on $\alpha_{265}$=11,000). UVmax=265 nm; MS: m/e 554.70 (M–H).

Example 29

Synthesis of 5-methylaminomethyl-UTP (00901013006)

Scheme 21

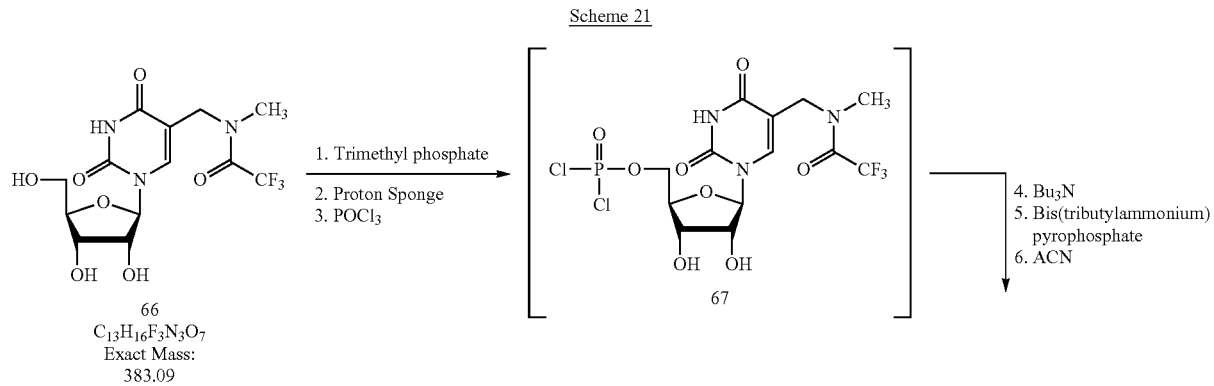

531

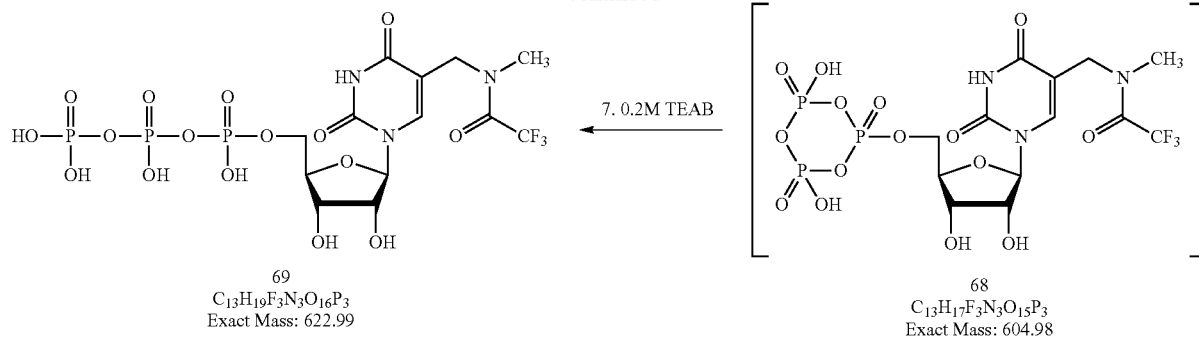

Scheme 22

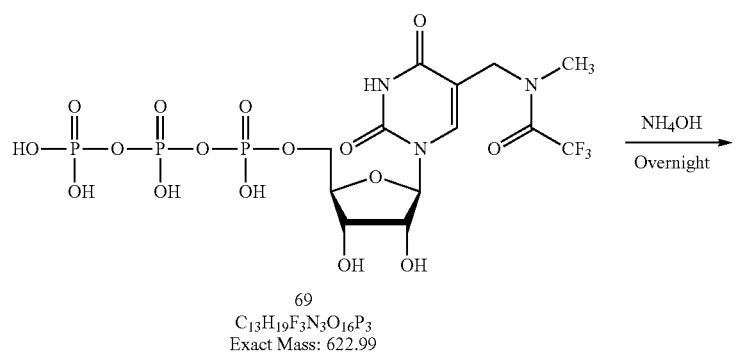

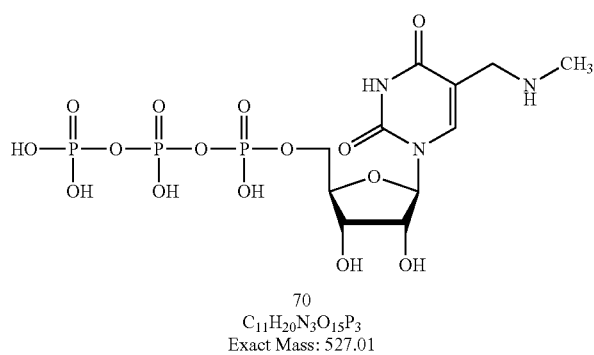

5-Methylaminomethyl-UTP: A solution of 5-N-TFA-N-Methylaminomethyl-uridine 66 (110.0 mg, 0.29 mmol; applied heat to make it soluble) and proton sponge (94.30 mg, 0.44 mmol, 1.5 equiv.) in trimethyl phosphate (0.8 mL) was stirred for 10.0 minutes at 0° C. Phosphorus oxychloride (54.13 µL, 0.58 mmol, 2.0 equiv.) was added dropwise to the solution and it was then kept stirring for 2.0 hours under $N_2$ atmosphere. A mixture of tributylamine (281.46 µL, 1.16 mmol, 4.0 equiv.) and bis(tributylammonium) pyrophosphate (477.34 mg, 0.87 mmol, 3.0 equiv.) in acetonitrile (2.5 mL) was added at once. After ~25 minutes, the reaction was quenched with 0.2 M TEAB buffer (13.7 mL) and the clear solution was stirred at room temperature for an hour. LCMS analysis indicated the formation of the corresponding triphosphate. To this above crude reaction mixture, about 22.0 mL of concentrated $NH_4OH$ was added and the reaction mixture was stirred at room temperature overnight. It was then lyophilized overnight and the crude reaction mixture was HPLC purified (Shimadzu, Phenomenex C18 preparative column, 250×30.0 mm, 5.0 micron; gradient (1%): 100% A for 3.0 min, then 1% B/min, A=100 mM TEAB buffer, B=ACN; flow rate: 20.0 mL/min; retention time: 14.89-16.11 min). Fractions containing the desired were pooled and lyophilized to yield the 5-Methylaminomethyl-UTP as a tetrakis(triethylammonium salt) (35.27 mg, 19.31% for two steps, based on $\alpha_{266}$=10,000). UVmax=266 nm; MS: m/e 525.70 (M−H).

Example 30

Synthesis of N4,N4,2'-O-trimethyl-CTP
(03601074029)

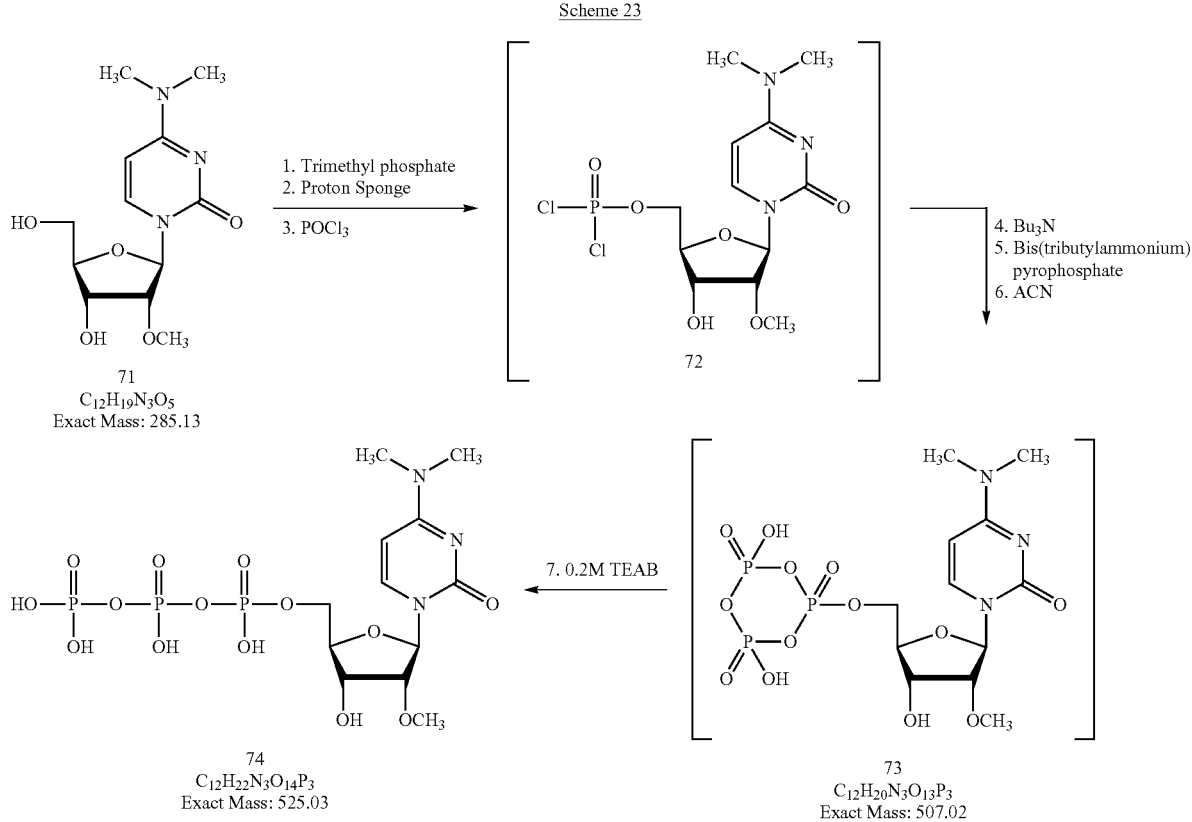

N4, N4, 2'-O-Trimethyl-CTP (74): A solution of N4, N4, 2'-O-trimethyl-cytidine 71 (101.5 mg, 0.36 mmol; applied heat to make it soluble) and proton sponge (115.7 mg, 0.54 mmol, 1.5 equiv.) in trimethyl phosphate (0.8 mL) was stirred for 10.0 minutes at 0° C. Phosphorus oxychloride (67.20 µL, 0.72 mmol, 2.0 equiv.) was added dropwise to the solution and it was then kept stirring for 2.0 hours under $N_2$ atmosphere. A mixture of tributylamine (349.40 µL, 1.44 mmol, 4.0 equiv.) and bis(tributylammonium) pyrophosphate (592.60 mg, 1.08 mmol, 3.0 equiv.) in acetonitrile (2.5 mL) was added at once. After ~25 minutes, the reaction was quenched with 0.2 M TEAB buffer (17.0 mL) and the clear solution was stirred at room temperature for an hour. LCMS analysis indicated the formation of the corresponding triphosphate. The reaction mixture was then lyophilized overnight. The crude reaction mixture was HPLC purified (Shimadzu, Phenomenex C18 preparative column, 250×30.0 mm, 5.0 micron; gradient (1%): 100% A for 3.0 min, then 1% B/min, A=100 mM TEAB buffer, B=ACN; flow rate: 20.0 mL/min; retention time: 18.67-19.38 min). Fractions containing the desired were pooled and lyophilized to yield the N4, N4, 2'-O-Trimethyl-CTP (74) as a tetrakis(triethylammonium salt) (30.22 mg, 16.11%, based on $\alpha_{278}$=9,000). UVmax=278 nm; MS: m/e 523.75 (M−H).

Example 31

Synthesis of
5-methoxycarbonylmethyl-2'-O-methyl-UTP
(00901073005)

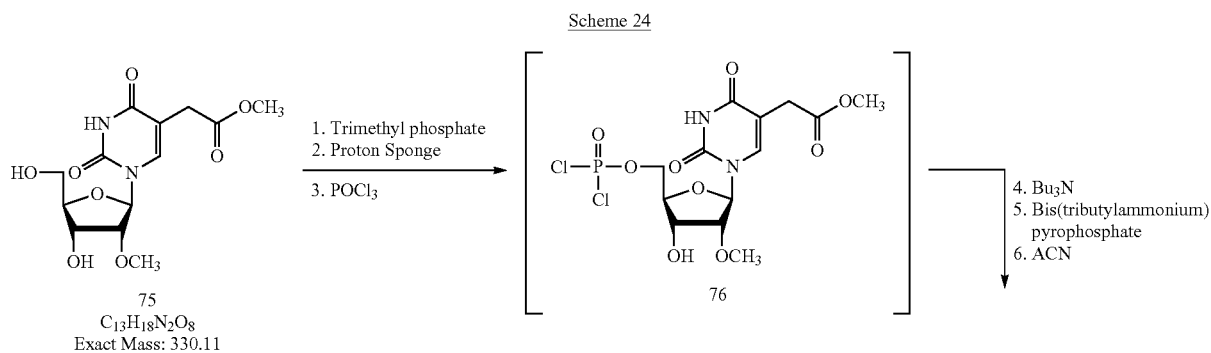

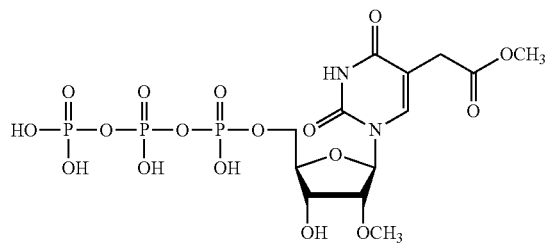

78
C₁₃H₂₁N₂O₁₇P₃
Exact Mass: 570.01

7. 0.2M TEAB ←

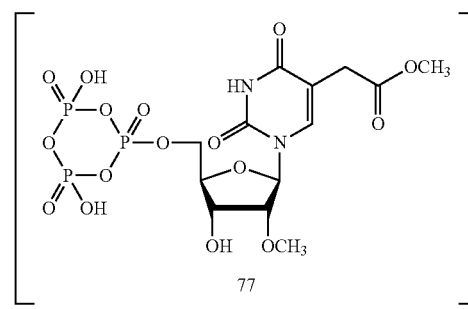

77
C₁₃H₁₉N₂O₁₆P₃
Exact Mass: 551.99

5-Methoxycarbonylmethyl-2'-O-methyl-UTP (78): A solution of 5-Methoxycarbonylmethyl-2'-O-methyl-uridine 75 (102.0 mg, 0.31 mmol; applied heat to make it soluble) and proton sponge (100.72 mg, 0.47 mmol, 1.5 equiv.) in trimethyl phosphate (0.8 mL) was stirred for 10.0 minutes at 0° C. Phosphorus oxychloride (57.87 μL, 0.62 mmol, 2.0 equiv.) was added dropwise to the solution and it was then kept stirring for 2.0 hours under $N_2$ atmosphere. A mixture of tributylamine (300.87 μL, 1.24 mmol, 4.0 equiv.) and bis(tributylammonium) pyrophosphate (510.26 mg, 0.93 mmol, 3.0 equiv.) in acetonitrile (2.5 mL) was added at once. After ~25 minutes, the reaction was quenched with 0.2 M TEAB buffer (14.64 mL) and the clear solution was stirred at room temperature for an hour. LCMS analysis indicated the formation of the corresponding triphosphate. The reaction mixture was then lyophilized overnight. The crude reaction mixture was HPLC purified (Shimadzu, Phenomenex C18 preparative column, 250×30.0 mm, 5.0 micron; gradient (1%): 100% A for 3.0 min, then 1% B/min, A=100 mM TEAB buffer, B=ACN; flow rate: 20.0 mL/min; retention time: 18.57-19.35 min). Fractions containing the desired were pooled and lyophilized to yield the 5-Methoxycarbonylmethyl-2'-O-methyl-UTP (78) as a tetrakis(triethylammonium salt) (54.60 mg, 30.97%, based on $\alpha_{265}$=11,000). UVmax=265 nm; MS: m/e 568.65 (M-H).

Example 32

Synthesis of 5-methoxy uridine (compound 15) and 5-methoxy UTP (NTP of said compound)

Scheme 25

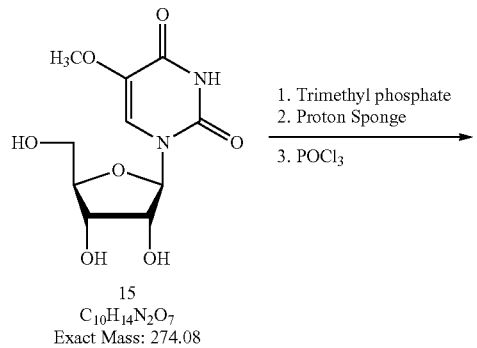

15
C₁₀H₁₄N₂O₇
Exact Mass: 274.08

1. Trimethyl phosphate
2. Proton Sponge
3. POCl₃
→

-continued

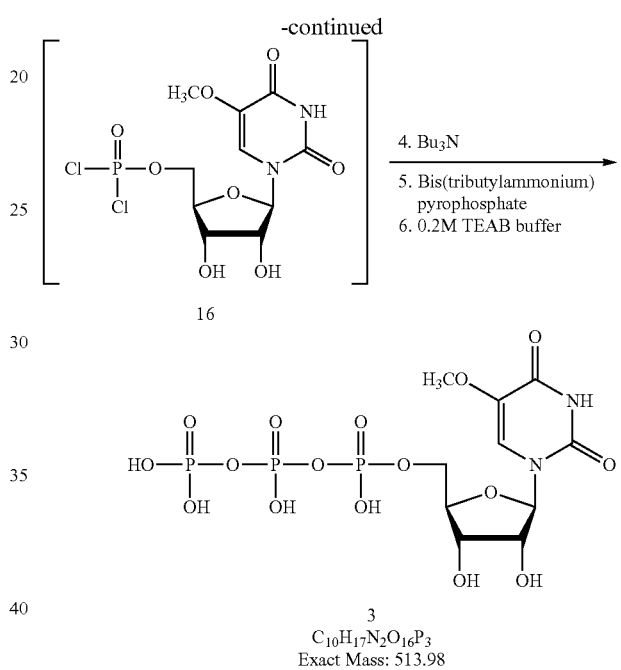

16

4. Bu₃N
5. Bis(tributylammonium) pyrophosphate
6. 0.2M TEAB buffer
→

3
C₁₀H₁₇N₂O₁₆P₃
Exact Mass: 513.98

A solution of 5-methoxy uridine (compound 15) (69.0 mg, 0.25 mmol, plus heat to make it soluble) was added to proton sponge (80.36 mg, 0.375 mmol, 1.50 equiv.) in 0.7 mL trimethylphosphate (TMP) and was stirred for 10 minutes at 0° C. Phosphorous oxychloride (POCl₃) (46.7 ul, 0.50 mmol, 2.0 equiv.) was added dropwise to the solution before being kept stirring for 2 hours under $N_2$ atmosphere. After 2 hours the solution was reacted with a mixture of bistributylammonium pyrophosphate (TBAPP or (n-Bu₃NH)₂ H₂P₂O₇) (894.60 mg, 1.63 mmol, 6.50 equiv.) and tributylamine (243.0 ul, 1.00 mmol, 4.0 equiv.) in 2.0 ml of dimethylformamide. After approximately 15 minutes, the reaction was quenched with 17.0 ml of 0.2M triethylammonium bicarbonate (TEAB) and the clear solution was stirred at room temperature for an hour. The reaction mixture was lyophilized overnight and the crude reaction mixture was purified by HPLC (Shimadzu, Kyoto Japan, Phenomenex C18 preparative column, 250×21.20 mm, 10.0 micron; gradient: 100% A for 3.0 min, then 1% B/min, A=100 mM TEAB buffer, B=ACN; flow rate: 10.0 mL/min; retention time: 16.57-17.51 min). Fractions containing the desired compound were pooled and lyophilized to produce the NTP of compound 15. The triphosphorylation reactions were carried out in a two-neck flask flame-dried under N₂ atmosphere. Nucleosides and the protein sponge were dried over P₂O₅ under vacuum overnight prior to use. The formation of monophosphates was monitored by LCMS.

Example 33

Synthesis of 6-Methylpseudouridine (03600015037)

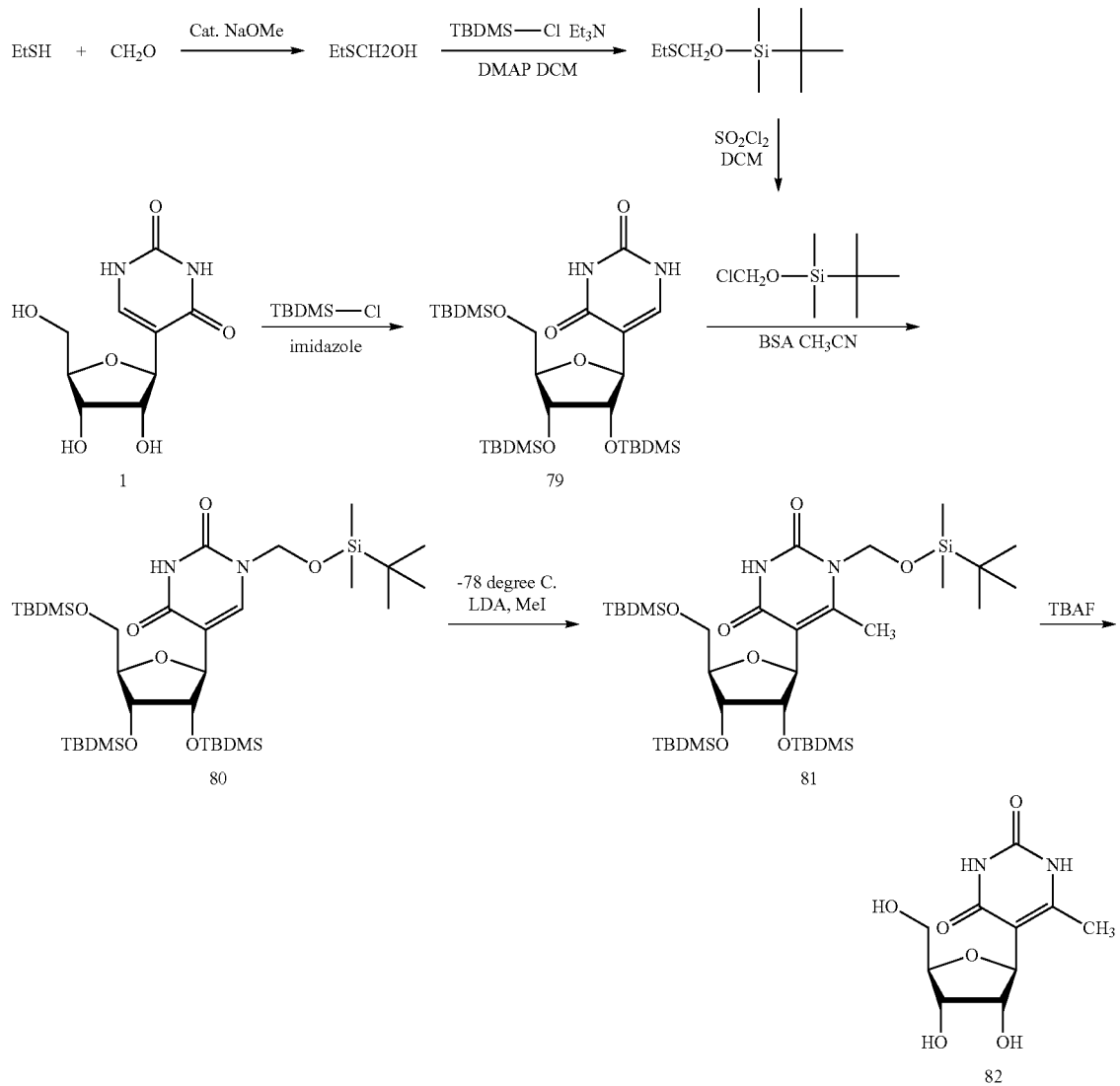

Ethylthiomethanol: To a stirred mixture of ethanethiol (7.4 ml, 6.2 g, 0.1 mol) and paraformaldehyde (3.0 g, 0.1 mol) was added 0.03 mL saturated sodium methoxide solution in methanol as catalyst. It was stirred at 40 C for 30 min, and cooled to give liquid product 9.2 g. It was used for next step without further purification.

(tert-Butyldimethylsilyloxy)methyl ethyl sulfide: To a solution of ethylthiomethanol (4.6 g, 50 mmol) in 50 mL of anhydrous dichloromethane was added tert-butyldimethylsilylchloride (8.31 g, 55 mmol), 4-(N,N-dimethylamino)pyridine (244 mg, 2 mmol) and triethylamine (8.35 ml, 60 mmol). The mixture was stirred at ambient temperature under nitrogen atmosphere for 4 h, and diluted with dichloromethane. The mixture was washed successively with water (×2) and saturated aqueous ammonium chloride (×2), and then dried over anhydrous sodium sulfate. The filtrate solution was concentrated under reduced pressure to give 8.72 g product as pale yellow oil in 84% yield. It was used in next step without further purification.

(tert-Butyldimethylsilyloxy)methyl Chloride: A solution of (tert-butyldimethylsilyloxy)methyl ethyl sulfide (5.1 mg, 25 mmol) in anhydrous dichloromethane was cooled to 0° C. Sulfury chloride (1.6 mL, 10 mmol) in 20 mL of anhydrous methylene chloride was added under stirring over 30 min. The reaction mixture was stirred at room temperature for an additional 10 min, and concentrated under reduced pressure giving 4.2 g product as pale yellow oil, which was used directly for next step without further purification.

Compound 79: A mixture of pseudouridine (1) (3.0 g, 12.3 mmol), imidazole (4.2 g, 61.5 mmol, 5.0 eq), and t-butyldimethylsilyl chloride (7.4 g, 49.2 mmol, 4.0 eq) in anhydrous DMF was stirred at 30° C. overnight. TLC (PE-EA=2:1) indicated completion of the reaction. The reaction mixture was treated with dichloromethane and saturated sodium carbonate solution. The organic phase was separated, and the aqueous phase was extracted with ethyl acetate. The combined organic phase was dried over anhydrous sodium sulfate. The filtrate was concentrated under reduced pressure. The crude product was purified by flash chromatography on a silica gel column using PE-EA (3:1) as eluent giving white foam product 79 which was used for next step without further purification and characterization.

Compound 80: A stirred mixture of trisilylated compound 79 (1.5 g, 2.56 mmol) in 20 mL of anhydrous acetonitrile and 8 mL of BSA was heated to 65° C. under nitrogen atmosphere for 6 h. t-(Butyldimethylsilyloxy)methyl chloride (1.8 g, 10 mmol) was added, and the resulting reaction mixture was stirred at 65° C. overnight. TLC (PE-EA=3:1) indicated completion of the reaction. The reaction mixture was cooled to room temperature and treated with dichloromethane and aqueous saturated sodium carbonate solution. The layers were separated, and the aqueous layer was extracted with dichloromethane (30 mL×3). The combined organic phase was dried over anhydrous sodium sulfate, and filtered. The solvent was evaporated under reduced pressure. The residue was purified by flash chromatography on a silica gel column giving 1.2 g desired product 80 in 64% yield.

Compound 81: N,N-Diisopropylamine (1.4 mL, 10 mmol) was dissolved in 20 mL of anhydrous THF. The solution was cooled to −78° C. under nitrogen atmosphere. n-Butyl lithium (4 mL, mmol; 2.5 M in hexane) was added dropwise under stirring over 1 h. A solution of compound 80 (2.2 g, 3 mmol) in 5 mL of anhydrous THF was added to the LDA solution prepared above. The resulting reaction mixture was stirred at −78° C. for an additional 2 h. During this time, a solution of iodomthane (1.25 mL, 20 mmol) in 10 mL of anhydrous THF was cooled to −78° C. under nitrogen atmosphere. The LDA solution of compound D at low temperature was directly transferred to this cooled iodomethane solution. The resulting reaction mixture was stirred at −78° C. for 30 min. The reaction mixture was treated with aqueous ammonium chloride solution, and it was allowed to warm to room temperature, followed by the treatment with ethyl acetate and aqueous sodium bicarbonate solution. The layers were separated, and the aqueous phase was extracted with ethyl acetate. The combined organic phase was tried over anhydrous sodium sulfate and filtered. The solution was concentrated under reduced pressure. The residue was purified by flash chromatography on a silica gel column providing 1.1 g desired 6-methylated product 82 in 49% yield.

6-Methylpseudouridine (82): Compound 81 (1.1 g, 1.48 mmol) was treated with 0.5 M TBAF solution in THF, and it was stirred at 30° C. overnight. TLC indicated completion of the reaction. The mixture was concentrated and purified by flash chromatography on a silica gel column providing 257 mg desired product in 67% yield with 99.42% HPLC purity. It was characterized by NMR and MS spectral analysis.

Example 34

Synthesis of 6, $N^1$-dimethylpseudouridine (03600015107)

Scheme 27

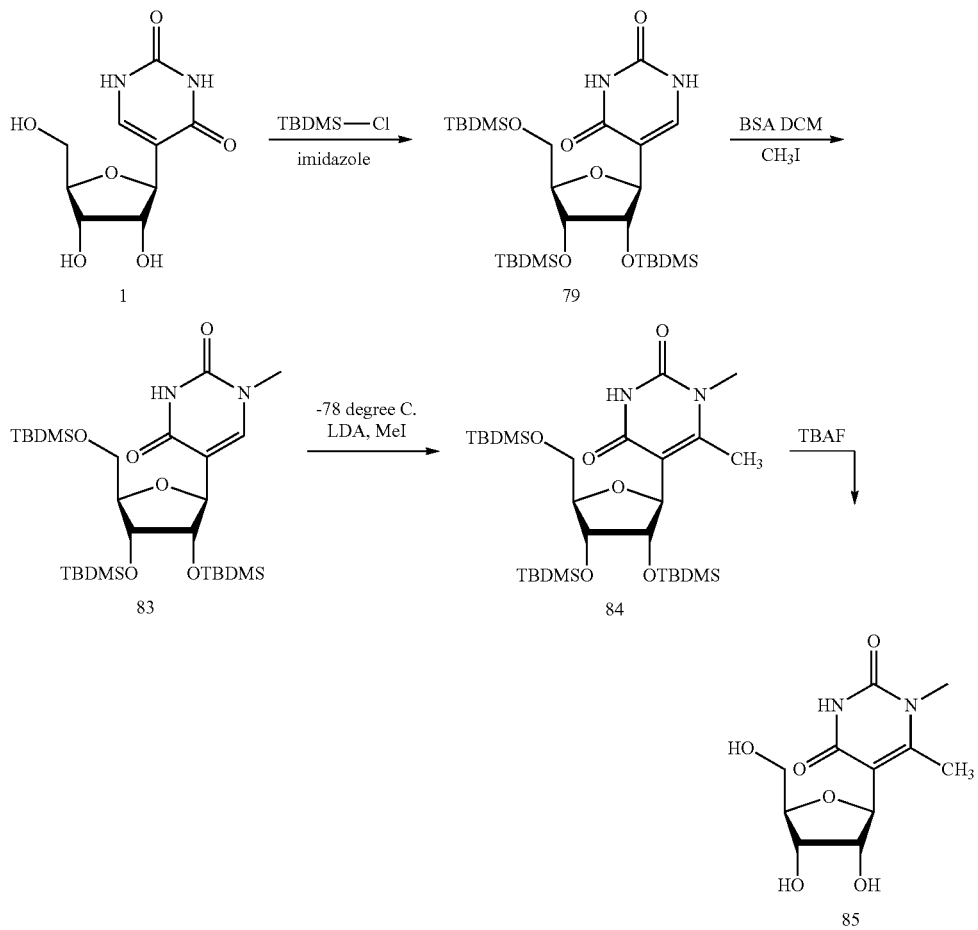

541

Compound 83: Compound 79 (5.87 g, 10 mmol) was dissolved in 100 mL of anhydrous dichloromethane, and 20 mL of BSA was added. The mixture was refluxed under nitrogen atmosphere for 4 h. iodomethane (2.56 g, 1.12 mL, 1.8 eq) was added, and the reaction mixture was continued to be heated at reflux temperature for 5 days. TLC (PE-EA=3:1) indicated trace starting material left. The reaction mixture was cooled to room temperature, and treated with dichloromethane and aqueous sodium bicarbonate solution. The layers were separated, and the aqueous phase was extracted with dichloromethane. The combined organic phase was dried over anhydrous sodium sulfate, and the filtrate was concentrated under reduced pressure. The residue was purified by flash chromatography on a silica gel column giving 3.9 g compound 83 as white foam in 65% yield. Some starting material was recovered.

Compound 84: N,N-Diisopropylamine (1.4 mL, 10 mmol) was dissolved in 20 mL of anhydrous THF. The solution was cooled to −78° C. under nitrogen atmosphere. n-Butyl lithium (4 mL, mmol; 2.5 M in hexane) was added dropwise under stirring over 1 h. A solution of compound 83 (1.8 g, 3 mmol) in 5 mL of anhydrous THF was added to the LDA solution prepared above. The resulting reaction mixture was stirred at −78° C. for an additional 2 h. During this time, a solution of iodomthane (1.25 mL, 20 mmol) in 10 mL of anhydrous THF was cooled to −78° C. under nitrogen atmosphere. The LDA solution of compound 83 at low temperature was directly transferred to this cooled iodomethane solution. The resulting reaction mixture was stirred at −78° C. for 30 min. The reaction mixture was treated with aqueous ammonium chloride solution, and it was allowed to warm to room temperature, followed by the treatment with ethyl acetate and aqueous sodium bicarbonate solution. The layers were separated, and the aqueous phase was extracted with ethyl acetate. The combined organic phase was tried over anhydrous sodium sulfate and filtered. The solution was concentrated under reduced pressure. The residue was purified by flash chromatography on a silica gel column providing 1.2 g desired product 84 as pale yellow foam in 65% yield.

1,6-Dimethylpseudouridine (85): Compound 84 (1.2 g, 1.95 mmol) was treated with 10 mL of 1 M TBAF solution in THF, and it was stirred at room temperature for 24 h. TLC indicated completion of the reaction. The mixture was concentrated and purified by flash chromatography on a silica gel column using methylene chloride-methanol (20:1) providing 240 mg desired product 85 with 99.61% HPLC purity. It was characterized by NMR and MS spectral analysis (see separate document for spectra).

Example 35

Synthesis of $N^1$-Allylpseudouridine (03600015151)

Scheme 28

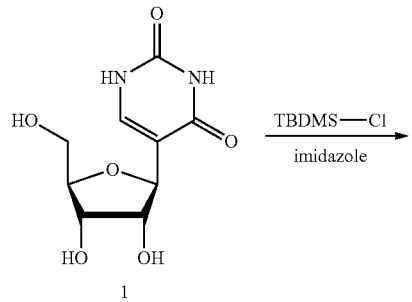

542

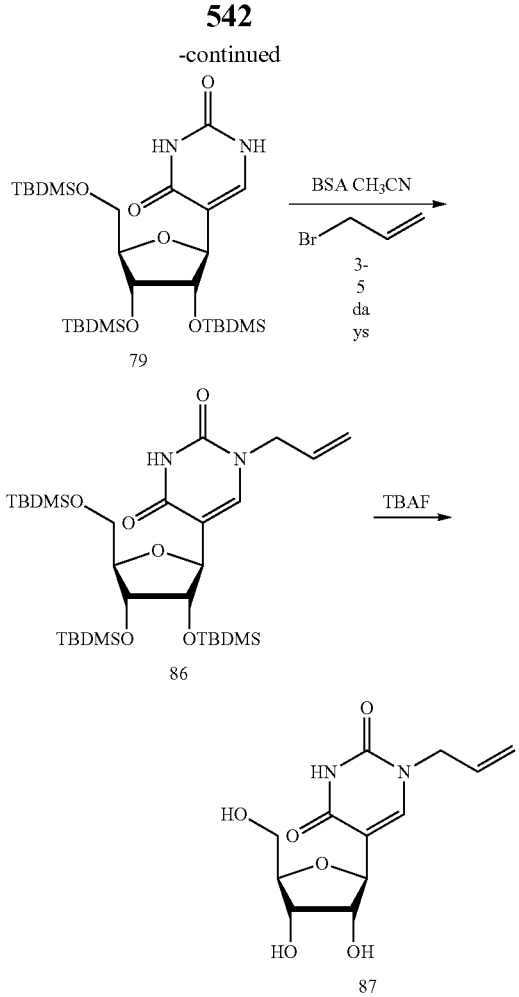

Compound 86: A stirred mixture of compound 79 (1.17 g, 2.0 mmol) in 20 mL of anhydrous acetonitrile and 10 mL of BSA was heated to 65° C. under nitrogen atmosphere for 4 h. Allyl bromide (0.5 mL, 0.7 g, 5.8 mmol) was added. The reaction mixture was stirred at 65° C. for an additional 24 h. TLC (PE-EA=3:1) indicated completion of the reaction. The cooled reaction mixture was treated with ethyl acetate and saturated sodium carbonate solution. The layers were separated, and the aqueous layer was extracted with ethyl acetate. The combined organic phase was dried over anhydrous sodium sulfate. The filtrate was concentrated under reduced pressure. The residue was purified by flash chromatography on a silica gel column using PE-EA as eluent giving 650 mg product 86 in 52% yield (some starting material was recovered).

1-Allyl-pseudouridine (87): Compound C (1.1 g, 1.75 mmol) was dissolved in 10 mL of THF, and 10 mL of 1M TBAF in THF was added. The reaction mixture was stirred at room temperature for 24 h. The solvent was concentrated, and the residue was purified by flash chromatography on a silica gel column giving 284 mg desired product 87 in 57% yield with 95.47% yield. It was characterized by NMR and MS spectral analysis (see different document for spectra).

Example 36

Synthesis of 1-Propargyl-pseudouridine (03600015153)

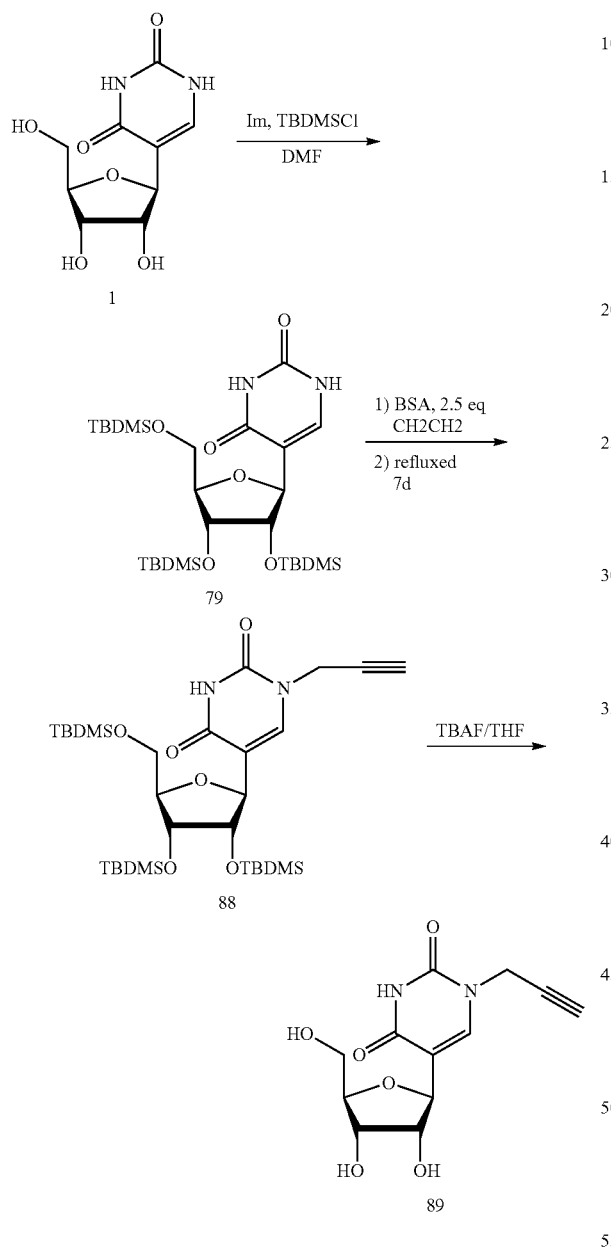

Scheme 29

Synthesis of compound 88: Bis-trimethylsilylacetamide (BSA, 10 ml) was added to a stirred solution of Compound 79 (1.5 g, 2.56 mmol) in DCM (20 mL). After stirring for four hour at 40 degree C., propargyl bromide (0.36 mL) was added to the solution, and the solution was then heated at reflux temperature for 24 h. The reaction mixture was concentrated to dryness under reduced pressure. The residue was purified via silica gel chromatography using petroleum ether (PE): ethyl acetate (EA)=20:1-8:1 to give 1.1 g compound 88 as light yellow foam in 81% yield.

1-Propargyl-pseudouridine (89): To a solution of Compound 88 (2.2 g, 1 eq) in THF was added TBAF in THF (1 M, 2 mL), and the mixture was stirred overnight at 30 degree C. The mixture was concentrated under reduced pressure to dryness. The resulted crude product was purified by silica gel chromatography using MeOH-DCM=1:50-1:25 to give 0.325 g product 89 as light pink solid in 32.7% yield. HPLC purity: 98.2%; $^1$H NMR (DMSO-d$_6$): δ11.4 (s, 1H), 7.81 (s, 1H), 4.97-4.99 (d, 1H, J=3.9 Hz), 4.77-4.78 (m, 2H), 4.46-4.50 (m, 3H), 3.83-3.93 (m, 2H), 3.59-3.71 (m, 2H), 3.42-3.50 (m, 2H).

Example 37

Synthesis of 1-Cyclopropylmethylpseudouridine (03600015030)

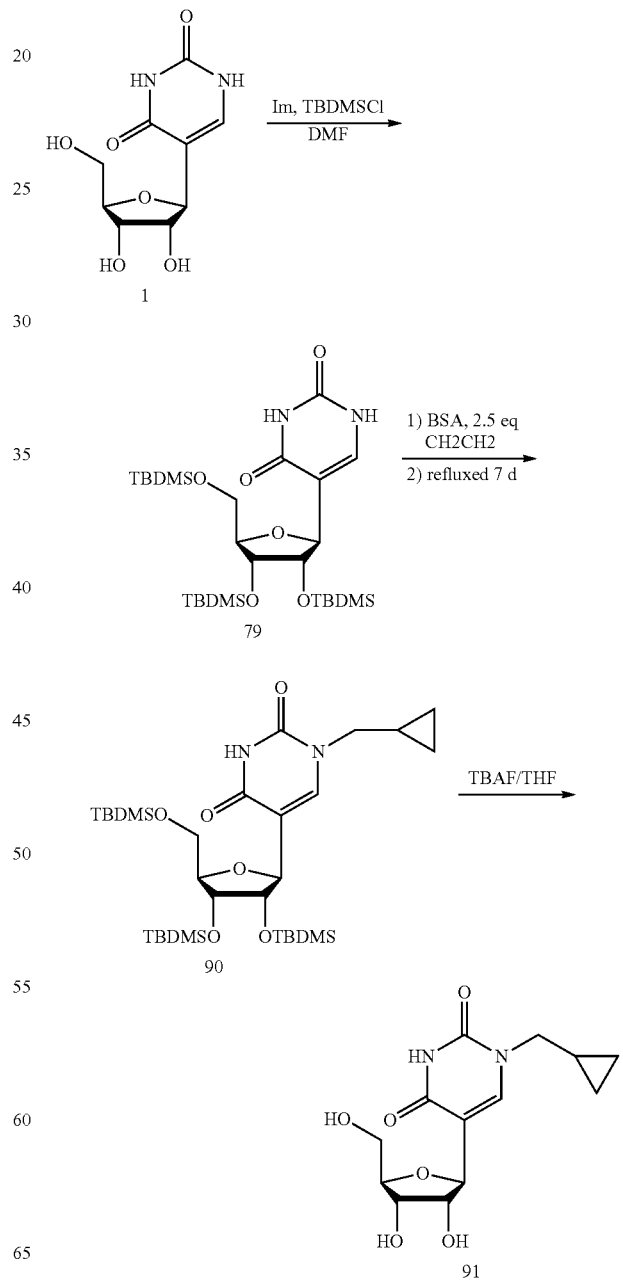

Scheme 30

Synthesis of compound 90: Bis-trimethylsilylacetamide (BSA, 5 ml) was added to a stirred solution of Compound 79 (1.5 g, 2.6 mmol) in DCM (15 mL). After stirring for four hour at 40 degree C., cyclopropylmethyl bromide (0.45 mL) was added to the solution, and the solution was then heated at reflux temperature for 5 days. The reaction mixture was concentrated to dryness under reduced pressure. The residue was purified via silica gel chromatography using PE:EA=20:1-8:1 to give 1.1 g product 90 as light yellow foam in 67% yield.

1-Cyclopropylmethylpseudouridine (91): To a solution of Compound 90 (1.2 g, 1 eq) in THF was added TBAF in THF (1 M, 2 mL), and the mixture was stirred overnight. The mixture was concentrated to dryness under reduced pressure. The resulting crude product was purified by silica gel chromatography using MeOH:DCM=1:50-1:25 to give 0.26 g product 91 as white solid in 46.6% yield. HPLC purity: 97.6%; $^1$H NMR (DMSO-d$_6$): δ 11.28 (s, 1H), 7.84 (s, 1H), 4.97-4.99 (d, 1H, J=3.6 Hz), 4.82-4.85 (t, 1H, J=4.5 Hz), 4.75-4.76 (d, 1H, J=4.5 Hz), 4.46-4.47 (d, 1H, J=3 Hz), 3.88-3.95 (m, 2H), 3.58-3.71 (m, 3H), 3.34-3.45 (m, 2H), 1.11 (1H), 0.45-0.48 (m, 2H), 0.32-0.35 (m, 2H).

Example 38

Synthesis of 6-Chloro-1-methylpseudouridine (03600015117)

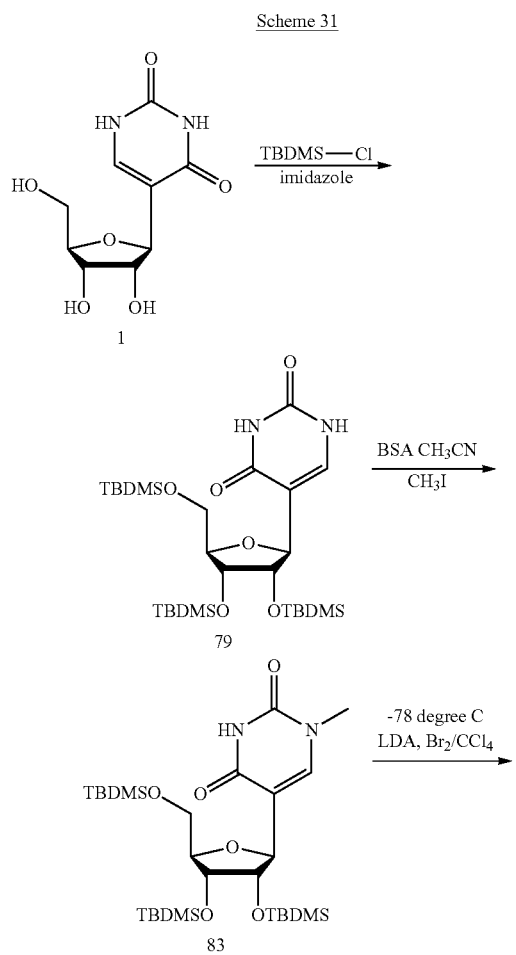

Scheme 31

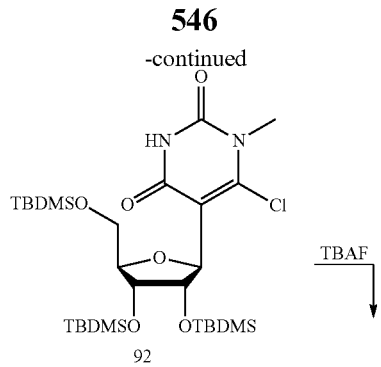

Compound 92: N,N-Diisopropylamine (1.4 mL, 10 mmol) was dissolved in 20 mL of anhydrous THF. The solution was cooled to −78° C. under nitrogen atmosphere. n-Butyl lithium (4 mL, mmol; 2.5 M in hexane) was added dropwise under stirring over 1 h. A solution of compound 83 (2.2 g, 3 mmol) in 5 mL of anhydrous THF was added to the LDA solution prepared above. The resulting reaction mixture was stirred at −78° C. for an additional 2 h. Bromine (5 mL) was dissolved in 10 mL of anhydrous carbon tetrachloride, and dried with molecular sieves. This bromine solution was added to the LDA solution of compound 83 under stirring at −78° C. until pale yellow color became orange. The reaction mixture was stirred at −78° C. for 30 min. TLC (PE-EA=3:1) indicated trace amount of starting material left. While still cold, the reaction mixture was poured into the mixture of sodium thiosulfate and sodium bicarbonate aqueous solution. It was extracted with ethyl acetate, and the organic phase was dried over anhydrous sodium sulfate and filtered. The solution was concentrated under reduced pressure. The residue was purified by flash chromatography on a silica gel column to give 1.6 g of 92.

6-Chloro-1-methylpseudouridine (93): 1.6 g of 92 obtained above was treated with 10 mL of 0.5 M TBAF solution in THF, and it was stirred at room temperature for 24 h and concentrated. The residue was purified by flash chromatography on a silica gel column using methylene chloride-methanol providing 120 mg product with 96.3% HPLC purity. It was characterized by NMR and MS spectral analysis to be the N1-methyl-6-chloro pseudouridine 93.

Example 39

Synthesis of 1-Benzyl-pseudouridine (03600015032)

Scheme 32

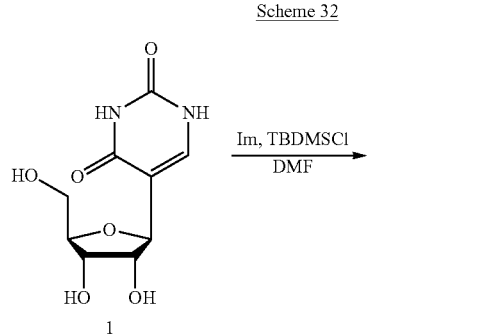

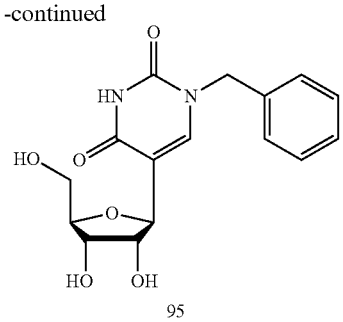

Compound 94: Bis-trimethylsilylacetamide (BSA, 10 mL) was added to a stirred solution of compound 79 (2.0 g, 3.4 mmol) in 20 mL of dichloromethane. After stirring for four hour at 40° C., benzyl bromide (0.5 mL) was added to the solution, and the solution was then heated at reflux temperature for 5 days. The reaction mixture was concentrated to dryness under reduced pressure. The residue was purified via silica gel chromatography using gradient eluent PE:EA=20:1-8:1 to give 1.4 g product 94 as a light yellow foam in 60.8% yield.

1-Benzyl-pseudouridine (95): To a solution of compound 94 (1.4 g, 1 eq) in THF was added TBAF in THF (1 M, 10 mL), and the mixture was stirred at room temperature overnight. The mixture was concentrated under reduced pressure to dryness. The crude product was purified by silica gel chromatography using MeOH:DCM=1:50-1:25 giving 0.309 g desired product 95 as a white solid in 51.0% yield. Purity: 97.9% (HPLC); H NMR (DMSO-$d_6$) δ 11.41 (s, 1H), 7.91 (s, 1H), 7.27-7.36 (m, 5H), 4.94-4.95 (d, 1H, J=3.6 Hz), 4.86 (s, 2H), 4.77-4.80 (t, 1H, J=4.2 Hz), 4.71-4.72 (d, 1H, J=4.2 Hz), 4.46-4.47 (d, 1H, J=3.3 Hz), 3.93-3.96 (m, 1H), 3.83-3.87 (m, 1H), 3.68-3.70 (m, 1H), 3.59-3.63 (m, 1H), 3.42-3.47 (m, 1H); Mass Spectrum: 335.1 (M+H)$^+$, 358.1 (M+Na)$^+$.

Example 40

Synthesis of 1-Methyl-3-(2-N-t-Boc-amino-3-t-butyloxycarbonyl) propyl pseudouridine (03600015036-Boc)

Scheme 33

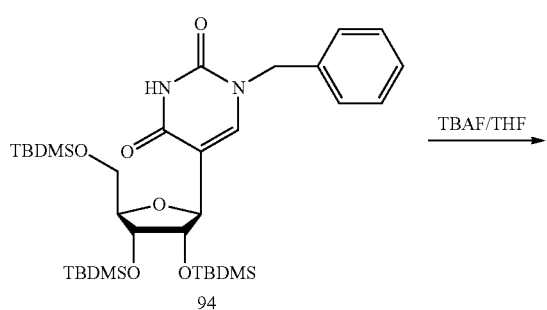

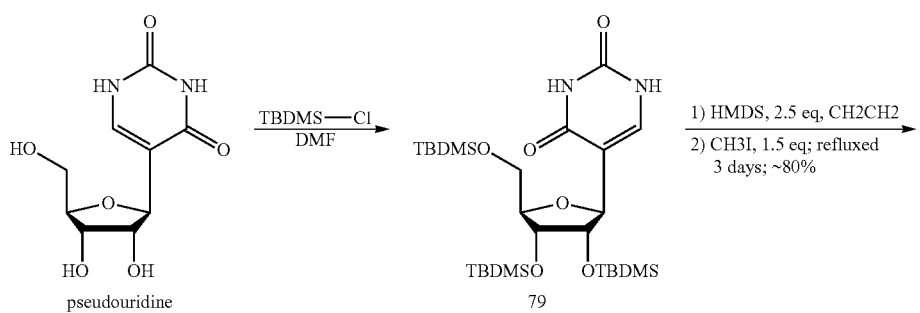

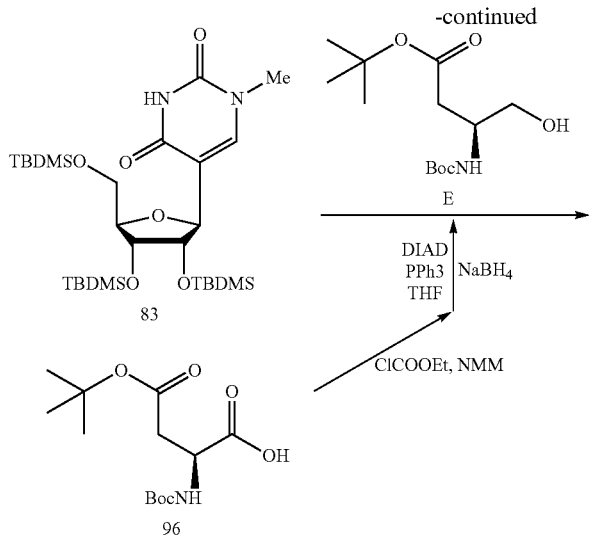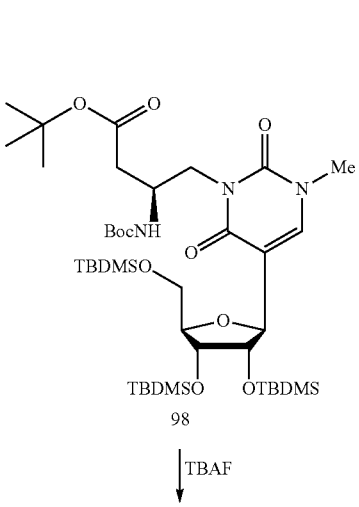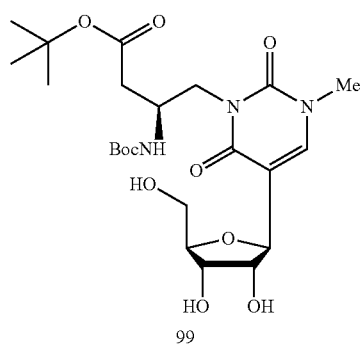

Synthesis compound 97: A solution of Boc-Asp(OtBu)-OH (96) (5.0 g, 17.3 mmol) in 50 ml dry THF was cooled to −10 degree C. N-Methylmorpholine (1.75 g, 17.3 mmol) was added. After 1 min, ClCO$_2$Et (1.65 ml, 17.3 mmol) was added dropwise. The reaction mixture was stirred for an additional 15 min at −5 degree C. The precipitated N-methylmorpholie hydrochloride was filtered off, and the filtrate was added to a solution of NaBH$_4$ (1.47 g, 38.9 mmol) in 20 mL of water at 5-10 degree C. within 10 min. The reaction mixture was stirred at room temperature for 3.5 h and then cooled to 5 degree C. 3M hydrochloric acid was added to give a pH of 2, and the mixture was extracted twice with ethyl acetate. The combined organic phase was washed twice with water and then dried with anhydrous Na$_2$SO$_4$. The product is dried in vacuo and purified via silica gel chromatography using EA: PE (1:2) as eluent to give 4.0 g product 97 as colorless oil in 85% yield.

Compound 98: Diisopropyl azodicarboxylate (1.6 g, 3 eq) was added to a stirred solution of compound 83 (1.60 g, 1.0 eq), compound 97 (0.83 g, 1.5 eq) and triphenylphosphine (2.1 g, 3 eq) in anhydrous THF (16 mL) at room temperature under N$_2$. The reaction mixture was stirred for 1 h, and the solvent was removed under reduced pressure. The residue was purified by silica gel chromatography using PE: EA (10:1-8:1) providing 1.6 g desired product 98 as pale yellow oil in 56.8% yield.

1-Methyl-3-(2-N-t-Boc-amino-3-t-butyloxycarbonyl) propyl psudouridine (99): To a solution of compound 98 (1.3 g, 1 eq) in THF was added TBAF in THF (1 M, 2 mL), and the mixture was stirred at room temperature for 2 h. The mixture was concentrated to dryness under reduced pressure. The crude product was purified by silica gel chromatography using MeOH:DCM=1:20-1:5 to give 0.46 g product 99 as white foam in 57.6% yield, with HPLC purity of 98%. $^1$H NMR (DMSO-d$_6$, 300 MHz): δ 7.77 (s, 1H), 6.25-6.64 (d, 1H, J=6.9 Hz), 4.93-4.95 (1H), 4.78-4.81 (m, 2H), 4.73-4.75 (d, 1H, J=4.8 Hz), 4.51-4.52 (d, 1H, J=2.4 Hz), 3.86-3.90 (m, 1H), 3.68-3.70 (m, 3H), 3.48-3.50 (m, 3H), 3.34 (s, 3H), 2.33-2.37 (m, 2H), 1.26-1.37 (18H); ES MS, m/z 537.7 (M+Na)$^+$.

Example 41

Synthesis of compound Pseudouridine 1-(2-ethanoic acid-Fm) (03600015034-Fm)

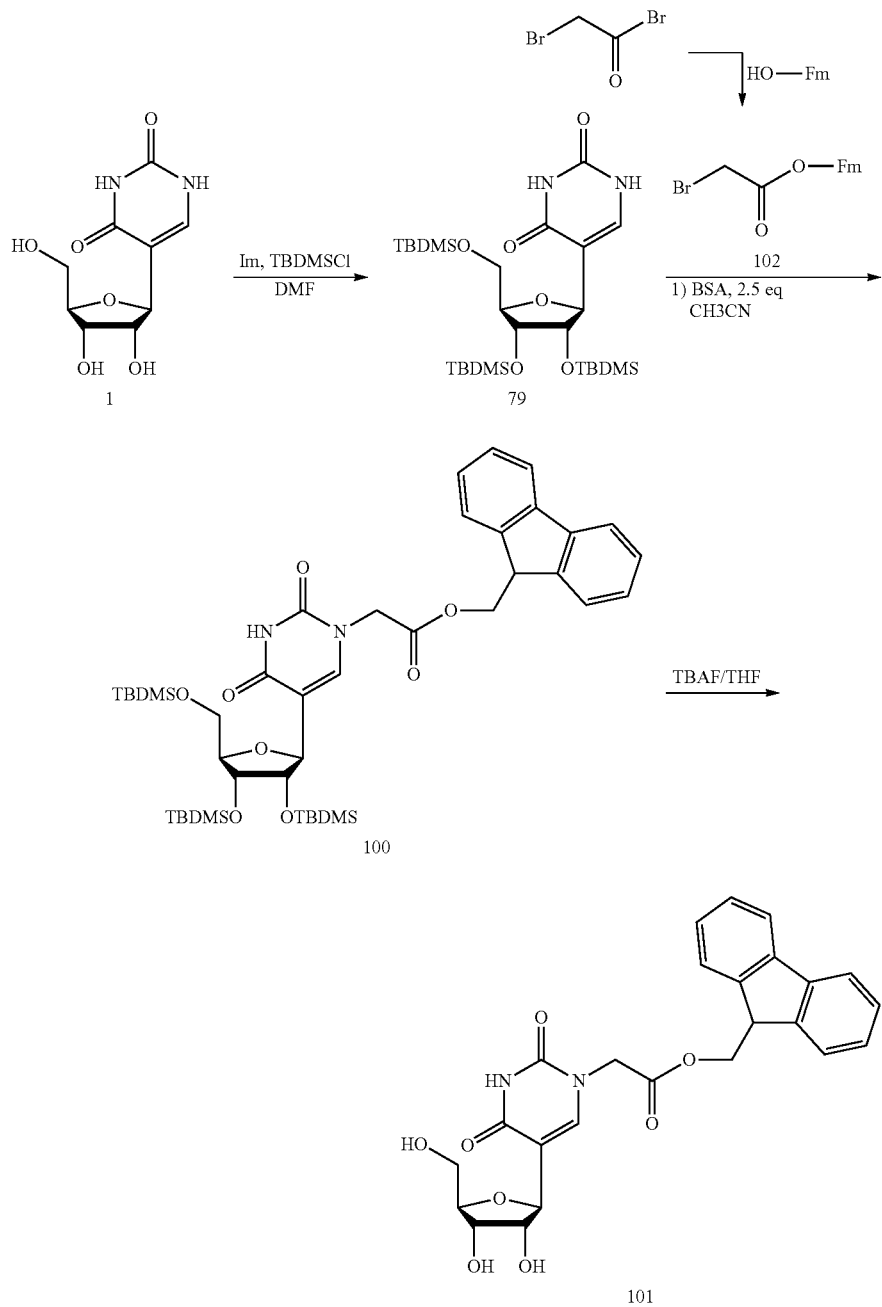

Scheme 34

Synthesis of Bromoacetic Acid Fm Ester (102): 9-Fluorenyl methanol (10 g, 1 eq) was dissolved in 100 mL of dichlormethane, and triethylamine (6.14 g, 1.19 eq) was added. The reaction mixture was cooled in ice bath, and a solution of bromoacetyl bromide (10.3 g, 1 eq) in 10 mL methylene chloride was added under stirring over 1 h. The cloudy mixture was warmed to room temperature, and stirred overnight. The mixture was washed with water (100 mL×3) and brine. The combined organic phase was dried and concentrated under reduced pressure. The crude product thus obtained was purified via silica gel chromatography (PE:EA=300:1-50:1) giving 6.4 g product 102 as a light yellow solid in 39.8% yield.

Compound 100: Bis-trimethylsilylacetamide (BSA, 20 mL) was added to a stirred solution of compound 79 (2.5 g, 3.4 mmol) in dichloromethane (25 mL). After stirring for four hours at 40° C., the bromo-compound 102 (2.43 g, 1.8 eq) in dichloromethane (2 mL) was added, and the solution was then heated at reflux temperature for 5 days. The reaction mixture was concentrated under reduced pressure to dryness. The residue was purified via silica gel chromatography using PE: EA=10:1-5:1 giving 0.8 g desired compound 100 as white foam. (1.7 g of compound 79 was recovered).

Pseudouridine 1-(2-ethanoic acid-Fm) (101): To a solution of compound 100 (0.8 g, 1 eq) in THF (20 mL) was added 1M HCl (1 mL), and the mixture was stirred at room temperature overnight. The mixture was concentrated under reduced pressure to dryness. The residue was purified by silica gel chromatography using MeOH:DCM=1:30-1:20 giving 0.30 g final product 101 as white solid in 64.2% yield.

Example 42

Synthesis of 5-Ethyl-cytidine (03600014039)

Scheme 35

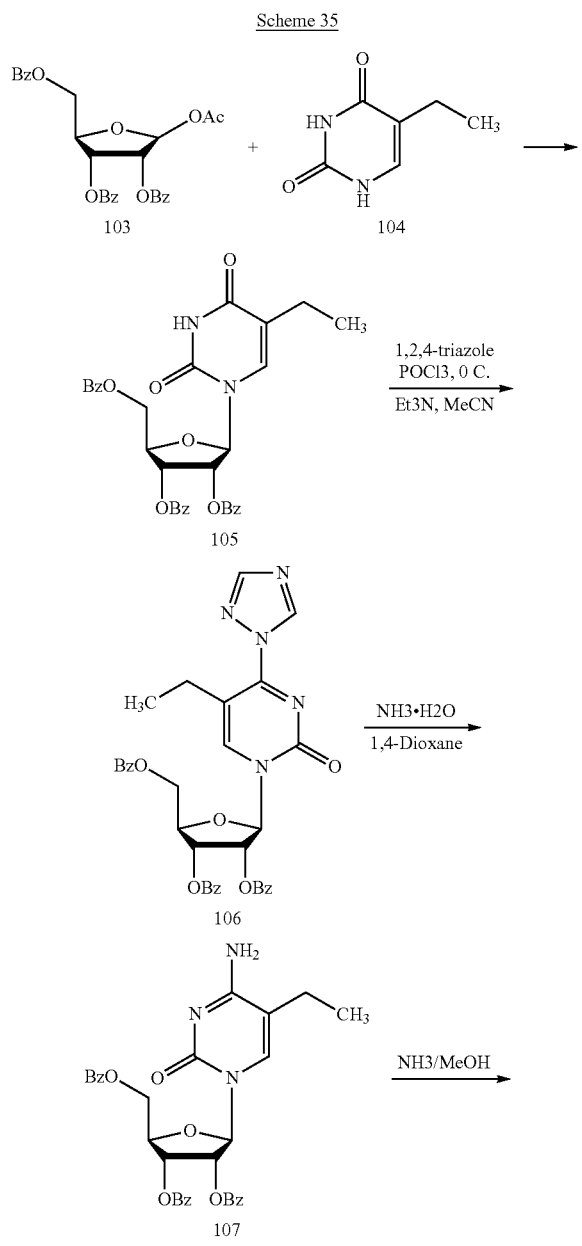

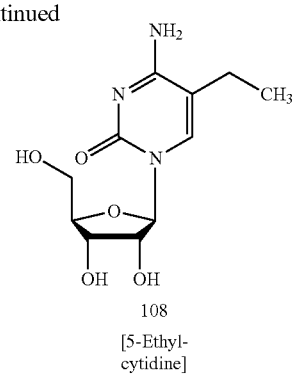

108
[5-Ethyl-cytidine]

Compound 105: To a solution of compound 104 (2.8 g, 20 mmol) in dry acetonitrile (30 mL) was added BSA (21 g, 100 mmol, 5 eq). The reaction mixture was stirred at 60° C. for 4 h and cooled to room temperature. To this reaction mixture were added compound 103 (10.1 g, 20 mmol), TMSOTf (10.8 mL, 60 mmol, 3 eq), and the resulted reaction mixture was stirred at 60° C. for 4 h. Upon completion of the reaction as monitored by TLC, the reaction mixture was treated with methylene chloride and saturated sodium bicarbonate. The organic phase was separated, and the aqueous phase was extracted with dichloromethane. The combined organic phase was dried over anhydrous $Na_2SO_4$. The drying agent was filtered off, and the filtrate was concentrated under reduced pressure. The crude product was purified by flash chromatography on a silica gel column giving 11 g desired compound 105 in 95% yield.

Compound 106: To a solution of 1,2,4-1H-triazole (19.36 g, 285 mmol), phosphorus oxychloride (5.8 mL 63 mmol) in dry methylene chloride (300 mL) was added slowly triethylamine (37.5 mL, 270 mmol) at 0° C. After the reaction mixture was warmed to room temperature, compound 105 (16.7 g, 30 mmol) was added. The reaction mixture was added and stirred at temperature for 2 h. Upon completion of the reaction as monitored by TLC, the reaction mixture was treated with methylene chloride and saturated sodium bicarbonate. The organic phase was separated, and the aqueous phase was extracted with methylene chloride. The combined organic phase was dried over anhydrous $Na_2SO_4$. The drying agent was filtered off, and the filtrate was concentrated under reduced pressure giving crude product compound 106 which was carried to the next step without further purification.

Compound 107: To a stirred solution of compound 106 (crude obtained above) in dioxane (135 mL) was added concentrated ammonia solution (19.4 mL). The reaction mixture was stirred at room temperature for 5 h. Upon completion of the reaction as monitored by TLC, the reaction mixture was concentrated under reduced pressure to give crude compound 107 which was carried to the next step without further purification.

5-Ethyl-cytidine (108): A solution of compound 107 (crude obtained above) in saturated ammonia methanol solution (100 mL) was stirred at room temperature in s sealed container for 24 h. Upon completion of the reaction as monitored by TLC, the reaction mixture was concentrated under reduced pressure to dryness. The crude product was purified by flash chromatography on a silica gel column resulting in the desired final product 108 which was was characterized by NMR, MS and UV spectral analyses. $^1$H NMR (DMSO-$d_6$) δ 7.8 (s, 1H), 7.3 (brs, 2H), 5.75 (s, 1H), 5.31 (s, 1H), 5.16 (s, 1H), 5.01 (s, 1H), 3.97 (s, 2H), 3.83 (s, 1H), 3.68 (d, 2H, J=12.0 Hz), 3.55 (d, 2H, J=12.4 Hz), 2.25 (q, 2H, J=7.2 Hz), 1.05 (t, 3H, J=7.2 Hz). Mass Spectrum: m/z 272.0 (M+H)$^+$.

Example 43

Synthesis of 5-Methoxy-cytidine (03600014030)

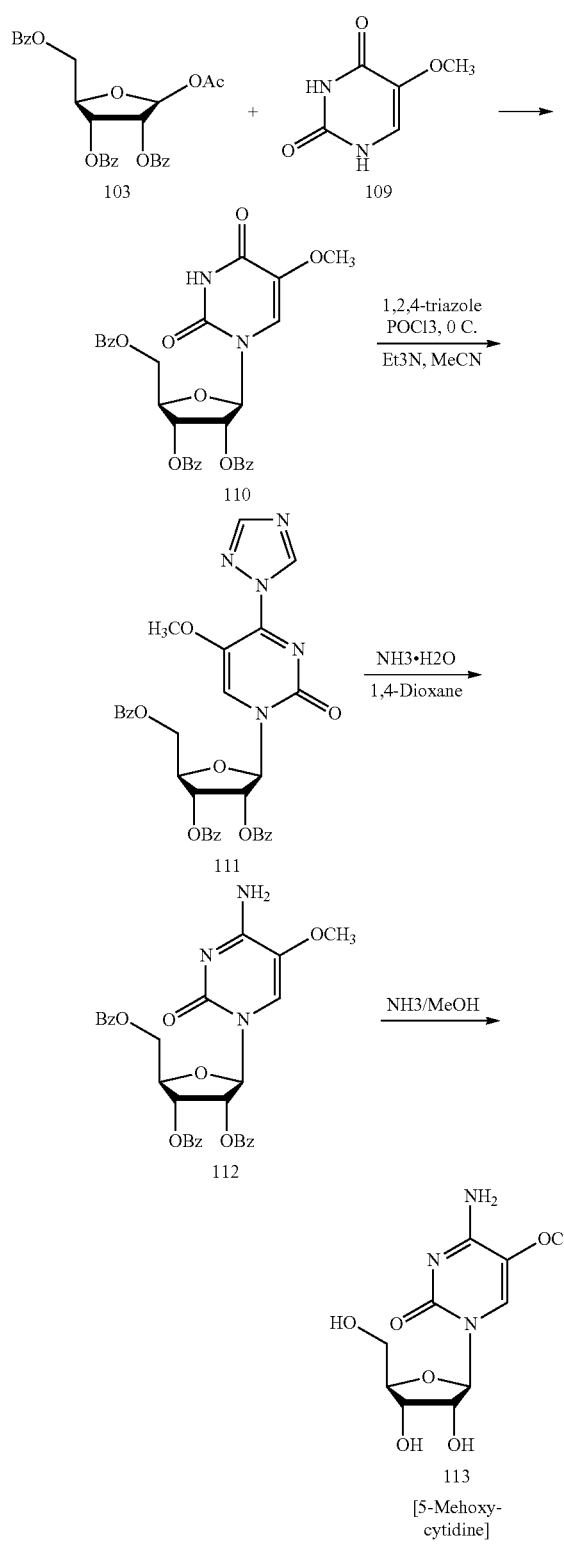

Compound 110: To a solution of compound 109 (1.42 g, 10 mmol) in dry acetonitrile (30 mL) was added BSA (10.5 g, 50 mmol). The reaction mixture was stirred at 60° C. for 4 h and cooled to room temperature. To the reaction mixture were added compound 103 (5.04 g, 10 mmol) and TMSOTf (2.7 mL, 15 mmol). The resulted reaction mixture was stirred at 60° C. for 4 h. Upon completion of the reaction as monitored by TLC, the reaction mixture was treated with methylene chloride and saturated sodium bicarbonate. The organic phase was separated, and the aqueous phase was extracted with methylene chloride. The combined organic phase was dried over anhydrous $Na_2SO_4$. The drying agent was filtered off, and the filtrate was concentrated under reduced pressure. The crude product was purified by flash chromatography on a silica gel column giving 3.8 g desired compound 110 in 65% yield.

Compound 111: To a solution of 1,2,4-1H-triazole (8.73 g, 126 mmol) and phosphorus oxychloride (2.6 mL 27.9 mmol) in dry methylene chloride (300 mL) was added slowly triethylamine (16.6 mL, 119.8 mmol) at 0° C. After the reaction mixture was warmed to room temperature, compound 110 (7.8 g, 13.3 mmol) was added. The reaction mixture was stirred at temperature for 2 h. Upon completion of the reaction as monitored by TLC, the reaction mixture was treated with methylene chloride and saturated sodium bicarbonate. The organic phase was separated, and the aqueous phase was extracted with methylene chloride. The combined organic phase was dried over anhydrous $Na_2SO_4$. The drying agent was filtered off, and the filtrate was concentrated under reduced pressure giving crude product compound 111 which was carried to the next step without further purification.

Compound 112: To a stirred solution of compound 111 (crude obtained above) in dioxane (60 mL) was added concentrated ammonia solution (8.6 mL). The reaction mixture was stirred at room temperature for 5 h. Upon completion of the reaction as monitored by TLC, the reaction mixture was concentrated under reduced pressure giving crude compound 112 which was carried to the next step without further purification.

5-Methoxy-cytidine (113): A solution of compound 112 (crude obtained above) in saturated ammonia methanol solution (80 mL) was stirred at room temperature in a sealed container for 24 h. Upon completion of the reaction as monitored by TLC, the reaction mixture was concentrated under reduced pressure to dryness. The crude product was purified by flash chromatography on a silica gel column resulting in the desired final product 113 which was characterized by LC-MS, UV and HNMR. $^1$H NMR (DMSO-$d_6$) δ 7.73 (s, 1H), 7.50 (s, 1H), 7.03 (s, 1H), 5.76 (d, 1H, J=3.6 Hz), 5.31 (s, 1H), 5.26 (d, 1H, J=4.0 Hz), 4.96 (d, 1H, J=4.8 Hz), 4.01 (d, 1H, J=4.4 Hz), 3.95 (s, 1H), 3.83 (d, 1H, J=2.8 Hz), 3.78 (d, 1H, J=12.0 Hz), 3.62 (s, 3H), 3.58 (d, 1H, J=12.4 Hz); Mass Spectrum: m/z 274.0 (M+H)$^+$.

Example 44

Synthesis of 2-Thio-5-amino(TFA)-methyl-Uridine (00900013015-TFA)

Scheme 37

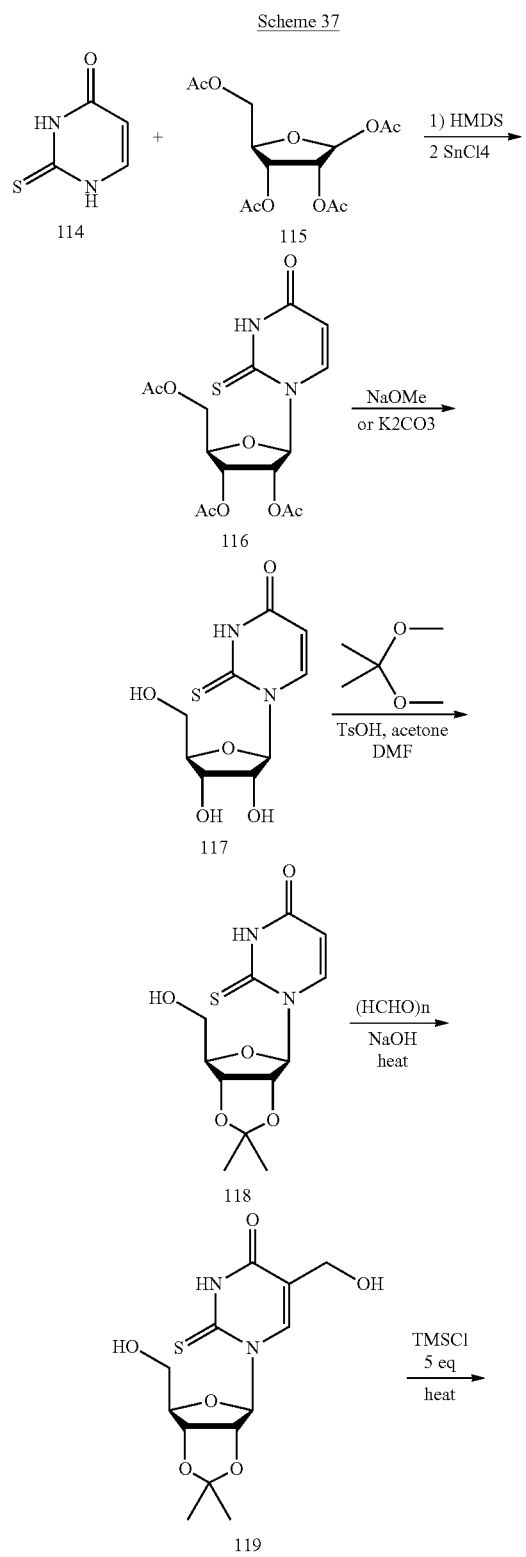

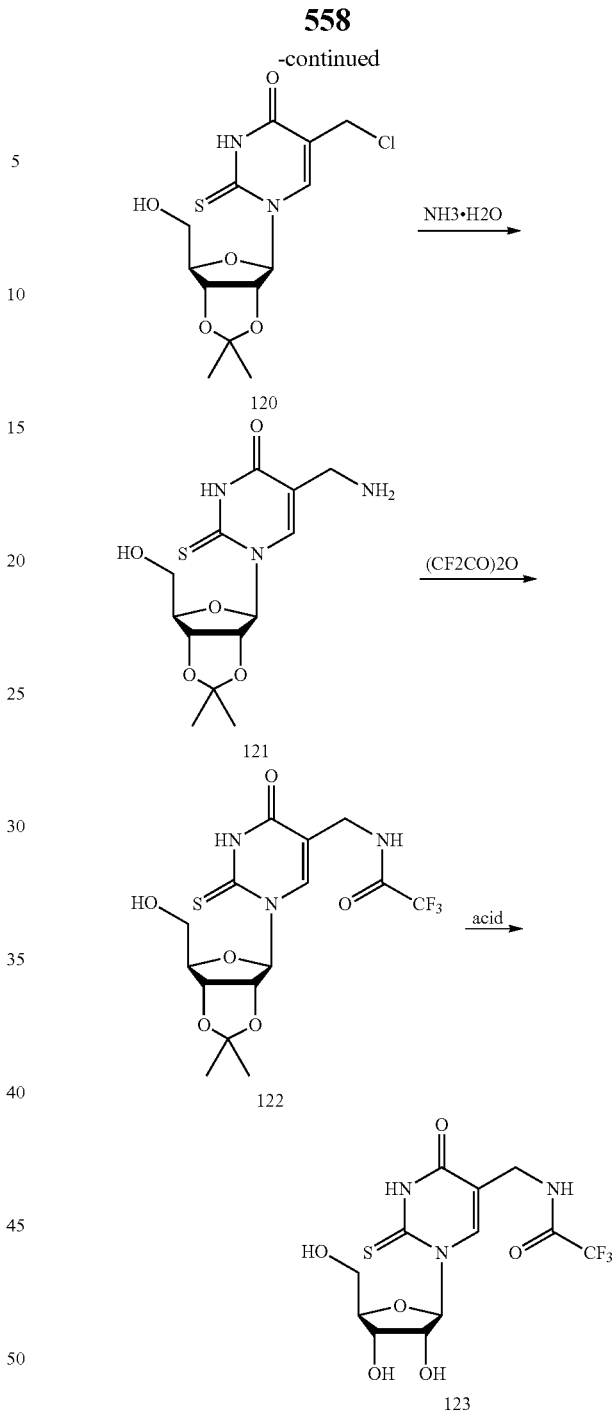

Compound 116: A mixture of 2-thiouracil 114 (6.0 g, 46.8 mmol), trimethyl chlorosilane (5.4 mL), hexamethyldisilazane (240 mL) and catalytic amount of ammonium sulfate were refluxed for 18 h. Upon the reaction mixture became clear, it was concentrated under reduced pressure to dryness at the temperature not greater than 45° C. To the resulted silylated thiouracil was dissolved in 1,2-dichloroethane (60 mL), and 1,2,3,5-tetra-O-acetyl-D-ribofuranose (16.5 g, 51.9 mmol) was added. It was stirred until homogeneous, stannic chloride (7.2 mL, 62.4 mmol) was added and stirred or 1 h. Upon completion of the reaction as monitored by TLC, the reaction mixture was poured into 150 mL of saturated sodium bicarbonate and stirred for 1 h. The mixture was filtered through a pad of Celite, and washed with methylene chloride. The organic phase was separated, and the aqueous was extracted with dichloromethane. The combined organic phase was dried over anhydrous Na$_2$SO$_4$. The drying agent was filtered off, and the filtrate was concentrated under reduced pressure. The crude product was purified by flash chromatography on a silica gel column using ethyl acetate-petroleum ether (1:2 to 1:1) resulting in compound 116 (15.0 g, 38.8 mmol) in 82.9% yield.

Compound 117: To a stirred solution of compound 116 (15.0 g, 38.8 mmol) in absolute methanol (150 mL) was added lithium hydroxide (3.7 g, 155.2 mmol, 4 eq), and the reaction mixture was stirred at room temperature for 30 min. Upon completion of the reaction as monitored by TLC, hydrochloric acid (3 N) was added to adjust to neutral. The mixture was concentrated under reduced pressure resulting in the white precipitate which was filtered giving 5 g of desired product. The filtrate was concentrated under reduced pressure to give crude product. The crude product was purified by flash chromatography on a silica gel column using methylene chloride-methanol (10:1 to 5:1) resulted compound 117 (1.2 g). 6.2 g (23.8 mmol) in 61.3% yield.

Compound 118: To a stirred solution of compound 117 (6.0 g, 23.1 mmol) in acetone (60 mL) was added p-toluenesulfonic acid (0.8 g, 4.7 mmol) and 2,2-Dimethyoxypropane (5.0 g 48.1 mmol). The resulted reaction mixture was stirred at room temperature for 2 h, and solid material disappeared. Upon completion of the reaction as monitored by TLC, sodium bicarbonate (1.5 g) was added, and it was stirred for 1 h. The solid was filtered off and washed with dichloromethane. The filtrate was concentrated under reduced pressure. The crude product was purified by flash chromatography on a silica gel column using methylene chloride-methanol (20:1 to 10:1) as eluent resulting in (6.4 g, 21.3 mmol) compound 118 in 92.2% yield.

Compound 119: To a stirred solution of compound 118 (6.0 g, 20 mmol) in aqueous potassium hydroxide (0.5 M, 100 mL) was added paraformaldehyde (3.0 g, 100 mmol). The resulted reaction mixture was stirred at 50° C. overnight. Upon completion of the reaction as monitored by TLC, hydrochloric acid (3 M) was added to adjust to neutral. The mixture was concentrated under reduced pressure to dryness. The crude product was purified by flash chromatography on a silica gel column using methylene chloridemethanol (20:1 to 10:1) resulting in (4.2 g, 12.7 mmol) compound 119 in 63.6% yield.

Compound 120: To a stirred solution of compound 119 (7.5 g, 22.7 mmol) in dioxane (50 mL) was added TMSCl (14.5 mL, 113 mmol, 5 eq). The reaction mixture was stirred at 50° C. under N$_2$ atmosphere overnight. Upon almost completion of the reaction as monitored by TLC, the reaction mixture was concentrated at the temperature not over 30° C. under reduced pressure. The crude product was dissolved in anhydrous acetone, and concentrated under reduced pressure to dryness. Thus resulted crude product compound 120 was used in next step without further purification.

Compound 121: To a stirred solution of compound 120 (crude obtained above) in dioxane (50 mL) was added ammonium hydroxide. The reaction mixture was stirred at room temperature overnight. Upon completion of the reaction as monitored by TLC, the reaction mixture was concentrated under reduced pressure to dryness. The crude product was purified by flash chromatography on a silica gel column using ethyl acetate-petroleum ether (1:3 to 1:1) as eluent resulting in compound 121 (3.1 g) which was used in next step directly.

Compound 122: A solution of compound 121 (3.1 g, 7 mmol) in dry pyridine (50 mL) was cooled to 0° C., and trifluoroacetic anhydride (18 g, 8 mmol) was added under N$_2$ atmosphere. The reaction mixture was stirred at room temperature for 1 h. Upon completion of the reaction as monitored by TLC, the reaction mixture was diluted with methylene chloride (100 mL) and aqueous sodium bicarbonate (100 mL, 5%). The organic phase was separated, and the aqueous phase was extracted with dichloromethane. The combined organic phase was dried over anhydrous Na$_2$SO$_4$. The drying agent was filtered off, and the filtrate was concentrated under reduced pressure to dryness. The crude product was purified by flash chromatography on a silica gel column using ethyl acetate-petroleum ether (1:5 to 1:3) as eluent resulting in compound 122 which was used directly in next step.

2-Thio-5-amino(TFA)-methyl-Uridine (123): 10 mL of hydrochloric acid (1 M) was added to a flask containing compound 122 (1.0 g). The mixture was stirred at room temperature for 30 min. The reaction mixture was neutralized with Na$_2$CO$_3$. The solid was filtered off, and the filtrate was concentrated under reduced pressure to dryness. The crude product was purified by flash chromatography on a silica gel column giving 290 mg desired final compound 123. Compound 123 was characterized by NMR, MS and UV with 99.0% HPLC purity: $^1$H NMR (DMSO-d$_6$) δ 12.73 (s, 1H), 9.56 (s, 1H), 8.17 (s, 1H), 6.57 (s, 1H), 5.42 (d, 1H, J=4.8 Hz), 5.17 (s, 1H), 5.12 (d, 1H, J=4.4 Hz), 4.02-3.97 (m, 4H), 3.92 (s, 1H), 3.71 (d, 1H, J=12.0 Hz), 3.60 (d, 1H, J=6.6 Hz); Mass Spectrum: m/z 385.7 (M+H)$^+$; 407.7 (M+Na)$^+$.

Example 45

Synthesis of 5-Formyl-2'-O-methylcytidine (03600074036)

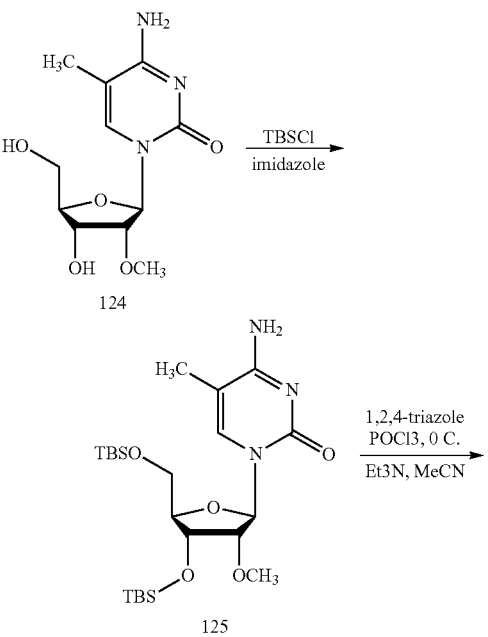

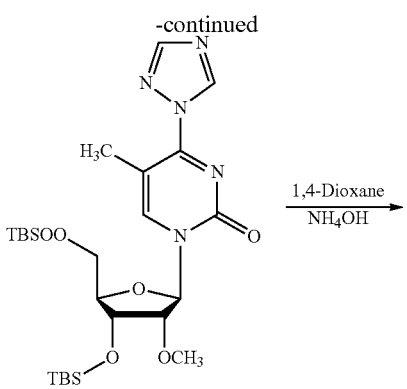

126

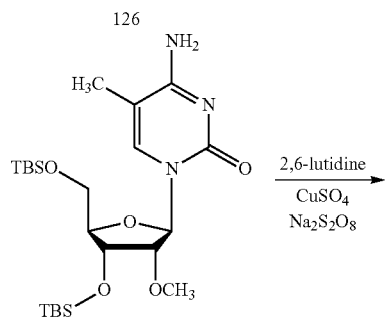

127

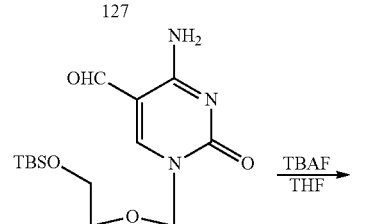

128

NH₂
OHC
HO
OH OCH₃
129

Compound 125: To a solution of compound 124 in dry N,N-dimethylformamide were added tert-Butyldimethylsilyl chloride (3 eq) and imidazole (4 eq). The reaction mixture was stirred at room temperature overnight and then quenched with water. The mixture was extracted with ethyl acetate, and the combined organic phase was washed with brine, and dried over anhydrous Na₂SO₄. The drying agent was filtered off, and the filtrate was concentrated to dryness under reduced pressure. The crude product thus obtained was purified by flash chromatography on a silica gel column giving compound 125.

Compound 126: To a solution of 1,2,4-1H-triazole (4.58 g, 66.3 mmol) in dry methylene chloride (500 mL) was added slowly phosphorus oxychloride (1.34 mL, 14.4 mmol) at room temperature. The mixture was cooled to 0° C., and triethylamine (8.7 mL) was added followed by the addition of compound 125 (3.5 g, 7 mmol) in dichloromethane. The reaction mixture was allowed to warm to room temperature, and stirred for 30 min. Upon completion of the reaction as monitored by TLC, the reaction mixture was treated with a mixture of triethylamine and water, followed by addition of saturated sodium bicarbonate. The organic phase was separated, and dried over anhydrous Na₂SO₄. The drying agent was filtered off, and the filtrate was concentrated under reduced pressure giving crude product compound 126 which was carried to the next step without further purification.

Compound 127: To a stirred solution of compound 126 (crude obtained above) in dioxane (25 mL) was added concentrated ammonium solution (4 mL). The reaction mixture was stirred at room temperature for 1 h. Upon completion of the reaction as monitored by TLC, the reaction mixture was concentrated under reduced pressure giving crude compound 127. The crude product was purified by flash chromatography on a silica gel column using methanol-dichloromethane (1:10) as eluent providing desired product 127.

Compound 128: To a stirred solution of compound 127 (5 g) in acetonitrile (70 mL) were added 2,6-lutidine (3.7 g), and an aqueous solution of sodium persulfate (4.76 g, 20 mL) and copper sulfate (0.638 g, aq. solution). The reaction mixture was stirred at 60° C. for 2 h. The mixture was extracted with dichloromethane. The organic phase was washed with brine and dried over anhydrous Na₂SO₄. The drying agent was filtered off, and the filtrate was concentrated to dryness under reduced pressure. The crude product thus obtained was purified by flash chromatography on a silica gel column giving desired compound 128.

5-Formyl-2'-O-methylcytidine (129): To a stirred solution of compound 128 (1 g, 2 mmol) in dry tetrahydrofuran (15 mL) were added a solution of tetrabutylammonium fluoride in tetrahydrofuran (1 M), followed by the addition of acetic acid (0.3 eq). The reaction mixture was stirred at room temperature. Upon completion of the reaction as monitored by TLC, the reaction mixture was concentrated under reduced pressure to dryness. The crude product was purified by flash chromatography on a silica gel column giving desired compound 129 with 99% HPLC purity. Compound 129 was characterized by NMR, MS and UV. $^1$H NMR (DMSO-d₆) δ 9.39 (s, 1H), 9.04 (s, 1H), 8.16 (s, 1H), 7.84 (s, 1H), 5.83 (s, 1H), 5.32 (s, 1H), 5.08 (d, 1H, J=6.4 Hz), 4.10 (d, 1H, J=4.8 Hz), 3.89 (d, 1H, J=6.8 Hz), 3.81 (s, 1H), 3.74 (s, 1H), 3.64 (d, 1H, J=5.0 Hz), 3.32 (s, 3H); Mass Spectrum: m/z 286 (M+H)+; 571 (2M+H)⁺.

Example 46

Synthesis of 2'-O-Methyl-2-thiouridine (00900073008)

Scheme 39

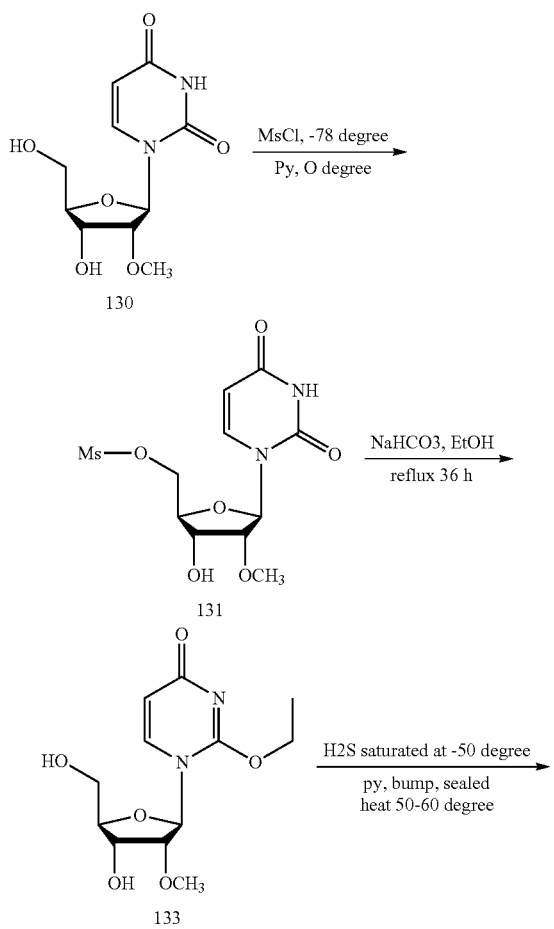

Compound 131: A solution of compound 130 (5.16 g, 20 mmol) in dry pyridine (100 mL) was cooled to −78° C., and MsCl (1.86 mL, 2.76 g, 24 mmol, 1.2 eq) was added dropwise. The reaction mixture was allowed to warm to room temperature, and continued to stir for 1 h. Upon completion of the reaction as monitored by TLC, the reaction mixture was quenched with methanol (1 mL), and concentrated under reduced pressure. The crude product was purified by flash chromatography on a silica gel column using dichloromethane-methanol (50:1 to 20:1) resulting in compound 131 (3.4 g, mmol) in 50% yield.

Compound 133: A mixture of compound 131 (3.36 g, 10 mmol) and sodium bicarbonate (2.1 g, 25 mmol) in ethanol (250 mL) was refluxed under $N_2$ atmosphere for 36 h. The reaction mixture was cooled to room temperature, and solid sodium bicarbonate was filtered off. The filtrate was concentrated under reduced pressure, and the crude product was purified by flash chromatography on a silica gel column using dichloromethane-methanol (50:1 to 20:1) resulting in 1.7 g of compound 133 in 59% yield. Some starting material was recovered. This product was verified by MS spectrum with good HPLC purity.

2'-O-Methyl-2-thiouridine (134): A solution of compound 133 (1.7 g, 5.94 mmol) in 500 mL of anhydrous pyridine in a high-pressure bump vessel was cooled to −50° C. The in house prepared and dried hydrogen sulfide gas was bubbled in the solution to make it saturated at low temperature. The high-pressure bump was sealed, and heated in an oil bath to 50° C. for 4 h, and then increased to 70° C. for 24 h. The reaction vessel was cooled to room temperature, and allowed to open to the air slowly. The reaction mixture was concentrated under reduced pressure, and the residue was purified by flash chromatography on a silica gel column providing desired final product 134 with 98.79% HPLC purity (some starting material was recovered). It was characterized by NMR, MS and UV. $^1$H NMR (DMSO-$d_6$) δ 12.66 (s, 1H), 8.20 (d, 1H, J=8.0 Hz), 6.60 (d, 1H, J=3.2 Hz), 6.00 (d, 1H, J=8.4 Hz), 5.28 (d, 1H, J=4.8 Hz), 5.17 (d, 1H, J=6.0 Hz), 4.10 (t, 1H, J=5.2 Hz), 3.90 (d, 1H, J=3.2 Hz), 3.80 (d, 1H, J=4.4 Hz), 3.75 (d, 1H, J=4.0 Hz), 3.62 (d, 1H, J=4.0 Hz), 3.45 (s, 3H); Mass Spectrum: m/z 275 (M+H)+; 297 (M+Na)+.

Example 47

Synthesis of 2-Selenouridine (03600013046)

Scheme 40

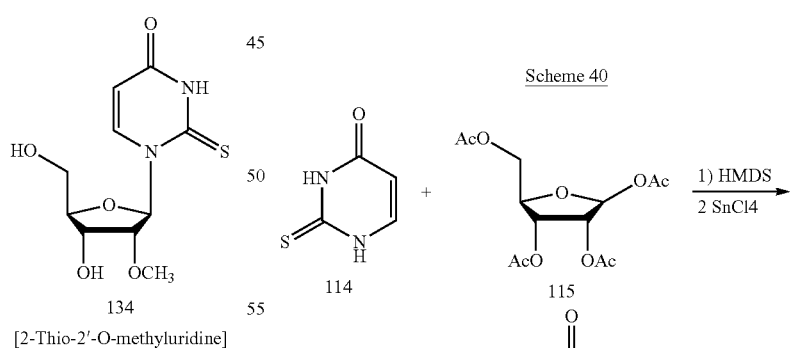

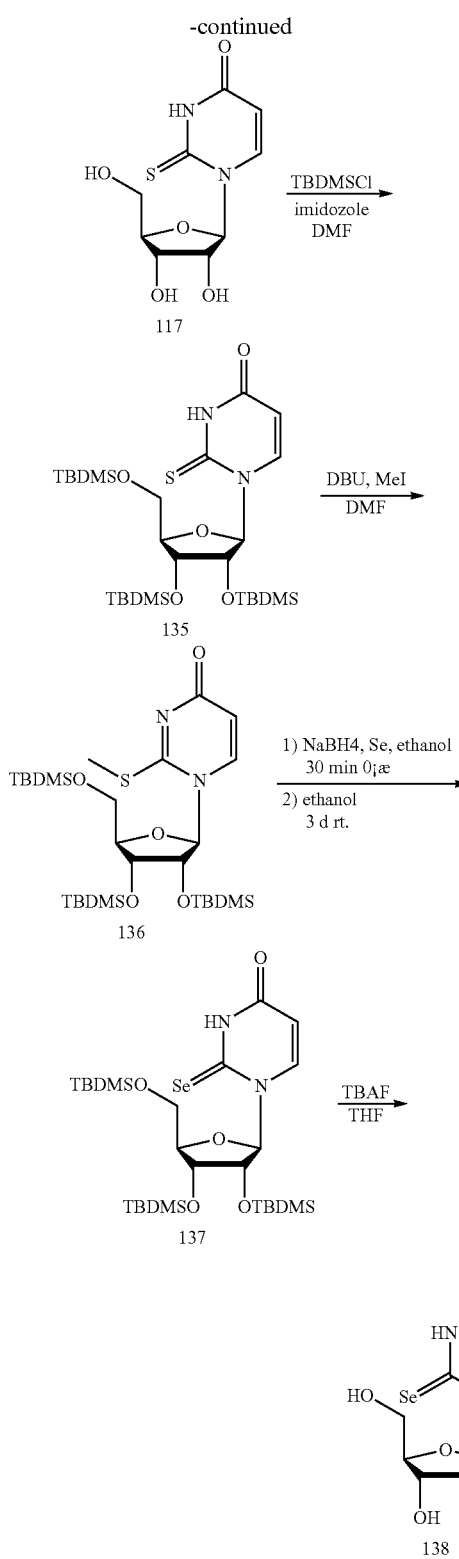

dichloromethane. The organic phase was dried over anhydrous sodium sulfate, and concentrated under reduced pressure. The residue was purified by flash chromatography on a silica gel column providing 20 g compound 135 in 72% yield.

Compound 136: To a solution of compound 135 (5 g, 8.3 mmol) in 50 mL of anhydrous DMF was added iodomethane (11.8 g, 83 mmol, 10 eq), followed by addition of DBU (1.9 g, 12.45 mmol, 1.5 eq). The reaction mixture was stirred at room temperature for 12 h, and quenched with water. The mixture was extracted with dichloromethane. The organic phase was dried over anhydrous sodium sulfate, and concentrated under reduced pressure. The residue was purified by flash chromatography on a silica gel column providing 2.0 g compound 136 in 39% yield.

Compound 137: A suspension of selenium (1.28 g, 16.2 mmol, 5 eq) and sodium borohydride (0.74 g, 19.44 mmol, 6 eq) in anhydrous ethanol was stirred at 0° C. under nitrogen flow for 30 minutes till clear colorless solution. A solution of compound 136 (2.0 g, 3.24 mmol) in 10 mL of ethanol was added to the selenium hydride system with syringe. The reaction mixture was stirred at room temperature for 3 days and monitored by TLC. It was quenched with water and extracted with methylene chloride. The organic phase was dried over anhydrous sodium sulfate and concentrated under reduced pressure. The residue was purified by flash chromatography on a silica gel column providing 1.8 g product 137 in 85% yield.

2-Selenouridine (138): To a solution of compound 137 (1.8 g, 2.7 mmol) in 10 mL of THF was added 17 mL of TBAF solution in THF (1 mol/L). It was stirred at room temperature for 2 hours. The reaction mixture was quenched with water and concentrated under reduced pressure to dryness. The residue was purified several times by flash chromatography on silica gel columns providing 260 mg of compound 138 with 96% HPLC purity. It was characterized by NMR, MS and UV spectral analyses. $^1$H NMR (DMSO) δ 13.9 (s, 1H), 8.21 (d, J=8.0 Hz, 1H), 6.70 (d, J=4.0 Hz, 1H), 6.13 (d, J=8.4 Hz, 1H), 5.42 (d, J=5.2 Hz, 1H), 5.26 (t, J=4.4 Hz, 1H), 5.11 (d, J=5.6 Hz, 1H), 4.11-4.06 (m, 1H), 4.01-3.95 (m, 1H), 3.94-3.90 (m, 1H), 3.75-3.67 (m, 1H), 3.64-3.56 (m, 1H). Mass Spectrum: m/z 308.8 (M+H)$^+$. 330.7 (M+Na)$^+$.

Example 48

Synthesis of 5-N-methyl-N-TFA-aminomethyl-2-thiouridine (00900013015-N-Me, N-TFA)

Scheme 41

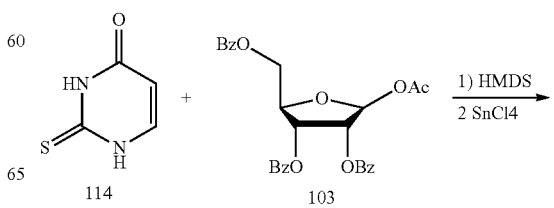

Compound 135: A solution of compound 117 (12 g, 46.1 mmol), t-butyldimethylsilyl chloride (70 g, 461.0 mmol, 10 eq), and imidazole (36.55 g, 553.2 mmol, 12 eq) in 150 mL of anhydrous DMF was stirred at 60° C. for 12 h. Upon completion of the reaction as monitored by TLC, the reaction mixture was quenched with water and extracted with

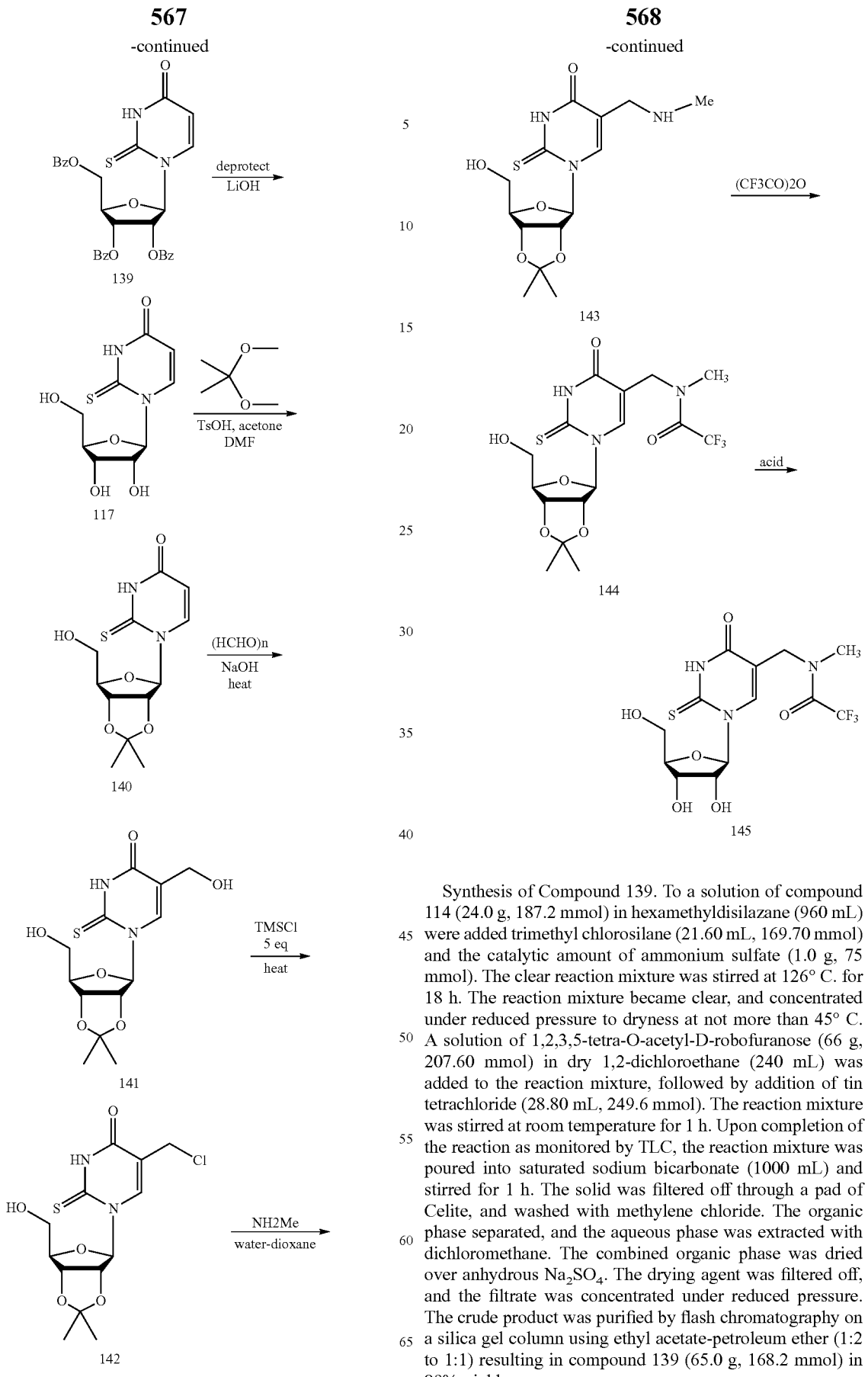

Synthesis of Compound 139. To a solution of compound 114 (24.0 g, 187.2 mmol) in hexamethyldisilazane (960 mL) were added trimethyl chlorosilane (21.60 mL, 169.70 mmol) and the catalytic amount of ammonium sulfate (1.0 g, 75 mmol). The clear reaction mixture was stirred at 126° C. for 18 h. The reaction mixture became clear, and concentrated under reduced pressure to dryness at not more than 45° C. A solution of 1,2,3,5-tetra-O-acetyl-D-robofuranose (66 g, 207.60 mmol) in dry 1,2-dichloroethane (240 mL) was added to the reaction mixture, followed by addition of tin tetrachloride (28.80 mL, 249.6 mmol). The reaction mixture was stirred at room temperature for 1 h. Upon completion of the reaction as monitored by TLC, the reaction mixture was poured into saturated sodium bicarbonate (1000 mL) and stirred for 1 h. The solid was filtered off through a pad of Celite, and washed with methylene chloride. The organic phase separated, and the aqueous phase was extracted with dichloromethane. The combined organic phase was dried over anhydrous $Na_2SO_4$. The drying agent was filtered off, and the filtrate was concentrated under reduced pressure. The crude product was purified by flash chromatography on a silica gel column using ethyl acetate-petroleum ether (1:2 to 1:1) resulting in compound 139 (65.0 g, 168.2 mmol) in 89% yield.

Synthesis of Compound 117. To a stirred solution of compound 139 (70 g, 181.17 mmol) in methanol (700 mL) was added lithium hydroxide (15 g, 625 mmol). It was stirred at room temperature for 1 min. Upon completion of the reaction as monitored by TLC, the reaction mixture was treated with hydrochloric acid (3 N) to adjust to neutral. The reaction mixture was concentrated under reduced pressure resulting in white solid precipitation. The precipitate was filtered giving 31.2 g compound 117 as white solid in 66.2% yield.

Synthesis of Compound 140. To a stirred solution of compound 117 (31.20 g, 119.88 mmol) in dry acetone (1000 mL) were added p-toluenesulfonic acid (3.06 g, 17.79 mmol) and 2,2-dimethoxypropane. The resulted reaction mixture was stirred at room temperature for 2 h till solid completely disappeared. Upon completion of the reaction as monitored by TLC, the reaction mixture was adjusted to neutral with by addition of saturated sodium bicarbonate (150 mL). The solid was filtered off, and washed with dichloromethane. The filtrate was concentrated under reduced pressure, and the crude product was purified by flash chromatography on a silica gel column using dichloromethane-methanol (20:1 to 10:1) to give final product compound 140 (33.97 g, 113.10 mmol) in 94.36% yield.

Synthesis of Compound 141. To a stirred mixture of compound 140 (26.0 g, 86.57 mmol) and aqueous potassium hydroxide (0.5 N, 200 mL) was added paraformaldehyde (20.0 g, 666.66 mmol). The reaction mixture was stirred at 50° C. overnight. Upon completion of the reaction as monitored by TLC, the reaction mixture was adjusted to neutral with hydrochloric acid (3 N). The reaction mixture was concentrated under reduced pressure to dryness. The crude product was purified by flash chromatography on a silica gel column using methylene chloride-methanol (20:1 to 10:1) resulting in compound 141 (25 g, 75.76 mmol) in 87.51% yield.

Synthesis of Compound 142. Compound 141 (16 g, 48.43 mmol) was dissolved in anhydrous dioxane (500 mL), and chlorotrimethylsilane (65 mL, 507 mmol) was added to the stirred solution. The reaction mixture was stirred overnight at 50° C. under $N_2$ atmosphere. The reaction mixture was concentrated under reduced pressure at not less than 30° C. giving crude product compound 142 which was carried to the next step without further purification.

Synthesis of Compound 143. To a stirred solution of compound 142 (crude obtained above) in dioxane (200 mL) was added methylamine $MeNH_2$ (200 mL, 40% aq. Solution, 2.32 mol, 48 eq). The reaction mixture was stirred at room temperature for 10 min. Upon completion of the reaction as monitored by TLC, the reaction mixture was concentrated under reduced pressure to dryness. The crude product was purified by flash chromatography on a silica gel column using methylene chloride-methanol (30:1 to 20:1) resulting in compound 143 (6.7 g 19.51 mmol) in 40.28% yield.

Synthesis of Compound 144. To a stirred solution of compound 143 (6.45 g, 18.78 mmol) in dry pyridine (100 mL) was added trifluoroacetic anhydride (7.94 mL, 56.32 mmol, 3 eq). The reaction mixture was stirred at room temperature for 10 h. Upon completion of the reaction as monitored by TLC, the reaction mixture was concentrated under reduced pressure to dryness. The crude product was purified by flash chromatography on a silica gel column using ethyl acetate-petroleum ether (1:5 to 1:2) resulting in compound 144 (7.5 g, 17.06 mmol) in 90.84% yield.

Synthesis of Compound 145. To a stirred solution of compound 144 (6 g, 13.65 mmol) in methanol (60 mL) was added hydrochloric acid (1 N, 35 mL). It was stirred at room temperature for 10 h, and then stirred at 80° C. for 0.5 h. Upon completion of the reaction as monitored by TLC, the reaction mixture was cooled to room temperature and treated with methylene chloride (10 mL). The reaction mixture was concentrated under reduced pressure to dryness. The crude product was purified by flash chromatography on a silica gel column using methylene chloride-methanol (30:1 to 20:1) resulting in 2.5 g of final product 145 in 45.86% yield with 99.29% HPLC purity. Compound 145 was characterized by NMR, MS and UV spectral analyses. $^1$H NMR (DMSO-$d_6$) δ s, 1H), 8.2 (d, J=6.9 Hz, 1H), 6.5 (t, J=2.1 Hz, 1H), 5.4 (d, J=3.9 Hz, 1H), 5.20-5.07 (m, 2H), 4.37-4.15 (m, 2H), 4.08-4.05 (dd, 1H), 3.99-3.91 (m, 2H), 3.75-3.57 (m, 2H), 3.1 (d, J=1.2 Hz, 2H), 2.9 (s, 1H). Mass Spectrum m/z 400 $(M+H)^+$. 422 $(M+Na)^+$. UV, λmax=278 nm.

Example 49

Synthesis of 5-(2-hydroxyethoxycarbonyl methyl)uridine (03600013047)

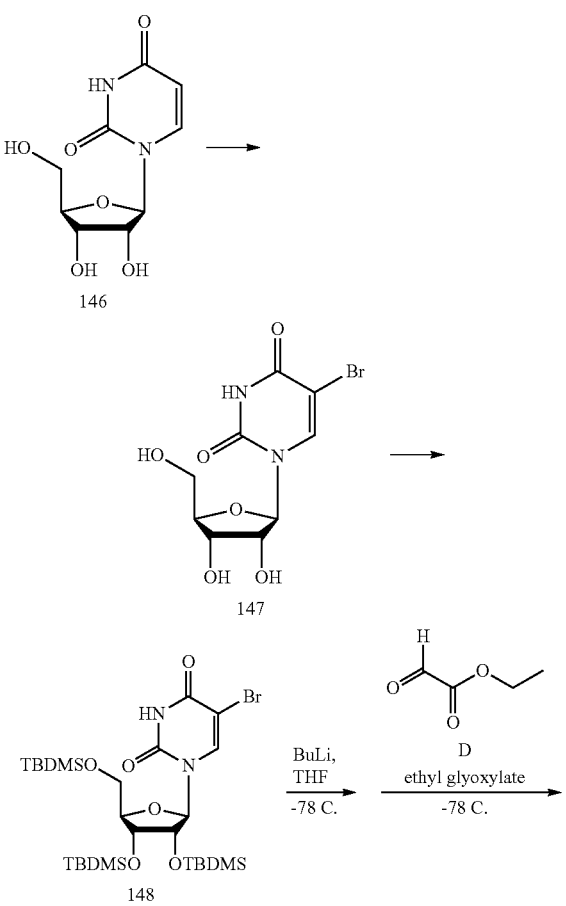

Scheme 42

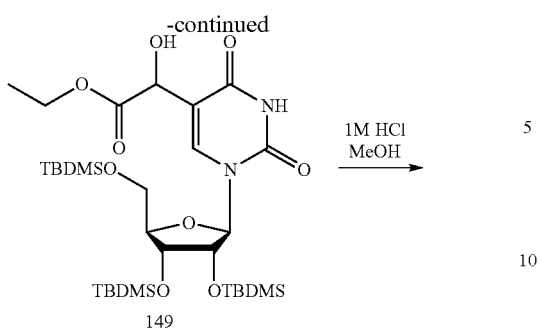

149

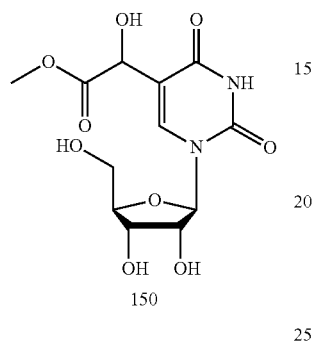

150

Synthesis of Compound 147: To a solution of uridine 146 (20.0 g, 82 mmol) and NBS (21.7 g, 0.12 mol) in anhydrous dimethylfomamide was added AIBN (0.1 eq) in anhydrous dimethylfomamide, then the solution was stirred at 80° C. for 4 h. Saturated sodium thiosulfate solution (20 mL) was added. After evaporation of the solvent, the residue was precipitation with methanol to give 22.0 g compound 147 as light yellow solid.

Synthesis of Compound 148: To the solution of compound 147 (22.0 g, 66 mmol), imidazole (23.0 g, 0.33 mol) in anhydrous dimethylfomamide (100 mL) was added TBDMSCl (50.0 g, 0.32 mol) in anhydrous dimethylfomamide (50.0 mL), then the solution was stirred at rt overnight. Saturated sodium bicarbonate solution (30 mL) was added. The aqueous phase was extracted with ethyl acetate (2×300 mL), and the combined organic phase was washed with brine, and dried over sodium sulfate. After evaporation of the solvent, the residue was purified by silica gel chromatography giving 40.0 g compound 148 as light yellow syrup.

Synthesis of Compound 149: To a solution of compound 148 (10.0 g, 15.0 mmol) in anhydrous THF (100 mL) at −78° C. was added n-BuLi (2.5 M in hexane, 24 mL). The solution was stirred for 1 h, and freshly distilled ethyl glyoxylate (32 mmol) was added. The mixture was stirred for 1 h at −78° C., warmed to room temperature, and stirred overnight. Saturated ammonium chloride (50 mL) was added. The aqueous phase was extracted with ethyl acetate (3×100 mL), and the combined organic phase was washed with brine, and dried over sodium sulfate. After evaporation of the solvent, the residue was purified by silica gel chromatography, eluting with 1-3% methanol in dichloromethane, giving 4.0 g compound 149 as light yellow syrup.

Synthesis of Compound 150: 5-(Ethoxycarbonyl)(hydroxy)methyl-2',3',5'-tris-O-(tert-butyldimethylsilyl)uridine compound 149 (4.0 g, 5.8 mmol) was treated added HCl saturated solution in methanol (0.5 M, 50 mL). The mixture was stirred at room temperature overnight. After concentrating the mixture to dryness under reduced pressure, the residue was purified by silica gel chromatography, eluting with 8-12% methanol in dichloromethane, giving compound 150 as light yellow foam. HPLC purity: 96%. ¹H NMR (300 MHz, DMSO-d₆) δ 11.46 (s, 1H), 7.89-7.93 (m, 1H), 5.80-5.86 (m, 2H), 5.39 (s, 1H), 5.06-5.12 (m, 2H), 4.83 (s, 1H), 3.55-3.95 (m, 8H); ESI mass spectrum m/z: 332.8 [M+H]⁺, 254.8 [M+Na]⁺. UV, λmax=270 nm.

Example 50

Synthesis of N⁴,2'-O-dimethyl Cytidine (00900074004)

Scheme 43

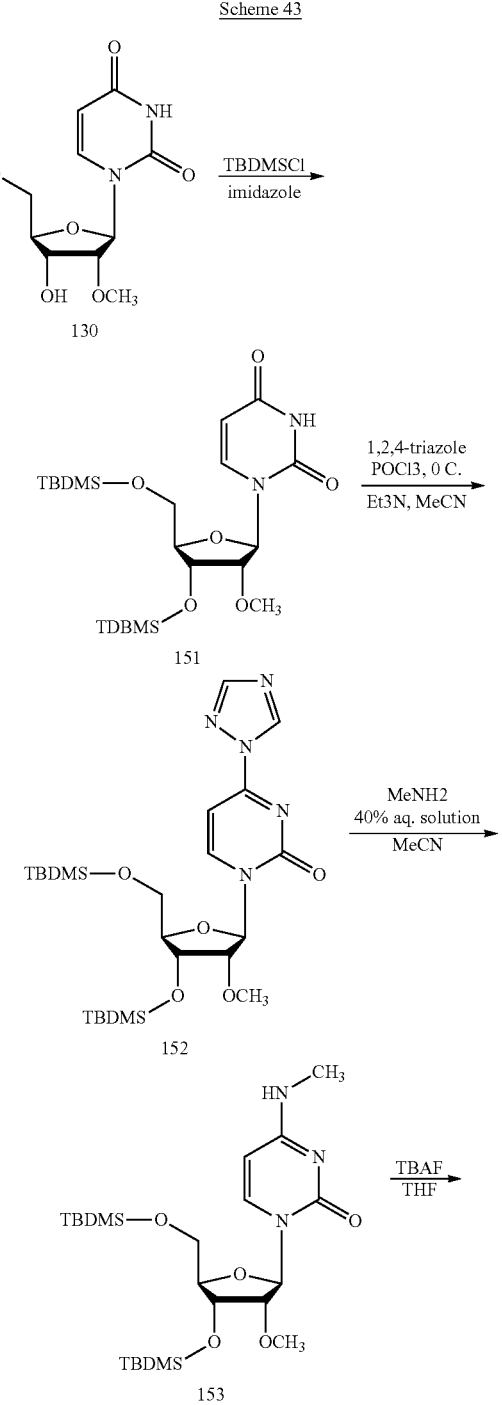

-continued

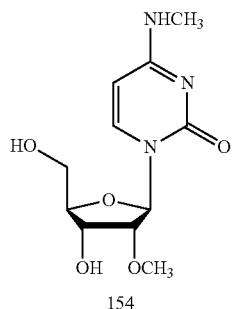

154

Synthesis of Compound 151. To a solution of compound 130 (5.16 g, 20.0 mmol) in dry DMF (50 mL) were added tert-butyldimethylsilyl chloride (12.0 g, 80 mmol) and imidazole (6.8 g, 100.0 mmol). The clear reaction mixture was stirred at room temperature for 24 h. Water was added, and the mixture was extracted with ethyl acetate. The combined organic phase was washed with brine, and dried over anhydrous $Na_2SO_4$. The drying agent was filtered off, and the filtrate was concentrated to dryness under reduced pressure. The crude product thus obtained was purified by flash chromatography on a silica gel column using petroleum ether-ethyl acetate (5:1 to 1:1) to give 8.3 g compound 151 as colorless oil in 85%.

Synthesis of Compound 152. To a stirred mixture of 1,2,4-triazole (2.24 g, 32.5 mmol) in anhydrous methylene chloride (20 mL) at 0° C. was added $POCl_3$ (1.04 g, 6.8 mmol) slowly. Triethylamine (3.09 g, 30.6 mmol) was then added dropwise. The resulted suspension was stirred for 30 min. A solution of compound 151 (1.7 g, 3.4 mmol) in anhydrous dichloromethane (5 mL) was added. The reaction mixture was then continuously stirred overnight and quenched with water. The mixture was extracted with dichloromethane. The combined organic phase was washed with brine and dried over anhydrous $Na_2SO_4$. The drying agent was filtered off, and the filtrate was concentrated under reduced pressure to give 1.9 g crude product compound 152 which was carried to the next step without further purification.

Synthesis of Compound 153. To a stirred solution of compound 152 (1.9 g, crude obtained above) in absolute ethanol (20 mL) was added methylamine $MeNH_2$ (20 mL, 40% aq. solution). The reaction mixture was stirred at room temperature for 30 min. The reaction mixture was concentrated under reduced pressure to dryness. The crude product was purified by flash chromatography on a silica gel column using petroleum ether-ethyl acetate (5:1 to 1:1) resulting in 1.5 g of compound 153 (86%) as a white solid.

Synthesis of $N^4$,2'-O-Dimethylcytidine (154). Tetrabutylammonium fluoride trihydrate (1.58 g, 6.0 mmol) was added to a stirred solution of compound 153 (1.5 g, 3.0 mmol) in dry THF (15 mL), and the reaction mixture was stirred at room temperature for 12 h. The mixture was then concentrated under reduced pressure. The crude product was purified by flash chromatography on a silica gel column using methylene chloride-methanol (20:1) to give final product compound 154 (500 mg, 61.4%) as a white solid. HPLC purity: 97.56%. $^1$H NMR (DMSO-$d_6$): δ 7.81 (d, 1H, J=7.6 Hz), 7.68 (m, 1H, NH), 5.86 (d, 1H, J=4.4 Hz), 5.72 (d, 1H, J=7.2 Hz), 5.07 (m, 2H, J=8.0 Hz), 4.05 (s, 1H), 3.81 (t, 1H, J=2.8 Hz), 3.60-3.70 (m, 2H), 3.53-3.58 (m, 1H), 3.36 (d, 3H, J=4.8 Hz), 2.74 (d, 3H, J=4.8 Hz). ESI MS, m/e 272 (M+H)$^+$, 273 (2M+H)$^+$. UV, $\lambda_{max}$=270.50 nm, ε=11557 L·mol$^{-1}$ cm$^{-1}$, y=11557x, $R^2$=0.9991 (C=2.7368× 10$^{-5}$8.2103×10$^{0.5}$ mol/L).

Example 51

Synthesis of 5-carbanoylmethyl uridine (03600013036)

Scheme 44

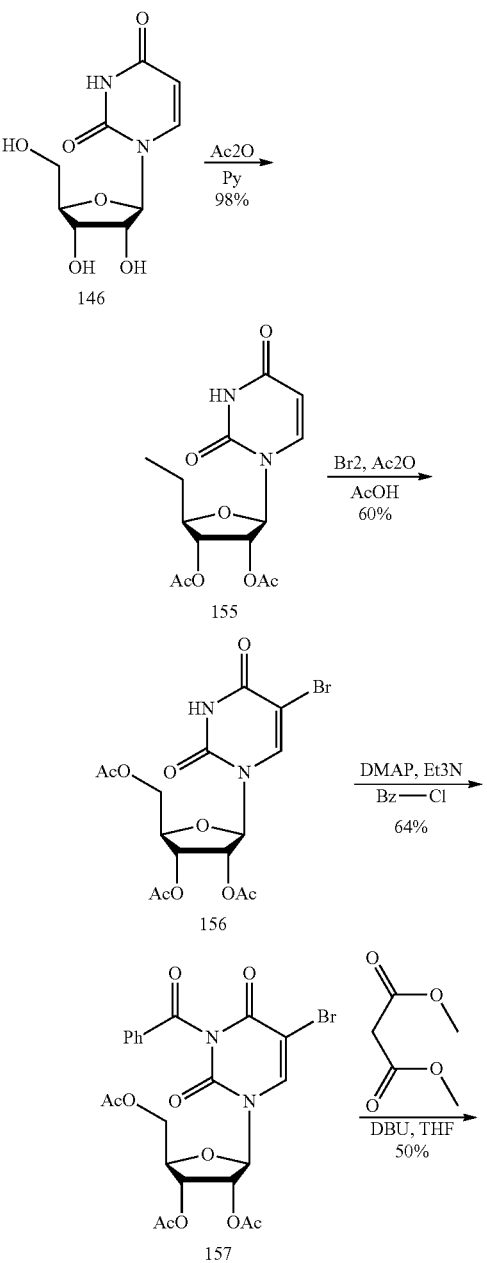

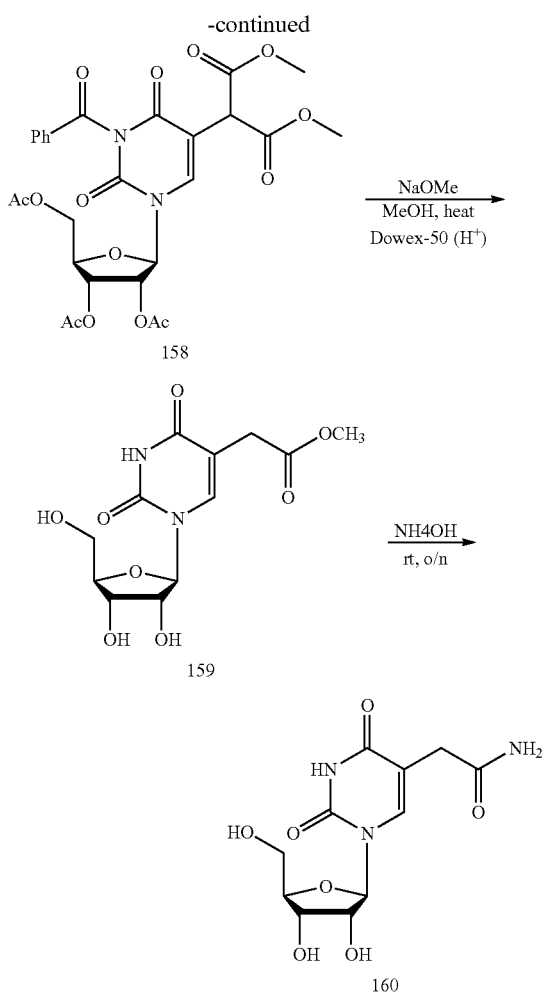

Synthesis of 2',3',5'-tri-O-acetyluridine (155). To a solution of uridine 146 (1.0 g, 4.0 mmol) in 20 mL of pyridine was added 2 mL (2.16 g, 21.0 mmol) of acetic anhydride. The resulting reaction mixture was heated to 60° C. for 3 h, and the TLC indicated its completion. The reaction mixture was concentrated, and the residue was purified by flash chromatography on a silica gel column using dichloromethane-methanol (80:1) as eluent giving 1.2 g desired product 155 in 79% yield.

Synthesis of 5-bromo-2',3',5'-tri-O-acetyluridine (156). Compound 155 (1.2 g, 3.0 mmol) was dissolved in 20 mL of acetic acid, and 1.2 mL (1.25 g, 11 mmol) acetic anhydride was added. The resulting mixture was cooled to 0° C. in an ice bath, and bromine (0.7 g, 4.0 mmol) was added slowly under stirring. The reaction flask was sealed, and the mixture was stirred at room temperature overnight. Ethanol was added slowly, and the mixture was concentrated under reduced pressure to dryness. The residue was co-evaporated with ethanol and purified by flash chromatography on a silica gel column using methylene chloride-methanol (80:1) as eluent providing 1.3 g desired bromo product 156 in 89% yield. $^1$H NMR (CDCl$_3$) δ 9.10 (br, 1H), 7.82 (s, 1H), 6.07 (m, 1H), 5.26-5.35 (m, 2H), 4.30-4.41 (m, 3H), 2.20 (s, 3H), 2.11 (s, 3H), 2.09 (s, 3H).

Synthesis of 5-bromo-N$^3$-benzoyl-2',3',5'-tri-O-acetyluridine (157). Compound 156 (1.3 g, 2.9 mmol) was dissolved in 40 mL of dichloromethane, and it was cooled to 0° C. To the stirred solution were added N,N-dimethylaminopyridine (DMAP) (0.50 g, 4.0 mmol) and triethylamine (0.41 mL, 0.303 g, 3.0 mmol). Benzoyl chloride (0.70 mL, 0.83 g, 5.79 mmol) was then added slowly. The reaction mixture was stirred at room temperature for 30 minutes, and treated with a mixture of pyridine and water. It was then extracted with dichloromethane. The organic phase was washed with water and dried over anhydrous sodium sulfate. The drying agent was filtered off, and the filtrate was concentrated under reduced pressure. The crude product was purified by flash chromatography on a silica gel column using methylene chloride-methanol (80:1) as eluent providing 1.4 g of desired product 157 as white foam in 87% yield.

Synthesis of N$^3$-benzoyl-2',3',5'-O-triacetyluridine-5-malonic acid dimethyl ester (compound 158). N3-Benzoyl-5-bromo-2',3',5'-tri-O-acetyluridine (157) (1.40 g, 2.53 mmol) was dissolved in anhydrous THF (20-30 mL). To this solution were added dimethyl malonate (320 uL, 2.8 mmol) and DBU (450 uL). The reaction mixture was stirred at room temperature overnight, and small amount of acetic acid was added to quench the reaction. The mixture was concentrated and the residue was purified by flash chromatography on a silica gel column using dichloromethane-methanol (80:1) as eluent providing 1.30 g desired product 158 as white foam in 84% yield.

Synthesis of 5-(methoxycarbonyl)methyluridine (uridine 5-acetic acid methyl ester) (159). To a solution of N$^3$-benzoyl-2',3',5'-tri-O-acetoxyuridine-5-malonic acid dimethyl ester (158) (1.30 g, 2.1 mmol) in 100 mL of absolute methanol was added sodium methoxide (25% in methanol, 3.5 mL). The reaction mixture was stirred at 50° C. for 16 h, and diluted with methanol. Sodium bicarbonate was added to the mixture, and the solid was filtered. The filtrate was concentrated under reduced pressure. The residue was purified by flash chromatography on a silica gel column using dichloromethane-methanol (20:1) as eluent providing 400 mg desired product 159 as white foam in about 70% yield. $^1$H NMR (DMSO-d$_6$): δ 11.46 (d, 1H, J=3.0 Hz), 7.56 (d, 1H, J=3.6 Hz), 4.91 (d, 1H, J=3.6 Hz), 4.79 (t, 1H, J=4.2 Hz), 4.70 (d, 1H, J=4.2 Hz), 4.49 (d, 1H, J=3.0 Hz), 3.82-3.88 (m, 2H), 3.66-3.67 (m, 1H), 3.57-3.61 (m, 1H), 3.40-3.47 (m, 1H), 3.09 (s, 3H). ESI mass spectrum m/z 339 (M+Na)$^+$.

Synthesis of Compound 160. A mixture of compound 159 (1.0 g) in ammonia saturated methanol solution (40 mL) was stirred for 2 days. Upon completion of the reaction as monitored by TLC, the reaction mixture was concentrated under reduced pressure to dryness. The crude product thus obtained was recrystallized from methanol giving the desired compound 160 with 95% HPLC purity. It was characterized by NMR, MS and UV spectral analyses. $^1$H NMR (D$_2$O): δ 7.77 (s, 1H), 5.82 (d, 1H, J=4.0 Hz), 4.22-4.28 (m, 1H), 4.11-4.20 (m, 1H), 3.95-4.05 (m, 1H), 3.60-3.80 (m, 1H), 3.20-3.30 (m, 2H). ESI mass spectrum m/z 302 (M+H)$^+$, 324 (M+Na)$^+$, 625 (2M+Na)$^+$. UV, λmax=260 nm.

Example 52

Synthesis of 5-(isopentenylamino(FTA)methyl)uridine (03600013044)

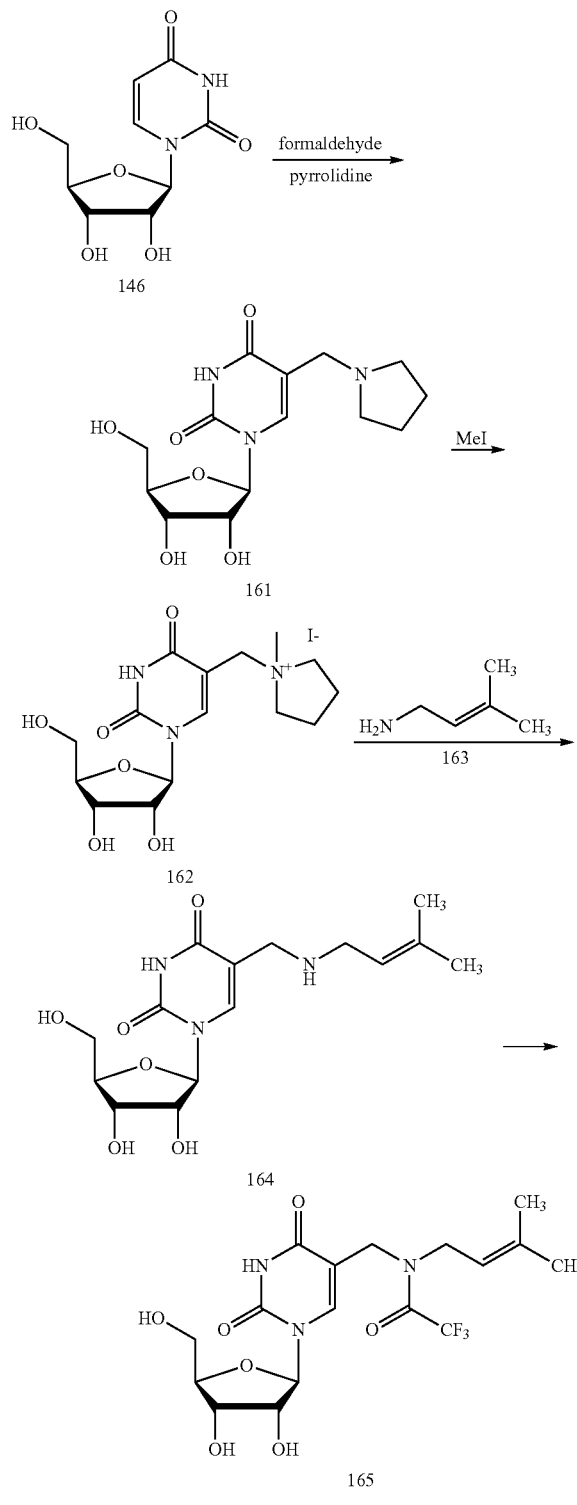

Scheme 45

Synthesis of Compound 161. A mixture of compound 146 (6.0 g, 24.6 mmol) and formaldehyde (12.28 g, 123 mmol, 30% aq. solution, 5 eq) was diluted with water (12 mL). The resulting reaction mixture was cooled to 10° C., and pyrrolidine (10.5 g 147 mmol, 6 eq) was added. The reaction mixture was stirred at 100° C. for 2 h. Upon completion of the reaction as monitored by TLC, the reaction mixture was concentrated under reduced pressure to dryness. The crude product was purified by flash chromatography on a silica gel column using methylene chloride-methanol (7:1 to 5:1) containing 0.2% ammonium hydroxide, resulting in compound F as white foam. This crude product thus obtained was recrystallized from isopropanol giving the desired compound 161 as a white solid with 97% HPLC purity.

Synthesis of Compound 162. To a stirred solution of compound 161 (3.0 g, 9 mmol) in absolute methanol (50 mL) was added methyl iodide (24 g). The reaction mixture was stirred at room temperature for 3 days. Upon completion of the reaction as monitored by TLC, the reaction mixture was concentrated under reduced pressure giving crude product compound 162 which was carried to the next step without further purification.

Synthesis of Compound 164. To a stirred solution of compound 162 (crude obtained above) in absolute methanol (45 mL) was added 1-bromo-3-methyl-2-butene 163 (5.4 g). The reaction mixture was stirred at room temperature for 1 h, and concentrated under reduced pressure to dryness. The crude product was purified by flash chromatography on a silica gel column using methylene chloride-methanol (7:1 to 5:1 to 4:1) resulting in 2.9 g compound 164.

Synthesis of Compound 165. To a solution of compound 164 (2.9 g 8.5 mmol) in dry pyridine (50 mL) was added trifluoroacetic anhydride (5 mL, 35.4 mmol, 4 eq). The reaction mixture was stirred at room temperature for 3 days as monitored by TLC for its completion. The reaction mixture was concentrated under reduced pressure to dryness. The crude product was purified by flash chromatography on a silica gel column using methylene chloride-methanol (25:1 to 15:1 with 0.2% ammonium hydroxide) giving final product compound 165 (410 mg, 10.2%) as a white solid. HPLC purity: 98%. The product was characterized by NMR, MS and UV spectral analyses. $^1$H NMR (DMSO-$d_6$ 400 Hz): δ 11.50 (d, 1H, NH), 7.55 (d, 1H, J=10.4 Hz), 5.98-6.02 (m, 1H), 5.44-5.59 (m, 2H), 5.08 (s, 1H), 4.94 (t, 1H, J=5.2 Hz), 3.91-4.22 (m, 6H), 3.75 (t, 1H, J=5.2 Hz), 3.52-3.61 (m, 2H), 1.58-1.70 (m, 6H). ESI MS, m/e 438 (M+H)$^+$, 460 (M+Na)$^+$, 897 (2M+Na)$^+$. UV, $\lambda_{max}$=275 nm.

Example 53

Synthesis of 5-{Isopentenylamino(TFA)methyl}2-thiouridine (03600013043)

Scheme 46

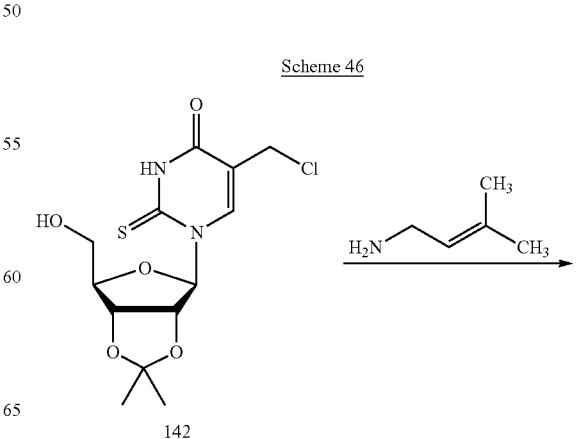

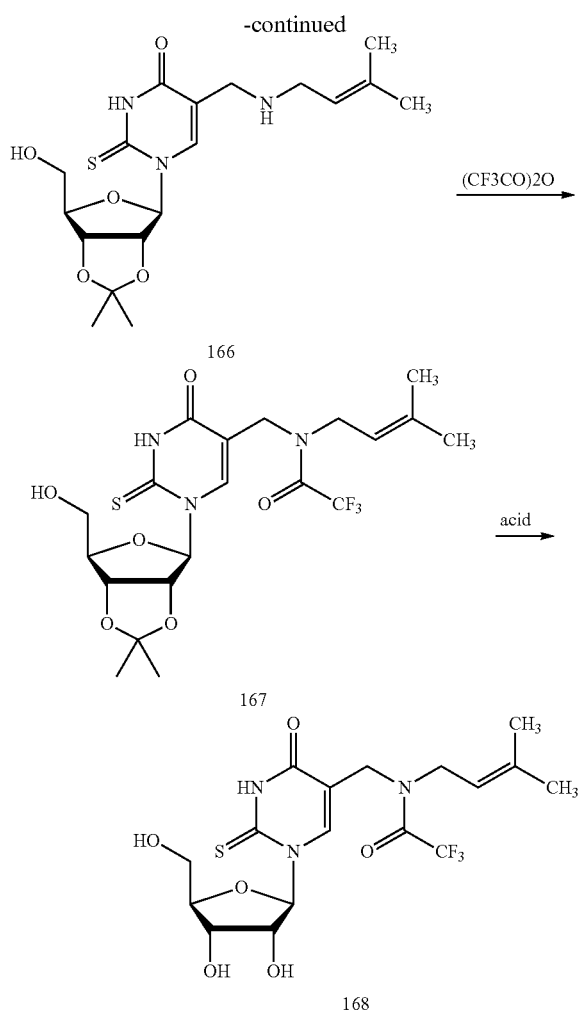

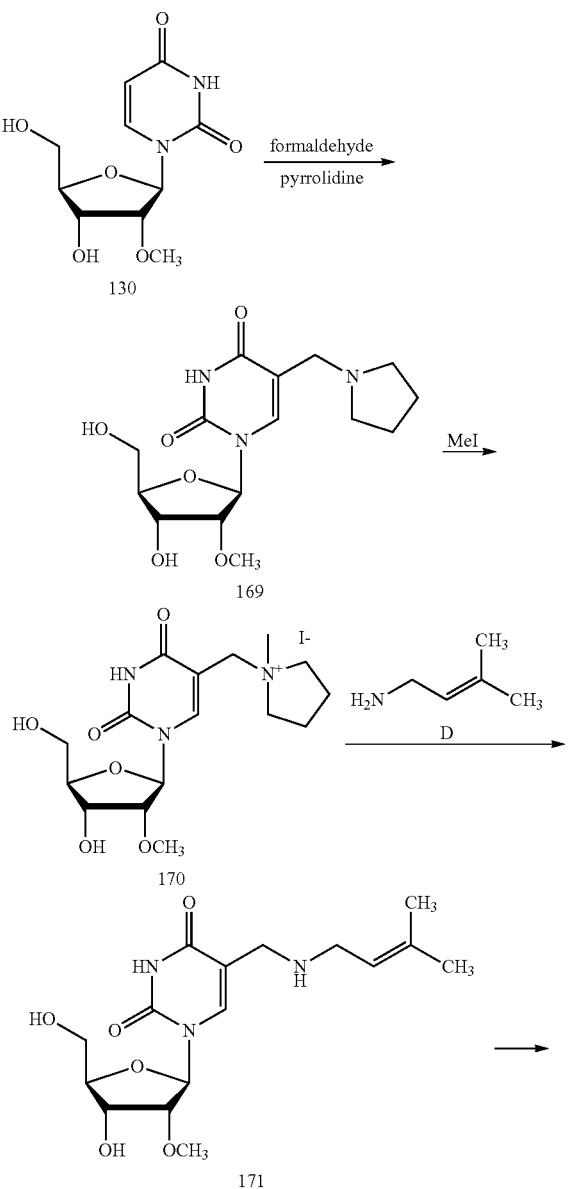

Synthesis of Compound 166. To a stirred solution of compound 142 (crude) in dioxane (50 mL) was added excess amount of 1-amino-3-methyl-2-butene. The reaction mixture was stirred at room temperature overnight. Upon completion of the reaction as monitored by TLC, the reaction mixture was concentrated under reduced pressure to dryness. The crude product was purified by flash chromatography on a silica gel column using ethyl acetate-petroleum ether (1:3 to 1:1) resulting in compound 166 (3.1 g) which was used for next step without further purification.

Synthesis of Compound 167. To a stirred solution of compound 166 (3.1 g, 7 mmol) in dry pyridine (50 mL) was cooled to 0° C., and trifluoroacetic anhydride (12 mL, 18 g, 8 mmol, 1.2 eq) was added under $N_2$ atmosphere. The reaction mixture was stirred at room temperature for 1 h. Upon completion of the reaction as monitored by TLC, the reaction mixture was treated with methylene chloride (100 mL) and sodium bicarbonate solution (100 mL, 5%). The organic phase was separated, and the aqueous phase was extracted with dichloromethane. The combined organic phase was dried over anhydrous $Na_2SO_4$. The drying agent was filtered off, and the filtrate was concentrated under reduced pressure to dryness. The crude product was purified by flash chromatography on a silica gel column using ethyl acetate-petroleum ether (1:5 to 1:3) resulting in desired compound 167 which was used for next step without further purification.

Synthesis of Compound 168. A mixture of compound 167 (1 g) and hydrochloric acid (1 M, 20 mL) was stirred at room temperature for 30 min. Sodium carbonate was added to neutralize the reaction mixture. The solid material was filtered off, and the filtrate was concentrated under reduced pressure to dryness. The crude product was purified by flash chromatography on a silica gel column giving the desired compound 168 (370 mg) with 98.27% HPLC purity. Compound 168 was characterized by HNMR, MS and UV spectral analyses. $^1$H NMR (DMSO-$d_6$ 400 Hz): δ 12.78 (d, 1H, NH), 8.10 (d, 1H, J=23.2 Hz), 6.53-6.56 (m, 1H), 5.42 (d, 1H, J=5.6 Hz), 5.06-5.16 (m, 3H), 3.90-4.23 (m, 7H), 3.59-3.68 (m, 2H), 1.56-1.69 (m, 6H). ESI MS, m/e 454 (M+H)$^+$, 476 (M+Na)$^+$. UV, $\lambda_{max}$=277 nm.

Example 54

Synthesis of 5-{Isopentenylamino(TFA)methyl}-2'-O-methyluridine (03600073043)

Scheme 47

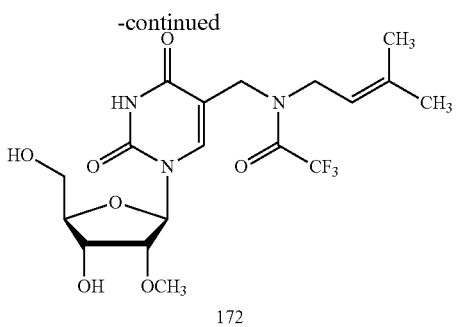

172

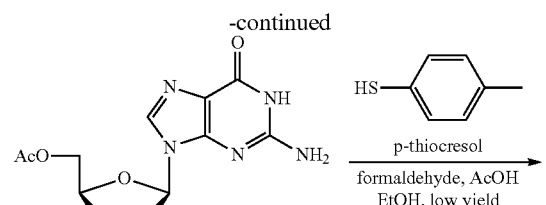

174

Synthesis of Compound 169. To a mixture of compound 130 (10.32 g, 40.0 mmol) and water (20 mL) were added pyrrolidine (14.2 g, 200.0 mmol) and paraformaldehyde (13.8 mL, 200.0 mmol). The reaction mixture was stirred at 105° C. for 48 h and concentrated under reduced pressure. The crude product was purified by silica gel chromatography (MeOH:DCM=1:15) on a silica gel column giving compound 169 (4.3 g, 32%) as oil.

Synthesis of Compound 170. Compound 169 (4.3 g, 12.6 mmol) was dissolved in MeOH (50 mL), and MeI (7.8 mL, 126.0 mL) was added. The reaction mixture was stirred at room temperature for 12 h, and then concentrated providing crude compound 170 which was used for next step without further purification.

Synthesis of Compound 171. The crude compound 170 (obtained above) was dissolved in MeOH (40 mL), and to the stirred solution was added compound D (3.2 g, 37.8 mmol). The reaction mixture was stirred at room temperature for 72 h and concentrated under the reduced pressure. The crude product was purified by silica gel chromatography (MeOH:DCM=1:40) giving compound 171 (1.0 g, 22%) as a white solid.

Synthesis of Compound 172. Compound 171 (1.0 g, 2.8 mmol) was dissolved in anhydrous pyridine (10 mL), and the solution was cooled to 0° C. The trifluoroacetic anhydride (2.3 g, 11.2 mmol) was added, and the reaction mixture was stirred at room temperature for 72 h. The solution was then concentrated, and the residue was purified by silica gel chromatography (EA:PE=3:2) on a silica gel column resulting in the desired compound 172 (0.33 g, 25%) as a white foam with 99.5% HPLC purity. It was characterized by NMR, MS and UV spectral analyses. $^1$H NMR (CDCl$_3$, 400 Hz): δ 8.94 (s, 1H), 8.34 (s, 1H), 5.96-5.97 (d, 1H, J=3.6 Hz), 5.06-5.09 (t, 1H, J=6.8 Hz), 4.29-4.41 (m, 1H), 3.78-4.23 (m, 8H), 3.56-3.60 (d, 3H, J=15 Hz), 3.35-3.82 (m, 1H), 2.75-2.77 (d, 1H, J=6.4 Hz), 1.63-1.74 (t, 6H, J=12.8 Hz). ESI MS, m/e 452 (M+H)$^+$, 474 (M+Na)$^+$. UV, $\lambda_{max}$=267 nm.

Example 55

Synthesis of N$^2$,2'-O-dimethylguanosine (00900072014)

Scheme 48

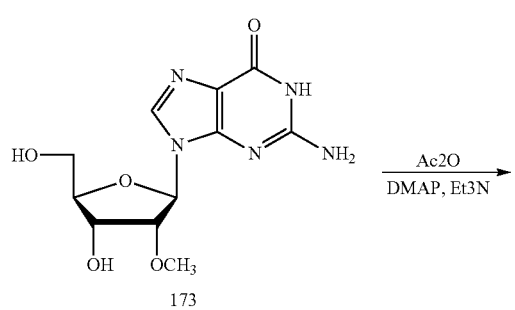

173

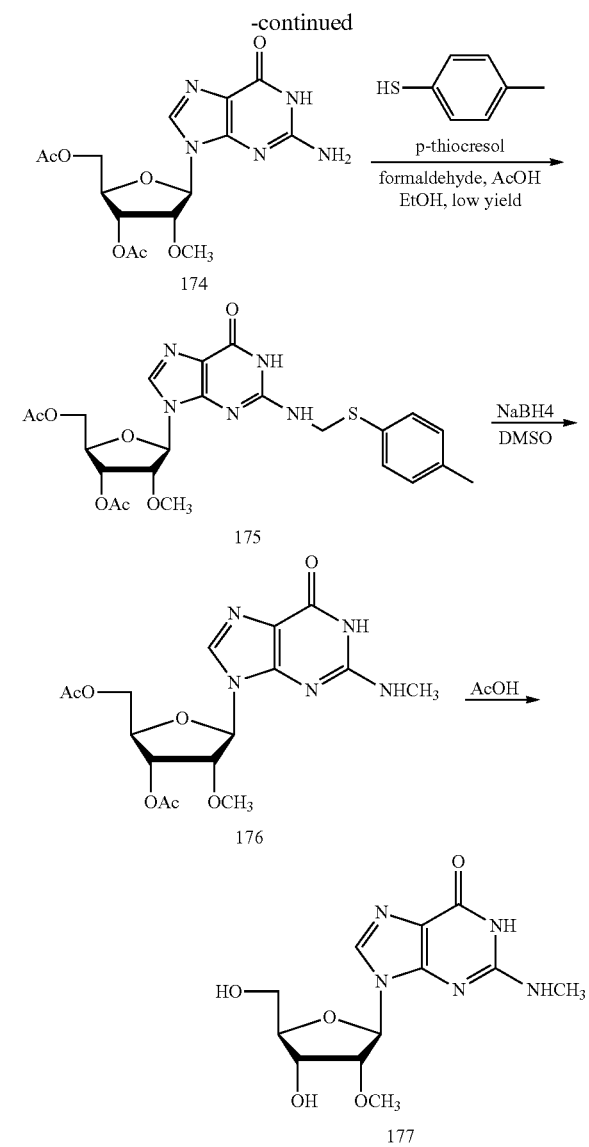

Synthesis of Compound 174: To a stirred solution of 2'-O-methylguanosine (compound 173, 3.0 g, 10.0 mmol) in anhydrous pyridine was added acetic anhydride (5.0 mL) at 0° C. The resulted reaction mixture was stirred at room temperature for 4 h. Ethanol (5.0 mL) was added, and the mixture was concentrated under reduced pressure. The residue was purified by flash chromatography on a silica gel column giving 3.0 g compound 174 as light yellow solid.

Synthesis of Compound 175: To a stirred solution of compound 174 (3.0 g, 7.8 mmol) in 60 mL of ethanol were added p-thiocresol (3.0 g, 24 mmol), 37% aqueous formaldehyde (1.0 ml, 24 mmol), and acetic acid (6 ml), and the resulted reaction mixture was refluxed for 4-6 hr as monitored by TLC. The reaction mixture was cooled, and the resulting colorless precipitate was collected by filtration giving 2.5 g compound 175 as light yellow solid.

Synthesis of Compound 177: Sodium borohydride (0.7 g, 18.0 mmol) was added to a solution of compound 175 (3.0 g, 5.8 mmol) in dimethyl sulfoxide (15 mL). The reaction mixture was heated at 100° C. for 1-2 hr, and then cooled to room temperature. It was then quenched with acetic acid/ ethanol (50 mL, v: v=1:10). The resulted colorless precipitate was filtrated out, and washed thoroughly with methanol. The crude product was dried under reduced pressure, and water was added. After further evaporation of water, the residue was crystallized from water to give $N^2$, 2'-dimethylguanosine 177 as a white solid (0.62 g, 43%). HPLC purity: 98%, ESI mass spectrum m/z 312.8 [M+H]$^+$, 623 [2M+1]$^+$, $^1$H NMR (300 MHz, DMSO-d6) δ 11.85 (br, 1H), 7.93 (s, 1H), 7.60 (br, 1H), 5.84 (d, J=3.9 Hz, 1H), 4.82-5.10 (br, 2H), 4.26-4.29 (m, 2H), 3.90 (s, 1H), 3.53-3.57 (m, 2H), 3.35 (s, 3H), 2.78 (s, 3H). ESI mass spectrum m/z 312 (M+H)$^+$, 623 (2M+H)$^+$. UV, max=258 nm.

Example 56

Synthesis of 5-methoxycarbonylmethyl-2-thiouridine (03600013035)

Scheme 49

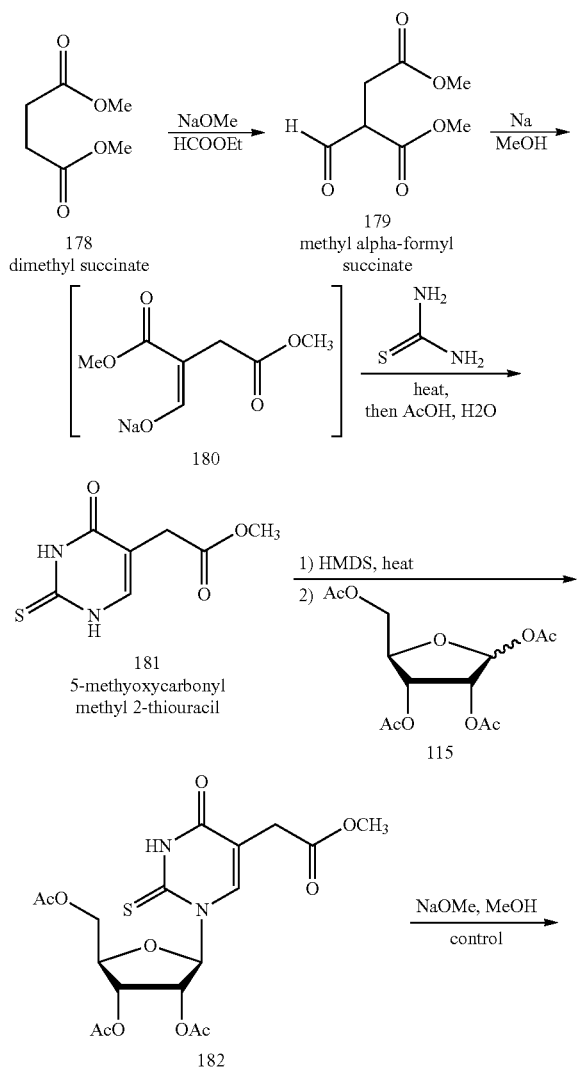

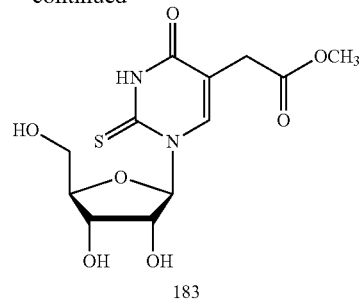

Synthesis of 5-Methoxycarbonylmethyl-2-thiouracil (181): A mixture of sodium methoxide (13.5 g, 0.25 mol) in 200 mL of diethyl ether was cooled to 0° C., and it was added slowly to a stirred mixture of dimethyl succinate 178 (36.5 g, 0.25 mol) and ethyl formate (18.5 g, 0.25 mol). The reaction mixture was stirred at 0° C. for 3 h, and at room temperature overnight. The solvent was evaporated, and the residue was washed thoroughly with petroleum ether resulting intermediate 180. The crude intermediate 180 was dissolved in methanol, and 19 g (0.25 mol) of thiourea was added. The reaction mixture was refluxed overnight. It was filtered, and the solid was washed with methanol. The filtrate was concentrated under reduced pressure. Flash chromatographic purification on a silica gel column resulting in the desired product 181 in 20% yield.

Synthesis of Glycosylated Compound 182: A mixture of 5-methoxycarbonyl methyl-2-thiouracil 181 (2.0 g, 10 mmol), 50 mL of HMDS, and catalytic amount of ammonium sulfate (50 mg) was refluxed at 130° C. After the mixture became clear solution, excess amount of HMDS was evaporated under reduced pressure. The residue was dissolved in 30 mL of 1,2-dichloromethane. To this solution was added protected riboside 115 (10.5 g), followed by addition of 1.73 mL (15 mmol) of SnCl$_4$. The reaction mixture was stirred at room temperature for 1 h, and treated with dichloromethane and saturated sodium bicarbonate. The organic phase was separated, and the aqueous phase was extracted with dichloromethane. The combined organic phase was extracted with dichloromethane. The combined organic phase was dried over anhydrous sodium sulfate. After concentrated under reduced pressure, the crude product was purified giving desired product 182.

Synthesis of Compound 183: 3 mL of sodium methoxide solution in methanol was added to a solution of compound 182 (1.2 g) in 100 mL of anhydrous methanol. The reaction mixture was stirred at room temperature for 1 h till solid disappeared. The reaction mixture was adjusted to week acid with diluted hydrochloric acid. It was then neutralized with sodium bicarbonate. The solvent was concentrated, and the residue was purified by flash chromatography on a silica gel column providing final product 182 with 99% HPLC purity. $^1$H NMR (400 MHz, DMSO$_{d6}$) δ 12.73 (s, 1H), 8.17 (s, 1H), 6.54-6.55 (d, 1H), 5.44-5.45 (d, 1H), 5.24-5.25 (d, 1H), 5.10-5.12 (d, 1H), 3.90-4.04 (m, 3H), 3.72-3.80 (m, 1H), 3.61 (s, 4H), 3.29 (s, 3H); Mass Spectrum: m/z 332.9.0 (M)$^+$, 333.8 (M+H)$^+$, 354.9 (M+Na-H)$^+$, 686.7 (2M+Na-H)$^+$. UV, λmax=260 nm.

Example 57

Synthesis of 5-methyl-N-TFA-aminomethyl-2-selenouridine (03600013048)

Scheme 50

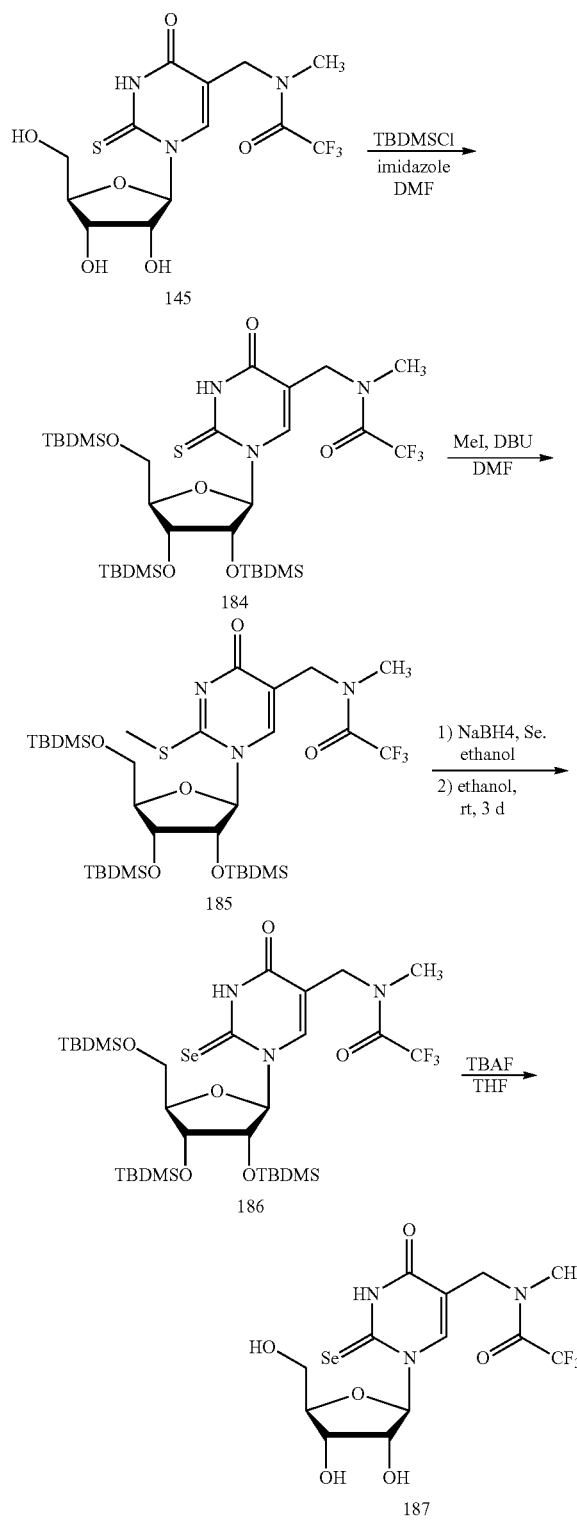

Synthesis of Compound 184: A mixture of compound 145 (3.80 g, 9.52 mmol), t-butyldimethylsilyl chloride (14.35 g, 95.2 mmol), imidazole (7.54 g, 114.24 mmol) in 20 ml of anhydrous DMF was stirred at 60° C. for 12 h. The solvent was concentrated under reduced pressure, and the residue was treated with water and ethyl acetate. The organic phase was separated and the aqueous phase was extracted with ethyl acetate. The organic phase was dried over anhydrous sodium sulfate. The drying agent was filtered off, and the filtrate was concentrated. The residue was purified by flash chromatography on a silica gel column providing 6.3 g product 184.

Synthesis of compound 185: Methyl iodide (9.56 g, 70.0 mmol, 10 eq) was added to the well stirred mixture of compound 184 (5.20 g, 7.0 mmol) and sodium bicarbonate (0.85 g, 10.12 mmol, 1.45 eq) in anhydrous DMF. The resulting reaction mixture was stirred at room temperature for 8-9 h, as indicated for the completion of the reaction by TLC. The reaction mixture was treated with dichloromethane and water. The organic phase was separated, and the aqueous phase was extracted with ethyl acetate. The organic phase was dried, and the solvent was concentrated. The residue was purified by flash chromatography on a silica gel column providing 5.60 g desired product 185.

Synthesis of compound 186: Compound 185 (5.0 g, 6.61 mmol) was dissolved in 20 mL of anhydrous ethanol. Sodium borohydride (1.30 g, 33.0 mmol) and metal selenium (2.10 g, 26.4 mmol, 8 eq) in a separate round bottom flask was cooled to 0° C. Under nitrogen protection and protection from light, 20 mL of anhydrous ethanol was added slowly. The reaction mixture was stirred for 30 min at 0° C. till the reaction mixture became clear orange solution. The solution of compound 185 in ethanol prepared above was added to the freshly prepared NaSeH$_4$ solution. The reaction mixture was stirred at room temperature for 2 days, and treated with dichloromethane and water. The organic phase was separated, and the aqueous phase was extracted with dichloromethane. The organic phase was concentrated, and the residue was purified by flash chromatography on a silica gel column providing 5.0 g of desired product 186.

Synthesis of compound 187: To a stirred solution of compound 186 (5.0 g, 6.34 mmol) in 20 mL of THF was added 38 mL tetrabutyl ammonium fluoride. The reaction mixture was stirred at room temperature for 2 h, and concentrated directly under reduced pressure. The residue was purified by flash chromatography on silica gel column. It was purified four times by column providing 120 mg of the desired final product 187 with 95% HPLC purity. MS ES, M/z 447 (M+H)$^+$, 469.8 (M+Na)$^+$. UV, $\lambda$max=315 nm.

Example 58

Synthesis of 5-methyl dihydrouridine (03600013039)

Scheme 51

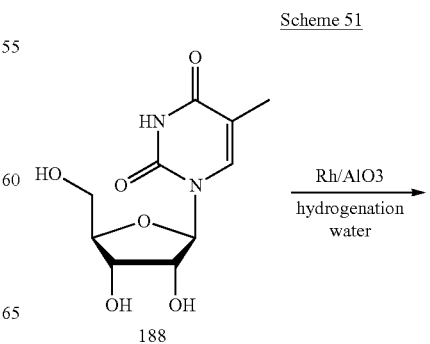

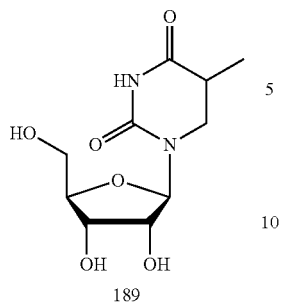

189

5-Methyl-5,6-dihydrouridine 189: To a solution of 5-methyluridine 188 (3.0 g) in water (500 mL) was added catalyst 5% Rh/C (936 mg). The mixture was shaken in an atmosphere of hydrogen (0.34 MPa) at room temperature for 12 h. The catalyst was filtered off, and the filtrate was concentrated under reduced pressure to dryness. Several recrystallization processes using ethanol/ethyl acetate solvent system yielded a mixture of stereoisomeric product 189 (2.5 g, 82%) with 99% HPLC purity, two isomers in total. Then further recrystallization from methanol/ether resulted in one isomer-enriched sample (150 mg) as indicated by NMR because HPLC could not separate these two peaks. $^1$H NMR (400 MHz, DMSO$_{d6}$) δ 10.20 (s, 1H), 5.60-5.70 (m, 1H), 5.02-5.10 (m, 1H), 4.88-4.93 (m, 1H), 4.75-4.85 (m, 1H), 3.89-4.02 (m, 1H), 3.82-3.88 (m, 1H), 3.63-3.70 (m, 1H), 3.32-3.55 (m, 3H), 2.95-3.10 (m, 1H), 2.52-2.65 (m, 1H); Mass Spectrum: m/z 261 (M+H), 283 (M+Na)+. UV, λmax=220 nm.

Example 59

Synthesis of Compound 5-ethynyl-cytidine (03600014012)

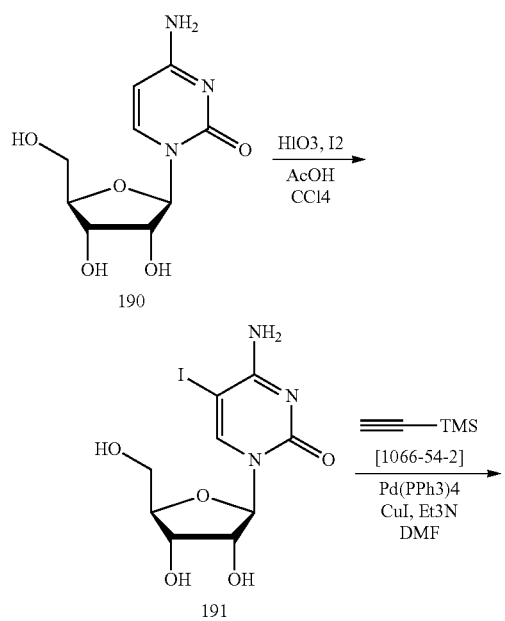

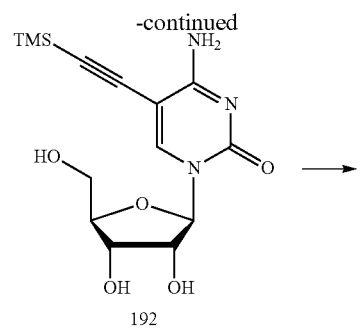

192

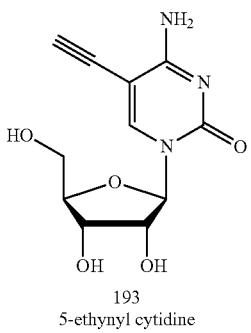

193
5-ethynyl cytidine

Synthesis of 5-iodocytidine 191: A mixture of cytidine 190 (15.0 g, 61.7 mmol) in 225 mL of acetic acid and 225 mL of carbon tetrachloride was warmed to 40° C., and iodine (9.6 g, 75.7 mmol) was added. To the stirred reaction mixture was added slowly a solution of iodic acid (9.6 g, 54.6 mmol) in 25 mL of water within 10 min. The reaction mixture was stirred at 40° C. for 6 h and stirred at room temperature overnight. Upon completion of the reaction as monitored by TLC, the reaction mixture was concentrated under reduced pressure. The residue was purified by flash chromatography on a silica gel column using dichloromethane-methanol (15:1 to 10:1 to 5:1) as gradient eluents resulting in 19.4 g (85.1%) desired product 5-iodocytidine (191).

Synthesis of compound 192: 5-Iodocytidine (191) (2.3 g, 6.2 mmol) was dissolved in anhydrous N,N-dimethylformamide (100 mL), and dried triethylamine (80 mL) was added. To the nitrogen-protected stirred reaction mixture were added CuI (0.8 g, 4.2 mmol), Pd(PPh$_3$)$_4$ (1.0 g, 0.87 mmol), and trimethylsilylacetylene (1.1 g, 11.2 mmol). The resulted reaction mixture was stirred at 35° C. for 4.5 h until the starting material was consumed as monitored by TLC. The volatiles were evaporated under reduced pressure, and the residue was treated with methanol. It was filtered through a pad of Celite, and the filtrate was concentrated. The residue was purified by flash chromatography on a silica gel column using dichloromethane-methanol (10:1 to 5:1 to 3:1) as gradient eluents giving 2.0 g (94%) compound 192.

Synthesis of compound 5-ethynyl-cytidine: Compound 192 obtained above was dissolved in 50 mL of methanol, and potassium carbonate (250 mg, 1.8 mmol) was added. The mixture was stirred at room temperature overnight. The mixture was filtered, and the filtrate was concentrated under reduced pressure. The residue was purified by flash chromatography on a silica gel column using dichloromethane-methanol (10:1 to 3:1) as gradient eluents resulting final product 193, 1.2 g (76.4%). It was further triturated with methanol resulting in pure product, 5-ethynyl-cytidine, with 98.9% HPLC purity. $^1$HNMR (400 MHz, DMSO-d$_6$) d 8.38 (s, 1H), 7.73 (bs, 1H), 6.85 (bs, 1H), 5.74 (d, 1H, J=3.2 Hz), 5.39 (d, 1H, J=4.4 Hz), 5.21 (t, 1H, J=4.8 Hz), 4.98-5.02 (m, 1H), 4.35 (s, 1H), 3.85-3.95 (m, 2H), 3.81-3.83 (m, 1H), 3.48-3.70 (m, 1H); MS (ESI) m/z 268 (M+H)⁺, 535 (2M+H)⁺, 557 (2M+Na)⁺. UV, $\lambda_{max}$ 210.5, 233.5 and 292.5 nm.

Example 60

Synthesis of 5-Vinyl Cytidine (03600014019)

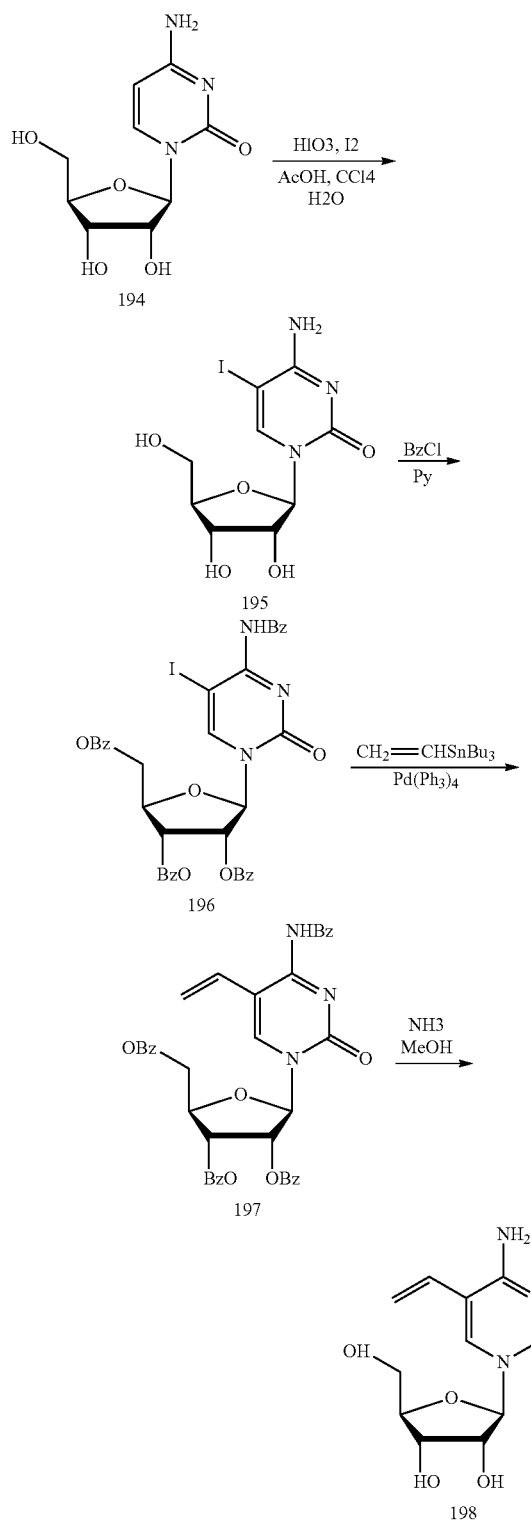

Synthesis of 5-iodocytidine (195): A mixture of cytidine (194) (15.0 g, 61.7 mmol) in 225 mL of acetic acid and 225 mL of carbon tetrachloride was warmed to 40° C., and iodine (9.6 g, 75.7 mmol) was added. To the stirred reaction mixture was added slowly a solution of iodic acid (9.6 g, 54.6 mmol) in 25 mL of water within 10 min. The reaction mixture was stirred at 40° C. for 6 h and stirred at room temperature overnight. Upon completion of the reaction as monitored by TLC, the reaction mixture was concentrated under reduced pressure. The residue was purified by flash chromatography on a silica gel column using dichloromethane-methanol (15:1 to 10:1 to 5:1) as gradient eluents resulting in 19.4 g (85.1%) desired product 5-iodocytidine (195).

Example 61

Synthesis of 5-Phenyl Cytidine (03600014021)

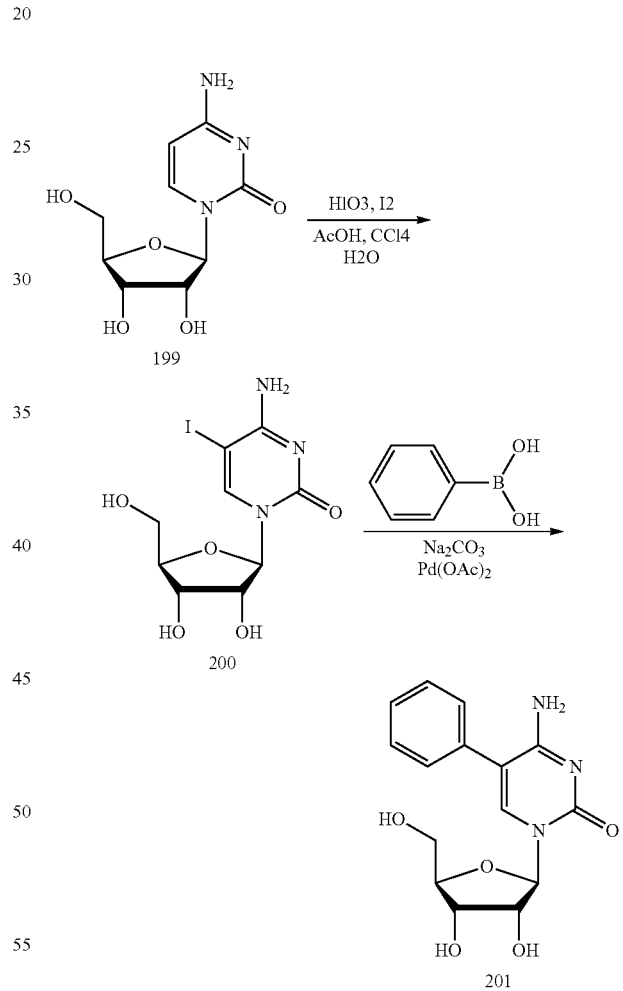

Synthesis of 5-iodocytidine (200): A mixture of cytidine (199) (15.0 g, 61.7 mmol) in 225 mL of acetic acid and 225 mL of carbon tetrachloride was warmed to 40° C., and iodine (9.6 g, 75.7 mmol) was added. To the stirred reaction mixture was added slowly a solution of iodic acid (9.6 g, 54.6 mmol) in 25 mL of water within 10 min. The reaction mixture was stirred at 40° C. for 6 h and stirred at room temperature overnight. Upon completion of the reaction as monitored by TLC, the reaction mixture was concentrated under reduced pressure. The residue was purified by flash chromatography on a silica gel column using dichloromethane-methanol (15:1 to 10:1 to 5:1) as gradient eluents resulting in 19.4 g (85.1%) desired product 5-iodocytidine (200).

Synthesis of 5-phenyl cytidine 201: To a stirred solution of 5-iodocytidine (200) (10.0 g, 27 mmol) in 100 mL of water and 50 mL acetonitrile was added Pd(Ac)$_2$ (0.58 g, 2.6 mmol), followed by the addition of phenyl boronic acid (4.68 g, 38.4 mmol) and potassium carbonate (7.0 g, 50.4 mmol). The resulted reaction mixture was stirred at 80° C. overnight and concentrated under reduced pressure to half volume. The precipitated solid was filtered off, and the filtrate was further concentrated. The residue was triturated with methanol, and filtered. The filtrate was concentrated partially, and the resulted solution was directly purified by flash chromatography on a silica gel column using dichloromethane-methanol (8:1 to 5:1) as gradient eluents giving 710 mg (8.1%) product, which was further treated with methanol giving product 201 with 96% purity. $^1$HNMR (400 MHz, DMSO-d$_6$); δ 8.06 (s, 1H), 7.66 (bs, 1H), 7.32-7.48 (m, 5H), 6.72 (bs, 1H), 5.81 (d, 1H, J=3.6 Hz), 5.37 (m, 1H), 5.67 (m, 1H), 4.99 (m, 1H), 3.97-4.02 (m, 3H), 3.83-3.86 (m, 1H), 3.50-3.68 (m, 2H); MS (ESI) m/z 320 (M+H)$^+$, 639 (2M+H)$^+$, 660 (2M+Na)$^+$. UV, λmax at 202, 232 and 282 nm.

Example 62

Synthesis of N4-Benzoyl cytidine (03600014013)

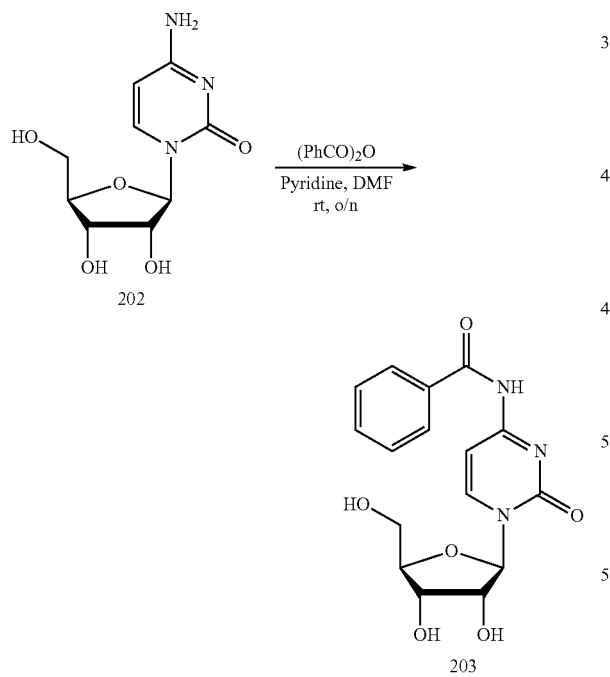

Synthesis of N4-Benzoylcytidine (203): To a stirred solution of cytidine (202) (2.43 g, 10 mmol) in anhydrous pyridine (80 mL) and DMF (30 mL) was added benzoic anhydride (3.39 g, 15 mmol). The reaction mixture was stirred at room temperature for 24 h, and treated with water. The volatiles were evaporated under reduced pressure, and the residue was purified by chromatographic column. The desired fractions were collected and concentrated. The product was treated with methanol giving 1.5 g final product 203 with 97% HPLC purity. $^1$HNMR (400 MHz, DMSO-d$_6$) δ 11.26 (s, 1H), 8.50-8.53 (m, 1H), 7.99-8.02 (m, 1H), 7.32-7.68 (m, 4H), 5.82 (d, 1H, J=2.8 Hz), 5.54 (d, 1H, J=4.8 Hz), 5.20 (t, 1H, J=5.2 Hz), 5.08 (d, 1H, J=5.6 Hz), 3.80-4.02 (m, 3H), 3.50-3.75 (m, 2H); MS (ESI) m/z 348 (M+H)$^+$, 370 (M+Na)$^+$, 717 (2M+Na)$^+$. UV, λmax at 259.5 and 302.5 nm.

Example 63

Synthesis of 5-beta-D-ribofuranosyl-2(1H)-pyridinone(07100015011)

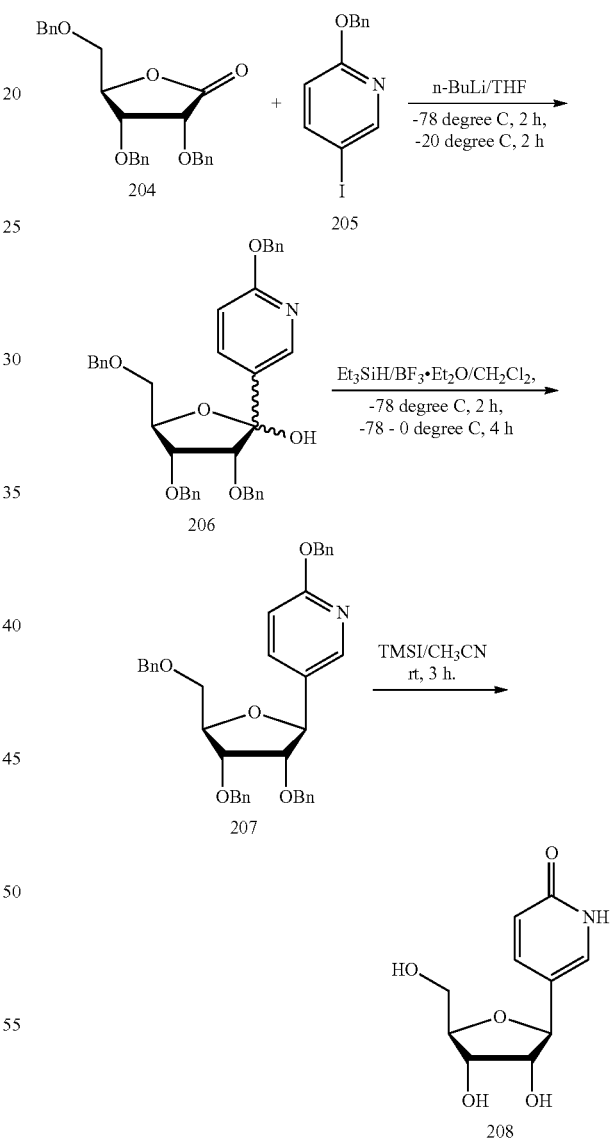

Synthesis of Compound 206. To a stirred solution of compound 205 (7.0 g, 22.5 mmol, 1 eq) in dry tetrahydrofuran (100 mL) was added slowly n-butyl lithium (2.5 M solution in hexane; 9.5 mL, 24.75 mmol, 1.1 eq) at −78° C. under N$_2$ atmosphere. It was stirred at −78° C. for 15 min, and a solution of compound 204 (9.0 g, 22.5 mmol, 1 eq) in anhydrous tetrahydrofuran (50 mL) was added. The temperature was raised to −20° C., and the reaction mixture was stirred for an additional hour. Upon completion of the reaction as monitored by TLC, the reaction was poured into aqueous saturated ammonium chloride solution. The mixture was extracted with ethyl acetate. The combined organic phase was dried over anhydrous Na$_2$SO$_4$. The drying agent was filtered off, and the filtrate was concentrated to dryness under reduced pressure. The crude product thus obtained was purified by flash chromatography on a silica gel column using ethyl acetate-petroleum ether (1:10 to 1:7) resulting in C—C glycosylated compound 206 (9.0 g).

Synthesis of Compound 207. To a stirred solution of compound 206 (9.0 g, 14.9 mmol, 1 eq) in dry dichloromethane (100 mL) was added Et$_3$SiH (13.8 mL, 149 mmol, 10 eq), followed by the slow addition of boron trifluoride-diethyl etherate complex (4.6 mL, 22.3 mmol, 1.5 eq) at −30° C. The temperature was raised to 0° C. Upon completion of the reaction as monitored by TLC, the reaction was quenched with saturated sodium bicarbonate. The mixture was extracted with dichloromethane. The combined organic phase was dried over anhydrous Na$_2$SO$_4$. The drying agent was filtered off, and the filtrate was concentrated to dryness under reduced pressure. The crude product thus obtained was purified by flash chromatography on a silica gel column using ethyl acetate-petroleum ether (1:15 to 1:10) resulting compound 207 (4.4 g) as pale yellow oil. The overall yield for two steps was 35%.

Synthesis of Compound 208. To a stirred solution of compound 207 (3.4 g, 5.8 mmol, 1 eq) in dry acetonitrile was added TMSI (12.0 mL, 87 mmol, 15 eq) at room temperature. It was stirred at room temperature for 4 h. Upon completion of the reaction as monitored by TLC, the reaction was quenched with water (10 mL). The combined organic phase was dried over anhydrous Na$_2$SO$_4$. The drying agent was filtered off, and the filtrate was concentrated to dryness under reduced pressure. The crude product thus obtained was purified by flash chromatography on a silica gel column using methanol-dichloromethane (1:15 to 1:5) resulting in the desired product 208 (880 mg) as white solid in 67% yield. HPLC purity: 100%. The product was characterized by NMR, MS and UV spectral analyses: $^1$H NMR (400 MHz, DMSO$_{d6}$): δ 11.48 (s, 1H), 7.48 (d, 1H, J=2.4 Hz), 7.29 (d, 1H, J=2.0 Hz), 6.31 (d, 1H, J=9.2 Hz), 4.85-4.91 (m, 2H), 4.80 (t, 1H, J=5.6 Hz), 4.32 (d, 1H, J=7.6 Hz), 3.88 (m, 1H), 3.49-3.75 (m, 2H), 3.49 (m, 2H); ESI MS m/z 228 (M+H), 455 (2M+H)$^+$, 477 (2M+Na)$^+$. UV, λ$_{max}$, 230.0 nm, 298.5 nm.

Example 64

6-fluoro-5-beta-D-ribofuranosyl-2(1H)-pyridinone
(07100015012)

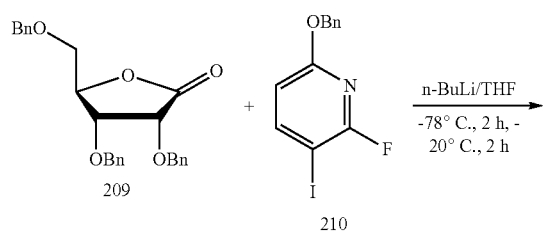

Synthesis of Compound 211. To a stirred solution of compound 210 (5.4 g, 16.4 mmol, 1.1 eq) in dry tetrahydrofuran (80 mL) was added slowly n-butyl lithium (2.5 M solution in hexane; 6.5 mL, 17.9 mmol, 1.2 eq) at −78° C. under N$_2$ atmosphere. It was stirred at −78° C. for 15 min, and a solution of compound 209 (6.2 g, 14.9 mmol, 1 eq) in anhydrous tetrahydrofuran (50 mL) was added. The temperature was raised to −20° C., and the reaction mixture was stirred for 1 h. Upon completion of the reaction as monitored by TLC, the reaction mixture was poured into saturated aqueous ammonium chloride solution. The mixture was extracted with ethyl acetate. The combined organic phase was dried over anhydrous Na$_2$SO$_4$. The drying agent was filtered off, and the filtrate was concentrated to dryness under reduced pressure. The crude product thus obtained was purified by flash chromatography on a silica gel column using ethyl acetate-petroleum ether (1:15 to 1:10) resulting in compound 211 (6.0 g) as yellow oil.

Synthesis of Compound 212. To a stirred solution of compound 211 (6.0 g, 9.6 mmol, 1 eq) in dry dichloromethane (80 mL) was added Et$_3$SiH (15.0 mL, 96 mmol, 10 eq), followed by the slow addition of boron trifluoride-diethyl etherate complex (5.2 mL, 19.2 mmol, 2 eq) at −30° C. The temperature was raised to 0° C. Upon completion of the reaction as monitored by TLC, the reaction was quenched with aqueous saturated sodium bicarbonate solution. The mixture was extracted with dichloromethane. The combined organic phase was dried over anhydrous Na$_2$SO$_4$. The drying agent was filtered off, and the filtrate was concentrated to dryness under reduced pressure. The crude product thus obtained was purified by flash chromatography on a silica gel column using ethyl acetate-petroleum ether (1:20 to 1:10) resulting in compound 212 (3.8 g) as yellow oil. The overall yield for two steps was 42.2%.

Synthesis of Compound 213. To a stirred solution of compound 212 (3.8 g, 6.27 mmol, 1 eq) in dry acetonitrile was added TMSI (15.0 mL, 125.4 mmol, 20 eq) at room temperature. It was stirred at room temperature for 4 h. Upon completion of the reaction as monitored by TLC, the reaction was quenched with water (10 mL). The mixture was concentrated to dryness under reduced pressure. The crude product thus obtained was purified by flash chromatography on a silica gel column using methanol-dichloromethane (1:15 to 1:10) resulting in compound 213 (270 mg) as white solid in 17.5% yield. HPLC purity: 95.6%. $^1$H NMR (400 MHz, DMSO$_{d6}$): δ 11.25 (s, 1H), 7.77-7.79 (m, 1H), 6.56 (d, 1H), 4.69-5.01 (m, 4H), 3.76-3.99 (m, 3H), 3.49-3.55 (m, 2H). ESI MS m/z 246 (M+H)$^+$, 268 (M+Na)$^+$. UV, $\lambda_{max}$, 217.5 nm, 274.0 nm.

Example 65

Synthesis of 3-methyl-5-beta-D-ribofuranosyl-2 (1H)-pyridinone (07100015017)

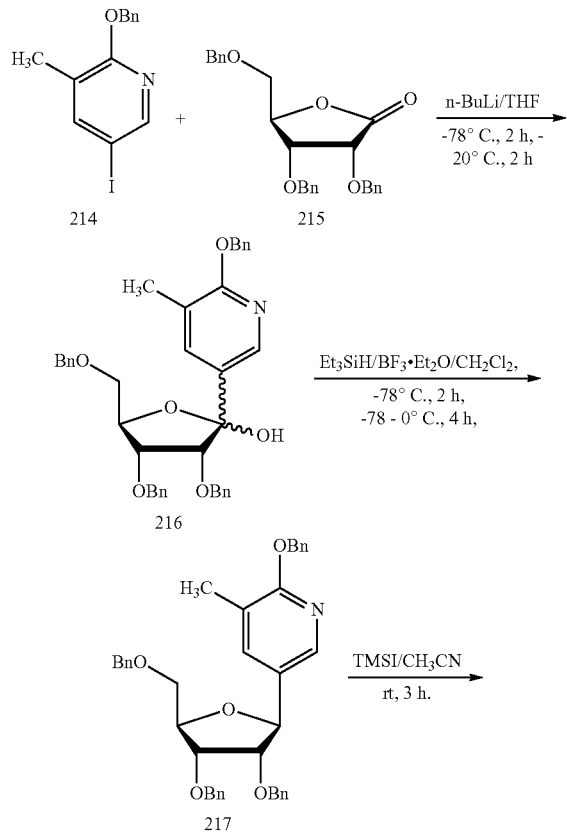

Synthesis of compound 216. Compound 214 (2.14 g, 6.6 mmol, 1.1 eq) was dissolved in anhydrous tetrahydrofuran (50 mL), and it was cooled to −78° C. under nitrogen atmosphere. n-Butyl lithium (2.5 M solution in hexane, 3.0 mL, 1.2 eq) was added slowly to the stirred solution at −78° C. The resulted reaction mixture was stirred at the low temperature for 15 min, and a solution of compound 215 (1.3 g) in anhydrous tetrahydrofuran (10 mL) was added. The temperature was raised to −20° C., and it was stirred for 1 h. Upon the completion of the reaction as monitored by TLC, the reaction mixture was poured in to aqueous saturated ammonium chloride solution. It was extracted with ethyl acetate, and the organic phase was dried over anhydrous sodium sulfate. The drying agent was filtered off, and the filtrate was concentrated under reduced pressure. The residue was purified by flash chromatography on a silica gel column using ethyl acetate-petroleum ether (1:10 to 1:7) resulting in the compound 216 (2.0 g, 52.6%).

Synthesis of compound 217: A solution of compound 216 (2.0 g, 3.2 mmol) in 20 mL of anhydrous dichloromethane was cooled to −30° C. To this stirred solution at the low temperature was added Et$_3$SiH (10 eq), followed by addition of boron trifluoride etherate (1.5 eq). The temperature was brought to 0° C. and continued to stir till completion as monitored by TLC. The reaction mixture was treated with saturated sodium bicarbonate solution, and extracted with dichloromethane. The combined organic phase was dried over anhydrous sodium sulfate. The drying agent was filtered off, and the filtrate was concentrated under reduced pressure. The resulted residue was purified by flash chromatography on a silica gel column using ethyl acetate-petroleum ether (1:15 to 1:10) resulting in the desired compound 217 (1.8 g, 92%).

Synthesis of compound 218: Compound 217 (1.0 g, 1.7 mmol) was dissolved in anhydrous acetonitrile, and TMSI (2.3 mL, 10 eq) was added at room temperature under stirring. The reaction mixture was stirred at room temperature for 3 h and treated with 5 mL of water to quench the reaction. The mixture was concentrated under reduced pressure, and the residue was purified by flash chromatography on a silica gel column using methanol-dichloromethane (1:15 to 1:10) as eluent giving the desired product 218 (350 mg, 87%). HPLC purity: 97%; $^1$H NMR (400 MHz, DMSO$_{d6}$): δ 11.34 (s, 1H), 7.34 (s, 1H), 7.16 (d, 1H, J=2.0 Hz), 4.79-4.95 (m, 3H), 4.26-4.30 (m, 3H), 4.85-4.88 (m, 1H), 3.67-3.74 (m, 2H), 3.35-3.50 (m, 2H), 1.97 (s, 3H). ESI MS m/z 242 (M+H)$^+$, 264 (M+Na)$^+$, 505 (2M+Na)$^+$. UV, $\lambda_{max}$, 232.5 nm, 297.5 nm.

Example 66

Synthesis of 6-methyl-5-beta-D-ribofuranosyl-2 (1H)-pyridinone (07100015013)

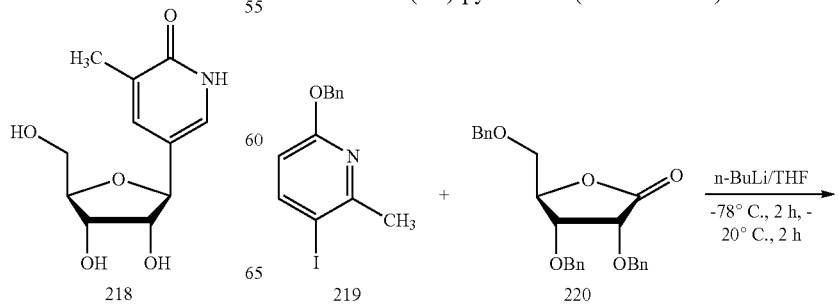

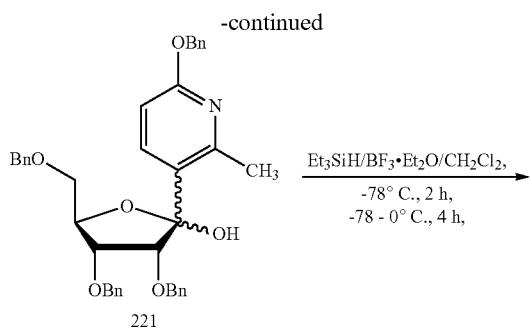

(4.68 g) in anhydrous tetrahydrofuran (30 mL) was added. The temperature was raised to −20° C., and it was stirred for 1 h. Upon the completion of the reaction as monitored by TLC, the reaction mixture was poured in to aqueous saturated ammonium chloride solution. It was extracted with ethyl acetate, and the organic phase was dried over anhydrous sodium sulfate. The drying agent was filtered off, and the filtrate was concentrated under reduced pressure. The residue was purified by flash chromatography on a silica gel column using ethyl acetate-petroleum ether (1:10 to 1:7) resulting in the compound 221 (4.2 g crude).

Synthesis of compound 222: A solution of crude compound 221 (4.2 g) in 40 mL of anhydrous dichloromethane was cooled to −30° C. To this stirred solution at the low temperature was added Et₃SiH (8.0 mL, 10 eq), followed by addition of boron trifluoride etherate (2.4 mL, 1.5 eq). The temperature was brought to 0° C. and continued to stir till completion as monitored by TLC. The reaction mixture was treated with saturated sodium bicarbonate solution, and extracted with dichloromethane. The combined organic phase was dried over anhydrous sodium sulfate. The drying agent was filtered off, and the filtrate was concentrated under reduced pressure. The resulted residue was purified by flash chromatography on a silica gel column using ethyl acetate-petroleum ether (1:15 to 1:10) resulting in the desired compound 222 (2.0 g).

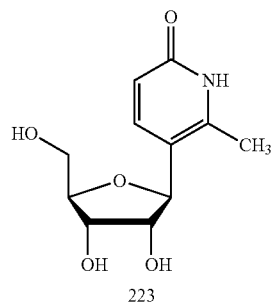

Synthesis of compound 223: Compound 222 (2.0 g, 3.4 mmol) was dissolved in anhydrous acetonitrile, and TMSI (4.6 mL, 10 eq) was added at room temperature under stirring. The reaction mixture was stirred at room temperature for 3 h and treated with 5 mL of water to quench the reaction. The mixture was concentrated under reduced pressure, and the residue was purified by flash chromatography on a silica gel column using methanol-dichloromethane (1:15 to 1:10) as eluent giving the desired product 223 (350 mg). After several more column purification, it was obtained with 96% HPLC purity; $^1$H NMR (400 MHz, DMSO$_{d6}$): δ 11.45 (s, 1H), 7.51 (d, 1H, J=8.5 Hz), 6.16 (d, 1H, J=9.6 Hz), 4.70-4.93 (m, 3H), 4.53-4.57 (m, 1H), 4.85-4.88 (m, 1H), 3.62-3.78 (m, 2H), 3.22-3.50 (m, 2H), 2.21 (s, 3H). ESI MS m/z 242 (M+H)⁺, 264 (M+Na)⁺, 505 (2M+Na)⁺. UV, λ$_{max}$, 233.0 nm, 303.5 nm.

Synthesis of compound 221. Compound 219 (4.0 g, 12.3 mmol, 1.1 eq) was dissolved in anhydrous tetrahydrofuran (80 mL), and it was cooled to −78° C. under nitrogen atmosphere. n-Butyl lithium (2.5 M solution in hexane, 5.4 mL, 1.2 eq) was added slowly to the stirred solution at −78° C. The resulted reaction mixture was stirred at the low temperature for 15 min, and a solution of compound 220

Example 67

Synthesis of 5-Ethyl-CTP (03601014039)

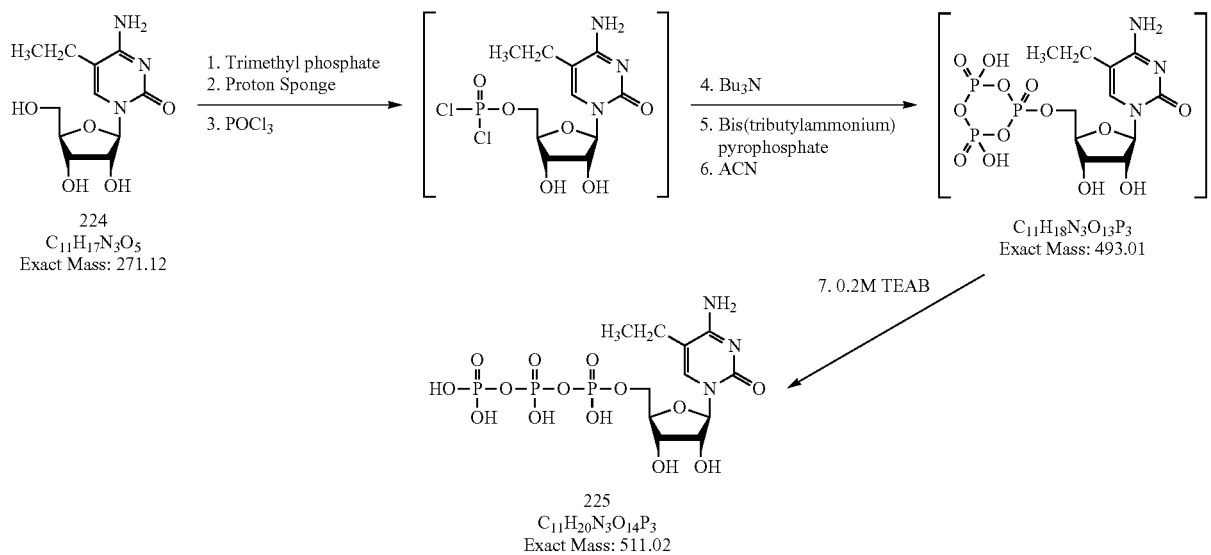

5-Ethyl-CTP (225): A solution of 5-ethyl-cytidine 224 (102.0 mg, 0.38 mmol; applied heat to make it soluble) and proton sponge (122.2 mg, 0.57 mmol, 1.5 equiv.) in trimethyl phosphate (0.8 mL) was stirred for 10.0 minutes at 0° C. Phosphorus oxychloride (70.96 μL, 0.76 mmol, 2.0 equiv.) was added dropwise to the solution and it was then kept stirring for 2.0 hours under $N_2$ atmosphere. A mixture of tributylamine (368.84 μL, 2.28 mmol, 4.0 equiv.) and bis(tributylammonium) pyrophosphate (625.5 mg, 1.14 mmol, 3.0 equiv.) in acetonitrile (2.5 mL) was added at once. After ~25 minutes, the reaction was quenched with 0.2 M TEAB buffer (15.0 mL) and the clear solution was stirred at room temperature for an hour. LCMS analysis indicated the formation of the corresponding triphosphate. The reaction mixture was then lyophilized overnight. The crude reaction mixture was purified by anion exchange followed by HPLC (Waters, Phenomenex C18 reverse-phase preparative column, 250×21.2 mm, 10.0 micron; gradient (1%): 100% A for 3.0 min, then 1% B/min, A=100 mM TEAA buffer, B=ACN; flow rate: 10.0 mL/min; retention time: 15.57-16.20 min). Fractions containing the desired were pooled together and lyophilized to yield the 5-ethyl-cytidine-TP (225) as a tetrakis(triethylammonium salt) (51.9 mg, 26.32%, based on $\varepsilon_{278}$=6,851.4 Lmol$^{-1}$ cm$^{-1}$). UVmax=278 nm; MS: m/e 509.90 (M–H).

Example 68

Synthesis of 5-Methoxy-CTP (03601014030)

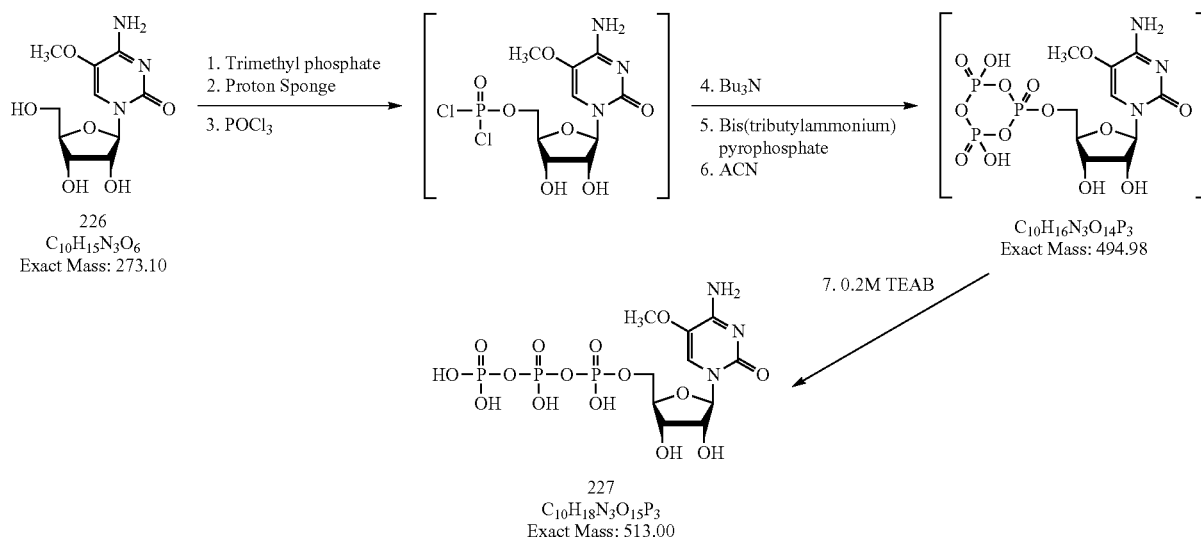

5-Methoxy-CTP (227): A solution of 5-methoxy-cytidine 226 (100.0 mg, 0.36 mmol; applied heat to make it soluble) and proton sponge (115.72 mg, 0.54 mmol, 1.5 equiv.) in trimethyl phosphate (0.8 mL) was stirred for 10.0 minutes at 0° C. Phosphorus oxychloride (67.23 μL, 0.72 mmol, 2.0 equiv.) was added dropwise to the solution and it was then kept stirring for 2.0 hours under $N_2$ atmosphere. A mixture of tributylamine (349.4 μL, 1.44 mmol, 4.0 equiv.) and bis(tributylammonium) pyrophosphate (592.56 mg, 1.08 mmol, 3.0 equiv.) in acetonitrile (2.5 mL) was added at once. After ~25 minutes, the reaction was quenched with 0.2 M TEAB buffer (14.2 mL) and the clear solution was stirred at room temperature for an hour. LCMS analysis indicated the formation of the corresponding triphosphate. The reaction mixture was then lyophilized overnight. The crude reaction mixture was purified by anion exchange followed by HPLC (Waters, Phenomenex C18 reverse-phase preparative column, 250×21.2 mm, 10.0 micron; gradient (1%): 100% A for 3.0 min, then 1% B/min, A=100 mM TEAA buffer, B=ACN; flow rate: 10.0 mL/min; retention time: 15.8-16.7 min). Fractions containing the desired were pooled together and lyophilized to yield the 5-methoxy-cytidine-TP (227) as a tetrakis(triethylammonium salt) (38.55 mg, 20.83%, based on $\varepsilon_{289}$=6,049.6 Lmol$^{-1}$ cm$^{-1}$). UVmax=289 nm; MS: m/e 511.90 (M–H).

Example 69

Synthesis of 5-ethynyl-cytidine (03601014012)

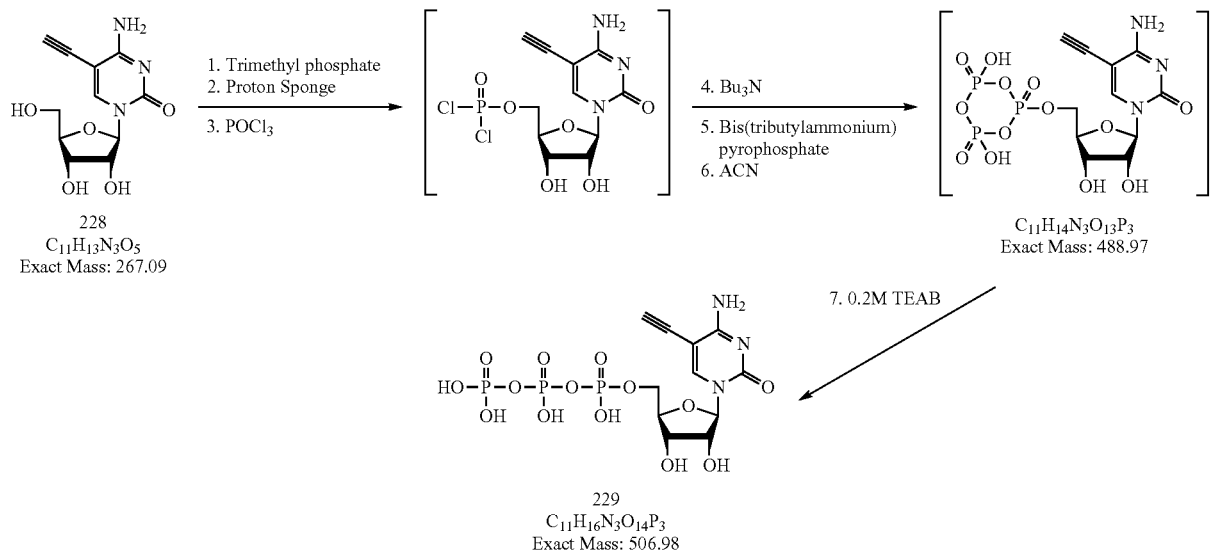

5-Ethynyl-CTP (229): A solution of 5-ethynyl-cytidine 228 (118.0 mg, 0.44 mmol; applied heat to make it soluble) and proton sponge (141.44 mg, 0.66 mmol, 1.5 equiv.) in trimethyl phosphate (0.9 mL) was stirred for 10.0 minutes at 0° C. Phosphorus oxychloride (82.16 µL, 0.88 mmol, 2.0 equiv.) was added dropwise to the solution and it was then kept stirring for 2.0 hours under $N_2$ atmosphere. A mixture of tributylamine (427.0 µL, 1.76 mmol, 4.0 equiv.) and bis(tributylammonium) pyrophosphate (724.24 mg, 1.32 mmol, 3.0 equiv.) in acetonitrile (3.0 mL) was added at once. After ~25 minutes, the reaction was quenched with 0.2 M TEAB buffer (17.3 mL) and the clear solution was stirred at room temperature for an hour. LCMS analysis indicated the formation of the corresponding triphosphate. The reaction mixture was then lyophilized overnight. The crude reaction mixture was purified by anion exchange followed by HPLC (Waters, Phenomenex C18 reverse-phase preparative column, 250×21.2 mm, 10.0 micron; gradient (1%): 100% A for 3.0 min, then 1% B/min, A=100 mM TEAA buffer, B=ACN; flow rate: 10.0 mL/min; retention time: 14.1-15.1 min). Fractions containing the desired were pooled together and lyophilized to yield the 5-ethynyl-cytidine-TP (229) as a tetrakis(triethylammonium salt) (53.05 mg, 22.72%, based on $\varepsilon_{292}$=6,308.3 $Lmol^{-1}$ $cm^{-1}$). UVmax=292 nm; MS: m/e 505.85 (M–H).

Example 70

Synthesis of 5-Fluoro-CTP (00901014041)

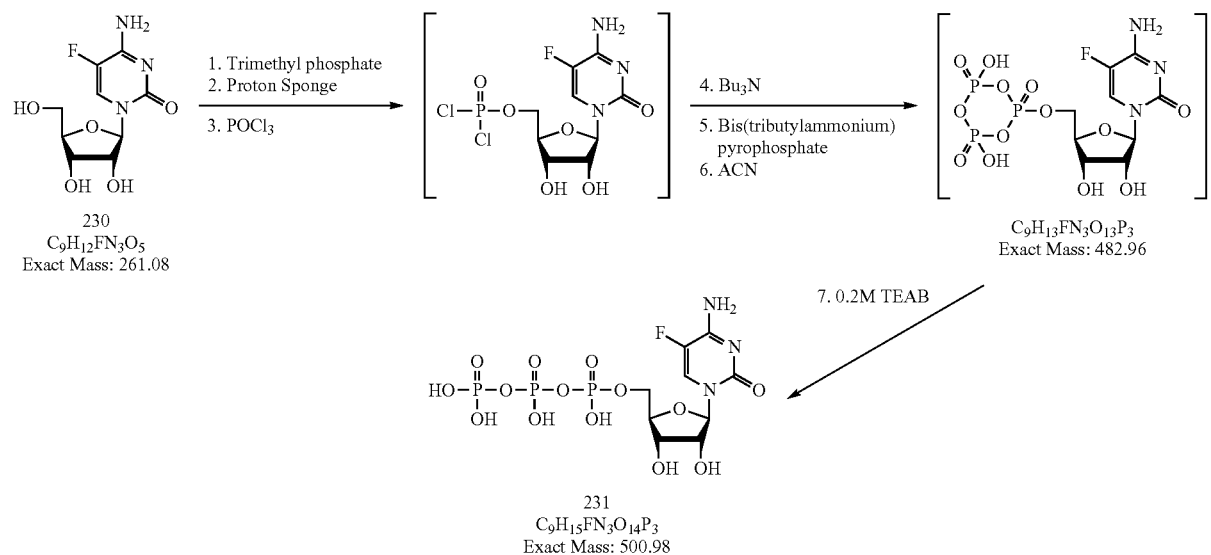

5-Fluoro-CTP (231): A solution of 5-fluoro-cytidine 230 (124.0 mg, 0.47 mmol; applied heat to make it soluble) and proton sponge (151.0 mg, 0.7 mmol, 1.5 equiv.) in trimethyl phosphate (0.9 mL) was stirred for 10.0 minutes at 0° C. Phosphorus oxychloride (87.76 μL, 0.94 mmol, 2.0 equiv.) was added dropwise to the solution and it was then kept stirring for 2.0 hours under $N_2$ atmosphere. A mixture of tributylamine (456.2 μL, 1.88 mmol, 4.0 equiv.) and bis(tributylammonium) pyrophosphate (773.6 mg, 1.41 mmol, 3.0 equiv.) in acetonitrile (3.0 mL) was added at once. After ~25 minutes, the reaction was quenched with 0.2 M TEAB buffer (18.5 mL) and the clear solution was stirred at room temperature for an hour. LCMS analysis indicated the formation of the corresponding triphosphate. The reaction mixture was then lyophilized overnight. The crude reaction mixture was purified by anion exchange followed by HPLC (Waters, Phenomenex C18 reverse-phase preparative column, 250×21.2 mm, 10.0 micron; gradient (1%): 100% A for 3.0 min, then 1% B/min, A=100 mM TEAA buffer, B=ACN; flow rate: 10.0 mL/min; retention time: 14.8-15.8 min). Fractions containing the desired were pooled together and lyophilized to yield the 5-fluoro-cytidine-TP (231) as a tetrakis(triethylammonium salt) (47.3 mg, 20.0%, based on $\varepsilon_{280}$=9,000.0 $Lmol^{-1}$ $cm^{-1}$). UVmax=280 nm; MS: m/e 499.80 (M−H).

Example 71

Synthesis of 5-Phenyl-CTP (03601014021)

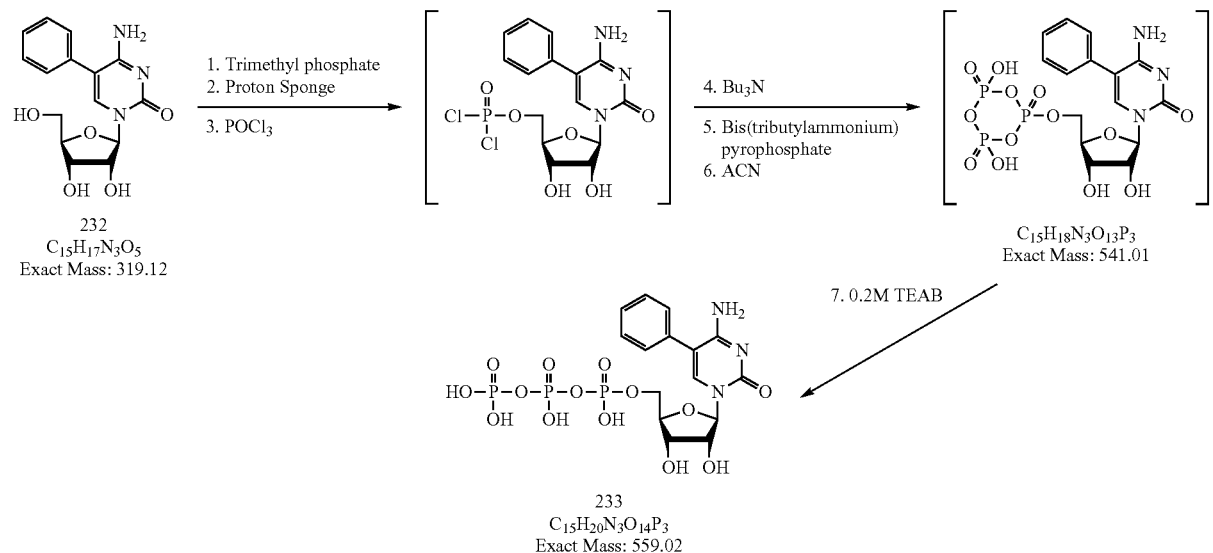

232
$C_{15}H_{17}N_3O_5$
Exact Mass: 319.12

$C_{15}H_{18}N_3O_{13}P_3$
Exact Mass: 541.01

233
$C_{15}H_{20}N_3O_{14}P_3$
Exact Mass: 559.02

5-Phenyl-CTP (233): A solution of 5-phenyl-cytidine 232 (102.0 mg, 0.32 mmol; applied heat to make it soluble) and proton sponge (102.68 mg, 0.48 mmol, 1.5 equiv.) in trimethyl phosphate (0.9 mL) was stirred for 10.0 minutes at 0° C. Phosphorus oxychloride (59.5 μL, 0.64 mmol, 2.0 equiv.) was added dropwise to the solution and it was then kept stirring for 2.0 hours under $N_2$ atmosphere. A mixture of tributylamine (304.4 μL, 1.28 mmol, 4.0 equiv.) and bis(tributylammonium) pyrophosphate (525.78 mg, 0.95 mmol, 3.0 equiv.) in acetonitrile (2.5 mL) was added at once. After ~25 minutes, the reaction was quenched with 0.2 M TEAB buffer (12.5 mL) and the clear solution was stirred at room temperature for an hour. LCMS analysis indicated the formation of the corresponding triphosphate. The reaction mixture was then lyophilized overnight. The crude reaction mixture was purified by anion exchange followed by HPLC (Waters, Phenomenex C18 reverse-phase preparative column, 250×21.2 mm, 10.0 micron; gradient (1%): 100% A for 3.0 min, then 1% B/min, A=100 mM TEAA buffer, B=ACN; flow rate: 10.0 mL/min; retention time: 18.1-19.2 min). Fractions containing the desired were pooled together and lyophilized to yield the 5-phenyl-cytidine-TP (233) as a tetrakis(triethylammonium salt) (29.5 mg, 16.56%, based on $\varepsilon_{285}$=7,052.2 $Lmol^{-1}$ $cm^{-1}$). UVmax=285 nm; MS: m/e 557.80 (M−H).

Example 72

Synthesis of $N^4$-Benzoyl-CTP (03601014013)

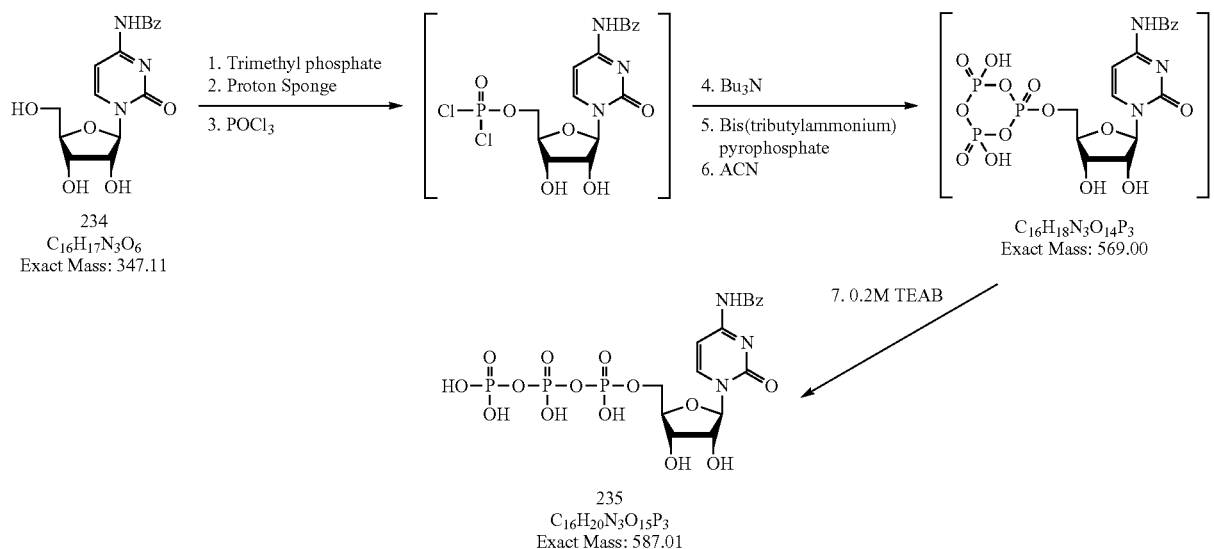

$N^4$-Benzoyl-CTP (235): A solution of $N^4$-benzoyl-cytidine 234 (154.0 mg, 0.44 mmol; applied heat to make it soluble) and proton sponge (141.44 mg, 0.66 mmol, 1.5 equiv.) in trimethyl phosphate (2.0 mL) was stirred for 10.0 minutes at 0° C. Phosphorus oxychloride (82.16 µL, 0.88 mmol, 2.0 equiv.) was added dropwise to the solution and it was then kept stirring for 2.0 hours under $N_2$ atmosphere. A mixture of tributylamine (427.0 µL, 1.76 mmol, 4.0 equiv.) and bis(tributylammonium) pyrophosphate (724.24 mg, 1.32 mmol, 3.0 equiv.) in acetonitrile (3.0 mL) was added at once. After ~25 minutes, the reaction was quenched with 0.2 M TEAB buffer (17.3 mL) and the clear solution was stirred at room temperature for an hour. LCMS analysis indicated the formation of the corresponding triphosphate. The reaction mixture was then lyophilized overnight. The crude reaction mixture was purified by anion exchange followed by HPLC (Waters, Phenomenex C18 reverse-phase preparative column, 250×21.2 mm, 10.0 micron; gradient (1%): 100% A for 3.0 min, then 1% B/min, A=100 mM TEAA buffer, B=ACN; flow rate: 10.0 mL/min; retention time: 18.0-19.7 min). Fractions containing the desired were pooled together and lyophilized to yield the $N^4$-benzoyl-cytidine-TP (235) as a tetrakis(triethylammonium salt) (35.25 mg, 13.64%, based on $\varepsilon_{259}$=22,886.0 Lmol$^{-1}$ cm$^{-1}$). UVmax=259 nm & 304 nm; MS: m/e 585.95 (M−H).

Example 73

Synthesis of $N^6$-Isopentenyl-ATP (00901011044)

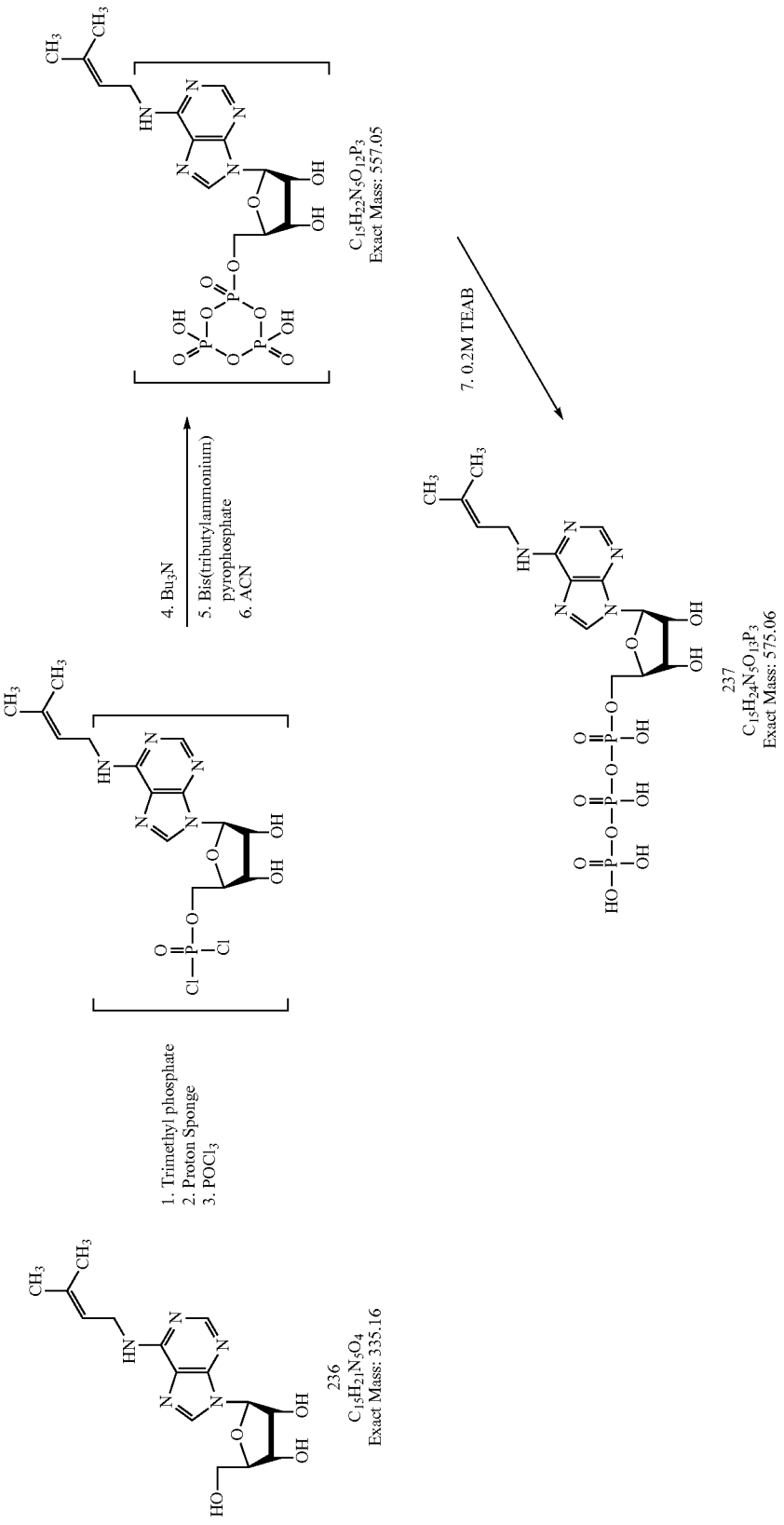

$N^6$-Isopentenyl-ATP (237): A solution of $N^6$-isopentenyl-adenosine 236 (146.0 mg, 0.44 mmol; applied heat to make it soluble) and proton sponge (139.95 mg, 0.65 mmol, 1.5 equiv.) in trimethyl phosphate (1.5 mL) was stirred for 10.0 minutes at 0° C. Phosphorus oxychloride (60.8 µL, 0.65 mmol, 2.0 equiv.) was added dropwise to the solution and it was then kept stirring for 2.0 hours under $N_2$ atmosphere. A mixture of tributylamine (414.0 µL, 1.74 mmol, 4.0 equiv.) and bis(tributylammonium) pyrophosphate (716.60 mg, 1.30 mmol, 3.0 equiv.) in acetonitrile (2.5 mL) was added at once. After ~25 minutes, the reaction was quenched with 0.2 M TEAB buffer (17.0 mL) and the clear solution was stirred at room temperature for an hour. LCMS analysis indicated the formation of the corresponding triphosphate. The reaction mixture was then lyophilized overnight. The crude reaction mixture was purified by anion exchange followed by HPLC (Waters, Phenomenex C18 reverse-phase preparative column, 250×21.2 mm, 10.0 micron; gradient (1%): 100% A for 3.0 min, then 1% B/min, A=100 mM TEAA buffer, B=ACN; flow rate: 10.0 mL/min; retention time: 28.0-31.0 min). Fractions containing the desired were pooled together and lyophilized to yield the $N^6$-isopentenyl-adenosine-TP (60) as a tetrakis(triethylammonium salt) (23.3 mg, 9.32%, based on $\varepsilon_{268}$=15,000.0 $Lmol^{-1}$ $cm^{-1}$). UVmax=268 nm; MS: m/e 573.90 (M−H).

Example 74

Synthesis of 8-Methyl-ATP (00901011045)

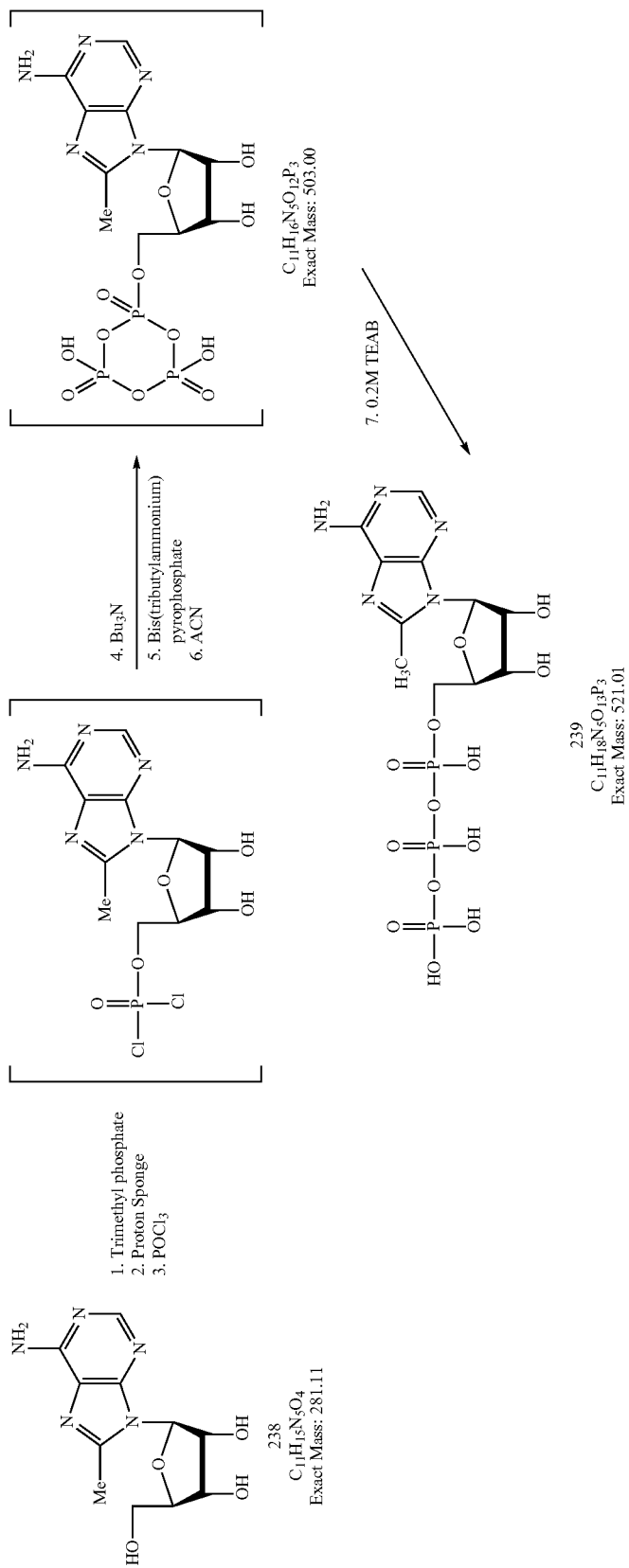

8-Methyl-ATP (239): A solution of 8-methyl-adenosine 238 (112.0 mg, 0.4 mmol; applied heat to make it soluble) and proton sponge (139.95 mg, 0.65 mmol, 1.5 equiv.) in trimethyl phosphate (0.9 mL) was stirred for 10.0 minutes at 0° C. Phosphorus oxychloride (74.23 µL, 0.8 mmol, 2.0 equiv.) was added dropwise to the solution and it was then kept stirring for 2.0 hours under $N_2$ atmosphere. A mixture of tributylamine (379.5 µL, 1.60 mmol, 4.0 equiv.) and bis(tributylammonium) pyrophosphate (655.43 mg, 1.20 mmol, 3.0 equiv.) in acetonitrile (2.5 mL) was added at once. After ~25 minutes, the reaction was quenched with 0.2 M TEAB buffer (15.5 mL) and the clear solution was stirred at room temperature for an hour. LCMS analysis indicated the formation of the corresponding triphosphate. The reaction mixture was then lyophilized overnight. The crude reaction mixture was purified by anion exchange followed by HPLC (Waters, Phenomenex C18 reverse-phase preparative column, 250×21.2 mm, 10.0 micron; gradient (1%): 100% A for 3.0 min, then 1% B/min, A=100 mM TEAA buffer, B=ACN; flow rate: 10.0 mL/min; retention time: 18.25-19.50 min). Fractions containing the desired were pooled together and lyophilized to yield the 8-methyl-adenosine-TP (239) as a tetrakis(triethylammonium salt) (7.56 mg, 3.25%, based on $\varepsilon_{259}$=15,000.0 $Lmol^{-1}$ $cm^{-1}$). UVmax=259 nm; MS: m/e 519.90 (M−H).

Example 75

Synthesis of 5-Isopentenyl-aminomethyl-UTP (00901013042)

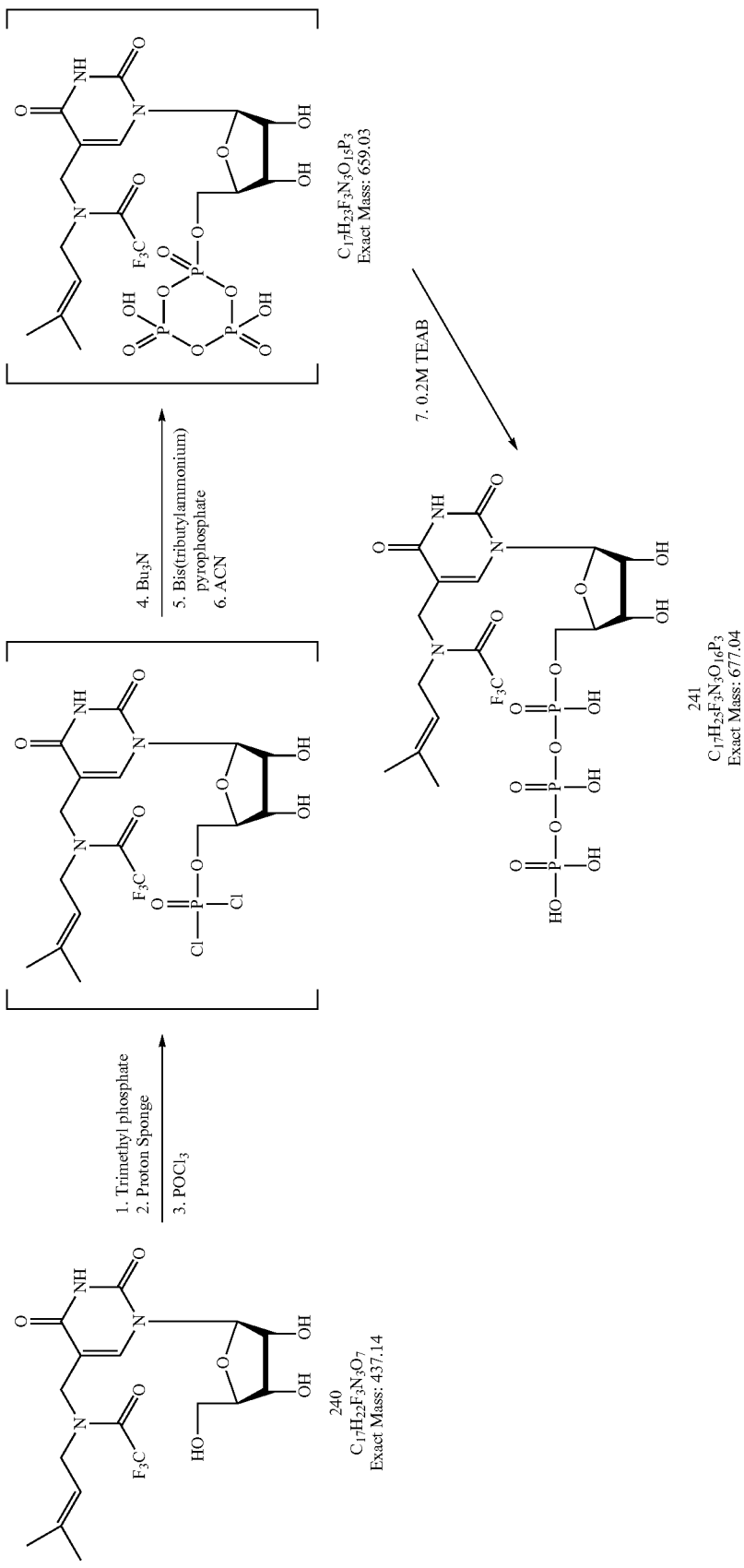

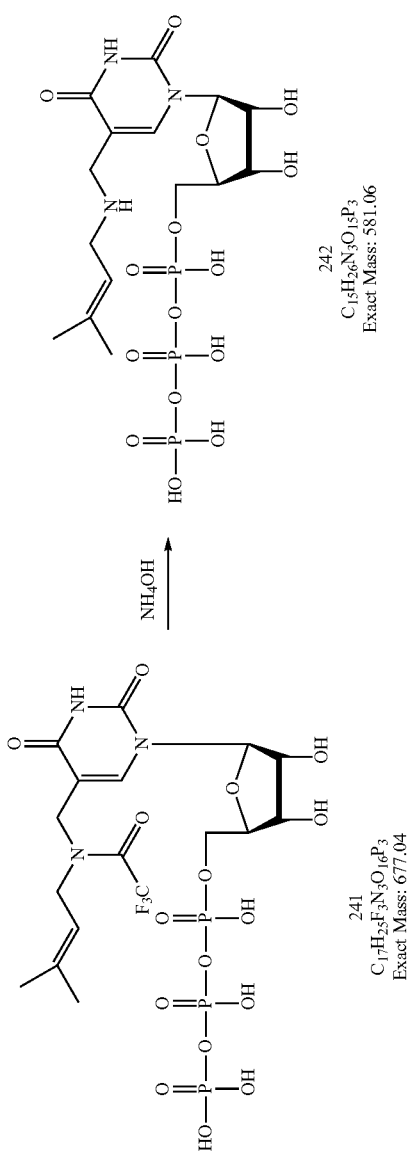

5-Isopentenyl-aminomethyl-UTP (242): A solution of 5-isopentenyl-amino(TFA)methyl-uridine 240 (116.0 mg, 0.26 mmol; applied heat to make it soluble) and proton sponge (85.3 mg, 0.39 mmol, 1.5 equiv.) in trimethyl phosphate (0.9 mL) was stirred for 10.0 minutes at 0° C. Phosphorus oxychloride (44.5 µL, 0.47 mmol, 1.8 equiv.) was added dropwise to the solution and it was then kept stirring for 2.0 hours under $N_2$ atmosphere. A mixture of tributylamine (252.0 µL, 1.06 mmol, 4.0 equiv.) and bis(tributylammonium) pyrophosphate (436.55 mg, 0.79 mmol, 3.0 equiv.) in acetonitrile (2.5 mL) was added at once. After ~25 minutes, the reaction was quenched with 0.2 M TEAB buffer (10.4 mL) and the clear solution was stirred at room temperature for an hour. LCMS analysis indicated the formation of the corresponding triphosphate. The reaction mixture was then treated with conc. $NH_4OH$ (22.0 mL) and stirred vigorously at room temperature overnight. The LCMS analysis showed the formation of the desired deprotected product. The solvent was then evaporated under rotavap and lyophilized overnight. The crude reaction mixture was purified by anion exchange followed by HPLC (Waters, Phenomenex C18 reverse-phase preparative column, 250×21.2 mm, 10.0 micron; gradient (1%): 100% A for 3.0 min, then 1% B/min, A=100 mM TEAA buffer, B=ACN; flow rate: 10.0 mL/min; retention time: 19.4-20.8 min). Fractions containing the desired were pooled together and lyophilized to yield the 5-isopentenyl-aminomethyl-uridine-TP (242) as a tetrakis(triethylammonium salt) (27.21 mg, 18.10%, based on $\varepsilon_{267}$=9,000.0 Lmol$^{-1}$ cm$^{-1}$). UVmax=267 nm; MS: m/e 579.85 (M–H).

Example 76

Synthesis of 5-Hydroxy-UTP (00901013054)

5-Hydroxy-UTP (244): A solution of 5-hydroxy-uridine 243 (121.0 mg, 0.46 mmol; applied heat to make it soluble) and proton sponge (149.48 mg, 0.69 mmol, 1.5 equiv.) in trimethyl phosphate (1.0 mL) was stirred for 10.0 minutes at 0° C. Phosphorus oxychloride (78.0 µL, 0.84 mmol, 1.8 equiv.) was added dropwise to the solution and it was then kept stirring for 2.0 hours under $N_2$ atmosphere. A mixture of tributylamine (443.0 µL, 1.86 mmol, 4.0 equiv.) and bis(tributylammonium) pyrophosphate (765.4 mg, 1.40 mmol, 3.0 equiv.) in acetonitrile (2.5 mL) was added at once. After ~25 minutes, the reaction was quenched with 0.2 M TEAB buffer (18.1 mL) and the clear solution was stirred at room temperature for an hour. LCMS analysis indicated the formation of the corresponding triphosphate. The reaction mixture was then lyophilized overnight. The crude reaction mixture was purified by anion exchange followed by HPLC (Waters, Phenomenex C18 reverse-phase preparative column, 250×21.2 mm, 10.0 micron; gradient (1%): 100% A for 3.0 min, then 1% B/min, A=100 mM TEAA buffer, B=ACN; flow rate: 10.0 mL/min; retention time: 11.20-12.50 min). Fractions containing the desired were pooled together and lyophilized to yield the 5-hydroxy-uridine-TP (244) as a tetrakis(triethylammonium salt) (9.42 mg, 4.13%, based on $\varepsilon_{280}$=9,000.0 Lmol$^{-1}$ cm$^{-1}$). UVmax=280 nm; MS: m/e 498.85 (M–H).

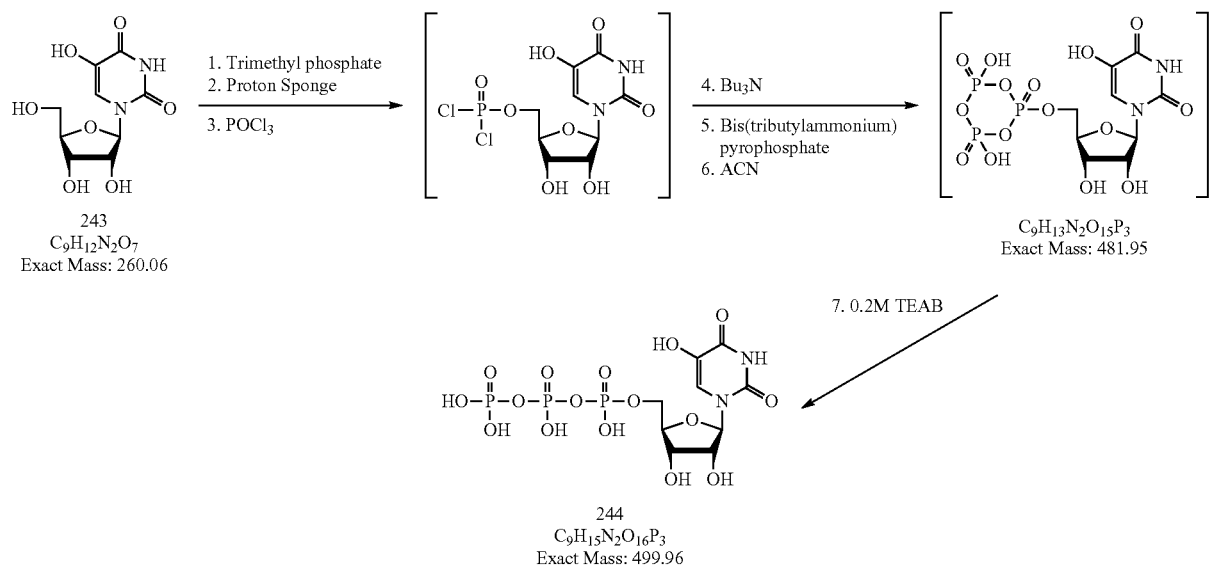

Example 77

Synthesis of 5-Carbamoylmethyl-UTP
(03601013036)

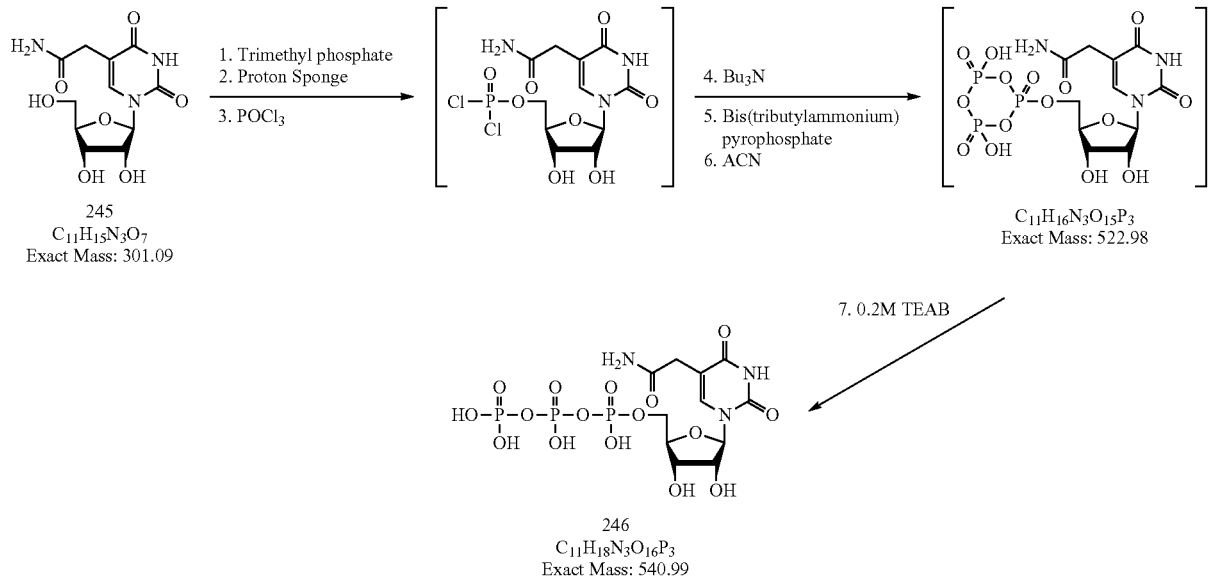

5-Carbamoylmethyl-UTP (246): A solution of 5-carbamoylmethyl-uridine 245 (114.0 mg, 0.38 mmol; applied heat to make it soluble) and proton sponge (121.6 mg, 0.57 mmol, 1.5 equiv.) in trimethyl phosphate (0.9 mL) was stirred for 10.0 minutes at 0° C. Phosphorus oxychloride (63.5 µL, 0.68 mmol, 1.8 equiv.) was added dropwise to the solution and it was then kept stirring for 2.0 hours under $N_2$ atmosphere. A mixture of tributylamine (360.0 µL, 1.51 mmol, 4.0 equiv.) and bis(tributylammonium) pyrophosphate (622.86 mg, 1.13 mmol, 3.0 equiv.) in acetonitrile (2.5 mL) was added at once. After ~25 minutes, the reaction was quenched with 0.2 M TEAB buffer (14.8 mL) and the clear solution was stirred at room temperature for an hour. LCMS analysis indicated the formation of the corresponding triphosphate. The reaction mixture was then lyophilized overnight. The crude reaction mixture was purified by anion exchange followed by HPLC (Waters, Phenomenex C18 reverse-phase preparative column, 250×21.2 mm, 10.0 micron; gradient (1%): 100% A for 3.0 min, then 1% B/min, A=100 mM TEAA buffer, B=ACN; flow rate: 10.0 mL/min; retention time: 10.4-11.40 min). Fractions containing the desired were pooled together and lyophilized to yield the 5-carbamoylmethyl-uridine-TP (246) as a tetrakis(triethylammonium salt) (21.46 mg, 10.52%, based on $\varepsilon_{265}$=9,000.0 $Lmol^{-1}$ $cm^{-1}$). UVmax=265 nm; MS: m/e 539.90 (M−H).

Example 78

Synthesis of
5-beta-D-Ribofuranosyl-2(1H)-pyridinone-TP
(07101015011)

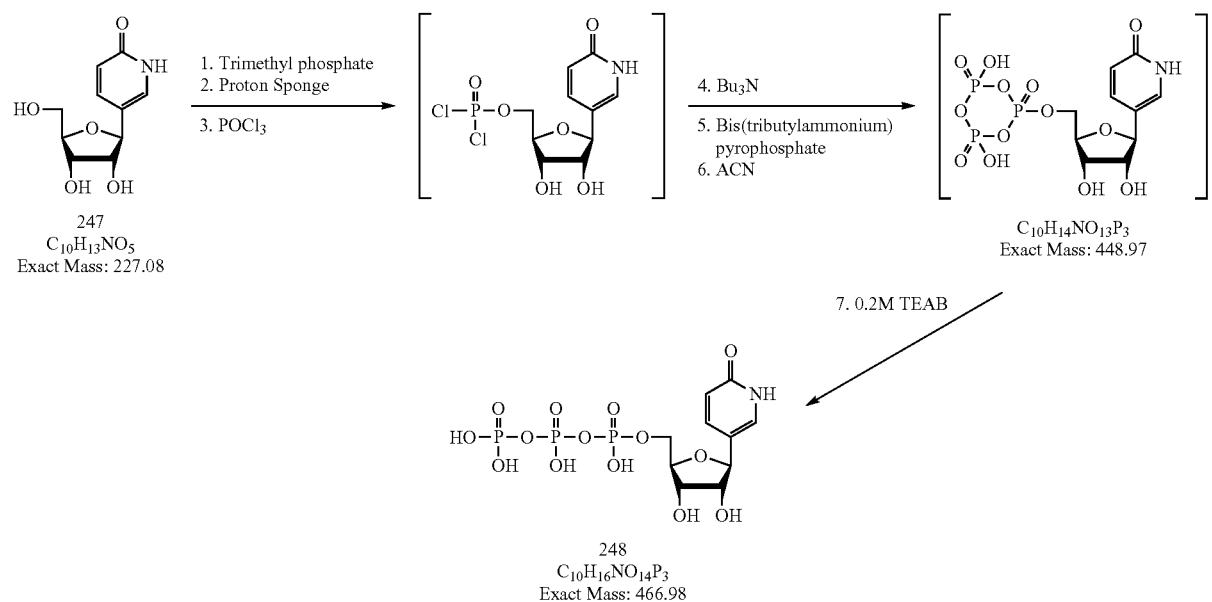

5-beta-D-Ribofuranosyl-2(1H)-pyridinone-TP (248): A solution of 5-((2S,3R,4S,5R)-3,4-dihydroxy-5-(hydroxymethyl)tetrahydrofuran-2-yl)pyridin-2(1H)-one 247 (101.0 mg, 0.44 mmol) in trimethyl phosphate (1.0 mL) was heated until fully dissolved. Proton sponge (140.0 mg, 0.66 mmol, 1.5 equiv.) was added and the resulting reaction mixture was cooled to 0° C. and stirred for 10 minutes. Phosphorus oxychloride (61.0 µL, 0.66 mmol, 1.5 equiv.) was added dropwise to the solution and it was then kept stirring for 1.5 hours under $N_2$ atmosphere. A mixture of tributylamine (0.44 mL) and bis(tributylammonium) pyrophosphate (720.0 mg, 1.32 mmol, 3 equiv.) in acetonitrile (2.0 mL) was added at once. After ~20 minutes, the reaction was quenched with 0.2 M TEAB buffer (12.0 mL) and the clear solution was stirred at room temperature for 1 hour. LCMS analysis indicated the formation of the corresponding triphosphate. The reaction mixture was concentrated under reduced pressure. The crude reaction mixture was purified by anion exchange followed by HPLC (Waters, Phenomenex C18 reverse-phase preparative column, 250×21.2 mm, 10.0 micron; gradient (1%): 100% A for 3.0 min, then 1% B/min, A=100 mM TEAA buffer, B=ACN; flow rate: 10.0 mL/min; retention time: 10.7-11.2 min). Fractions containing the desired triphosphate were pooled and lyophilized to yield 2-pyridinone-TP (248) as a tetrakis(triethylammonium) salt (0.77 mg, based on $\varepsilon_{299}$=5,969.8 Lmol$^{-1}$ cm$^{-1}$). UVmax=299 nm; MS: m/e 465.85 (M–H).

Example 79

Synthesis of 6-Fluoro-5-beta-D-ribofuranosyl-2 (1H)-pyridinone-TP (07101015012)

6-Fluoro-5-beta-D-ribofuranosyl-2(1H)-pyridinone-TP (250): A solution of 5-((2S,3R,4S,5R)-3,4-dihydroxy-5-(hydroxymethyl)tetrahydrofuran-2-yl)-6-fluoropyridin-2(1H)-one 249 (105.0 mg, 0.43 mmol) in trimethyl phosphate (1.0 mL) was heated until fully dissolved. Proton sponge (140.0 mg, 0.65 mmol, 1.5 equiv.) was added and the resulting reaction mixture was cooled to 0° C. and stirred for 10 minutes. Phosphorus oxychloride (61.0 µL, 0.65 mmol, 1.5 equiv.) was added dropwise to the solution and it was then kept stirring for 2 hours under $N_2$ atmosphere. A mixture of tributylamine (0.42 mL) and bis(tributylammonium) pyrophosphate (710.0 mg, 1.29 mmol, 3 equiv.) in acetonitrile (2.0 mL) was added at once. After ~20 minutes, the reaction was quenched with 0.2 M TEAB buffer (12.0 mL) and the clear solution was stirred at room temperature for 1 hour. LCMS analysis indicated the formation of the corresponding triphosphate. The reaction mixture was concentrated under reduced pressure. The crude reaction mixture was purified by anion exchange followed by HPLC (Waters, Phenomenex C18 reverse-phase preparative column, 250×21.2 mm, 10.0 micron; gradient (1%): 100% A for 3.0 min, then 1% B/min, A=100 mM TEAA buffer, B=ACN; flow rate: 10.0 mL/min; retention time: 11.1-11.5 min). Fractions containing the desired triphosphate were pooled and lyophilized to yield 6-fluoro-2-pyridinone-TP (250) as a tetrakis(triethylammonium) salt (1.99 mg, based on $\varepsilon_{274}$=5,468.2 Lmol$^{-1}$ cm$^{-1}$). UVmax=291 nm; MS: m/e 483.8 (M–H).

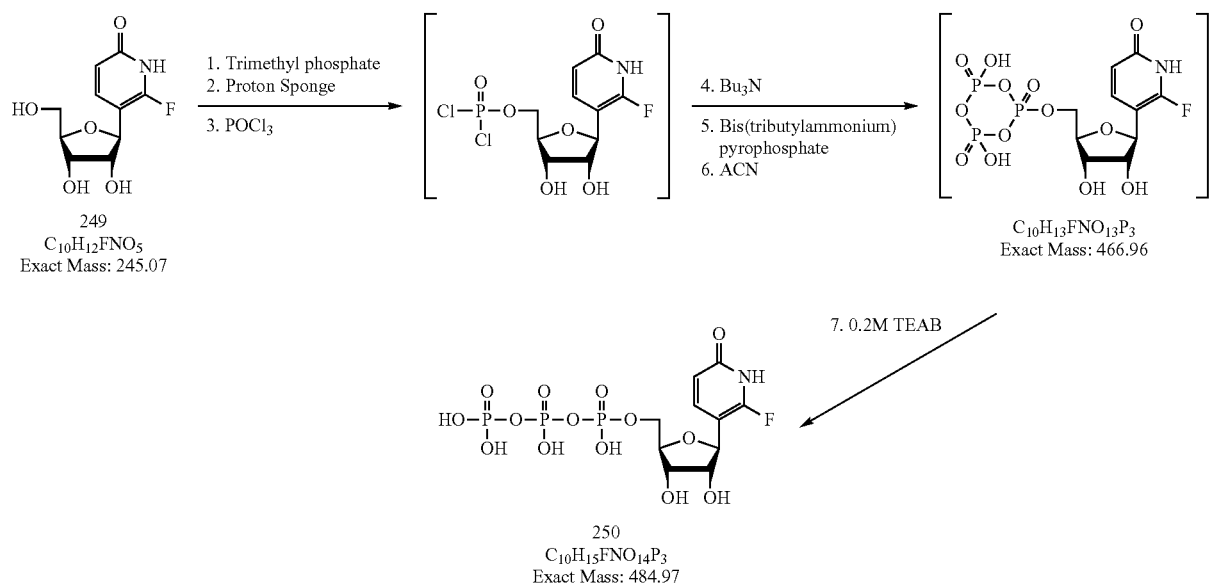

Example 80

Synthesis of 3-Methyl-5-beta-D-ribofuranosyl-2 (1H)-pyridinone-TP (07101015017)

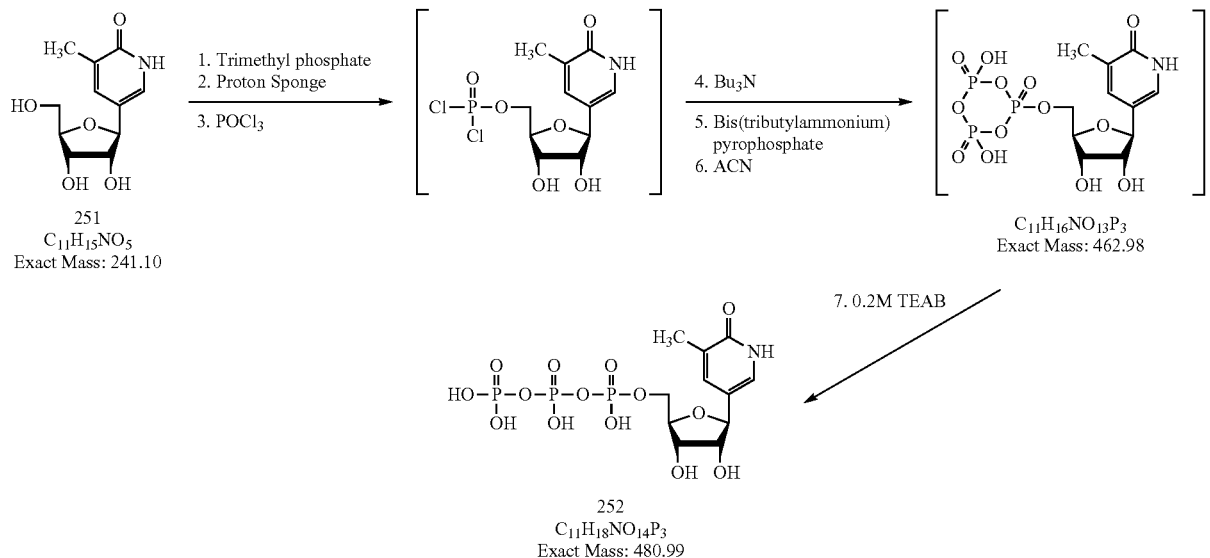

3-Methyl-5-beta-D-ribofuranosyl-2(1H)-pyridinone-TP (252): A solution of 5-((2S,3R,4S,5R)-3,4-dihydroxy-5-(hydroxymethyl)tetrahydrofuran-2-yl)-3-methylpyridin-2(1H)-one 251 (109.0 mg, 0.45 mmol) in trimethyl phosphate (1.1 mL) was heated until fully dissolved. Proton sponge (145.0 mg, 0.68 mmol, 1.5 equiv.) was added and the resulting reaction mixture was cooled to 0° C. and stirred for 10 minutes. Phosphorus oxychloride (63.0 µL, 0.68 mmol, 1.5 equiv.) was added dropwise to the solution and it was then kept stirring for 1.5 hours under $N_2$ atmosphere. A mixture of tributylamine (0.44 mL) and bis(tributylammonium) pyrophosphate (740.0 mg, 1.35 mmol, 3 equiv.) in acetonitrile (2.0 mL) was added at once. After ~20 minutes, the reaction was quenched with 0.2 M TEAB buffer (12.0 mL) and the clear solution was stirred at room temperature for 1 hour. LCMS analysis indicated the formation of the corresponding triphosphate. The reaction mixture was concentrated under reduced pressure. The crude reaction mixture was purified by anion exchange followed by HPLC (Waters, Phenomenex C18 reverse-phase preparative column, 250× 21.2 mm, 10.0 micron; gradient (1%): 100% A for 3.0 min, then 1% B/min, A=100 mM TEAA buffer, B=ACN; flow rate: 10.0 mL/min; retention time: 11.0-11.55 min). Fractions containing the desired triphosphate were pooled and lyophilized to yield 3-methyl-2-pyridinone-TP (252) as a tetrakis(triethylammonium) salt (1.2 mg, based on $\epsilon_{298}$=5, 849.8 $Lmol^{-1}$ $cm^{-1}$). UVmax=298 nm; MS: m/e 479.85 (M−H).

Example 81

Synthesis of 6-Methyl-5-beta-D-ribofuranosyl-2 (1H)-pyridinone-TP (07101015013)

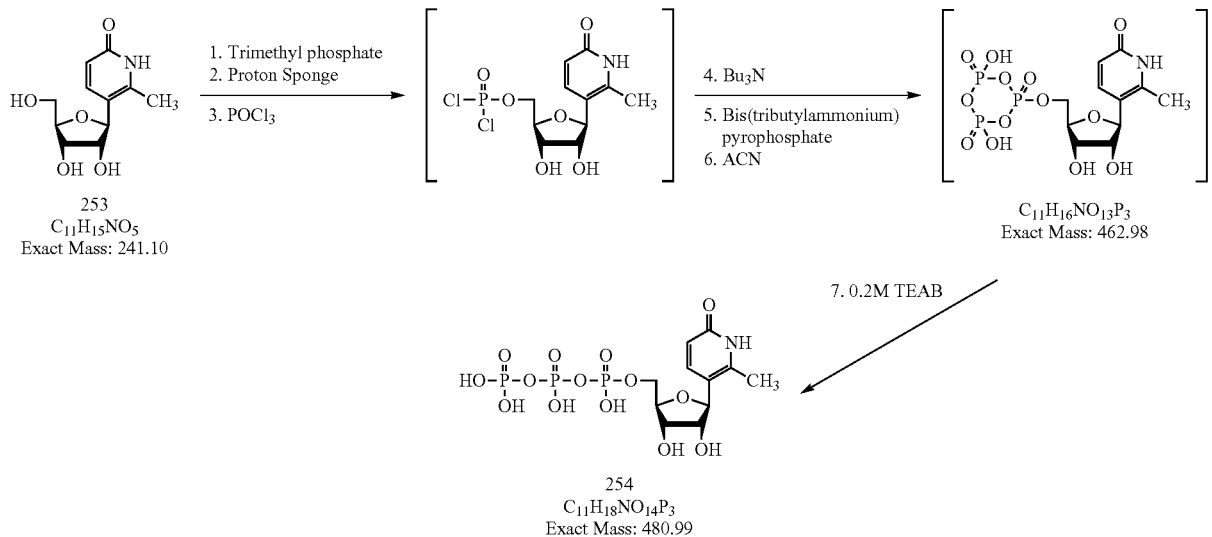

6-Methyl-5-beta-D-ribofuranosyl-2(1H)-pyridinone-TP (254): 5-((2S,3R,4S,5R)-3,4-dihydroxy-5-(hydroxymethyl)tetrahydrofuran-2-yl)-6-methylpyridin-2(1H)-one 253 (101.0 mg, 0.42 mmol) in trimethyl phosphate (0.96 mL) was heated until fully dissolved. Proton sponge (135.0 mg, 0.63 mmol, 1.5 equiv.) was added and the resulting reaction mixture was cooled to 0° C. and stirred for 10 minutes. Phosphorus oxychloride (59.0 μL, 0.63 mmol, 1.5 equiv.) was added dropwise to the solution and it was then kept stirring for 1.5 hours under $N_2$ atmosphere. A mixture of tributylamine (0.42 mL) and bis(tributylammonium) pyrophosphate (690.0 mg, 1.26 mmol, 3 equiv.) in acetonitrile (2.0 mL) was added at once. After ~20 minutes, the reaction was quenched with 0.2 M TEAB buffer (12.0 mL) and the clear solution was stirred at room temperature for 1 hour. LCMS analysis indicated the formation of the corresponding triphosphate. The reaction mixture was concentrated under reduced pressure. The crude reaction mixture was purified by anion exchange followed by HPLC (Waters, Phenomenex C18 reverse-phase preparative column, 250×21.2 mm, 10.0 micron; gradient (1%): 100% A for 3.0 min, then 1% B/min, A=100 mM TEAA buffer, B=ACN; flow rate: 10.0 mL/min; retention time: 4.75-5.1 min). Fractions containing the desired triphosphate were pooled and lyophilized to yield 6-methyl-2-pyridinone-TP (254) as a tetrakis(triethylammonium) salt (1.14 mg, based on $\varepsilon_{304}$=7,897.7 $Lmol^{-1}$ $cm^{-1}$). UVmax=304 nm; MS: m/e 479.85 (M−H).

Example 82

DNA and mRNA Sequences for Constructs Used to Screen Compounds of the Invention GCSF DNA
SEQ ID NO: 1
GGGAGATCAGAGAGAAAAGAAGAGTAAGAAGAAATATAAGAGCCACCATG
GCCGGTCCCGCGACCCAAAGCCCCATGAAACTTATGGCCCTGCAGTTGCT
GCTTTGGCACTCGGCCCTCTGGACAGTCCAAGAAGCGACTCCTCTCGGAC
CTGCCTCATCGTTGCCGCAGTCATTCCTTTTGAAGTGTCTGGAGCAGGTG
CGAAAGATTCAGGGCGATGGAGCCGCACTCCAAGAGAAGCTCTGCGCGAC
ATACAAACTTTGCCATCCCGAGGAGCTCGTACTGCTCGGGCACAGCTTGG
GGATTCCCTGGGCTCCTCTCTCGTCCTGTCCGTCGCAGGCTTTGCAGTTG
GCAGGGTGCCTTTCCCAGCTCCACTCCGGTTTGTTCTTGTATCAGGGACT
GCTGCAAGCCCTTGAGGGAATCTCGCCAGAATTGGGCCCGACGCTGGACA
CGTTGCAGCTCGACGTGGCGGATTTCGCAACAACCATCTGGCAGCAGATG
GAGGAACTGGGGATGGCACCCGCGCTGCAGCCCACGCAGGGGGCAATGCC
GGCCTTTGCGTCCGCGTTTCAGCGCAGGGCGGGTGGAGTCCTCGTAGCGA
GCCACCTTCAATCATTTTTGGAAGTCTCGTACCGGGTGCTGAGACATCTT
GCGCAGCCGTGATAATAGGCTGGAGCCTCGGTGGCCATGCTTCTTGCCCC
TTGGGCCTCCCCCCAGCCCCTCCTCCCCTTCCTGCACCCGTACCCCGTG
GTCTTTGAATAAAGTCTGAGTGGGCGGCTCTAGA GCSF mRNA
SEQ ID NO: 2
GGGAGAUCAGAGAGAAAAGAAGAGUAAGAAGAAAUAUAAGAGCCACCAUG
GCCGGUCCCGCGACCCAAAGCCCCAUGAAACUUAUGGCCCUGCAGUUGCU
GCUUUGGCACUCGGCCCUCUGGACAGUCCAAGAAGCGACUCCUCUCGGAC
CUGCCUCAUCGUUGCCGCAGUCAUUCCUUUUGAAGUGUCUGGAGCAGGUG
CGAAAGAUUCAGGGCGAUGGAGCCGCACUCCAAGAGAAGCUCUGCGCGAC
AUACAAACUUUGCCAUCCCGAGGAGCUCGUACUGCUCGGGCACAGCUUGG
GGAUUCCCUGGGCUCCUCUCUCGUCCUGUCCGUCGCAGGCUUUGCAGUUG
GCAGGGUGCCUUUCCCAGCUCCACUCCGGUUUGUUCUUGUAUCAGGGACU
GCUGCAAGCCCUUGAGGGAAUCUCGCCAGAAUUGGGCCCGACGCUGGACA
CGUUGCAGCUCGACGUGGCGGAUUUCGCAACAACCAUCUGGCAGCAGAUG
GAGGAACUGGGGAUGGCACCCGCGCUGCAGCCCACGCAGGGGGCAAUGCC
GGCCUUUGCGUCCGCGUUUCAGCGCAGGGCGGGUGGAGUCCUCGUAGCGA
GCCACCUUCAAUCAUUUUUGGAAGUCUCGUACCGGGUGCUGAGACAUCUU
GCGCAGCCGUGAUAAUAGGCUGGAGCCUCGGUGGCCAUGCUUCUUGCCCC
UUGGGCCUCCCCCCAGCCCCUCCUCCCCUUCCUGCACCCGUACCCCGUG
GUCUUUGAAUAAAGUCUGAGUGGGCGGCUCUAGA Luciferase DNA
SEQ ID NO: 3
GGGAAATAAGAGAGAAAAGAAGAGTAAGAAGAAATATAAGAGCCACCATG
GAAGATGCGAAGAACATCAAGAAGGGACCTGCCCCGTTTTACCCTTTGGA
GGACGGTACAGCAGGAGAACAGCTCCACAAGGCGATGAAACGCTACGCCC
TGGTCCCCGGAACGATTGCGTTTACCGATGCACATATTGAGGTAGACATC
ACATACGCAGAATACTTCGAAATGTCGGTGAGGCTGGCGGAAGCGATGAA
GAGATATGGTCTTAACACTAATCACCGCATCGTGGTGTGTTCGGAGAACT
CATTGCAGTTTTTCATGCCGGTCCTTGGAGCACTTTTCATCGGGGTCGCA
GTCGCGCCAGCGAACGACATCTACAATGAGCGGGAACTCTTGAATAGCAT
GGGAATCTCCCAGCCGACGGTCGTGTTTGTCTCCAAAAAGGGGCTGCAGA
AAATCCTCAACGTGCAGAAGAAGCTCCCCATTATTCAAAAGATCATCATT
ATGGATAGCAAGACAGATTACCAAGGGTTCCAGTCGATGTATACCTTTGT
GACATCGCATTTGCCGCCAGGGTTTAACGAGTATGACTTCGTCCCCGAGT
CATTTGACAGAGATAAAACCATCGCGCTGATTATGAATTCCTCGGGTAGC
ACCGGTTTGCCAAAGGGGGTGGCGTTGCCCCACCGCACTGCTTGTGTGCG
GTTCTCGCACGCTAGGGATCCTATCTTTGGTAATCAGATCATTCCCGACA
CAGCAATCCTGTCCGTGGTACCTTTTCATCACGGTTTTGGCATGTTCACG
ACTCTCGGCTATTTGATTTGCGGTTTCAGGGTCGTACTTATGTATCGGTT
CGAGGAAGAACTGTTTTTGAGATCCTTGCAAGATTACAAGATCCAGTCGG
CCCTCCTTGTGCCAACGCTTTTCTCATTCTTTGCGAAATCGACACTTATT
GATAAGTATGACCTTTCCAATCTGCATGAGATTGCCTCAGGGGGAGCGCC
GCTTAGCAAGGAAGTCGGGGAGGCAGTGGCCAAGCGCTTCCACCTTCCCG
GAATTCGGCAGGGATACGGGCTCACGGAGACAACATCCGCGATCCTTATC
ACGCCCGAGGGTGACGATAAGCCGGGAGCCGTCGGAAAAGTGGTCCCCTT
CTTTGAAGCCAAGGTCGTAGACCTCGACACGGGAAAAACCCTCGGAGTGA
ACCAGAGGGGCGAGCTCTGCGTGAGAGGGCCGATGATCATGTCAGGTTAC
GTGAATAACCCTGAAGCGACGAATGCGCTGATCGACAAGGATGGGTGGTT GCATTCGGGAGACATTGCCTATTGGGATGAGGATGAGCACTTCTTTATCG
TAGATCGACTTAAGAGCTTGATCAAATACAAAGGCTATCAGGTAGCGCCT
GCCGAGCTCGAGTCAATCCTGCTCCAGCACCCCAACATTTTCGACGCCGG
AGTGGCCGGGTTGCCCGATGACGACGCGGGTGAGCTGCCAGCGGCCGTGG
TAGTCCTCGAACATGGGAAAACAATGACCGAAAAGGAGATCGTGGACTAC
GTAGCATCACAAGTGACGACTGCGAAGAAACTGAGGGGAGGGGTAGTCTT
TGTGGACGAGGTCCCGAAAGGCTTGACTGGGAAGCTTGACGCTCGCAAAA
TCCGGGAAATCCTGATTAAGGCAAAGAAAGGCGGGAAAATCGCTGTCTGA
TAATAGGCTGGAGCCTCGGTGGCCATGCTTCTTGCCCCTTGGGCCTCCCC
CCAGCCCCTCCTCCCCTTCCTGCACCCGTACCCCGTGGTCTTTGAATAA
AGTCTGAGTGGGCGGCTCTAGA Luciferase mRNA
SEQ ID NO: 4
GGGAAAUAAGAGAGAAAAGAAGAGUAAGAAGAAAUAUAAGAGCCACCAUG
GAAGAUGCGAAGAACAUCAAGAAGGGACCUGCCCCGUUUUACCCUUUGGA
GGACGGUACAGCAGGAGAACAGCUCCACAAGGCGAUGAAACGCUACGCCC
UGGUCCCCGGAACGAUUGCGUUUACCGAUGCACAUAUUGAGGUAGACAUC
ACAUACGCAGAAUACUUCGAAAUGUCGGUGAGGCUGGCGGAAGCGAUGAA
GAGAUAUGGUCUUAACACUAAUCACCGCAUCGUGGUGUGUUCGGAGAACU
CAUUGCAGUUUUCAUGCCGGUCCUUGGAGCACUUUCAUCGGGUCGCA
GUCGCGCCAGCGAACGACAUCUACAAUGAGCGGGAACUCUUGAAUAGCAU
GGGAAUCUCCCAGCCGACGGUCGUGUUUGUCUCCAAAAAGGGGCUGCAGA
AAAUCCUCAACGUGCAGAAGAAGCUCCCCAUUAUUCAAAAGAUCAUCAUU
AUGGAUAGCAAGACAGAUUACCAAGGGUUCCAGUCGAUGUAUACCUUUGU
GACAUCGCAUUUGCCGCCAGGGUUUAACGAGUAUGACUUCGUCCCCGAGU
CAUUUGACAGAGAUAAAACCAUCGCGCUGAUUAUGAAUUCCUCGGGUAGC
ACCGGUUUGCCAAAGGGGGUGGCGUUGCCCCACCGCACUGCUUGUGUGCG
GUUCUCGCACGCUAGGGAUCCUAUCUUUGGGUAAUCAGAUCAUUCCCGACA
CAGCAAUCCUGUCCGUGGUACCUUUUCAUCACGGUUUUGGCAUGUUCACG
ACUCUCGGCUAUUUGAUUUGCGGUUUCAGGGUCGUACUUUAUGUAUCGGUU
CGAGGAAGAACUGUUUUUGAGAUCCUUGCAAGAUUACAAGAUCCAGUCGG
CCCUCCUUGUGCCAACGCUUUUCUCAUUCUUUGCGAAAUCGACACUUAUU
GAUAAGUAUGACCUUUCCAAUCUGCAUGAGAUUGCCUCAGGGGGAGCGCC
GCUUAGCAAGGAAGUCGGGGAGGCAGUGGCCAAGCGCUUCCACCUUCCCG
GAAUUCGGCAGGGAUACGGGCUCACGGAGACAACAUCCGCGAUCCUUAUC
ACGCCCGAGGGUGACGAUAAGCCGGGAGCCGUCGAAAAGUGGUCCCCUU
CUUUGAAGCCAAGGUCUAGACCUCGACACGGAAAAACCCUCGGAGUGA
ACCAGAGGGCGAGCUCUGCGUGAGAGGGCCGAUGAUCAUGUCAGGUUAC
GUGAAUAACCCUGAAGCGACGAAUGCGCUGAUCGACAAGGAUGGGUGGUU
GCAUUCGGGAGACAUUGCCUAUUGGGAUGAGGAUGAGCACUUCUUUAUCG
UAGAUCGACUUAAGAGCUUGAUCAAAUACAAAGGCUAUCAGGUAGCGCCU
GCCGAGCUCGAGUCAAUCCUGCUCCAGCACCCCAACAUUUUCGACGCCGG AGUGGCCGGGUUGCCCGAUGACGACGCGGGUGAGCUGCCAGCGGCCGUGG
UAGUCCUCGAACAUGGGAAAACAAUGACCGAAAAGGAGAUCGUGGACUAC
GUAGCAUCACAAGUGACGACUGCGAAGAAACUGAGGGGAGGGGUAGUCUU
UGUGGACGAGGUCCCGAAAGGCUUGACUGGGAAGCUUGACGCUCGCAAAA
UCCGGGAAAUCCUGAUUAAGGCAAAGAAAGGCGGGAAAAUCGCUGUCUGA
UAAUAGGCUGGAGCCUCGGUGGCCAUGCUUCUUGCCCCUUGGGCCUCCCC
CCAGCCCCUCCUCCCCUUCCUGCACCCGUACCCCGUGGUCUUUGAAUAA
AGUCUGAGUGGGCGGCUCUAGA EPO DNA
SEQ ID NO: 5
GGGAAATAAGAGAGAAAAGAAGAGTAAGAAGAAATATAAGAGCCACCATG
GGAGTGCACGAGTGTCCCGCGTGGTTGTGGTTGCTGCTGTCGCTCTTGAG
CCTCCCACTGGGACTGCCTGTGCTGGGGCACCACCCAGATTGATCTGCG
ACTCACGGGTACTTGAGAGGTACCTTCTTGAAGCCAAAGAAGCCGAAAAC
ATCACAACCGGATGCGCCGAGCACTGCTCCCTCAATGAGAACATTACTGT
ACCGGATACAAAGGTCAATTTCTATGCATGGAAGAGAATGGAAGTAGGAC
AGCAGGCCGTCGAAGTGTGGCAGGGGCTCGCGCTTTTGTCGGAGGCGGTG
TTGCGGGGTCAGGCCCTCCTCGTCAACTCATCACAGCCGTGGGAGCCCCT
CCAACTTCATGTCGATAAAGCGGTGTCGGGGCTCCGCAGCTTGACGACGT
TGCTTCGGGCTCTGGGCGCACAAAAGGAGGCTATTTCGCCGCCTGACGCG
GCCTCCGCGGCACCCCTCCGAACGATCACCGCGGACACGTTTAGGAAGCT
TTTTAGAGTGTACAGCAATTTCCTCCGCGGAAAGCTGAAATTGTATACTG
GTGAAGCGTGTAGGACAGGGGATCGCTGATAATAGGCTGGAGCCTCGGTG
GCCATGCTTCTTGCCCCTTGGGCCTCCCCCCAGCCCCTCCTCCCCTTCCT
GCACCCGTACCCCGTGGTCTTTGAATAAAGTCTGAGTGGGCGGCTCTAG
A EPO mRNA
SEQ ID NO: 6
GGGAAAUAAGAGAGAAAAGAAGAGUAAGAAGAAAUAUAAGAGCCACCAUG
GGAGUGCACGAGUGUCCCGCGUGGUUGUGGUUGCUGCUGUCGCUCUUGAG
CCUCCCACUGGGACUGCCUGUGCUGGGGGCACCACCCAGAUUGAUCUGCG
ACUCACGGGUACUUGAGAGGUACCUUCUUGAAGCCAAAGAAGCCGAAAAC
AUCACAACCGGAUGCGCCGAGCACUGCUCCCUCAAUGAGAACAUUACUGU
ACCGGAUACAAAGGUCAAUUUCUAUGCAUGGAAGAGAAUGGAAGUAGGAC
AGCAGGCCGUCGAAGUGUGGCAGGGGCUCGCGCUUUUGUCGGAGGCGGUG
UUGCGGGGUCAGGCCCUCCUCGUCAACUCAUCACAGCCGUGGGAGCCCCU
CCAACUUCAUGUCGAUAAAGCGGUGUCGGGGCUCCGCAGCUUGACGACGU
UGCUUCGGGCUCUGGGCGCACAAAAGGAGGCUAUUUCGCCGCCUGACGCG
GCCUCCGCGGCACCCCUCCGAACGAUCACCGCGGACACGUUUAGGAAGCU
UUUUAGAGUGUACAGCAAUUUCCUCCGCGGAAAGCUGAAAUUGUAUACUG
GUGAAGCGUGUAGGACAGGGGAUCGCUGAUAAUAGGCUGGAGCCUCGGUG
GCCAUGCUUCUUGCCCCUUGGGCCUCCCCCCAGCCCCUCCUCCCCUUCCU -continued

GCACCCGUACCCCCGUGGUCUUUGAAUAAAGUCUGAGUGGGCGGCUCUAGA mCherry DNA

SEQ ID NO: 7

TCAAGCTTTTGGACCCTCGTACAGAAGCTAATACGACTCACTATAGGGAAATAAGAGAGAAAAGAAGAGTAAGAAGAAATATAAGAGCCACCATGGTATCCAAGGGGGAGGAGGACAACATGGCGATCATCAAGGAGTTCATGCGATTCAAGGTGCACATGGAAGGTTCGGTCAACGGACACGAATTTGAAATCGAAGGAGAGGGTGAAGGAAGGCCCTATGAAGGGACACAGACCGCGAAACTCAAGGTCACGAAAGGGGGACCACTTCCTTTCGCCTGGGACATTCTTTCGCCCCAGTTTATGTACGGGTCCAAAGCATATGTGAAGCATCCCGCCGATATTCCTGACTATCTGAAACTCAGCTTTCCCGAGGGATTCAAGTGGGAGCGGGTCATGAACTTTGAGGACGGGGGTGTAGTCACCGTAACCCAAGACTCAAGCCTCCAAGACGGCGAGTTCATCTACAAGGTCAAACTGCGGGGGACTAACTTTCCGTCGGATGGGCCGGTGATGCAGAAGAAAACGATGGGATGGGAAGCGTCATCGGAGAGGATGTACCCAGAAGATGGTGCATTGAAGGGGGAGATCAAGCAGAGACTGAAGTTGAAAGATGGGGACATTATGATGCCGAGGTGAAAACGACATACAAAGCGAAAAAGCCGGTGCAGCTTCCCGGAGCGTATAATGTGAATATCAAGTTGGATATTACTTCACACAATGAGGACTACACAATTGTCGAACAGTACGAACGCGCTGAGGGTAGACACTCGACGGGAGGCATGGACGAGTTGTACAAATGATAATAGGCTGGAGCCTCGGTGGCCATGCTTCTTGCCCCTTGGGCCTCCCCCCAGCCCCTCCTCCCCTTCCTGCACCCGTACCCCCGTGGTCTTTGAATAAAGTCTGAGTGGGCGGCTCTAGA nanoluc DNA

SEQ ID NO: 8

TCAAGCTTTTGGACCCTCGTACAGAAGCTAATACGACTCACTATAGGGAAATAAGAGAGAAAAGAAGAGTAAGAAGAAATATAAGAGCCACCATGGTTTTTACCCTCGAAGATTTTGTCGGAGATTGGAGACAGACTGCCGGATACAACCTTGACCAAGTCCTCGAGCAAGGCGGTGTGTCGTCACTCTTCCAAAACCTGGGTGTGTCCGTGACTCCCATCCAGCGCATCGTCCTGAGCGGCGAAAATGGGTTGAAGATCGACATCCATGTGATCATTCCATACGAGGGACTGTCCGGGGACCAGATGGGTCAGATCGAAAAGATTTTCAAAGTGGTGTACCCGGTCGACGATCATCACTTCAAGGTGATCCTGCACTACGGAACGCTGGTGATCGATGGGGTGACCCCGAACATGATTGACTATTTCGGACGGCCTTACGAGGGCATCGCAGTGTTCGACGGAAAGAAGATCACCGTGACCGGCACTCTGTGGAATGGAAACAAAATCATCGACGAACGCCTGATCAATCCGGATGGCTCGCTGTTGTTCCGGGTGACCATTAACGGAGTCACTGGATGGAGGCTCTGCGAGCGCATCCTTGCGTGATAATAGGCTGGAGCCTCGGTGGCCATGCTTCTTGCCCCTTGGGCCTCCCCCAGCCCCTCCTCCCCTTCCTGCACCCGTACCCCCGTGGTCTTTGAATAAAGTCTGAGTGGGCGGCTCTAGA

Human EPO DNA

SEQ ID NO: 9

TCAAGCTTTTGGACCCTCGTACAGAAGCTAATACGACTCACTATAGGGAAATAAGAGAGAAAAGAAGAGTAAGAAGAAATATAAGAGCCACCATGGGAGTGCACGAGTGTCCCGCGTGGTTGTGGTTGCTGCTGTCGCTCTTGAGCCTCCCACTGGGACTGCCTGTGCTGGGGGCACCACCCAGATTGATCTGCGACTCACGGGTACTTGAGAGGTACCTTCTTGAAGCCAAAGAAGCCGAAAACATCACAACCGGATGCGCCGAGCACTGCTCCCTCAATGAGAACATTACTGTACCGGATACAAAGGTCAATTTCTATGCATGGAAGAGAATGGAAGTAGGACAGCAGGCCGTCGAAGTGTGGCAGGGGCTCGCGCTTTTGTCGGAGGCGGTGTTGCGGGGTCAGGCCCTCCTCGTCAACTCATCACAGCCGTGGGAGCCCCTCCAACTTCATGTCGATAAAGCGGTGTCGGGGCTCCGCAGCTTGACGACGTTGCTTCGGGCTCTGGGCGCACAAAAGGAGGCTATTTCGCCGCCTGACGCGGCCTCCGCGGCACCCCTCCGAACGATCACCGCGGACACGTTTAGGAAGCTTTTTAGAGTGTACAGCAATTTCCTCCGCGGAAAGCTGAAATTGTATACTGGTGAAGCGTGTAGGACAGGGGATCGCTGATAATAGGCTGGAGCCTCGGTGGCCATGCTTCTTGCCCCTTGGGCCTCCCCCCAGCCCCTCCTCCCCTTCCTGCACCCGTACCCCCGTGGTCTTTGAATAAAGTCTGAGTGGGCGGCTCTAGA

Mouse EPO DNA

SEQ ID NO: 10

TCAAGCTTTTGGACCCTCGTACAGAAGCTAATACGACTCACTATAGGGAAATAAGAGAGAAAAGAAGAGTAAGAAGAAATATAAGAGCCACCATGGGGGTGCCCGAACGTCCCACCCTGCTGCTTTTACTCTCCTTGCTACTGATTCCTCTGGGCCTCCCAGTCCTCTGTGCTCCCCCACGCCTCATCTGCGACAGTCGAGTTCTGGAGAGGTACATCTTAGAGGCCAAGGAGGCAGAAAATGTCACGATGGGTTGTGCAGAAGGTCCCAGACTGAGTGAAAATATTACAGTCCCAGATACCAAAGTCAACTTCTATGCTTGGAAAAGAATGGAGGTGGAAGAACAGGCCATAGAAGTTTGGCAAGGCCTGTCCCTGCTCTCAGAAGCCATCCTGCAGGCCCAGGCCCTGCTAGCCAATTCCTCCCAGCCACCAGAGACCCTTCAGCTTCATATAGACAAAGCCATCAGTGGTCTACGTAGCCTCACTTCACTGCTTCGGGTACTGGGAGCTCAGAAGGAATTGATGTCGCCTCCAGATACCACCCCACCTGCTCCACTCCGAACACTCACAGTGGATACTTTCTGCAAGCTCTTCCGGGTCTACGCCAACTTCCTCCGGGGAAACTGAAGCTGTACACGGGAGAGGTCTGCAGGAGAGGGGACAGGTGATAATAGGCTGGAGCCTCGGTGGCCATGCTTCTTGCCCCTTGGGCCTCCCCCCAGCCCCTCCTCCCCTTCCTGCACCCGTACCCCCGTGGTCTTTGAATAAAGTCTGAGTGGGCGGCTCTAGA

Example 83

In Vitro Transcription Yields

Yields were targeted to be 0.2 mg. See Example 2 for protocol.

TABLE 23

In vitro Transcription Yields.

| Compound # | Chemical Alterations | Luc In Vitro Transcription yield(mg) | EPO In Vitro Transcription yield(mg) | GCSF In Vitro Transcription yield(mg) |
|---|---|---|---|---|
| 00902015001 | PseudoU-alpha-thio-TP | 0.6479 | 0.8632 | 0.5522 |
| 00902015002 | 1-Methyl-pseudo-U-alpha-thio-TP | 0.6011 | 0.7679 | 0.6582 |
| 03601015003 | 1-Ethyl-pseudo-UTP | 0.6304 | 1.095 | 0.5464 |
| 03601015004 | 1-Propyl-pseudo-UTP | 0.4971 | 0.9920 | 0.5976 |
| 03601015005 | 1-(2,2,2-Trifluoroethyl)pseudo-UTP | 0.4388 | 0.3379 | 0.2332 |
| 00901015006 | 2-Thio-pseudo-UTP | 0.6123 | 1.081 | 0.5207 |
| 00901013002 | 5-Trifluoromethyl-UTP | 0.3662 | 0.3830 | 0.5102 |
| 00901014003 | 5-Trifluoromethyl-CTP | 0.5097 | 0.7886 | 0.7710 |
| 00901015187 | 3-Methyl-pseudo-UTP | 0.0152 | 0.0125 | 0.0120 |
| 00901013004 | 5-Methyl-2-thio-UTP | 0.7580 | 0.8717 | 0.4682 |
| 00901014004 | N4-methyl CTP | 1.124 | 1.154 | 0.9028 |
| 00901014005 | 5-Hydroxymethyl-CTP | 0.4073 | 0.7778 | 0.6391 |
| 00901014006 | 3-Methyl-CTP | 0.0068 | 0.0060 | 0.0141 |
| 00901013004 | UTP-5-oxyacetic acid Me ester | 0.6348 | 0.3859 | 0.3836 |
| 00901013005 | 5-Methoxy carbonyl methyl-UTP | 0.8825 | 0.6432 | 0.6475 |
| 00901013006 | 5-Methylaminomethyl-UTP | 0.2914 | 0.3060 | 0.3494 |
| 00901013007 | 5-methoxy-UTP | 0.3817 | 0.1727 | 0.1546 |
| 00901014007 | N4-Ac-CTP | 0.4394 | 0.4351 | 0.3658 |
| 00901012008 | N1-Me-GTP | 0.0059 | 0.0032 | 0.0050 |
| 03601011002 | 2-Amino-ATP | 0.1215 | 0.2612 | 0.1567 |
| 00901011003 | 8-Aza-ATP | 0.0262 | 0.0055 | 0.03 |
| 00901012003 | Xanthosine | 0.0054 | 0.0032 | 0.0041 |
| 03601014008 | 5-Bromo-CTP | 0.5161 | 0.3454 | 0.3685 |
| 03601014009 | 5-Aminoallyl-CTP | 0.3471 | 0.4943 | 0.4567 |
| 03601012004 | 2-Aminopurine-riboside TP | 0.0690 | 0.0125 | 0.2919 |
| 00901013008 | 2-Thio-UTP | 0.2792 | 0.3630 | 0.3359 |
| 00901013009 | 5-Bromo-UTP | 0.3352 | 0.2617 | 0.3566 |
| 00901014010 | 2-Thio-CTP | 0.0073 | 0.0061 | 0.0076 |
| 00902014001 | Alpha-thio-CTP | 0.3352 | 0.2669 | 0.2650 |
| 00901013010 | 5-Aminoallyl-UTP | 0.3513 | 0.3732 | 0.4206 |
| 00902013001 | Alpha-thio-UTP | 0.3510 | 0.2666 | 0.2605 |
| 00901013011 | 4-Thio-UTP | 0.1625 | 0.0416 | 0.0759 |
| 00901014003/ 00901015002 | 5-Trifluoromethyl-CTP/ 1-Methyl-pseudo-UTP | 0.3405 | 0.4471 | 0.2966 |
| 00901014005/ 00901015002 | 5-Hydroxymethyl-CTP/ 1-Methyl-pseudo-UTP | 0.3270 | 0.3149 | 0.3705 |
| 03601014008/ 00901015002 | 5-Bromo-CTP/ 1-Methyl-pseudo-UTP | 0.2594 | 0.3073 | 0.3958 |
| 00901014003/ 00901015001 | 5-Trifluoromethyl-CTP/ Pseudo-UTP | 0.3316 | 0.4486 | 0.4197 |
| 03601014008/ 00901015001 | 5-Bromo-CTP/Pseudo-UTP | 0.3265 | 0.4879 | 0.2982 |
| 00901014003/ 00901015002 | 75% 5-Trifluoromethyl-CTP + 25% CTP/1-Methyl-pseudo-UTP | 0.3316 | 0.4008 | 0.4777 |
| 00901014003/ 00901015002 | 50% 5-Trifluoromethyl-CTP + 50% CTP/1-Methyl-pseudo-UTP | 0.3884 | 0.3990 | 0.4130 |
| 00901014003/ 00901015002 | 25% 5-Trifluoromethyl-CTP + 75% CTP/1-Methyl-pseudo-UTP | 0.3157 | 0.3913 | 0.5430 |
| 03601014008/ 00901015002 | 50% 5-Bromo-CTP + 50% CTP/ 1-Methyl-pseudo-UTP | 0.2897 | 0.4181 | 0.3894 |
| 03601014008/ 00901015002 | 25% 5-Bromo-CTP + 75% CTP/ 1-Methyl-pseudo-UTP | 0.3258 | 0.3930 | 0.4911 |
| 00901014005/ 00901015002 | 50% 5-Hydroxymethyl-CTP + 50% CTP/1-Methyl-pseudo-UTP | 0.4535 | 0.4546 | 0.4414 |
| 00901014007/ 00901015001 | N4Ac-CTP/1-Methyl-pseudo-UTP | 0.3213 | 0.2257 | 0.3696 |
| 00901014007/ 00901013007 | N4Ac-CTP/5-Methoxy-UTP | 0.2747 | 0.3903 | 0.2972 |
| 00901014002/ 00901015002 | 75% 5-Methyl-CTP + 25% CTP/ 1-Methyl-pseudo-UTP | 0.19 | 0.17 | 0.25 |
| 00901014002/ 00901015002 | 50% 5-Methyl-CTP + 50% CTP/ 1-Methyl-pseudo-UTP | 0.22 | 0.19 | 0.44 |
| 00901014002/ 00901015002 | 25% 5-Methyl-CTP + 75% CTP/ 1-Methyl-pseudo-UTP | 0.24 | 0.25 | 0.25 |
| 00901014002/ 00901015002 | 12.5% 5-Methyl-CTP + 87.5% CTP/1-Methyl-pseudo-UTP | 0.26 | 0.3 | 0.27 |
| 00901014002/ 00901015001 | 75% 5-Methyl-CTP + 25% CTP/ Pseudo-UTP | 0.29 | 0.19 | 0.36 |
| 00901014002/ 00901015001 | 50% 5-Methyl-CTP + 50% CTP/ Pseudo-UTP | 0.22 | 0.15 | 0.29 |
| 00901014002/ 00901015001 | 25% 5-Methyl-CTP + 75% CTP/ Pseudo-UTP | 0.28 | 0.19 | 0.25 |

TABLE 23-continued

In vitro Transcription Yields.

| Compound # | Chemical Alterations | Luc In Vitro Transcription yield(mg) | EPO In Vitro Transcription yield(mg) | GCSF In Vitro Transcription yield(mg) |
|---|---|---|---|---|
| 00901014035/ 00901015002 | 5-Iodo-CTP/1-Methyl-pseudo-UTP | .09 | 0.07 | 0.1 |
| 00901014035/ 00901015002 | 75% 5-Iodo-CTP + 25% CTP/ 1-Methyl-pseudo-UTP | 0.15 | 0.13 | 0.16 |
| 00901014035/ 00901015002 | 50% 5-Iodo-CTP + 50% CTP/ 1-Methyl-pseudo-UTP | 0.21 | 0.15 | 0.19 |
| 00901014035/ 00901015002 | 25% 5-Iodo-CTP + 75% CTP/ 1-Methyl-pseudo-UTP | 0.21 | 0.18 | 0.35 |
| 03601014008/ 00901015002 | 75% 5-Bromo-CTP + 25% CTP/ 1-Methyl-pseudo-UTP | 0.11 | N/A | |
| 03601014008/ 00901015001 | 75% 5-Bromo-CTP + 25% CTP/ Pseudo-UTP | 0.17 | N/A | |
| 03601014008/ 00901015001 | 50% 5-Bromo-CTP + 50% CTP/ Pseudo-UTP | 0.14 | N/A | |
| 03601014008/ 00901015001 | 25% 5-Bromo-CTP + 75% CTP/ Pseudo-UTP | 0.11 | N/A | |
| 00901014003/ 00901013007 | 5-Trifluoro-methyl-CTP/ 5-Methoxy-UTP | 0.06 | N/A | |
| 12201014040/ 00901013007 | 5-Hydroxy-methyl-CTP/ 5-Methoxy-UTP | 0.05 | N/A | |
| 03601014008/ 00901013007 | 5-Bromo-CTP/5-Methoxy-UTP | 0.06 | N/A | |
| 00901014002/ 00901013008 | 5-Methyl-CTP/75% 2-Thio-UTP + 25% UTP | 0.12 | 0.17 | |
| 00901014002/ 00901013008 | 5-Methyl-CTP/25% 2-Thio-UTP + 75% UTP | 0.15 | 0.15 | |
| 00901014002/ 00901013008 | 75% 5-Methyl-CTP + 25% CTP/ 2-Thio-UTP | 0.11 | 0.18 | |
| 00901014002/ 00901013008 | 50% 5-Methyl-CTP + 50% CTP/ 2-Thio-UTP | 0.11 | 0.18 | |
| 00901014002/ 00901013008 | 25% 5-Methyl-CTP + 75% CTP/ 2-Thio-UTP | 0.09 | 0.13 | |
| 00901014002/ 00901013008 | 75% 5-Methyl-CTP + 25% CTP/ 75% 2-Thio-UTP + 25% UTP | 0.18 | 0.21 | |
| 00901014002/ 00901013008 | 50% 5-Methyl-CTP + 50% CTP/ 75% 2-Thio-UTP + 25% UTP | 0.15 | 0.18 | |
| 00901014002/ 00901013008 | 25% 5-Methyl-CTP + 75% CTP/ 75% 2-Thio-UTP + 25% UTP | 0.17 | 0.14 | |
| 00901014002/ 00901013008 | 75% 5-Methyl-CTP + 25% CTP/ 50% 2-Thio-UTP + 50% UTP | 0.14 | 0.21 | |
| 00901014002/ 00901013008 | 50% 5-Methyl-CTP + 50% CTP/ 50% 2-Thio-UTP + 50% UTP | 0.16 | 0.14 | |
| 00901014002/ 00901013008 | 25% 5-Methyl-CTP + 75% CTP/ 50% 2-Thio-UTP + 50% UTP | 0.14 | 0.16 | |
| 00901014002/ 00901013008 | 75% 5-Methyl-CTP + 25% CTP/ 25% 2-Thio-UTP + 75% UTP | 0.12 | 0.19 | |
| 00901014002/ 00901013008 | 50% 5-Methyl-CTP + 50% CTP/ 25% 2-Thio-UTP + 75% UTP | 0.16 | 0.19 | |
| 00901014002/ 00901013008 | 25% 5-Methyl-CTP + 75% CTP/ 25% 2-Thio-UTP + 75% UTP | 0.13 | 0.19 | |
| 00901013008 | CTP/75% 2-Thio-UTP + 25% UTP | 0.19 | 0.23 | |
| 00901013008 | CTP/50% 2-Thio-UTP + 50% UTP | 0.21 | 0.23 | |
| 00901013008 | CTP/25% 2-Thio-UTP + 75% UTP | 0.21 | 0.24 | |
| 03601014008/ 00901015002 | 75% 5-Bromo-CTP + 25% CTP/ 1-Methyl-pseudo-UTP | 0.11 | N/A | |

TABLE 24

In vitro Transcription Yields.

| Compound # | Chemical Alterations | mCherry In Vitro Transcription yield(mg) | nanoLuc In Vitro Transcription yield(mg) |
|---|---|---|---|
| 00901014005/ 00901015001 | 5-Hydroxymethyl-CTP/Pseudo-UTP | 0.13 | 0.15 |
| 00901014035/ 00901015001 | 5-Iodo-CTP/Pseudo-UTP | 0.01 | 0.11 |

TABLE 24-continued

In vitro Transcription Yields.

| Compound # | Chemical Alterations | mCherry In Vitro Transcription yield(mg) | nanoLuc In Vitro Transcription yield(mg) |
|---|---|---|---|
| 00901014007/ 00901015001 | N4-Ac-CTP/Pseudo-UTP | 0.12 | 0.22 |
| 00901014035/ 00901013007 | 5-Iodo-CTP/5-Methoxy-UTP | 0.07 | 0.04 |
| 07101015011 | 2-Pyridinone-TP | 0 | 0 |
| 07101015012 | 6-Fluoro-2-pyridinone-TP | 0 | 0 |
| 07101015017 | 3-Methyl-2-pyridinone-TP | 0 | 0 |
|  | 5'-Amino-UTP | 0 | 0 |
| 00901014002/ | 5-Methyl-CTP/5'-Amino-UTP | 0 | 0 |
| 07101015013 | 6-Methyl-2-pyridinone-TP | 0 | 0 |
| 00901014002/ 07101015011 | 5-Methyl-CTP/2-Pyridinone-TP | 0 | 0 |
| 00901014002/ 07101015012 | 5-Methyl-CTP/6-Fluoro-2-pyridinone-TP | 0 | 0 |
| 00901014002/ 07101015017 | 5-Methyl-CTP/3-Methyl-2-pyridinone-TP | 0 | 0 |
| 00901014002/ 07101015013 | 5-Methyl-CTP/6-Methyl-2-pyridinone-TP | 0 | 0 |
| 03601015032 | 1-Benzyl-pseudo-UTP | 0 | 0 |
| 00901014002/ 03601015003 | 5-Methyl-CTP/1-Ethyl-pseudo-UTP | 0.2 | 0.2 |
| 00901014002/ 03601015004 | 5-Methyl-CTP/1-Propyl-pseudo-UTP | 0.2 | 0.12 |
| 00901014002/ 03601015032 | 5-Methyl-CTP/1-Benzyl-pseudo-UTP | 0 | 0 |
| 00901014002/ 00901013007 | 5-Methyl-CTP/75% 5-Methoxy-UTP + 25% UTP | 0.23 | 0.27 |
| 00901014002/ 00901013007 | 5-Methyl-CTP/50% 5-Methoxy-UTP + 50% UTP | 0.27 | 0.22 |
| 00901014002/ 00901013007 | 5-Methyl-CTP/25% 5-Methoxy-UTP + 75% UTP | 0.2 | 0.24 |
| 00901014002/ 00901013007 | 75% 5-Methyl-CTP + 25% CTP/ 5-Methoxy-UTP | 0.2 | 0.18 |
| 00901014002/ 00901013007 | 50% 5-Methyl-CTP + 50% CTP/ 5-Methoxy-UTP | 0.35 | 0.36 |
| 00901014002/ 00901013007 | 25% 5-Methyl-CTP + 75% CTP/ 5-Methoxy-UTP | 0.23 | 0.16 |
| 00901014002/ 00901013007 | 75% 5-Methyl-CTP + 25% CTP/75% 5-Methoxy-UTP + 25% UTP | 0.21 | 0.23 |
| 00901014002/ 00901013007 | 50% 5-Methyl-CTP + 50% CTP/75% 5-Methoxy-UTP + 25% UTP | 0.25 | 0.25 |
| 00901014002/ 00901013007 | 25% 5-Methyl-CTP + 75% CTP/75% 5-Methoxy-UTP + 25% UTP | 0.25 | 0.22 |
| 00901014002/ 00901013007 | 75% 5-Methyl-CTP + 25% CTP/50% 5-Methoxy-UTP + 50% UTP | 0.27 | 0.18 |
| 00901014002/ 00901013007 | 50% 5-Methyl-CTP + 50% CTP/50% 5-Methoxy-UTP + 50% UTP | 0.25 | 0.24 |
| 00901014002/ 00901013007 | 25% 5-Methyl-CTP + 75% CTP/50% 5-Methoxy-UTP + 50% UTP | 0.2 | 0.3 |
| 00901014002/ 00901013007 | 75% 5-Methyl-CTP + 25% CTP/25% 5-Methoxy-UTP + 75% UTP | 0.32 | 0.23 |
| 00901014002/ 00901013007 | 50% 5-Methyl-CTP + 50% CTP/25% 5-Methoxy-UTP + 75% UTP | 0.23 | 0.19 |
| 00901014002/ 00901013007 | 25% 5-Methyl-CTP + 75% CTP/25% 5-Methoxy-UTP + 75% UTP | 0.22 | 0.18 |
| 00901013007 | CTP/75% 5-Methoxy-UTP + 25% UTP | 0.22 | 0.25 |
| 00901013007 | CTP/50% 5-Methoxy-UTP + 50% UTP | 0.24 | 0.2 |
| 00901013007 | CTP/25% 5-Methoxy-UTP + 75% UTP | 0.18 | 0.24 |
| 00901013007 | CTP/5-Methoxy-UTP (No cap) | 0.18 | 0.14 |
| 00901013007 | CTP/5-Methoxy-UTP (cap 0) | 0.17 | 0.17 |
| 00901014002/ 00901013007 | 5-Methyl-CTP/5-Methoxy-UTP (No cap) | 0.09 | 0.1 |
| 00901014002/ 00901013007 | 5-Methyl-CTP/5-Methoxy-UTP (cap 0) | 0.1 | 0.1 |
|  | CTP/UTP (No cap) | 0.17 | 0.18 |
|  | CTP/UTP (cap 0) | 0.2 | 0.22 |
| 00901014002/ 00901015001 | 5-Methyl-CTP/Pseudo-UTP (No cap) | 0.17 | 0.21 |
| 00901014002/ 00901015001 | 5-Methyl-CTP/Pseudo-UTP (cap 0) | 0.13 | 0.22 |
| 00901014002/ 00901015002 | 5-Methyl-CTP/1-Methyl-pseudo-UTP (No cap) | 0.13 | 0.17 |

TABLE 24-continued

In vitro Transcription Yields.

| Compound # | Chemical Alterations | mCherry In Vitro Transcription yield(mg) | nanoLuc In Vitro Transcription yield(mg) |
|---|---|---|---|
| 00901014002/ 00901015002 | 5-Methyl-CTP/1-Methyl-pseudo-UTP (cap 0) | 0.14 | 0.18 |
| 00901015002 | CTP/1-Methyl-pseudo-UTP (No cap) | 0.17 | 0.28 |
| 00901015002 | CTP/1-Methyl-pseudo-UTP (cap 0) | 0.15 | 0.14 |
|  | CTP/UTP/ATP/GTP (cap ARCA) | 0.09 | 0.06 |
| 00901014002/ 00901015001 | 5-Methyl-CTP/Pseudo-UTP (cap ARCA) | 0.07 | 0.07 |
| 00901014002/ 00901015002 | 5-Methyl-CTP/1-Methyl-pseudo-UTP (cap ARCA) | 0.09 | 0.14 |
| 00901015002 | CTP/1-Methyl-pseudo-UTP (cap ARCA) | 0.09 | 0.14 |
| 00902011001 | Alpha-Thio-ATP | 0 | 0 |
| 00901014002/ 00901015001/ 00902011001 | 5-Methyl-CTP/Pseudo-UTP/ Alpha-Thio-ATP | 0.13 | 0.1 |
| 00901014002/ 00901015002/ 00902011001 | 5-Methyl-CTP/1-Methyl-pseudo-UTP/ Alpha-Thio-ATP | 0 | 0 |
| 00901015002/ 00902011001 | 1-Methyl-pseudo-UTP/Alpha-Thio-ATP | 0 | 0 |
| 00901013007/ 00902011001 | 5-Methoxy-UTP/Alpha-Thio-ATP | 0 | 0 |
| 00901014002/ 00901013007/ 00902011001 | 5-Methyl-CTP/5-Methoxy-UTP/ Alpha-Thio-ATP | 0 | 0 |
| 00902012001 | Alpha-Thio-GTP | 0.19 | 0.18 |
| 00901014002/ 00901015001/ 00902012001 | 5-Methyl-CTP/Pseudo-UTP/ Alpha-Thio-GTP | 0.13 | 0.17 |
| 00901014002/ 00901015002/ 00902012001 | 5-Methyl-CTP/1-Methyl-pseudo-UTP/ Alpha-Thio-GTP | 0.04 | 0.11 |
| 00901015002/ 00902012001 | 1-Methyl-pseudo-UTP/Alpha-Thio-GTP | 0.14 | 0.06 |
| 00901013007/ 00902012001 | 5-Methoxy-UTP/Alpha-Thio-GTP | 0.07 | 0.11 |
| 00901014002/ 00901013007/ 00902012001 | 5-Methyl-CTP/5-Methoxy-UTP/ Alpha-Thio-GTP | 0.07 | 0.11 |
| 00901011006 | N6-Me-ATP | 0.22 | 0.2 |
| 00901014002/ 00901015001/ 00901011006 | 5-Methyl-CTP/Pseudo-UTP/N6-Me-ATP | 0.15 | 0.14 |
| 00901014002/ 00901015002/ 00901011006 | 5-Methyl-CTP/1-Methyl-pseudo-UTP/ N6-Me-ATP | 0.06 | 0.06 |
| 00901015002/ 00901011006 | 1-Methyl-pseudo-UTP/N6-Me-ATP | 0.18 | 0.07 |
| 00901013007/ 00901011006 | 5-Methoxy-UTP/N6-Me-ATP | 0.19 | 0.14 |
| 00901014002/ 00901013007/ 00901011006 | 5-Methyl-CTP/5-Methoxy-UTP/ N6-Me-ATP | 0.3 | 0.14 |
| 03601014039 | 5-Ethyl-CTP | 0.3 | 0.26 |
| 03601014039/ 00901015002 | 5-Ethyl-CTP/1-Methyl-pseudo-UTP | 0.26 | 0.23 |
| 03601014039/ 00901013007 | 5-Ethyl-CTP/5-Methoxy-UTP | 0.24 | 0.23 |
| 03601014030 | 5-Methoxy-CTP | 0.21 | 0.17 |
| 03601014030/ 00901015002 | 5-Methoxy-CTP/1-Methyl-pseudo-UTP | 0.17 | 0.17 |
| 03601014030/ 00901013007 | 5-Methoxy-CTP/5-Methoxy-UTP | 0.16 | 0.17 |
| 03601014011 | 5-Ethynyl-CTP | 0.26 | 0.23 |
| 03601014011/ 00901015002 | 5-Ethynyl-CTP/1-Methyl-pseudo-UTP | 0.19 | 0.24 |
| 03601014011/ 00901013007 | 5-Ethynyl-CTP/5-Methoxy-UTP | 0.14 | 0.16 |
| 03601014011/ 00901015001 | 5-Ethynyl-CTP/Pseudo-UTP | 0.12 | 0.09 |
| 03601014011/ 00901013007/ 00901015002 | 5-Methyl-CTP/75% 5-Methoxy-UTP + 25% 1-Methyl-pseudo-UTP | 0.33 | 0.35 |

TABLE 24-continued

In vitro Transcription Yields.

| Compound # | Chemical Alterations | mCherry In Vitro Transcription yield(mg) | nanoLuc In Vitro Transcription yield(mg) |
|---|---|---|---|
| 03601014011/ 00901013007/ 00901015002 | 5-Methyl-CTP/50% 5-Methoxy-UTP + 50% 1-Methyl-pseudo-UTP | 0.23 | 0.49 |
| 03601014011/ 00901013007/ 00901015002 | 5-Methyl-CTP/25% 5-Methoxy-UTP + 75% 1-Methyl-pseudo-UTP | 0.3 | 0.29 |
| 03601014011/ 00901013007/ 00901015002 | 75% 5-Methyl-CTP + 25% CTP/75% 5-Methoxy-UTP + 25% 1-Methyl-pseudo-UTP | 0.12 | 0.19 |
| 03601014011/ 00901013007/ 00901015002 | 50% 5-Methyl-CTP + 50% CTP/75% 5-Methoxy-UTP + 25% 1-Methyl-pseudo-UTP | 0.23 | 0.32 |
| 03601014011/ 00901013007/ 00901015002 | 25% 5-Methyl-CTP + 75% CTP/75% 5-Methoxy-UTP + 25% 1-Methyl-pseudo-UTP | 0.1 | 0.19 |
| 03601014011/ 00901013007/ 00901015002 | 75% 5-Methyl-CTP + 25% CTP/50% 5-Methoxy-UTP + 50% 1-Methyl-pseudo-UTP | 0.24 | 0.27 |
| 03601014011/ 00901013007/ 00901015002 | 50% 5-Methyl-CTP + 50% CTP/50% 5-Methoxy-UTP + 50% 1-Methyl-pseudo-UTP | 0.28 | 0.57 |
| 03601014011/ 00901013007/ 00901015002 | 25% 5-Methyl-CTP + 75% CTP/50% 5-Methoxy-UTP + 50% 1-Methyl-pseudo-UTP | 0.45 | 0.44 |
| 03601014011/ 00901013007/ 00901015002 | 75% 5-Methyl-CTP + 25% CTP/25% 5-Methoxy-UTP + 75% 1-Methyl-pseudo-UTP | 0.29 | 0.38 |
| 03601014011/ 00901013007/ 00901015002 | 50% 5-Methyl-CTP + 50% CTP/25% 5-Methoxy-UTP + 75% 1-Methyl-pseudo-UTP | 0.21 | 0.27 |
| 03601014011/ 00901013007/ 00901015002 | 25% 5-Methyl-CTP + 75% CTP/25% 5-Methoxy-UTP + 75% 1-Methyl-pseudo-UTP | 0.21 | 0.52 |
| 00901013007/ 00901015002 | CTP/75% 5-Methoxy-UTP + 25% 1-Methyl-pseudo-UTP | 0.22 | 0.25 |
| 00901013007/ 00901015002 | CTP/50% 5-Methoxy-UTP + 50% 1-Methyl-pseudo-UTP | 0.35 | 0.34 |
| 00901013007/ 00901015002 | CTP/25% 5-Methoxy-UTP + 75% 1-Methyl-pseudo-UTP | 0.32 | 0.29 |
| 00901014004/ 00901015002 | N4-Methyl-CTP/1-Methyl-pseudo-UTP | 0.27 | 0.1 |
| 00902014001/ 00901015002 | Alpha-thio-CTP/1-Methyl-pseudo-UTP | 0 | 0.06 |
|  | 5-Methyl-5,6-dihydro-UTP | 0.02 | 0 |
| 00901015002/ 00902012001 | 1-Methyl-pseudo-UTP/2% Alpha-Thio-GTP + 98% GTP | 0.13 | 0.07 |
| 00901015002/ 00902012001 | 1-Methyl-pseudo-UTP/5% Alpha-Thio-GTP + 95% GTP | 0.22 | 0.27 |
| 00901015002/ 00902012001 | 1-Methyl-pseudo-UTP/10% Alpha-Thio-GTP + 90% GTP | 0.17 | 0.26 |
| 00901015002/ 00902012001 | 1-Methyl-pseudo-UTP/25% Alpha-Thio-GTP + 75% GTP | 0.22 | 0.25 |
| 00901015002/ 00902012001 | 1-Methyl-pseudo-UTP/50% Alpha-Thio-GTP + 50% GTP | 0.24 | 0.26 |
| 00901015002/ 00902011001 | 1-Methyl-pseudo-UTP/2% Alpha-Thio-ATP + 98% ATP | 0.18 | 0.17 |
| 00901015002/ 00902011001 | 1-Methyl-pseudo-UTP/5% Alpha-Thio-ATP + 95% ATP | 0.20 | 0.15 |
| 00901015002/ 00902011001 | 1-Methyl-pseudo-UTP/10% Alpha-Thio-ATP + 90% ATP | 0.19 | 0.22 |
| 00901015002/ 00902011001 | 1-Methyl-pseudo-UTP/25% Alpha-Thio-ATP + 75% ATP | 0.03 | 0.04 |
| 00901015002/ 00902011001 | 1-Methyl-pseudo-UTP/50% Alpha-Thio-ATP + 50% ATP | 0.11 | 0.12 |
| 00901015002 | 75% 1-Methyl-pseudo-UTP + 25% UTP | 0.12 | 0.23 |
| 00901015002 | 50% 1-Methyl-pseudo-UTP + 50% UTP | 0.18 | 0.28 |
| 00901015001 | 75% Pseudo-UTP + 25% UTP | 0.19 | 0.2 |
| 00901015001 | 50% Pseudo-UTP + 50% UTP | 0.19 | 2.4 |
| 00901015001 | 25% Pseudo-UTP + 75% UTP | 0.18 | 2.3 |
| 03601013014 | 75% 5-Methyl-UTP + 25% UTP | 0.19 | 2.1 |
| 03601013014 | 50% 5-Methyl-UTP + 50% UTP | 0.24 | 0.39 |
| 03601013014 | 25% 5-Methyl-UTP + 75% UTP | 0.19 | 0.2 |
| 00901013003 | 75% 5-Methyl-2-thio-UTP + 25% UTP | 0.22 | 0.49 |

TABLE 24-continued

In vitro Transcription Yields.

| Compound # | Chemical Alterations | mCherry In Vitro Transcription yield(mg) | nanoLuc In Vitro Transcription yield(mg) |
| --- | --- | --- | --- |
| 00901013003 | 50% 5-Methyl-2-thio-UTP + 50% UTP | 2 | 0.27 |
| 00901013003 | 25% 5-Methyl-2-thio-UTP + 75% UTP | 1.6 | 0.22 |
| 00901013011 | 75% 4-Thio-UTP + 25% UTP | 0.19 | 0.16 |
| 00901013011 | 50% 4-Thio-UTP + 50% UTP | 0.23 | 0.21 |
| 00901013011 | 25% 4-Thio-UTP + 75% UTP | 0.26 | 0.19 |
| 00901013009 | 75% 5-Methoxy-carbonylmethyl-UTP + 25% UTP | 0.28 | 0.15 |
| 00901013009 | 50% 5-Methoxy-carbonylmethyl-UTP + 50% UTP | 0.27 | 0.17 |
| 00901013009 | 25% 5-Methoxy-carbonylmethyl-UTP + 75% UTP | 0.24 | 0.12 |
| 03601014011 | 75% 5-Methyl-CTP + 25% CTP | 0.19 | 0.28 |
| 03601014011 | 50% 5-Methyl-CTP + 50% CTP | 0.21 | 0.15 |
| 03601014011 | 25% 5-Methyl-CTP + 75% CTP | 0.2 | 0.18 |
| 03601014011/ 00901015002 | 75% 5-Methyl-CTP + 25% CTP/ 1-Methyl-pseudo-UTP | 0.19 | 0.19 |
| 03601014011/ 00901015002 | 50% 5-Methyl-CTP + 50% CTP/ 1-Methyl-pseudo-UTP | 0.15 | 0.14 |
| 03601014011/ 00901015002 | 25% 5-Methyl-CTP + 75% CTP/ 1-Methyl-pseudo-UTP | 0.09 | 0.07 |
| 00901011045 | 8-Me-ATP | 0.01 | 0.01 |
| 00901015002/ 00901011045 | 1-Methyl-pseudo-UTP/8-Me-ATP | 0.01 | 0.01 |
| 00901015002/ 00902011001/ 00902012001 | 1-Methyl-pseudo-UTP/2% Alpha-Thio-ATP + 98% ATP/2% Alpha-Thio-GTP + 98% GTP | 0.07 | 0.13 |
| 00901015002/ 00902011001/ 00902012001 | 1-Methyl-pseudo-UTP/5% Alpha-Thio-ATP + 95% ATP/5% Alpha-Thio-GTP + 95% GTP | 0.14 | 0.13 |
| 00901015002/ 00902011001/ 00902012001 | 1-Methyl-pseudo-UTP/2% Alpha-Thio-ATP + 98% ATP/5% Alpha-Thio-GTP + 95% GTP | 0.12 | 0.10 |
| 00901015002/ 00902011001/ 00902012001 | 1-Methyl-pseudo-UTP/5% Alpha-Thio-ATP + 95% ATP/2% Alpha-Thio-GTP + 98% GTP | 0.11 | 0.08 |
| 00901015002/ 00902011001/ 00902012001 | 1-Methyl-pseudo-UTP/10% Alpha-Thio-ATP + 90% ATP/2% Alpha-Thio-GTP + 98% GTP | 0.12 | 0.08 |
| 00901015002/ 00902011001/ 00902012001 | 1-Methyl-pseudo-UTP/2% Alpha-Thio-ATP + 98% ATP/10% Alpha-Thio-GTP + 90% GTP | 0.11 | 0.08 |
| 00901015002/ 00902011001/ 00902012001 | 1-Methyl-pseudo-UTP/10% Alpha-Thio-ATP + 90% ATP/5% Alpha-Thio-GTP + 95% GTP | 0.09 | 0.07 |
| 00901015002/ 00902011001/ 00902012001 | 1-Methyl-pseudo-UTP/5% Alpha-Thio-ATP + 95% ATP/10% Alpha-Thio-GTP + 90% GTP | 0.11 | 0.06 |
| 00901015002/ 00902011001/ 00902012001 | 1-Methyl-pseudo-UTP/10% Alpha-Thio-ATP + 90% ATP/10% Alpha-Thio-GTP + 90% GTP | 0.10 | 0.08 |
| 00901014041 | 5-Fluoro-CTP | 0.30 | 0.21 |
| 00901014041/ 00901015002 | 5-Fluoro-CTP/1-Methyl-pseudo-UTP | 0.21 | 0.20 |
| 00901014041/ 00901013007 | 5-Fluoro-CTP/5-Methoxy-UTP | 0.20 | 0.20 |
| 03601014021 | 5-Phenyl-CTP | 0.13 | 0.07 |
| 03601014021/ 00901015002 | 5-Phenyl-CTP/1-Methyl-pseudo-UTP | 0.07 | 0.04 |
| 03601014021/ 00901013007 | 5-Phenyl-CTP/5-Methoxy-UTP | 0.06 | 0.07 |
| 03601014013 | N4-Bz-CTP | 0.16 | 0.12 |
| 03601014013/ 00901015002 | N4-Bz-CTP/1-Methyl-pseudo-UTP | 0.11 | 0.11 |
| 03601014013/ 00901013007 | N4-Bz-CTP/5-Methoxy-UTP | 0.02 | 0.02 |
| 00901011044 | N6-Isopentenyl-ATP | 0.04 | 0.04 |
| 00901015002/ 00901011044 | 1-Methyl-pseudo-UTP/N6-Isopentenyl-ATP | 0.01 | 0.02 |
| 00901013007/ 00901011044 | 5-Methoxy-UTP/N6-Isopentenyl-ATP | 0.02 | 0.02 |
| 03601013036 | 5-Carbamoyl-methyl-UTP | 0.27 | 0.16 |
| 03601013036 | 75% 5-Carbamoyl-methyl-UTP + 25% UTP | 0.19 | 0.18 |

TABLE 24-continued

In vitro Transcription Yields.

| Compound # | Chemical Alterations | mCherry In Vitro Transcription yield(mg) | nanoLuc In Vitro Transcription yield(mg) |
|---|---|---|---|
| 03601013036 | 50% 5-Carbamoyl-methyl-UTP + 50% UTP | 0.26 | 0.13 |
| 03601013036 | 25% 5-Carbamoyl-methyl-UTP + 75% UTP | 0.18 | 0.11 |
| 00901013054 | 75% 5-Hydroxy-UTP + 25% UTP | 0.18 | 0.17 |
| 00901013054 | 50% 5-Hydroxy-UTP + 50% UTP | 0.18 | 0.20 |
| 00901013054 | 25% 5-Hydroxy-UTP + 75% UTP | 0.21 | 0.23 |
| 00901014007/ 00901013007 | 25% N4-Ac-CTP + 75% CTP/25% 5-Methoxy-UTP + 75% UTP | 0.21 | 0.30 |
| 00901014007/ 00901013007 | 75% N4-Ac-CTP + 25% CTP/25% 5-Methoxy-UTP + 75% UTP | 0.21 | 0.30 |
| 00901014007/ 00901013007 | 25% N4-Ac-CTP + 75% CTP/75% 5-Methoxy-UTP + 25% UTP | 0.20 | 0.25 |
| 00901014007/ 00901013007 | 75% N4-Ac-CTP + 25% CTP/75% 5-Methoxy-UTP + 25% UTP | 0.15 | 0.13 |
| 00901014005/ 00901013007 | 25% 5-Hydroxymethyl-CTP + 75% CTP/ 25% 5-Methoxy-UTP + 75% UTP | 0.33 | 0.25 |
| 00901014005/ 00901013007 | 75% 5-Hydroxymethyl-CTP + 25% CTP/ 25% 5-Methoxy-UTP + 75% UTP | 0.28 | 0.27 |
| 00901014005/ 00901013007 | 25% 5-Hydroxymethyl-CTP + 75% CTP/ 75% 5-Methoxy-UTP + 25% UTP | 0.27 | 0.37 |
| 00901014005/ 00901013007 | 75% 5-Hydroxymethyl-CTP + 25% CTP/ 75% 5-Methoxy-UTP + 25% UTP | 0.37 | 0.33 |
| 00901014004/ 00901013007 | N4-Methyl-CTP/5-Methoxy-UTP | 0.39 | 0.27 |
| 00901014004/ 00901013007 | 25% N4-Methyl-CTP + 75% CTP/25% 5-Methoxy-UTP + 75% UTP | 0.42 | 0.35 |
| 00901014004/ 00901013007 | 75% N4-Methyl-CTP + 25% CTP/25% 5-Methoxy-UTP + 75% UTP | 0.44 | 0.24 |
| 00901014004/ 00901013007 | 25% N4-Methyl-CTP + 75% CTP/75% 5-Methoxy-UTP + 25% UTP | 0.41 | 0.23 |
| 00901014004/ 00901013007 | 75% N4-Methyl-CTP + 25% CTP/75% 5-Methoxy-UTP + 25% UTP | 0.34 | 0.30 |
| 00901014003/ 00901013007 | 25% 5-Trifluoromethyl-CTP + 75% CTP/ 25% 5-Methoxy-UTP + 75% UTP | 0.34 | 0.13 |
| 00901014003/ 00901013007 | 75% 5-Trifluoromethyl-CTP + 25% CTP/ 25% 5-Methoxy-UTP + 75% UTP | 0.42 | 0.15 |
| 00901014003/ 00901013007 | 25% 5-Trifluoromethyl-CTP + 75% CTP/ 75% 5-Methoxy-UTP + 25% UTP | 0.53 | 0.25 |
| 00901014003/ 00901013007 | 75% 5-Trifluoromethyl-CTP + 25% CTP/ 75% 5-Methoxy-UTP + 25% UTP | 0.28 | 0.27 |
| 03601014008/ 00901013007 | 25% 5-Bromo-CTP + 75% CTP/25% 5-Methoxy-UTP + 75% UTP | 0.29 | 0.26 |
| 03601014008/ 00901013007 | 75% 5-Bromo-CTP + 25% CTP/25% 5-Methoxy-UTP + 75% UTP | 0.23 | 0.19 |
| 03601014008/ 00901013007 | 25% 5-Bromo-CTP + 75% CTP/75% 5-Methoxy-UTP + 25% UTP | 0.18 | 0.15 |
| 03601014008/ 00901013007 | 75% 5-Bromo-CTP + 25% CTP/75% 5-Methoxy-UTP + 25% UTP | 0.18 | 0.14 |
| 00901014035/ 00901013007 | 5-Iodo-CTP/5-Methoxy-UTP | 0.11 | 0.12 |
| 00901014035/ 00901013007 | 25% 5-Iodo-CTP + 75% CTP/25% 5-Methoxy-UTP + 75% UTP | 0.20 | 0.18 |
| 00901014035/ 00901013007 | 75% 5-Iodo-CTP + 25% CTP/25% 5-Methoxy-UTP + 75% UTP | 0.17 | 0.08 |
| 00901014035/ 00901013007 | 25% 5-Iodo-CTP + 75% CTP/75% 5-Methoxy-UTP + 25% UTP | 0.19 | 0.16 |
| 00901014035/ 00901013007 | 75% 5-Iodo-CTP + 25% CTP/75% 5-Methoxy-UTP + 25% UTP | 0.14 | 0.11 |
| 03601014039/ 00901013007 | 25% 5-Ethyl-CTP + 75% CTP/25% 5-Methoxy-UTP + 75% UTP | 0.30 | 0.18 |
| 03601014039/ 00901013007 | 75% 5-Ethyl-CTP + 25% CTP/25% 5-Methoxy-UTP + 75% UTP | 0.27 | 0.19 |
| 03601014039/ 00901013007 | 25% 5-Ethyl-CTP + 75% CTP/75% 5-Methoxy-UTP + 25% UTP | 0.21 | 0.19 |
| 03601014039/ 00901013007 | 75% 5-Ethyl-CTP + 25% CTP/75% 5-Methoxy-UTP + 25% UTP | 0.17 | 0.13 |
| 03601014030/ 00901013007 | 25% 5-Methoxy-CTP + 75% CTP/25% 5-Methoxy-UTP + 75% UTP | 0.18 | 0.21 |
| 03601014030/ 00901013007 | 75% 5-Methoxy-CTP + 25% CTP/25% 5-Methoxy-UTP + 75% UTP | 0.21 | 0.17 |
| 03601014030/ 00901013007 | 25% 5-Methoxy-CTP + 75% CTP/75% 5-Methoxy-UTP + 25% UTP | 0.14 | 0.15 |

TABLE 24-continued

In vitro Transcription Yields.

| Compound # | Chemical Alterations | mCherry In Vitro Transcription yield(mg) | nanoLuc In Vitro Transcription yield(mg) |
|---|---|---|---|
| 03601014030/ 00901013007 | 75% 5-Methoxy-CTP + 25% CTP/75% 5-Methoxy-UTP + 25% UTP | 0.09 | 0.12 |
| 03601014012/ 00901013007 | 25% 5-Ethynyl-CTP + 75% CTP/25% 5-Methoxy-UTP + 75% UTP | 0.27 | 0.13 |
| 03601014012/ 00901013007 | 75% 5-Ethynyl-CTP + 25% CTP/25% 5-Methoxy-UTP + 75% UTP | 0.24 | 0.12 |
| 03601014012/ 00901013007 | 25% 5-Ethynyl-CTP + 75% CTP/75% 5-Methoxy-UTP + 25% UTP | 0.23 | 0.07 |
| 03601014012/ 00901013007 | 75% 5-Ethynyl-CTP + 25% CTP/75% 5-Methoxy-UTP + 25% UTP | 0.14 | 0.19 |
| 00901014014/ 00901013007 | Pseudo-iso-CTP/5-Methoxy-UTP | 0.2 | 0.15 |
| 00901014014/ 00901013007 | 25% Pseudo-iso-CTP + 75% CTP/25% 5-Methoxy-UTP + 75% UTP | 0.18 | 0.16 |
| 00901014014/ 00901013007 | 75% Pseudo-iso-CTP + 25% CTP/25% 5-Methoxy-UTP + 75% UTP | 0.18 | 0.15 |
| 00901014014/ 00901013007 | 25% Pseudo-iso-CTP + 75% CTP/75% 5-Methoxy-UTP + 25% UTP | 0.22 | 0.16 |
| 00901014014/ 00901013007 | 75% Pseudo-iso-CTP + 25% CTP/75% 5-Methoxy-UTP + 25% UTP | 0.21 | 0.13 |
| 00901014036/ 00901013007 | 5-Formyl-CTP/5-Methoxy-UTP | 0.17 | 0.16 |
| 00901014036/ 00901013007 | 25% 5-Formyl-CTP + 75% CTP/25% 5-Methoxy-UTP + 75% UTP | 0.16 | 0.11 |
| 00901014036/ 00901013007 | 75% 5-Formyl-CTP + 25% CTP/25% 5-Methoxy-UTP + 75% UTP | 0.19 | 0.15 |
| 00901014036/ 00901013007 | 25% 5-Formyl-CTP + 75% CTP/75% 5-Methoxy-UTP + 25% UTP | 0.2 | 0.13 |
| 00901014036/ 00901013007 | 75% 5-Formyl-CTP + 25% CTP/75% 5-Methoxy-UTP + 25% UTP | 0.2 | 0.12 |
| 03601014009/ 00901013007 | 5-Aminoallyl-CTP/5-Methoxy-UTP | 0.11 | 0.07 |
| 03601014009/ 00901013007 | 25% 5-Aminoallyl-CTP + 75% CTP/25% 5-Methoxy-UTP + 75% UTP | 0.26 | 0.19 |
| 03601014009/ 00901013007 | 75% 5-Aminoallyl-CTP + 25% CTP/25% 5-Methoxy-UTP + 75% UTP | 0.18 | 0.15 |
| 03601014009/ 00901013007 | 25% 5-Aminoallyl-CTP + 75% CTP/75% 5-Methoxy-UTP + 25% UTP | 0.19 | 0.16 |
| 03601014009/ 00901013007 | 75% 5-Aminoallyl-CTP + 25% CTP/75% 5-Methoxy-UTP + 25% UTP | 0.18 | 0.15 |
| 00901014041/ 00901013007 | 25% 5-Fluoro-CTP + 75% CTP/25% 5-Methoxy-UTP + 75% UTP | 0.29 | 0.31 |
| 00901014041/ 00901013007 | 75% 5-Fluoro-CTP + 25% CTP/25% 5-Methoxy-UTP + 75% UTP | 0.23 | 0.23 |
| 00901014041/ 00901013007 | 25% 5-Fluoro-CTP + 75% CTP/75% 5-Methoxy-UTP + 25% UTP | 0.18 | 0.22 |
| 00901014041/ 00901013007 | 75% 5-Fluoro-CTP + 25% CTP/75% 5-Methoxy-UTP + 25% UTP | 0.18 | 0.30 |
| 03601014021/ 00901013007 | 25% 5-Phenyl-CTP + 75% CTP/25% 5-Methoxy-UTP + 75% UTP | 0.20 | 0.41 |
| 03601014021/ 00901013007 | 75% 5-Phenyl-CTP + 25% CTP/25% 5-Methoxy-UTP + 75% UTP | 0.17 | 0.22 |
| 03601014021/ 00901013007 | 25% 5-Phenyl-CTP + 75% CTP/75% 5-Methoxy-UTP + 25% UTP | 0.05 | 0.05 |
| 03601014021/ 00901013007 | 75% 5-Phenyl-CTP + 25% CTP/75% 5-Methoxy-UTP + 25% UTP | 0.14 | 0.10 |
| 03601014013/ 00901013007 | 25% N4-Bz-CTP + 75% CTP/25% 5-Methoxy-UTP + 75% UTP | 0.30 | 0.30 |
| 03601014013/ 00901013007 | 75% N4-Bz-CTP + 25% CTP/25% 5-Methoxy-UTP + 75% UTP | 0.27 | 0.19 |
| 03601014013/ 00901013007 | 25% N4-Bz-CTP + 75% CTP/75% 5-Methoxy-UTP + 25% UTP | 0.21 | 0.19 |
| 03601014013/ 00901013007 | 75% N4-Bz-CTP + 25% CTP/75% 5-Methoxy-UTP + 25% UTP | 0.17 | 0.13 |
| 03601014041/ 00901013007 | 5-Carboxy-CTP/5-Methoxy-UTP | 0.03 | 0.05 |
| 03601014041/ 00901013007 | 25% 5-Carboxy-CTP + 75% CTP/25% 5-Methoxy-UTP + 75% UTP | 0.21 | 0.17 |
| 03601014041/ 00901013007 | 75% 5-Carboxy-CTP + 25% CTP/25% 5-Methoxy-UTP + 75% UTP | 0.21 | 0.17 |
| 03601014041/ 00901013007 | 25% 5-Carboxy-CTP + 75% CTP/75% 5-Methoxy-UTP + 25% UTP | 0.14 | 0.15 |

TABLE 24-continued

In vitro Transcription Yields.

| Compound # | Chemical Alterations | mCherry In Vitro Transcription yield(mg) | nanoLuc In Vitro Transcription yield(mg) |
|---|---|---|---|
| 03601014041/ 00901013007 | 75% 5-Carboxy-CTP + 25% CTP/75% 5-Methoxy-UTP + 25% UTP | 0.09 | 0.12 |
| 00901013007/ 00901012007 | 5-Methoxy-UTP/O6-Me-GTP | 0 | 0 |
| 00901013007/ 00901012007 | 25% 5-Methoxy-UTP + 75% UTP/25% O6-Me-GTP + 75% GTP | 0.8 | 0.14 |
| 00901013007/ 00901012007 | 25% 5-Methoxy-UTP + 75% UTP/75% O6-Me-GTP + 25% GTP | 0 | 0 |
| 00901013007/ 00901012007 | 75% 5-Methoxy-UTP + 25% UTP/25% O6-Me-GTP + 75% GTP | 0 | 0 |
| 00901013007/ 00901012007 | 75% 5-Methoxy-UTP + 25% UTP/75% O6-Me-GTP + 25% GTP | 0 | 0 |
| 00901013007/ 00901012035 | 5-Methoxy-UTP/7-Deaza-GTP | 0 | 0 |
| 00901013007/ 00901012035 | 25% 5-Methoxy-UTP + 75% UTP/25% 7-Deaza-GTP + 75% GTP | 0 | 0 |
| 00901013007/ 00901012035 | 25% 5-Methoxy-UTP + 75% UTP/75% 7-Deaza-GTP + 25% GTP | 0 | 0 |
| 00901013007/ 00901012035 | 75% 5-Methoxy-UTP + 25% UTP/25% 7-Deaza-GTP + 75% GTP | 0 | 0 |
| 00901013007/ 00901012035 | 75% 5-Methoxy-UTP + 25% UTP/75% 7-Deaza-GTP + 25% GTP | 0 | 0 |
| 00901013007/ 00901012010 | 5-Methoxy-UTP/2-Amino-6-Cl-purine-TP | 0 | 0 |
| 00901013007/ 00901012010 | 25% 5-Methoxy-UTP + 75% UTP/25% 2-Amino-6-Cl-purine-TP + 75% GTP | 0.16 | 0.32 |
| 00901013007/ 00901012010 | 25% 5-Methoxy-UTP + 75% UTP/75% A2-mino-6-Cl-purine-TP + 25% GTP | 0 | 0 |
| 00901013007/ 00901012010 | 75% 5-Methoxy-UTP + 25% UTP/25% 2-Amino-6-Cl-purine-TP + 75% GTP | 0 | 0 |
| 00901013007/ 00901012010 | 75% 5-Methoxy-UTP + 25% UTP/75% 2-Amino-6-Cl-purine-TP + 25% GTP | 0 | 0 |
| 00901013007/ 00901011004 | 5-Methoxy-UTP/N6-Me-2-amino purine-TP | 0 | 0 |
| 00901013007/ 00901011004 | 25% 5-Methoxy-UTP + 75% UTP/25% N6-Me-2-aminopurine-TP + 75% ATP | 0.13 | 0.08 |
| 00901013007/ 00901011004 | 25% 5-Methoxy-UTP + 75% UTP/75% N6-Me-2-amino purine-TP + 25% ATP | 0 | 0 |
| 00901013007/ 00901011004 | 75% 5-Methoxy-UTP + 25% UTP/25% N6-Me-2-amino purine-TP + 75% ATP | 0 | 0 |
| 00901013007/ 00901011004 | 75% 5-Methoxy-UTP + 25% UTP/75% N6-Me-2-amino purine-TP + 25% ATP | 0 | 0 |
| 00901013007/ 00901012004 | 5-Methoxy-UTP/2-amino purine-TP | 0.01 | 0.10 |
| 00901013007/ 00901012004 | 25% 5-Methoxy-UTP + 75% UTP/25% 2-aminopurine-TP + 75% ATP | 0.28 | 0.26 |
| 00901013007/ 00901012004 | 25% 5-Methoxy-UTP + 75% UTP/75% 2-amino purine-TP + 25% ATP | 0.14 | 0.19 |
| 00901013007/ 00901012004 | 75% 5-Methoxy-UTP + 25% UTP/25% 2-amino purine-TP + 75% ATP | 0.08 | 0.15 |
| 00901013007/ 00901012004 | 75% 5-Methoxy-UTP + 25% UTP/75% 2-amino purine-TP + 25% ATP | 0.23 | 0.14 |
| 00901013007/ 00901011005 | 5-Methoxy-UTP/8-Azido-ATP | 0.01 | 0.12 |
| 00901013007/ 00901011005 | 25% 5-Methoxy-UTP + 75% UTP/25% 8-Azido-ATP + 75% ATP | 0.12 | 0.18 |
| 00901013007/ 00901011005 | 25% 5-Methoxy-UTP + 75% UTP/75% 8-Azido-ATP + 25% ATP | 0.09 | 0.08 |
| 00901013007/ 00901011005 | 75% 5-Methoxy-UTP + 25% UTP/25% 8-Azido-ATP + 75% ATP | 0.17 | 0.16 |
| 00901013007/ 00901011005 | 75% 5-Methoxy-UTP + 25% UTP/75% 8-Azido-ATP + 25% ATP | 0.06 | 0.11 |
| 00901013007/ 00901012012 | 5-Methoxy-UTP/N7-Me-GTP | 0.02 | 0.14 |
| 00901013007/ 00901012012 | 25% 5-Methoxy-UTP + 75% UTP/25% N7-Me-GTP + 75% GTP | 0.21 | 0.18 |
| 00901013007/ 00901012012 | 25% 5-Methoxy-UTP + 75% UTP/75% N7-Me-GTP + 25% GTP | 0.12 | 0.19 |
| 00901013007/ 00901012012 | 75% 5-Methoxy-UTP + 25% UTP/25% N7-Me-GTP + 75% GTP | 0.10 | 0.19 |

TABLE 24-continued

In vitro Transcription Yields.

| Compound # | Chemical Alterations | mCherry In Vitro Transcription yield(mg) | nanoLuc In Vitro Transcription yield(mg) |
|---|---|---|---|
| 00901013007/ 00901012012 | 75% 5-Methoxy-UTP + 25% UTP/75% N7-Me-GTP + 25% GTP | 0.13 | 0.13 |
| 00901013042 | 5-Isopentenyl-aminomethyl-UTP | 0.01 | 0.05 |
| 00901013042 | 75% 5-Isopentenyl-aminomethyl-UTP + 25% UTP | 0.21 | 0.21 |
| 00901013042 | 50% 5-Isopentenyl-aminomethyl-UTP + 50% UTP | 0.22 | 0.17 |
| 00901013042 | 25% 5-Isopentenyl-aminomethyl-UTP + 75% UTP | 0.20 | 0.15 |
| 00901014002/ 00901013042 | 5-Me-CTP/5-Isopentenyl-aminomethyl-UTP | 0.01 | 0.12 |

TABLE 25

In vitro Transcription Yields.

| Compound # | Chemical Alterations | mEPO In Vitro Transcription yield(mg) | hEPO In Vitro Transcription yield(mg) |
|---|---|---|---|
| 00901013007 | 5-Methoxy-UTP | 0.13 | 0.33 |
| 00901014002/ 00901013007 | 5-Me-CTP/5-Methoxy-UTP | 0.22 | 0.22 |
| 00901014002/ 00901013007 | 5-Methyl-CTP/75% 5-Methoxy-UTP + 25% UTP | 0.26 | 0.17 |
| 00901014002/ 00901013007 | 5-Methyl-CTP/50% 5-Methoxy-UTP + 50% UTP | 0.27 | 0.24 |
| 00901014002/ 00901013007 | 5-Methyl-CTP/25% 5-Methoxy-UTP + 75% UTP | 0.15 | 0.25 |
| 00901014002/ 00901013007 | 75% 5-Methyl-CTP + 25% CTP/5-Methoxy-UTP | 0.15 | 0.25 |
| 00901014002/ 00901013007 | 50% 5-Methyl-CTP + 50% CTP/5-Methoxy-UTP | 0.21 | 0.29 |
| 00901014002/ 00901013007 | 25% 5-Methyl-CTP + 75% CTP/5-Methoxy-UTP | 0.15 | 0.23 |
| 00901014002/ 00901013007 | 75% 5-Methyl-CTP + 25% CTP/75% 5-Methoxy-UTP + 25% UTP | 0.2 | 0.02 |
| 00901014002/ 00901013007 | 50% 5-Methyl-CTP + 50% CTP/75% 5-Methoxy-UTP + 25% UTP | 0.24 | 0.02 |
| 00901014002/ 00901013007 | 25% 5-Methyl-CTP + 75% CTP/75% 5-Methoxy-UTP + 25% UTP | 0.4 | 0.11 |
| 00901014002/ 00901013007 | 75% 5-Methyl-CTP + 25% CTP/50% 5-Methoxy-UTP + 50% UTP | 0.34 | 0.11 |
| 00901014002/ 00901013007 | 50% 5-Methyl-CTP + 50% CTP/50% 5-Methoxy-UTP + 50% UTP | 0.14 | 0.19 |
| 00901014002/ 00901013007 | 25% 5-Methyl-CTP + 75% CTP/50% 5-Methoxy-UTP + 50% UTP | 0.19 | 0.23 |
| 00901014002/ 00901013007 | 75% 5-Methyl-CTP + 25% CTP/25% 5-Methoxy-UTP + 75% UTP | 0.13 | 0.09 |
| 00901014002/ 00901013007 | 50% 5-Methyl-CTP + 50% CTP/25% 5-Methoxy-UTP + 75% UTP | 0.13 | 0.1 |
| 00901014002/ 00901013007 | 25% 5-Methyl-CTP + 75% CTP/25% 5-Methoxy-UTP + 75% UTP | 0.13 | 0.2 |
| 00901013007 | CTP/75% 5-Methoxy-UTP + 25% UTP | 0.15 | 0.2 |
| 00901013007 | CTP/50% 5-Methoxy-UTP + 50% UTP | 0.19 | 0.3 |
| 00901013007 | CTP/25% 5-Methoxy-UTP + 75% UTP | 0.16 | 0.24 |

Example 84

In Vitro Translation Screen

The in vitro translation assay was done with the Rabbit Reticulocyte Lysate (nuclease-treated) kit (Promega, Madison, Wis.; Cat. # L4960) according to the manufacturer's instructions. The reaction buffer was a mixture of equal amounts of the amino acid stock solutions devoid of Leucine or Methionine provided in the kit. This resulted in a reaction mix containing sufficient amounts of both amino acids to allow effective in vitro translation.

The modRNAs of firefly Luciferase, human GCSF and human EPO, harboring chemical alterations on either the bases or the ribose units, were diluted in sterile nuclease-free water to a final concentration of 250 ng in 2.5 ul (Stock 100 ng/µl). The modRNA (250 ng) was added to the mixture of freshly prepared Rabbit Reticulocyte Lysate and reaction buffer. The in vitro translation reaction was done in a standard 0.2 ml polypropylene 96-well PCR plates (USA Scientific, Ocala, Fla.; Cat. #1402-9596) at 30° C. in a Thermocycler (MJ Research PCT-100, Watertown, Mass.).

After 45 min incubation, the reaction was stopped by placing the plate on ice. Aliquots of the in vitro translation reaction containing luciferase modRNA were transferred to white opaque polystyrene 96-well plates (Corning, Manassas, Va.; Cat. # CLS3912) and combined with 100 ul complete luciferase assay solution (Promega, Madison, Wis.). The volumes of the in vitro translation reactions were adjusted or diluted until no more than 2 million relative light units per well were detected for the strongest signal producing samples. The background signal of the plates without reagent was about 200 relative light units per well. The plate reader was a BioTek Synergy H1 (BioTek, Winooski, Vt.).

Aliquots of the in vitro translation reaction containing human GCSF modRNA or human EPO mRNA were transferred and analyzed with a human GCSF-specific or EPO ELISA kit (both from R&D Systems, Minneapolis, Minn.; Cat. #s SCS50, DEP00 respectively) according to the manufacturer instructions. All samples were diluted until the determined values were within the linear range of the human GCSF or EPO ELISA standard curve.

TABLE 26

| | | In vitro Translation Data. | | | | | |
|---|---|---|---|---|---|---|---|
| Compound # | Chemical Alterations | Luc Expression (RLUs) | Luc Std Dev | Epo Expression (pg/ml) | Epo Std Dev | GCSF Expression (pg/ml) | GSCF Std Dev |
| 00902015001 | PseudoU-alpha-thio-TP | 5221 | 480 | 2669 | 492 | 7763 | 538 |
| 00902015002 | 1-Methyl-pseudo-U-alpha-thio-TP | 1201 | 840 | 1694 | 143 | 4244 | 44 |
| 03601015003 | 1-Ethyl-pseudo-UTP | 122 | 36 | 7894 | 383 | 5700 | 288 |
| 03601015004 | 1-Propyl-pseudo-UTP | 140 | 7 | 838 | 36 | 1613 | 75 |
| 00901015006 | 2-Thio-pseudo-UTP | 2198 | 297 | 12310 | 2602 | 5988 | 238 |
| 00901014003 | 5-Trifluoromethyl-CTP | 23340 | 294 | 10200 | 817 | 31510 | 156 |
| 00901013004 | 5-Methyl-2-thio-UTP | 235 | 30 | 1100 | 11 | 2319 | 44 |
| 00901014005 | 5-Hydroxymethyl-CTP | 154000 | 5090 | 9425 | 442 | 26600 | 462 |
| 00901013004 | UTP-5-oxyacetic acid Me ester | 162 | 30 | 544 | 32 | 4388 | 775 |
| 00901013007 | 5-methoxy-UTP | 306600 | 619 | 17530 | 3678 | 26440 | 344 |
| 00901014007 | N4-Ac-CTP | 167600 | 1461 | 8675 | 1790 | 8794 | 131 |
| 03601014008 | 5-Bromo-CTP | 194900 | 5665 | 8581 | 143 | 13510 | 1706 |
| 03601014009 | 5-Aminoallyl-CTP | 887 | 242 | 169 | 3 | 1806 | 181 |
| 03601012004 | 2-Aminopurine-riboside TP | 107000 | 28420 | 22180 | 362 | 8675 | 1025 |
| 00901013008 | 2-Thio-UTP | 1181 | 222 | 1894 | 92 | 3744 | 244 |
| 00901013009 | 5-Bromo-UTP | 218500 | 11290 | 18220 | 6 | 21530 | 1231 |
| 00902014001 | Alpha-thio-CTP | 142900 | 20660 | 17000 | 1671 | 26930 | 281 |
| 00901013010 | 5-Aminoallyl-UTP | 14870 | 2587 | 1863 | 54 | 3706 | 706 |
| 00902013001 | Alpha-thio-UTP | 51180 | 4835 | 14260 | 1465 | 20530 | 1381 |
| 00901014003/ 00901015002 | 5-Trifluoromethyl-CTP/1-Methyl-pseudo-UTP | | | | | | 281 |
| 0090101400/ 00901015002 | 5-Hydroxymethyl-CTP/1-Methyl-pseudo-UTP | | | | | | 706 |
| 0360101400/ 00901015002 | 5-Bromo-CTP/1-Methyl-pseudo-UTP | | | | | | 1381 |
| 00901014002/ 00901015002 | 75% 5-Methyl-CTP + 25% CTP/1-Methyl-pseudo-UTP | | | 123784.09 | 3671.05 | | |
| 00901014002/ 00901015002 | 50% 5-Methyl-CTP + 50% CTP/1-Methyl-pseudo-UTP | | | 122397.73 | 8593.01 | | |
| 00901014002/ 00901015002 | 25% 5-Methyl-CTP + 75% CTP/1-Methyl-pseudo-UTP | | | 134988.64 | 8945.90 | | |
| 00901014002/ 00901015002 | 12.5% 5-Methyl-CTP + 87.5% CTP/1-Methyl-pseudo-UTP | | | 146261.36 | 1569.59 | | |
| 00901014002/ 00901015001 | 75% 5-Methyl-CTP + 25% CTP/Pseudo-UTP | | | 90477.27 | 1758.97 | | |
| 00901014002/ 00901015001 | 50% 5-Methyl-CTP + 50% CTP/Pseudo-UTP | | | 105772.73 | 706.92 | | |
| 00901014002/ 00901015001 | 25% 5-Methyl-CTP + 75% CTP/Pseudo-UTP | | | 122204.55 | 1707.45 | | |
| 00901014035/ 00901015002 | 5-Iodo-CTP/1-Methyl-pseudo-UTP | 38787.75 | 696.85 | 50375.00 | 610.80 | | |
| 00901014035/ 00901015002 | 75% 5-Iodo-CTP + 25% CTP/1-Methyl-pseudo-UTP | | | 63034.09 | 921.39 | | |

TABLE 26-continued

In vitro Translation Data.

| Compound # | Chemical Alterations | Luc Expression (RLUs) | Luc Std Dev | Epo Expression (pg/ml) | Epo Std Dev | GCSF Expression (pg/ml) | GSCF Std Dev |
|---|---|---|---|---|---|---|---|
| 00901014035/ 00901015002 | 50% 5-Iodo-CTP + 50% CTP/1-Methyl-pseudo-UTP | | | 74159.09 | 1004.21 | | |
| 00901014035/ 00901015002 | 25% 5-Iodo-CTP + 75% CTP/1-Methyl-pseudo-UTP | | | 98147.73 | 562.10 | | |
| 03601014008/ 00901015002 | 75% 5-Bromo-CTP + 25% CTP/1-Methyl-pseudo-UTP | | | 36208 | 446 | | |
| 03601014008/ 00901015001 | 75% 5-Bromo-CTP + 25% CTP/Pseudo-UTP | | | 24515 | 1601 | | |
| 03601014008/ 00901015001 | 50% 5-Bromo-CTP + 50% CTP/Pseudo-UTP | | | 33896 | 2220 | | |
| 03601014008/ 00901015001 | 25% 5-Bromo-CTP + 75% CTP/Pseudo-UTP | | | 43143 | 117 | | |
| 00901014003/ 00901013007 | 5-Trifluoro-methyl-CTP/5-Methoxy-UTP | | | 29120 | 1933 | | |
| 12201014040/ 00901013007 | 5-Hydroxy-methyl-CTP/5-Methoxy-UTP | | | 18398 | 3813 | | |
| 03601014008/ 00901013007 | 5-Bromo-CTP/5-Methoxy-UTP | | | 23204 | 882 | | |
| 00901014002/ 00901013008 | 5-Methyl-CTP/75% 2-Thio-UTP + 25% UTP | | | 15466 | 1041 | −1170 | −42 |
| 00901014002/ 00901013008 | 5-Methyl-CTP/25% 2-Thio-UTP + 75% UTP | | | 65466 | 2491 | 19485 | 741 |
| 00901014002/ 00901013008 | 75% 5-Methyl-CTP + 25% CTP/2-Thio-UTP | | | 1409 | 89 | −4523 | −75 |
| 00901014002/ 00901013008 | 50% 5-Methyl-CTP + 50% CTP/2-Thio-UTP | | | 614 | 12 | −4208 | −147 |
| 00901014002/ 00901013008 | 25% 5-Methyl-CTP + 75% CTP/2-Thio-UTP | | | 886 | 0 | −4028 | −12 |
| 00901014002/ 00901013008 | 75% 5-Methyl-CTP + 25% CTP/75% 2-Thio-UTP + 25% UTP | | | 78500 | 4338 | 56250 | 2511 |
| 00901014002/ 00901013008 | 50% 5-Methyl-CTP + 50% CTP/75% 2-Thio-UTP + 25% UTP | | | 61886 | 239 | 81000 | 1619 |
| 00901014002/ 00901013008 | 25% 5-Methyl-CTP + 75% CTP/75% 2-Thio-UTP + 25% UTP | | | 78318 | 6068 | 130568 | 2050 |
| 00901014002/ 00901013008 | 75% 5-Methyl-CTP + 25% CTP/50% 2-Thio-UTP + 50% UTP | | | 36989 | 2095 | 32130 | 966 |
| 00901014002/ 00901013008 | 50% 5-Methyl-CTP + 50% CTP/50% 2-Thio-UTP + 50% UTP | | | 51625 | 11043 | 54158 | 1992 |

TABLE 26-continued

In vitro Translation Data.

| Compound # | Chemical Alterations | Luc Expression (RLUs) | Luc Std Dev | Epo Expression (pg/ml) | Epo Std Dev | GCSF Expression (pg/ml) | GSCF Std Dev |
|---|---|---|---|---|---|---|---|
| 00901014002/ 00901013008 | 25% 5-Methyl-CTP + 75% CTP/50% 2-Thio-UTP + 50% UTP | | | 63864 | 1847 | 99158 | 3010 |
| 00901014002/ 00901013008 | 75% 5-Methyl-CTP + 25% CTP/25% 2-Thio-UTP + 75% UTP | | | 58875 | 5575 | 62888 | 4864 |
| 00901014002/ 00901013008 | 50% 5-Methyl-CTP + 50% CTP/25% 2-Thio-UTP + 75% UTP | | | 56489 | 3144 | 95130 | 3620 |
| 00901014002/ 00901013008 | 25% 5-Methyl-CTP + 75% CTP/25% 2-Thio-UTP + 75% UTP | | | 62432 | 369 | 129600 | 2980 |
| 00901013008 | CTP/75% 2-Thio-UTP + 25% UTP | | | 66148 | 1097 | | |
| 00901013008 | CTP/50% 2-Thio-UTP + 50% UTP | | | 111693 | 3905 | | |
| 00901013008 | CTP/25% 2-Thio-UTP + 75% UTP | | | 116784 | 2846 | | |

TABLE 27

In vitro Translation Data.

| Chemical Alterations | In Vitro Translation Luc Expression (RLUs) | In Vitro Translation hEpo Expression (pg/ml) | In Vitro Translation hGCSF Expression (pg/ml) |
|---|---|---|---|
| 75% 5-Bromo-CTP 25% CTP 1-Methyl-pseudo-UTP | 372909 | 36208 | 21330 |
| 75% 5-Bromo-CTP 25% CTP Pseudo-UTP | 863775 | 24515 | 14760 |
| 50% 5-Bromo-CTP 50% CTP Pseudo-UTP | 1593328 | 33896 | 32040 |
| 25% 5-Bromo-CTP 75% CTP Pseudo-UTP | 193009 | 43143 | 63360 |
| 5-Trifluoromethyl-CTP 5-Methoxy-UTP | 43541 | 29120 | 115470 |
| 5-Hydroxymethyl-CTP 5-Methoxy-UTP | 121836 | 18398 | 26595 |
| 5-Bromo-CTP 5-Methoxy-UTP | 83463 | 23204 | 12330 |

TABLE 28

In vitro Translation Data.

| Compund # | Chemical Alterations | mCherry Expression (pg/mL) | mCherry Std Dev | nanoLuc Expression (RLUs) | nanoLuc Std Dev |
|---|---|---|---|---|---|
| 00901014005/ 00901015001 | 5-Hydroxymethyl-CTP/Pseudo-UTP | 1613.50 | 27.58 | 139336.75 | 23352.56 |
| 00901014035/ 00901015001 | 5-Iodo-CTP/Pseudo-UTP | 240.50 | 2.12 | 37553.75 | 1801.35 |
| 00901014007/ 00901015001 | N4-Ac-CTP/Pseudo-UTP | 2156.50 | 463.15 | 180876.25 | 29259.73 |
| 00901014035/ 00901013007 | 5-Iodo-CTP/5-Methoxy-UTP | 302.00 | 9.90 | 24770.50 | 1690.69 |
| 00901014002/ | 5-Methyl-CTP/5'-Amino-UTP | 794.00 | 25.46 | | |
| 00901014002/ 03601015003 | 5-Methyl-CTP/1-Ethyl-pseudo-UTP | 211.00 | 9.90 | 1757.00 | 152.03 |

TABLE 28-continued

In vitro Translation Data.

| Compund # | Chemical Alterations | mCherry Expression (pg/mL) | mCherry Std Dev | nanoLuc Expression (RLUs) | nanoLuc Std Dev |
|---|---|---|---|---|---|
| 00901014002/ 03601015004 | 5-Methyl-CTP/1-Propyl-pseudo-UTP | 214.00 | 42.43 | 288.50 | 36.06 |
| 00901014002/ 00901013007 | 5-Methyl-CTP/75% 5-Methoxy-UTP + 25% UTP | 1433.50 | 53.03 | 74113.50 | 1583.92 |
| 00901014002/ 00901013007 | 5-Methyl-CTP/50% 5-Methoxy-UTP + 50% UTP | 1564.00 | 145.66 | 77203.50 | 4840.85 |
| 00901014002/ 00901013007 | 5-Methyl-CTP/25% 5-Methoxy-UTP + 75% UTP | 1507.00 | 135.76 | 107758.25 | 4727.36 |
| 00901014002/ 00901013007 | 75% 5-Methyl-CTP + 25% CTP/ 5-Methoxy-UTP | 1169.00 | 117.38 | 48217.00 | 2466.39 |
| 00901014002/ 00901013007 | 50% 5-Methyl-CTP + 50% CTP/ 5-Methoxy-UTP | 1312.50 | 91.22 | 74865.25 | 4357.55 |
| 00901014002/ 00901013007 | 25% 5-Methyl-CTP + 75% CTP/ 5-Methoxy-UTP | 990.00 | 196.58 | 84744.25 | 12448.26 |
| 00901014002/ 00901013007 | 75% 5-Methyl-CTP + 25% CTP/75% 5-Methoxy-UTP + 25% UTP | 1231.00 | 18.38 | 104817.75 | 10710.90 |
| 00901014002/ 00901013007 | 50% 5-Methyl-CTP + 50% CTP/75% 5-Methoxy-UTP + 25% UTP | 1278.50 | 50.20 | 72832.25 | 41.37 |
| 00901014002/ 00901013007 | 25% 5-Methyl-CTP + 75% CTP/75% 5-Methoxy-UTP + 25% UTP | 1248.50 | 33.23 | 121615.00 | 11422.60 |
| 00901014002/ 00901013007 | 75% 5-Methyl-CTP + 25% CTP/50% 5-Methoxy-UTP + 50% UTP | 1937.50 | 376.89 | 63651.00 | 7326.33 |
| 00901014002/ 00901013007 | 50% 5-Methyl-CTP + 50% CTP/50% 5-Methoxy-UTP + 50% UTP | 1374.00 | 175.36 | 145398.50 | 27595.55 |
| 00901014002/ 00901013007 | 25% 5-Methyl-CTP + 75% CTP/50% 5-Methoxy-UTP + 50% UTP | 1375.00 | 89.10 | 241049.25 | 33588.63 |
| 00901014002/ 00901013007 | 75% 5-Methyl-CTP + 25% CTP/25% 5-Methoxy-UTP + 75% UTP | 1146.50 | 228.40 | 230246.75 | 25576.41 |
| 00901014002/ 00901013007 | 50% 5-Methyl-CTP + 50% CTP/25% 5-Methoxy-UTP + 75% UTP | 1875.00 | 592.56 | 271458.00 | 8507.20 |
| 00901014002/ 00901013007 | 25% 5-Methyl-CTP + 75% CTP/25% 5-Methoxy-UTP + 75% UTP | 1906.00 | 74.95 | 258728.50 | 7619.08 |
| 00901013007 | CTP/75% 5-Methoxy-UTP + 25% UTP | 1546.00 | 19.80 | 165573.75 | 2294.21 |
| 00901013007 | CTP/50% 5-Methoxy-UTP + 50% UTP | 1544.00 | 158.39 | 250344.25 | 420.37 |
| 00901013007 | CTP/25% 5-Methoxy-UTP + 75% UTP | 2023.00 | 243.24 | 336602.50 | 13238.45 |
| 00901013007 | CTP/5-Methoxy-UTP (No cap) | 660.00 | 14.14 | 18313.50 | 2438.81 |
| 00901013007 | CTP/5-Methoxy-UTP (cap 0) | 2423.50 | 294.86 | 75928.75 | 331.99 |
| 00901014002/ 00901013007 | 5-Methyl-CTP/5-Methoxy-UTP (No cap) | 853.00 | 25.46 | 6760.25 | 228.04 |
| 00901014002/ 00901013007 | 5-Methyl-CTP/5-Methoxy-UTP (cap 0) | 3142.50 | 532.45 | 19865.25 | 492.50 |
|  | CTP/UTP (No cap) | 1859.00 | 18.38 | 29651.75 | 2075.00 |
|  | CTP/UTP (cap 0) | 5093.00 | 268.70 | 139465.00 | 1797.47 |
| 00901014002/ 00901015001 | 5-Methyl-CTP/Pseudo-UTP (No cap) | 1557.00 | 19.80 | 12815.50 | 1076.22 |
| 00901014002/ 00901015001 | 5-Methyl-CTP/Pseudo-UTP (cap 0) | 5814.50 | 307.59 | 56361.25 | 3894.39 |
| 00901014002/ 00901015002 | 5-Methyl-CTP/1-Methyl-pseudo-UTP (No cap) | 1131.00 | 96.17 | 11691.25 | 270.47 |
| 00901014002/ 00901015002 | 5-Methyl-CTP/1-Methyl-pseudo-UTP (cap 0) | 3807.50 | 173.24 | 47763.00 | 383.25 |
| 00901015002 | CTP/1-Methyl-pseudo-UTP (No cap) | 3045.00 | 429.92 | 37563.25 | 4984.75 |
| 00901015002 | CTP/1-Methyl-pseudo-UTP (cap 0) | 9539.50 | 648.42 | 259230.50 | 19467.36 |
|  | CTP/UTP/ATP/GTP (cap ARCA) | 5588.50 | 190.21 | 168298.75 | 9877.22 |
| 00901014002/ 00901015001 | 5-Methyl-CTP/Pseudo-UTP (cap ARCA) | 5052.00 | 89.10 | 86986.50 | 273.65 |
| 00901014002/ 00901015002 | 5-Methyl-CTP/1-Methyl-pseudo-UTP (cap ARCA) | 3016.00 | 152.74 | 80634.25 | 324.21 |
| 00901015002 | CTP/1-Methyl-pseudo-UTP (cap ARCA) | 8347.00 | 1387.34 | 199318.25 | 8366.84 |
| 00901014002/ 00901015001/ 00902011001 | 5-Methyl-CTP/Pseudo-UTP/ Alpha-Thio-ATP | 1045.50 | 113.84 | 49016.00 | 958.84 |
| 00902012001 | Alpha-Thio-GTP | 1401.50 | 200.11 | 128260.75 | 15595.59 |
| 00901014002/ 00901015001/ 00902012001 | 5-Methyl-CTP/Pseudo-UTP/ Alpha-Thio-GTP | 1401.00 | 196.58 | 65491.75 | 3069.20 |
| 00901014002/ 00901015002/ 00902012001 | 5-Methyl-CTP/1-Methyl-pseudo-UTP/ Alpha-Thio-GTP | 648.50 | 26.16 | 42249.25 | 902.62 |
| 00901015002/ 00902012001 | 1-Methyl-pseudo-UTP/Alpha-Thio-GTP | 2615.00 | 15.56 | 213356.00 | 3404.72 |
| 00901013007/ 00902012001 | 5-Methoxy-UTP/Alpha-Thio-GTP | 714.00 | 33.94 | 41532.00 | 0.00 |

TABLE 28-continued

In vitro Translation Data.

| Compund # | Chemical Alterations | mCherry Expression (pg/mL) | mCherry Std Dev | nanoLuc Expression (RLUs) | nanoLuc Std Dev |
|---|---|---|---|---|---|
| 00901014002/ 00901013007/ 00902012001 | 5-Methyl-CTP/5-Methoxy-UTP/ Alpha-Thio-GTP | 820.50 | 68.59 | 21421.00 | 0.00 |
| 00901011006 | N6-Me-ATP | 94.00 | 12.73 | 2057.00 | 0.00 |
| 00901014002/ 00901015001/ 00901011006 | 5-Methyl-CTP/Pseudo-UTP/N6-Me-ATP | 92.00 | 1.41 | 984.00 | 0.00 |
| 00901014002/ 00901015002/ 00901011006 | 5-Methyl-CTP/1-Methyl-pseudo-UTP/ N6-Me-ATP | 90.50 | 3.54 | 1248.50 | 500.63 |
| 00901015002/ 00901011006 | 1-Methyl-pseudo-UTP/N6-Me-ATP | 113.00 | 11.31 | 817.00 | 100.41 |
| 00901013007/ 00901011006 | 5-Methoxy-UTP/N6-Me-ATP | 80.50 | 9.19 | 362.25 | 71.77 |
| 00901014002/ 00901013007/ 00901011006 | 5-Methyl-CTP/5-Methoxy-UTP/ N6-Me-ATP | 94.50 | 20.51 | 648.50 | 116.67 |
| 03601014039 | 5-Ethyl-CTP | 1718.00 | 347.90 | 20473.50 | 2481.24 |
| 03601014039/ 00901015002 | 5-Ethyl-CTP/1-Methyl-pseudo-UTP | 1856.50 | 23.33 | 11843.00 | 1278.45 |
| 03601014039/ 00901013007 | 5-Ethyl-CTP/5-Methoxy-UTP | 667.00 | 80.61 | 5166.00 | 458.91 |
| 03601014030 | 5-Methoxy-CTP | 1069.50 | 178.90 | 13888.25 | 1154.35 |
| 03601014030/ 00901015002 | 5-Methoxy-CTP/1-Methyl-pseudo-UTP | 794.50 | 159.10 | 7416.50 | 675.29 |
| 03601014030/ 00901013007 | 5-Methoxy-CTP/5-Methoxy-UTP | 683.00 | 203.65 | 5084.00 | 1538.66 |
| 03601014011 | 5-Ethynyl-CTP | 1440.50 | 16.26 | 14288.25 | 3900.05 |
| 03601014011/ 00901015002 | 5-Ethynyl-CTP/1-Methyl-pseudo-UTP | 355.00 | 29.70 | 6226.00 | 808.22 |
| 03601014011/ 00901013007 | 5-Ethynyl-CTP/5-Methoxy-UTP | 372.00 | 43.84 | 8274.50 | 2757.72 |
| 03601014011/ 00901015001 | 5-Ethynyl-CTP/Pseudo-UTP | 609.50 | 30.41 | 1433.00 | 127.99 |
| 03601014011/ 00901013007/ 00901015002 | 5-Methyl-CTP/75% 5-Methoxy-UTP + 25% 1-Methyl-pseudo-UTP | 1156.00 | 65.05 | 31772.00 | 4555.18 |
| 03601014011/ 00901013007/ 00901015002 | 5-Methyl-CTP/50% 5-Methoxy-UTP + 50% 1-Methyl-pseudo-UTP | 1271.00 | 41.01 | 36720.00 | 1120.06 |
| 03601014011/ 00901013007/ 00901015002 | 5-Methyl-CTP/25% 5-Methoxy-UTP + 75% 1-Methyl-pseudo-UTP | 1500.50 | 334.46 | 37789.00 | 21064.71 |
| 03601014011/ 00901013007/ 00901015002 | 75% 5-Methyl-CTP + 25% CTP/75% 5-Methoxy-UTP + 25% 1-Methyl-pseudo-UTP | 965.50 | 24.75 | 31655.00 | 1865.35 |
| 03601014011/ 00901013007/ 00901015002 | 50% 5-Methyl-CTP + 50% CTP/75% 5-Methoxy-UTP + 25% 1-Methyl-pseudo-UTP | 935.00 | 147.08 | 49602.00 | 1702.71 |
| 03601014011/ 00901013007/ 00901015002 | 25% 5-Methyl-CTP + 75% CTP/75% 5-Methoxy-UTP + 25% 1-Methyl-pseudo-UTP | 1412.50 | 79.90 | 82699.00 | 1813.02 |
| 03601014011/ 00901013007/ 00901015002 | 75% 5-Methyl-CTP + 25% CTP/50% 5-Methoxy-UTP + 50% 1-Methyl-pseudo-UTP | 1524.00 | 22.63 | 60087.50 | 3038.44 |
| 03601014011/ 00901013007/ 00901015002 | 50% 5-Methyl-CTP + 50% CTP/50% 5-Methoxy-UTP + 50% 1-Methyl-pseudo-UTP | 1835.50 | 321.73 | 86481.50 | 2905.50 |
| 03601014011/ 00901013007/ 00901015002 | 25% 5-Methyl-CTP + 75% CTP/50% 5-Methoxy-UTP + 50% 1-Methyl-pseudo-UTP | 1757.50 | 270.82 | 85345.50 | 512.65 |
| 03601014011/ 00901013007/ 00901015002 | 75% 5-Methyl-CTP + 25% CTP/25% 5-Methoxy-UTP + 75% 1-Methyl-pseudo-UTP | 1855.00 | 309.71 | 71842.00 | 280.01 |
| 03601014011/ 00901013007/ 00901015002 | 50% 5-Methyl-CTP + 50% CTP/25% 5-Methoxy-UTP + 75% 1-Methyl-pseudo-UTP | 1184.00 | 278.60 | 55291.50 | 2399.21 |
| 03601014011/ 00901013007/ 00901015002 | 25% 5-Methyl-CTP + 75% CTP/25% 5-Methoxy-UTP + 75% 1-Methyl-pseudo-UTP | 1884.00 | 82.02 | 102894.50 | 10720.45 |
| 00901013007/ 00901015002 | CTP/75% 5-Methoxy-UTP + 25% 1-Methyl-pseudo-UTP | 646.50 | 36.06 | 54569.00 | 1962.93 |
| 00901013007/ 00901015002 | CTP/50% 5-Methoxy-UTP + 50% 1-Methyl-pseudo-UTP | 1468.00 | 265.87 | 103184.50 | 1434.72 |

TABLE 28-continued

In vitro Translation Data.

| Compund # | Chemical Alterations | mCherry Expression (pg/mL) | mCherry Std Dev | nanoLuc Expression (RLUs) | nanoLuc Std Dev |
|---|---|---|---|---|---|
| 00901013007/ 00901015002 | CTP/25% 5-Methoxy-UTP + 75% 1-Methyl-pseudo-UTP | 1721.50 | 368.40 | 123827.00 | 4921.46 |
| 00901014004/ 00901015002 | N4-Methyl-CTP/1-Methyl-pseudo-UTP | 9203.50 | 2590.13 | 203918.00 | 19535.95 |
| 00902014001/ 00901015002 | 1-Methyl-pseudo-UTP/2% Alpha-Thio-GTP + 98% GTP | 5835.00 | 719.83 | 88144.00 | 10417.10v |
| 00902014001/ 00901015002 | 1-Methyl-pseudo-UTP/5% Alpha-Thio-GTP + 95% GTP | 6561.50 | 0.71 | 112307.00 | 30432.46 |
| 00901015002/ 00902012001 | 1-Methyl-pseudo-UTP/10% Alpha-Thio-GTP + 90% GTP | 4411.00 | 642.05 | 122696.00 | 4791.36 |
| 00901015002/ 00902012001 | 1-Methyl-pseudo-UTP/25% Alpha-Thio-GTP + 75% GTP | 4056.50 | 391.03 | 74470.00 | 1998.28 |
| 00901015002/ 00902012001 | 1-Methyl-pseudo-UTP/50% Alpha-Thio-GTP + 50% GTP | 4339.00 | 552.96 | 61497.50 | 4448.41 |
| 00901015002/ 00902011001 | 1-Methyl-pseudo-UTP/2% Alpha-Thio-ATP + 98% ATP | 5146.00 | 769.33 | 122779.00 | 11023.79 |
| 00901015002/ 00902011001 | 1-Methyl-pseudo-UTP/5% Alpha-Thio-ATP + 95% ATP | 5846.50 | 795.50 | 98961.00 | 15034.50 |
| 00901015002/ 00902011001 | 1-Methyl-pseudo-UTP/10% Alpha-Thio-ATP + 90% ATP | 6378.00 | 53.74 | 149039.50 | 15402.91 |
| 00901015002/ 00902011001 | 1-Methyl-pseudo-UTP/25% Alpha-Thio-ATP + 75% ATP | 5380.50 | 78.49 | 71078.50 | 6557.00 |
| 00901015002/ 00902011001 | 1-Methyl-pseudo-UTP/50% Alpha-Thio-ATP + 50% ATP | 5967.50 | 587.61 | 98998.00 | 27495.14 |
| 00901015002 | 75% 1-Methyl-pseudo-UTP + 25% UTP | 5284.50 | 552.25 | 122283.00 | 9775.04 |
| 00901015002 | 50% 1-Methyl-pseudo-UTP + 50% UTP | 4553.50 | 45.96 | 107640.00 | 14789.85 |
| 00901015001 | 75% Pseudo-UTP + 25% UTP | 5499.00 | 226.27 | 153386.00 | 5263.70 |
| 00901015001 | 50% Pseudo-UTP + 50% UTP | 4320.50 | 1559.17 | 118446.00 | 6133.44 |
| 00901015001 | 25% Pseudo-UTP + 75% UTP | 5927.50 | 519.72 | 99486.00 | 5593.21 |
| 03601013014 | 75% 5-Methyl-UTP + 25% UTP | 2613.00 | 76.37 | 92869.00 | 931.97 |
| 03601013014 | 50% 5-Methyl-UTP + 50% UTP | 3623.00 | 65.05 | 117837.00 | 11620.59 |
| 03601013014 | 25% 5-Methyl-UTP + 75% UTP | 3504.50 | 690.84 | 124512.00 | 14829.44 |
| 00901013003 | 75% 5-Methyl-2-thio-UTP + 25% UTP | 440.50 | 4.95 | 11348.00 | 612.35 |
| 00901013003 | 50% 5-Methyl-2-thio-UTP + 50% UTP | 867.50 | 101.12 | 23585.00 | 535.99 |
| 00901013003 | 25% 5-Methyl-2-thio-UTP + 75% UTP | 1188.00 | 19.80 | 83997.50 | 2346.89 |
| 00901013011 | 75% 4-Thio-UTP + 25% UTP | 8276.00 | 674.58 | 261483.50 | 37563.63 |
| 00901013011 | 50% 4-Thio-UTP + 50% UTP | 9816.00 | 316.78 | 408404.00 | 54952.10 |
| 00901013011 | 25% 4-Thio-UTP + 75% UTP | 8812.00 | 22.63 | 445430.00 | 23982.23 |
| 00901013009 | 75% 5-Methoxy-carbonylmethyl-UTP + 25% UTP | 589.00 | 19.80 | 28154.00 | 3461.99 |
| 00901013009 | 50% 5-Methoxy-carbonylmethyl-UTP + 50% UTP | 3179.00 | 169.71 | 145500.00 | 25536.45 |
| 00901013009 | 25% 5-Methoxy-carbonylmethyl-UTP + 75% UTP | 10241.00 | 1238.85 | 232518.50 | 45703.85 |
| 03601014011 | 75% 5-Methyl-CTP + 25% CTP | 9613.00 | 1006.92 | 228234.00 | 44888.55 |
| 03601014011 | 50% 5-Methyl-CTP + 50% CTP | 10413.50 | 252.44 | 284277.00 | 10789.04 |
| 03601014011 | 25% 5-Methyl-CTP + 75% CTP | 7868.00 | 530.33 | 306557.00 | 16677.82 |
| 03601014011/ 00901015002 | 75% 5-Methyl-CTP + 25% CTP/ 1-Methyl-pseudo-UTP | 8258.50 | 573.46 | 182035.50 | 62016.80 |
| 03601014011/ 00901015002 | 50% 5-Methyl-CTP + 50% CTP/ 1-Methyl-pseudo-UTP | 7701.50 | 564.98 | 218864.00 | 49249.99 |
| 03601014011/ 00901015002 | 25% 5-Methyl-CTP + 75% CTP/ 1-Methyl-pseudo-UTP | 5977.50 | 395.27 | 178608.00 | 2786.00 |
| 00901011045 | 1-Methyl-pseudo-UTP/2% Alpha-Thio-ATP + 98% ATP/2% Alpha-Thio-GTP + 98% GTP | 12779.50 | 826.61 | 147196.50 | 4141.52 |
| 00901015002/ 00901011045 | 1-Methyl-pseudo-UTP/5% Alpha-Thio-ATP + 95% ATP/5% Alpha-Thio-GTP + 95% GTP | 13173.50 | 78.49 | 161822.00 | 20969.96 |
| 00901015002/ 00902011001/ 00902012001 | 1-Methyl-pseudo-UTP/2% Alpha-Thio-ATP + 98% ATP/5% Alpha-Thio-GTP + 95% GTP | 14117.50 | 622.96 | 162037.00 | 16477.00 |
| 00901015002/ 00902011001/ 00902012001 | 1-Methyl-pseudo-UTP/5% Alpha-Thio-ATP + 95% ATP/2% Alpha-Thio-GTP + 98% GTP | 14301.00 | 482.25 | 180665.00 | 19412.91 |
| 00901015002/ 00902011001/ 00902012001 | 1-Methyl-pseudo-UTP/10% Alpha-Thio-ATP + 90% ATP/2% Alpha-Thio-GTP + 98% GTP | 13998.00 | 41.01 | 175482.00 | 5283.50 |
| 00901015002/ 00902011001/ 00902012001 | 1-Methyl-pseudo-UTP/2% Alpha-Thio-ATP + 98% ATP/10% Alpha-Thio-GTP + 90% GTP | 13546.00 | 584.07 | 149344.50 | 9207.24 |
| 00901015002/ 00902011001/ 00902012001 | 1-Methyl-pseudo-UTP/10% Alpha-Thio-ATP + 90% ATP/5% Alpha-Thio-GTP + 95% GTP | 12181.50 | 464.57 | 166917.00 | 13071.58 |

TABLE 28-continued

In vitro Translation Data.

| Compund # | Chemical Alterations | mCherry Expression (pg/mL) | mCherry Std Dev | nanoLuc Expression (RLUs) | nanoLuc Std Dev |
|---|---|---|---|---|---|
| 00901015002/ 00902011001/ 00902012001 | 1-Methyl-pseudo-UTP/5% Alpha-Thio-ATP + 95% ATP/10% Alpha-Thio-GTP + 90% GTP | 13638.00 | 1018.23 | 143875.50 | 6087.48 |
| 00901015002/ 00902011001/ 00902012001 | 1-Methyl-pseudo-UTP/10% Alpha-Thio-ATP + 90% ATP/10% Alpha-Thio-GTP + 90% GTP | 10480.00 | 285.67 | 139291.00 | 14927.02 |
| 00901014041 | 5-Fluoro-CTP | 14941.50 | 499.92 | 153088.00 | 48740.87 |
| 00901014041/ 00901015002 | 5-Fluoro-CTP/1-Methyl-pseudo-UTP | 16286.50 | 6660.24 | 132525.00 | 31988.10 |
| 00901014041/ 00901013007 | 5-Fluoro-CTP/5-Methoxy-UTP | 5573.00 | 1479.27 | 44264.50 | 6397.20 |
| 03601014021 | 5-Phenyl-CTP | 182.50 | 21.92 | 195.00 | 70.71 |
| 03601014021/ 00901015002 | 5-Phenyl-CTP/1-Methyl-pseudo-UTP | 366.00 | 60.81 | 162.50 | 14.85 |
| 03601014021/ 00901013007 | 5-Phenyl-CTP/5-Methoxy-UTP | 228.50 | 127.99 | 225.50 | 105.36 |
| 03601014013 | N4-Bz-CTP | 5134.00 | 4846.51 | 25258.00 | 6164.56 |
| 03601014013/ 00901015002 | N4-Bz-CTP/1-Methyl-pseudo-UTP | 2836.50 | 748.83 | 26432.50 | 5636.35 |
| 03601014013/ 00901013007 | N4-Bz-CTP/5-Methoxy-UTP | 315.50 | 13.44 | 2029.00 | 759.43 |
| 00901011044 | N6-Isopentenyl-ATP | 270.50 | 28.99 | 202.50 | 7.78 |
| 00901015002/ 00901011044 | 1-Methyl-pseudo-UTP/ N6-Isopentenyl-ATP | 319.00 | 16.97 | 222.00 | 33.94 |
| 00901013007/ 00901011044 | 5-Methoxy-UTP/N6-Isopentenyl-ATP | 357.00 | 0.00 | 168.50 | 75.66 |
| 03601013036 | 5-Carbamoyl-methyl-UTP | 387.50 | 26.16 | 1712.50 | 277.89 |
| 03601013036 | 75% 5-Carbamoyl-methyl-UTP + 25% UTP | 3992.50 | 9.19 | 104300.50 | 12595.69 |
| 03601013036 | 50% 5-Carbamoyl-methyl-UTP + 50% UTP | 9169.50 | 514.07 | 132913.00 | 2983.99 |
| 03601013036 | 25% 5-Carbamoyl-methyl-UTP + 75% UTP | 5889.00 | 687.31 | 201641.50 | 10463.06 |
| 00901013054 | 75% 5-Hydroxy-UTP + 25% UTP | 552.50 | 24.75 | 7232.50 | 1344.21 |
| 00901013054 | 50% 5-Hydroxy-UTP + 50% UTP | 1286.00 | 106.07 | 31038.50 | 6930.35 |
| 00901013054 | 25% 5-Hydroxy-UTP + 75% UTP | 3345.50 | 320.32 | 66768.50 | 7694.03 |
| 00901014007/ 00901013007 | 25% N4-Ac-CTP + 75% CTP/25% 5-Methoxy-UTP + 75% UTP | 6505.00 | 601.04 | 108477.00 | 1175.21 |
| 00901014007/ 00901013007 | 75% N4-Ac-CTP + 25% CTP/25% 5-Methoxy-UTP + 75% UTP | 5788.00 | 206.48 | 61520.50 | 1248.04 |
| 00901014007/ 00901013007 | 25% N4-Ac-CTP + 75% CTP/75% 5-Methoxy-UTP + 25% UTP | 5437.50 | 794.08 | 71288.50 | 1205.62 |
| 00901014007/ 00901013007 | 75% N4-Ac-CTP + 25% CTP/75% 5-Methoxy-UTP + 25% UTP | 4935.00 | 487.90 | 43981.50 | 4200.92 |
| 00901014005/ 00901013007 | 25% 5-Hydroxymethyl-CTP + 75% CTP/25% 5-Methoxy-UTP + 75% UTP | 6426.00 | 1008.33 | 113720.50 | 574.88 |
| 00901014005/ 00901013007 | 75% 5-Hydroxymethyl-CTP + 25% CTP/25% 5-Methoxy-UTP + 75% UTP | 5181.50 | 910.05 | 79721.00 | 8513.57 |
| 00901014005/ 00901013007 | 25% 5-Hydroxymethyl-CTP + 75% CTP/75% 5-Methoxy-UTP + 25% UTP | 8964.00 | 516.19 | 109908.00 | 9466.75 |
| 00901014005/ 00901013007 | 75% 5-Hydroxymethyl-CTP + 25% CTP/75% 5-Methoxy-UTP + 25% UTP | 6052.00 | 376.18 | 26563.50 | 915.70 |
| 00901014004/ 00901013007 | N4-Methyl-CTP/5-Methoxy-UTP | 6270.00 | 124.45 | 134668.50 | 8003.74 |
| 00901014004/ 00901013007 | 25% N4-Methyl-CTP + 75% CTP/25% 5-Methoxy-UTP + 75% UTP | 10099.00 | 1015.41 | 218004.50 | 5741.00 |
| 00901014004/ 00901013007 | 75% N4-Methyl-CTP + 25% CTP/25% 5-Methoxy-UTP + 75% UTP | 13926.00 | 2556.90 | 224345.50 | 12830.45 |
| 00901014004/ 00901013007 | 25% N4-Methyl-CTP + 75% CTP/75% 5-Methoxy-UTP + 25% UTP | 4609.50 | 659.73 | 141414.50 | 918.53 |
| 00901014004/ 00901013007 | 75% N4-Methyl-CTP + 25% CTP/75% 5-Methoxy-UTP + 25% UTP | 9540.00 | 1013.99 | 226181.50 | 2830.55 |
| 00901014003/ 00901013007 | 25% 5-Trifluoromethyl-CTP + 75% CTP/25% 5-Methoxy-UTP + 75% UTP | 10280.00 | 147.08 | 120197.50 | 5175.31 |
| 00901014003/ 00901013007 | 75% 5-Trifluoromethyl-CTP + 25% CTP/25% 5-Methoxy-UTP + 75% UTP | 11881.00 | 527.50 | 124028.00 | 7937.98 |
| 00901014003/ 00901013007 | 25% 5-Trifluoromethyl-CTP + 75% CTP/75% 5-Methoxy-UTP + 25% UTP | 8479.50 | 912.87 | 88625.50 | 6510.33 |
| 00901014003/ 00901013007 | 75% 5-Trifluoromethyl-CTP + 25% CTP/75% 5-Methoxy-UTP + 25% UTP | 7671.00 | 941.87 | 93162.00 | 4992.17 |
| 03601014008/ 00901013007 | 25% 5-Bromo-CTP + 75% CTP/25% 5-Methoxy-UTP + 75% UTP | 4125.50 | 101.12 | 35287.50 | 6706.91 |
| 03601014008/ 00901013007 | 75% 5-Bromo-CTP + 25% CTP/25% 5-Methoxy-UTP + 75% UTP | 3850.50 | 194.45 | 23939.50 | 1941.01 |

TABLE 28-continued

In vitro Translation Data.

| Compund # | Chemical Alterations | mCherry Expression (pg/mL) | mCherry Std Dev | nanoLuc Expression (RLUs) | nanoLuc Std Dev |
|---|---|---|---|---|---|
| 03601014008/ 00901013007 | 25% 5-Bromo-CTP + 75% CTP/75% 5-Methoxy-UTP + 25% UTP | 1311.50 | 152.03 | 20229.00 | 1234.61 |
| 03601014008/ 00901013007 | 75% 5-Bromo-CTP + 25% CTP/75% 5-Methoxy-UTP + 25% UTP | 1614.00 | 196.58 | 9198.50 | 195.87 |
| 00901014035/ 00901013007 | 5-Iodo-CTP/5-Methoxy-UTP | 463.00 | 57.98 | 3053.00 | 281.43 |
| 00901014035/ 00901013007 | 25% 5-Iodo-CTP + 75% CTP/25% 5-Methoxy-UTP + 75% UTP | 1372.50 | 57.28 | 25003.00 | 814.59 |
| 00901014035/ 00901013007 | 75% 5-Iodo-CTP + 25% CTP/25% 5-Methoxy-UTP + 75% UTP | 1390.50 | 194.45 | 6973.00 | 159.81 |
| 00901014035/ 00901013007 | 25% 5-Iodo-CTP + 75% CTP/75% 5-Methoxy-UTP + 25% UTP | 1813.00 | 445.48 | 16492.00 | 1004.09 |
| 00901014035/ 00901013007 | 75% 5-Iodo-CTP + 25% CTP/75% 5-Methoxy-UTP + 25% UTP | 525.50 | 84.15 | 9455.50 | 1443.20 |
| 03601014039/ 00901013007 | 25% 5-Ethyl-CTP + 75% CTP/25% 5-Methoxy-UTP + 75% UTP | 3145.50 | 58.69 | 52020.00 | 3887.67 |
| 03601014039/ 00901013007 | 75% 5-Ethyl-CTP + 25% CTP/25% 5-Methoxy-UTP + 75% UTP | 2057.50 | 188.80 | 20969.00 | 623.67 |
| 03601014039/ 00901013007 | 25% 5-Ethyl-CTP + 75% CTP/75% 5-Methoxy-UTP + 25% UTP | 1619.00 | 103.24 | 30453.50 | 57.28 |
| 03601014039/ 00901013007 | 75% 5-Ethyl-CTP + 25% CTP/75% 5-Methoxy-UTP + 25% UTP | 885.50 | 89.80 | 9986.50 | 289.21 |
| 03601014030/ 00901013007 | 25% 5-Methoxy-CTP + 75% CTP/25% 5-Methoxy-UTP + 75% UTP | 4211.00 | 22.63 | 45195.00 | 10565.59 |
| 03601014030/ 00901013007 | 75% 5-Methoxy-CTP + 25% CTP/25% 5-Methoxy-UTP + 75% UTP | 1925.50 | 910.05 | 15223.00 | 2003.94 |
| 03601014030/ 00901013007 | 25% 5-Methoxy-CTP + 75% CTP/75% 5-Methoxy-UTP + 25% UTP | 4893.50 | 1058.54 | 23719.00 | 2326.38 |
| 03601014030/ 00901013007 | 75% 5-Methoxy-CTP + 25% CTP/75% 5-Methoxy-UTP + 25% UTP | 1251.00 | 363.45 | 12230.00 | 226.27 |
| 03601014012/ 00901013007 | 25% 5-Ethynyl-CTP + 75% CTP/25% 5-Methoxy-UTP + 75% UTP | 4148.00 | 879.64 | 57475.00 | 14485.79 |
| 03601014012/ 00901013007 | 75% 5-Ethynyl-CTP + 25% CTP/25% 5-Methoxy-UTP + 75% UTP | 2571.00 | 53.74 | 21206.50 | 1709.08 |
| 03601014012/ 00901013007 | 25% 5-Ethynyl-CTP + 75% CTP/75% 5-Methoxy-UTP + 25% UTP | 3849.50 | 89.80 | 29513.50 | 4302.74 |
| 03601014012/ 00901013007 | 75% 5-Ethynyl-CTP + 25% CTP/75% 5-Methoxy-UTP + 25% UTP | 2117.50 | 342.95 | 15010.00 | 50.91 |
| 00901014014/ 00901013007 | Pseudo-iso-CTP/5-Methoxy-UTP | 994.00 | 200.82 | 43574.00 | 10889.44 |
| 00901014014/ 00901013007 | 25% Pseudo-iso-CTP + 75% CTP/25% 5-Methoxy-UTP + 75% UTP | 5758.00 | 1137.03 | 64159.50 | 13939.20 |
| 00901014014/ 00901013007 | 75% Pseudo-iso-CTP + 25% CTP/25% 5-Methoxy-UTP + 75% UTP | 5744.00 | 1473.61 | 75250.00 | 10786.21 |
| 00901014014/ 00901013007 | 25% Pseudo-iso-CTP + 75% CTP/75% 5-Methoxy-UTP + 25% UTP | 4564.00 | 1221.88 | 68965.00 | 612.35 |
| 00901014014/ 00901013007 | 75% Pseudo-iso-CTP + 25% CTP/75% 5-Methoxy-UTP + 25% UTP | 3404.00 | 354.97 | 72361.50 | 8914.50 |
| 00901014036/ 00901013007 | 5-Formyl-CTP/5-Methoxy-UTP | 1682.50 | 67.18 | 9101.00 | 1731.00 |
| 00901014036/ 00901013007 | 25% 5-Formyl-CTP + 75% CTP/25% 5-Methoxy-UTP + 75% UTP | 3506.50 | 593.26 | 82689.00 | 7773.93 |
| 00901014036/ 00901013007 | 75% 5-Formyl-CTP + 25% CTP/25% 5-Methoxy-UTP + 75% UTP | 6395.50 | 47.38 | 33731.50 | 737.51 |
| 00901014036/ 00901013007 | 25% 5-Formyl-CTP + 75% CTP/75% 5-Methoxy-UTP + 25% UTP | 3669.00 | 637.81 | 44983.50 | 3263.30 |
| 00901014036/ 00901013007 | 75% 5-Formyl-CTP + 25% CTP/75% 5-Methoxy-UTP + 25% UTP | 2148.50 | 96.87 | 23180.50 | 2706.10 |
| 03601014009/ 00901013007 | 5-Aminoallyl-CTP/5-Methoxy-UTP | 837.00 | 118.79 | 5671.50 | 1010.46 |
| 03601014009/ 00901013007 | 25% 5-Aminoallyl-CTP + 75% CTP/ 25% 5-Methoxy-UTP + 75% UTP | 6035.00 | 1721.10 | 37859.00 | 2343.35 |
| 03601014009/ 00901013007 | 75% 5-Aminoallyl-CTP + 25% CTP/ 25% 5-Methoxy-UTP + 75% UTP | 3008.50 | 669.63 | 15405.50 | 3845.95 |
| 03601014009/ 00901013007 | 25% 5-Aminoallyl-CTP + 75% CTP/ 75% 5-Methoxy-UTP + 25% UTP | 3920.00 | 400.22 | 27443.50 | 415.07 |
| 03601014009/ 00901013007 | 75% 5-Aminoallyl-CTP + 25% CTP/ 75% 5-Methoxy-UTP + 25% UTP | 1501.50 | 60.10 | 10076.00 | 1750.80 |
| 00901014041/ 00901013007 | 25% 5-Fluoro-CTP + 75% CTP/25% 5-Methoxy-UTP + 75% UTP | 4648.50 | 846.41 | 417808.00 | 193564.82 |
| 00901014041/ 00901013007 | 75% 5-Fluoro-CTP + 25% CTP/25% 5-Methoxy-UTP + 75% UTP | 4002.00 | 461.03 | 308582.00 | 29708.38 |
| 00901014041/ 00901013007 | 25% 5-Fluoro-CTP + 75% CTP/75% 5-Methoxy-UTP + 25% UTP | 3922.00 | 1349.16 | 267008.50 | 81295.36 |

TABLE 28-continued

In vitro Translation Data.

| Compund # | Chemical Alterations | mCherry Expression (pg/mL) | mCherry Std Dev | nanoLuc Expression (RLUs) | nanoLuc Std Dev |
|---|---|---|---|---|---|
| 00901014041/ 00901013007 | 75% 5-Fluoro-CTP + 25% CTP/75% 5-Methoxy-UTP + 25% UTP | 3708.00 | 1219.05 | 190718.00 | 28246.09 |
| 03601014021/ 00901013007 | 25% 5-Phenyl-CTP + 75% CTP/25% 5-Methoxy-UTP + 75% UTP | 698.00 | 48.08 | 32906.50 | 16101.53 |
| 03601014021/ 00901013007 | 75% 5-Phenyl-CTP + 25% CTP/25% 5-Methoxy-UTP + 75% UTP | 264.00 | 35.36 | 253.00 | 103.24 |
| 03601014021/ 00901013007 | 25% 5-Phenyl-CTP + 75% CTP/75% 5-Methoxy-UTP + 25% UTP | 814.00 | 56.57 | 27021.00 | 9814.64 |
| 03601014021/ 00901013007 | 75% 5-Phenyl-CTP + 25% CTP/75% 5-Methoxy-UTP + 25% UTP | 318.00 | 76.37 | 166.50 | 9.19 |
| 03601014013/ 00901013007 | 25% N4-Bz-CTP + 75% CTP/25% 5-Methoxy-UTP + 75% UTP | 6042.00 | 1090.36 | 285219.00 | 86337.74 |
| 03601014013/ 00901013007 | 75% N4-Bz-CTP + 25% CTP/25% 5-Methoxy-UTP + 75% UTP | 7217.50 | 480.13 | 147815.50 | 23530.39 |
| 03601014013/ 00901013007 | 25% N4-Bz-CTP + 75% CTP/75% 5-Methoxy-UTP + 25% UTP | 5635.00 | 210.72 | 141056.00 | 19653.33 |
| 03601014013/ 00901013007 | 75% N4-Bz-CTP + 25% CTP/75% 5-Methoxy-UTP + 25% UTP | 3451.50 | 178.90 | 113487.50 | 24649.04 |
| 03601014041/ 00901013007 | 5-Carboxy-CTP/5-Methoxy-UTP | 1990.50 | 408.00 | 17398.50 | 12186.99 |
| 03601014041/ 00901013007 | 25% 5-Carboxy-CTP + 75% CTP/25% 5-Methoxy-UTP + 75% UTP | 6752.00 | 1552.81 | 416950.50 | 35645.96 |
| 03601014041/ 00901013007 | 75% 5-Carboxy-CTP + 25% CTP/25% 5-Methoxy-UTP + 75% UTP | 1945.00 | 697.21 | 83756.00 | 33170.38 |
| 03601014041/ 00901013007 | 25% 5-Carboxy-CTP + 75% CTP/75% 5-Methoxy-UTP + 25% UTP | 5107.50 | 1935.35 | 282742.50 | 32543.18 |
| 03601014041/ 00901013007 | 75% 5-Carboxy-CTP + 25% CTP/75% 5-Methoxy-UTP + 25% UTP | 3646.50 | 1383.81 | 193.00 | 70.71 |
| 00901013007/ 00901012007 | 25% 5-Methoxy-UTP + 75% UTP/25% O6-Me-GTP + 75% GTP | 3348.50 | 275.06 | 99921.00 | 4922.88 |
| 00901013007/ 00901012007 | 75% 5-Methoxy-UTP + 25% UTP/25% O6-Me-GTP + 75% GTP | 758.00 | 124.45 | 159261.50 | 6166.68 |
| 00901013007/ 00901012035 | 25% 5-Methoxy-UTP + 75% UTP/25% 7-Deaza-GTP + 75% GTP | | | 238760.00 | 20470.74 |
| 00901013007/ 00901012010 | 25% 5-Methoxy-UTP + 75% UTP/25% 2-Amino-6-Cl-purine-TP + 75% GTP | 7114.50 | 1137.73 | 74409.50 | 9843.63 |
| 00901013007/ 00901012010 | 25% 5-Methoxy-UTP + 75% UTP/75% 2-Amino-6-Cl-purine-TP + 25% GTP | 767.00 | 59.40 | 118015.50 | 7197.64 |
| 00901013007/ 00901012010 | 75% 5-Methoxy-UTP + 25% UTP/75% 2-Amino-6-Cl-purine-TP + 25% GTP | | | 68928.00 | 17768.18 |
| 00901013007/ 00901011004 | 25% 5-Methoxy-UTP + 75% UTP/25% N6-Me-2-aminopurine-TP + 75% ATP | 21140.00 | 3135.31 | 172191.50 | 6347.70 |
| 00901013007/ 00901011004 | 25% 5-Methoxy-UTP + 75% UTP/75% N6-Me-2-amino purine-TP + 25% ATP | 7155.00 | 562.86 | 85361.00 | 4201.63 |
| 00901013007/ 00901011004 | 75% 5-Methoxy-UTP + 25% UTP/25% N6-Me-2-amino purine-TP + 75% ATP | | | 135911.00 | 7761.20 |
| 00901013007/ 00901011004 | 75% 5-Methoxy-UTP + 25% UTP/75% N6-Me-2-amino purine-TP + 25% ATP | | | 161490.00 | 9041.07 |
| 00901013007/ 00901012004 | 5-Methoxy-UTP/2-amino purine-TP | 318.00 | 2.83 | 288.50 | 0.71 |
| 00901013007/ 00901012004 | 25% 5-Methoxy-UTP + 75% UTP/25% 2-aminopurine-TP + 75% ATP | 3201.50 | 509.82 | 31898.50 | 3615.44 |
| 00901013007/ 00901012004 | 25% 5-Methoxy-UTP + 75% UTP/75% 2-amino purine-TP + 25% ATP | 4383.50 | 70.00 | 53125.00 | 6772.67 |
| 00901013007/ 00901012004 | 75% 5-Methoxy-UTP + 25% UTP/25% 2-amino purine-TP + 75% ATP | 1945.50 | 51.62 | 33986.00 | 15980.61 |
| 00901013007/ 00901012004 | 75% 5-Methoxy-UTP + 25% UTP/75% 2-amino purine-TP + 25% ATP | 2156.00 | 25.46 | 36032.00 | 19221.99 |
| 00901013007/ 00901011005 | 5-Methoxy-UTP/8-Azido-ATP | 332.00 | 14.14 | 170.50 | 84.15 |
| 00901013007/ 00901011005 | 25% 5-Methoxy-UTP + 75% UTP/25% 8-Azido-ATP + 75% ATP | 2125.50 | 282.14 | 88743.00 | 6638.32 |
| 00901013007/ 00901011005 | 25% 5-Methoxy-UTP + 75% UTP/75% 8-Azido-ATP + 25% ATP | 1184.00 | 69.30 | 57991.50 | 17361.59 |
| 00901013007/ 00901011005 | 75% 5-Methoxy-UTP + 25% UTP/25% 8-Azido-ATP + 75% ATP | 2396.00 | 651.95 | 49592.00 | 6083.95 |
| 00901013007/ 00901011005 | 75% 5-Methoxy-UTP + 25% UTP/75% 8-Azido-ATP + 25% ATP | 1148.00 | 275.77 | 94738.50 | 29371.09 |
| 00901013007/ 00901012012 | 5-Methoxy-UTP/N7-Me-GTP | 292.00 | 36.77 | 198.00 | 41.01 |
| 00901013007/ 00901012012 | 25% 5-Methoxy-UTP + 75% UTP/25% N7-Me-GTP + 75% GTP | 2610.00 | 84.85 | 91309.50 | 18029.10 |
| 00901013007/ 00901012012 | 25% 5-Methoxy-UTP + 75% UTP/75% N7-Me-GTP + 25% GTP | 984.00 | 154.15 | 17814.00 | 3616.14 |

TABLE 28-continued

In vitro Translation Data.

| Compund # | Chemical Alterations | mCherry Expression (pg/mL) | mCherry Std Dev | nanoLuc Expression (RLUs) | nanoLuc Std Dev |
|---|---|---|---|---|---|
| 00901013007/ 00901012012 | 75% 5-Methoxy-UTP + 25% UTP/25% N7-Me-GTP + 75% GTP | 1166.50 | 48.79 | 22419.00 | 2610.64 |
| 00901013007/ 00901012012 | 75% 5-Methoxy-UTP + 25% UTP/75% N7-Me-GTP + 25% GTP | 1000.50 | 62.93 | 9455.50 | 4025.56 |
| 00901013042 | 5-Isopentenyl-aminomethyl-UTP | 313.50 | 10.61 | 196.00 | 12.73 |
| 00901013042 | 75% 5-Isopentenyl-aminomethyl-UTP + 25% UTP | 2296.00 | 470.93 | 109067.00 | 10542.96 |
| 00901013042 | 50% 5-Isopentenyl-aminomethyl-UTP + 50% UTP | 3804.00 | 104.65 | 82844.50 | 10885.91 |
| 00901013042 | 25% 5-Isopentenyl-aminomethyl-UTP + 75% UTP | 1457.50 | 149.20 | 59094.50 | 9946.87 |
| 00901014002/ 00901013042 | 5-Me-CTP/5-Isopentenyl-aminomethyl-UTP | 319.50 | 27.58 | 180.00 | 52.33 |

The day before transfection, 20.000 HeLa cells (ATCC no. CCL-2; Manassas, Va.) were harvested by treatment with Trypsin-EDTA solution (LifeTechnologies, Grand Island, N.Y.) and seeded in a total volume of 100 ul EMEM medium (supplemented with 10% FCS and 1× Glutamax) per well in a 96-well cell culture plate (Corning, Manassas, Va.). The cells were grown at 37° C. in 5% $CO_2$ atmosphere overnight. Next day, 83 ng of Luciferase modRNA or 250 ng of human GCSF modRNA, harboring chemical alterations on the bases or the ribose units, were diluted in 10 ul final volume of OPTI-MEM (LifeTechnologies, Grand Island, N.Y.). Lipofectamine 2000 (LifeTechnologies, Grand Island, N.Y.) was used as transfection reagent and 0.2 µl were diluted in 10 ul final volume of OPTI-MEM. After 5 min incubation at room temperature, both solutions were combined and incubated additional 15 min at room temperature. Then the 20 µl were added to the 100 ul cell culture medium containing the HeLa cells. The plates were then incubated as described before. For transfection with mCherry or nanoLuc, a mixture of mRNA expressing mCherry or nanoLuc is mixed with 0.5 uL of Lipofectamine2000 (Life Technologies; cat#11668019) and OptiMem (Life Tehnologies; cat#31985062). A final volume of 20 uL of this mixture is added to 100 uL of cells. The final amount of human EPO, G-CSF, Firefly Luciferase, mCherry and nanoLuc mRNA used per well is 250 ng except for nanoLuc mRNA which we used at 25 ng per well, respectively.

After 18 h to 22 h incubation, cells expressing luciferase were lysed with 100 µl Passive Lysis Buffer (Promega, Madison, Wis.) according to manufacturer instructions. Aliquots of the lysates were transferred to white opaque polystyrene 96-well plates (Corning, Manassas, Va.) and combined with 100 ul complete luciferase assay solution (Promega, Madison, Wis.). The lysate volumes were adjusted or diluted until no more than 2 mio relative light units per well were detected for the strongest signal producing samples. The background signal of the plates without reagent was about 200 relative light units per well. The plate reader was a BioTek Synergy H1 (BioTek, Winooski, Vt.).

For the cells transfected with nanoLuc mRNA, the media is removed and washed once with sterile 100 uL of PBS pH7.4 (Life Technologies; cat #10010049). The cells are lysed with 100 uL of 1× Glo Lysis buffer (Promega; cat # E2661). The lysate is diluted 100 fold in Nano-Glo Luciferase substrate (Promega; cat#N1110) and read in a luminometer. For cells transfected with FireFly luciferase, the luminescence activity is measured according to manufacturer's protocol (Promega, cat# E1501).

For the cells transfected with mCherry, mCherry fluorescence reading is measured directly of the cells at excitation of 585 nm and emission of 615 nm wavelength.

After 18 h to 22 h incubation, cell culture supernatants of cells expressing human GCSF or human EPO were collected and centrifuged at 10.000 rcf for 2 min. The cleared supernatants were transferred and analyzed with a human GCSF-specific or EPO ELISA kit (both from R&D Systems, Minneapolis, Minn.; Cat. #s SCS50, DEP00, respectively) according to the manufacturer instructions. All samples were diluted until the determined values were within the linear range of the human GCSF or EPO ELISA standard curve.

TABLE 29

HeLa Cell Transfection Data.

| Compound # | Chemical Alterations | Luc Expression (RLUs) | Luc Std Dev | Epo Expression (pg/ml) | Epo Std Dev | GCSF Expression (pg/ml) | GSCF Std Dev |
|---|---|---|---|---|---|---|---|
| 00902015001 | PseudoU-alpha-thio-TP | 2015 | 131.5 | 302800 | 2544 | 320000 | 1687 |
| 00902015002 | 1-Methyl-pseudo-U-alpha-thio-TP | 4900 | 325.3 | 348600 | 7151 | 372100 | 4637 |
| 03601015003 | 1-Ethyl-pseudo-UTP | 130.50 | 34.65 | 52780 | 1491 | 209300 | 3033 |
| 03601015004 | 1-Propyl-pseudo-UTP | | | 0.00 | 0.00 | 10000 | 74.07 |
| 00901015006 | 2-Thio-pseudo-UTP | 1999 | 384.7 | 380600 | 4607 | 239300 | 10490 |
| 00901014003 | 5-Trifluoromethyl-CTP | 32250 | 808.9 | 668100 | 2155 | 1039000 | 9891 |
| 00901013004 | 5-Methyl-2-thio-UTP | | | 8333 | 57.47 | 16420 | 0.00 |
| 00901014004 | N4-methyl CTP | | | 90280 | 885.1 | | |
| 00901014005 | 5-Hydroxymethyl-CTP | 22160 | 754.5 | 440300 | 1931 | 1151000 | 39860 |

TABLE 29-continued

HeLa Cell Transfection Data.

| Compound # | Chemical Alterations | Luc Expression (RLUs) | Luc Std Dev | Epo Expression (pg/ml) | Epo Std Dev | GCSF Expression (pg/ml) | GSCF Std Dev |
|---|---|---|---|---|---|---|---|
| 00901013004 | UTP-5-oxyacetic acid Me ester | | | 8333 | 402.3 | 5714 | 221.5 |
| 00901013005 | 5-Methoxy carbonyl methyl-UTP | | | 8333 | 172.4 | | |
| 00901013007 | 5-methoxy-UTP | 31580 | 1241 | 1116000 | 18170 | 1399000 | 2004 |
| 00901014007 | N4-Ac-CTP | 141300 | 4463 | 2907000 | 41750 | 2094000 | 6826 |
| 03601014008 | 5-Bromo-CTP | 125700 | 28470 | 3263000 | 42000 | 1003000 | 2605 |
| 03601014009 | 5-Aminoallyl-CTP | 319.00 | 8.49 | 3488 | 23.41 | 24290 | 571.43 |
| 03601012004 | 2-Aminopurine-riboside TP | 713.50 | 3.54 | 56980 | 292.2 | 39290 | 205.7 |
| 00901013008 | 2-Thio-UTP | 423.00 | 16.97 | 182600 | 1808 | 214300 | 4915 |
| 00901013009 | 5-Bromo-UTP | 2731 | 36.06 | 210500 | 3218 | 118600 | 3926 |
| 00902014001 | Alpha-thio-CTP | 1845 | 1.41 | 195400 | 3733 | 285000.00 | 6925 |
| 00901013010 | 5-Aminoallyl-UTP | 1946 | 63.64 | 67440 | 1984 | 40710 | 211.0 |
| 00902013001 | Alpha-thio-UTP | 937.0 | 57.98 | 190700 | 8612 | 73570 | 923.5 |
| 00901014003/ 00901015002 | 5-Trifluoromethyl-CTP/1-Methyl-pseudo-UTP | 1668 | 254.6 | 492.2 | 2750 | 427100 | 5002 |
| 00901014005/ 00901015002 | 5-Hydroxymethyl-CTP/1-Methyl-pseudo-UTP | 22530 | 349.3 | 164800 | 17320 | 1666000 | 23170 |
| 03601014008/ 00901015002 | 5-Bromo-CTP/1-Methyl-pseudo-UTP | 28210 | 420.70 | 1248000 | 21190 | 474300 | 4124 |
| 00901014003/ 00901015001 | 5-Trifluoromethyl-CTP/Pseudo-UTP | 1340 | 231.2 | 429900 | 879 | 431400 | 4013 |
| 03601014008/ 00901015001 | 5-Bromo-CTP/Pseudo-UTP | 19340 | 224.9 | 859700 | 2097 | 355700 | 14150 |
| 00901014003/ 00901015002 | 75% 5-Trifluoromethyl-CTP + 25% CTP/1-Methyl-pseudo-UTP | 1086 | 166.2 | 577900 | 4792 | 754300 | |
| 00901014003/ 00901015002 | 50% 5-Trifluoromethyl-CTP + 50% CTP/1-Methyl-pseudo-UTP | 3932 | 89.09 | 1043000 | 20620 | 1267000 | 8739 |
| 00901014003/ 00901015002 | 25% 5-Trifluoromethyl-CTP + 75% CTP/1-Methyl-pseudo-UTP | 15190 | 159.1 | 1991000 | 38850 | 2271000 | |
| 03601014008/ 00901015002 | 50% 5-Bromo-CTP + 50% CTP/1-Methyl-pseudo-UTP | 45140 | 2274 | 2114000 | 59190 | 1921000 | 14350 |
| 03601014008/ 00901015002 | 25% 5-Bromo-CTP + 75% CTP/1-Methyl-pseudo-UTP | 76360 | 175.4 | 2782000 | 2903 | 2717000 | 4819 |
| 00901014005/ 00901015002 | 50% 5-Hydroxymethyl-CTP + 50% CTP/1-Methyl-pseudo-UTP | 54390 | 628.6 | 2307000 | 23850 | 2624000 | 25380 |
| 00901014007/ 00901015002 | N4Ac-CTP/1-Methyl-pseudo-UTP | 112200 | 633.6 | 2005000 | 4713 | 2074000 | 52510 |
| 00901014007/ 00901013007 | N4Ac-CTP/5-Methoxy-UTP | 7990 | 2724 | 420800 | 24440 | 611400 | 2199 |
| 00901014002/ 00901015002 | 75% 5-Methyl-CTP + 25% CTP/1-Methyl-pseudo-UTP | 1232354 | 17485 | 2139785 | 18117 | 2775714 | 87625 |
| 00901014002/ 00901015002 | 50% 5-Methyl-CTP + 50% CTP/1-Methyl-pseudo-UTP | 1432767 | 61397 | 1379570 | 8750 | 1448571 | 42152 |
| 00901014002/ 00901015002 | 25% 5-Methyl-CTP + 75% CTP/1-Methyl-pseudo-UTP | 787045 | 42863 | 1843011 | 1992 | 1748571 | 14205 |
| 00901014002/ 00901015002 | 12.5% 5-Methyl-CTP + 87.5% CTP/1-Methyl-pseudo-UTP | 989431 | 5967 | 883871 | 11071 | 1493571 | 30837 |
| 00901014002/ 00901015001 | 75% 5-Methyl-CTP + 25% CTP/Pseudo-UTP | 572903 | 39627 | 1165591 | 1911 | 655714 | 1865 |
| 00901014002/ 00901015001 | 50% 5-Methyl-CTP + 50% CTP/Pseudo-UTP | 77502 | 4088 | 1663441 | 8895 | 177857 | 922 |
| 00901014002/ 00901015001 | 25% 5-Methyl-CTP + 75% CTP/Pseudo-UTP | 27416 | 950 | 2523656 | 57933 | 324286 | 6036 |
| 00901014035/ 00901015002 | 5-Iodo-CTP/1-Methyl-pseudo-UTP | 112268 | 6635 | −43689 | −1440 | 1815714 | 41343 |
| 00901014035/ 00901015002 | 75% 5-Iodo-CTP + 25% CTP/1-Methyl-pseudo-UTP | 341089 | 43209 | −29126 | −6045 | −20714 | 0 |
| 00901014035/ 00901015002 | 50% 5-Iodo-CTP + 50% CTP/1-Methyl-pseudo-UTP | 0 | 0 | −31068 | −7170 | −20714 | −384 |
| 00901014035/ 00901015002 | 25% 5-Iodo-CTP + 75% CTP/1-Methyl-pseudo-UTP | 0 | 0 | −29126 | −6595 | −12857 | −1621 |
| 03601014008/ 00901015002 | 75% 5-Bromo-CTP + 25% CTP/1-Methyl-pseudo-UTP | 534332 | 8808 | 2294872 | 79216 | 1510500 | 14432 |
| 03601014008/ 00901015001 | 75% 5-Bromo-CTP + 25% CTP/Pseudo-UTP | 729830 | 12556 | 1650000 | 31618 | 882500 | 0 |
| 03601014008/ 00901015001 | 50% 5-Bromo-CTP + 50% CTP/Pseudo-UTP | 1023504 | 154028 | 1442308 | 28916 | 1486000 | 13942 |
| 03601014008/ 00901015001 | 25% 5-Bromo-CTP + 75% CTP/Pseudo-UTP | 153026 | 1945 | 1358974 | 9198 | 1801500 | 3872 |

TABLE 29-continued

HeLa Cell Transfection Data.

| Compound # | Chemical Alterations | Luc Expression (RLUs) | Luc Std Dev | Epo Expression (pg/ml) | Epo Std Dev | GCSF Expression (pg/ml) | GSCF Std Dev |
|---|---|---|---|---|---|---|---|
| 00901014003/ 00901013007 | 5-Trifluoro-methyl-CTP/5-Methoxy-UTP | 16168 | 1645 | 67949 | 388 | 351500 | 4276 |
| 12201014040/ 00901013007 | 5-Hydroxy-methyl-CTP/5-Methoxy-UTP | 152072 | 3198 | 921795 | 9865 | 1367500 | 17249 |
| 03601014008/ 00901013007 | 5-Bromo-CTP/5-Methoxy-UTP | 61114 | 3684 | 951282 | 6606 | 338500 | 6804 |
| 00901014002/ 00901013008 | 5-Methyl-CTP/75% 2-Thio-UTP + 25% UTP | 17763 | 344 | 477000 | 1529 | 382500 | 2045 |
| 00901014002/ 00901013008 | 5-Methyl-CTP/25% 2-Thio-UTP + 75% UTP | 219065 | 6966 | 1396000 | 17190 | 1317500 | 27008 |
| 00901014002/ 00901013008 | 75% 5-Methyl-CTP + 25% CTP/2-Thio-UTP | 1404 | 1 | 49000 | 0 | 63125 | 799 |
| 00901014002/ 00901013008 | 50% 5-Methyl-CTP + 50% CTP/2-Thio-UTP | 1001 | 10 | 48000 | 246 | 67500 | 0 |
| 00901014002/ 00901013008 | 25% 5-Methyl-CTP + 75% CTP/2-Thio-UTP | 2203 | 234 | 62000 | 890 | 83750 | 1241 |
| 00901014002/ 00901013008 | 75% 5-Methyl-CTP + 25% CTP/75% 2-Thio-UTP + 25% UTP | 112628 | 238 | 1820000 | 21281 | 1730000 | 23829 |
| 00901014002/ 00901013008 | 50% 5-Methyl-CTP + 50% CTP/75% 2-Thio-UTP + 25% UTP | 111285 | 2110 | 2283000 | 16911 | 2017500 | 3598 |
| 00901014002/ 00901013008 | 25% 5-Methyl-CTP + 75% CTP/75% 2-Thio-UTP + 25% UTP | 135131 | 6386 | 1923000 | 40875 | 2150625 | 30663 |
| 00901014002/ 00901013008 | 75% 5-Methyl-CTP + 25% CTP/50% 2-Thio-UTP + 50% UTP | 103382 | 8355 | 1208000 | 15156 | 1520000 | 7103 |
| 00901014002/ 00901013008 | 50% 5-Methyl-CTP + 50% CTP/50% 2-Thio-UTP + 50% UTP | 62049 | 3425 | 1823000 | 9254 | 1693750 | 28566 |
| 00901014002/ 00901013008 | 25% 5-Methyl-CTP + 75% CTP/50% 2-Thio-UTP + 50% UTP | 83620 | 8239 | 1941000 | 7437 | 1821250 | 11943 |
| 00901014002/ 00901013008 | 75% 5-Methyl-CTP + 25% CTP/25% 2-Thio-UTP + 75% UTP | 88292 | 1126 | 1959000 | 0 | 2106875 | 48662 |
| 00901014002/ 00901013008 | 50% 5-Methyl-CTP + 50% CTP/25% 2-Thio-UTP + 75% UTP | 102207 | 5544 | 1665000 | 23891 | 2145000 | 7214 |
| 00901014002/ 00901013008 | 25% 5-Methyl-CTP + 75% CTP/25% 2-Thio-UTP + 75% UTP | 121186 | 2148 | 2053000 | 46659 | 2340000 | 19299 |
| 00901013008 | CTP/75% 2-Thio-UTP + 25% UTP | 34637 | 1022 | 1561290 | 0 | 1230714 | 22497 |
| 00901013008 | CTP/50% 2-Thio-UTP + 50% UTP | 41617 | 586 | 824731 | 4567 | 1251429 | 32462 |
| 00901013008 | CTP/25% 2-Thio-UTP + 75% UTP | 25957 | 192 | 604301 | 3463 | 1103571 | 14434 |
| 03601014008/ 00901015002 | 75% 5-Bromo-CTP + 25% CTP/1-Methyl-pseudo-UTP | 534332 | 8808 | 2294872 | 79216 | 1510500 | 14432 |
| 03601014008/ 00901015001 | 75% 5-Bromo-CTP + 25% CTP/Pseudo-UTP | 729830 | 12556 | 1650000 | 31618 | 882500 | 0 |
| 03601014008/ 00901015001 | 50% 5-Bromo-CTP + 50% CTP/Pseudo-UTP | 1023504 | 154028 | 1442308 | 28916 | 1486000 | 13942 |
| 03601014008/ 00901015001 | 25% 5-Bromo-CTP + 75% CTP/Pseudo-UTP | 153026 | 1945 | 1358974 | 9198 | 1801500 | 3872 |
| 00901014003/ 00901013007 | 5-Trifluoro-methyl-CTP/5-Methoxy-UTP | 16168 | 1645 | 67949 | 388 | 351500 | 4276 |
| 12201014040/ 00901013007 | 5-Hydroxy-methyl-CTP/5-Methoxy-UTP | 152072 | 3198 | 921795 | 9865 | 1367500 | 17249 |
| 03601014008/ 00901013007 | 5-Bromo-CTP/5-Methoxy-UTP | 61114 | 3684 | 951282 | 6606 | 338500 | 6804 |
| 00901014002/ 00901013008 | 5-Methyl-CTP/75% 2-Thio-UTP + 25% UTP | 17763 | 344 | 477000 | 1529 | 382500 | 2045 |
| 00901014002/ 00901013008 | 5-Methyl-CTP/25% 2-Thio-UTP + 75% UTP | 219065 | 6966 | 1396000 | 17190 | 1317500 | 27008 |
| 00901014002/ 00901013008 | 75% 5-Methyl-CTP + 25% CTP/2-Thio-UTP | 1404 | 1 | 49000 | 0 | 63125 | 799 |
| 00901014002/ 00901013008 | 50% 5-Methyl-CTP + 50% CTP/2-Thio-UTP | 1001 | 10 | 48000 | 246 | 67500 | 0 |
| 00901014002/ 00901013008 | 25% 5-Methyl-CTP + 75% CTP/2-Thio-UTP | 2203 | 234 | 62000 | 890 | 83750 | 1241 |

TABLE 29-continued

HeLa Cell Transfection Data.

| Compound # | Chemical Alterations | Luc Expression (RLUs) | Luc Std Dev | Epo Expression (pg/ml) | Epo Std Dev | GCSF Expression (pg/ml) | GSCF Std Dev |
|---|---|---|---|---|---|---|---|
| 00901014002/ 00901013008 | 75% 5-Methyl-CTP + 25% CTP/75% 2-Thio-UTP + 25% UTP | 112628 | 238 | 1820000 | 21281 | 1730000 | 23829 |
| 00901014002/ 00901013008 | 50% 5-Methyl-CTP + 50% CTP/75% 2-Thio-UTP + 25% UTP | 111285 | 2110 | 2283000 | 16911 | 2017500 | 3598 |
| 00901014002/ 00901013008 | 25% 5-Methyl-CTP + 75% CTP/75% 2-Thio-UTP + 25% UTP | 135131 | 6386 | 1923000 | 40875 | 2150625 | 30663 |
| 00901014002/ 00901013008 | 75% 5-Methyl-CTP + 25% CTP/50% 2-Thio-UTP + 50% UTP | 103382 | 8355 | 1208000 | 15156 | 1520000 | 7103 |
| 00901014002/ 00901013008 | 50% 5-Methyl-CTP + 50% CTP/50% 2-Thio-UTP + 50% UTP | 62049 | 3425 | 1823000 | 9254 | 1693750 | 28566 |
| 00901014002/ 00901013008 | 25% 5-Methyl-CTP + 75% CTP/50% 2-Thio-UTP + 50% UTP | 83620 | 8239 | 1941000 | 7437 | 1821250 | 11943 |
| 00901014002/ 00901013008 | 75% 5-Methyl-CTP + 25% CTP/25% 2-Thio-UTP + 75% UTP | 88292 | 1126 | 1959000 | 0 | 2106875 | 48662 |
| 00901014002/ 00901013008 | 50% 5-Methyl-CTP + 50% CTP/25% 2-Thio-UTP + 75% UTP | 102207 | 5544 | 1665000 | 23891 | 2145000 | 7214 |
| 00901014002/ 00901013008 | 25% 5-Methyl-CTP + 75% CTP/25% 2-Thio-UTP + 75% UTP | 121186 | 2148 | 2053000 | 46659 | 2340000 | 19299 |
| 00901013008 | CTP/75% 2-Thio-UTP + 25% UTP | 34637 | 1022 | 1561290 | 0 | 1230714 | 22497 |
| 00901013008 | CTP/50% 2-Thio-UTP + 50% UTP | 41617 | 586 | 824731 | 4567 | 1251429 | 32462 |
| 00901013008 | CTP/25% 2-Thio-UTP + 75% UTP | 25957 | 192 | 604301 | 3463 | 1103571 | 14434 |

TABLE 30

HeLa cell transfection data.

| Compound # | Chemical Alterations | mCherry Expression (pg/mL) | mCherry Std Dev | nanoLuc Expression (RLUs) | nanoLuc Std Dev |
|---|---|---|---|---|---|
| 00901014005/ 00901015001 | 5-Hydroxymethyl-CTP/Pseudo-UTP | 754.5 | 174.66 | 18716350 | 1611567 |
| 00901014035/ 00901015001 | 5-Iodo-CTP/Pseudo-UTP | 31.5 | 3.54 | 80495000 | 2012426 |
| 00901014007/ 00901015001 | N4-Ac-CTP/Pseudo-UTP | 1830.5 | 120.92 | 23107500 | 9565741 |
| 00901014035/ 00901013007 | 5-Iodo-CTP/5-Methoxy-UTP | 168.5 | 4.95 | 17474000 | 94752.31 |
| 00901014002/ 03601015004 | 5-Methyl-CTP/1-Propyl-pseudo-UTP | 33 | 0 | 175500 | 16263.46 |
| 00901014002/ 00901013007 | 5-Methyl-CTP/75% 5-Methoxy-UTP + 25% UTP | 1104.5 | 78.49 | 3898000 | 229527 |
| 00901014002/ 00901013007 | 5-Methyl-CTP/50% 5-Methoxy-UTP + 50% UTP | 1896 | 86.27 | 8598100 | 1025446 |
| 00901014002/ 00901013007 | 5-Methyl-CTP/25% 5-Methoxy-UTP + 75% UTP | 2348 | 77.78 | 14881300 | 216375 |
| 00901014002/ 00901013007 | 75% 5-Methyl-CTP + 25% CTP/ 5-Methoxy-UTP | 0 | 0 | 2555850 | 896541 |
| 00901014002/ 00901013007 | 50% 5-Methyl-CTP + 50% CTP/ 5-Methoxy-UTP | 1123.5 | 7.78 | 2229400 | 43134 |
| 00901014002/ 00901013007 | 25% 5-Methyl-CTP + 75% CTP/ 5-Methoxy-UTP | 1395.5 | 36.06 | 1185700 | 201101 |
| 00901014002/ 00901013007 | 75% 5-Methyl-CTP + 25% CTP/75% 5-Methoxy-UTP + 25% UTP | 1658.5 | 61.52 | 9555300 | 3433569 |
| 00901014002/ 00901013007 | 50% 5-Methyl-CTP + 50% CTP/75% 5-Methoxy-UTP + 25% UTP | 0 | 0 | 4134200 | 1555918 |
| 00901014002/ 00901013007 | 25% 5-Methyl-CTP + 75% CTP/75% 5-Methoxy-UTP + 25% UTP | 1742.5 | 75.66 | 9920150 | 5418913 |

TABLE 30-continued

HeLa cell transfection data.

| Compound # | Chemical Alterations | mCherry Expression (pg/mL) | mCherry Std Dev | nanoLuc Expression (RLUs) | nanoLuc Std Dev |
|---|---|---|---|---|---|
| 00901014002/ 00901013007 | 75% 5-Methyl-CTP + 25% CTP/50% 5-Methoxy-UTP + 50% UTP | 2055.5 | 71.42 | 9705650 | 4237903 |
| 00901014002/ 00901013007 | 50% 5-Methyl-CTP + 50% CTP/50% 5-Methoxy-UTP + 50% UTP | 2276.5 | 187.38 | 11126100 | 6158759 |
| 00901014002/ 00901013007 | 25% 5-Methyl-CTP + 75% CTP/50% 5-Methoxy-UTP + 50% UTP | 0 | 0 | 21769050 | 3721715 |
| 00901014002/ 00901013007 | 75% 5-Methyl-CTP + 25% CTP/25% 5-Methoxy-UTP + 75% UTP | 2437 | 239.00 | 25706850 | 4158141 |
| 00901014002/ 00901013007 | 50% 5-Methyl-CTP + 50% CTP/25% 5-Methoxy-UTP + 75% UTP | 2586.5 | 173.24 | 30849100 | 4655450 |
| 00901014002/ 00901013007 | 25% 5-Methyl-CTP + 75% CTP/25% 5-Methoxy-UTP + 75% UTP | 3248 | 151.32 | 22711150 | 3111906 |
| 00901013007 | CTP/75% 5-Methoxy-UTP + 25% UTP | 0 | 0 | 10641950 | 2563049.9 |
| 00901013007 | CTP/50% 5-Methoxy-UTP + 50% UTP | 2669 | 107.48 | 15843050 | 2751423 |
| 00901013007 | CTP/25% 5-Methoxy-UTP + 75% UTP | 3398.5 | 232.64 | 10717000 | 1483934 |
| 00901013007 | CTP/5-Methoxy-UTP(No cap) | 27 | 5.66 | 3550 | 353.55 |
| 00901013007 | CTP/5-Methoxy-UTP (cap 0) | 1170.5 | 62.93 | 322200 | 1697.06 |
| 00901014002/ 00901013007 | 5-Methyl-CTP/5-Methoxy-UTP(No cap) | 28.5 | 4.95 | 22700 | 1272.79 |
| 00901014002/ 00901013007 | 5-Methyl-CTP/5-Methoxy-UTP(cap 0) | 754 | 106.07 | 385000 | 12869.34 |
|  | CTP/UTP(No cap) | 26.5 | 2.12 | 6900 | 989.95 |
|  | CTP/UTP(cap 0) | 200 | 14.14 | 1521900 | 512511 |
| 00901014002/ 00901015001 | 5-Methyl-CTP/Pseudo-UTP(No cap) | 41.5 | 3.54 | 23300 | 3535.53 |
| 00901014002/ 00901015001 | 5-Methyl-CTP/Pseudo-UTP (cap 0) | 1364.5 | 14.85 | 1690850 | 90014.69 |
| 00901014002/ 00901015002 | 5-Methyl-CTP/1-Methyl-pseudo-UTP (No cap) | 35.5 | 4.95 | 9000 | 565.69 |
| 00901014002/ 00901015002 | 5-Methyl-CTP/1-Methyl-pseudo-UTP (cap 0) | 1385 | 114.55 | 355800 | 53598.69 |
| 00901015002 | CTP/1-Methyl-pseudo-UTP (No cap) | 48.5 | 4.95 | 31800 | 3535.53 |
| 00901015002 | CTP/1-Methyl-pseudo-UTP (cap 0) | 1894 | 268.70 | 6829100 | 209445.0 |
|  | CTP/UTP/ATP/GTP (cap ARCA) | 104.5 | 4.95 | 405650 | 27365.03 |
| 00901014002/ 00901015001 | 5-Methyl-CTP/Pseudo-UTP (cap ARCA) | 908 | 178.19 | 5030600 | 919238.8 |
| 00901014002/ 00901015002 | 5-Methyl-CTP/1-Methyl-pseudo-UTP (cap ARCA) | 817 | 36.77 | 2396050 | 30334.88 |
| 00901015002 | CTP/1-Methyl-pseudo-UTP (cap ARCA) | 876.5 | 231.22 | 4904800 | 617445.6 |
| 00902011001 | Alpha-Thio-ATP | 28.5 | 3.54 | 900 | 141.42 |
| 00901014002/ 00901015001/ 00902011001 | 5-Methyl-CTP/Pseudo-UTP/ Alpha-Thio-ATP | 26 | 0 | 4500 | 424.26 |
| 00901014002/ 00901015002/ 00902011001 | 5-Methyl-CTP/1-Methyl-pseudo-UTP/ Alpha-Thio-ATP | 27.5 | 2.12 | 700 | 141.42 |
| 00901015002/ 00902011001 | 1-Methyl-pseudo-UTP/Alpha-Thio-ATP | 27.5 | 2.12 | 1100 | 282.84 |
| 00901013007/ 00902011001 | 5-Methoxy-UTP/Alpha-Thio-ATP | 24 | 2.83 | 900 | 282.84 |
| 00901014002/ 00901013007/ 00902011001 | 5-Methyl-CTP/5-Methoxy-UTP/ Alpha-Thio-ATP | 25.5 | 3.54 | 850 | 212.13 |
| 00902012001 | Alpha-Thio-GTP | 54.5 | 0.71 | 4500 | 565.69 |
| 00901014002/ 00901015001/ 00902012001 | 5-Methyl-CTP/Pseudo-UTP/ Alpha-Thio-GTP | 306 | 43.84 | 13650 | 2899.14 |
| 00901014002/ 00901015002/ 00902012001 | 5-Methyl-CTP/1-Methyl-pseudo-UTP/ Alpha-Thio-GTP | 135 | 7.07 | 8350 | 1343.50 |
| 00901015002/ 00902012001 | 1-Methyl-pseudo-UTP/Alpha-Thio-GTP | 100 | 19.80 | 19450 | 2757.72 |
| 00901013007/ 00902012001 | 5-Methoxy-UTP/Alpha-Thio-GTP | 101.5 | 21.92 | 1800 | 424.26 |
| 00901014002/ 00901013007/ 00902012001 | 5-Methyl-CTP/5-Methoxy-UTP/ Alpha-Thio-GTP | 183.5 | 26.16 | 2200 | 282.84 |
| 00901011006 | N6-Me-ATP | 26 | 2.83 | 950 | 70.71 |
| 00901014002/ 00901015001/ 00901011006 | 5-Methyl-CTP/Pseudo-UTP/ N6-Me-ATP | 26.5 | 4.95 | 750 | 353.55 |
| 00901014002/ 00901015002/ 00901011006 | 5-Methyl-CTP/1-Methyl-pseudo-UTP/ N6-Me-ATP | 29 | 1.41 | 800 | 0 |

TABLE 30-continued

HeLa cell transfection data.

| Compound # | Chemical Alterations | mCherry Expression (pg/mL) | mCherry Std Dev | nanoLuc Expression (RLUs) | nanoLuc Std Dev |
|---|---|---|---|---|---|
| 00901015002/ 00901011006 | 1-Methyl-pseudo-UTP/N6-Me-ATP | 28 | 2.83 | 1850 | 636.40 |
| 00901013007/ 00901011006 | 5-Methoxy-UTP/N6-Me-ATP | 23 | 2.83 | 1200 | 424.26 |
| 00901014002/ 00901013007/ 00901011006 | 5-Methyl-CTP/5-Methoxy-UTP/ N6-Me-ATP | 22.5 | 2.12 | 700 | 0 |
| 03601014039 | 5-Ethyl-CTP | 1556.5 | 256.68 | 3690400 | 717713.3 |
| 03601014039/ 00901015002/ | 5-Ethyl-CTP/1-Methyl-pseudo-UTP | 324.5 | 23.33 | 993550 | 270751.1 |
| 03601014039/ 00901013007 | 5-Ethyl-CTP/5-Methoxy-UTP | 324 | 22.63 | 254400 | 98429.26 |
| 03601014030 | 5-Methoxy-CTP | 645.5 | 350.02 | 7304450 | 1760342.3 |
| 03601014030/ 00901015002 | 5-Methoxy-CTP/1-Methyl-pseudo-UTP | 316 | 178.19 | 4611050 | 1119137.9 |
| 03601014030/ 00901013007 | 5-Methoxy-CTP/5-Methoxy-UTP | 225.5 | 118.09 | 1271200 | 384666.09 |
| 03601014011 | 5-Ethynyl-CTP | 368.5 | 301.93 | 6232300 | 1554645 |
| 03601014011/ 00901015002 | 5-Ethynyl-CTP/1-Methyl-pseudo-UTP | 58.5 | 7.78 | 1244950 | 424759.04 |
| 03601014011/ 00901013007 | 5-Ethynyl-CTP/5-Methoxy-UTP | 87 | 21.21 | 569150 | 154927.1 |
| 03601014011/ 00901015001 | 5-Ethynyl-CTP/Pseudo-UTP | 97.5 | 36.06 | 158450 | 29486.35 |
| 03601014011/ 00901013007/ 00901015002 | 5-Methyl-CTP/75% 5-Methoxy-UTP + 25% 1-Methyl-pseudo-UTP | 307100 | 8343.86 | 1884.5 | 31.82 |
| 03601014011/ 00901013007/ 00901015002 | 5-Methyl-CTP/50% 5-Methoxy-UTP + 50% 1-Methyl-pseudo-UTP | 200800 | 7778.17 | 1667 | 74.95 |
| 03601014011/ 00901013007/ 00901015002 | 5-Methyl-CTP/25% 5-Methoxy-UTP + 75% 1-Methyl-pseudo-UTP | 334450 | 7566.04 | 2217.5 | 96.87 |
| 03601014011/ 00901013007/ 00901015002 | 75% 5-Methyl-CTP + 25% CTP/75% 5-Methoxy-UTP + 25% 1-Methyl-pseudo-UTP | 221100 | 19374.73 | 1879.5 | 334.46 |
| 03601014011/ 00901013007/ 00901015002 | 50 5-Methyl-CTP + 50% CTP/75% 5-Methoxy-UTP + 25% 1-Methyl-pseudo-UTP | 316700 | 35496.76 | 1913.5 | 17.68 |
| 03601014011/ 00901013007/ 00901015002 | 25% 5-Methyl-CTP + 75% CTP/75% 5-Methoxy-UTP + 25% 1-Methyl-pseudo-UTP | 820150 | 106419.6 | 2527 | 93.34 |
| 03601014011/ 00901013007/ 00901015002 | 75% 5-Methyl-CTP + 25% CTP/50% 5-Methoxy-UTP + 50% 1-Methyl-pseudo-UTP | 699550 | 124804.4 | 2721.5 | 108.19 |
| 03601014011/ 00901013007/ 00901015002 | 50 5-Methyl-CTP + 50% CTP/50% 5-Methoxy-UTP + 50% 1-Methyl-pseudo-UTP | 776650 | 60881.89 | 2803.5 | 273.65 |
| 03601014011/ 00901013007/ 00901015002 | 25% 5-Methyl-CTP + 75% CTP/50% 5-Methoxy-UTP + 50% 1-Methyl-pseudo-UTP | 753050 | 18738.33 | 2535 | 4.24 |
| 03601014011/ 00901013007/ 00901015002 | 75% 5-Methyl-CTP + 25% CTP/25% 5-Methoxy-UTP + 75% 1-Methyl-pseudo-UTP | 709150 | 777.82 | 3184.5 | 150.61 |
| 03601014011/ 00901013007/ 00901015002 | 50 5-Methyl-CTP + 50% CTP/25% 5-Methoxy-UTP + 75% 1-Methyl-pseudo-UTP | 499100 | 59538.39 | 1992 | 70.71 |
| 03601014011/ 00901013007/ 00901015002 | 25% 5-Methyl-CTP + 75% CTP/25% 5-Methoxy-UTP + 75% 1-Methyl-pseudo-UTP | 925050 | 79832.36 | 2302.5 | 157.68 |
| 00901013007/ 00901015002 | CTP/75% 5-Methoxy-UTP + 25% 1-Methyl-pseudo-UTP | 429250 | 59891.94 | 1423 | 45.25 |
| 00901013007/ 00901015002 | CTP/50% 5-Methoxy-UTP + 50% 1-Methyl-pseudo-UTP | 867750 | 25243.71 | 2241.5 | 125.16 |
| 00901013007/ 00901015002 | CTP/25% 5-Methoxy-UTP + 75% 1-Methyl-pseudo-UTP | 1097100 | 23617.37 | 2767.5 | 147.79 |
| 00901014004/ 00901015002 | N4-Methyl-CTP/1-Methyl-pseudo-UTP | 113 | 19.80 | 190550 | 23263.81 |
| 00902014001/ 00901015002 | Alpha-thio-CTP/1-Methyl-pseudo-UTP | 31.5 | 7.78 | 350 | 70.71 |
| 00901015002/ 00902012001 | 1-Methyl-pseudo-UTP/2% Alpha-Thio-GTP + 98% GTP | 1232 | 306.88 | 1952950 | 90580.38 |
| 00901015002/ 00902012001 | 1-Methyl-pseudo-UTP/5% Alpha-Thio-GTP + 95% GTP | 1703.5 | 75.66 | 1518750 | 97651.45 |

TABLE 30-continued

HeLa cell transfection data.

| Compound # | Chemical Alterations | mCherry Expression (pg/mL) | mCherry Std Dev | nanoLuc Expression (RLUs) | nanoLuc Std Dev |
|---|---|---|---|---|---|
| 00901015002/ 00902012001 | 1-Methyl-pseudo-UTP/10% Alpha-Thio-GTP + 90% GTP | 850 | 53.74 | 1869050 | 45749.81 |
| 00901015002/ 00902012001 | 1-Methyl-pseudo-UTP/25% Alpha-Thio-GTP + 75% GTP | 340.5 | 13.44 | 688150 | 29486.35 |
| 00901015002/ 00902012001 | 1-Methyl-pseudo-UTP/50% Alpha-Thio-GTP + 50% GTP | 444 | 36.77 | 537150 | 9828.78 |
| 00901015002/ 00902011001 | 1-Methyl-pseudo-UTP/2% Alpha-Thio-ATP + 98% ATP | 1063.5 | 214.25 | 2748350 | 107692.4 |
| 00901015002/ 00902011001 | 1-Methyl-pseudo-UTP/5% Alpha-Thio-ATP + 95% ATP | 1702 | 56.57 | 2098700 | 254275.6 |
| 00901015002/ 00902011001 | 1-Methyl-pseudo-UTP/10% Alpha-Thio-ATP + 90% ATP | 1771 | 340.83 | 3053950 | 52396.61 |
| 00901015002/ 00902011001 | 1-Methyl-pseudo-UTP/25% Alpha-Thio-ATP + 75% ATP | 167 | 14.14 | 986750 | 50133.87 |
| 00901015002/ 00902011001 | 1-Methyl-pseudo-UTP/50% Alpha-Thio-ATP + 50% ATP | 413.5 | 37.48 | 713250 | 65690.22 |
| 00901015002 | 75% 1-Methyl-pseudo-UTP + 25% UTP | 232.5 | 50.20 | 4297950 | 92843.12 |
| 00901015002 | 50% 1-Methyl-pseudo-UTP + 50% UTP | 390.5 | 20.51 | 1792550 | 701520.6 |
| 00901015001 | 75% Pseudo-UTP + 25% UTP | 225.5 | 3.54 | 1831700 | 20364.67 |
| 00901015001 | 50% Pseudo-UTP + 50% UTP | 149 | 12.73 | 467750 | 22839.54 |
| 00901015001 | 25% Pseudo-UTP + 75% UTP | 314.5 | 13.44 | 392900 | 18243.35 |
| 03601013014 | 75% 5-Methyl-UTP + 25% UTP | 144 | 11.31 | 137900 | 2262.74 |
| 03601013014 | 50% 5-Methyl-UTP + 50% UTP | 143.5 | 13.44 | 388800 | 8202.44 |
| 03601013014 | 25% 5-Methyl-UTP + 75% UTP | 89.5 | 21.92 | 197750 | 41365.74 |
| 00901013003 | 75% 5-Methyl-2-thio-UTP + 25% UTP | 113 | 22.63 | 625450 | 132299.6 |
| 00901013003 | 50% 5-Methyl-2-thio-UTP + 50% UTP | 109.5 | 2.12 | 821650 | 205980.2 |
| 00901013003 | 25% 5-Methyl-2-thio-UTP + 75% UTP | 84.5 | 4.95 | 821350 | 105429.6 |
| 00901013011 | 75% 4-Thio-UTP + 25% UTP | 364.5 | 269.41 | 876950 | 45466.96 |
| 00901013011 | 50% 4-Thio-UTP + 50% UTP | 1387.5 | 6.36 | 1298700 | 257386.8 |
| 00901013011 | 25% 4-Thio-UTP + 75% UTP | 247 | 183.85 | 1123450 | 179958.6 |
| 00901013009 | 75% 5-Methoxy-carbonylmethyl-UTP + 25% UTP | 27 | 7.07 | 6850 | 494.97 |
| 00901013009 | 50% 5-Methoxy-carbonylmethyl-UTP + 50% UTP | 141 | 55.15 | 108250 | 31749.09 |
| 00901013009 | 25% 5-Methoxy-carbonylmethyl-UTP + 75% UTP | 448.5 | 249.61 | 531050 | 131875.4 |
| 03601014011 | 75% 5-Methyl-CTP + 25% CTP | 148.5 | 91.22 | 671750 | 81529.41 |
| 03601014011 | 50% 5-Methyl-CTP + 50% CTP | 122.5 | 68.59 | 711350 | 34436.10 |
| 03601014011 | 25% 5-Methyl-CTP + 75% CTP | 118.5 | 6.36 | 464200 | 58831.28 |
| 03601014011/ 00901015002 | 75% 5-Methyl-CTP + 25% CTP/ 1-Methyl-pseudo-UTP | 1366.5 | 51.62 | 416850 | 12374.36 |
| 03601014011/ 00901015002 | 50% 5-Methyl-CTP + 50% CTP/ 1-Methyl-pseudo-UTP | 1238.5 | 92.63 | 481450 | 26940.76 |
| 03601014011/ 00901015002 | 25% 5-Methyl-CTP + 75% CTP/ 1-Methyl-pseudo-UTP | 1026.5 | 185.97 | 469850 | 35850.31 |
| 00901011045 | 8-Me-ATP | 25 | 5.66 | 500 | 141.42 |
| 00901015002/ 00901011045 | 1-Methyl-pseudo-UTP/8-Me-ATP | 24.5 | 4.95 | 450 | 70.71 |
| 00901015002/ 00902011001/ 00902012001 | 1-Methyl-pseudo-UTP/2% Alpha-Thio-ATP + 98% ATP/2% Alpha-Thio-GTP + 98% GTP | 2024 | 545.89 | 3095100 | 271104.7 |
| 00901015002/ 00902011001/ 00902012001 | 1-Methyl-pseudo-UTP/5% Alpha-Thio-ATP + 95% ATP/5% Alpha-Thio-GTP + 95% GTP | 1550 | 39.60 | 2704350 | 394070.6 |
| 00901015002/ 00902011001/ 00902012001 | 1-Methyl-pseudo-UTP/2% Alpha-Thio-ATP + 98% ATP/5% Alpha-Thio-GTP + 95% GTP | 2325.5 | 301.93 | 2386850 | 694873.8 |
| 00901015002/ 00902011001/ 00902012001 | 1-Methyl-pseudo-UTP/5% Alpha-Thio-ATP + 95% ATP/2% Alpha-Thio-GTP + 98% GTP | 1955 | 330.93 | 2172700 | 828729.1 |
| 00901015002/ 00902011001/ 00902012001 | 1-Methyl-pseudo-UTP/10% Alpha-Thio-ATP + 90% ATP/2% Alpha-Thio-GTP + 98% GTP | 2376 | 96.17 | 2417950 | 531249.3 |
| 00901015002/ 00902011001/ 00902012001 | 1-Methyl-pseudo-UTP/2% Alpha-Thio-ATP + 98% ATP/10% Alpha-Thio-GTP + 90% GTP | 1891.5 | 441.94 | 1809950 | 156058.4 |
| 00901015002/ 00902011001/ 00902012001 | 1-Methyl-pseudo-UTP/10% Alpha-Thio-ATP + 90% ATP/5% Alpha-Thio-GTP + 95% GTP | 1446 | 602.45 | 1846750 | 762190.3 |
| 00901015002/ 00902011001/ 00902012001 | 1-Methyl-pseudo-UTP/5% Alpha-Thio-ATP + 95% ATP/10% Alpha-Thio-GTP + 90% GTP | 1214.5 | 119.50 | 1516800 | 430203.7 |

TABLE 30-continued

HeLa cell transfection data.

| Compound # | Chemical Alterations | mCherry Expression (pg/mL) | mCherry Std Dev | nanoLuc Expression (RLUs) | nanoLuc Std Dev |
|---|---|---|---|---|---|
| 00901015002/ 00902011001/ 00902012001 | 1-Methyl-pseudo-UTP/10% Alpha-Thio-ATP + 90% ATP/10% Alpha-Thio-GTP + 90% GTP | 1537 | 513.36 | 1388350 | 257599.0 |
| 00901014041 | 5-Fluoro-CTP | 361.5 | 30.41 | 1898750 | 90438.95 |
| 00901014041/ 00901015002 | 5-Fluoro-CTP/1-Methyl-pseudo-UTP | 1426 | 415.78 | 2392400 | 25880.10 |
| 00901014041/ 00901013007 | 5-Fluoro-CTP/5-Methoxy-UTP | 732.5 | 260.92 | 206100 | 1131.37 |
| 03601014021 | 5-Phenyl-CTP | 24.5 | 4.95 | 650 | 70.71 |
| 03601014021/ 00901015002 | 5-Phenyl-CTP/1-Methyl-pseudo-UTP | 30 | 5.66 | 3050 | 3181.98 |
| 03601014021/ 00901013007 | 5-Phenyl-CTP/5-Methoxy-UTP | 31 | 4.24 | 650 | 212.13 |
| 03601014013 | N4-Bz-CTP | 233 | 130.11 | 13800 | 3959.80 |
| 03601014013/ 00901015002 | N4-Bz-CTP/1-Methyl-pseudo-UTP | 126 | 69.30 | 23100 | 707.12 |
| 03601014013/ 00901013007 | N4-Bz-CTP/5-Methoxy-UTP | 34.5 | 0.71 | 800 | 0 |
| 00901011044 | N6-Isopentenyl-ATP | 29.5 | 7.78 | 700 | 0 |
| 00901015002/ 00901011044 | 1-Methyl-pseudo-UTP/ N6-Isopentenyl-ATP | 35 | 7.07 | 700 | 0 |
| 00901013007/ 00901011044 | 5-Methoxy-UTP/N6-Isopentenyl-ATP | 27 | 5.66 | 850 | 70.71 |
| 03601013036 | 5-Carbamoyl-methyl-UTP | 43.5 | 2.12 | 3350 | 212.13 |
| 03601013036 | 75% 5-Carbamoyl-methyl-UTP + 25% UTP | 388 | 63.64 | 652800 | 52184.48 |
| 03601013036 | 50% 5-Carbamoyl-methyl-UTP + 50% UTP | 302 | 21.21 | 1230150 | 102459.7 |
| 03601013036 | 25% 5-Carbamoyl-methyl-UTP + 75% UTP | 139.5 | 17.68 | 873800 | 6505.38 |
| 00901013054 | 75% 5-Hydroxy-UTP + 25% UTP | 28 | 0 | 1100 | 141.42 |
| 00901013054 | 50% 5-Hydroxy-UTP + 50% UTP | 34 | 9.90 | 8750 | 353.55 |
| 00901013054 | 25% 5-Hydroxy-UTP + 75% UTP | 35 | 5.66 | 36700 | 3252.69 |
| 00901014007/ 00901013007 | 25% N4-Ac-CTP + 75% CTP/25% 5-Methoxy-UTP + 75% UTP | 35 | 0 | 333400 | 30264.17 |
| 00901014007/ 00901013007 | 75% N4-Ac-CTP + 25% CTP/25% 5-Methoxy-UTP + 75% UTP | 122.5 | 34.65 | 532750 | 353.55 |
| 00901014007/ 00901013007 | 25% N4-Ac-CTP + 75% CTP/75% 5-Methoxy-UTP + 25% UTP | 966 | 156.98 | 585450 | 116601.9 |
| 00901014007/ 00901013007 | 75% N4-Ac-CTP + 25% CTP/75% 5-Methoxy-UTP + 25% UTP | 1017.5 | 41.72 | 345900 | 42002.14 |
| 00901014005/ 00901013007 | 25% 5-Hydroxymethyl-CTP + 75% CTP/25% 5-Methoxy-UTP + 75% UTP | 31.5 | 6.36 | 189000 | 62791.08 |
| 00901014005/ 00901013007 | 75% 5-Hydroxymethyl-CTP + 25% CTP/25% 5-Methoxy-UTP + 75% UTP | 42 | 2.83 | 339900 | 103096.1 |
| 00901014005/ 00901013007 | 25% 5-Hydroxymethyl-CTP + 75% CTP/75% 5-Methoxy-UTP + 25% UTP | 749 | 223.45 | 757400 | 182716.3 |
| 00901014005/ 00901013007 | 75% 5-Hydroxymethyl-CTP + 25% CTP/75% 5-Methoxy-UTP + 25% UTP | 1206.5 | 228.40 | 279600 | 81175.85 |
| 00901014004/ 00901013007 | N4-Methyl-CTP/5-Methoxy-UTP | 94.5 | 16.26 | 111600 | 14000.71 |
| 00901014004/ 00901013007 | 25% N4-Methyl-CTP + 75% CTP/25% 5-Methoxy-UTP + 75% UTP | 44.5 | 14.85 | 534400 | 97156.47 |
| 00901014004/ 00901013007 | 75% N4-Methyl-CTP + 25% CTP/25% 5-Methoxy-UTP + 75% UTP | 28 | 7.07 | 157600 | 19374.72 |
| 00901014004/ 00901013007 | 25% N4-Methyl-CTP + 75% CTP/75% 5-Methoxy-UTP + 25% UTP | 581 | 42.43 | 458950 | 188443.9 |
| 00901014004/ 00901013007 | 75% N4-Methyl-CTP + 25% CTP/75% 5-Methoxy-UTP + 25% UTP | 364 | 97.58 | 363300 | 141987.0 |
| 00901014003/ 00901013007 | 25% 5-Trifluoromethyl-CTP + 75% CTP/25% 5-Methoxy-UTP + 75% UTP | 196 | 80.61 | 411450 | 138663.6 |
| 00901014003/ 00901013007 | 75% 5-Trifluoromethyl-CTP + 25% CTP/25% 5-Methoxy-UTP + 75% UTP | 1613.5 | 161.93 | 241550 | 58760.57 |
| 00901014003/ 00901013007 | 25% 5-Trifluoromethyl-CTP + 75% CTP/75% 5-Methoxy-UTP + 25% UTP | 1654.5 | 62.93 | 373300 | 124167.9 |
| 00901014003/ 00901013007 | 75% 5-Trifluoromethyl-CTP + 25% CTP/75% 5-Methoxy-UTP + 25% UTP | 902 | 100.41 | 145100 | 19233.30 |
| 03601014008/ 00901013007 | 25% 5-Bromo-CTP + 75% CTP/25% 5-Methoxy-UTP + 75% UTP | 116.5 | 12.02 | 642600 | 15414.92 |
| 03601014008/ 00901013007 | 75% 5-Bromo-CTP + 25% CTP/25% 5-Methoxy-UTP + 75% UTP | 419.5 | 85.56 | 686200 | 14142.13 |
| 03601014008/ 00901013007 | 25% 5-Bromo-CTP + 75% CTP/75% 5-Methoxy-UTP + 25% UTP | 301 | 35.36 | 526150 | 59609.10 |

TABLE 30-continued

HeLa cell transfection data.

| Compound # | Chemical Alterations | mCherry Expression (pg/mL) | mCherry Std Dev | nanoLuc Expression (RLUs) | nanoLuc Std Dev |
|---|---|---|---|---|---|
| 03601014008/ 00901013007 | 75% 5-Bromo-CTP + 25% CTP/75% 5-Methoxy-UTP + 25% UTP | 346.5 | 3.54 | 325400 | 35921.02 |
| 00901014035/ 00901013007 | 5-Iodo-CTP/5-Methoxy-UTP | 116 | 1.41 | 52250 | 5586.14 |
| 00901014035/ 00901013007 | 25% 5-Iodo-CTP + 75% CTP/25% 5-Methoxy-UTP + 75% UTP | 455 | 48.08 | 975850 | 9121.68 |
| 00901014035/ 00901013007 | 75% 5-Iodo-CTP + 25% CTP/25% 5-Methoxy-UTP + 75% UTP | 549 | 48.08 | 412950 | 30052.03 |
| 00901014035/ 00901013007 | 25% 5-Iodo-CTP + 75% CTP/75% 5-Methoxy-UTP + 25% UTP | 367.5 | 40.31 | 405300 | 2545.58 |
| 00901014035/ 00901013007 | 75% 5-Iodo-CTP + 25% CTP/75% 5-Methoxy-UTP + 25% UTP | 73.5 | 9.19 | 281050 | 4171.93 |
| 03601014039/ 00901013007 | 25% 5-Ethyl-CTP + 75% CTP/25% 5-Methoxy-UTP + 75% UTP | 82.5 | 12.02 | 401450 | 43062.80 |
| 03601014039/ 00901013007 | 75% 5-Ethyl-CTP + 25% CTP/25% 5-Methoxy-UTP + 75% UTP | 161.5 | 14.85 | 346500 | 48083.26 |
| 03601014039/ 00901013007 | 25% 5-Ethyl-CTP + 75% CTP/75% 5-Methoxy-UTP + 25% UTP | 466.5 | 41.72 | 433800 | 13010.76 |
| 03601014039/ 00901013007 | 75% 5-Ethyl-CTP + 25% CTP/75% 5-Methoxy-UTP + 25% UTP | 195 | 29.70 | 119900 | 2404.16 |
| 03601014030/ 00901013007 | 25% 5-Methoxy-CTP + 75% CTP/25% 5-Methoxy-UTP + 75% UTP | 284 | 84.85 | 565850 | 24960.86 |
| 03601014030/ 00901013007 | 75% 5-Methoxy-CTP + 25% CTP/25% 5-Methoxy-UTP + 75% UTP | 508.5 | 164.76 | 1005400 | 37900.92 |
| 03601014030/ 00901013007 | 25% 5-Methoxy-CTP + 75% CTP/75% 5-Methoxy-UTP + 25% UTP | 1023.5 | 210.01 | 524900 | 10040.91 |
| 03601014030/ 00901013007 | 75% 5-Methoxy-CTP + 25% CTP/75% 5-Methoxy-UTP + 25% UTP | 292.5 | 17.68 | 459250 | 12091.52 |
| 03601014012/ 00901013007 | 25% 5-Ethynyl-CTP + 75% CTP/25% 5-Methoxy-UTP + 75% UTP | 1582 | 178.19 | 593200 | 15132.08 |
| 03601014012/ 00901013007 | 75% 5-Ethynyl-CTP + 25% CTP/25% 5-Methoxy-UTP + 75% UTP | 872.5 | 4.95 | 193950 | 17041.27 |
| 03601014012/ 00901013007 | 25% 5-Ethynyl-CTP + 75% CTP/75% 5-Methoxy-UTP + 25% UTP | 1612.5 | 96.87 | 348900 | 26304.37 |
| 03601014012/ 00901013007 | 75% 5-Ethynyl-CTP + 25% CTP/75% 5-Methoxy-UTP + 25% UTP | 659 | 100.41 | 115800 | 8485.281 |
| 00901014014/ 00901013007 | Pseudo-iso-CTP/5-Methoxy-UTP | 67.5 | 2.12 | 19150 | 1626.35 |
| 00901014014/ 00901013007 | 25% Pseudo-iso-CTP + 75% CTP/25% 5-Methoxy-UTP + 75% UTP | 1068 | 132.94 | 728150 | 72054.18 |
| 00901014014/ 00901013007 | 75% Pseudo-iso-CTP + 25% CTP/25% 5-Methoxy-UTP + 75% UTP | 1037 | 83.44 | 535400 | 33234.01 |
| 00901014014/ 00901013007 | 25% Pseudo-iso-CTP + 75% CTP/75% 5-Methoxy-UTP + 25% UTP | 811 | 209.30 | 396050 | 19869.70 |
| 00901014014/ 00901013007 | 75% Pseudo-iso-CTP + 25% CTP/75% 5-Methoxy-UTP + 25% UTP | 232.5 | 21.92 | 127750 | 3323.40 |
| 00901014036/ 00901013007 | 5-Formyl-CTP/5-Methoxy-UTP | 31.5 | 2.12 | 550 | 70.71 |
| 00901014036/ 00901013007 | 25% 5-Formyl-CTP + 75% CTP/25% 5-Methoxy-UTP + 75% UTP | 35 | 4.24 | 20500 | 6081.12 |
| 00901014036/ 00901013007 | 75% 5-Formyl-CTP + 25% CTP/25% 5-Methoxy-UTP + 75% UTP | 40 | 7.07 | 1250 | 70.71 |
| 00901014036/ 00901013007 | 25% 5-Formyl-CTP + 75% CTP/75% 5-Methoxy-UTP + 25% UTP | 70 | 12.73 | 6450 | 212.13 |
| 00901014036/ 00901013007 | 75% 5-Formyl-CTP + 25% CTP/75% 5-Methoxy-UTP + 25% UTP | 27.5 | 6.36 | 2600 | 707.11 |
| 03601014009/ 00901013007 | 5-Aminoallyl-CTP/5-Methoxy-UTP | 61.5 | 2.12 | 11650 | 3181.98 |
| 03601014009/ 00901013007 | 25% 5-Aminoallyl-CTP + 75% CTP/ 25% 5-Methoxy-UTP + 75% UTP | 325.5 | 325.5 | 594550 | 63568.89 |
| 03601014009/ 00901013007 | 75% 5-Aminoallyl-CTP + 25% CTP/ 25% 5-Methoxy-UTP + 75% UTP | 152.5 | 0.71 | 103900 | 13152.18 |
| 03601014009/ 00901013007 | 25% 5-Aminoallyl-CTP + 75% CTP/ 75% 5-Methoxy-UTP + 25% UTP | 1149 | 15.56 | 438850 | 43062.80 |
| 03601014009/ 00901013007 | 75% 5-Aminoallyl-CTP + 25% CTP/ 75% 5-Methoxy-UTP + 25% UTP | 168.5 | 20.51 | 97550 | 4596.19 |
| 00901014041/ 00901013007 | 25% 5-Fluoro-CTP + 75% CTP/25% 5-Methoxy-UTP + 75% UTP | 156 | 8.49 | 1231300 | 115541.2 |
| 00901014041/ 00901013007 | 75% 5-Fluoro-CTP + 25% CTP/25% 5-Methoxy-UTP + 75% UTP | 556 | 69.30 | 114622.00 | 224082.1 |
| 00901014041/ 00901013007 | 25% 5-Fluoro-CTP + 75% CTP/75% 5-Methoxy-UTP + 25% UTP | 2229 | 343.65 | 2397200 | 317773.8 |
| 00901014041/ 00901013007 | 75% 5-Fluoro-CTP + 25% CTP/75% 5-Methoxy-UTP + 25% UTP | 1735.5 | 409.41 | 2815000 | 685186.4 |

TABLE 30-continued

HeLa cell transfection data.

| Compound # | Chemical Alterations | mCherry Expression (pg/mL) | mCherry Std Dev | nanoLuc Expression (RLUs) | nanoLuc Std Dev |
|---|---|---|---|---|---|
| 03601014021/ 00901013007 | 25% 5-Phenyl-CTP + 75% CTP/25% 5-Methoxy-UTP + 75% UTP | 36.5 | 4.95 | 10450 | 1202.081 |
| 03601014021/ 00901013007 | 75% 5-Phenyl-CTP + 25% CTP/25% 5-Methoxy-UTP + 75% UTP | 33.5 | 2.12 | 800 | 141.42 |
| 03601014021/ 00901013007 | 25% 5-Phenyl-CTP + 75% CTP/75% 5-Methoxy-UTP + 25% UTP | 54 | 4.24 | 7900 | 989.95 |
| 03601014021/ 00901013007 | 75% 5-Phenyl-CTP + 25% CTP/75% 5-Methoxy-UTP + 25% UTP | 29.5 | 12.02 | 900 | 0 |
| 03601014013/ 00901013007 | 25% N4-Bz-CTP + 75% CTP/25% 5-Methoxy-UTP + 75% UTP | 903 | 100.41 | 1291000 | 338421.3 |
| 03601014013/ 00901013007 | 75% N4-Bz-CTP + 25% CTP/25% 5-Methoxy-UTP + 75% UTP | 217 | 38.18 | 216950 | 20576.80 |
| 03601014013/ 00901013007 | 25% N4-Bz-CTP + 75% CTP/75% 5-Methoxy-UTP + 25% UTP | 1804 | 548.71 | 533750 | 77286.77 |
| 03601014013/ 00901013007 | 75% N4-Bz-CTP + 25% CTP/75% 5-Methoxy-UTP + 25% UTP | 519 | 66.47 | 77800 | 707.11 |
| 03601014041/ 00901013007 | 5-Carboxy-CTP/5-Methoxy-UTP | 211.5 | 10.61 | 75350 | 1343.50 |
| 03601014041/ 00901013007 | 25% 5-Carboxy-CTP + 75% CTP/25% 5-Methoxy-UTP + 75% UTP | 158 | 39.60 | 851550 | 126501.4 |
| 03601014041/ 00901013007 | 75% 5-Carboxy-CTP + 25% CTP/25% 5-Methoxy-UTP + 75% UTP | 1285 | 197.99 | 645850 | 97368.60 |
| 03601014041/ 00901013007 | 25% 5-Carboxy-CTP + 75% CTP/75% 5-Methoxy-UTP + 25% UTP | 1673.5 | 477.30 | 1049650 | 125511.4 |
| 03601014041/ 00901013007 | 75% 5-Carboxy-CTP + 25% CTP/75% 5-Methoxy-UTP + 25% UTP | 1245 | 255.97 | 850 | 70.71 |
| 00901013007/ 00901012007 | 25% 5-Methoxy-UTP + 75% UTP/25% O6-Me-GTP + 75% GTP | 185 | 132.94 | 1002650 | 145451.8 |
| 00901013007/ 00901012007 | 75% 5-Methoxy-UTP + 25% UTP/25% O6-Me-GTP + 75% GTP | 146 | 5.66 | 663500 | 212273.4 |
| 00901013007/ 00901012035 | 25% 5-Methoxy-UTP + 75% UTP/25% 7-Deaza-GTP + 75% GTP | | | 526450 | 148280.2 |
| 00901013007/ 00901012010 | 25% 5-Methoxy-UTP + 75% UTP/25% 2-Amino-6-Cl-purine-TP + 75% GTP | 233 | 45.25 | 727900 | 19091.88 |
| 00901013007/ 00901012010 | 25% 5-Methoxy-UTP + 75% UTP/75% 2-Amino-6-Cl-purine-TP + 25% GTP | 178.5 | 30.41 | 978000 | 125582.1 |
| 00901013007/ 00901012010 | 75% 5-Methoxy-UTP + 25% UTP/75% 2-Amino-6-Cl-purine-TP + 25% GTP | | | 696200 | 112429.9 |
| 00901013007/ 00901011004 | 25% 5-Methoxy-UTP + 75% UTP/25% N6-Me-2-aminopurine-TP + 75% ATP | 127 | 18.38 | 222600 | 13152.18 |
| 00901013007/ 00901011004 | 25% 5-Methoxy-UTP + 75% UTP/75% N6-Me-2-amino purine-TP + 25% ATP | 36.5 | 0.71 | 25600 | 424.26 |
| 00901013007/ 00901011004 | 75% 5-Methoxy-UTP + 25% UTP/25% N6-Me-2-amino purine-TP + 75% ATP | | | 78800 | 4242.64 |
| 00901013007/ 00901011004 | 75% 5-Methoxy-UTP + 25% UTP/75% N6-Me-2-amino purine-TP + 25% ATP | | | 15250 | 1343.50 |
| 00901013007/ 00901012004 | 25% 5-Methoxy-UTP + 75% UTP/25% 2-aminopurine-TP + 75% ATP | 58.5 | 17.68 | 382050 | 28072.13 |
| 00901013007/ 00901012004 | 25% 5-Methoxy-UTP + 75% UTP/75% 2-amino purine-TP + 25% ATP | 109.5 | 26.16 | 324000 | 11737.97 |
| 00901013007/ 00901012004 | 75% 5-Methoxy-UTP + 25% UTP/25% 2-amino purine-TP + 75% ATP | 668.5 | 123.74 | 350900 | 29415.64 |
| 00901013007/ 00901012004 | 75% 5-Methoxy-UTP + 25% UTP/75% 2-amino purine-TP + 25% ATP | 211.5 | 58.69 | 94750 | 8414.57 |
| 00901013007/ 00901011005 | 25% 5-Methoxy-UTP + 75% UTP/25% 8-Azido-ATP + 75% ATP | 79 | 14.14 | 262100 | 21920.31 |
| 00901013007/ 00901011005 | 25% 5-Methoxy-UTP + 75% UTP/75% 8-Azido-ATP + 25% ATP | 58 | 2.83 | 358200 | 8626.70 |
| 00901013007/ 00901011005 | 75% 5-Methoxy-UTP + 25% UTP/25% 8-Azido-ATP + 75% ATP | 744.5 | 197.28 | 849850 | 13081.47 |
| 00901013007/ 00901011005 | 75% 5-Methoxy-UTP + 25% UTP/75% 8-Azido-ATP + 25% ATP | 273.5 | 7.78 | 995150 | 6576.09 |
| 00901013007/ 00901012012 | 25% 5-Methoxy-UTP + 75% UTP/25% N7-Me-GTP + 75% GTP | 50 | 7.07 | 226200 | 32668.33 |
| 00901013007/ 00901012012 | 25% 5-Methoxy-UTP + 75% UTP/75% N7-Me-GTP + 25% GTP | 48.5 | 10.61 | 259200 | 9758.07 |
| 00901013007/ 00901012012 | 75% 5-Methoxy-UTP + 25% UTP/25% N7-Me-GTP + 75% GTP | 697.5 | 180.31 | 283400 | 76367.53 |
| 00901013007/ 00901012012 | 75% 5-Methoxy-UTP + 25% UTP/75% N7-Me-GTP + 25% GTP | 340 | 65.05 | 124150 | 20152.54 |
| 00901013042 | 75% 5-Isopentenyl-aminomethyl-UTP + 25% UTP | 105 | 15.56 | 600650 | 33728.99 |
| 00901013042 | 50% 5-Isopentenyl-aminomethyl-UTP + 50% UTP | 67 | 8.49 | 291250 | 7000.36 |

TABLE 30-continued

HeLa cell transfection data.

| Compound # | Chemical Alterations | mCherry Expression (pg/mL) | mCherry Std Dev | nanoLuc Expression (RLUs) | nanoLuc Std Dev |
|---|---|---|---|---|---|
| 00901013042 | 25% 5-Isopentenyl-aminomethyl-UTP + 75% UTP | 35 | 0 | 98650 | 8273.15 |

TABLE 31

HeLa Cell Transfection Data.

| Compound IP# | Chemical Alterations | mEPO Expression (pg/mL) | mEPO Std Dev | hEPO Expression (RLUs) | hEPO Std Dev |
|---|---|---|---|---|---|
| 00901013007 | 5-Methoxy-UTP | 4015985.00 | 206711.35 | 98064.00 | 2885.00 |
| 00901014002/ 00901013007 | 5-Me-CTP/5-Methoxy-UTP | 2673065.00 | 1217.64 | 105491.00 | 1161.07 |
| 00901014002/ 00901013007 | 5-Methyl-CTP/75% 5-Methoxy-UTP + 25% UTP | 3104257.00 | 269064.03 | 130192.00 | 998.43 |
| 00901014002/ 00901013007 | 5-Methyl-CTP/50% 5-Methoxy-UTP + 50% UTP | 3363823.00 | 119199.82 | 174280.00 | 4522.65 |
| 00901014002/ 00901013007 | 5-Methyl-CTP/25% 5-Methoxy-UTP + 75% UTP | 4138876.00 | 24332.96 | 109296.00 | 37827.38 |
| 00901014002/ 00901013007 | 75% 5-Methyl-CTP + 25% CTP/5-Methoxy-UTP | 3156205.00 | 91314.36 | 91250.00 | 6774.08 |
| 00901014002/ 00901013007 | 50% 5-Methyl-CTP + 50% CTP/5-Methoxy-UTP | 3223483.00 | 18292.85 | 59120.00 | 26191.24 |
| 00901014002/ 00901013007 | 25% 5-Methyl-CTP + 75% CTP/5-Methoxy-UTP | 2823962.00 | 23362.81 | 61455.00 | 12254.16 |
| 00901014002/ 00901013007 | 75% 5-Methyl-CTP + 25% CTP/75% 5-Methoxy-UTP + 25% UTP | 3513664.00 | 137738.74 | 113442.00 | 4681.05 |
| 00901014002/ 00901013007 | 50% 5-Methyl-CTP + 50% CTP/75% 5-Methoxy-UTP + 25% UTP | 3483574.00 | 195104.90 | 95106.00 | 1151.17 |
| 00901014002/ 00901013007 | 25% 5-Methyl-CTP + 75% CTP/75% 5-Methoxy-UTP + 25% UTP | 3988525.00 | 16230.93 | 106624.00 | 4590.54 |
| 00901014002/ 00901013007 | 75% 5-Methyl-CTP + 25% CTP/50% 5-Methoxy-UTP + 50% UTP | 3953938.00 | 80649.77 | 140778.00 | 7379.37 |
| 00901014002/ 00901013007 | 50% 5-Methyl-CTP + 50% CTP/50% 5-Methoxy-UTP + 50% UTP | 4573939.00 | 35800.82 | 165648.00 | 29562.72 |
| 00901014002/ 00901013007 | 25% 5-Methyl-CTP + 75% CTP/50% 5-Methoxy-UTP + 50% UTP | 4551109.00 | 88536.84 | 111585.00 | 13060.26 |
| 00901014002/ 00901013007 | 75% 5-Methyl-CTP + 25% CTP/25% 5-Methoxy-UTP + 75% UTP | 3660725.00 | 294839.49 | 180139.00 | 7120.57 |
| 00901014002/ 00901013007 | 50% 5-Methyl-CTP + 50% CTP/25% 5-Methoxy-UTP + 75% UTP | 3930557 | 400161.62 | 168004 | 25750.00 |
| 00901014002/ 00901013007 | 25% 5-Methyl-CTP + 75% CTP/25% 5-Methoxy-UTP + 75% UTP | 4745109 | 230699.24 | 133501 | 14748.83 |
| 00901013007 | CTP/75% 5-Methoxy-UTP + 25% UTP | 3694885.00 | 291176.67 | 96485.00 | 15829.29 |
| 00901013007 | CTP/50% 5-Methoxy-UTP + 50% UTP | 4053770 | 325025.87 | 140196.00 | 1467.95 |
| 00901013007 | CTP/25% 5-Methoxy-UTP + 75% UTP | 4233164.00 | 337207.91 | 112796.00 | 2126.98 |

Example 86

PBMC Cytokine Assay

A. PBMC isolation and Culture 50 mL of human blood from three donors was received from Research Blood Components (Brighton, Mass.) in sodium heparin tubes. For each donor, the blood was pooled and diluted to 70 mL with DPBS (Life Technologies, Grand Island, N.Y., 14190-250) and split evenly between two 50 mL conical tubes. 10 mL of Ficoll Paque (GE Healthcare, Fairfield, Conn., 17-5442-03) was gently dispensed below the blood layer. The tubes were centrifuged at 2000 rpm for 30 minutes with low acceleration and braking (Thermo, Waltham, Mass., 75004506). The tubes were removed and the buffy coat PBMC layers were gently transferred to a fresh 50 mL conical and washed with DPBS. The tubes were centrifuged at 1450 rpm for 10 minutes.

The supernatant was aspirated and the PBMC pellets were resuspended and washed in 50 mL of DPBS. The tubes were centrifuged at 1450 rpm for 10 minutes. This wash step was repeated, and the PBMC pellets were resuspended in 5 mL of OptiMEM (LifeTechnologies, 31985088) and counted. The cell suspensions were adjusted to a concentration of $3.0 \times 10^6$ cells/mL live cells.

These cells were then plated on 96 well tissue culture treated round bottom plates (Corning Costar, Tewksbury Mass., 3799) per donor at 50 µL per well. Within 30 minutes, transfection mixtures were added to each well at a volume of 50 µL per well.

B. Transfection Preparation

Alternative mRNA encoding firefly Luciferase (mRNA SEQ ID NO: 4), human G-CSF (mRNA sequence shown in SEQ ID NO: 2; polyA tail of approximately 140 nucleotides not shown in sequence; 5' cap, Cap1) or human EPO (mRNA sequence shown in SEQ ID NO: 6; polyA tail of approximately 140 nucleotides not shown in sequence; 5' cap, Cap1) were diluted to 100 ng/μL in a final volume of 30 μL of sterile water.

Separately, for each mRNA sample, 2.4 μL of Lipofectamine 2000 (LifeTechnologies 11668019) was diluted with 268 μL OptiMEM. In a 96 well plate the aliquots of 30 μL of each mRNA was added to 270.4 μL of the diluted Lipofectamine 2000. The plate containing the mRNA to be transfected was incubated for 20 minutes. The transfection mixtures were then transferred to each of the human PBMC plates at 50 μL per well (6 wells per mRNA sample). The plates were then incubated at 37° C. After 2 hours incubation, 11 μl of heat-inactivated FCS (LifeTechnologies, 16140071) was added to each well (10% FCS final concentration).

The plates were further incubated at 37° C, 5% $CO_2$ for additional 18-20 hs. In order to harvest the supernatant, plates were centrifuged at 1450 rpm for 5 min in a swinging plate rotor. The supernatant of 6 wells transfected with the same mRNA was carefully harvested and pooled in a single well of a fresh 96-well plate. Supernatants were either frozen or used fresh until ELISA analysis was done.

Innate Immune Response Analysis

The ability of unaltered and alternative mRNA to trigger innate immune recognition as measured by interferon-alpha production. Use of in vitro PBMC cultures is an accepted way to determine the immunostimulatory potential of oligonucleotides (Robbins et al., Oligonucleotides 2009 19:89-102). The release of interferon was measured with an IFN-alpha multi-subtype ELISA (PBL interferonsource, Pisctaway, N.J., 11668019) following the instructions of the manufacturer. The data is shown in Table 32.

TABLE 32

PBMC Assay Data.

| Compound # | Chemical Alterations | Luc (3 Donor samples) pg/ml | hEPO (3 Donor samples) pg/ml | hGCSF (3 Donor samples) pg/ml |
|---|---|---|---|---|
| 00902015001 | PseudoU-alpha-thio-TP | 20<br>170<br>−90 | −190<br>75<br>400 | 50<br>508.33<br>640 |
| 00902015002 | 1-Methyl-pseudo-U-alpha-thio-TP | 180<br>500<br>180 | −290<br>512.5<br>475 | 425<br>916.66<br>1250 |
| 00901015006 | 2-Thio-pseudo-UTP | 530<br>1180<br>1400 | −210<br>675<br>362.5 | 358.33<br>166.66<br>490 |
| 00901016002 | 5-Trifluoromethyl-CTP | 6670<br>2190<br>6410 | 4440<br>3100<br>1412.5 | 6253.33<br>6725<br>6280 |
| 00901014005 | 5-Hydroxymethyl-CTP | 7130<br>3680<br>8990 | 4960<br>3100<br>2412.5 | 6575<br>5800<br>8180 |
| 00901013007 | 5-methoxy-UTP | 390<br>−70<br>−170 | −210<br>162.5<br>150 | 350<br>−41.66<br>40 |
| 00901014007 | N4-Ac-CTP | 7170<br>2500<br>5879 | 4050<br>2137.5<br>5850 | 5683.33<br>4883.33<br>4590 |
| 03601014008 | 5-Bromo-CTP | 5470<br>1080<br>5420 | 2300<br>487.5<br>500 | 2808.33<br>2266.67<br>1650 |
| 00901014003/<br>00901015002 | 5-Trifluoromethyl-CTP/1-Methyl-pseudo-UTP | 0<br>−184<br>25 | −13<br>−61<br>−121 | 61.11<br>13.88 |

TABLE 32-continued

PBMC Assay Data.

| Compound # | Chemical Alterations | Luc (3 Donor samples) pg/ml | hEPO (3 Donor samples) pg/ml | hGCSF (3 Donor samples) pg/ml |
|---|---|---|---|---|
| 00901014005/<br>00901015002 | 5-Hydroxymethyl-CTP/1-Methyl-pseudo-UTP | 775<br>762<br>1163 | 135<br>3<br>3 | 108.33<br>13.88 |
| 03601014008/<br>00901015002 | 5-Bromo-CTP/1-Methyl-pseudo-UTP | −178<br>−140<br>27.77 | 13<br>−33<br>−27 | −27.77<br>−36.11 |
| 00901014003/<br>00901015001 | 5-Trifluoromethyl-CTP/Pseudo-UTP | 118.75<br>237.5<br>186.1 | 97<br>12<br>30 | 102.77<br>111.11 |
| 03601014008/<br>00901015001 | 5-Bromo-CTP/Pseudo-UTP | 1296<br>706.2<br>800 | 165<br>9<br>12 | 513.8<br>280.5 |
| 00901014003/<br>00901015002 | 75% 5-Trifluoromethyl-CTP + 25% CTP/1-Methyl-pseudo-UTP | −181.25<br>−206.25<br>0 | −100<br>−58<br>−64 | −19.44<br>−213.8 |
| 00901014003/<br>00901015002 | 50% 5-Trifluoromethyl-CTP + 50% CTP/1-Methyl-pseudo-UTP | 37.5<br>−193.75<br>5.555 | −52<br>−70<br>−130 | −55.55<br>−47.22 |
| 00901014003/<br>00901015002 | 25% 5-Trifluoromethyl-CTP + 75% CTP/1-Methyl-pseudo-UTP | 1006<br>1175<br>663.8 | 216<br>39<br>−79 | 41.66<br>−19.44 |
| 03601014008/<br>00901015002 | 50% 5-Bromo-CTP + 50% CTP/1-Methyl-pseudo-UTP | 200<br>190.6<br>50 | −39<br>−130 | 27.77<br>−36.11 |
| 03601014008/<br>00901015002 | 25% 5-Bromo-CTP + 75% CTP/1-Methyl-pseudo-UTP | 318.7<br>446.8<br>130.5 | 148<br>−58<br>−73 | −166.6<br>−8.333 |
| 00901014005/<br>00901015002 | 50% 5-Hydroxymethyl-CTP + 50% CTP/1-Methyl-pseudo-UTP | 1650<br>1370<br>752.7 | 806<br>115<br>224 | 580.55<br>83.33 |
| 00901014007/<br>00901015002 | N4Ac-CTP/1-Methyl-pseudo-UTP | −96<br>−65<br>−33 | −77<br>−136<br>−136 | −19.44<br>−36.11 |
| 00901014007/<br>00901013007 | N4Ac-CTP/5-Methoxy-UTP | −171.8<br>−84<br>−75 | −87<br>−155<br>−155 | 8.333<br>30.55 |
| 03601014008/<br>00901015002 | 75% 5-Bromo-CTP 25% CTP 1-Methyl-pseudo-UTP | −19<br>−80<br>−33 | −38<br>56<br>78 | 56<br>78<br>−4 |
| 03601014008/<br>00901015001 | 75% 5-Bromo-CTP 25% CTP Pseudo-UTP | −2<br>−145<br>33 | 33<br>85<br>120 | 85<br>120<br>1 |
| 03601014008/<br>00901015001 | 50% 5-Bromo-CTP 50% CTP Pseudo-UTP | 102<br>−135<br>56 | 56<br>76<br>92 | 76<br>92<br>44 |
| 03601014008/<br>00901015001 | 25% 5-Bromo-CTP 75% CTP Pseudo-UTP | −34<br>−135<br>−18 | −18<br>149<br>213 | 149<br>213<br>420 |
| 00901014003/<br>00901013007 | 5-Trifluoromethyl-CTP 5-Methoxy-UTP | −169<br>−170<br>−72 | −72<br>41<br>39 | 41<br>39<br>27 |

TABLE 32-continued

PBMC Assay Data.

| Compound # | Chemical Alterations | Luc (3 Donor samples) pg/ml | hEPO (3 Donor samples) pg/ml | hGCSF (3 Donor samples) pg/ml |
|---|---|---|---|---|
| 00901014005/ 00901013007 | 5-Hydroxymethyl-CTP 5-Methoxy-UTP | −176 −140 −116 | −116 36 109 | 36 109 −8 |
| 03601014008/ 00901013007 | 5-Bromo-CTP 5-Methoxy-UTP | −165 −197 −111 | −111 −27 88 | 27 88 −6 |
| 03601014008/ 00901015002 | 75% 5-Bromo-CTP + 25% CTP/1-Methyl-pseudo-UTP | 0 0 0 | 0 56 78 | 56 78 0 |
| 03601014008/ 00901015001 | 75% 5-Bromo-CTP + 25% CTP/Pseudo-UTP | 0 0 33 | 33 85 120 | 85 120 1 |
| 03601014008/ 00901015001 | 50% 5-Bromo-CTP + 50% CTP/Pseudo-UTP | 102 0 56 | 56 76 92 | 76 92 44 |
| 03601014008/ 00901015001 | 25% 5-Bromo-CTP + 75% CTP/Pseudo-UTP | 0 0 0 | 0 149 213 | 149 213 420 |
| 00901014003/ 00901013007 | 5-Trifluoro-methyl-CTP/5-Methoxy-UTP | 0 0 0 | 0 41 39 | 41 39 27 |
| 12201014040/ 00901013007 | 5-Hydroxy-methyl-CTP/5-Methoxy-UTP | 0 0 0 | 0 36 109 | 36 109 0 |
| 03601014008/ 00901013007 | 5-Bromo-CTP/5-Methoxy-UTP | 0 0 0 | 0 27 88 | 27 88 0 |

Example 87

Cytokine Screen of modRNA with Novel Chemistries in BJ Fibroblast Cells

At 2 or 3 days prior to transfection, 100,000 BJ fibroblast cells (ATCC no. CRL-2522; Manassas, Va.) were harvested by treatment with trypsin-EDTA solution (LifeTechnologies, Grand Island, N.Y.) and seeded in a total volume of 500 ul EMEM medium (supplemented with 10% FCS and 10% Glutamax, both LifeTechnologies, Grand Island, N.Y.) per well in 24-well cell culture plates (Corning, Manassas, Va.). The cells were grown at 37° C. in a 5% $CO_2$ atmosphere overnight. On the next day, 500 ng modRNA, harboring chemical alterations on the bases or the ribose units, were diluted in 25 ul final volume of OPTI-MEM (LifeTechnologies, Grand Island, N.Y.). Lipofectamine 2000 (LifeTechnologies, Grand Island, N.Y.) was used as transfection reagent and 1.0 ul was diluted in 25 ul final volume of OPTI-MEM. After 5 min incubation at room temperature, both solutions were combined and incubated an additional 15 min at room temperature. The 50 ul were added to the 500 ul cell culture medium containing the BJ fibroblast cells. The plates were then incubated as described above.

After 18 h to 22 h incubation, cell culture supernatants were collected and centrifuged at 10,000 rcf for 2 min. The cleared supernatants were transferred and analyzed with a human IFN-beta ELISA (R&D Systems, Minneapolis, Minn.; Cat. #s 41410-2) and human CCL-5/RANTES ELISA (R&D Systems, Minneapolis, Minn.; Cat. #s SRN00B) according to the manufacturer instructions. All samples were diluted until the determined values were within the linear range of the ELISA standard curves using a BioTek Synergy H1 plate reader (BioTek, Winooski, Vt.).

The data is shown in Tables 33-36

TABLE 33

Cytokine screen results in BJ Fibroblast cells.

| mRNA Chemistry | Luc mRNA RANTES [pg/ml] | hEpo mRNA RANTES [pg/ml] | hGCSF mRNA RANTES [pg/ml] |
|---|---|---|---|
| N4-acetyl-cytidine TP, ATP, GTP, UTP | 2546 | 4360 | 4103 |
| 5-methoxy-uridine TP, ATP, GTP, UTP | 33.33 | −6.66 | −6.66 |
| pseudouridine TP, ATP, GTP, CTP | 4600 | 5490 | 5016 |
| 1-methyl-pseudouridine TP, ATP, GTP, CTP | 5473 | 8780 | 4816 |
| 2-thio-pseudouridine TP, ATP, GTP, CTP | 1706 | 5440 | 2106 |
| 5-hydroxymethyl-cytidine TP, ATP, GTP, UTP | 9826 | 2160 | 9063 |
| 5-bromocytidine TP, ATP, GTP, UTP | 1380 | 1343 | 1900 |
| 5-trifluromethylcytidine TP, ATP, GTP, UTP | 2303 | 7593 | 4203 |

TABLE 34

Cytokine screen results in BJ Fibroblast cells.

| Compound # | Chemical Alterations | IFN-β (Luciferase) | IFN-β (Luciferase) Std Dev |
|---|---|---|---|
| 00901014002/ 00901013008 | 5-Methyl-CTP/75% 2-Thio-UTP + 25% UTP | 174.88 | 6.03 |
| 00901014002/ 00901013008 | 5-Methyl-CTP/25% 2-Thio-UTP + 75% UTP | 366.99 | 15.43 |
| 00901014002/ 00901013008 | 75% 5-Methyl-CTP + 25% CTP/2-Thio-UTP | 11.51 | 3.12 |
| 00901014002/ 00901013008 | 50% 5-Methyl-CTP + 50% CTP/2-Thio-UTP | 5.35 | 2.11 |
| 00901014002/ 00901013008 | 25% 5-Methyl-CTP + 75% CTP/2-Thio-UTP | 32.36 | 0.63 |
| 00901014002/ 00901013008 | 75% 5-Methyl-CTP + 25% CTP/75% 2-Thio-UTP + 25% UTP | 778.00 | 8.67 |
| 00901014002/ 00901013008 | 50% 5-Methyl-CTP + 50% CTP/75% 2-Thio-UTP + 25% UTP | 769.01 | 4.04 |

TABLE 34-continued

Cytokine screen results in BJ Fibroblast cells.

| Compound # | Chemical Alterations | IFN-β (Luciferase) | IFN-β (Luciferase) Std Dev |
|---|---|---|---|
| 00901014002/ 00901013008 | 25% 5-Methyl-CTP + 75% CTP/75% 2-Thio-UTP + 25% UTP | 1078.77 | 44.09 |
| 00901014002/ 00901013008 | 75% 5-Methyl-CTP + 25% CTP/50% 2-Thio-UTP + 50% UTP | 359.69 | 13.45 |
| 00901014002/ 00901013008 | 50% 5-Methyl-CTP + 50% CTP/50% 2-Thio-UTP + 50% UTP | 699.19 | 32.86 |
| 00901014002/ 00901013008 | 25% 5-Methyl-CTP + 75% CTP/50% 2-Thio-UTP + 50% UTP | 549.7 | 25.12 |
| 00901014002/ 00901013008 | 75% 5-Methyl-CTP + 25% CTP/25% 2-Thio-UTP + 75% UTP | 645.30 | 23.20 |
| 00901014002/ 00901013008 | 50% 5-Methyl-CTP + 50% CTP/25% 2-Thio-UTP + 75% UTP | 735.98 | 111.95 |
| 00901014002/ 00901013008 | 25% 5-Methyl-CTP + 75% CTP/25% 2-Thio-UTP + 75% UTP | 1064.22 | 3.09 |

TABLE 35

Cytokine screen results in BJ Fibroblast cells.

| Compound # | Chemical Alterations | IFN-β (mCherry) | IFN-β (mCherry) Std Dev | IFN-β (nanoLuc) | IFN-β (nanoLuc) Std Dev |
|---|---|---|---|---|---|
| 00901014002/ 00901013007 | 5-Methyl-CTP/75% 5-Methoxy-UTP + 25% UTP | 26.36 | 1.74 | −17 | −1 |
| 00901014002/ 00901013007 | 5-Methyl-CTP/50% 5-Methoxy-UTP + 50% UTP | 17.27 | 0.30 | 30 | 3 |
| 00901014002/ 00901013007 | 5-Methyl-CTP/25% 5-Methoxy-UTP + 75% UTP | 376.36 | 49.82 | 100 | 2 |
| 00901014002/ 00901013007 | 75% 5-Methyl-CTP + 25% CTP/5-Methoxy-UTP | 6.36 | 0.00 | 8.33 | 0.48 |
| 00901014002/ 00901013007 | 50% 5-Methyl-CTP + 50% CTP/5-Methoxy-UTP | 6.36 | 0.12 | 10 | 0.07 |
| 00901014002/ 00901013007 | 25% 5-Methyl-CTP + 75% CTP/5-Methoxy-UTP | 7.27 | 0.03 | 11.67 | 0.66 |
| 00901014002/ 00901013007 | 75% 5-Methyl-CTP + 25% CTP/75% 5-Methoxy-UTP + 2% UTP | 4.55 | 0.08 | 18.33 | 0.75 |
| 00901014002/ 00901013007 | 50% 5-Methyl-CTP + 50% CTP/75% 5-Methoxy-UTP + 25% UTP | 17.27 | 0.30 | 3.33 | 0.17 |
| 00901014002/ 00901013007 | 25% 5-Methyl-CTP + 75% CTP/75% 5-Methoxy-UTP + 25% UTP | 15.45 | 0.27 | 141.67 | 7.73 |
| 00901014002/ 00901013007 | 75% 5-Methyl-CTP + 25% CTP/50% 5-Methoxy-UTP + 50% UTP | 83.64 | 0.27 | 68.33 | 6.21 |
| 00901014002/ 00901013007 | 50% 5-Methyl-CTP + 50% CTP/50% 5-Methoxy-UTP + 50% UTP | 366.36 | 20.22 | 175 | 1.46 |
| 00901014002/ 00901013007 | 25% 5-Methyl-CTP + 75% CTP/50% 5-Methoxy-UTP + 50% UTP | 208.18 | 7.54 | 1031.67 | 43.78 |
| 00901014002/ 00901013007 | 75% 5-Methyl-CTP + 25% CTP/25% 5-Methoxy-UTP + 75% UTP | 434.55 | 25.78 | 686.67 | 16.32 |
| 00901014002/ 00901013007 | 50% 5-Methyl-CTP + 50% CTP/25% 5-Methoxy-UTP + 75% UTP | 538.18 | 3.34 | 951.67 | 5.39 |
| 00901014002/ 00901013007 | 25% 5-Methyl-CTP + 75% CTP/25% 5-Methoxy-UTP + 75% UTP | 674.55 | 3.53 | 930 | 38.92 |
| 00901013007 | CTP/75% 5-Methoxy-UTP + 25% UTP | 9.09 | 0.12 | 258.33 | 7.13 |
| 00901013007 | CTP/50% 5-Methoxy-UTP + 50% UTP | 1002.73 | 13.72 | 1610 | 10.24 |
| 00901013007 | CTP/25% 5-Methoxy-UT+ 75% UTP | 1996.36 | 128.45 | 2126.67 | 149.21 |
| 00901013007 | CTP/5-Methoxy-UTP (No cap) | 20 | 0.81 | 9 | 0 |

TABLE 35-continued

Cytokine screen results in BJ Fibroblast cells.

| Compound # | Chemical Alterations | IFN-β (mCherry) | IFN-β (mCherry) Std Dev | IFN-β (nanoLuc) | IFN-β (nanoLuc) Std Dev |
|---|---|---|---|---|---|
| 00901013007 | CTP/5-Methoxy-UTP (cap 0) | 27.86 | 1.77 | 3 | 0 |
| 00901014002/ 00901013007 | 5-Methyl-CTP/5-Methoxy-UTP (No cap) | −1.43 | −0.03 | 17.33 | 0.63 |
| 00901014002/ 00901013007 | 5-Methyl-CTP/5-Methoxy-UTP (cap 0) | 4.29 | 0.12 | 12.00 | 0.19 |
| | CTP/UTP (No cap) | 2255.71 | 4.64 | 1940.0 | 54.9 |
| | CTP/UTP (cap 0) | 1918.57 | 55.64 | 1407.3 | 163.1 |
| 00901014002/ 00901015001 | 5-Methyl-CTP/Pseudo-UTP (No cap) | 92.14 | 0.99 | 569.3 | 54.1 |
| 00901014002/ 00901015001 | 5-Methyl-CTP/Pseudo-UTP (cap 0) | 132.86 | 4.62 | 391.3 | 12.5 |
| 00901014002/ 00901015002 | 5-Methyl-CTP/1-Methyl-pseudo-UTP (No cap) | 9.29 | 0.14 | 2.7 | 0.0 |
| 00901014002/ 00901015002 | 5-Methyl-CTP/1-Methyl-pseudo-UTP (cap 0) | 4.29 | 0.02 | 19.3 | 0.4 |
| 00901015002 | CTP/1-Methyl-pseudo-UTP (No cap) | 343.57 | 8.52 | 423.3 | 7.4 |
| 00901015001 | CTP/1-Methyl-pseudo-UTP (cap 0) | 347.86 | 9.50 | 567.3 | 17.8 |
| | CTP/UTP/ATP/GTP (cap ARCA) | 1722.14 | 46.68 | 2563.3 | 180.2 |
| 00901014002/ 00901015001 | 5-Methyl-CTP/Pseudo-UTP (cap ARCA) | 733.57 | 5.77 | 1231.3 | 56.2 |
| 00901014002/ 00901015002 | 5-Methyl-CTP/1-Methyl-pseudo-UTP (cap ARCA) | 31.43 | 0.33 | 70.7 | 1.3 |
| 00901015002 | CTP/1-Methyl-pseudo-UTP (cap ARCA) | 427.86 | 17.24 | 305.3 | 1.5 |
| 00902011001 | Alpha-Thio-ATP | 10 | 0.04 | | |
| 00901014002/ 00901015001/ 00902011001 | 5-Methyl-CTP/ Pseudo-UTP/Alpha-Thio-ATP | 631.43 | 6.15 | | |
| 00901014002/ 00901015002/ 00902011001 | 5-Methyl-CTP/ 1-Methyl-pseudo-UTP/ Alpha-Thio-ATP | 7.14 | 0.08 | | |
| 00901015002/ 00902011001 | 1-Methyl-pseudo-UTP/Alpha-Thio-ATP | 5.71 | 0.02 | | |
| 00901013007/ 00902011001 | 5-Methoxy-UTP/ Alpha-Thio-ATP | −0.71 | −0.01 | | |
| 00901014002/ 00901013007/ 00902011001 | 5-Methyl-CTP/5-Methoxy-UTP/Alpha-Thio-ATP | 4.29 | 0.02 | | |
| 00902012001 | Alpha-Thio-GTP | 1215 | 1.25 | | |
| 00901014002/ 00901015001/ 00902012001 | 5-Methyl-CTP/Pseudo-UTP/Alpha-Thio-GTP | 314.29 | 2.29 | | |
| 00901014002/ 00901015002/ 00902012001 | 5-Methyl-CTP/1-Methyl-pseudo-UTP/Alpha-Thio-GTP | 18.57 | 0.34 | | |
| 00901015002/ 00902012001 | 1-Methyl-pseudo-UTP/ Alpha-Thio-GTP | 1635.71 | 61.30 | | |
| 00901013007/ 00902012001 | 5-Methoxy-UTP/Alpha-Thio-GTP | 258 | 1.01 | | |
| 00901014002/ 00901013007/ 00902012001 | 5-Methyl-CTP/5-Methoxy-UTP/Alpha-Thio-GTP | −19 | −0.57 | | |
| 00901011006 | N6-Me-ATP | 1282 | 86.92 | | |
| 00901014002/ 00901015001/ 00901011006 | 5-Methyl-CTP/Pseudo-UTP/N6-Me-ATP | 229 | 7.14 | | |
| 00901014002/ 00901015002/ 00901011006 | 5-Methyl-CTP/1-Methyl-pseudo-UTP/N6-Me-ATP | −11 | −0.05 | | |
| 00901015002/ 00901011006 | 1-Methyl-pseudo-UTP/ N6-Me-ATP | −11 | −0.41 | | |

TABLE 35-continued

Cytokine screen results in BJ Fibroblast cells.

| Compound # | Chemical Alterations | IFN-β (mCherry) | IFN-β (mCherry) Std Dev | IFN-β (nanoLuc) | IFN-β (nanoLuc) Std Dev |
|---|---|---|---|---|---|
| 00901013007/ 00901011006 | 5-Methoxy-UTP/N6-Me-ATP | −9 | −0.26 | | |
| 00901014002/ 00901013007/ 00901011006 | 5-Methyl-CTP/5-Methoxy-UTP/N6-Me-ATP | −4 | −0.13 | | |
| 03601014039 | 5-Ethyl-CTP | 182 | 4.23 | | |
| 03601014039/ 00901015002 | 5-Ethyl-CTP/1-Methyl-pseudo-UTP | 5 | 0.03 | | |
| 03601014039/ 00901013007 | 5-Ethyl-CTP/5-Methoxy-UTP | 9 | 0.12 | | |
| 03601014030 | 5-Methoxy-CTP | 38 | 4.27 | | |
| 03601014030/ 00901015002 | 5-Methoxy-CTP/1-Methyl-pseudo-UTP | −7 | −0.30 | | |
| 03601014030/ 00901013007 | 5-Methoxy-CTP/5-Methoxy-UTP | −10 | −0.18 | | |
| 03601014011 | 5-Ethynyl-CTP | 128 | 1.53 | | |
| 03601014011/ 00901015002 | 5-Ethynyl-CTP/1-Methyl-pseudo-UTP | −17 | −0.50 | | |
| 03601014011/ 00901013007 | 5-Ethynyl-CTP/5-Methoxy-UTP | 568 | 20.50 | | |
| 03601014011/ 00901015001 | 5-Ethynyl-CTP/Pseudo-UTP | 13 | 0 | | |
| 03601014011/ 00901013007/ 00901015002 | 5-Methyl-CTP/75% 5-Methoxy-UTP + 25% 1-Methyl-pseudo-UTP | 9 | 0 | −14.17 | −0.40 |
| 03601014011/ 00901013007/ 00901015002 | 5-Methyl-CTP/50% 5-Methoxy-UTP + 50% 1-Methyl-pseudo-UTP | −4 | −0.01 | −26.67 | −0.70 |
| 03601014011/ 00901013007/ 00901015002 | 5-Methyl-CTP/25% 5-Methoxy-UTP + 75% 1-Methyl-pseudo-UTP | | | −43.33 | −2.12 |
| 03601014011/ 00901013007/ 00901015002 | 75% 5-Methyl-CTP + 25% CTP/75% 5-Methoxy-UTP + 25% 1-Methyl-pseudo-UTP | | | 1020.8 | 39.8 |
| 03601014011/ 00901013007/ 00901015002 | 50% 5-Methyl-CTP + 50% CTP/75% 5-Methoxy-UTP + 25% 1-Methyl-pseudo-UTP | | | −4.2 | −0.3 |
| 03601014011/ 00901013007/ 00901015002 | 25% 5-Methyl-CTP + 75% CTP/75% 5-Methoxy-UTP + 25% 1-Methyl-pseudo-UTP | | | −25.0 | −0.3 |
| 03601014011/ 00901013007/ 00901015002 | 75% 5-Methyl-CTP + 25% CTP/50% 5-Methoxy-UTP + 50% 1-Methyl-pseudo-UTP | | | −13.3 | 0.0 |
| 03601014011/ 00901013007/ 00901015002 | 50% 5-Methyl-CTP + 50% CTP/50% 5-Methoxy-UTP + 50% 1-Methyl-pseudo-UTP | | | −29.2 | −0.3 |
| 03601014011/ 00901013007/ 00901015002 | 25% 5-Methyl-CTP + 75% CTP/50% 5-Methoxy-UTP + 50% 1-Methyl-pseudo-UTP | | | −25.8 | −0.3 |
| 03601014011/ 00901013007/ 00901015002 | 75% 5-Methyl-CTP + 25% CTP/25% 5-Methoxy-UTP + 75% 1-Methyl-pseudo-UTP | | | −17.5 | −0.3 |
| 03601014011/ 00901013007/ 00901015002 | 50% 5-Methyl-CTP + 50% CTP/25% 5-Methoxy-UTP + 75% 1-Methyl-pseudo-UTP | | | 0.0 | 0.0 |
| 03601014011/ 00901013007/ 00901015002 | 25% 5-Methyl-CTP + 75% CTP/25% 5-Methoxy-UTP + 75% 1-Methyl-pseudo-UTP | | | 39.2 | 1.5 |
| 00901013007/ 00901015002 | CTP/75% 5-Methoxy-UTP + 25% 1-Methyl-pseudo-UTP | | | 3.3 | 0.0 |
| 00901013007/ 00901015002 | CTP/50% 5-Methoxy-UTP + 50% 1-Methyl-pseudo-UTP | | | −15.8 | −0.5 |

TABLE 35-continued

Cytokine screen results in BJ Fibroblast cells.

| Compound # | Chemical Alterations | IFN-β (mCherry) | IFN-β (mCherry) Std Dev | IFN-β (nanoLuc) | IFN-β (nanoLuc) Std Dev |
|---|---|---|---|---|---|
| 00901013007/ 00901015002 | CTP/25% 5-Methoxy-UTP + 75% 1-Methyl-pseudo-UTP | | | 15.8 | 0.3 |
| | 5-Methyl-5,6-dihydro-UTP | 5 | 0 | 30 | 1.23 |
| 00901015002/ 00902012001 | 1-Methyl-pseudo-UTP/2% Alpha-Thio-GTP + 98% GTP | 612.5 | 1.80 | 1407.5 | 38.37 |
| 00901015002/ 00902012001 | 1-Methyl-pseudo-UTP/5% Alpha-Thio-GTP + 95% GTP | 478.75 | 7.52 | 127.5 | 0.69 |
| 00901015002/ 00902012001 | 1-Methyl-pseudo-UTP/10% Alpha-Thio-GTP + 90% GTP | 353.75 | 6.73 | 170 | 1.68 |
| 00901015002/ 00902012001 | 1-Methyl-pseudo-UTP/25% Alpha-Thio-GTP + 75% GTP | 992.5 | 6.05 | 510 | 12.07 |
| 00901015002/ 00902012001 | 1-Methyl-pseudo-UTP/50% Alpha-Thio-GTP + 50% GTP | 1238.75 | 30.42 | 860 | 14.39 |
| 00901015002/ 00902011001 | 1-Methyl-pseudo-UTP/2% Alpha-Thio-ATP + 98% ATP | 1468.75 | 136.65 | 650 | 23.10 |
| 00901015002/ 00902011001 | 1-Methyl-pseudo-UTP/5% Alpha-Thio-ATP + 95% ATP | 891.25 | 40.47 | 372.5 | 1.32 |
| 00901015002/ 00902011001 | 1-Methyl-pseudo-UTP/10% Alpha-Thio-ATP + 90% ATP | 837.5 | 19.48 | 320 | 12.21 |
| 00901015002/ 00902011001 | 1-Methyl-pseudo-UTP/25% Alpha-Thio-ATP + 75% ATP | 1146.25 | 75.59 | 1560 | 24.70 |
| 00901015002/ 00902011001 | 1-Methyl-pseudo-UTP/50% Alpha-Thio-ATP + 50% ATP | 1085 | 71.79 | 1360 | 8.02 |
| 00901015002 | 75% 1-Methyl-pseudo-UTP + 25% UTP | 1358 | 55.43 | | |
| 00901015002 | 50% 1-Methyl-pseudo-UTP + 50% UTP | 2248 | 52.52 | | |
| 00901015001 | 75% Pseudo-UTP + 25% UTP | 2242 | 88.05 | | |
| 00901015001 | 50% Pseudo-UTP + 50% UTP | 2308 | 15.31 | | |
| 00901015001 | 25% Pseudo-UTP + 75% UTP | 1968 | 58.03 | | |
| 03601013014 | 75% 5-Methyl-UTP + 25% UTP | 2476 | 60.14 | | |
| 03601013014 | 50% 5-Methyl-UTP + 50% UTP | 2364 | 46.09 | | |
| 03601013014 | 25% 5-Methyl-UTP + 75% UTP | 2666 | 62.48 | | |
| 00901013003 | 75% 5-Methyl-2-thio-UTP + 25% UTP | 1690 | 25.80 | | |
| 00901013003 | 50% 5-Methyl-2-thio-UTP + 50% UTP | 2190 | 77.61 | | |
| 00901013003 | 25% 5-Methyl-2-thio-UTP + 75% UTP | 2650 | 218.52 | | |
| 00901013011 | 75% 4-Thio-UTP + 25% UTP | | | 1847.5 | 59.95 |
| 00901013011 | 50% 4-Thio-UTP + 50% UTP | | | 2057.5 | 132.52 |
| 00901013011 | 25% 4-Thio-UTP + 75% UTP | | | 1488.75 | 98.39 |
| 00901013009 | 75% 5-Methoxy-carbonylmethyl-UTP + 25% UTP | | | 1632.5 | 19.70 |
| 00901013009 | 50% 5-Methoxy-carbonylmethyl-UTP + 50% UTP | | | 1290 | 36.01 |
| 00901013009 | 25% 5-Methoxy-carbonylmethyl-UTP + 75% UTP | | | 1462.5 | 58.24 |
| 03601014011 | 75% 5-Methyl-CTP + 25% CTP | | | 1796.25 | 14.39 |

TABLE 35-continued

Cytokine screen results in BJ Fibroblast cells.

| Compound # | Chemical Alterations | IFN-β (mCherry) | IFN-β (mCherry) Std Dev | IFN-β (nanoLuc) | IFN-β (nanoLuc) Std Dev |
|---|---|---|---|---|---|
| 03601014011 | 50% 5-Methyl-CTP + 50% CTP | | | 1411.25 | 18.24 |
| 03601014011 | 25% 5-Methyl-CTP + 75% CTP | | | 2065 | 42.69 |
| 03601014011/ 00901015002 | 75% 5-Methyl-CTP + 25% CTP/1-Methyl-pseudo-UTP | | | 77.5 | 1.88 |
| 03601014011/ 00901015002 | 50% 5-Methyl-CTP + 50% CTP/1-Methyl-pseudo-UTP | | | 67.5 | 0.56 |
| 03601014011/ 00901015002 | 25% 5-Methyl-CTP + 75% CTP/1-Methyl-pseudo-UTP | | | 38.75 | 0.54 |
| 00901011045 | 8-Me-ATP | | | −1.25 | −0.01 |
| 00901015002/ 00901011045 | 1-Methyl-pseudo-UTP/8-Me-ATP | | | −1.25 | −0.03 |
| 00901015002/ 00902011001/ 00902012001 | 1-Methyl-pseudo-UTP/2% Alpha-Thio-ATP + 98% ATP/2% Alpha-Thio-GTP + 98% GTP | | | 358.75 | 2.29 |
| 00901015002/ 00902011001/ 00902012001 | 1-Methyl-pseudo-UTP/5% Alpha-Thio-ATP + 95% ATP/5% Alpha-Thio-GTP + 95% GTP | | | 282.5 | 6.92 |
| 00901015002/ 00902011001/ 00902012001 | 1-Methyl-pseudo-UTP/2% Alpha-Thio-ATP + 98% ATP/5% Alpha-Thio-GTP + 95% GTP | | | 282.5 | 23.54 |
| 00901015002/ 00902011001/ 00902012001 | 1-Methyl-pseudo-UTP/5% Alpha-Thio-ATP + 95% ATP/2% Alpha-Thio-GTP + 98% GTP | | | 213.75 | 4.24 |
| 00901015002/ 00902011001/ 00902012001 | 1-Methyl-pseudo-UTP/10% Alpha-Thio-ATP + 90% ATP/2% Alpha-Thio-GTP + 98% GTP | | | 237.5 | 19.15 |
| 00901015002/ 00902011001/ 00902012001 | 1-Methyl-pseudo-UTP/2% Alpha-Thio-ATP + 98% ATP/10% Alpha-Thio-GTP + 90% GTP | | | 383.75 | 8.63 |
| 00901015002/ 00902011001/ 00902012001 | 1-Methyl-pseudo-UTP/10% Alpha-Thio-ATP + 90% ATP/5% Alpha-Thio-GTP + 95% GTP | | | 340 | 3.00 |
| 00901015002/ 00902011001/ 00902012001 | 1-Methyl-pseudo-UTP/5% Alpha-Thio-ATP + 95% ATP/10% Alpha-Thio-GTP + 90% GTP | | | 437.5 | 21.38 |
| 00901015002/ 00902011001/ 00902012001 | 1-Methyl-pseudo-UTP/10% Alpha-Thio-ATP + 90% ATP/10% Alpha-Thio-GTP + 90% GTP | | | 401.25 | 5.58 |
| 00901014041 | 5-Fluoro-CTP | 2808.46 | 102.10 | | |
| 00901014041/ 00901015002 | 5-Fluoro-CTP/1-Methyl-pseudo-UTP | 188.46 | 3.02 | | |
| 00901014041/ 00901013007 | 5-Fluoro-CTP/5-Methoxy-UTP | 4.62 | 0.12 | | |
| 03601014021 | 5-Phenyl-CTP | 865.38 | 26.34 | | |
| 03601014021/ 00901015002 | 5-Phenyl-CTP/1-Methyl-pseudo-UTP | −20 | −0.09 | | |
| 03601014021/ 00901013007 | 5-Phenyl-CTP/5-Methoxy-UTP | −16.92 | −0.36 | | |
| 03601014013 | N4-Bz-CTP | −17.69 | −0.46 | | |
| 03601014013/ 00901015002 | N4-Bz-CTP/1-Methyl-pseudo-UTP | −23.08 | −0.10 | | |
| 03601014013/ 00901013007 | N4-Bz-CTP/5-Methoxy-UTP | −17.69 | −0.15 | | |
| 03601013036 | 5-Carbamoyl-methyl-UTP | 1445.38 | 98.89 | | |
| 03601013036 | 75% 5-Carbamoyl-methyl-UTP + 25% UTP | 2341.54 | 121.37 | | |
| 00901013054 | 50% 5-Carbamoyl-methyl-UTP + 50% UTP | 3471.54 | 131.06 | | |
| 00901013054 | 25% 5-Carbamoyl-methyl-UTP + 75% UTP | 2246.92 | 106.12 | | |
| 00901013054 | 75% 5-Hydroxy-UTP + 25% UTP | 3277.69 | 195.96 | | |

TABLE 35-continued

Cytokine screen results in BJ Fibroblast cells.

| Compound # | Chemical Alterations | IFN-β (mCherry) | IFN-β (mCherry) Std Dev | IFN-β (nanoLuc) | IFN-β (nanoLuc) Std Dev |
|---|---|---|---|---|---|
| 00901014007/ 00901013007 | 50% 5-Hydroxy-UTP + 50% UTP | 3347.69 | 266.68 | | |
| 00901014007/ 00901013007 | 25% 5-Hydroxy-UTP + 75% UTP | 2800.77 | 122.21 | | |
| 00901014007/ 00901013007 | 25% N4-Ac-CTP + 75% CTP/25% 5-Methoxy-UTP + 75% UTP | | | 2245 | 66 |
| 00901014007/ 00901013007 | 75% N4-Ac-CTP + 25% CTP/25% 5-Methoxy-UTP + 75% UTP | | | 181 | 15 |
| 00901014005/ 00901013007 | 25% N4-Ac-CTP + 75% CTP/75% 5-Methoxy-UTP + 25% UTP | | | 1790 | 92 |
| 00901014005/ 00901013007 | 75% N4-Ac-CTP + 25% CTP/75% 5-Methoxy-UTP + 25% UTP | | | 21 | 1 |
| 00901014005/ 00901013007 | 25% 5-Hydroxymethyl-CTP + 75% CTP/25% 5-Methoxy-UTP + 75% UTP | | | 1603.64 | 60.64 |
| 00901014005/ 00901013007 | 75% 5-Hydroxymethyl-CTP + 25% CTP/25% 5-Methoxy-UTP + 75% UTP | | | 2502.73 | 245.56 |
| 00901014004/ 00901013007 | 25% 5-Hydroxymethyl-CTP + 75% CTP/75% 5-Methoxy-UTP + 25% UTP | | | 440.00 | 37.53 |
| 00901014004/ 00901013007 | 75% 5-Hydroxymethyl-CTP + 25% CTP/75% 5-Methoxy-UTP + 25% UTP | | | 20.00 | 0.06 |
| 00901014004/ 00901013007 | N4-Methyl-CTP/5-Methoxy-UTP | | | 2.73 | 0.12 |
| 00901014004/ 00901013007 | 25% N4-Methyl-CTP + 75% CTP/25% 5-Methoxy-UTP + 75% UTP | | | 1795.45 | 49.96 |
| 00901014004/ 00901013007 | 75% N4-Methyl-CTP + 25% CTP/25% 5-Methoxy-UTP + 75% UTP | | | 2277.27 | 43.45 |
| 00901014003/ 00901013007 | 25% N4-Methyl-CTP + 75% CTP/75% 5-Methoxy-UTP + 25% UTP | | | 610.00 | 28.17 |
| 00901014003/ 00901013007 | 75% N4-Methyl-CTP + 25% CTP/75% 5-Methoxy-UTP + 25% UTP | | | 608.18 | 56.29 |
| 00901014003/ 00901013007 | 25% 5-Trifluoromethyl-CTP + 75% CTP/25% 5-Methoxy-UTP + 75% UTP | | | 2207.27 | 52.12 |
| 00901014003/ 00901013007 | 75% 5-Trifluoromethyl-CTP + 25% CTP/25% 5-Methoxy-UTP + 75% UTP | | | 2226.36 | 67.42 |
| 03601014008/ 00901013007 | 25% 5-Trifluoromethyl-CTP + 75% CTP/75% 5-Methoxy-UTP + 25% UTP | | | 1080.91 | 139.93 |
| 03601014008/ 00901013007 | 75% 5-Trifluoromethyl-CTP + 25% CTP/75% 5-Methoxy-UTP + 25% UTP | | | 0 | 0 |
| 03601014008/ 00901013007 | 25% 5-Bromo-CTP + 75% CTP/25% 5-Methoxy-UTP + 75% UTP | | | 1823.75 | 165.4 |
| 03601014008/ 00901013007 | 75% 5-Bromo-CTP + 25% CTP/25% 5-Methoxy-UTP + 75% UTP | | | 0 | 0 |
| 00901014035/ 00901013007 | 25% 5-Bromo-CTP + 75% CTP/75% 5-Methoxy-UTP + 25% UTP | | | 0 | 0 |
| 00901014035/ 00901013007 | 75% 5-Bromo-CTP + 25% CTP/75% 5-Methoxy-UTP + 25% UTP | | | 0 | 0 |
| 00901014035/ 00901013007 | 5-Iodo-CTP/5-Methoxy-UTP | | | 0 | 0 |
| 00901014035/ 00901013007 | 25% 5-Iodo-CTP + 75% CTP/25% 5-Methoxy-UTP + 75% UTP | | | 570 | 5.907 |
| 00901014035/ 00901013007 | 75% 5-Iodo-CTP + 25% CTP/25% 5-Methoxy-UTP + 75% UTP | | | 0 | 0 |

TABLE 35-continued

| Cytokine screen results in BJ Fibroblast cells. | | | | | |
|---|---|---|---|---|---|
| Compound # | Chemical Alterations | IFN-β (mCherry) | IFN-β (mCherry) Std Dev | IFN-β (nanoLuc) | IFN-β (nanoLuc) Std Dev |
| 03601014039/ 00901013007 | 25% 5-Iodo-CTP + 75% CTP/75% 5-Methoxy-UTP + 25% UTP | | | 0 | 0 |
| 03601014039/ 00901013007 | 75% 5-Iodo-CTP + 25% CTP/75% 5-Methoxy-UTP + 25% UTP | | | 0 | 0 |
| 03601014039/ 00901013007 | 25% 5-Ethyl-CTP + 75% CTP/25% 5-Methoxy-UTP + 75% UTP | | | 1877.5 | 20.65 |
| 03601014039/ 00901013007 | 75% 5-Ethyl-CTP + 25% CTP/25% 5-Methoxy-UTP + 75% UTP | | | 17.5 | 0.318 |
| 03601014030/ 00901013007 | 25% 5-Ethyl-CTP + 75% CTP/75% 5-Methoxy-UTP + 25% UTP | | | 82.5 | 0.864 |
| 03601014030/ 00901013007 | 75% 5-Ethyl-CTP + 25% CTP/75% 5-Methoxy-UTP + 25% UTP | | | 0 | 0 |
| 03601014030/ 00901013007 | 25% 5-Methoxy-CTP + 75% CTP/25% 5-Methoxy-UTP + 75% UTP | | | 2893.75 | 14.3 |
| 03601014030/ 00901013007 | 75% 5-Methoxy-CTP + 25% CTP/25% 5-Methoxy-UTP + 75% UTP | | | 2.5 | 0 |
| 03601014012/ 00901013007 | 25% 5-Methoxy-CTP + 75% CTP/75% 5-Methoxy-UTP + 25% UTP | | | 0 | 0 |
| 03601014012/ 00901013007 | 75% 5-Methoxy-CTP + 25% CTP/75% 5-Methoxy-UTP + 25% UTP | | | 0 | 0 |
| 03601013036 | 25% 5-Ethynyl-CTP + 75% CTP/25% 5-Methoxy-UTP + 75% UTP | | | 884.17 | 6.55 |
| 03601013036 | 75% 5-Ethynyl-CTP + 25% CTP/25% 5-Methoxy-UTP + 75% UTP | | | 0 | 0 |
| 03601014012/ 00901013007 | 25% 5-Ethynyl-CTP + 75% CTP/75% 5-Methoxy-UTP + 25% UTP | | | 0 | 0 |
| 03601014012/ 00901013007 | 75% 5-Ethynyl-CTP + 25% CTP/75% 5-Methoxy-UTP + 25% UTP | | | 6.67 | 0.16 |
| 00901014014/ 00901013007 | Pseudo-iso-CTP/5-Methoxy-UTP | | | 0 | 0 |
| 00901014014/ 00901013007 | 25% Pseudo-iso-CTP + 75% CTP/25% 5-Methoxy-UTP + 75% UTP | | | 2384.17 | 106 |
| 00901014014/ 00901013007 | 75% Pseudo-iso-CTP + 25% CTP/25% 5-Methoxy-UTP + 75% UTP | | | 978.33 | 59.52 |
| 00901014014/ 00901013007 | 25% Pseudo-iso-CTP + 75% CTP/75% 5-Methoxy-UTP + 25% UTP | | | 127.5 | 1.15 |
| 00901014014/ 00901013007 | 75% Pseudo-iso-CTP + 25% CTP/75% 5-Methoxy-UTP + 25% UTP | | | 0 | 0 |
| 00901014036/ 00901013007 | 5-Formyl-CTP/5-Methoxy-UTP | | | 0 | 0 |
| 00901014036/ 00901013007 | 25% 5-Formyl-CTP + 75% CTP/25% 5-Methoxy-UTP + 75% UTP | | | 2692.5 | 188.2 |
| 00901014036/ 00901013007 | 75% 5-Formyl-CTP + 25% CTP/25% 5-Methoxy-UTP + 75% UTP | | | 440.83 | 60.36 |
| 00901014036/ 00901013007 | 25% 5-Formyl-CTP + 75% CTP/75% 5-Methoxy-UTP + 25% UTP | | | 30 | 1.57 |
| 00901014036/ 00901013007 | 75% 5-Formyl-CTP + 25% CTP/75% 5-Methoxy-UTP + 25% UTP | | | 0 | 0 |
| 03601014009/ 00901013007 | 5-Aminoallyl-CTP/5-Methoxy-UTP | | | 0 | 0 |

TABLE 35-continued

Cytokine screen results in BJ Fibroblast cells.

| Compound # | Chemical Alterations | IFN-β (mCherry) | IFN-β (mCherry) Std Dev | IFN-β (nanoLuc) | IFN-β (nanoLuc) Std Dev |
|---|---|---|---|---|---|
| 03601014009/ 00901013007 | 25% 5-Aminoallyl-CTP + 75% CTP/25% 5-Methoxy-UTP + 75% UTP | | | 410.83 | 18.91 |
| 03601014009/ 00901013007 | 75% 5-Aminoallyl-CTP + 25% CTP/25% 5-Methoxy-UTP + 75% UTP | | | 0 | 0 |
| 03601014009/ 00901013007 | 25% 5-Aminoallyl-CTP + 75% CTP/75% 5-Methoxy-UTP + 25% UTP | | | 6.67 | 0.11 |
| 03601014009/ 00901013007 | 75% 5-Aminoallyl-CTP + 25% CTP/75% 5-Methoxy-UTP + 25% UTP | | | 0 | 0 |
| 00901014041/ 00901013007 | 25% 5-Fluoro-CTP + 75% CTP/25% 5-Methoxy-UTP + 75% UTP | | | 2364.17 | 87.84 |
| 00901014041/ 00901013007 | 75% 5-Fluoro-CTP + 25% CTP/25% 5-Methoxy-UTP + 75% UTP | | | 1472.5 | 35.88 |
| 00901014041/ 00901013007 | 25% 5-Fluoro-CTP + 75% CTP/75% 5-Methoxy-UTP + 25% UTP | | | 304.17 | 1.87 |
| 00901014041/ 00901013007 | 75% 5-Fluoro-CTP + 25% CTP/75% 5-Methoxy-UTP + 25% UTP | | | 27.5 | 0.17 |
| 03601014021/ 00901013007 | 25% 5-Phenyl-CTP + 75% CTP/25% 5-Methoxy-UTP + 75% UTP | | | 1820 | 103.94 |
| 03601014021/ 00901013007 | 75% 5-Phenyl-CTP + 25% CTP/25% 5-Methoxy-UTP + 75% UTP | | | 200 | 4.95 |
| 03601014021/ 00901013007 | 25% 5-Phenyl-CTP + 75% CTP/75% 5-Methoxy-UTP + 25% UTP | | | 105 | 4.34 |
| 03601014021/ 00901013007 | 75% 5-Phenyl-CTP + 25% CTP/75% 5-Methoxy-UTP + 25% UTP | | | 0 | 0 |
| 03601014013/ 00901013007 | 25% N4-Bz-CTP + 75% CTP/25% 5-Methoxy-UTP + 75% UTP | | | 2194.17 | 135.35 |
| 03601014013/ 00901013007 | 75% N4-Bz-CTP + 25% CTP/25% 5-Methoxy-UTP + 75% UTP | | | 492.5 | 51.72 |
| 03601014013/ 00901013007 | 25% N4-Bz-CTP + 75% CTP/75% 5-Methoxy-UTP + 25% UTP | | | 324.17 | 25.01 |
| 03601014013/ 00901013007 | 75% N4-Bz-CTP + 25% CTP/75% 5-Methoxy-UTP + 25% UTP | | | 0 | 0 |
| 03601014041/ 00901013007 | 5-Carboxy-CTP/5-Methoxy-UTP | | | 10 | 0.24 |
| 03601014041/ 00901013007 | 25% 5-Carboxy-CTP + 75% CTP/25% 5-Methoxy-UTP + 75% UTP | | | 2575.83 | 126.66 |
| 03601014041/ 00901013007 | 75% 5-Carboxy-CTP + 25% CTP/25% 5-Methoxy-UTP + 75% UTP | | | 839.17 | 32.48 |
| 03601014041/ 00901013007 | 25% 5-Carboxy-CTP + 75% CTP/75% 5-Methoxy-UTP + 25% UTP | | | 330 | 0.48 |
| 03601014041/ 00901013007 | 75% 5-Carboxy-CTP + 25% CTP/75% 5-Methoxy-UTP + 25% UTP | | | 0 | 0 |

TABLE 36

Cytokine screen results in BJ Fibroblast cells.

| Compound # | Chemical Alterations | IFN-β (mEPO) | IFN-β (mEPO) Std Dev | IFN-β (hEPO) | IFN-β (hEPO) Std Dev |
|---|---|---|---|---|---|
| 00901013007 | 5-Methoxy-UTP | −3.33 | −0.03 | 15 | 0.15 |
| 00901014002/ 00901013007 | 5-Me-CTP/5-Methoxy-UTP | −1.67 | −0.03 | 5 | 0 |
| 00901014002/ 00901013007 | 5-Methyl-CTP/75% 5-Methoxy-UTP + 25% UTP | 6.67 | 0.07 | 42.5 | 0.20 |
| 00901014002/ 00901013007 | 5-Methyl-CTP/50% 5-Methoxy-UTP + 50% UTP | 0.00 | 0.00 | −7.5 | −0.35 |
| 00901014002/ 00901013007 | 5-Methyl-CTP/25% 5-Methoxy-UTP + 75% UTP | 0.00 | 0.00 | 0 | 0 |
| 00901014002/ 00901013007 | 75% 5-Methyl-CTP + 25% CTP/5-Methoxy-UTP | −8.33 | −0.13 | −2.5 | −0.01 |
| 00901014002/ 00901013007 | 50% 5-Methyl-CTP + 50% CTP/5-Methoxy-UTP | −3.33 | −0.03 | −2.5 | −0.01 |
| 00901014002/ 00901013007 | 25% 5-Methyl-CTP + 75% CTP/5-Methoxy-UTP | 1.67 | 0.08 | −10 | −0.21 |
| 00901014002/ 00901013007 | 75% 5-Methyl-CTP + 25% CTP/75% 5-Methoxy-UTP + 25% UTP | −10.00 | −0.21 | 5 | 0 |
| 00901014002/ 00901013007 | 50% 5-Methyl-CTP + 50% CTP/75% 5-Methoxy-UTP + 25% UTP | −8.33 | −0.04 | 30 | 0.58 |
| 00901014002/ 00901013007 | 25% 5-Methyl-CTP + 75% CTP/75% 5-Methoxy-UTP + 25% UTP | 30 | 0.56 | 10 | 0.4 |
| 00901014002/ 00901013007 | 75% 5-Methyl-CTP + 25% CTP/50% 5-Methoxy-UTP + 50% UTP | 10 | 0.10 | 25 | 0 |
| 00901014002/ 00901013007 | 50% 5-Methyl-CTP + 50% CTP/50% 5-Methoxy-UTP + 50% UTP | 6.67 | 0 | 2.5 | 0.01 |
| 00901014002/ 00901013007 | 25% 5-Methyl-CTP + 75% CTP/50% 5-Methoxy-UTP + 50% UTP | −1.67 | −0.03 | 10 | 0.1 |
| 00901014002/ 00901013007 | 75% 5-Methyl-CTP + 25% CTP/25% 5-Methoxy-UTP + 75% UTP | 6.67 | 0.2 | 27.5 | 0.93 |
| 00901014002/ 00901013007 | 50% 5-Methyl-CTP + 50% CTP/25% 5-Methoxy-UTP + 75% UTP | −11.67 | −0.19 | −7.5 | −0.04 |
| 00901014002/ 00901013007 | 25% 5-Methyl-CTP + 75% CTP/25% 5-Methoxy-UTP + 75% UTP | 450 | 17.38 | 12.5 | 0.06 |
| 00901013007 | CTP/75% 5-Methoxy-UTP + 25% UTP | −1.67 | −0.01 | 5 | 0.10 |
| 00901013007 | CTP/50% 5-Methoxy-UTP + 50% UTP | 43.33 | 0.78 | 20 | 0.78 |
| 00901013007 | CTP/25% 5-Methoxy-UTP + 75% UTP | 148.33 | 3.64 | 35 | 0.67 |

Example 88

In Vivo Assays with Human EPO Containing Alternative Nucleotides

Formulation

Alternative hEPO mRNAs were formulated in lipid nanoparticles (LNPs) comprising DLin-KC2-DMA, DSPC, Cholesterol, and PEG-DMG at 50:10:38.5:1.5 mol % respectively (Table 37). The LNPs were made by direct injection utilizing nanoprecipitation of ethanol solubilized lipids into a pH 4.0 50 mM citrate mRNA solution. The EPO LNP particle size distributions were characterized by DLS. Encapsulation efficiency (EE) was determined using a Ribogreen™ fluorescence-based assay for detection and quantification of nucleic acids. The sample details are shown in Table 38.

TABLE 37

Formulation Conditions

| Ionizable Lipid 2-(2,2-di((9Z,12Z)-octadeca-9,12-dien-1yl)-1,3-diocolan-4-yl)-N,N-dimethylethanamine (Lipid/Mol %) | Phospholipid 1,2-distearoyl-sn-glycero-3-phosphocholine (Lipid/Mol %) | Cholesterol cholest-5-en-3β-ol (Lipid/Mol %) | PEG Lipid 1,2-Dimyristoyl-sn-glycerol, methoxypolyethylene Glycol (Lipid/Mol %) |
|---|---|---|---|
| DLin-KC2-DMA 50 | DSPC 10 | Cholesterol 38.5 | PEG-DMG 1.5 |

TABLE 38

Sample Details

| Batch Size (ug) | Sample Name | mRNA Chemistry | Z-average (d · nm) | PDI | % EE |
|---|---|---|---|---|---|
| 100 | hEPO 597 1 | 5-methoxy-UTP/CTP/ATP/GTP | 84.44 | 0.131 | 97 |
| 100 | hEPO 597 2 | 5-methoxy-UTP/5-methyl-CTP/ATP/GTP | 81.77 | 0.108 | 97 |
| 100 | hEPO 597 3 | 75% 5-methoxy-UTP/5-methyl-CTP/ATP/GTP | 89.22 | 0.162 | 94 |
| 100 | hEPO 597 4 | 50% 5-methoxy-UTP/5-methyl-CTP/ATP/GTP | 86.24 | 0.124 | 98 |
| 100 | hEPO 597 5 | 25% 5-methoxy-UTP/5-methyl-CTP/ATP/GTP | 86.67 | 0.144 | 97 |
| 50 | hEPO 597 6 | 5-methoxy-UTP/75% 5-methyl-CTP/ATP/GTP | 99.25 | 0.162 | 81 |
| 100 | hEPO 597 7 | 5-methoxy-UTP/50% 5-methyl-CTP/ATP/GTP | 89.32 | 0.123 | 95 |
| 100 | hEPO 597 8 | 5-methoxy-UTP/25% 5-methyl-CTP/ATP/GTP | 87.38 | 0.134 | 97 |
| 100 | hEPO 597 9 | 75% 5-methoxy-UTP/75% 5-methyl-CTP/ATP/GTP | 86.66 | 0.139 | 97 |
| 100 | hEPO 597 10 | 75% 5-methoxy-UTP/50% 5-methyl-CTP/ATP/GTP | 86.54 | 0.124 | 97 |
| 100 | hEPO 597 11 | 75% 5-methoxy-UTP/25% 5-methyl-CTP/ATP/GTP | 86.07 | 0.143 | 97 |
| 100 | hEPO 597 12 | 50% 5-methoxy-UTP/75% 5-methyl-CTP/ATP/GTP | 87.54 | 0.114 | 98 |
| 100 | hEPO 597 13 | 50% 5-methoxy-UTP/50% 5-methyl-CTP/ATP/GTP | 87.66 | 0.123 | 97 |
| 100 | hEPO 597 14 | 50% 5-methoxy-UTP/25% 5-methyl-CTP/ATP/GTP | 85.96 | 0.156 | 97 |
| 100 | hEPO 597 15 | 25% 5-methoxy-UTP/75% 5-methyl-CTP/ATP/GTP | 90.03 | 0.113 | 98 |
| 50 | hEPO 597 16 | 25% 5-metoxy-UTP/50% 5-methyl-CTP/ATP/GTP | 94.52 | 0.201 | 93 |
| 100 | hEPO 597 17 | 25% 5-methoxy-UTP/25% 5-methyl-CTP/ATP/GTP | 86.66 | 0.096 | 96 |
| 100 | hEPO 597 18 | 75% 5-methoxy-UTP/CTP/ATP/GTP | 86.13 | 0.164 | 97 |
| 100 | hEPO 597 19 | 50% 5-methoxy-UTP/CTP/ATP/GTP | 85.57 | 0.157 | 98 |
| 100 | hEPO 597 20 | 25% 5-methoxy-UTP/CTP/ATP/GTP | 88.36 | 0.127 | 98 |
| 100 | hEPO 597 21 | UTP/CTP/ATP/GTP | 87.39 | 0.126 | 98 |
| 50 | hEPO 597 22 | pseudo-UTP/5-methyl-CTP/ATP/GTP | 100.8 | 0.136 | 91 |
| 100 | hEPO 597 23 | 1-methyl-pseudo-UTP/5-methyl-CTP/ATP/GTP | 87.13 | 0.141 | 98 |
| 100 | hEPO 597 24 | 1-methyl-pseudo-UTP/CTP/ATP/GTP | 87.92 | 0.098 | 98 |

Methods and Data

Female Balb/c mice (n=5) were administered 0.05 mg/kg IM (50 ul in the quadriceps) or IV (100 ul in the tail vein) of human EPO mRna. At time 8 hours after the injection mice were euthanized and blood was collected in serum separator tubes. The samples were spun and serum samples were then run on an EPO ELISA following the kit protocol (Stem Cell Technologies Catalog #01630). The results are shown in Table 39.

TABLE 39

Results of In vivo assay

| Sample Name | hEPO IV (pg/ml) | hEPO IM (pg/ml) |
|---|---|---|
| hEPO 597 1 | 2205 | 1068 |
| hEPO 597 2 | 9618 | 2045 |
| hEPO 597 3 | 12583 | 2315 |

TABLE 39-continued

Results of In vivo assay

| Sample Name | hEPO IV (pg/ml) | hEPO IM (pg/ml) |
|---|---|---|
| hEPO 597 4 | 11617 | 3537 |
| hEPO 597 5 | 42259 | 6388 |
| hEPO 597 6 | 3693 | 1591 |
| hEPO 597 7 | 7226 | 1722 |
| hEPO 597 8 | 3432 | 1258 |
| hEPO 597 9 | 11736 | 1883 |
| hEPO 597 10 | 6860 | 1832 |
| hEPO 597 11 | 7779 | 2156 |
| hEPO 597 12 | 11894 | 2791 |
| hEPO 597 13 | 17942 | 2945 |
| hEPO 597 15 | 19171 | 4860 |
| hEPO 597 16 | 10842 | 2014 |
| hEPO 597 17 | 20685 | 3534 |
| hEPO 597 18 | 2389 | 777 |
| hEPO 597 19 | 6808 | 1777 |
| hEPO 597 20 | 9138 | 2369 |
| hEPO 597 21 | 35819 | 3708 |
| hEPO 597 22 | 1350 | 344 |
| hEPO 597 23 | 27438 | 3183 |
| hEPO 597 24 | 43755 | 3826 |

Other Embodiments

It is to be understood that while the present disclosure has been described in conjunction with the detailed description thereof, the foregoing description is intended to illustrate and not limit the scope of the present disclosure, which is defined by the scope of the appended claims. Other aspects, advantages, and modifications are within the scope of the following claims.

The invention claimed is:

1. An mRNA encoding a polypeptide, wherein at least one base is 1-methyl-pseudouracil and one base is 5-methoxy-uracil.

2. A pharmaceutical composition comprising the mRNA of claim 1 and a pharmaceutically acceptable excipient.

3. A method of expressing a polypeptide in a mammalian cell, said method comprising the steps of:
   (i) providing an mRNA of claim 1; and
   (ii) introducing said mRNA to a mammalian cell under conditions that permit the expression of the polypeptide by the mammalian cell,
thereby expressing the polypeptide in the mammalian cell.

4. The mRNA of claim 1, wherein about 25% of the uracils are 1-methyl-pseudouracil and about 75% of the uracils are 5-methoxy-uracil.

5. The mRNA of claim 1, wherein about 50% of the uracils are 1-methyl-pseudouracil and about 50% of the uracils are 5- methoxy-uracil.

6. The mRNA of claim 1, wherein about 75% of the uracils are 1-methyl-pseudouracil and about 25% of the uracils are 5-methoxy-uracil.

7. The mRNA of claim 1, wherein at least one base is 5-methyl-cytosine.

8. The mRNA of claim 1, wherein at least one nucleotide is alpha-thio-adenosine or alpha-thio-guanosine.

9. The mRNA of claim 8, wherein about 2-100% of the adenosines and/or guanosines in the mRNA are alpha-thio-adenosine and/or alpha-thio-guanosine.

10. The mRNA of claim 9, wherein about 2% of the adenosines and/or guanosines in the mRNA are alpha-thio-adenosine and/or alpha-thio-guanosine.

11. The mRNA of claim 1 further comprising:
   (i) at least one 5'-cap structure;
   (ii) a 5'-UTR optionally comprising a Kozak sequence; and
   (iii) a 3'-UTR.

12. The mRNA of claim 11, wherein the at least one 5'-cap structure is Cap0, Cap1, ARCA, inosine, N1-methyl-guanosine, 2'-fluoro-guanosine, 7-deaza-guanosine, 8-oxo-guanosine, 2-amino-guanosine, LNA-guanosine, or 2-azido-guanosine.

13. The mRNA of claim 11 further comprising a poly-A tail.

14. The mRNA of claim 1, wherein the mRNA is codon optimized.

* * * * *

SEQUENCE LISTING

<160> NUMBER OF SEQ ID NOS: 14

<210> SEQ ID NO 1
<211> LENGTH: 784
<212> TYPE: DNA
<213> ORGANISM: Homo sapiens

<400> SEQUENCE: 1

```
gggagatcag agagaaaaga agagtaagaa gaaatataag agccaccatg gccggtcccg      60
cgacccaaag ccccatgaaa cttatggccc tgcagttgct gctttggcac tcggccctct     120
ggacagtcca agaagcgact cctctcggac ctgcctcatc gttgccgcag tcattccttt     180
tgaagtgtct ggagcaggtg cgaaagattc agggcgatgg agccgcactc caagagaagc     240
tctgcgcgac atacaaactt tgccatcccg aggagctcgt actgctcggg cacagcttgg     300
ggattccctg ggctcctctc tcgtcctgtc cgtcgcaggc tttgcagttg gcagggtgcc     360
tttcccagct ccactccggt ttgttcttgt atcagggact gctgcaagcc cttgagggaa     420
tctcgccaga attgggcccg acgctggaca cgttgcagct cgacgtggcg gatttcgcaa     480
caaccatctg gcagcagatg gaggaactgg ggatggcacc cgcgctgcag cccacgcagg     540
gggcaatgcc ggccttttgcg tccgcgtttc agcgcagggc gggtggagtc ctcgtagcga     600
gccaccttca atcattttg gaagtctcgt accgggtgct gagacatctt gcgcagccgt     660
gataataggc tggagcctcg gtggccatgc ttcttgcccc ttgggcctcc ccccagcccc     720
tcctcccctt cctgcacccg tacccccgtg gtctttgaat aaagtctgag tgggcggctc     780
taga                                                                  784
```

<210> SEQ ID NO 2
<211> LENGTH: 784
<212> TYPE: RNA
<213> ORGANISM: Homo sapiens

<400> SEQUENCE: 2

```
gggagaucag agagaaaaga agaguaagaa gaaauauaag agccaccaug gccggucccg      60
cgacccaaag ccccaugaaa cuuauggccc ugcaguugcu gcuuuggcac ucggcccucu     120
ggacagucca agaagcgacu ccucucggac cugccucauc guugccgcag ucauuccuuu     180
ugaaguaucu ggagcaggug cgaaagauuc agggcgaugg agccgcacuc caagagaagc     240
ucugcgcgac auacaaacuu ugccaucccg aggagcucgu acugcucggg cacagcuugg     300
```

| | |
|---|---|
| ggauucccug ggcuccucuc ucguccuguc cgucgcaggc uuugcaguug gcagggugcc | 360 |
| uuucccagcu ccacuccggu uuguucuugu aucagggacu gcugcaagcc cuugagggaa | 420 |
| ucucgccaga auugggcccg acgcuggaca cguugcagcu cgacguggcg gauuucgcaa | 480 |
| caaccaucug gcagcagaug gaggaacugg ggauggcacc cgcgcugcag cccacgcagg | 540 |
| gggcaaugcc ggccuuugcg uccgcguuuc agcgcagggc ggguggaguc cucguagcga | 600 |
| gccaccuuca aucauuuuug gaagucucgu accggguget gagacaucuu gcgcagccgu | 660 |
| gauaauaggc uggagccucg guggccaugc uucuugcccc uugggccucc ccccagcccc | 720 |
| uccuccccuu ccugcacccg uaccccgug gucuuugaau aaagucugag ugggcggcuc | 780 |
| uaga | 784 |

<210> SEQ ID NO 3
<211> LENGTH: 1822
<212> TYPE: DNA
<213> ORGANISM: Homo sapiens

<400> SEQUENCE: 3

| | |
|---|---|
| gggaaauaag agagaaaaga agaguaagaa gaaauauaag agccaccaug aagaugcga | 60 |
| agaacaucaa gaagggaccu gccccguuuu acccuuugga ggacgguaca gcaggagaac | 120 |
| agcuccacaa ggcgaugaaa cgcuacgccc uggucccggg aacgauugcg uuuaccgaug | 180 |
| cacauauuga ggtagacauc acauacgcag aauacuucga aauguccggug aggcuggcgg | 240 |
| aagcgaugaa gagauauggu cuuaacacua aucaccgcau cguggugugu ucggagaacu | 300 |
| cauugcaguu uuucaugccg guccuuggag cacuuuucau cggggucgca gucgcgccag | 360 |
| cgaacgacau cuacaaugag cgggaacucu ugaauagcau gggaaucucc cagccgacgg | 420 |
| ucgugguugu cucccaaaaag gggcugcaga aaauccucaa cguggcagaag aagcucccca | 480 |
| uuauucaaaa gaucaucauu augggauagca agacagauua ccaagggguuc cagucgaugu | 540 |
| auaccuuugu gacaucgcau uugccgccag ggtuuaacga guaugacuuc gucccgagu | 600 |
| cauuugacag agauaaaaacc aucgcgcuga uuaugaauuc cucgggguagc accgguuugc | 660 |
| caaagggggu ggcguugccc caccgcacug cuugugugcg guucucgcac gcuagggauc | 720 |
| cuaucuuugg uaaucagauc auucccgaca cagcaauccu guccguggua ccuuuucauc | 780 |
| acgguuuugg cauguucacg acucucggcu auuugauuug cgguuucagg gucguacuua | 840 |
| ugauaucgguu cgaggaagaa cuguuuuuga gauccuugca agauuacaag auccagucgg | 900 |
| cccuccuugu gccaacgcuu uucucauucu uugcgaaauc gacacuauu gauaaguaug | 960 |
| accuuuccaa ucugcaugag auugccucag gggagcgcc gcuuagcaag gaagucgggg | 1020 |
| aggcaguggc caagcgcuuc caccuucccg gaauucggca gggauacggg cucacgagag | 1080 |
| caacauccgc gauccuuauc acgcccgagg gugacgauaa gccgggagcc gucggaaaag | 1140 |
| ugguccccuu cuuugaagcc aagguccguag accucgacac gggaaaaacc cucggaguga | 1200 |
| accagagggg cgagcucugc gugagagggc cgaugaucau gucaggucuac guagaauaacc | 1260 |
| cugaagcgac gaaugcgcug aucgacaagg augggugguu gcauucggga gacauugccu | 1320 |
| auugggauga ggaugagcac uucuuuaucg uagaucgacu uaagagcuug aucaaauaca | 1380 |
| aaggcuauca ggtagcgccu gccgagcucg agucaaucccu gcuccagcac cccaacauuu | 1440 |
| ucgacgccgg aguggccggg uugcccgaug acgacgcggg ugагcuпgccа gcggccguga | 1500 |
| uaguccucga acauggaaaa acaaugaccg aaaaggagau cguggacuac guagcaucac | 1560 |
| aаguагсgас uсgcаагаaа cugaggggag gguагucuu uguuгасgаg gucccgaaag | 1620 |

```
gcttgactgg gaagcttgac gctcgcaaaa tccgggaaat cctgattaag gcaaagaaag      1680
gcgggaaaat cgctgtctga taataggctg gagcctcggt ggccatgctt cttgcccctt      1740
gggcctcccc ccagcccctc ctccccttcc tgcacccgta ccccgtggt ctttgaataa       1800 agtctgagtg ggcggctcta ga                                              1822
```

<210> SEQ ID NO 4
<211> LENGTH: 1822
<212> TYPE: RNA
<213> ORGANISM: Homo sapiens

<400> SEQUENCE: 4

```
gggaaauaag agagaaaaga agaguaagaa gaaauauaag agccaccaug gaagaugcga       60
agaacaucaa gaagggaccu gccccguuuu acccuuugga ggacgguaca gcaggagaac      120
agcuccacaa ggcgaugaaa cgcuacgccc uggucccgg aacgauugcg uuuaccgaug       180
cacauauuga gguagacauc acauacgcag aauacuucga aaugucggug aggcuggcgg      240
aagcgaugaa gagauauggu cuuaacacua aucaccgcau cguggugugu ucggagaacu      300
cauugcaguu uuucaugccg guccuuggag cacuuuucau cggggucgca gucgcgccag      360
cgaacgacau cuacaaugag cgggaacucu ugaauagcau gggaaucccc agccgacgg       420 ucguguuugu cuccaaaaag gggcugcaga aaauccucaa cgugcagaag aagcuccccca     480 uuauucaaaa gaucaucauu auggaugca agacagauua ccaagggucuc cagucgaugu     540 auaccuuugu gacaucgcau uugccgccag ggauuaacga guaugacuuc gucccccgagu    600 cauuugacag agauaaaacc aucgcgcuga uuaugaauuc ucggguagc accgguuugc      660 caaagggggu ggcguugccc caccgcacug cuugugugcg guucucgcac gcuagggauc     720
cuaucuuugg uaaucagauc auucccgaca cagcaauccu guccgugguaa ccuuuucauc     780 acgguuuugg caguguacg cacucucggcu auuugauuug cgguucagg gucguacuua     840 uguaucgguu cgaggaagaa cuguuuuuga gauccuugca agauuacaag auccagucgg      900
cccuccuugu gccaacgcuu uucucauucu uugcgaaauc gacacuuauu gauaaguaug      960
accuuuccaa ucugcaugag auugcccag ggggagcgcc gcuuagcaag gaagucgggg       1020 aggcagugc caagcgcuuc caccuucccg gaauucggca gggauacggg cucacggaga       1080
caacauccgc gauccuuauc acgcccgagg gugacgauaa gccggagcc gucgaaaag       1140 uggucccuu cuuugaagcc aaggucuag accucgacac gggaaaaaacc cucggagugu      1200 accagagggg cgagcucugc gugagggggc cgaugaucau gucagguuac gugaauaacc     1260
cugaagcgac gaaugcgcug aucgacaagg augggguggu ucauuugga gacauugccu      1320 auugggauga ggaugagcac uucuuuaucg uagaucgacu uaagagcuug aucaaauaca     1380
aagcuaauca gguagcgccu gccgagcucg agucaauccu gcuccagcac cccaacauuu     1440
ucgacgccgg aguggccggg uugcccgaug acgacgcggg ugagcugcca gcggccgugg    1500
uagcccucga acaugggaaa acaaugaccg aaaaggagau cguggacuac guagcaucac    1560
aagugacgac ugcgaagaaa cugaggggag gguagucuu ugggacgag ucccgaaag       1620 gcuugacugg gaagcuugac gcucgcaaaa uccgggaaau ccugauuaag gcaaagaaag    1680
gcgggaaaau cgcugucuga uaauaggcug gagccucgggu ggccaugcuu cuugccccuu   1740 gggcucccc ccagcccuc cuccccuucc ugcacccguua ccccguggu cuuugaauaa       1800 agucugagug ggcggcucua ga                                              1822
```

```
<210> SEQ ID NO 5
<211> LENGTH: 751
<212> TYPE: DNA
<213> ORGANISM: Homo sapiens

<400> SEQUENCE: 5 gggaataag  agagaaaaga  agagtaagaa  gaaatataag  agccaccatg  ggagtgcacg      60
agtgtcccgc  gtggttgtgg  ttgctgctgt  cgctcttgag  cctcccactg  ggactgcctg     120 tgctggggc   accacccaga  ttgatctgcg  actcacgggt  acttgagagg  taccttcttg     180
aagccaaaga  agccgaaaac  atcacaaccg  gatgcgccga  gcactgctcc  ctcaatgaga     240
acattactgt  accggataca  aaggtcaatt  tctatgcatg  gaagagaatg  gaagtaggac     300
agcaggccgt  cgaagtgtgg  caggggctcg  cgcttttgtc  ggaggcggtg  ttgcggggtc     360
aggccctcct  cgtcaactca  tcacagccgt  gggagcccct  ccaacttcat  gtcgataaag     420
cggtgtcggg  gctccgcagc  ttgacgacgt  tgcttcgggc  tctgggcgca  caaaaggagg     480
ctatttcgcc  gcctgacgcg  gcctccgcgg  caccccctcg  aacgatcacc  gcggacacgt     540
ttaggaagct  ttttagagtg  tacagcaatt  tcctccgcgg  aaagctgaaa  ttgtatactg     600
gtgaagcgtg  taggacaggg  gatcgctgat  aataggctgg  agcctcggtg  gccatgcttc     660
ttgccccttg  ggcctccccc  cagcccctcc  tccccttcct  gcacccgtac  ccccgtggtc     720
tttgaataaa  gtctgagtgg  gcggctctag  a                                     751

<210> SEQ ID NO 6
<211> LENGTH: 751
<212> TYPE: RNA
<213> ORGANISM: Homo sapiens

<400> SEQUENCE: 6 gggaauaag   agagaaaaga  agaguaagaa  gaaauauaag  agccaccaug  ggagugcacg      60 aguguccgc   gugguugugg  uugcugcugu  cgcucuugag  ccucccacug  ggacugccug     120 ugcuggggc   accacccaga  uugaucugcg  acucacgggu  acuugagagg  uaccuucuug     180
aagccaaaga  agccgaaaac  aucacaaccg  gaugcgccga  gcacugcucc  cucaaugaga     240
acauuacugu  accggauaca  aaggucaauu  ucuaugcaug  gaagagaaug  gaaguaggac     300
agcaggccgu  cgaagugugg  caggggcucg  cgcuuuuguc  ggaggcggug  uugcgggguc     360
aggcccuccu  cgucaacuca  ucacagccgu  gggagcccu   ccaacuucau  gucgauaaag     420 cgguguucggg gcuccgcagc  uugacgacgu  ugcuucgggc  ucugggcgca  caaaaggagg     480
cuauuucgcc  gccugacgcg  gccuccgcgg  caccccuccg  aacgaucacc  gcggacacgu     540
uuaggaagcu  uuuuagagug  uacagcaauu  uccuccgcgg  aaagcugaaa  uuguauacug     600
gugaagcgug  uaggacaggg  gaucgcugau  aauaggcugg  agccucggug  gccaugcuuc     660
uugccccuug  ggccuccccc  cagccccucc  ucccuucuu   gcacccguac  ccccgugguc     720
uuugaauaaa  gucugagugg  gcggcucuag  a                                     751

<210> SEQ ID NO 7
<211> LENGTH: 925
<212> TYPE: DNA
<213> ORGANISM: Homo sapiens

<400> SEQUENCE: 7
tcaagctttt  ggaccctcgt  acagaagcta  atacgactca  ctatagggaa  ataagagaga      60 aagaagagt   aagaagaaat  ataagagcca  ccatggtatc  caggggggag  gaggacaaca     120
```

| | |
|---|---|
| tggcgatcat caaggagttc atgcgattca aggtgcacat ggaaggttcg gtcaacggac | 180 |
| acgaatttga aatcgaagga gagggtgaag gaaggcccta tgaagggaca cagaccgcga | 240 |
| aactcaaggt cacgaaaggg ggaccacttc ctttcgcctg ggacattctt tcgcccagt | 300 |
| ttatgtacgg gtccaaagca tatgtgaagc atcccgccga tattcctgac tatctgaaac | 360 |
| tcagctttcc cgagggattc aagtgggagc gggtcatgaa ctttgaggac ggggggtgtag | 420 |
| tcaccgtaac ccaagactca agcctccaag acggcgagtt catctacaag gtcaaactgc | 480 |
| gggggactaa ctttccgtcg gatgggccgg tgatgcagaa gaaaacgatg ggatgggaag | 540 |
| cgtcatcgga gaggatgtac ccagaagatg gtgcattgaa gggggagatc aagcagagac | 600 |
| tgaagttgaa agatggggga cattatgatg ccgaggtgaa aacgacatac aaagcgaaaa | 660 |
| agccggtgca gcttcccgga gcgtataatg tgaatatcaa gttggatatt acttcacaca | 720 |
| atgaggacta cacaattgtc gaacagtacg aacgcgctga gggtagacac tcgacgggag | 780 |
| gcatggacga gttgtacaaa tgataatagg ctggagcctc ggtggccatg cttcttgccc | 840 |
| cttgggcctc cccccagccc ctcctcccct tcctgcaccc gtaccccgt ggtctttgaa | 900 |
| taaagtctga gtgggcggct ctaga | 925 |

<210> SEQ ID NO 8
<211> LENGTH: 730
<212> TYPE: DNA
<213> ORGANISM: Homo sapiens

<400> SEQUENCE: 8

| | |
|---|---|
| tcaagctttt ggaccctcgt acagaagcta atacgactca ctatagggaa ataagagaga | 60 |
| aaagaagagt aagaagaaat ataagagcca ccatggtttt taccctcgaa gattttgtcg | 120 |
| gagattggag acagactgcc ggatacaacc ttgaccaagt cctcgagcaa ggcggtgtgt | 180 |
| cgtcactctt ccaaaacctg ggtgtgtccg tgactcccat ccagcgcatc gtcctgagcg | 240 |
| gcgaaaatgg gttgaagatc gacatccatg tgatcattcc atacgaggga ctgtccgggg | 300 |
| accagatggg tcagatcgaa aagattttca agtggtgta cccggtcgac gatcatcact | 360 |
| tcaaggtgat cctgcactac ggaacgctgg tgatcgatgg ggtgaccccg aacatgattg | 420 |
| actatttcgg acggccttac gagggcatcg cagtgttcga cggaaagaag atcaccgtga | 480 |
| ccggcactct gtggaatgga aacaaaatca tcgacgaacg cctgatcaat ccggatggct | 540 |
| cgctgttgtt ccgggtgacc attaacggag tcactggatg gaggctctgc gagcgcatcc | 600 |
| ttgcgtgata ataggctgga gcctcggtgg ccatgcttct tgccccttgg gcctcccccc | 660 |
| agcccctcct ccccttcctg caccgtacc cccgtggtct ttgaataaag tctgagtggg | 720 |
| cggctctaga | 730 |

<210> SEQ ID NO 9
<211> LENGTH: 796
<212> TYPE: DNA
<213> ORGANISM: Homo sapiens

<400> SEQUENCE: 9

| | |
|---|---|
| tcaagctttt ggaccctcgt acagaagcta atacgactca ctatagggaa ataagagaga | 60 |
| aaagaagagt aagaagaaat ataagagcca ccatgggagt gcacgagtgt cccgcgtggt | 120 |
| tgtggttgct gctgtcgctc ttgagcctcc cactgggact gctgtgctg ggggcaccac | 180 |
| ccagattgat ctgcgactca cgggtacttg agaggtacct tcttgaagcc aaagaagccg | 240 |
| aaaacatcac aaccggatgc gccgagcact gctccctcaa tgagaacatt actgtaccgg | 300 |

```
atacaaaggt caatttctat gcatggaaga gaatggaagt aggacagcag gccgtcgaag    360
tgtggcaggg gctcgcgctt ttgtcggagg cggtgttgcg gggtcaggcc ctcctcgtca    420
actcatcaca gccgtgggag cccctccaac ttcatgtcga taaagcggtg tcggggctcc    480
gcagcttgac gacgttgctt cgggctctgg gcgcacaaaa ggaggctatt tcgccgcctg    540
acgcggcctc cgcggcaccc ctccgaacga tcaccgcgga cacgtttagg aagctttta    600 gagtgtacag caatttcctc cgcggaaagc tgaaattgta tactggtgaa gcgtgtagga    660
caggggatcg ctgataatag gctggagcct cggtggccat gcttcttgcc ccttgggcct    720
ccccccagcc cctcctcccc ttcctgcacc cgtaccccg tggtctttga ataaagtctg     780
agtgggcggc tctaga                                                    796

<210> SEQ ID NO 10
<211> LENGTH: 793
<212> TYPE: DNA
<213> ORGANISM: Mus musculus

<400> SEQUENCE: 10
tcaagctttt ggaccctcgt acagaagcta atacgactca ctatagggaa ataagagaga     60
aaagaagagt aagaagaaat ataagagcca ccatgggggt gcccgaacgt cccaccctgc    120
tgcttttact ctccttgcta ctgattcctc tgggcctccc agtcctctgt gctcccccac    180
gcctcatctg cgacagtcga gttctggaga ggtacatctt agaggccaag gaggcagaaa    240
atgtcacgat gggttgtgca gaaggtccca gactgagtga aaatattaca gtcccagata    300
ccaaagtcaa cttctatgct tggaaaagaa tggaggtgga agaacaggcc atagaagttt    360
ggcaaggcct gtccctgctc tcagaagcca tcctgcaggc ccaggccctg ctagccaatt    420
cctcccagcc accagagacc cttcagcttc atatagacaa agccatcagt ggtctacgta    480
gcctcacttc actgcttcgg gtactgggag ctcagaagga attgatgtcg cctccagata    540
ccaccccacc tgctccactc cgaacactca cagtggatac tttctgcaag ctcttccggg    600
tctacgccaa cttcctccgg gggaaactga agctgtacac gggagaggtc tgcaggagag    660
gggacaggtg ataataggct ggagcctcgg tggccatgct tcttgcccct tgggcctccc    720
cccagcccct cctccccttc ctgcaccgt accccgtgg tctttgaata aagtctgagt     780
gggcggctct aga                                                      793

<210> SEQ ID NO 11
<211> LENGTH: 10
<212> TYPE: DNA
<213> ORGANISM: Artificial Sequence
<220> FEATURE:
<223> OTHER INFORMATION: 3' U-rich region

<400> SEQUENCE: 11
tttttctttt                                                            10

<210> SEQ ID NO 12
<211> LENGTH: 11
<212> TYPE: DNA
<213> ORGANISM: Artificial Sequence
<220> FEATURE:
<223> OTHER INFORMATION: 3' U-rich region

<400> SEQUENCE: 12
ttttgctttt t                                                          11
```

```
<210> SEQ ID NO 13
<211> LENGTH: 10
<212> TYPE: DNA
<213> ORGANISM: Artificial Sequence
<220> FEATURE:
<223> OTHER INFORMATION: 3' U-rich region

<400> SEQUENCE: 13
ttttgctttt                                                              10

<210> SEQ ID NO 14
<211> LENGTH: 11
<212> TYPE: DNA
<213> ORGANISM: Artificial Sequence
<220> FEATURE:
<223> OTHER INFORMATION: 3' A-rich region

<400> SEQUENCE: 14
aaaaagcaaa a                                                            11
```